US009533982B2

(12) United States Patent
Conn et al.

(10) Patent No.: US 9,533,982 B2
(45) Date of Patent: Jan. 3, 2017

(54) SUBSTITUTED BICYCLIC HETEROARYL CARBOXAMIDE ANALOGS AS MGLUR5 NEGATIVE ALLOSTERIC MODULATORS

(71) Applicant: Vanderbilt University, Nashville, TN (US)

(72) Inventors: P. Jeffrey Conn, Nashville, TN (US); Craig W. Lindsley, Brentwood, CA (US); Kyle A. Emmitte, Spring Hill, TN (US); Andrew S. Felts, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/664,792

(22) Filed: Mar. 20, 2015

(65) Prior Publication Data
US 2015/0266866 A1    Sep. 24, 2015

Related U.S. Application Data

(60) Provisional application No. 61/968,323, filed on Mar. 20, 2014.

(51) Int. Cl.
C07D 401/14    (2006.01)
A61K 31/506    (2006.01)
C07D 417/14    (2006.01)
C07D 403/14    (2006.01)

(52) U.S. Cl.
CPC ........... *C07D 417/14* (2013.01); *A61K 31/506* (2013.01); *C07D 401/14* (2013.01); *C07D 403/14* (2013.01)

(58) Field of Classification Search
CPC ... C07D 401/14; C07D 403/14; C07D 417/14; A61K 31/506
USPC .................................. 544/333; 514/249, 256
See application file for complete search history.

(56) References Cited

U.S. PATENT DOCUMENTS

| 6,638,953 | B2 | 10/2003 | Gaster et al. |
| 6,846,827 | B1 | 1/2005 | Cumming |
| 7,414,060 | B2 | 8/2008 | Jaeschke et al. |
| 8,501,757 | B2 | 8/2013 | Conn et al. |
| 8,569,308 | B2 | 10/2013 | Conn et al. |
| 8,598,345 | B2 | 12/2013 | Conn et al. |
| 8,796,295 | B2 | 8/2014 | Conn et al. |
| 9,085,562 | B2 | 7/2015 | Conn et al. |
| 2003/0134843 | A1 | 7/2003 | Lubisch et al. |
| 2006/0199828 | A1 | 9/2006 | Jaeschke et al. |
| 2006/0199858 | A1 | 9/2006 | Durst et al. |
| 2006/0235035 | A1 | 10/2006 | Hogberg et al. |
| 2006/0235069 | A1 | 10/2006 | Duggan et al. |
| 2007/0149547 | A1 | 6/2007 | Bonnefous et al. |
| 2007/0293457 | A1 | 12/2007 | Baker et al. |
| 2009/0042855 | A1 | 2/2009 | Conn et al. |
| 2009/0047296 | A1 | 2/2009 | Doronina et al. |
| 2009/0124625 | A1 | 5/2009 | Bessis et al. |
| 2009/0197883 | A1 | 8/2009 | Armstrong et al. |
| 2010/0179121 | A1 | 7/2010 | Chen et al. |
| 2010/0227887 | A1 | 9/2010 | Jaeschke et al. |
| 2010/0317643 | A1 | 12/2010 | Goodacre et al. |
| 2011/0152299 | A1 | 6/2011 | Conn et al. |
| 2011/0166158 | A1 | 7/2011 | Conn et al. |
| 2011/0172247 | A1 | 7/2011 | Conn et al. |
| 2011/0172248 | A1 | 7/2011 | Conn et al. |
| 2012/0129812 | A1 | 5/2012 | Kawata et al. |
| 2012/0178742 | A1 | 7/2012 | Henrich et al. |

FOREIGN PATENT DOCUMENTS

| AU | 2012223720 | 3/2012 |
| AU | 2014353150 | 11/2014 |
| BE | 10817936.7 | 9/2010 |
| CA | 2774372 | 9/2010 |
| CA | 2774373 | 9/2010 |
| CA | 2774374 | 9/2010 |
| CA | 2774515 | 9/2010 |
| CA | 2828877 | 3/2012 |
| CA | 2931097 | 11/2014 |
| CH | 10817936.7 | 9/2010 |
| DE | 10817936.7 | 9/2010 |
| DK | 10817936.7 | 9/2010 |
| EP | 10817928.4 | 9/2010 |
| EP | 10817936.7 | 9/2010 |
| EP | 10817950.8 | 9/2010 |
| EP | 10817954.0 | 9/2010 |
| EP | 12752374.4 | 3/2012 |
| EP | 2447630 A2 | 5/2012 |
| EP | 2477629 A1 | 7/2012 |
| ES | 10817936.7 | 9/2010 |

(Continued)

OTHER PUBLICATIONS

Ulrich, Crystallization, Kirk-Othmer Encyclopedia of Chemical Technology, pp. 1-7, 2002.*
Vippagunta et al., Crystalline Solids, Advanced Drug Delivery Reviews 48 (2001), pp. 3-26.*
Abdel-Magid et al. (1996) Reductive Amination of Aldehydes and Ketones with Sodium Triacetoxyborohydride. Studies on Direct and Indirect Reductive Amination Procedures(1). *J. Org. Chem.* 61: 3849-3862.
Awad et al. (2000) Activation of metabotropic glutamate receptor 5 has direct excitatory effects and potentiates NMDA receptor currents in neurons of the subthalamic nucleus. *J. Neurosci.* 20: 7871-7879.

(Continued)

*Primary Examiner* — Deepak Rao
(74) *Attorney, Agent, or Firm* — Ballard Spahr LLP

(57) ABSTRACT

Disclosed are negative allosteric modulators of the metabotropic glutamate receptor subtype 5 (mGluR5); synthetic methods for making the compounds; pharmaceutical compositions comprising the compounds; and methods of treating neurological and psychiatric disorders associated with glutamate dysfunction using the compounds and compositions. This abstract is intended as a scanning tool for purposes of searching in the particular art and is not intended to be limiting of the present invention.

20 Claims, 2 Drawing Sheets

(56) References Cited

FOREIGN PATENT DOCUMENTS

| | | |
|---|---|---|
| FR | 1472619 A | 3/1967 |
| FR | 10817936.7 | 9/2010 |
| GB | 10817936.7 | 9/2010 |
| IE | 10817936.7 | 9/2010 |
| IT | 10817936.7 | 9/2010 |
| JP | 2007-524682 A | 8/2007 |
| JP | 2012-529943 | 9/2010 |
| JP | 2012-529946 | 9/2010 |
| JP | 2013-556618 | 3/2012 |
| JP | 5792173 B2 | 10/2015 |
| JP | 2016-123582 | 6/2016 |
| NL | 10817936.7 | 9/2010 |
| SE | 10817936.7 | 9/2010 |
| TR | 10817936.7 | 9/2010 |
| WO | WO-03/059258 A2 | 7/2003 |
| WO | WO-2004/037789 A2 | 5/2004 |
| WO | WO-2005/004863 A1 | 1/2005 |
| WO | WO-2005/079802 A1 | 9/2005 |
| WO | WO-2006/091639 A2 | 8/2006 |
| WO | WO-2006/094691 A1 | 9/2006 |
| WO | WO-2006/115895 A2 | 11/2006 |
| WO | WO-2008/092072 A2 | 7/2008 |
| WO | WO-2009/010454 A2 | 1/2009 |
| WO | WO-2009/047296 A2 | 4/2009 |
| WO | WO-2009/135758 A1 | 11/2009 |
| WO | PCT/US10/049358 | 9/2010 |
| WO | PCT/US10/049373 | 9/2010 |
| WO | PCT/US10/049400 | 9/2010 |
| WO | PCT/US10/049407 | 9/2010 |
| WO | WO-2010/142752 A1 | 12/2010 |
| WO | WO-2011/035186 A1 | 3/2011 |
| WO | WO-2011/035209 A1 | 3/2011 |
| WO | WO-2011/035214 A1 | 3/2011 |
| WO | PCT/US12/000119 | 3/2012 |
| WO | PCT/US14/066207 | 11/2014 |

OTHER PUBLICATIONS

Bloch, R. (1998) Additions of Organometallic Reagents to C=N Bonds: Reactivity and Selectivity. *Chem. Rev.* 98: 1407-1438.

Botteghi et al. (2001) Rhodium catalyzed hydroformylation of 1,1-bis(p-fluorophenyl)allyl or propargyl alcohol: a key step in the synthesis of *Fluspirilen* and *Penfluridol*. *Tetrahedron* 57: 1631-1637.

Broekkamp et al. (1986) Major tranquillizers can be distinguished from minor tranquillizers on the basis of effects on marble burying and swim-induced grooming in mice. *Eur. J. Pharmacol.* 126: 223-229.

Brookhart and Studabaker (1987) Cyclopropanes from reactions of transition metal carbene complexes with olefins. *Chem. Rev.* 87: 411-432.

Burkhard et al. (2010) Synthesis and structural analysis of a new class of azaspiro[3.3]heptanes as building blocks for medicinal chemistry. *Org. Lett.* 12: 1944-1947.

Cella, J. A. (1982) Reductive alkylation/arylation of arylcarbinols and ketonsd with organosilicon compounds. *J. Org. Chem.* 47: 2125-2130.

Chiamulera et al. (2001) Reinforcing and locomotor stimulant effects of cocaine are absent in mGluR5 null mutant mice. *Nature Neurosci.* 4: 873-874.

Christlieb et al. (2001) The stereoselective synthesis of oxetanes; exploration of a new, Mitsonobu-style procedure for the cyclisation of 1,3-diols. *J. Chem. Soc. Perkin Trans.* 1: 2983-2996.

Ciaccio et al. (2003) "Instant Methylide" Modification of the Corey-Chaykovsky Epoxide Synthesis. *Synthetic Comm.* 33: 2135-2143.

De and Gibbs (2005) Bismuth(III) Chloride-Catalyzed Direct Deoxygenative Allylation of Substituted Benzylic Alcohols with Allyltrimethylsilane. *Tetrahedron Lett.* 46: 8345-8350.

De Kimpe and De Smaele (1994) Synthesis of aziridines and azetidines from N-(ω-haloalkyl). *Tetrahedron Lett.* 35: 8023-8026.

de Vrij et al. (2008) Rescue of behavioral phenotype and neuronal protrusion morphology in Fmr1 KO mice. *Neurobiol. Disease* 31(1): 127-132.

Deacon, R. M. J. (2006) Digging and marble burying in mice: simplest methods for in vivo identification of biological impacts. *Nature Protocols* 1: 122-124.

Dolbier et al. (2004) Trimethylsilyl fluorosulfonyldifluoroacetate (TFDA): a new, highly efficient difluorocarbene reagent. *J. Fluorine Chem.* 125: 459-469.

Fleming and Urch (1985) Stereospecific cyclopropane synthesis from γ-stannyl alcohols. *J. Organomet. Chem.* 285: 173-191.

Gass et al. (2009) mGluR5 antagonism attenuates methamphetamine reinforcement and prevents reinstatement of methamphetamine-seeking behavior in rats. *Neuropsychopharmacology* 34: 820-833.

Grant No. 5R01-NS031373-15 awarded by NINDS. (Abstract).
Grant No. 1R01-DA023947-01 awarded by NIDA. (Abstract).
Grant No. 2R01-MH062646-12 awarded by NIMH. (Abstract).
Grant No. 5R01-MH073676-04 awarded by NIMH. (Abstract).

Groundwater et al. (2001) A novel synthesis of imidazoles via the cycloaddition of nitrile ylides to their imidoyl chloride precursors. *J. Chem. Soc., Perkin Trans.* 1: 2781-2787.

Gribble and Leese (1997) Reactions of Sodium Borohydride in Acidic Media; IV. Reduction of Diarylmethanols and Triarylmethanols in Trifluoroacetic Acid 1-3. *Synthesis-stuttgart* 172-176.

Grygorenko et al. (2011) Trifluoromethyl-substituted cyclopropanes. *Tetrahedron* 67: 803-823.

Ishiyama et al. (1995) Palladium(0)-Catalyzed Cross-Coupling Reaction of Alkoxydiboron with Haloarenes: A Direct Procedure for Arylboronic Esters. *J. Org. Chem.* 60: 7508-7510.

Jensen et al. (2005) Transient lower esophageal sphincter relaxations in dogs are inhibited by a metabotropic glutamate receptor 5 antagonist. *Eur. J. Pharmacol.* 519: 154-157.

Kawai, H. (2010) Cinchona alkaloid-catalyzed asymmetric trigluoromethylation of alkynyl ketones with trimethylsilyl trifluoromethane. *Org. Lett.* 12: 5104-5107.

Kotlinska and Bochenski (2007) Comparison of the effects of mGluR1 and mGluR5 antagonists on the expression of behavioral sensitization to the locomotor effect of morphine and the morphine withdrawal jumping in mice. *Eur. J. Pharmacol.* 448: 113-118.

Lominac et al. (2006) Behavioral and neurochemical interactions between Group 1 mGluR antagonists and ethanol: potential insight into their anti-addictive properties. *Drug Alcohol Depend.* 85: 142-156.

Mannaioni et al. (2001) Metabotropic glutamate receptors 1 and 5 differentially regulate CA1 pyramidal cell function. *J. Neurosci.* 21: 5925-5934.

Molander and Rivero (2002) Suzuki cross-coupling reactions of potassium alkenyltrifluoroborates. *Org. Lett.* 4: 107-109.

Murayama et al. (1984) The Reaction of Trimethylstannylmethllithium with Electrophiles. *Chem. Lett.* 1897-1900.

Nemoto et al. (1995) A novel and efficient route to chiral A-ring aromatic trichothecanes—The first enantiocontrolled total synthesis of (−)-debromofiliformin and (−)-filiformin. *Tetrahedron* 51: 5511-5522.

Nicolas et al. (2006) A combined marble burying-locomotor activity test in mice: a practical screening test with sensitivity to different classes of anxiolytics and antidepressants. *Eur. J. Pharmacol.* 547: 106-115.

Nishizono, N. (2007) Synthesis of thietane nucleosides by glycosidation of thietanose derivatives with nucleobases. *Tetrahedron* 63: 11622-11625.

Niswender et al. (2008) A novel assay of Gi/o-linked G protein-coupled receptor coupling to potassium channels provides new insights into the pharmacology of the group III metabotropic glutamate receptors. *Mol. Pharmacol.* 73: 1213-1224.

Njung'e and Handley (1991) Effects of 5-HT uptake inhibitors, agonists and antagonists on the burying of harmless objects by mice; a putative test for anxiolytic agents. *Brit. J. Pharmacol.* 104: 105-112.

(56) References Cited

OTHER PUBLICATIONS

Obrey et al. (2001) Aluminum Alkoxides as Synthons for Methalumoxane (MAO): Product-Catalyzed Thermal Decomposition of [Me$_2$Al(μ-OCPh$_3$)]$_2$. Organometallics 20: 5162-5170.

Orfanopoulos and Smonou (1988) Selective Reduction of Diaryl or Aryl Alkyl Alcohols in the Presence of Primary Hydroxyl or Ester Groups by Etherated Boron Trifluoride-Triethylsilane System. Synth. Comm. 18: 833-839.

Ossowska et al. (2001) Blockade of the metabotropic glutamate receptor subtype 5 (mGluR5) produces antiparkinsonian-like effects in rats. Neuropharmacol. 41: 413-420.

Periasamy et al. (2001) Novel synthesis of cyclobutanone derivatives via dimetalation of iminium ions with the TiCl$_4$-trialkylamine reagent system. Chem. Commun. 1728-1729.

Periasamy et al. (2005) Simple and Efficient Methods of Synthesis of 3,3-Diarylcyclobutanone and 3,3-Diarylcyclobutylamine Derivatives Using the TiCl$_4$/R$_3$N Reagent System. J. Org. Chem. 70: 5420-5425.

Picard et al. (1981) An Efficient One-Pot Synthesis of Oxetanes from 1,3-Diols. Synthesis 550-551.

Prakash et al. (1989) Synthetic methods and reactions. 141. Fluoride-induced trifluoromethylation of carbonyl compounds with trifluoromethyltrimethylsilane (TMS-CF3). A trifluoromethide equivalent. J. Am. Chem. Soc. 111: 393-395.

Rollin et al. (1993) J. Organom. Chem. 461: 9-13.

Romano et al. (1996) Metabotropic glutamate receptor 5 is a disulfide-linked dimer. J. Biol. Chem. 271(45): 28612-28616.

Ross and Bartsch (2003) High-Intensity Ultrasound-Promoted Reformatsky Reactions. J. Org. Chem. 68: 360-366.

Saidi and Nazari (2004) Aminoalkylation with Aldehydes Mediated by Solkid Lithium Perchlorate. Monatshefte fur Chem. 135: 309-312.

Salt and Binns (2001) Contributions of mGlu1 and mGlu5 receptors to interactions with N-methyl-D-aspartate receptor-mediated responses and nociceptive sensory responses of rat thalamic neurons. Neuroscience 100: 375-380.

Singh et al. (1997) Catalytic Enantioselective Cyclopropanation of Olegins Using Carbenoid Chemistry. Synthesis 137-149.

Singh et al. (1999) Cesium Fluoride Catalyzed Trifluoromethylation of Esters, Aldehydes, and Ketones with (Trifluoromethyl)trimethylsilane. J. Org. Chem. 64: 2873-2876.

Sorensen et al. (2003) Synthesis and Structure-Activity Relationship Studies of Novel 2-Diarylethyl Substituted (2-Carboxycycloprop-1-yl)glycines as Hih-Affinity Group II Metabotropic Glutamate Receptor Ligands. Bioorg. Med. Chem. 11: 197-205.

Spooren et al. (2000) Anxiolytic-like effects of the prototypica metabotropic glutamate receptor 5 antagonist 2-methyl-6-(phenylethynyl)pyridine in rodents. J. Pharmacol. Exp. Therapeut. 295: 1267-1275.

Srivastava et al. (2007) Application of Polymer-Supported Triphenylphosphine and Microwave Irradiation to the Palladium-Catalyzed Cyanation of Aryl Triflates. Synthetic Comm. 37: 431-438.

Stafford and McMurry (1988) An efficient method for the preparation of alkylidenecyclopropanes. Tetrahedron Lett. 29: 2531-2534.

Suh and Rieke (2004) Synthesis of β-hydroxy esters using highly active manganese. Tetrahedron Lett. 45: 1807-1809.

Suri et al. (2005) New Application of Bromotrimethylsilane: Elaboration of Aldehydes/Ketones into Homologous α, β-Unsaturated Esters via β-Hydroxy Esters. Synth. Comm. 37: 379-387.

Tanaka and Shishido (2007) Synthesis of aromatic compounds containing a 1,1-dialkyl-2-trifluoromethyl group, a bioisostere of the tert-alkyl moiety. Bioorg. Med. Chem. Lett. 17: 6079-6085.

Tatarczynska et al. (2001) Potential anxiolytic- and antidepressant-like effects of MPEP, a potent, selective and systemically active mGlu5 receptor antagonist. Br. J. Pharmacol. 132: 1423-1430.

Tronci et al. (2010) The effects of the mGluR5 receptor antagonist 6-methyl-2-(phenylethynyl)-pyridine (MPEP) on behavioural responses to nicotine. Psychopharmacology 211: 33-42.

Virender and Sain (2005) Indium-mediated, highly efficient cyclopropanation of olefins using CH$_2$I$_2$ as methylene transfer reagent. Tetrahedron Lett. 46: 37-38.

Winter, B. (2004) Spirocyclic Ethers Related to Ambrox®: Synthesis and Structure-Odor Relationships. Helv. Chim. Acta 87: 1616-1627.

Yan et al. (2005) Suppression of two major Fragile X Syndrome mouse model phenotypes by the mGluR5 antagonist MPEP. Neuropharmacol. 49(7): 1053-1066.

Yoshida et al. (1997) J. Chem. Soc., Perkin Trans 1 643-648.

Almarasson O, et al. (2004) Crystal engineering of the composition of pharmaceutical phases. Do Pharmaceutical co-crystals represent a new path to improved medicines? The Royal Society of Chemistry, 1889-1896.

Bonnefous C, et al. (2005) Dipyridyl amides: potent metabotropic glutamate subtype 5 (mGlu5) receptor antagonists. Biorganic & Medicinal ; Chemistry Letters, 15: 1197-1200.

Burkhard et al. (2010) Synthesis of azaspirocycles and their evaluation ind rug discovery. Angew. Chem. Int. Ed. 49: 3524-3527.

Caron S, et al. (2000) A practical, effecient, and rapid method for the oxidation of electron deficient pyridines using trifluoroacetic anhydride and hydrogen peroxide-urea complex. Tetrahedron Lett. 41: 2299-2302.

Ceccarelli, et al., "Rational design, synthesis, and structure-activity relationship of benzoxazolones: New potent mglu5 receptor antagonists based on the fenobam structure", Bioorganic & Medicinal Chemistry Letters,vol. 17, No. 5, Feb. 14, 2007 (Feb. 14, 2007), pp. 1302-1306.

Communication enclosing the Extended European Search Report for European Patent Application No. 10817928.4, dated Apr. 4, 2013.

Communication pursuant to Rules 70(2) and 70a(2) EPC issued by the European Patent Office on Apr. 23, 2013 for Application No. 10817950.8 filed ; on Sep. 17, 2010 (Applicants—Vanderbilt University; Inventors—Conn, et al.) (1 page).

Conn PJ, et al. (2009) Allosteric modulators of GPCRs: a novel approach for the treatment of CNS disorders. Nature Reviews, 8: 41-54.

Conn, et al., "Allosteric modulators of GPCRs: a novel approach for the treatment of CNS disorders", Nature Reviews Drug Discovery, vol. 8, No. 1, Jan. 1, 2009 (Jan. 1, 2009), pp. 41-54.

Cosford ND, et al. (2003a) 3-[(2-Methyl-1,3-thiazol-4-yl)ethynyl]-pyridine: a potent and highly selective metabotropic glutamate subtype 5 receptor antagonist with anxiolytic activity. J. Med. Chem. 46: 204-206.

European Search Report issued Jan. 13, 2015 for Application No. 12752374.4 (Applicant—Vanderbilt University//Inventor—P. Jeffrey Conn//) (8 pages).

Extended European Search Report issued by the European Patent Office on Apr. 4, 2013 for Application No. 10817950.8 filed on Sep. 17, 2010 ; (Applicants—Vanderbilt University; Inventors—Conn, et al.) (13 pages).

Extended European Search Report issued on Apr. 9, 2013 for application EP 10817954.0, filed on Sep. 17, 2010 and published as EP 2477631 on Jul. 25, 2012 (Applicant—Vanderbilt University // Inventor—Conn, et al.) (14 pages).

Felts, et al., "3-Cyano-5-fluoro-N-arylbenzamides as negative allosteric modulators of mGiu5: Identification of easily prepared tool compounds with CNS exposure in rats", Bioorganic & Medicinal Chemistry Letters, vol. 20, No. 15, Aug. 1, 2010 (Aug. 1, 2010), pp. 4390-4394.

Fife WK. (1983) Regioselective cyanation of pyridine 1-oxides with trimethylsilanecarbonitrile: a modified Reissert-Henze reaction. J. Org. Chem. 48: 1375-1377.

Final Official Action issued by the JPO on Feb. 22, 2016 for application JP 2013-556618, filed on Mar. 5, 2012 and published as JP 2014-515008 on Jun. 26, 2014 (Applicant—Vanderbilt University // Inventor—Conn, et al.) (2 pages).

Grant No. 1U19-MH097056-01 awarded by the National Institute of Mental Health (NIMH).

Hamilton et al. (2014) "Metabotropic glutamate receptor 5 knock-out reduces cognitive impairment and pathogenesis in a mouse model of Alzheimer's disease." Molecular Brain 7: 40.

(56) References Cited

OTHER PUBLICATIONS

Hughes et al. (2013) "Negative allosteric modulation of metabotropic glutamate receptor 5 results in broad spectrum activity relevant to treatment resistant depression." Neuropharmacology 66: 202-214.
International Preliminary Report on Patentability and Written Opinion from International Application No. PCT/US10/49373, issued Mar. 20, 2012.
International Preliminary Report on Patentability from International Application No. PCT/US10/049400, issued on Mar. 20, 2012.
International Preliminary Report on Patentability from International Application No. PCT/US10/049407, issued on Mar. 20, 2012 (6 pp).
International Preliminary Report on Patentability issued Feb. 27, 2012 by the International Searching Authority for International Patent Application PCT/US2012/000119 filed Jul. 9, 2011 and which published as WO 2012/118563 on Sep. 7, 202(Inventor—Jeffrey Conn // Applicant—Vanderbilt University) (9 pages).
International Preliminary Report on Patentability issued in corresponding International Application No. PCT/US201 0/049358 on Mar. 20, 2012.
International Preliminary Report on Patentability issued on May 24, 2016 for application PCT/US14/066207, filed on Nov. 18, 2014 and published as WO 2015/077246 on May 28, 2015 (Applicant—Vanderbilt Univ. // Inventor—Emmitt, et al.) (7 pages).
International Search Report and Written Opinion issued in corresponding International Application No. PCT/US2010/049358 mailed Oct. 25, 2010 (7 pages).
International Search Report and Written Opinion issued on Jan. 27, 2015 for application PCT/US14/066207, filed on Nov. 18, 2014 and published as WO 2015/077246 on May 28, 2015 (Applicant—Vanderbilt Univ. // Inventor—Emmitt, et al.) (15 pages).
International Search Report from International Application No. PCT/US1 0/049400, mailed Nov. 9, 2010.
International Search Report from International Application No. PCT/US10/049407, mailed Nov. 1, 2010 (1 page).
International Search Report from International Application No. PCT/US10/49373, dated Nov. 9, 2010.
International Search Report issued Feb. 27, 2012 by the International Searching Authority for International Patent Application PCT/US2012/000119 filed Jul. 9, 2011 and which published as WO 2012/118563 on Sep. 7, 2012 (Inventor—Jeffrey Conn //Applicant—Vanderbilt University) (5 pages).
Jaeschke, et al., "mGlu5 receptor antagonists and their therapeutic potential," Expert Opinion, Informa Healthcare, 2008 (20 pages).
Jingami, et al., "Structure of the metabotropic glutamate receptor," Current Opinions in Neurobiology, 2003, vol. 13 pp. 271-287.
Kew JNC, et al. (2004) Positive and negative allosteric modulation of metabotropic glutamate receptors: emerging therapeutic potential. Pharmacology & Threapeutics, 104: 233-244.
Kew, et al., "Positive and negative allosteric modulation of metabotropic glutamate receptors: emerging therapeutic potential", Pharmacology and Therapeutics, vol. 104, No. 3, Dec. 1, 2004 (Dec. 1, 2004), pp. 233-244.
Klodzinska et al. (2004) "Anxiolytic-like effects of MTEP, a potent and selective mGlu5 receptor agonist does not involve GABA(A) signaling." Neuropharmacology 47: 342.
Kulkarni et al., "Design and Synthesis of Novel Heterobiaryl Amides as Metabotrophic Glutamate Receptor Subtype 5 Antagonists," Bioorg. Med. Chem. Lett.vol. 17(7), pp. 2074-2079, 2007 (From NIH Public Access pp. 1-16).
Kumaresan et al. (2009) "Metabotropic glutamate receptor 5 (mGluR5) antagonists attenuate cocaine priming- and cue-induced reinstatement of cocaine seeking." Behav. Brain Res. 202: 238-244.
Li F, et al. (2005) Synthesis of Diaryl Ethers, Diaryl Sulfides, Heteroaryl Ethers and heteroaryl Sulfides under Mircrowave Dielectric Heating. ; Synthesis, 8: 1305-1313.
Lindsley CW, et al. (2008) Recent progress in the discovery and development of negative allosteric modulators of mGluR5. Current Opinion in Drug Discovery & Development 12(4): 440-452.
Lindsley et al. (2011) "(3-Cyano-5-fluorophenyl)biaryl negative allosteric modulators of mGlu(5): Discovery of a new tool compound with activity in the OSS mouse model of addiction." ACS Chem. Neurosci. 2: 471.
Martin-Fardon et al. (2009) "Dissociation of the effects of MTEP [3-[(2-methyl-1,3-thiazol-4-yl)ethynyl]piperidine] on conditioned reinstatement and reinforcement: comparison between cocaine and a conventional reinforce." J. Pharmacol. Exp. Ther. 329: 1084.
Michalon et al. (2012) "Chronic Pharmacological mGlu5 Inhibition Corrects Fragile X in Adult Mice." Neuron 74: 49-56.
Morin et al. (2010) "Effect of the metabotropic glutamate receptor type 5 antagonists MPEP and MTEP in parkinsonian monkeys." Neuropharmacology 58: 981-986.
Non-Final Office Action issued on Apr. 24, 2013 for U.S. Appl. No. 12/885,378, filed Sep. 17, 2010 and granted as U.S. Pat. No. 8,796,295 on Aug. 5, 2014 (Applicant—Vanderbilt University // Inventor—Conn, et al.) (7 pages).
Non-Final Office Action issued on Nov. 13, 2012 for U.S. Appl. No. 12/885,289, filed Sep. 17, 2010 and granted as U.S. Pat. No. 8,598,345 on Dec. 3, 2013 (Applicant—Vanderbilt Univ. // Inventor—Conn, et al.) (58 pages).
Non-Final Office Action issued on Nov. 8, 2012 for U.S. Appl. No. 12/885,245, filed Sep. 17, 2010 and granted as U.S. Pat. No. 8,569,308 on Oct. 29, 2013 (Applicant—Vanderbilt Univ. // Inventor—Conn, et al.) (8 pages).
Non-Final Office Action issued on Sep. 17, 2014 for U.S. Appl. No. 14/002,309, filed Mar. 17, 2014 and granted as U.S. Pat. No. 9,085,562 on Jul. 21, 2015 (Applicant—Vanderbilt University // Inventor—Conn, et al.) (33 pages).
Notice of Allowance issued on Jul. 31, 2013 for U.S. Appl. No. 12/885,289, filed Sep. 17, 2010 and granted as U.S. Pat. No. 8,598,345 on Dec. 3, 2013 (Applicant—Vanderbilt Univ. // Inventor—Conn, et al.) (6 pages).
Notice of Allowance issued on Jun. 20, 2013 for U.S. Appl. No. 12/885,245, filed Sep. 17, 2010 and granted as U.S. Pat. No. 8,569,308 on Oct. 29, 2013 (Applicant—Vanderbilt Univ. // Inventor—Conn, et al.) (10 pages).
Notice of Allowance issued on Mar. 16, 2015 for U.S. Appl. No. 14/002,309, filed Mar. 17, 2014 and granted as U.S. Pat. No. 9,085,562 on Jul. 21, 2015 (Applicant—Vanderbilt University // Inventor—Conn, et al.) (5 pages).
Notice of Allowance issued on May 23, 2013 for U.S. Appl. No. 12/885,420, filed Sep. 17, 2010 and granted as U.S. Pat. No. 8,501,757 on Aug. 6, 2013 (Applicant—Vanderbilt University // Inventor—Conn, et al.) (14 pages).
Notice of Allowance issued on Nov. 20, 2013 for U.S. Appl. No. 12/885,378, filed Sep. 17, 2010 and granted as U.S. Pat. No. 8,796,295 on Aug. 5, 2014 (Applicant—Vanderbilt University // Inventor—Conn, et al.) (7 pages).
Official Action issued by the JPO on Aug. 19, 2015 for application JP 2013-556618, filed on Mar. 5, 2012 and published as JP 2014-515008 on Jun. 26, 2014 (Applicant—Vanderbilt University // Inventor—Conn, et al.) (3 pages).
Pietraszek et al. (2005) "Anxiolytic-like effects of mGlu1 and mGlu5 receptor antagonists in rats." Eur. J. Pharmacol. 514: 25.
Requirement for Restriction or Election issued on Feb. 24, 2016 for U.S. Appl. No. 14/664,792, filed Mar. 20, 2015 and published as US 2015-0266866 A1 on Sep. 24, 2015 (Applicant—Vanderbilt Univ. // Inventor—Conn, et al.) (9 pages).
Response to Non-Final Office Action filed on May 13, 2013 for U.S. Appl. No. 12/885,289, filed Sep. 17, 2010 and granted as U.S. Pat. No. 8,598,345 on Dec. 3, 2013 (Applicant—Vanderbilt Univ. // Inventor—Conn, et al.) (6 pages).
Response to Non-Final Office Action filed on May 7, 2013 for U.S. Appl. No. 12/885,245, filed Sep. 17, 2010 and granted as U.S. Pat. No. 8,569,308 on Oct. 29, 2013 (Applicant—Vanderbilt Univ. // Inventor—Conn, et al.) (4 pages).
Response to Non-Final Office Action filed on Ocotber 20, 2015 for U.S. Appl. No. 14/002,309, filed Mar. 17, 2014 and granted as U.S. Pat. No. 9,085,562 on Jul. 21, 2015 (Applicant—Vanderbilt University // Inventor—Conn, et al.) (23 pages).

(56) References Cited

OTHER PUBLICATIONS

Response to Non-Final Office Action filed on Oct. 24, 2013 for U.S. Appl. No. 12/885,378, filed Sep. 17, 2010 and granted as U.S. Pat. No. 8,796,295 on Aug. 5, 2014 (Applicant—Vanderbilt University // Inventor—Conn, et al.) (9 pages).

Silverman et al. (2010) "Repetitive Self-Grooming Behavior in the BTBR Mouse Model of Autism is Blocked by the mGluR5 Antagonist MPEP." Neuropsychopharmacology 35: 976-989.

Silverman et al. (2012) "Negative Allosteric Modulation of the mGluR5 Receptor Reduces Repetitive Behaviors and Rescues Social Deficits in Mouse Models of Autism." Sci. Transl. Med. 4: 131ra51.

Taylor EC and Crovetti AJ. (1956) 3-Methyl-4-nitropyridine-1-oxide. Organic Syntheses, 36: 53.

Written Opinion issued Feb. 27, 2012 by the International Searching Authority for International Patent Application PCT/US2012/000119 filed Jul. 9, 2011 and which published as WO 2012/118563 on Sep. 7, 2012 (Inventor—Jeffrey Conn //Applicant—Vanderbilt University) (8 pages).

Written Opinion of the International Searching Authority from International Application No. PCT/US1 0/049400, mailed Nov. 9, 2010.

Written Opinion of the International Searching Authority from International Application No. PCT/US10/049400, mailed Nov. 1, 2010 (5 pp).

Zhou, et al., "Synthesis and SAR of novel, non-MPEP chemotype mGiuR5 NAMs identified by functional HTS", Bioorganic & Medicinal Chemistry Letters, vol. 19, No. 23, Dec. 1, 2009 (Dec. 1, 2009 ), pp. 6502-6506.

Non-Final Office Action issued on May 23, 2016 for U.S. Appl. No. 14/873,869, filed Oct. 2, 2015 and published as US-2016-0096833-A1 on Apr. 7, 2016 (Applicant—Vanderbilt Univ. // Inventor—Emmitte, et al.) (14 pages).

U.S. Appl. No. 61/243,378, filed Sep. 17, 2009, Weaver (Vanderbilt University).

U.S. Appl. No. 61/449,017, filed Mar. 3, 2011, Conn (Vanderbilt University).

U.S. Appl. No. 61/906,393, filed Nov. 19, 2013, Conn (Vanderbilt University).

U.S. Appl. No. 15/037,320, filed Nov. 18, 2014, Emmitte (Vanderbilt University).

U.S. Appl. No. 62/152,631, filed Apr. 24, 2015, Lindsley (Vanderbilt University).

U.S. Appl. No. 62/107,308, filed Jan. 23, 2015, Bornhop (Vanderbilt University).

U.S. Appl. No. 61/788,697, filed Mar. 15, 2013, Felts (Vanderbilt University).

U.S. Appl. No. 61/968,323, filed Mar. 20, 2014, Conn (Vanderbilt University).

U.S. Appl. No. 14/873,869, filed Oct. 2, 2015, Emmitte (Vanderbilt University).

U.S. Appl. No. 61/788,697, filed Mar. 15, 2013, P. Jeffrey Conn.

U.S. Appl. No. 61/968,323, filed Mar. 20, 2014, P. Jeffrey Conn.

* cited by examiner

SUBSTITUTED BICYCLIC HETEROARYL CARBOXAMIDE ANALOGS AS MGLUR5 NEGATIVE ALLOSTERIC MODULATORS

CROSS-REFERENCE TO RELATED APPLICATIONS

This application claims the benefit of U.S. Provisional Application No. 61/968,323, filed on Mar. 20, 2014, which is incorporated herein by reference in its entirety.

STATEMENT REGARDING FEDERALLY SPONSORED RESEARCH

This invention was made with government support under Grant No. 2R01-MH062646-12 awarded by the National Institute of Mental Health (NIMH), under Grant No. 5R01-MH073676-04 awarded by the National Institute of Mental Health (NIMH), under Grant No. 5R01-NS031373-15 awarded by the National Institute of Neurological Disorders and Stroke (NINDS), and Grant no. 1R01-DA023947-01 awarded by the National Institute on Drug Abuse (NIDA). The United States government has certain rights in the invention.

BACKGROUND

Glutamate (L-glutamic acid) is the major excitatory transmitter in the mammalian central nervous system, exerting its effects through both ionotropic and metabotropic glutamate receptors. The metabotropic glutamate receptors (mGluRs) belong to family C (also known as family 3) of the G-protein-coupled receptors (GPCRs). They are characterized by a seven transmembrane (7TM) α-helical domain connected via a cysteine rich-region to a large bi-lobed extracellular amino-terminal domain (FIG. 1). While the orthosteric binding site is contained in the amino-terminal domain, currently known allosteric binding sites reside in the 7TM domain. The mGluR family comprises eight known mGluRs receptor types (designated as mGluR1 through mGluR8). Several of the receptor types are expressed as specific splice variants, e.g. mGluR5a and mGluR5b or mGluR8a, mGluR8b and mGluR8c. The family has been classified into three groups based on their structure, preferred signal transduction mechanisms, and pharmacology. Group I receptors (mGluR1 and mGluR5) are coupled to Gαq, a process that results in stimulation of phospholipase C and an increase in intracellular calcium and inositol phosphate levels. Group II receptors (mGluR2 and mGluR3) and group III receptors (mGluR4, mGluR6, mGluR7, and mGluR8) are coupled to Gαi, which leads to decreases in cyclic adenosine monophosphate (cAMP) levels. While the Group I receptors are predominately located postsynaptically and typically enhance postsynaptic signaling, the group II and III receptors are located presynaptically and typically have inhibitory effects on neurotransmitter release. Without wishing to be bound by theory, increasing evidence indicates mGluRs play an important role in lasting changes in synaptic transmission, and studies of synaptic plasticity in the Fmr1 knockout mouse have identified a connection between the fragile X phenotype and mGluR signaling.

The identification of small molecule mGluR antagonists that bind at the orthosteric site has greatly increased the understanding of the roles played by these receptors and their corresponding relation to disease. Because the majority of these antagonists were designed as analogs of glutamate, they typically lack desired characteristics for drugs targeting mGluR such as oral bioavailability and/or distribution to the central nervous system (CNS). Moreover, because of the highly conserved nature of the glutamate binding site, most orthosteric antagonists lack selectivity among the various mGluRs.

A more recent strategy that has been able to successfully deal with the aforementioned issues has been the design of compounds that bind the mGluR at a site that is topographically distinct from the orthosteric binding site, or an allosteric binding site. Selective negative allosteric modulators (NAMs) are compounds that do not directly deactivate receptors by themselves, but decrease the affinity of a glutamate-site agonist at its extracellular N-terminal binding site. Negative allosteric modulation is thus an attractive mechanism for inhibiting appropriate physiological receptor activation. Among the most studied and characterized small molecules are the mGluR5 NAMs, 2-methyl-6-(phenylethynyl)pyridine (MPEP) and 3-[(2-methyl-1,3-thiazol-4-yl)ethynyl]pyridine (MTEP). Both MPEP and MTEP have proven efficacious in numerous rodent models of disease, including those for drug addiction and pain as well as anxiety. The compounds were also able to inhibit transient lower esophageal sphincter relaxation (TLESD), the major cause of gastroesophageal reflux disease (GERD), in dogs and ferrets. In addition, MPEP was efficacious in mouse models of fragile X syndrome (FXS) and Parkinson's disease (PD) as well as a baboon model of binge-eating disorder.

Although the utility of MPEP and MTEP as tool compounds has been clearly demonstrated, both molecules have issues that complicate or prevent their further development as therapeutic molecules. MPEP has been shown to directly inhibit the N-methyl-D-aspartate (NMDA) receptor activity at higher concentrations and is a positive allosteric modulator of mGluR4. While these selectivity issues are mitigated with MTEP, it is a potent inhibitor of cytochrome P450 1A2 and is efficiently cleared following intravenous administration to rhesus monkeys.

Potential adverse effects of known mGluR5 NAMs, however, could reduce their ultimate therapeutic utility. Further, conventional mGluR5 receptor modulators which target the orthosteric binding site can lack satisfactory aqueous solubility, exhibit poor oral bioavailability, and/or exhibit adverse effects. Therefore, there remains a need for methods and compositions that overcome these deficiencies and that effectively provide selective negative allosteric modulators for the mGluR5 receptor.

SUMMARY

In accordance with the purpose(s) of the invention, as embodied and broadly described herein, the invention, in one aspect, relates to compounds useful as negative allosteric modulators of the metabotropic glutamate receptor subtype 5 (mGluR5), methods of making same, pharmaceutical compositions comprising same, and methods of treating disorders associated with glutamate dysfunction using same.

Disclosed are compounds having a structure represented by a formula:

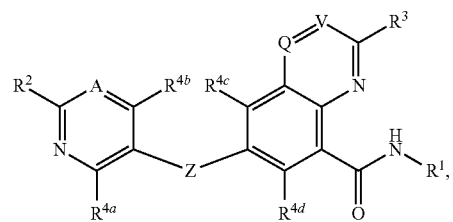

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8(O)_rR^9$—, —$CR^8NR^{10a}R^{10b}$—, —(C=O)—, and a structure represented by a formula:

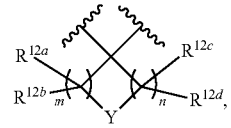

wherein Y is selected from —$CR^8R^9$—, —O—, —$S(O)_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —$S(O)_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O)$R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —NR$^{54a}$R$^{54b}$; wherein each occurrence of each of R$^{54a}$ and R$^{54b}$, when present, is independently selected from hydrogen, C1-C3 alkyl, C1-C3 monohaloalkyl, C1-C3 polyhaloalkyl, and cyclopropyl; or wherein R$^{54a}$ and R$^{54b}$, when present, are optionally covalently bonded and, together with nitrogen atom to which they are attached, comprise a 3- to 6-membered heterocycle; wherein each occurrence of R$^{53}$, when present, is independently from C1-C3 alkyl, C1-C3 monohaloalkyl, C1-C3 polyhaloalkyl, cyclopropyl, and, —NR$^{55a}$R$^{55b}$; wherein each occurrence of each of R$^{55a}$ and R$^{55b}$, when present, is independently selected from hydrogen, C1-C3 alkyl, C1-C3 monohaloalkyl, C1-C3 polyhaloalkyl, and cyclopropyl; or wherein R$^{55a}$ and R$^{55b}$, when present, are optionally covalently bonded and, together with nitrogen atom to which they are attached, comprise a 3- to 6-membered heterocycle; wherein R$^2$ is selected from hydrogen, C1-C3 alkyl, C1-C3 monohaloalkyl, C1-C3 polyhaloalkyl, and cyclopropyl; wherein R$^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$, is independently selected from hydrogen and fluoro; or a pharmaceutically acceptable salt, solvate, or polymorph thereof, wherein the compound exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound.

Also disclosed are pharmaceutical compositions comprising a therapeutically effective amount of a disclosed compound and a pharmaceutically acceptable carrier.

Also disclosed are methods for manufacturing a medicament comprising combining at least one disclosed compound with a pharmaceutically acceptable carrier or diluent.

Also disclosed are methods for the treatment of a disorder associated with metabotropic glutamate receptor activity in a mammal comprising the step of administering to the mammal a therapeutically effective amount of a compound having a structure represented by a formula:

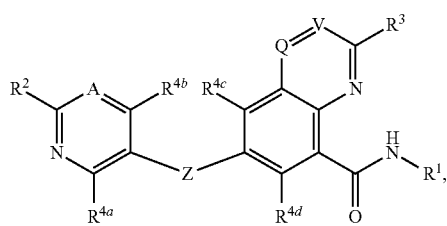

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein Q is selected from N and CR$^6$; wherein R$^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle; wherein R$^{32}$, when present, is selected from C1-C3 alkyl, C1-C3 monohaloalkyl, C1-C3 polyhaloalkyl, cyclopropyl, and, —NR$^{34a}$R$^{34b}$; wherein each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with nitrogen atom to which they are attached, comprise a 3- to 6-membered heterocycle; wherein R$^{33}$, when present, is selected from C1-C3 alkyl, C1-C3 monohaloalkyl, C1-C3 polyhaloalkyl, cyclopropyl, and, —NR$^{35a}$R$^{35b}$; wherein each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8(O)_rR^9$—, —$CR^8NR^{10a}R^{10b}$—, —(C=O)—, and a structure represented by a formula:

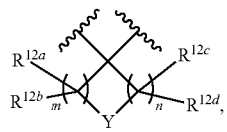

wherein Y is selected from —$CR^8R^9$—, —O—, —S(O)$_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —S(O)$_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O) $R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —$NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, —$NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof.

Also disclosed are methods for decreasing metabotropic glutamate receptor activity in a mammal comprising the step of administering to the mammal a therapeutically effective amount of at least one compound having a structure represented by a formula:

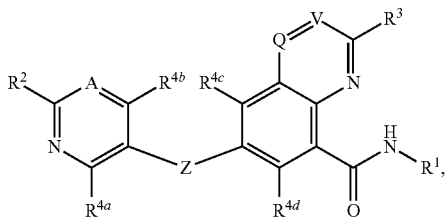

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8(O)_rR^9$—, —$CR^8NR^{10a}R^{10b}$—, —(C=O)—, and a structure represented by a formula:

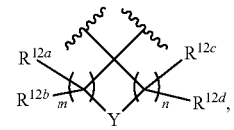

wherein Y is selected from —$CR^8R^9$—, —O—, —$S(O)_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —$S(O)_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O)

R$^{53}$; wherein each occurrence of R$^{50}$, when present, is independently selected from hydrogen, C1-C3 alkyl, C1-C3 monohaloalkyl, C1-C3 polyhaloalkyl, and cyclopropyl; wherein each occurrence of each of R$^{51a}$ and R$^{51b}$, when present, is independently selected from hydrogen, C1-C3 alkyl, C1-C3 monohaloalkyl, C1-C3 polyhaloalkyl, and cyclopropyl; or wherein R$^{51a}$ and R$^{51b}$, when present, are optionally covalently bonded and, together with nitrogen atom to which they are attached, comprise a 3- to 6-membered heterocycle; wherein each occurrence of R$^{52}$, when present, is independently selected from C1-C3 alkyl, C1-C3 monohaloalkyl, C1-C3 polyhaloalkyl, cyclopropyl, and, —NR$^{54a}$R$^{54b}$; wherein each occurrence of each of R$^{54a}$ and R$^{54b}$, when present, is independently selected from hydrogen, C1-C3 alkyl, C1-C3 monohaloalkyl, C1-C3 polyhaloalkyl, and cyclopropyl; or wherein R$^{54a}$ and R$^{54b}$, when present, are optionally covalently bonded and, together with nitrogen atom to which they are attached, comprise a 3- to 6-membered heterocycle; wherein each occurrence of R$^{53}$, when present, is independently from C1-C3 alkyl, C1-C3 monohaloalkyl, C1-C3 polyhaloalkyl, cyclopropyl, and, —NR$^{55a}$R$^{55b}$; wherein each occurrence of each of R$^{55a}$ and R$^{55b}$, when present, is independently selected from hydrogen, C1-C3 alkyl, C1-C3 monohaloalkyl, C1-C3 polyhaloalkyl, and cyclopropyl; or wherein R$^{55a}$ and R$^{55b}$, when present, are optionally covalently bonded and, together with nitrogen atom to which they are attached, comprise a 3- to 6-membered heterocycle; wherein R$^2$ is selected from hydrogen, C1-C3 alkyl, C1-C3 monohaloalkyl, C1-C3 polyhaloalkyl, and cyclopropyl; wherein R$^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$, is independently selected from hydrogen and fluoro; or a pharmaceutically acceptable salt, solvate, or polymorph thereof.

Also disclosed are methods for inhibiting metabotropic glutamate receptor activity in a mammal comprising the step of administering to the mammal a therapeutically effective amount of least one compound having a structure represented by a formula:

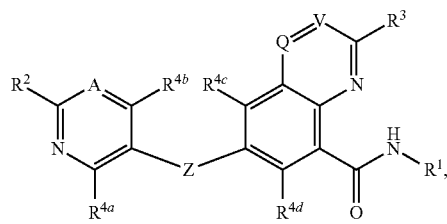

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein Q is selected from N and CR$^6$; wherein R$^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle; wherein R$^{32}$, when present, is selected from C1-C3 alkyl, C1-C3 monohaloalkyl, C1-C3 polyhaloalkyl, cyclopropyl, and, —NR$^{34a}$R$^{34b}$; wherein each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with nitrogen atom to which they are attached, comprise a 3- to 6-membered heterocycle; wherein R$^{33}$, when present, is selected from C1-C3 alkyl, C1-C3 monohaloalkyl, C1-C3 polyhaloalkyl, cyclopropyl, and, —NR$^{35a}$R$^{35b}$; wherein each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —$(C=O)R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8(O)_rR^9$—, —$CR^8NR^{10a}R^{10b}$—, —(C=O)—, and a structure represented by a formula:

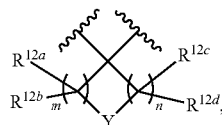

wherein Y is selected from —$CR^8R^9$—, —O—, —$S(O)_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —$S(O)_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O) $R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —$NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, —$NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof.

Also disclosed are methods for negative allosteric modulation of metabotropic glutamate receptor activity in a mammal comprising the step of administering to the mammal a therapeutically effective amount of at least one compound having a structure represented by a formula:

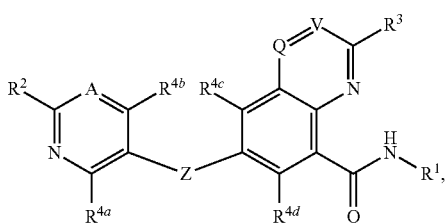

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein Q is selected from N and CR$^6$; wherein R$^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle; wherein R$^{32}$, when present, is selected from C1-C3 alkyl, C1-C3 monohaloalkyl, C1-C3 polyhaloalkyl, cyclopropyl, and, —NR$^{34a}$R$^{34b}$; wherein each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with nitrogen atom to which they are attached, comprise a 3- to 6-membered heterocycle; wherein R$^{33}$, when present, is selected from C1-C3 alkyl, C1-C3 monohaloalkyl, C1-C3 polyhaloalkyl, cyclopropyl, and, —NR$^{35a}$R$^{35b}$; wherein each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; wherein V is selected from N and CR$^7$, provided that Q and V are not simultaneously N; wherein R$^7$, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and, —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and, —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with nitrogen atom to which they are attached, comprise a 3- to 6-membered heterocycle; wherein Z is selected from —CR$^8$(O)$_r$R$^9$—, —CR$^8$NR$^{10a}$R$^{10b}$—, —(C=O)—, and a structure represented by a formula:

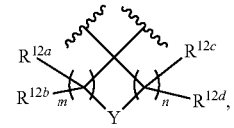

wherein Y is selected from —CR$^8$R$^9$—, —O—, —S(O)$_q$—, and —NR$^8$—; wherein m is an integer selected from 0, 1, and 2; wherein n is an integer selected from 0 and 1; wherein the sum of m and n is 1 or 2 when Y is —CR$^8$R$^9$—; wherein the sum of m and n is 2 when Y is —O—, —S(O)$_q$—, and —NR$^8$—; wherein q is 0, 1, or 2; wherein r is 0 or 1; wherein R$^8$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^8$ is not halogen; wherein R$^9$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^9$ is not halogen; wherein each of R$^{10a}$ and R$^{10b}$, when present, is independently selected from hydrogen, C1-C3 alkyl, C1-C3 monohaloalkyl, C1-C3 polyhaloalkyl, and cyclopropyl; wherein each occurrence of R$^{12a}$, R$^{12a}$, R$^{12a}$, and R$^{12a}$, when present, is independently selected from hydrogen, halogen, C1-C3 alkyl, C1-C3 monohaloalkyl, and C1-C3 polyhaloalkyl; wherein R$^1$ is selected from aryl and heteroaryl, and wherein R$^1$ is substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)

R⁵³; wherein each occurrence of R⁵⁰, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of R⁵², when present, is independently selected from C1-C3 alkyl, C1-C3 monohaloalkyl, C1-C3 polyhaloalkyl, cyclopropyl, and, $-NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of R⁵³, when present, is independently from C1-C3 alkyl, C1-C3 monohaloalkyl, C1-C3 polyhaloalkyl, cyclopropyl, and, $-NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein R² is selected from hydrogen, C1-C3 alkyl, C1-C3 monohaloalkyl, C1-C3 polyhaloalkyl, and cyclopropyl; wherein R³ is selected from hydrogen, halogen, —CN, C1-C3 alkyl, C1-C3 monohaloalkyl, C1-C3 polyhaloalkyl, cyclopropyl, $-OR^{60}$, $-NR^{61a}R^{61b}$, $-SO_2R^{62}$, and $-(C=O)R^{63}$; wherein R⁶⁰, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein R⁶², when present, is selected from C1-C3 alkyl, C1-C3 monohaloalkyl, C1-C3 polyhaloalkyl, cyclopropyl, and, $-NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein R⁶³, when present, is selected from C1-C3 alkyl, C1-C3 monohaloalkyl, C1-C3 polyhaloalkyl, cyclopropyl, and, $-NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof.

Also disclosed are methods for partial antagonism of metabotropic glutamate receptor activity in a mammal comprising the step of administering to the mammal a therapeutically effective amount of least one compound having a structure represented by a formula:

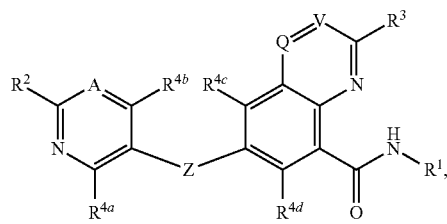

wherein A is selected from N and CR⁵; wherein R⁵, when present, is selected from hydrogen, halogen, —CN, C1-C3 alkyl, C1-C3 monohaloalkyl, C1-C3 polyhaloalkyl, cyclopropyl, $-OR^{20}$, $-NR^{21a}R^{21b}$, $-SO_2R^{22}$, and $-(C=O)R^{23}$; wherein R²⁰, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein R²², when present, is selected from C1-C3 alkyl, C1-C3 monohaloalkyl, C1-C3 polyhaloalkyl, cyclopropyl, and, $-NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein R²³, when present, is selected from C1-C3 alkyl, C1-C3 monohaloalkyl, C1-C3 polyhaloalkyl, cyclopropyl, and, $-NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and CR⁶; wherein R⁶, when present, is selected from hydrogen, halogen, —CN, C1-C3 alkyl, C1-C3 monohaloalkyl, C1-C3 polyhaloalkyl, cyclopropyl, $-OR^{30}$, $-NR^{31a}R^{31b}$, $-SO_2R^{32}$, and $-(C=O)R^{33}$; wherein R³⁰, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein R³², when present, is selected from C1-C3 alkyl, C1-C3 monohaloalkyl, C1-C3 polyhaloalkyl, cyclopropyl, and, $-NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein R³³, when present, is selected from C1-C3 alkyl, C1-C3 monohaloalkyl, C1-C3 polyhaloalkyl, cyclopropyl, and, $-NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and CR$^7$, provided that Q and V are not simultaneously N; wherein R$^7$, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and, —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and, —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with nitrogen atom to which they are attached, comprise a 3- to 6-membered heterocycle; wherein Z is selected from —CR$^8$(O)$_r$R$^9$—, —CR$^8$NR$^{10a}$R$^{10b}$—, —(C=O)—, and a structure represented by a formula:

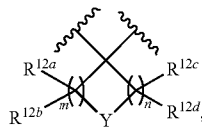

wherein Y is selected from —CR$^8$R$^9$—, —O—, —S(O)$_q$—, and —NR$^8$—; wherein m is an integer selected from 0, 1, and 2; wherein n is an integer selected from 0 and 1; wherein the sum of m and n is 1 or 2 when Y is —CR$^8$R$^9$—; wherein the sum of m and n is 2 when Y is —O—, —S(O)$_q$—, and —NR$^8$—; wherein q is 0, 1, or 2; wherein r is 0 or 1; wherein R$^8$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^8$ is not halogen; wherein R$^9$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^9$ is not halogen; wherein each of R$^{10a}$ and R$^{10b}$, when present, is independently selected from hydrogen, C1-C3 alkyl, C1-C3 monohaloalkyl, C1-C3 polyhaloalkyl, and cyclopropyl; wherein each occurrence of R$^{12a}$, R$^{12a}$, R$^{12a}$, and R$^{12a}$, when present, is independently selected from hydrogen, halogen, C1-C3 alkyl, C1-C3 monohaloalkyl, and C1-C3 polyhaloalkyl; wherein R$^1$ is selected from aryl and heteroaryl, and wherein R$^1$ is substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$; wherein each occurrence of R$^{50}$, when present, is independently selected from hydrogen, C1-C3 alkyl, C1-C3 monohaloalkyl, C1-C3 polyhaloalkyl, and cyclopropyl; wherein each occurrence of each of R$^{51a}$ and R$^{51b}$, when present, is independently selected from hydrogen, C1-C3 alkyl, C1-C3 monohaloalkyl, C1-C3 polyhaloalkyl, and cyclopropyl; or wherein R$^{51a}$ and R$^{51b}$, when present, are optionally covalently bonded and, together with nitrogen atom to which they are attached, comprise a 3- to 6-membered heterocycle; wherein each occurrence of R$^{52}$, when present, is independently selected from C1-C3 alkyl, C1-C3 monohaloalkyl, C1-C3 polyhaloalkyl, cyclopropyl, and, —NR$^{54a}$R$^{54b}$; wherein each occurrence of each of R$^{54a}$ and R$^{54b}$, when present, is independently selected from hydrogen, C1-C3 alkyl, C1-C3 monohaloalkyl, C1-C3 polyhaloalkyl, and cyclopropyl; or wherein R$^{54a}$ and R$^{54b}$, when present, are optionally covalently bonded and, together with nitrogen atom to which they are attached, comprise a 3- to 6-membered heterocycle; wherein each occurrence of R$^{53}$, when present, is independently from C1-C3 alkyl, C1-C3 monohaloalkyl, C1-C3 polyhaloalkyl, cyclopropyl, and, —NR$^{55a}$R$^{55b}$; wherein each occurrence of each of R$^{55a}$ and R$^{55b}$, when present, is independently selected from hydrogen, C1-C3 alkyl, C1-C3 monohaloalkyl, C1-C3 polyhaloalkyl, and cyclopropyl; or wherein R$^{55a}$ and R$^{55b}$, when present, are optionally covalently bonded and, together with nitrogen atom to which they are attached, comprise a 3- to 6-membered heterocycle; wherein R$^2$ is selected from hydrogen, C1-C3 alkyl, C1-C3 monohaloalkyl, C1-C3 polyhaloalkyl, and cyclopropyl; wherein R$^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$, is independently selected from hydrogen and fluoro; or a pharmaceutically acceptable salt, solvate, or polymorph thereof.

Also disclosed are methods for modulating mGluR5 activity in a mammal comprising the step of administering to the mammal a therapeutically effective amount of least one compound having a structure represented by a formula:

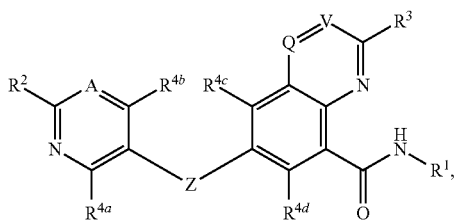

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein Q is selected from N and CR$^6$; wherein R$^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle; wherein R$^{32}$, when present, is selected from C1-C3 alkyl, C1-C3 monohaloalkyl, C1-C3 polyhaloalkyl, cyclopropyl, and, —NR$^{34a}$R$^{34b}$; wherein each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with nitrogen atom to which they are attached, comprise a 3- to 6-membered heterocycle; wherein R$^{33}$, when present, is selected from C1-C3 alkyl, C1-C3 monohaloalkyl, C1-C3 polyhaloalkyl, cyclopropyl, and, —NR$^{35a}$R$^{35b}$; wherein each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; wherein V is selected from N and CR$^7$, provided that Q and V are not simultaneously N; wherein R$^7$, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and, —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and, —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with nitrogen atom to which they are attached, comprise a 3- to 6-membered heterocycle; wherein Z is selected from —CR$^8$(O)$_r$R$^9$—, —CR$^8$NR$^{10a}$R$^{10b}$—, —(C=O)—, and a structure represented by a formula:

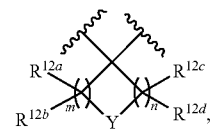

wherein Y is selected from —CR$^8$R$^9$—, —O—, —S(O)$_q$—, and —NR$^8$—; wherein m is an integer selected from 0, 1, and 2; wherein n is an integer selected from 0 and 1; wherein the sum of m and n is 1 or 2 when Y is —CR$^8$R$^9$—; wherein the sum of m and n is 2 when Y is —O—, —S(O)$_q$—, and —NR$^8$—; wherein q is 0, 1, or 2; wherein r is 0 or 1; wherein R$^8$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^8$ is not halogen; wherein R$^9$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^9$ is not halogen; wherein each of R$^{10a}$ and R$^{10b}$, when present, is independently selected from hydrogen, C1-C3 alkyl, C1-C3 monohaloalkyl, C1-C3 polyhaloalkyl, and cyclopropyl; wherein each occurrence of R$^{12a}$, R$^{12a}$, R$^{12a}$, and R$^{12a}$, when present, is independently selected from hydrogen, halogen, C1-C3 alkyl, C1-C3 monohaloalkyl, and C1-C3 polyhaloalkyl; wherein R$^1$ is selected from aryl and heteroaryl, and wherein R$^1$ is substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)

$R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, $-NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, $-NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, $-OR^{60}$, $-NR^{61a}R^{61b}$, $-SO_2R^{62}$, and $-(C=O)R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, $-NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, $-NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof.

Also disclosed are methods for modulating mGluR5 activity in at least one cell, comprising the step of contacting the at least one cell with an effective amount of least one compound having a structure represented by a formula:

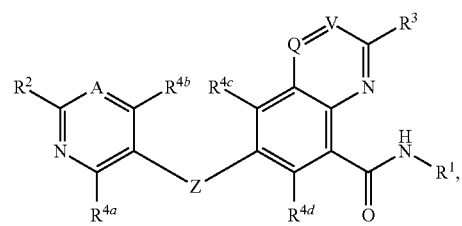

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, $-OR^{20}$, $-NR^{21a}R^{21b}$, $-SO_2R^{22}$, and $-(C=O)R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, $NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, $-NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, $-OR^{30}$, $-NR^{31a}R^{31b}$, $-SO_2R^{32}$, and $-(C=O)R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, $-NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, $-NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —$(C=O)R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8(O)_rR^9$—, —$CR^8NR^{10a}R^{10b}$—, —(C=O)—, and a structure represented by a formula:

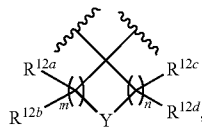

wherein Y is selected from —$CR^8R^9$—, —O—, —$S(O)_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —$S(O)_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O) $R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —$NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, —$NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof.

Also disclosed are methods for inhibiting mGluR5 activity in at least one cell, comprising the step of contacting the at least one cell with at least one compound having a structure represented by a formula:

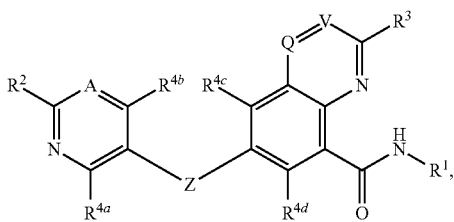

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein Q is selected from N and CR$^6$; wherein R$^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle; wherein R$^{32}$, when present, is selected from C1-C3 alkyl, C1-C3 monohaloalkyl, C1-C3 polyhaloalkyl, cyclopropyl, and, —NR$^{34a}$R$^{34b}$; wherein each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with nitrogen atom to which they are attached, comprise a 3- to 6-membered heterocycle; wherein R$^{33}$, when present, is selected from C1-C3 alkyl, C1-C3 monohaloalkyl, C1-C3 polyhaloalkyl, cyclopropyl, and, —NR$^{35a}$R$^{35b}$; wherein each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; wherein V is selected from N and CR$^7$, provided that Q and V are not simultaneously N; wherein R$^7$, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and, —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and, —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with nitrogen atom to which they are attached, comprise a 3- to 6-membered heterocycle; wherein Z is selected from —CR$^8$(O)$_r$R$^9$—, —CR$^8$NR$^{10a}$R$^{10b}$—, —(C=O)—, and a structure represented by a formula:

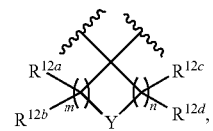

wherein Y is selected from —CR$^8$R$^9$—, —O—, —S(O)$_q$—, and —NR$^8$—; wherein m is an integer selected from 0, 1, and 2; wherein n is an integer selected from 0 and 1; wherein the sum of m and n is 1 or 2 when Y is —CR$^8$R$^9$—; wherein the sum of m and n is 2 when Y is —O—, —S(O)$_q$—, and —NR$^8$—; wherein q is 0, 1, or 2; wherein r is 0 or 1; wherein R$^8$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^8$ is not halogen; wherein R$^9$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^9$ is not halogen; wherein each of R$^{10a}$ and R$^{10b}$, when present, is independently selected from hydrogen, C1-C3 alkyl, C1-C3 monohaloalkyl, C1-C3 polyhaloalkyl, and cyclopropyl; wherein each occurrence of R$^{12a}$, R$^{12a}$, R$^{12a}$, and R$^{12a}$, when present, is independently selected from hydrogen, halogen, C1-C3 alkyl, C1-C3 monohaloalkyl, and C1-C3 polyhaloalkyl; wherein R$^1$ is selected from aryl and heteroaryl, and wherein R$^1$ is substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$; wherein each occurrence of R$^{50}$, when present, is independently selected from hydrogen, C1-C3 alkyl, C1-C3 monohaloalkyl, C1-C3 polyhaloalkyl, and cyclopropyl; wherein each occurrence of each of R$^{51a}$ and R$^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —NR$^{54a}$R$^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, —NR$^{55a}$R$^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C═O)R$^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —NR$^{64a}$R$^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —NR$^{65a}$R$^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof.

Also disclosed are uses of a compound having a structure represented by a formula:

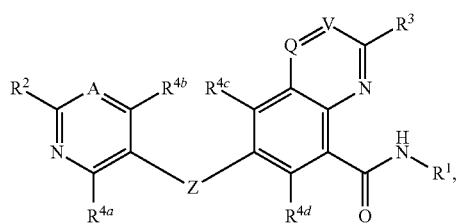

wherein A is selected from N and CR$^5$; wherein $R^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C═O) R$^{23}$; wherein $R^{20}$, when present, is selected from C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —NR$^{24a}$R$^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —NR$^{25a}$R$^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and CR$^6$; wherein $R^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C═O)R$^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —NR$^{34a}$R$^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —NR$^{35a}$R$^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and CR$^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C═O)R$^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, $-NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, $-NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from $-CR^8(O)_rR^9-$, $-CR^8NR^{10a}R^{10b}-$, $-(C=O)-$, and a structure represented by a formula:

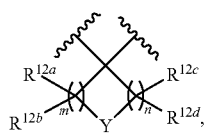

wherein Y is selected from $-CR^8R^9-$, $-O-$, $-S(O)_q-$, and $-NR^8-$; wherein m is an integer selected from 0, 1, and 2; wherein n is an integer selected from 0 and 1; wherein the sum of m and n is 1 or 2 when Y is $-CR^8R^9-$; wherein the sum of m and n is 2 when Y is $-O-$, $-S(O)_q-$, and $-NR^8-$; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is $-CR^8(O)_rR^9-$ and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is $-CR^8(O)_rR^9-$ and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, $-CN$, C1-C3 alkyl, C1-C3 monohaloalkyl, C1-C3 polyhaloalkyl, cyclopropyl, $-OR^{50}$, $-NR^{51a}R^{51b}$, $-SO_2R^{52}$, and $-(C=O)R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, $-NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, $-NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, $-CN$, C1-C3 alkyl, C1-C3 monohaloalkyl, C1-C3 polyhaloalkyl, cyclopropyl, $-OR^{60}$, $-NR^{61a}R^{61b}$, $-SO_2R^{62}$, and $-(C=O)R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, $-NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, $-NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof, in the manufacture of a medicament for the treatment of a disorder associated with glutamate dysfunction in a mammal.

Also disclosed are kits comprising at least one compound having a structure represented by a formula:

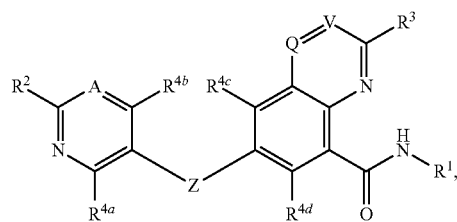

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O) R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein Q is selected from N and CR$^6$; wherein R$^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle; wherein R$^{32}$, when present, is selected from C1-C3 alkyl, C1-C3 monohaloalkyl, C1-C3 polyhaloalkyl, cyclopropyl, and, —NR$^{34a}$R$^{34b}$; wherein each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with nitrogen atom to which they are attached, comprise a 3- to 6-membered heterocycle; wherein R$^{33}$, when present, is selected from C1-C3 alkyl, C1-C3 monohaloalkyl, C1-C3 polyhaloalkyl, cyclopropyl, and, —NR$^{35a}$R$^{35b}$; wherein each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; wherein V is selected from N and CR$^7$, provided that Q and V are not simultaneously N; wherein R$^7$, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and, —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and, —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with nitrogen atom to which they are attached, comprise a 3- to 6-membered heterocycle; wherein Z is selected from —CR$^8$(O),R$^9$—, —CR$^8$NR$^{10a}$R$^{10b}$—, —(C=O)—, and a structure represented by a formula:

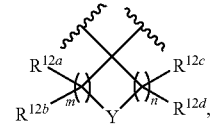

wherein Y is selected from —CR$^8$R$^9$—, —O—, —S(O)$_q$—, and —NR$^8$—; wherein m is an integer selected from 0, 1, and 2; wherein n is an integer selected from 0 and 1; wherein the sum of m and n is 1 or 2 when Y is —CR$^8$R$^9$—; wherein the sum of m and n is 2 when Y is —O—, —S(O)$_q$—, and —NR$^8$—; wherein q is 0, 1, or 2; wherein r is 0 or 1; wherein R$^8$, when present, is selected from hydrogen, halogen, C1-C3 alkyl, C1-C3 monohaloalkyl, C1-C3 polyhaloalkyl, and cyclopropyl; provided that, when Z is —CR$^8$(O),R$^9$— and r is 1, R$^8$ is not halogen; wherein R$^9$, when present, is selected from hydrogen, halogen, C1-C3 alkyl, C1-C3 monohaloalkyl, C1-C3 polyhaloalkyl, and cyclopropyl; provided that, when Z is —CR$^8$(O),R$^9$— and r is 1, R$^9$ is not halogen; wherein each of R$^{10a}$ and R$^{10b}$, when present, is independently selected from hydrogen, C1-C3 alkyl, C1-C3 monohaloalkyl, C1-C3 polyhaloalkyl, and cyclopropyl; wherein each occurrence of R$^{12a}$, R$^{12a}$, R$^{12a}$, and R$^{12a}$, when present, is independently selected from hydrogen, halogen, C1-C3 alkyl, C1-C3 monohaloalkyl, and C1-C3 polyhaloalkyl; wherein R$^1$ is selected from aryl and heteroaryl, and wherein R$^1$ is substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O) R$^{53}$; wherein each occurrence of R$^{50}$, when present, is independently selected from hydrogen, C1-C3 alkyl, C1-C3 monohaloalkyl, C1-C3 polyhaloalkyl, and cyclopropyl; wherein each occurrence of each of R$^{51a}$ and R$^{51b}$, when present, is independently selected from hydrogen, C1-C3 alkyl, C1-C3 monohaloalkyl, C1-C3 polyhaloalkyl, and cyclopropyl; or wherein R$^{51a}$ and R$^{51b}$, when present, are optionally covalently bonded and, together with nitrogen atom to which they are attached, comprise a 3- to 6-membered heterocycle; wherein each occurrence of R$^{52}$, when present, is independently selected from C1-C3 alkyl, C1-C3 monohaloalkyl, C1-C3 polyhaloalkyl, cyclopropyl, and, —NR$^{54a}$R$^{54b}$; wherein each occurrence of each of R$^{54a}$ and R$^{54b}$, when present, is independently selected from hydrogen, C1-C3 alkyl, C1-C3 monohaloalkyl, C1-C3 polyhaloalkyl, and cyclopropyl; or wherein R$^{54a}$ and R$^{54b}$, when present, are optionally covalently bonded and, together with nitrogen atom to which they are attached, comprise a 3- to 6-membered heterocycle; wherein each occurrence of R$^{53}$, when present, is independently from C1-C3 alkyl, C1-C3 monohaloalkyl, C1-C3 polyhaloalkyl, cyclopropyl, and, —NR$^{55a}$R$^{55b}$; wherein each occurrence of each of R$^{55a}$ and R$^{55b}$, when present, is independently selected from hydrogen, C1-C3 alkyl, C1-C3 monohaloalkyl, C1-C3 polyhaloalkyl, and cyclopropyl; or wherein R$^{55a}$ and R$^{55b}$, when present, are optionally covalently bonded and, together with nitrogen atom to which they are attached, comprise a 3- to 6-membered heterocycle; wherein R$^2$ is selected from hydrogen, C1-C3 alkyl, C1-C3 monohaloalkyl, C1-C3 polyhaloalkyl, and cyclopropyl; wherein R$^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$, is independently selected from hydrogen and fluoro; or a pharmaceutically acceptable salt, solvate, or polymorph thereof, and one or more of: (a) at least one agent known to increase mGluR5 activity; (b) at least one agent known to decrease mGluR5 activity; (c) at least one agent known to treat a neurological and/or psychiatric disorder; (d) at least one agent known to treat a disease of uncontrolled cellular proliferation; or (e) instructions for treating a disorder associated with glutamate dysfunction.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
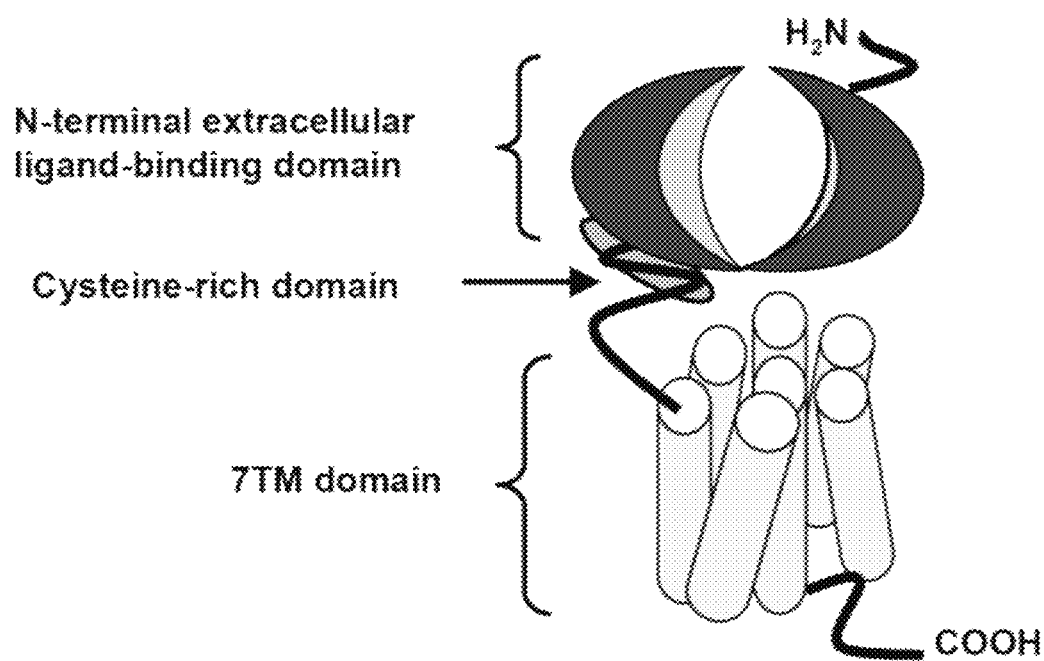
FIG. 1 is a schematic representation of an mGluR.
Figure 2:
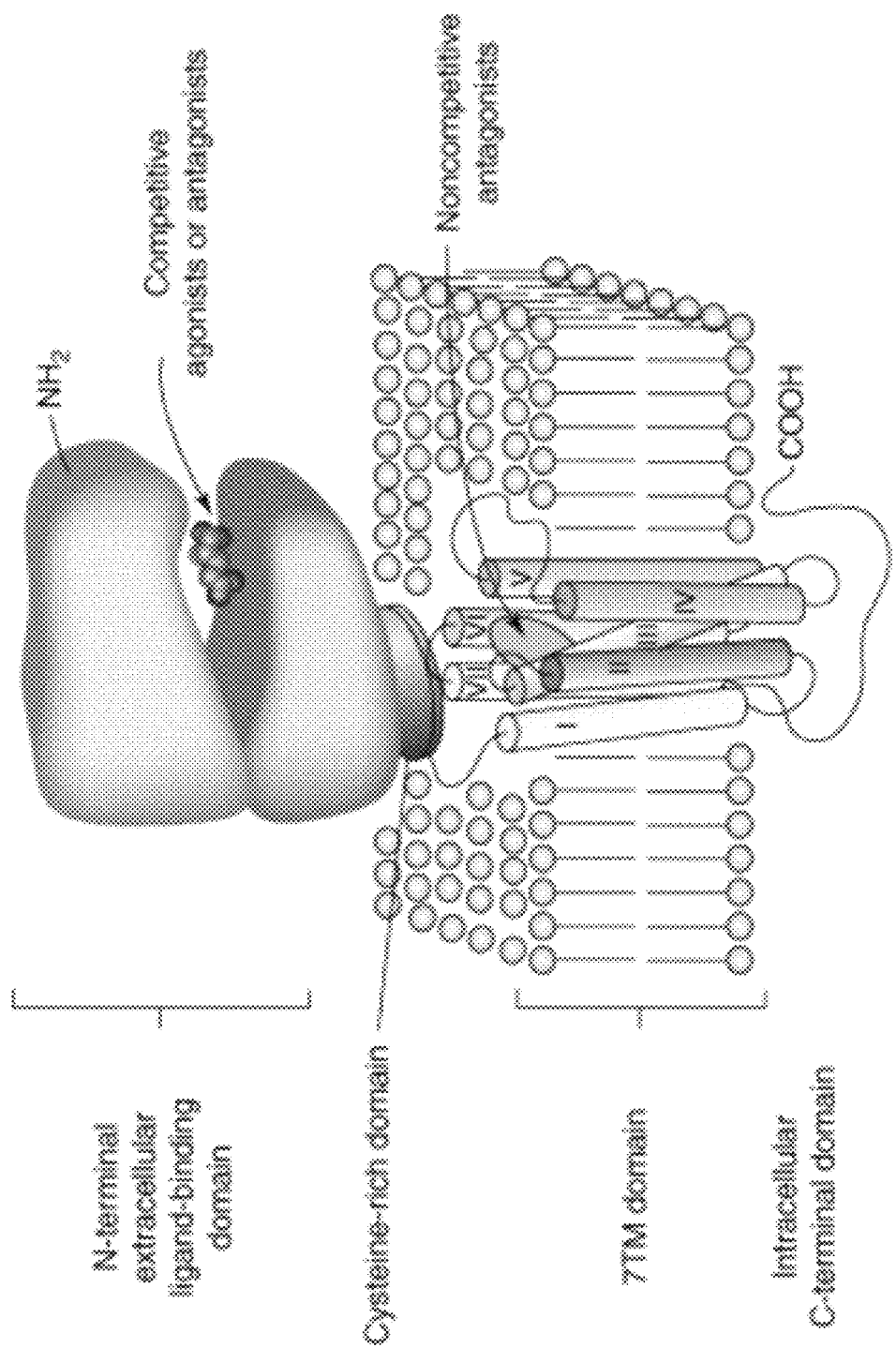
FIG. 2 illustrates allosteric modulation of mGluR5.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples and Figures included herein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "orthosteric site" refers to the primary binding site on a receptor that is recognized by the endogenous ligand or agonist for that receptor. For example, the orthosteric site in the mGluR5 receptor is the site that glutamate binds.

As used herein, the term "mGluR5 receptor negative allosteric modulator" refers to any exogenously administered compound or agent that directly or indirectly inhibits the activity of the mGluR5 receptor in the presence of the endogenous ligand (such as glutamate) in an animal, in particular a mammal, for example a human. The term is synonymous with the terms "mGluR5 receptor allosteric inhibitor," "mGluR5 receptor noncompetitive inhibitor," "mGluR5 receptor allosteric antagonist," and "mGluR5 receptor noncompetitive antagonist."

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated with glutamate dysfunction prior to the administering step. In some aspects of the disclosed method, the subject has been diagnosed with a need for negative allosteric modulation of metabotropic glutamate receptor activity prior to the administering step. In some aspects of the disclosed method, the subject has been diagnosed with a need for partial antagonism of metabotropic glutamate receptor activity prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

For example, "diagnosed with a disorder treatable by modulation of mGluR5" means having been subjected to a physical examination by a person of skill, for example, a physician, and found to have a condition that can be diagnosed or treated by a compound or composition that can modulate mGluR5. As a further example, "diagnosed with a need for modulation of mGluR5" refers to having been subjected to a physical examination by a person of skill, for example, a physician, and found to have a condition characterized by mGluR5 activity. Such a diagnosis can be in reference to a disorder, such as a neurodegenerative disease, and the like, as discussed herein. For example, the term "diagnosed with a need for negative allosteric modulation of metabotropic glutamate receptor activity" refers to having been subjected to a physical examination by a person of skill, for example, a physician, and found to have a condition that can be diagnosed or treated by negative allosteric modulation of metabotropic glutamate receptor activity. For example, "diagnosed with a need for partial antagonism of metabotropic glutamate receptor activity" means having been subjected to a physical examination by a person of skill, for example, a physician, and found to have a condition that can be diagnosed or treated by partial antagonism of metabotropic glutamate receptor activity. For example, "diagnosed with a need for treatment of one or more neurological and/or psychiatric disorder associated with glutamate dysfunction" means having been subjected to a physical examination by a person of skill, for example, a physician, and found to have one or more neurological and/or psychiatric disorder associated with glutamate dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to mGluR5 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target metabotropic glutamate receptor, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications.

Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response. In a yet further aspect, the response is in vitro. In a still further aspect, the response is in a human embryonic kidney cell transfected with human mGluR5. In a yet further aspect, the response is a human embryonic kidney cell transfected with rat mGluR5. In an even further aspect, the response is in a human embryonic kidney cell transfected with a mammalian mGluR5.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance. In a yet further aspect, the inhibition is measured in vitro. In a still further aspect, the inhibition is measured in a human embryonic kidney cell transfected with human mGluR5. In a yet further aspect, the inhibition is measured in a human embryonic kidney cell transfected with rat mGluR5. In an even further aspect, the inhibition is measured in a human embryonic kidney cell transfected with a mammalian mGluR5.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $-NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group is independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), is independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of Rt is independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

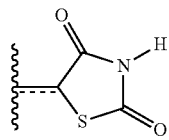

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, monosubstituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

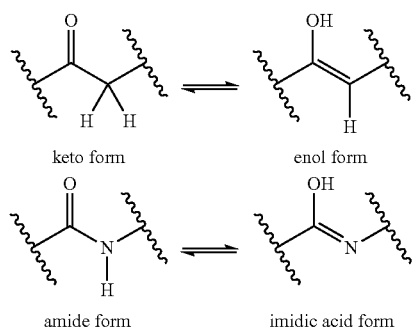

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

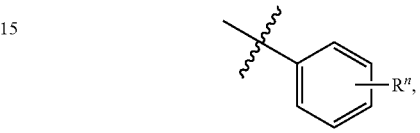

which is understood to be equivalent to a formula:

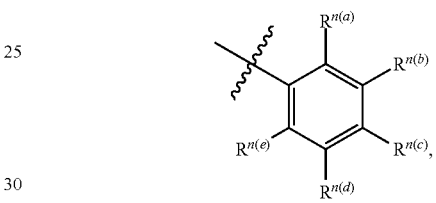

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^n(a)$ is halogen, then $R^n(b)$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

The following abbreviations are used herein. AcOH: acetic acid. DMF: N,N-dimethyl formamide. DMSO: dimethylsulfoxide. ES-MS: electrospray mass spectrometry. EtOAc: ethyl acetate. IPA: isopropyl alcohol. LC-MS or LCMS: liquid chromatography/mass spectrometry. [M+H]+: protonated mass of the free base of the compound. MeOH: methanol. NMR: nuclear magnetic resonance. TEA: triethylamine. THF: tetrahydrofuran. TLC: thin layer chromatography.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. mGLUR5 Negative Allosteric Modulators

In one aspect, the invention relates to compounds useful as negative allosteric modulators of the metabotropic glutamate receptor subtype 5 (mGluR5). Negative allosteric modulators are noncompetitive antagonists and can include a range of maximal antagonist activity from partial antagonists to inverse agonists. In one aspect, the present invention relates to compounds that allosterically modulate mGluR5 receptor activity, affecting the sensitivity of mGluR5 receptors to agonists without acting as orthosteric agonists themselves. The compounds can, in one aspect, exhibit subtype selectivity. The compounds of the invention can be useful in the treatment neurological and psychiatric disorders associated with glutamate dysfunction and other diseases in which metabotropic glutamate receptors are involved, as further described herein. Generally, the disclosed compounds exhibit negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In further aspect, the human embryonic kidney cells are transfected with human mGluR5. In yet a further aspect, human embryonic kidney cells are transfected with mGluR5 of a mammal.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to compounds, or pharmaceutically acceptable salts thereof, having a structure represented by a formula:

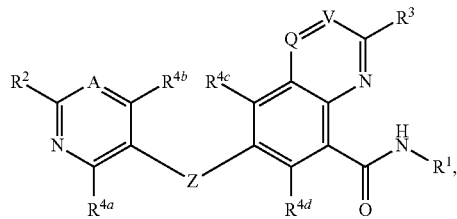

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8(O)_rR^9$—, —$CR^8NR^{10a}R^{10b}$—, —(C=O)—, and a structure represented by a formula:

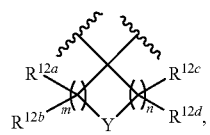

wherein Y is selected from —$CR^8R^9$—, —O—, —$S(O)_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —$S(O)_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O)$R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —$NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, —$NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$, is independently selected from hydrogen and fluoro; or a pharmaceutically acceptable salt, solvate, or polymorph thereof, wherein the compound exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound.

In a further aspect, the compound exhibits partial inhibition of mGluR5 response. In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits noncompetitive antagonism. In a still further aspect, the compound exhibits negative allosteric modulation. In a yet further aspect, the compound exhibits noncompetitive inhibition. In an even further aspect, the compound exhibits allosteric antagonism.

In a further aspect, the compound exhibits negative allosteric modulation with an IC$_{50}$ of less than about 30×10$^{-6}$ M. In an even further aspect, the compound exhibits negative allosteric modulation with an IC$_{50}$ of less than about 10×10$^{-6}$ M. In a yet further aspect, the compound exhibits negative allosteric modulation with an IC$_{50}$ of less than about 1.0×10$^{-6}$ M. In a still further aspect, the compound exhibits negative allosteric modulation with an IC$_{50}$ of less than about 1.0×10$^{-7}$ M. In an even further aspect, the compound exhibits negative allosteric modulation with an IC$_{50}$ of less than about 1.0×10$^{-8}$ M. In a yet further aspect, the compound exhibits negative allosteric modulation with an IC$_{50}$ of less than about 1.0×10$^{-9}$ M. In a still further aspect, the compound exhibits negative allosteric modulation inhibition with an IC$_{50}$ of between about 1×10$^{-5}$ M to about 1×10$^{-9}$ M. In an even further aspect, the compound exhibits negative allosteric modulation with an IC$_{50}$ of between about from about 1×10$^{-6}$ M to about 1×10$^{-9}$ M. In a yet further aspect, the compound exhibits negative allosteric modulation with an IC$_{50}$ of between about from about 1×10$^{-7}$ M to about 1×10$^{-9}$ M. In a still further aspect, the compound exhibits negative allosteric modulation with an IC$_{50}$ of between about 1×10$^{-8}$ M to about 1×10$^{-9}$ M.

In a further aspect, the compound exhibits partial or total inhibition with an IC$_{50}$ of less than about 30×10$^{-6}$ M. In an even further aspect, the compound exhibits partial or total inhibition with an IC$_{50}$ of less than about 10×10$^{-6}$ M. In a yet further aspect, the compound exhibits partial or total inhibition with an IC$_{50}$ of less than about 1.0×10$^{-6}$ M. In a still further aspect, the compound exhibits partial or total inhibition with an IC$_{50}$ of less than about 1.0×10$^{-7}$ M. In an even further aspect, the compound exhibits partial or total inhibition with an IC$_{50}$ of less than about 1.0×10$^{-8}$ M. In a yet further aspect, the compound exhibits partial or total inhibition with an IC$_{50}$ of less than about 1.0×10$^{-9}$ M. In a still further aspect, the compound exhibits partial or total inhibition with an IC$_{50}$ of between about 1×10$^{-5}$ M to about 1×10$^{-9}$ M. In an even further aspect, the compound exhibits partial or total inhibition with an IC$_{50}$ of between about from about 1×10$^{-6}$ M to about 1×10$^{-9}$ M. In a yet further aspect, the compound exhibits partial or total inhibition with an IC$_{50}$ of between about from about 1×10$^{-7}$ M to about 1×10$^{-9}$ M. In a still further aspect, the compound exhibits partial or total inhibition with an IC$_{50}$ of between about 1×10$^{-8}$ M to about 1×10$^{-9}$ M.

In a further aspect, a pharmaceutical composition comprising a therapeutically effective amount of a disclosed compound or product of a disclosed method of making and a pharmaceutically acceptable carrier.

In a further aspect, a compound has a structure represented by a formula:

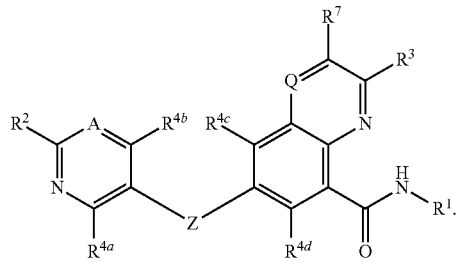

In a further aspect, a compound has a structure represented by a formula:

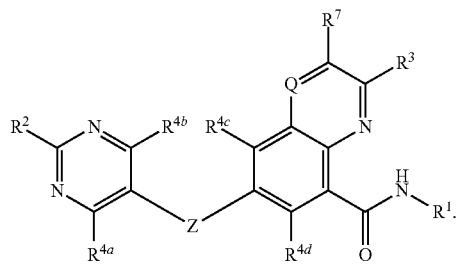

In further aspect, a compound has a structure represented by a formula:

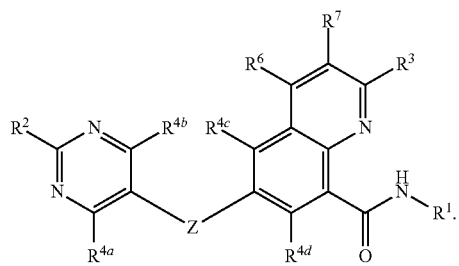

In a further aspect, a compound has a structure represented by a formula:

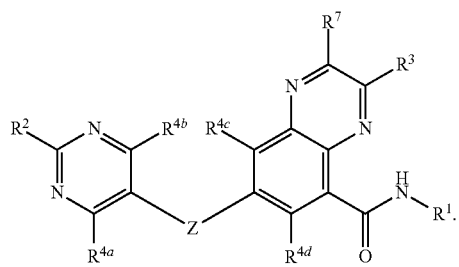

In a further aspect, a compound has a structure selected from:
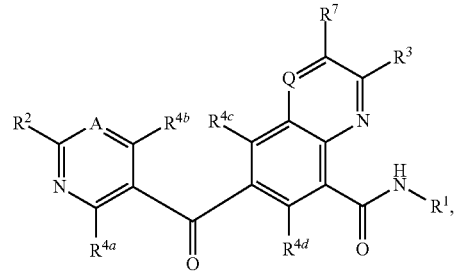
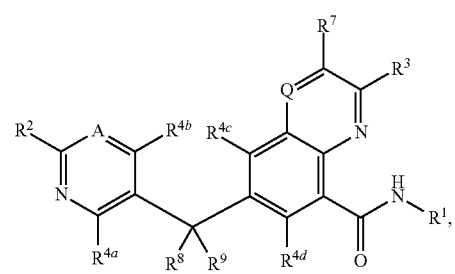
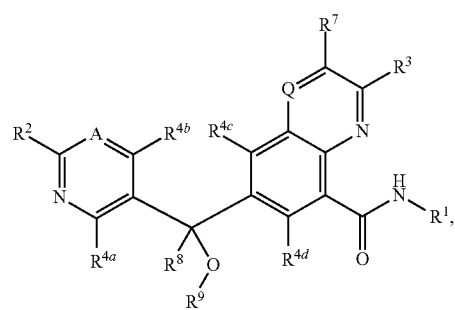
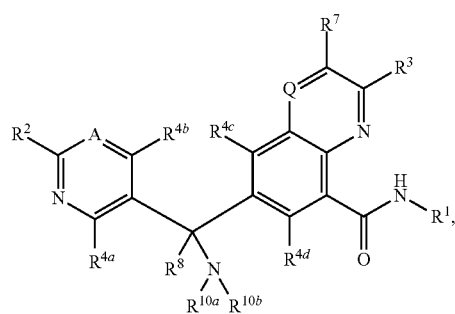
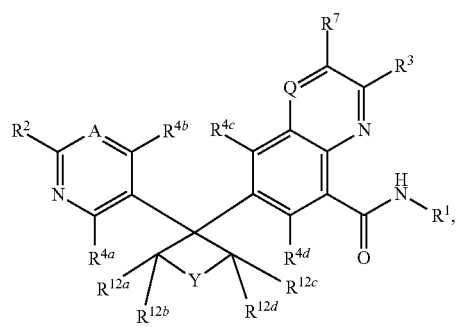
-continued
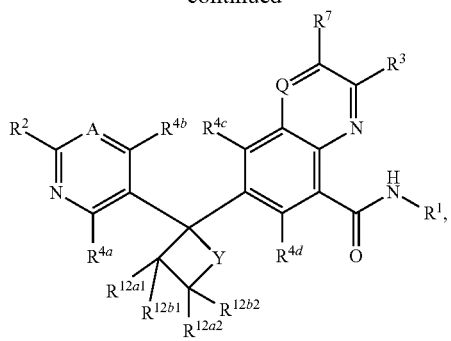
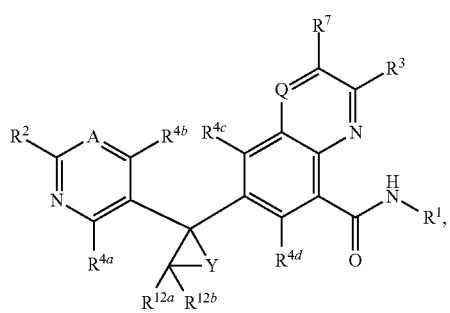
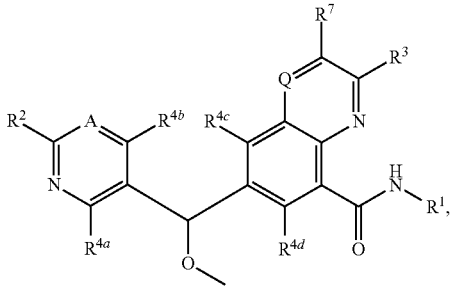
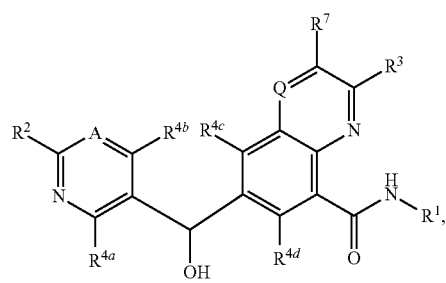
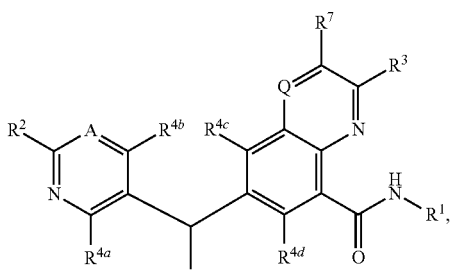

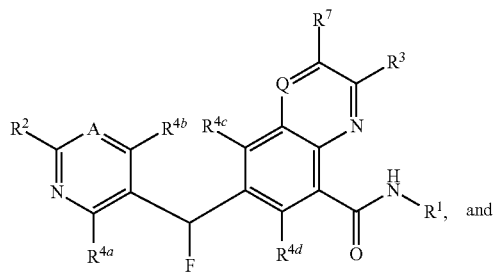
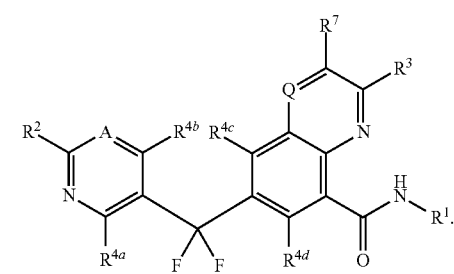
In a further aspect, a compound has a structures selected from:
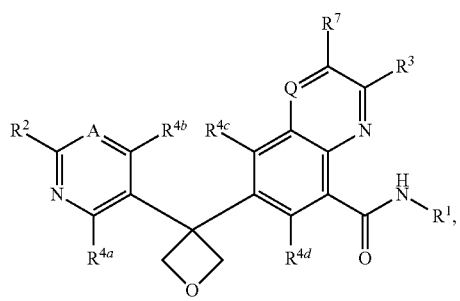
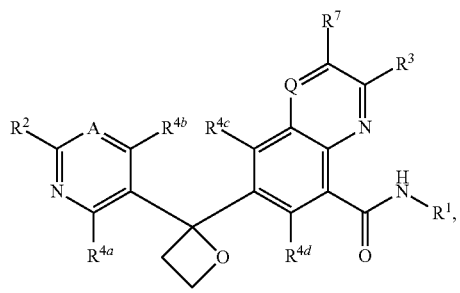
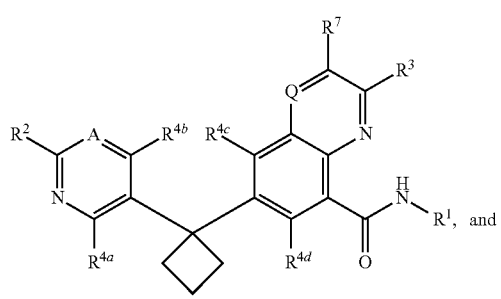
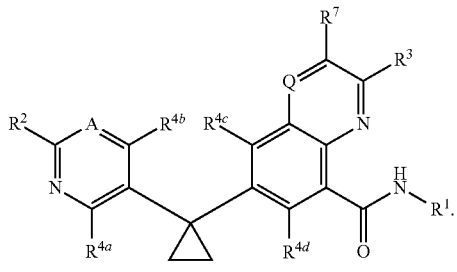
In a further aspect, a compound has a structure selected from:
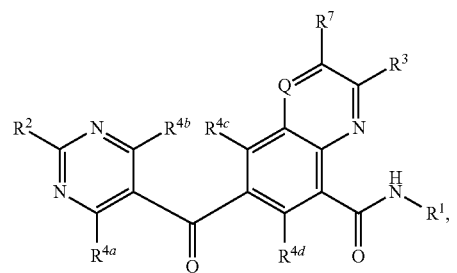
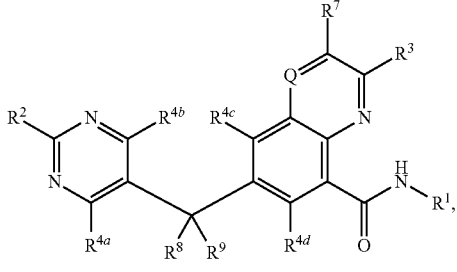
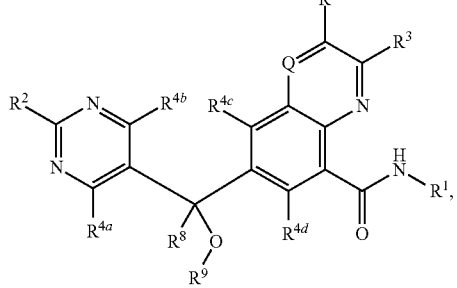
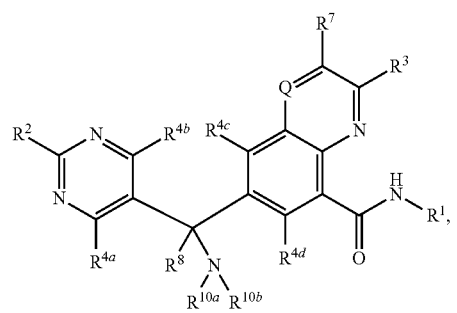

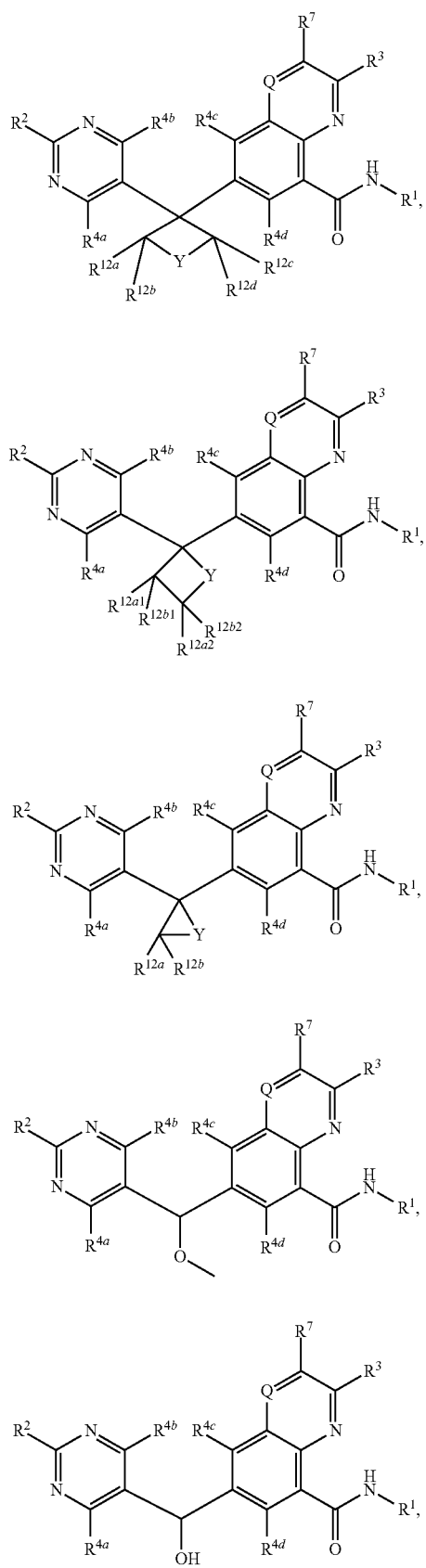
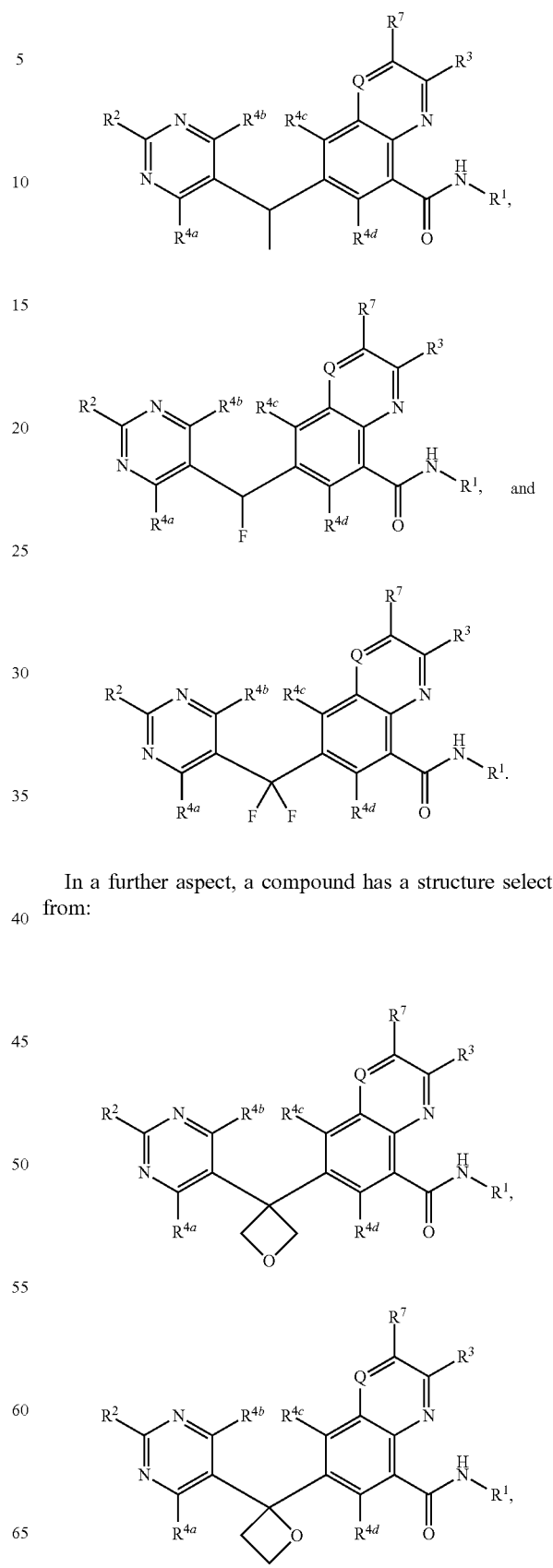
In a further aspect, a compound has a structure selected from:

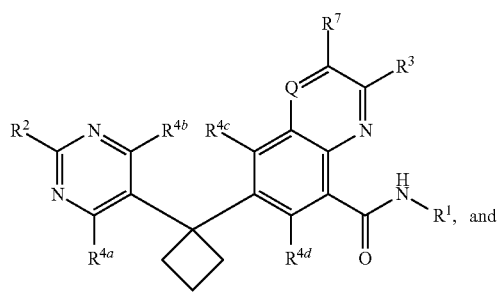
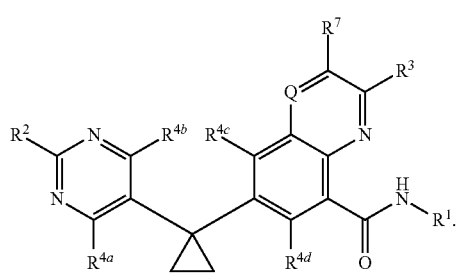
In a further aspect, a compound has a structure selected from:
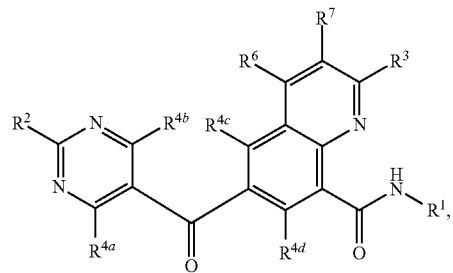
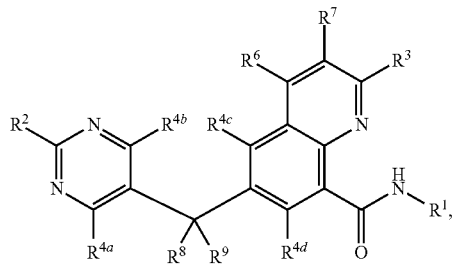
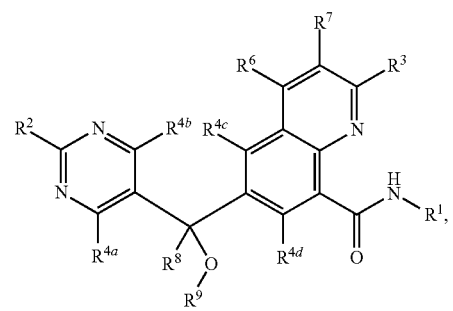
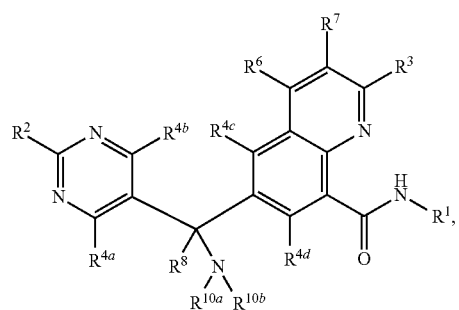
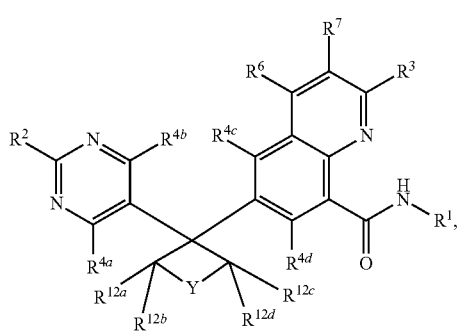
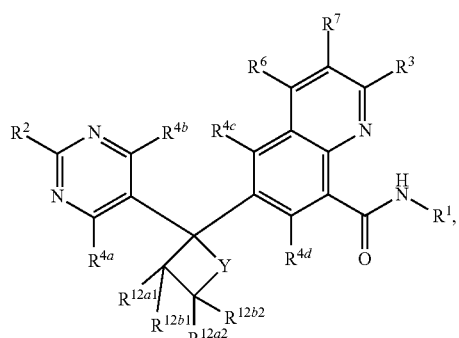
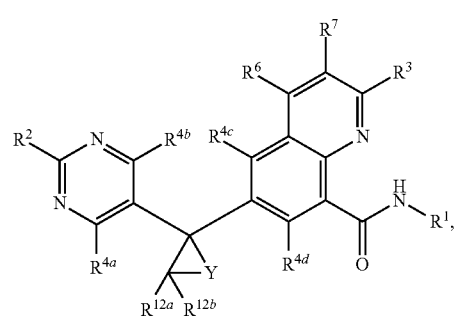
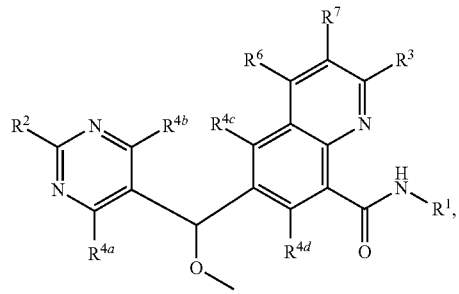

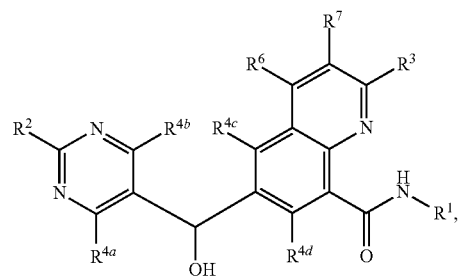
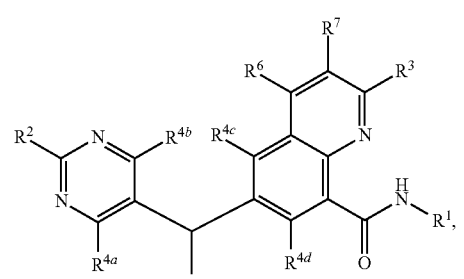
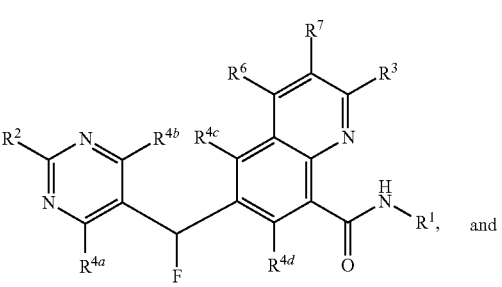
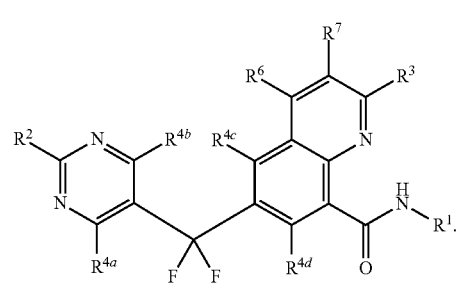
In a further aspect, a compound has a structure selected from:
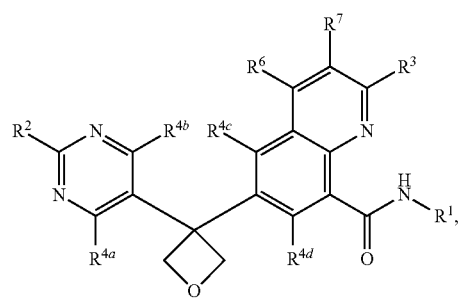
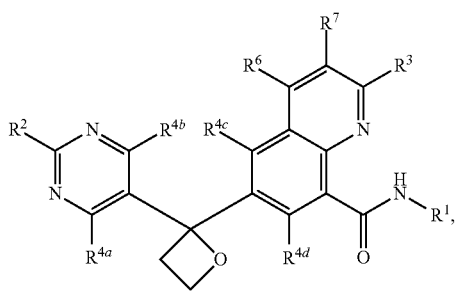
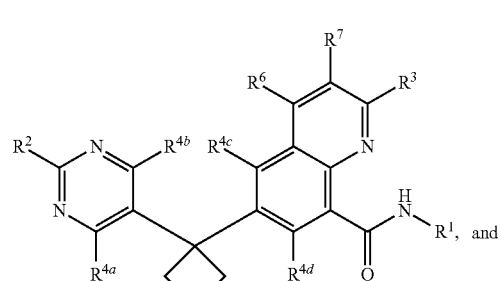
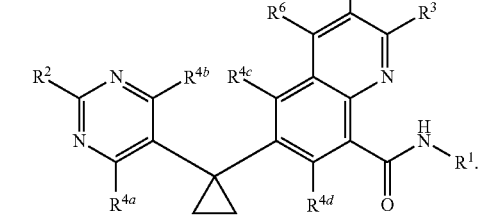
In a further aspect, a compound has a structure selected from:
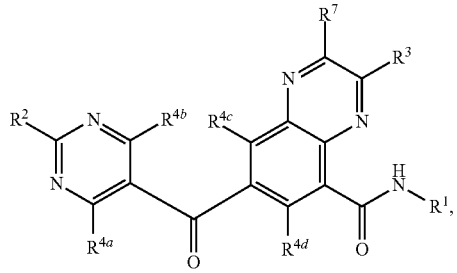
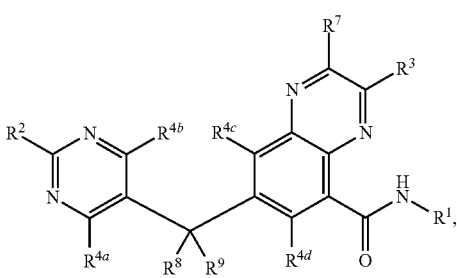

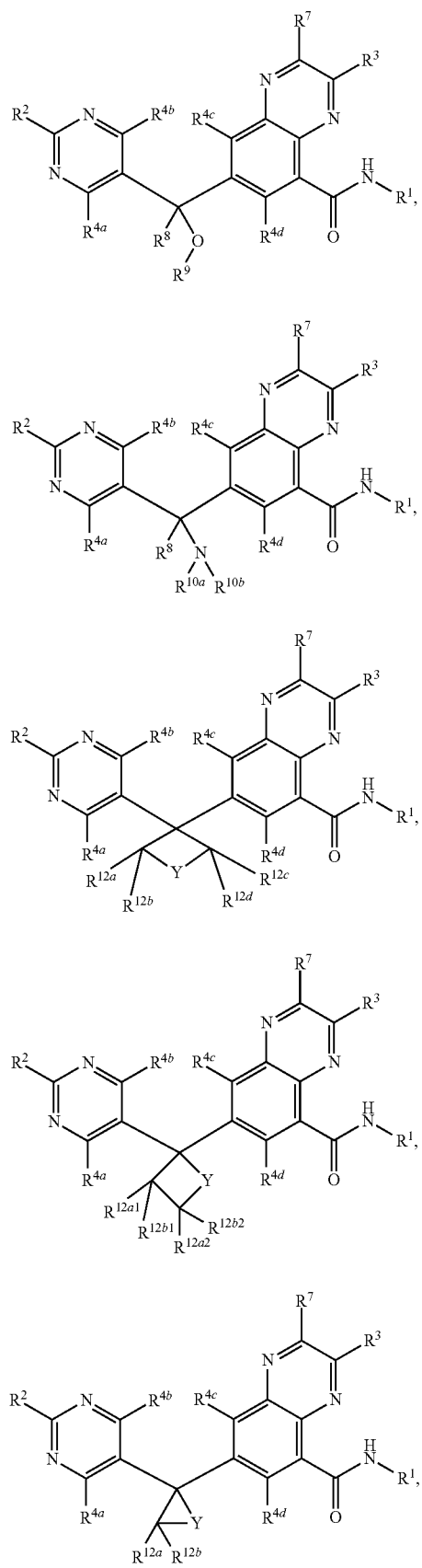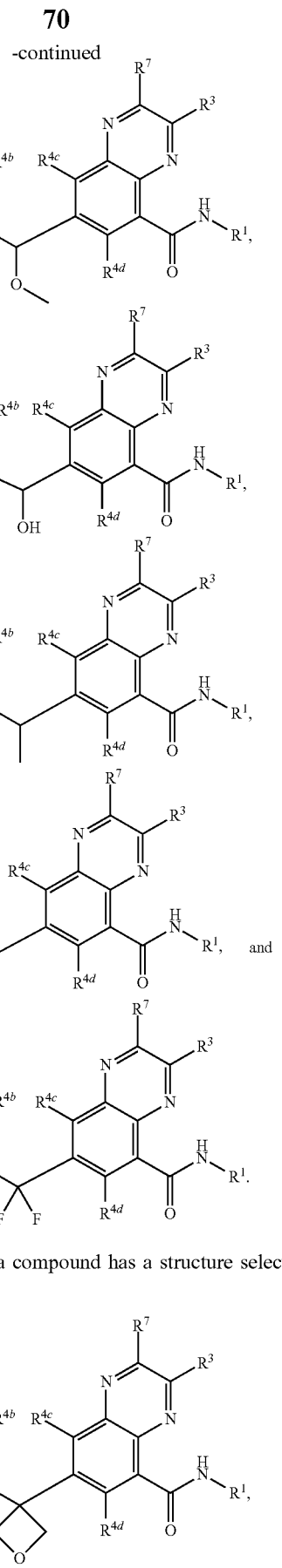
In a further aspect, a compound has a structure selected from:
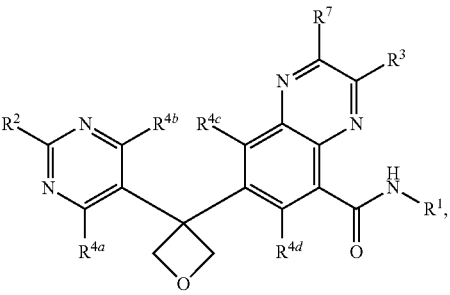

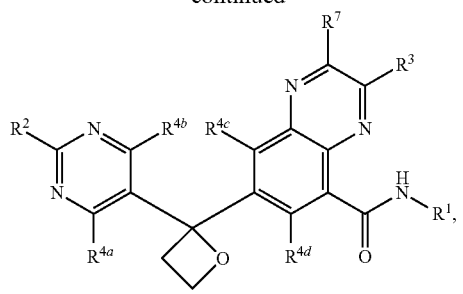
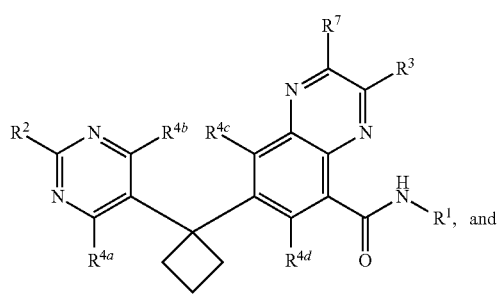
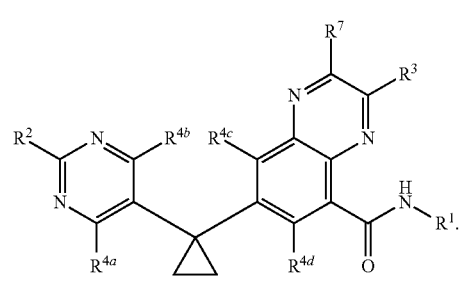
In a further aspect, a compound has a structure selected from:
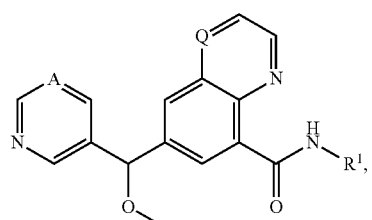
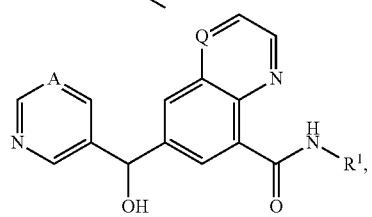
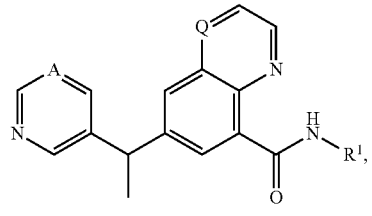
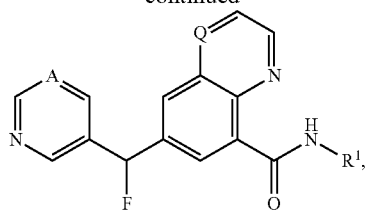
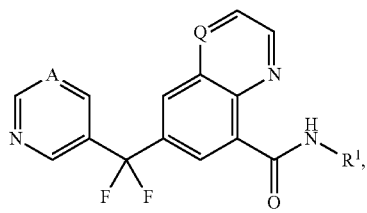
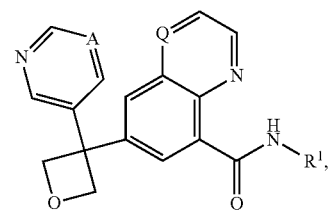
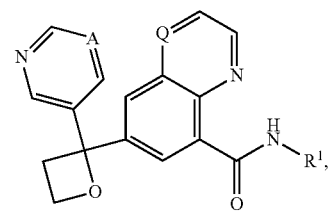
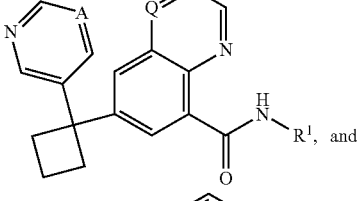
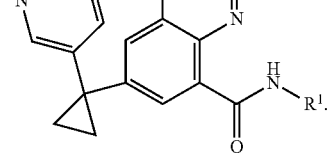
In a further aspect, a compound has a structure selected from:
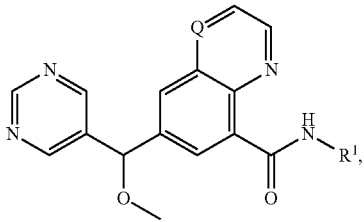

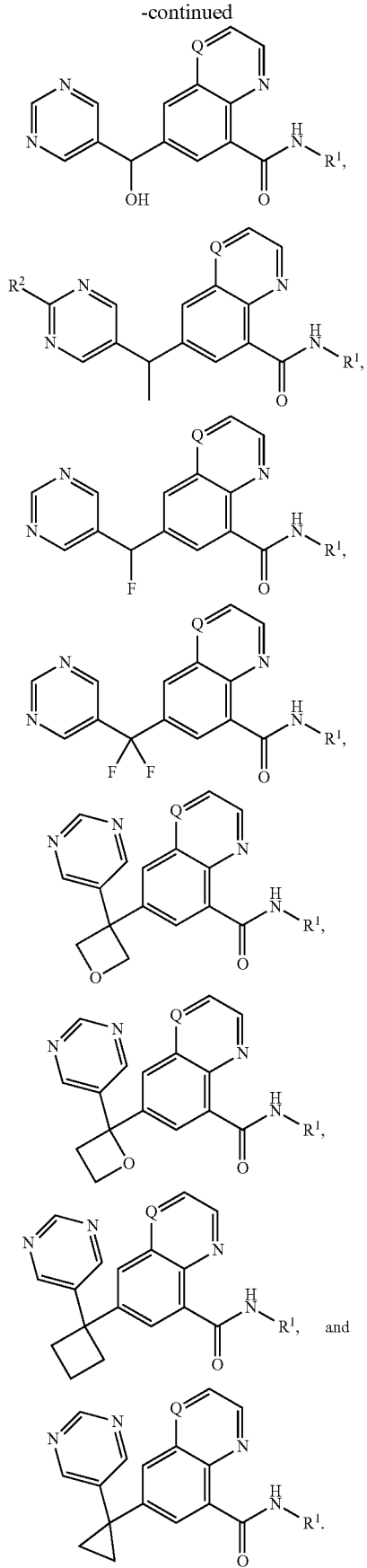
In a further aspect, a compound has a structure selected from:
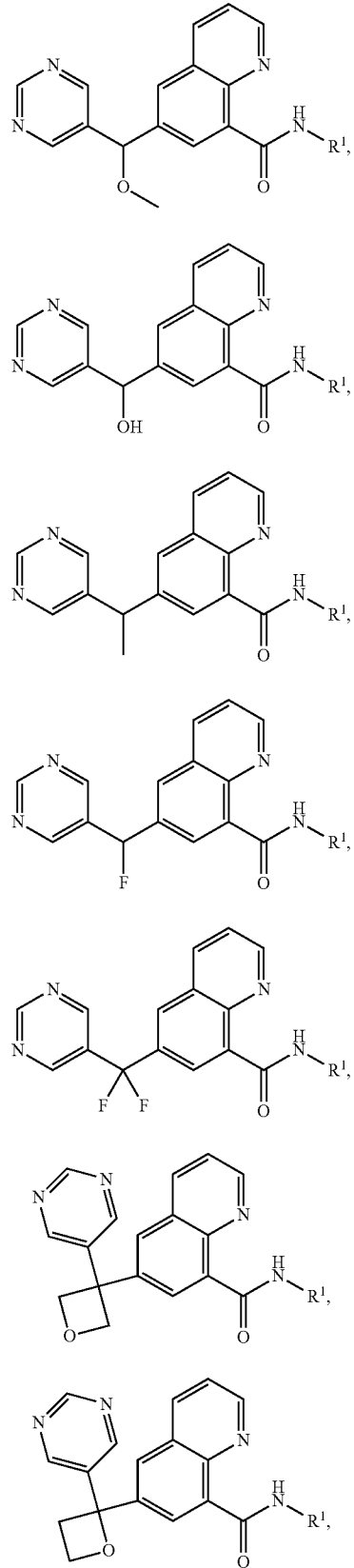

-continued
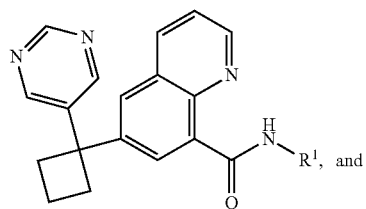
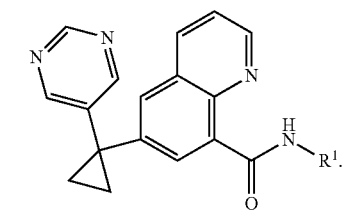
In a further aspect, a compound has a structure selected from:
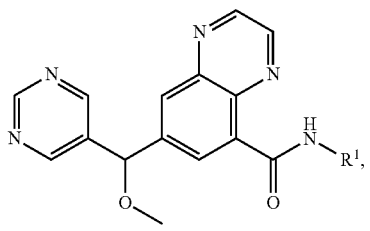
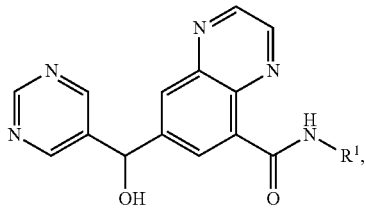
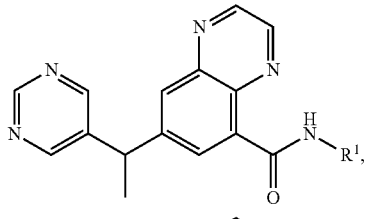
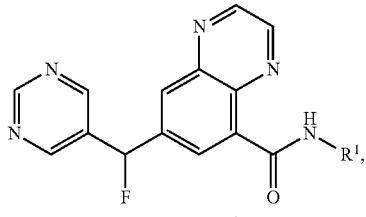
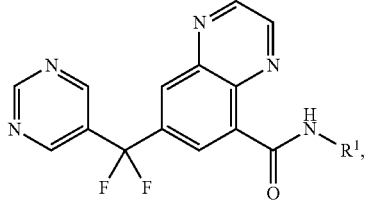
-continued
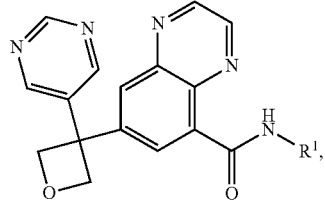
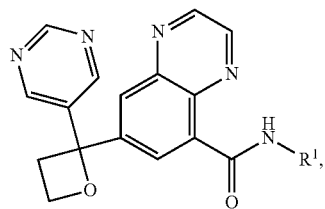
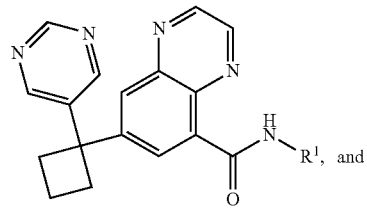
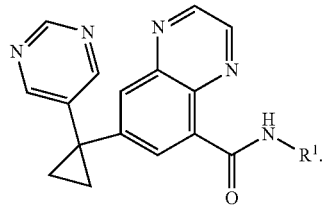
In a further aspect, a compound has a structure represented by a formula:
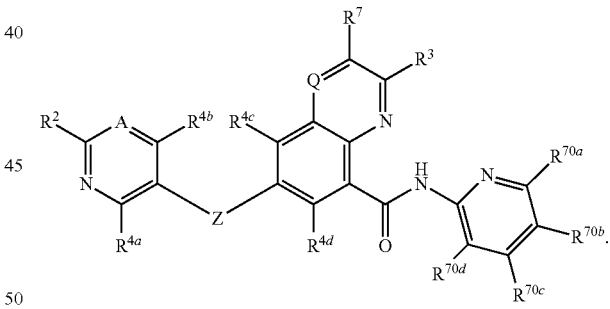
In a further aspect, a compound has a structure represented by a formula:
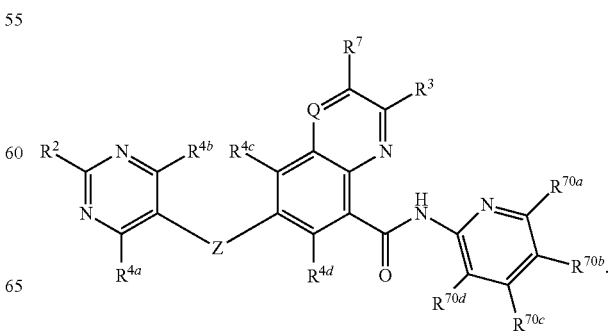

In a further aspect, a compound has a structure represented by a formula:
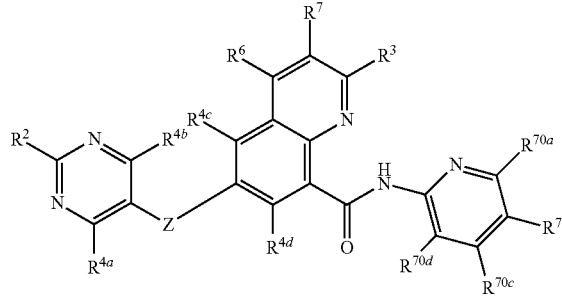
In a further aspect, a compound has a structure represented by a formula:
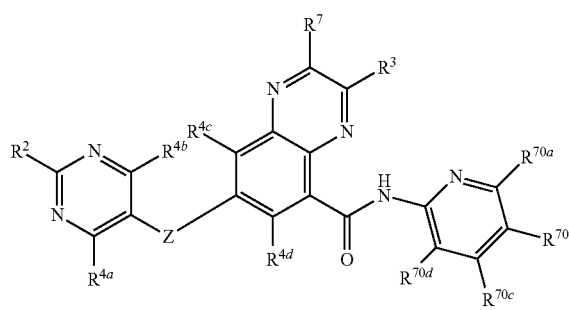
In a further aspect, a compound has a structure selected from:
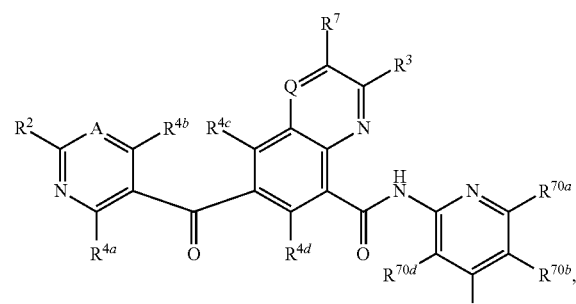
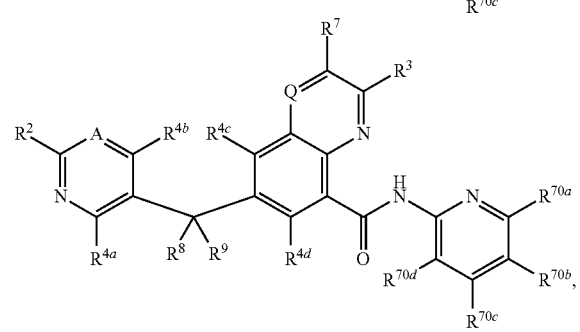
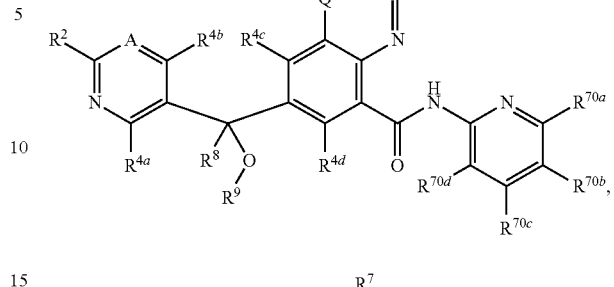
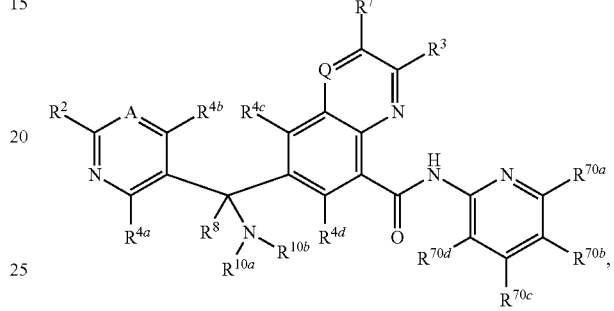
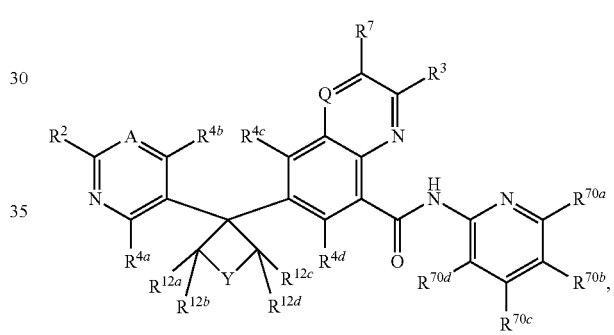
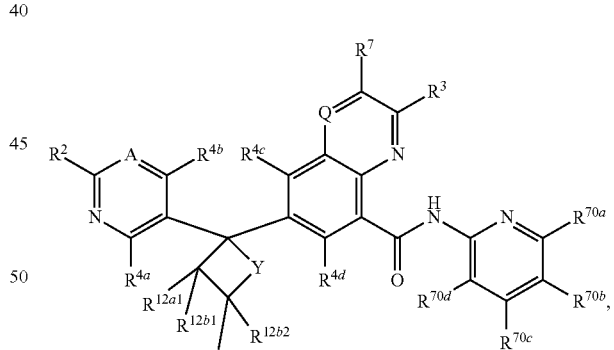
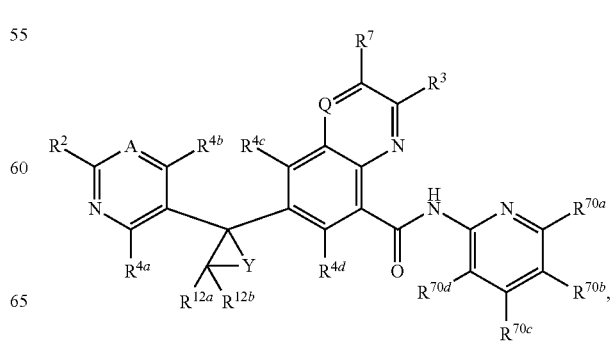

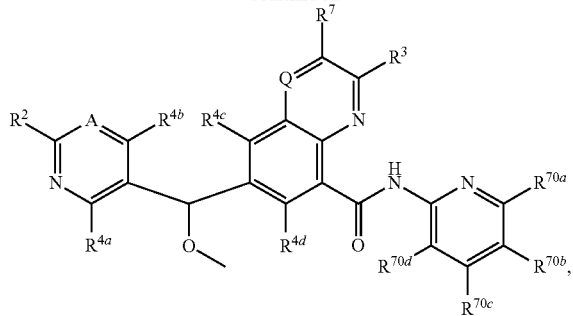
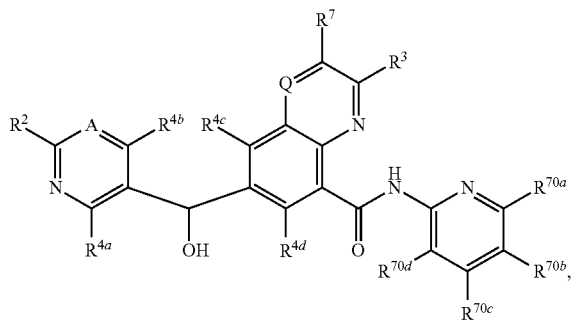
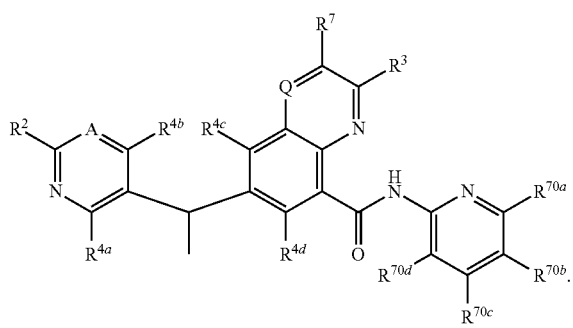
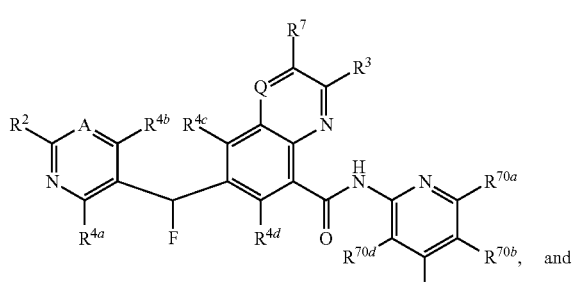
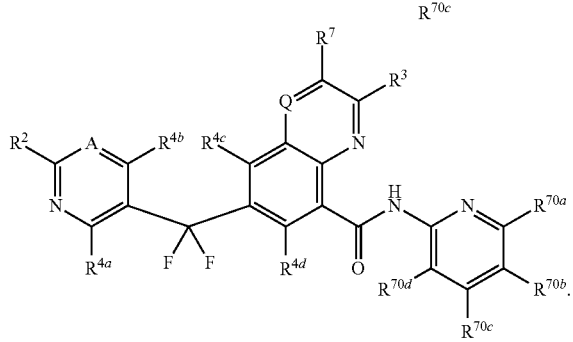
In a further aspect, a compound has a structure selected from:
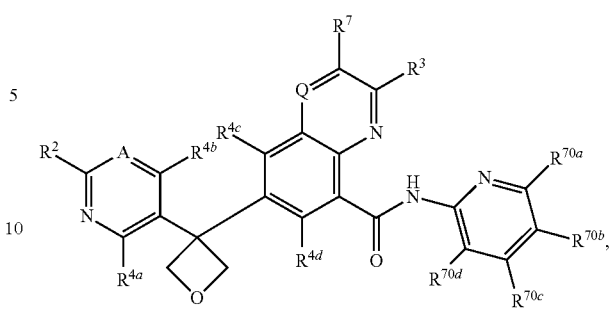
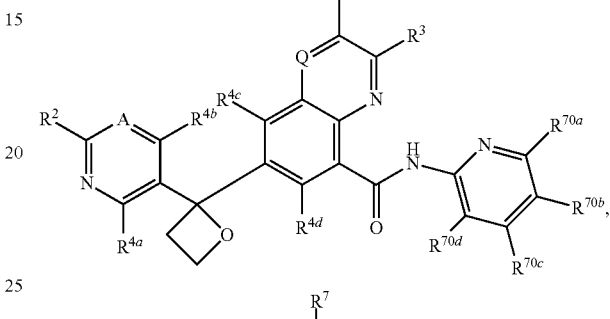
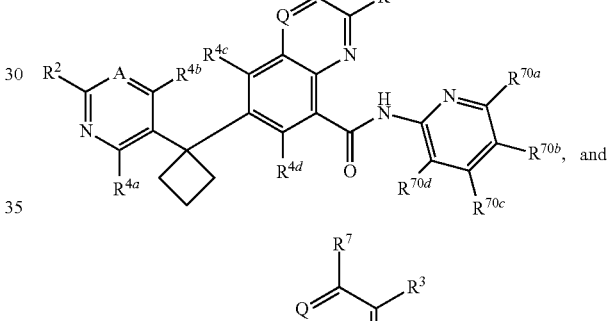
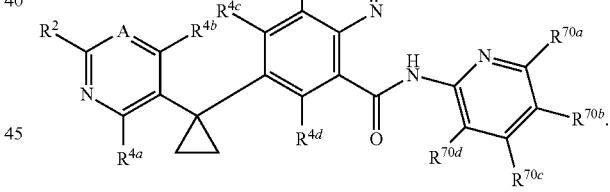
In a further aspect, a compound has a structure selected from:
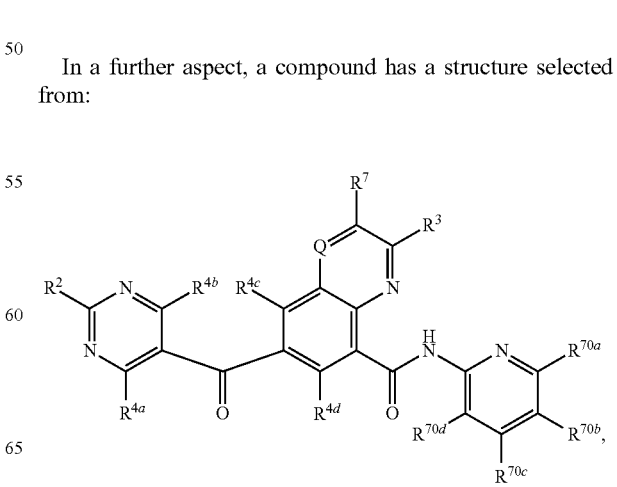

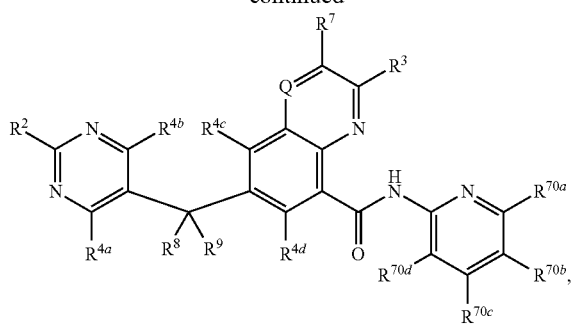
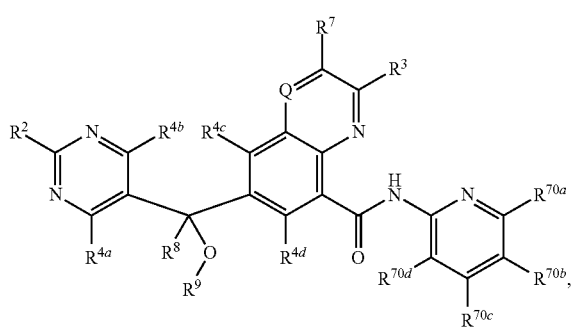
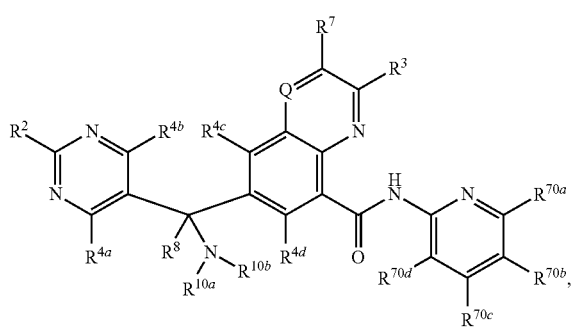
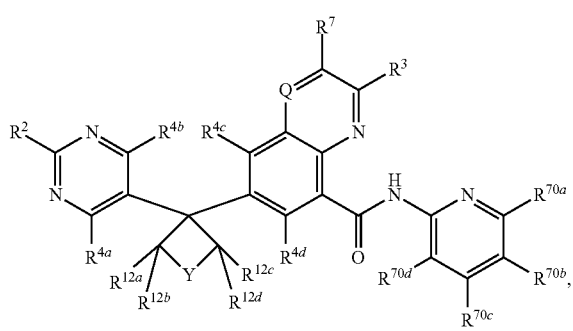
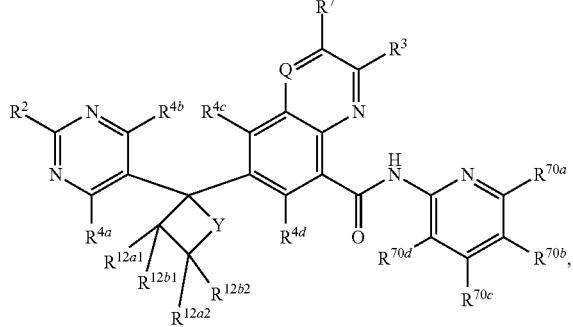
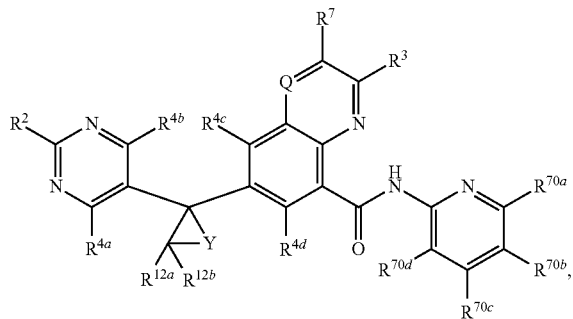
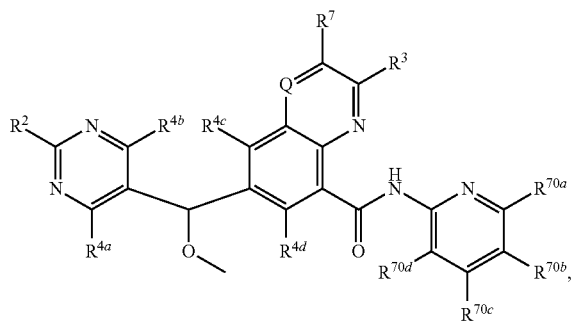
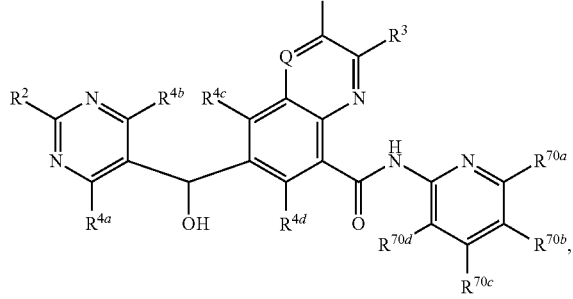
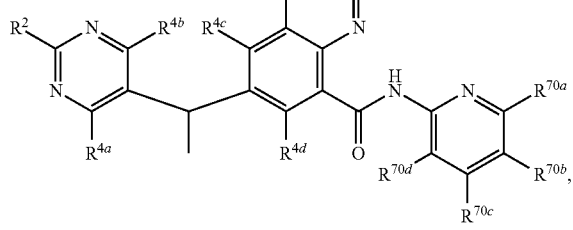
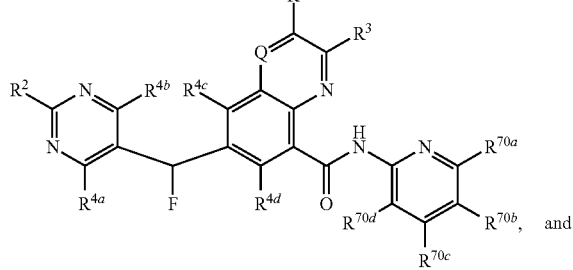
and

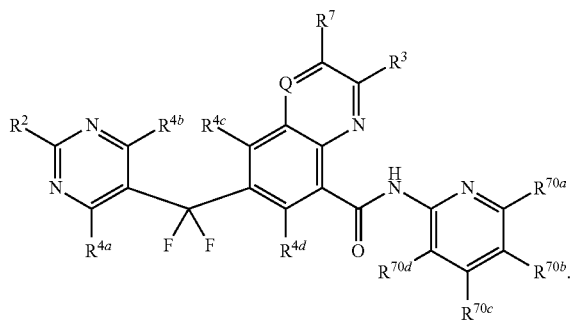
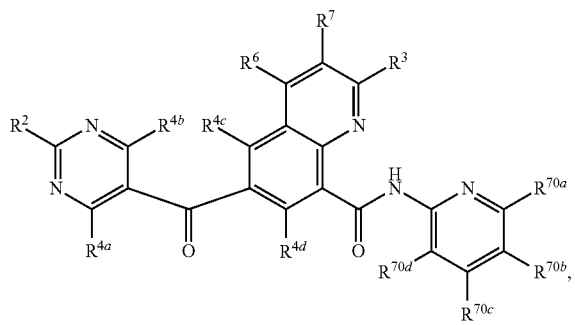
In a further aspect, a compound has a structure selected from:
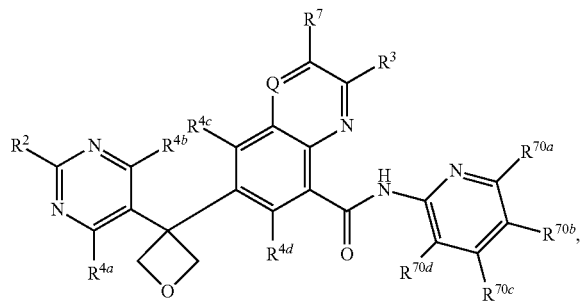
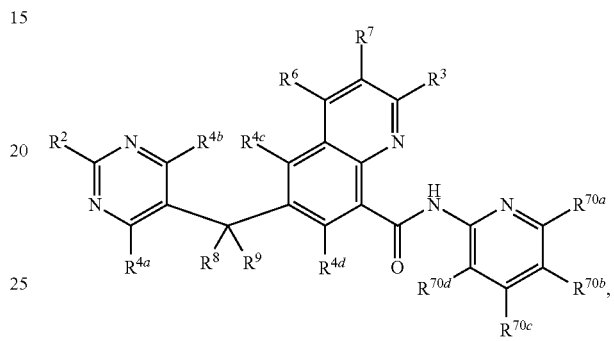
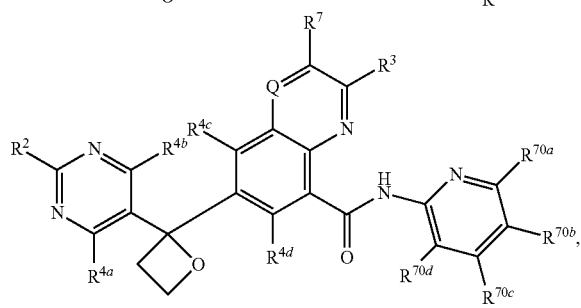
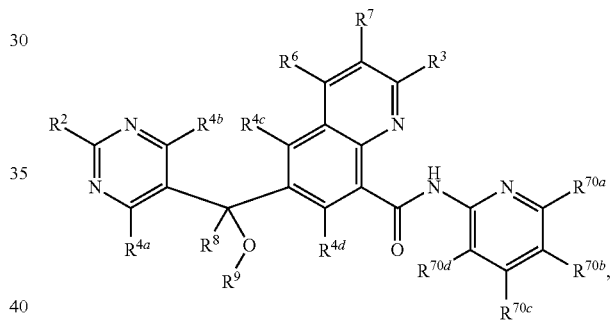
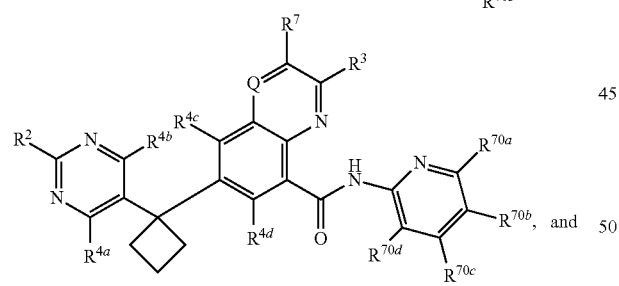
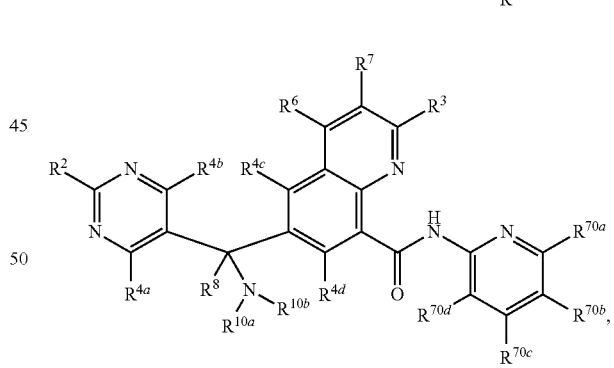
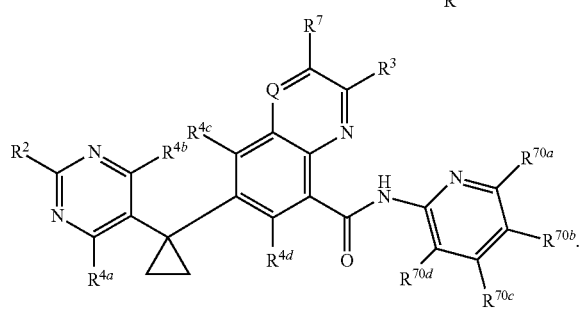
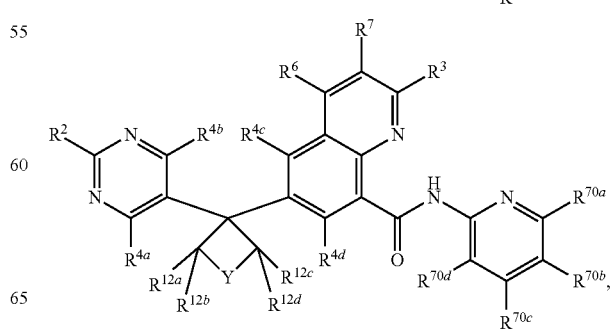
In a further aspect, a compound has a structure selected from:

-continued
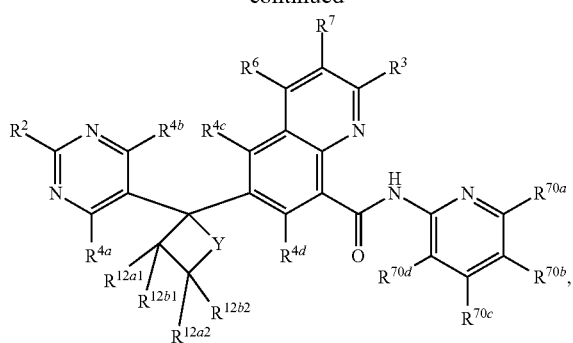
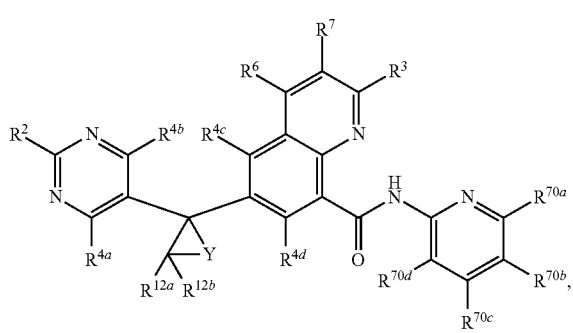
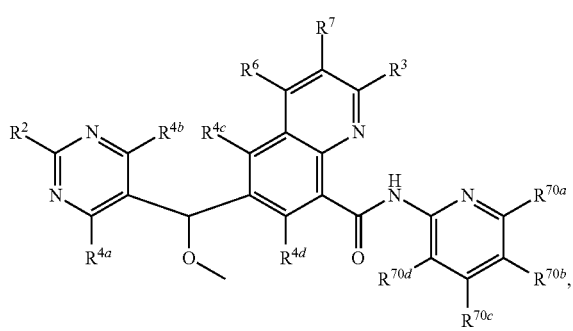
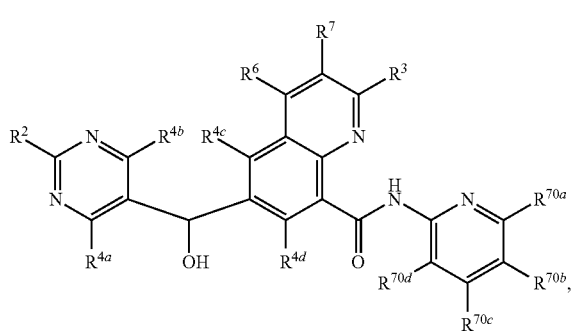
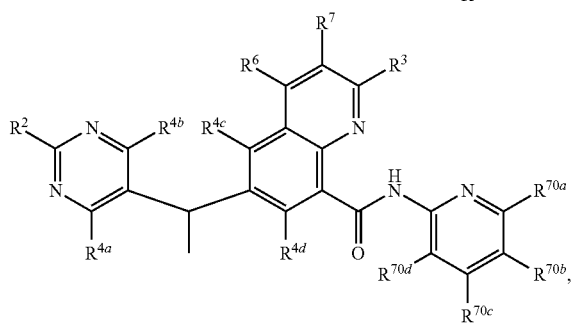
-continued
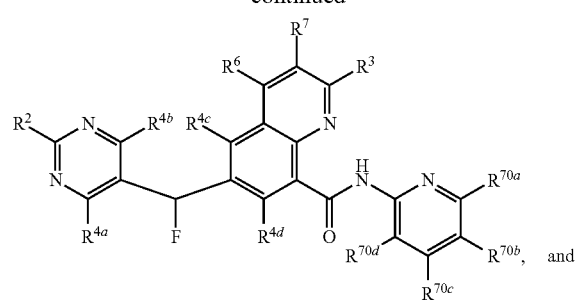
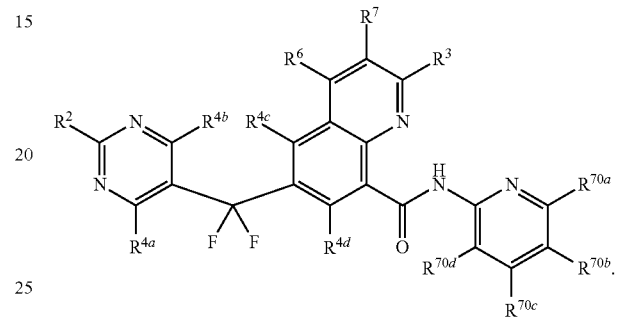
In a further aspect, a compound has a structure selected from:
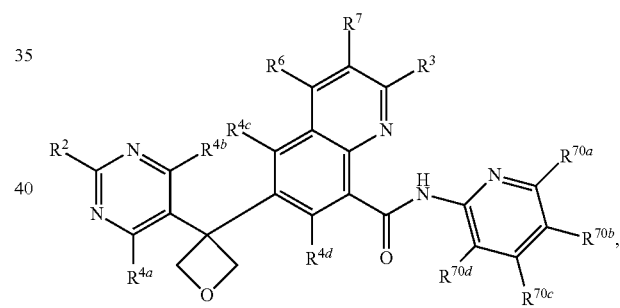
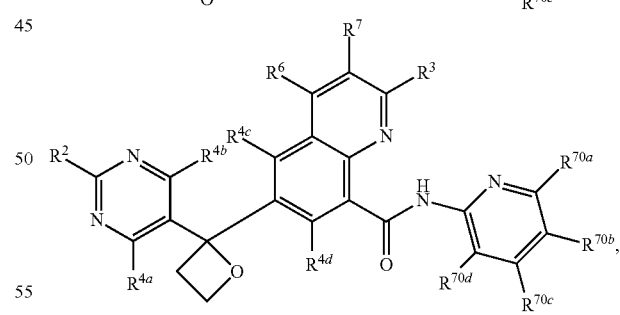
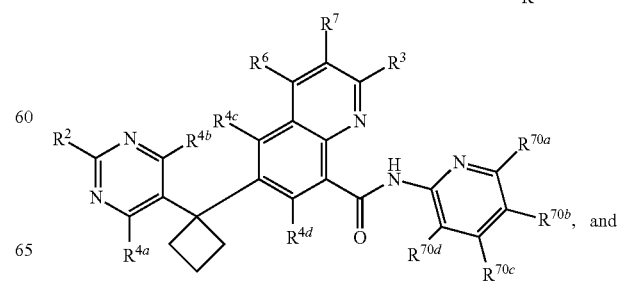

87
-continued
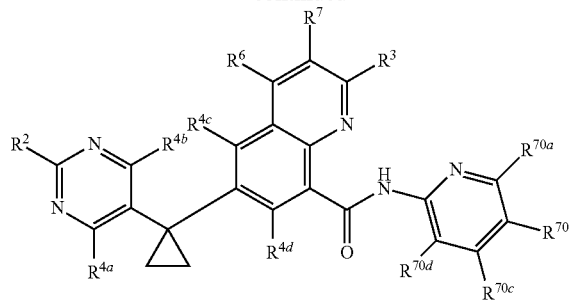
In a further aspect, a compound has a structure selected from:
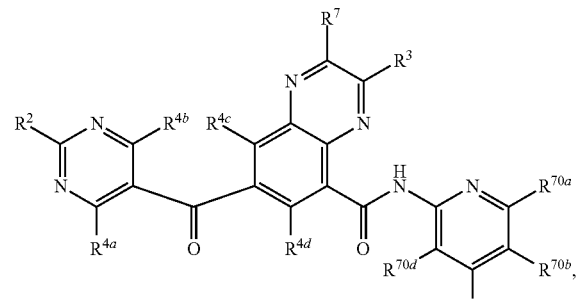
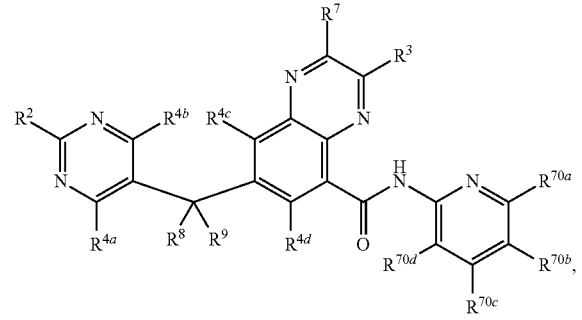
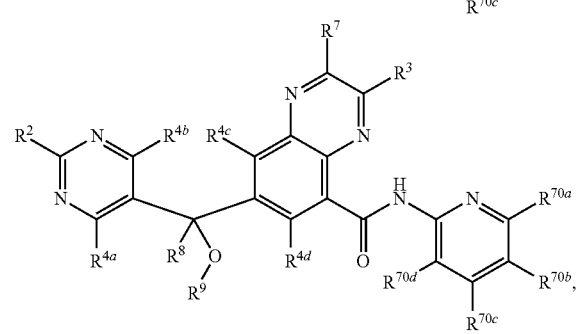
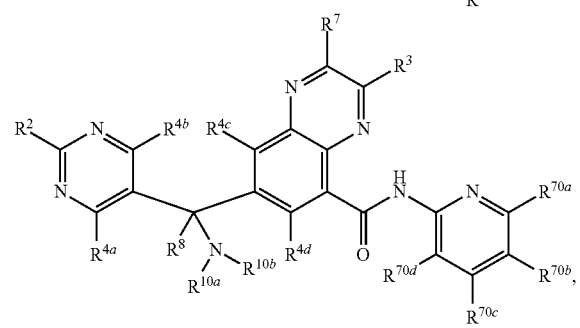
88
-continued
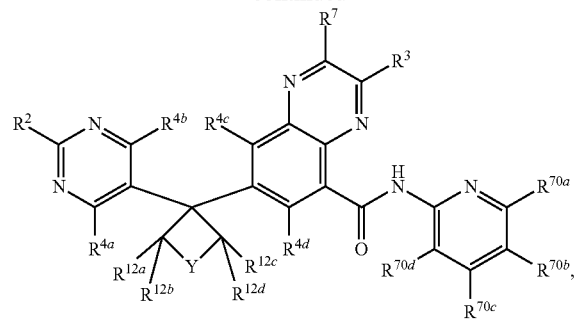
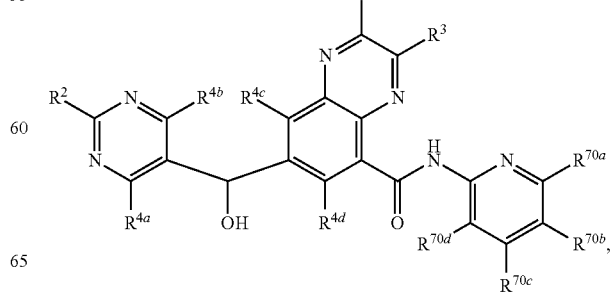

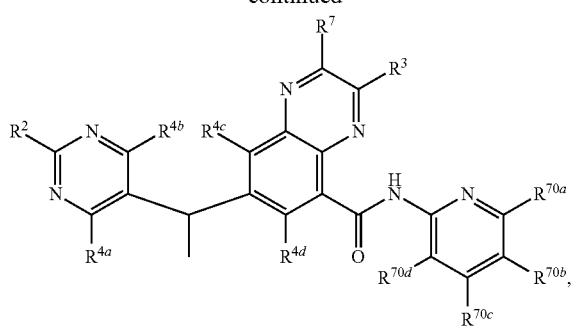
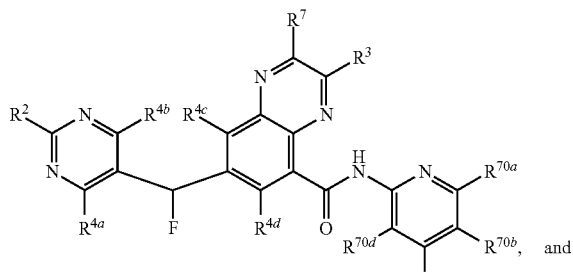
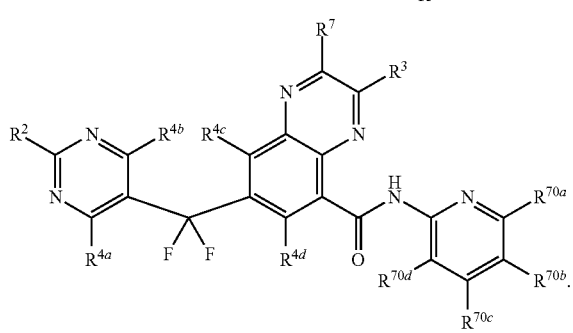
In a further aspect, a compound has a structure selected from:
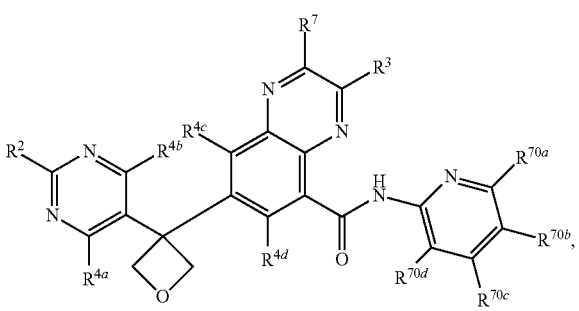
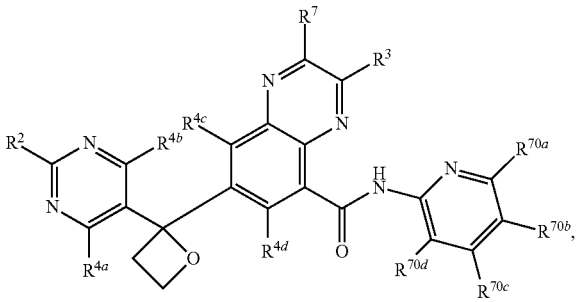
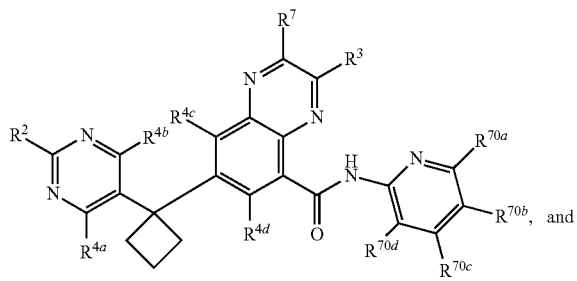
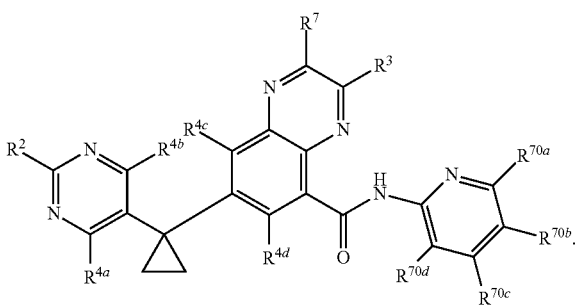
In a further aspect, a compound has a structure represented by a formula:
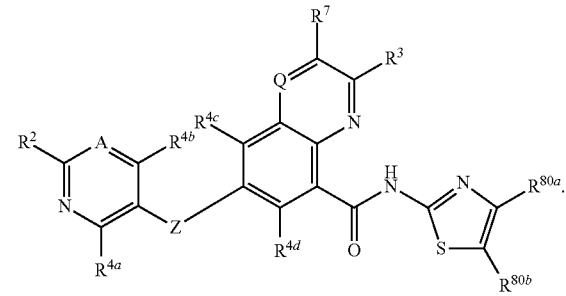
In another aspect, a compound has a structure represented by a formula:
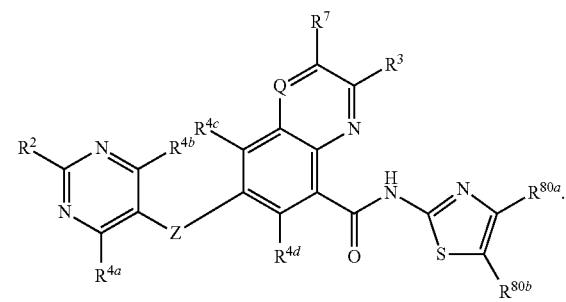
In another aspect, a compound has a structure represented by a formula:

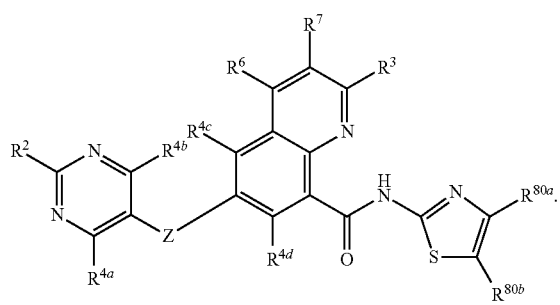
In another aspect, a compound has a structure represented by a formula:
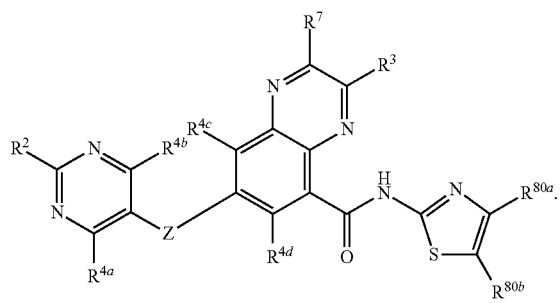
In another aspect, a compound has a structure selected from:
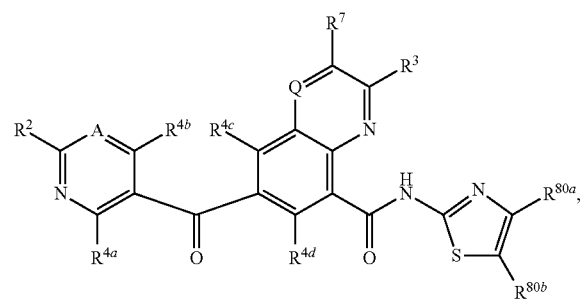
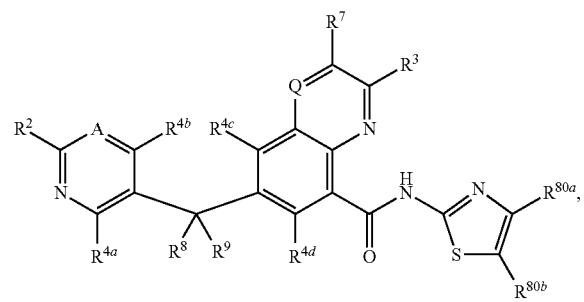
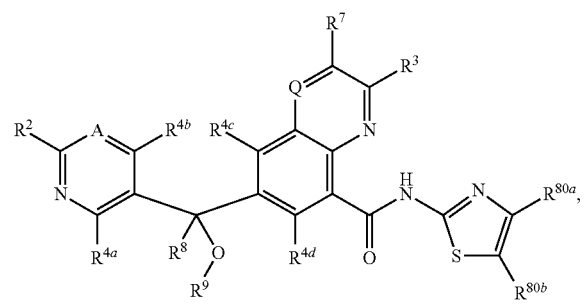
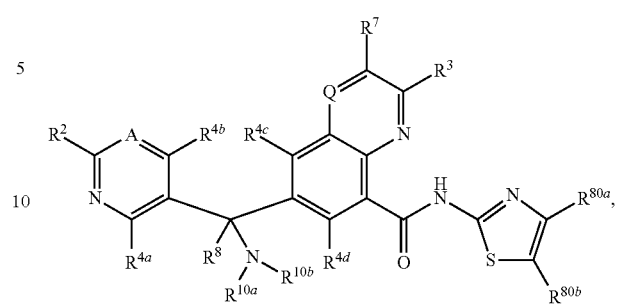
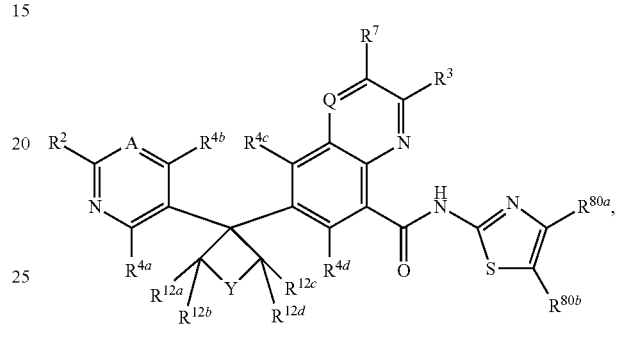
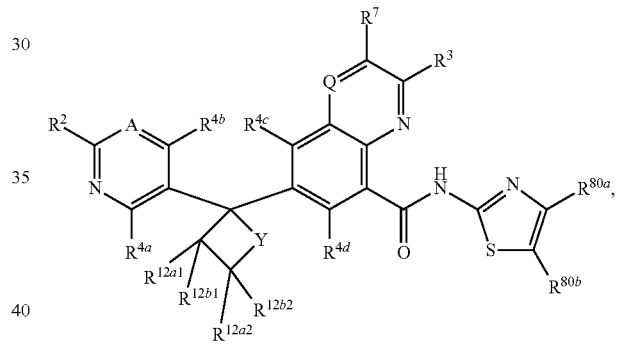
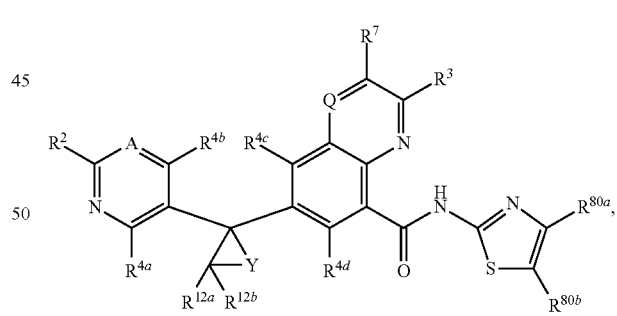
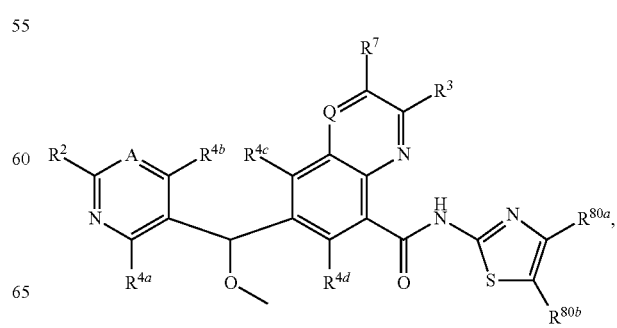

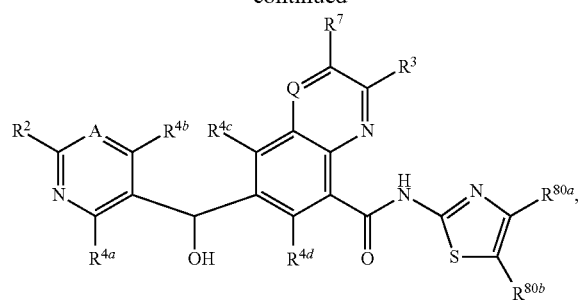
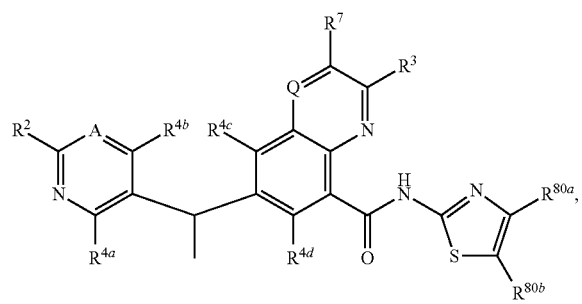
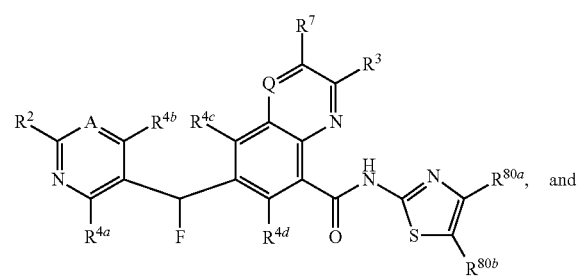
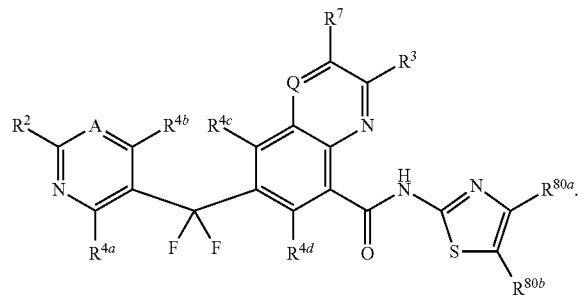
In a further aspect, a compound has a structure selected from:
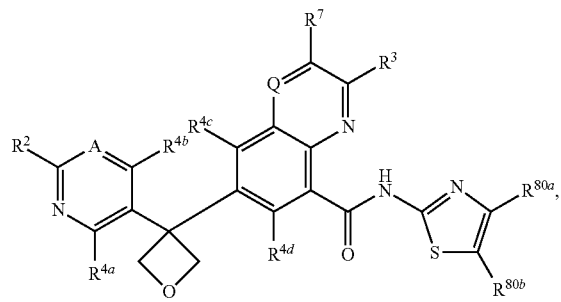
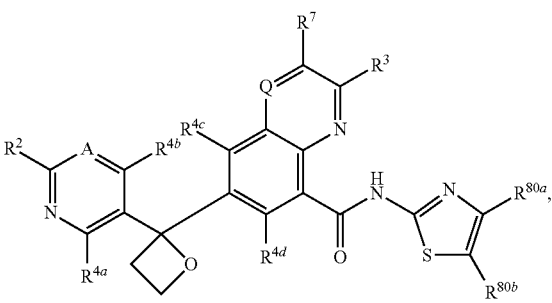
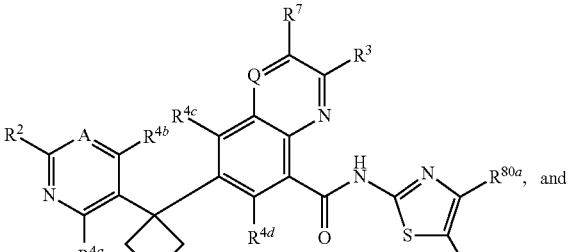
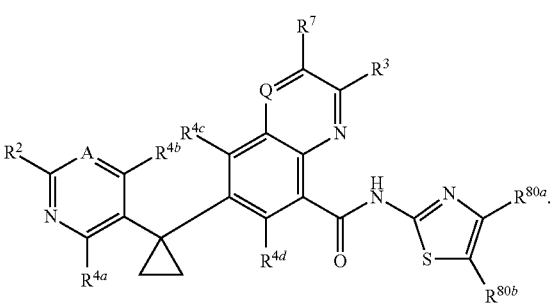
In another aspect, a compound has a structure selected from:
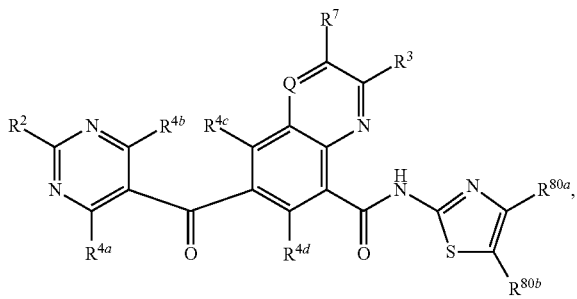
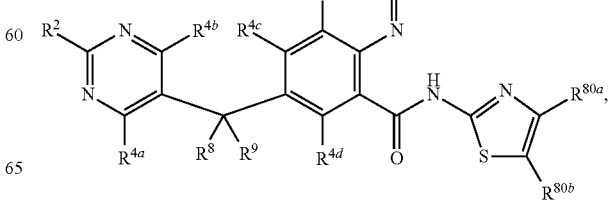

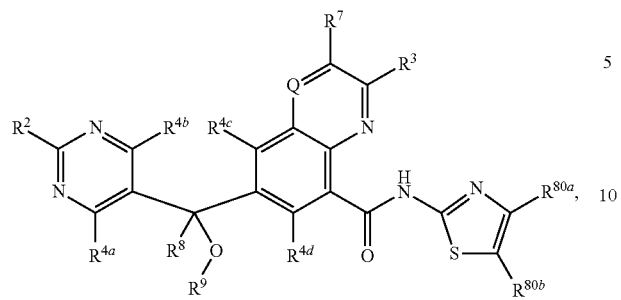
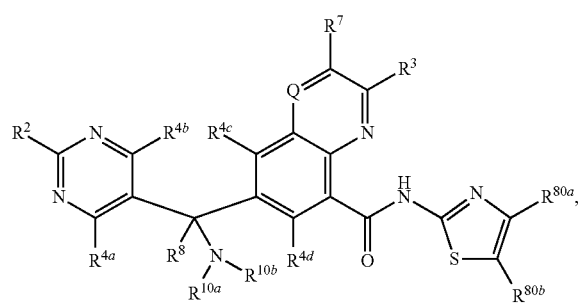
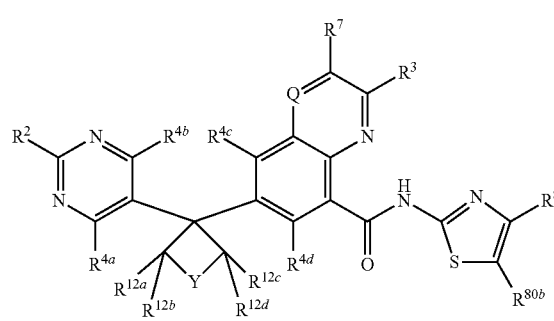
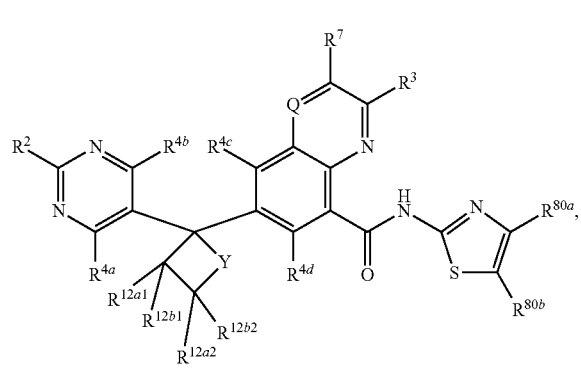
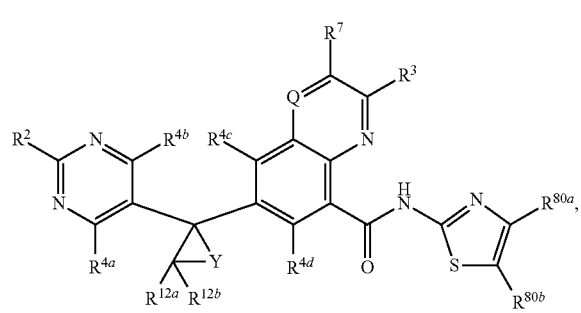
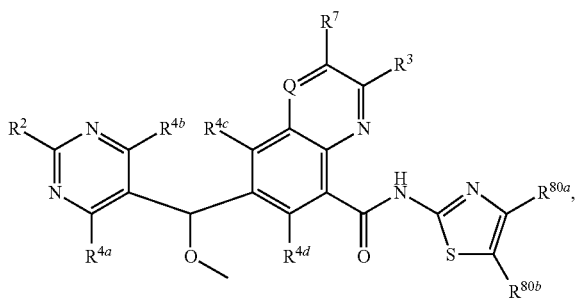
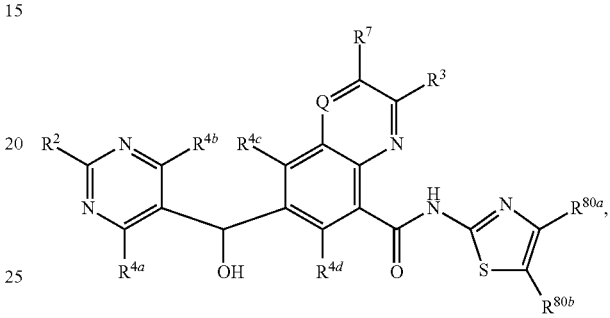
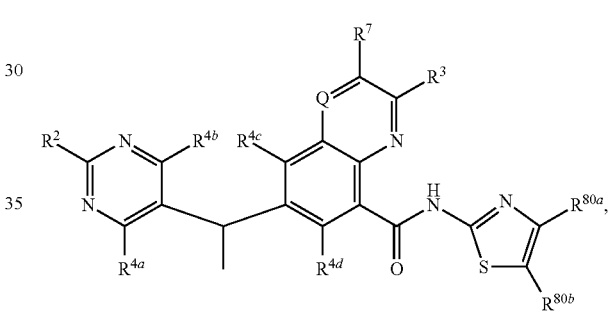
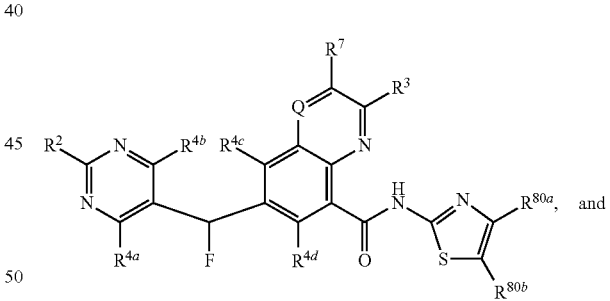
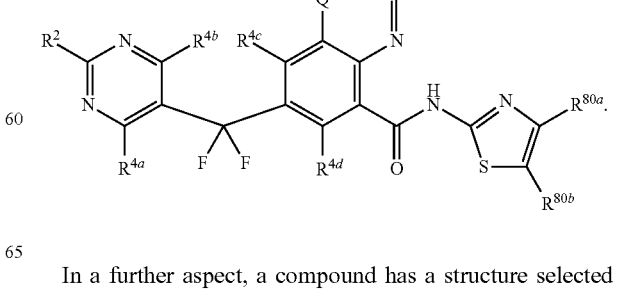
In a further aspect, a compound has a structure selected from:

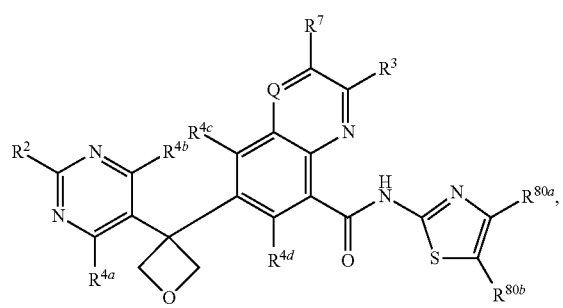
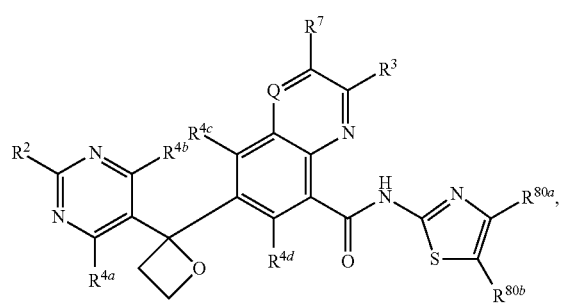
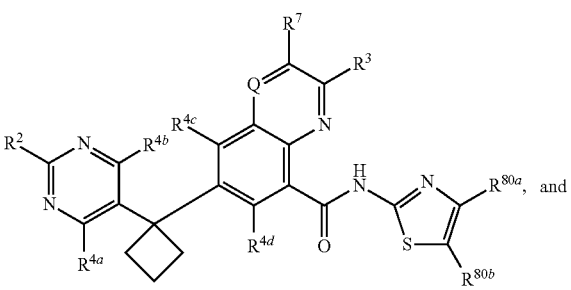
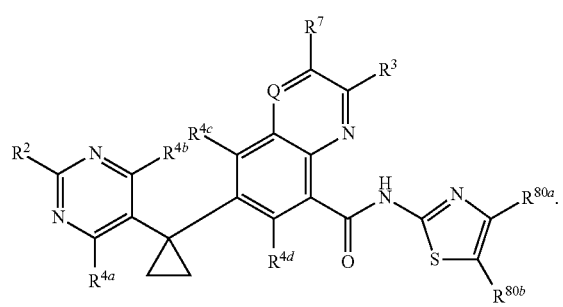
In another aspect, a compound has a structure selected from:
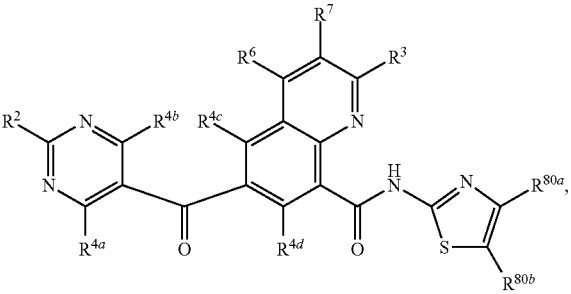
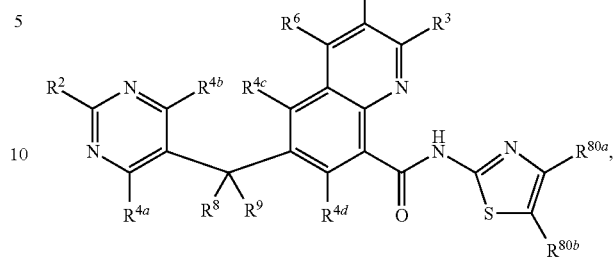
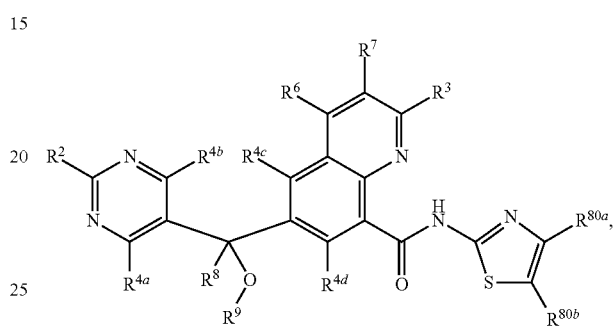

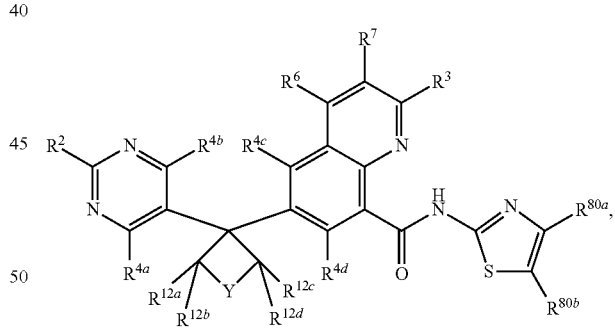
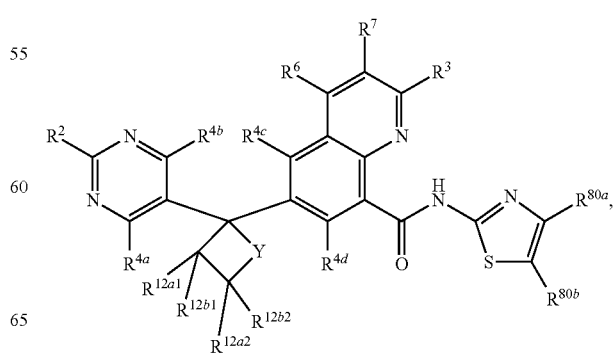

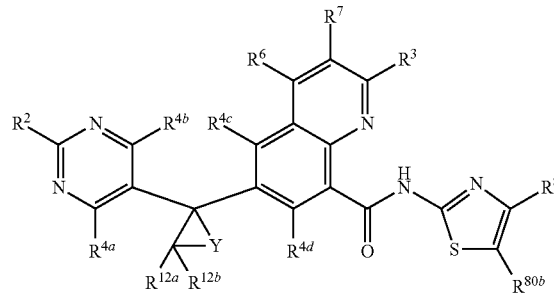
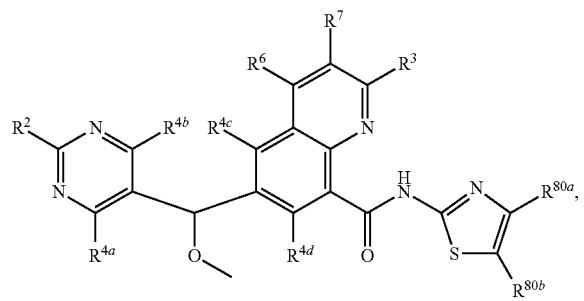
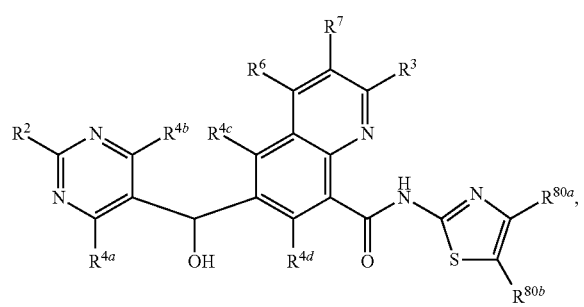
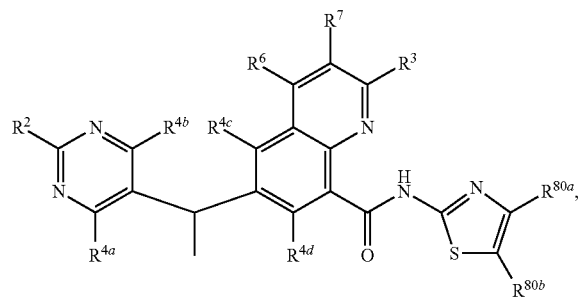
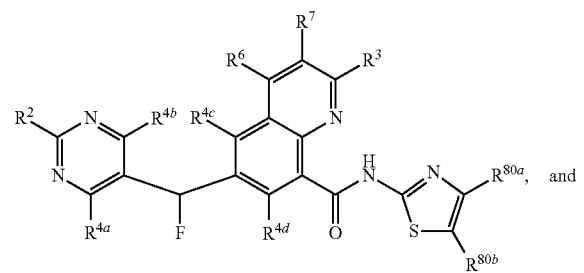
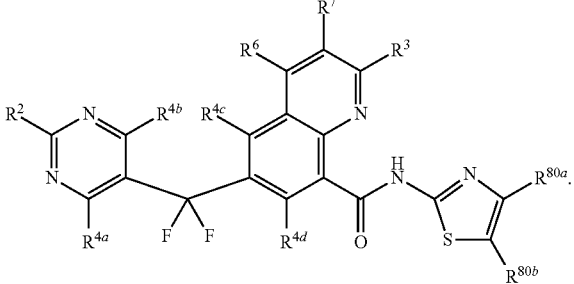
In a further aspect, a compound has a structure selected from:
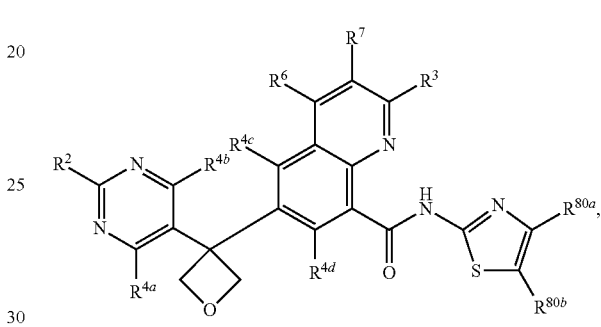
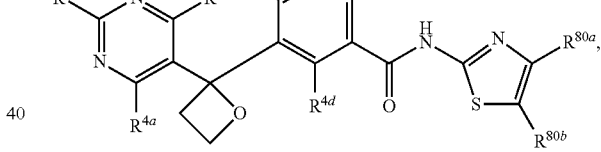
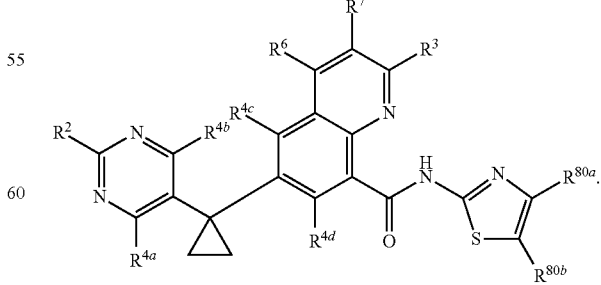
In another aspect, a compound has a structure selected from:

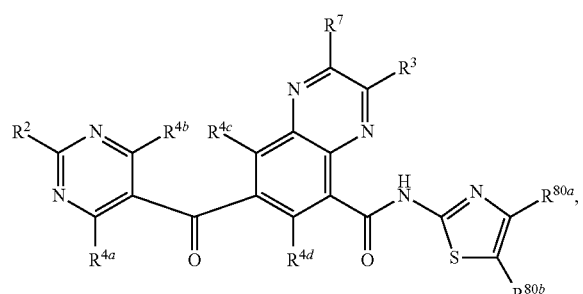
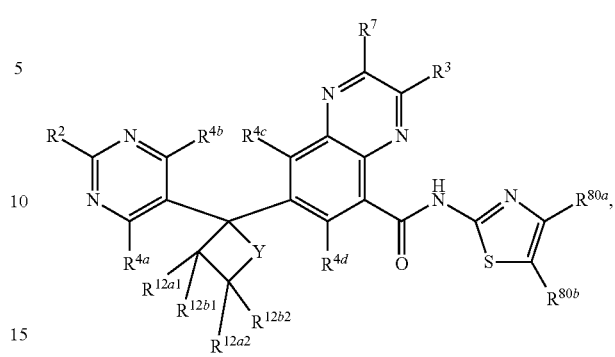
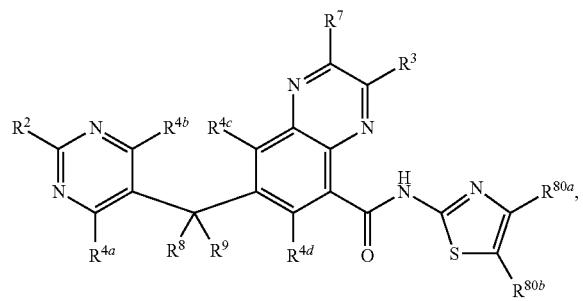
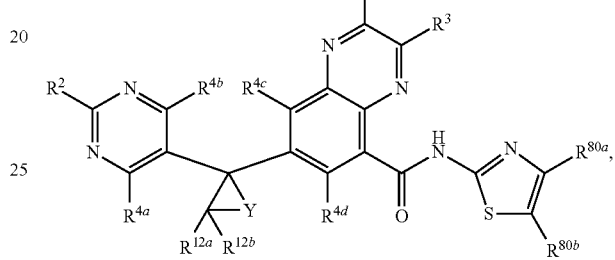
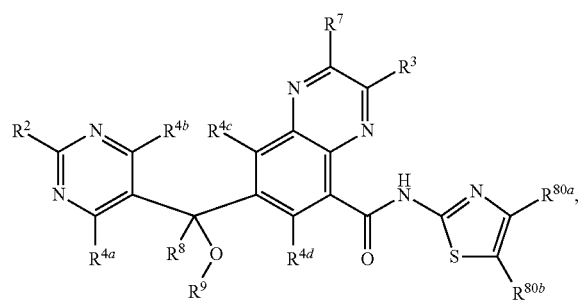
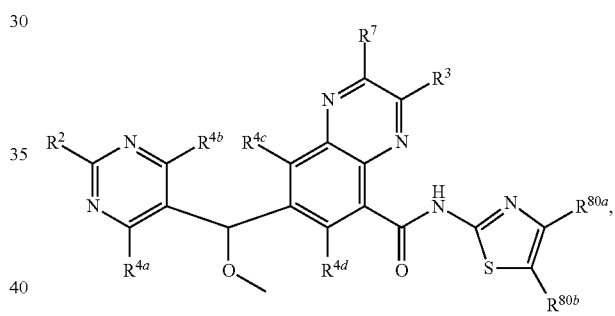
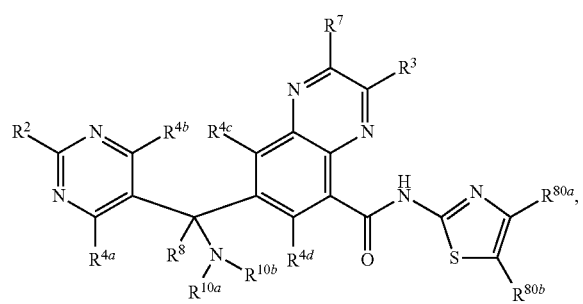
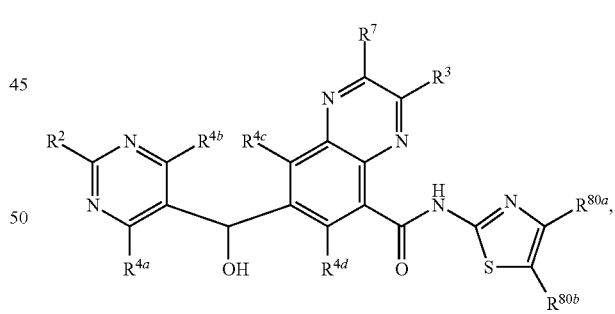
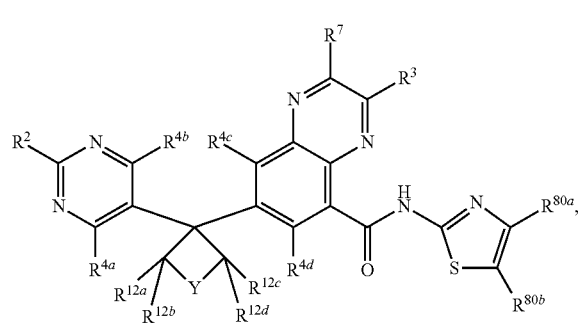
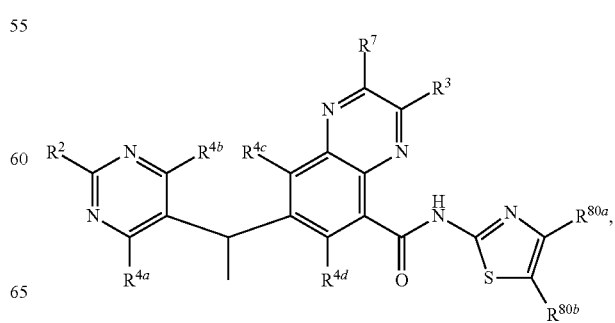

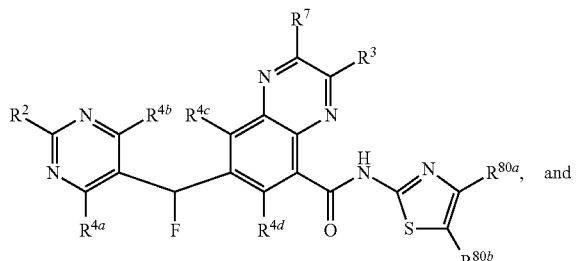
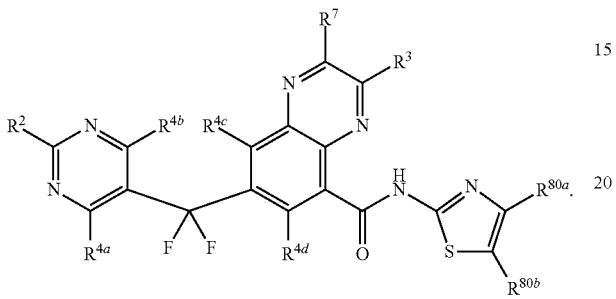
In a further aspect, a compound has a structure selected from:
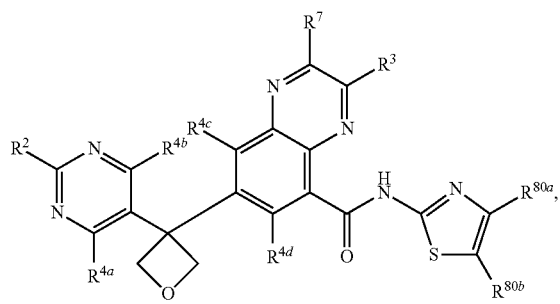
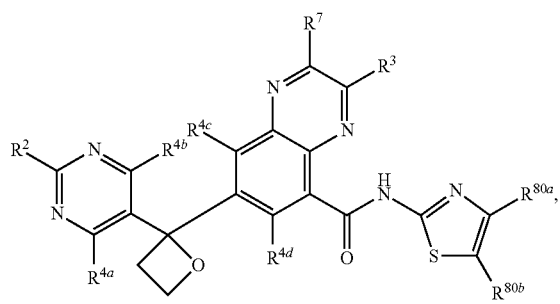
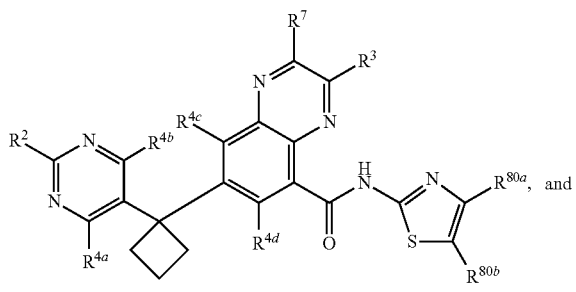
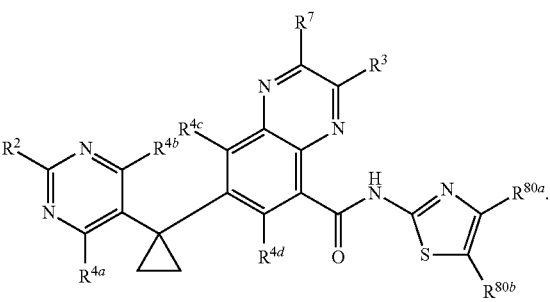
In a further aspect, a compound has a structure selected from:
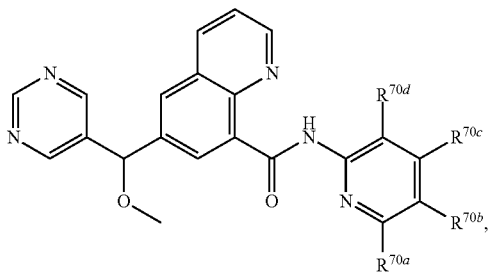
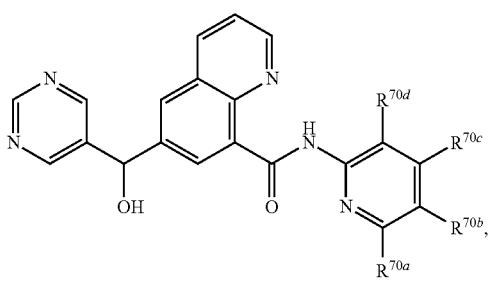
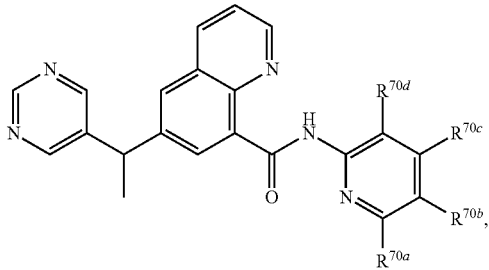
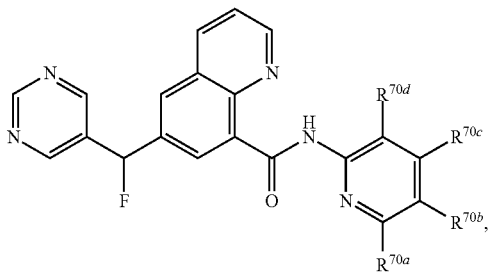

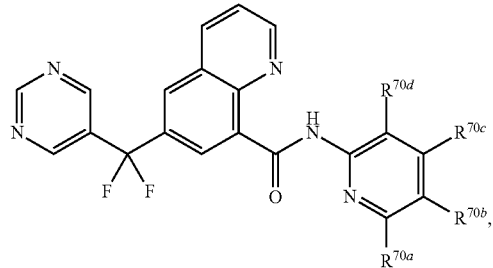
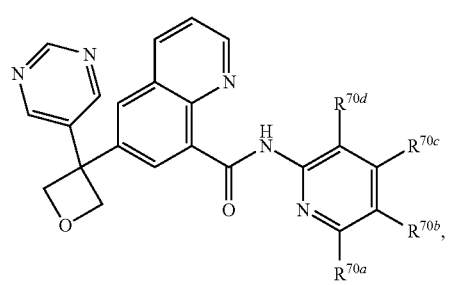
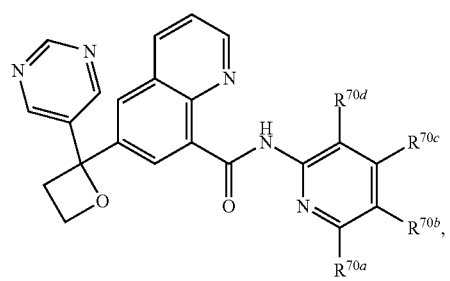
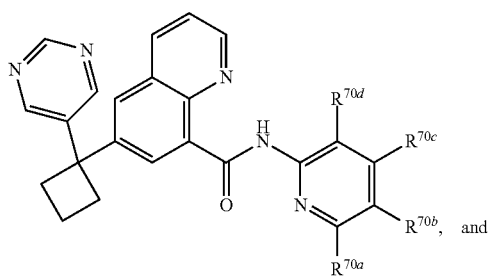
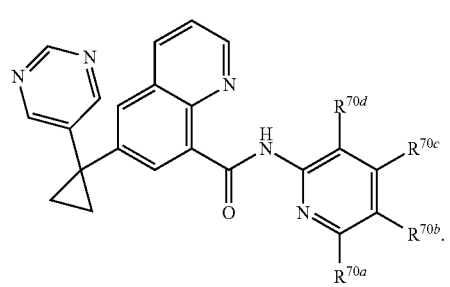
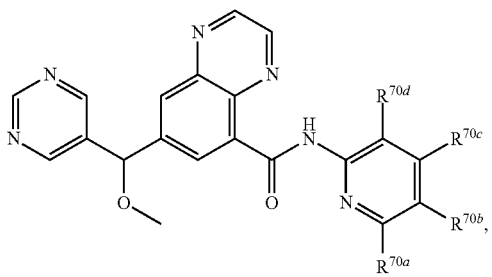
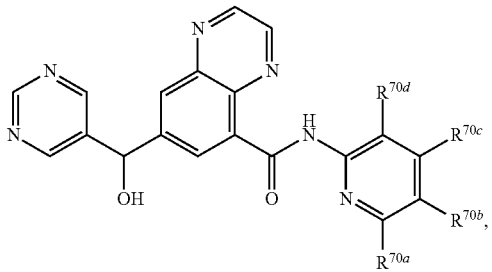

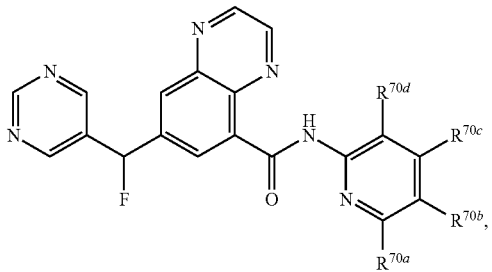
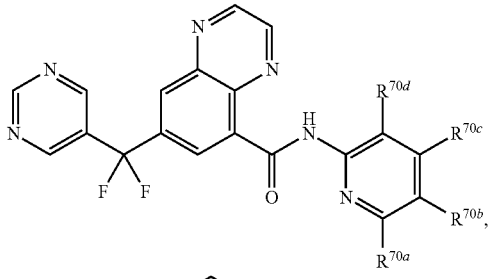
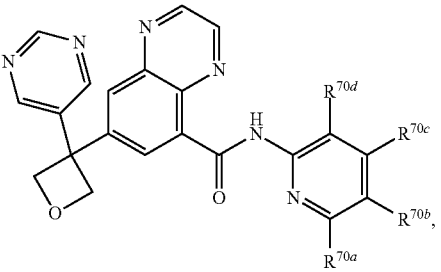
In a further aspect, a compound has a structure selected from:

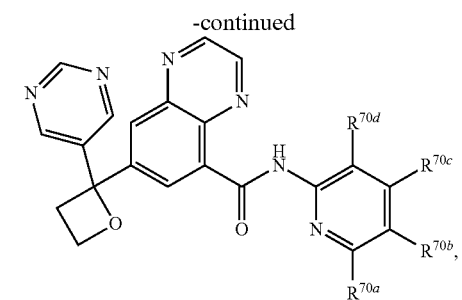
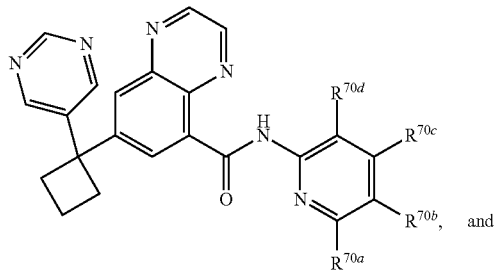 and
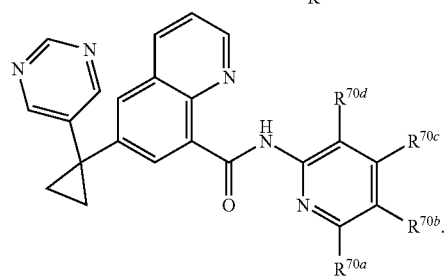
In a further aspect, a compound has a structure selected from:
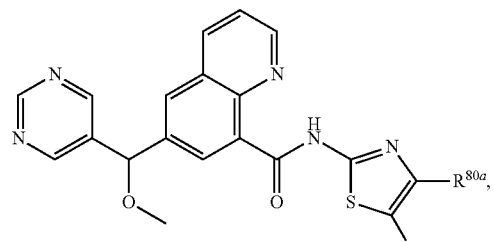
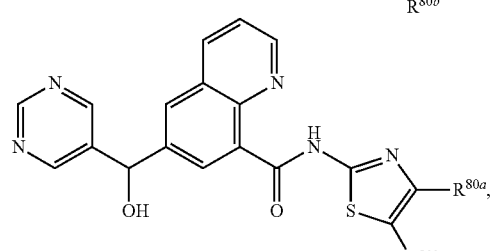
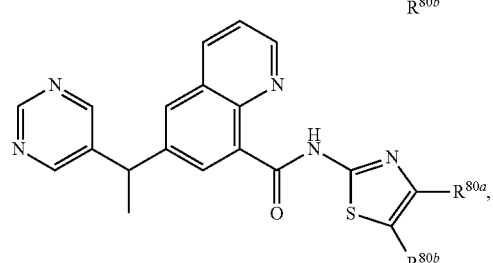
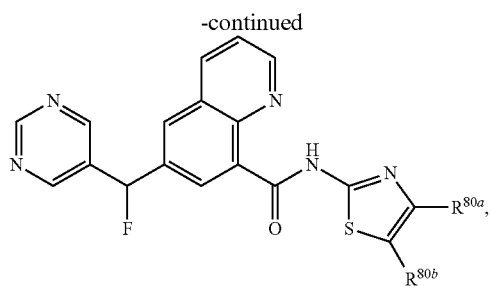
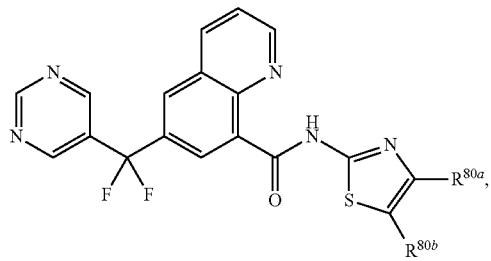
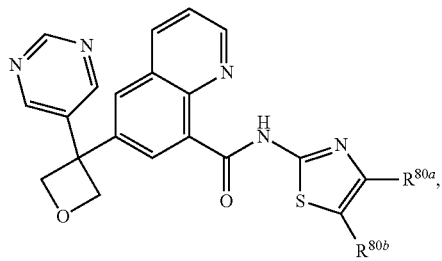
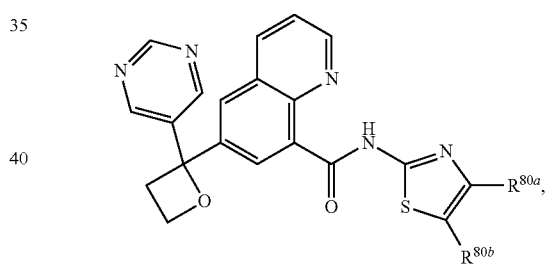 and
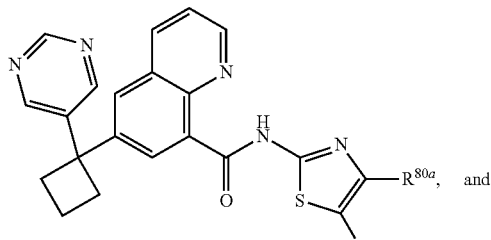
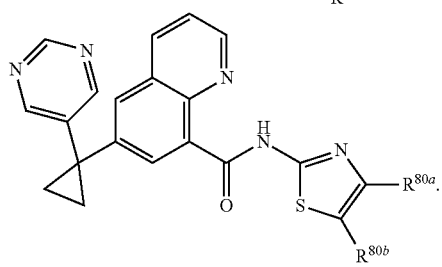
In a further aspect, a compound has a structure selected from:

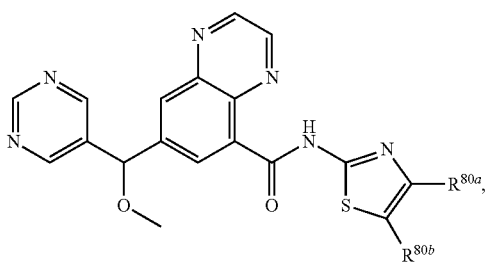
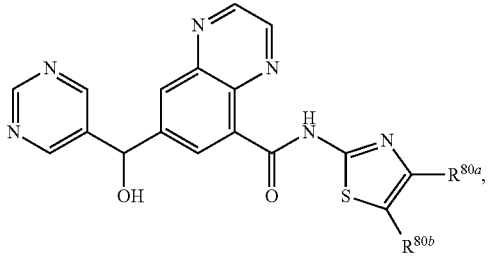
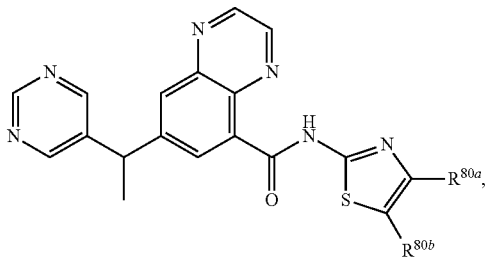
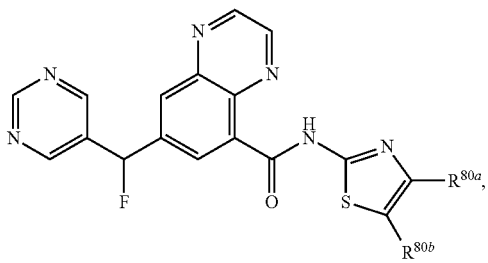
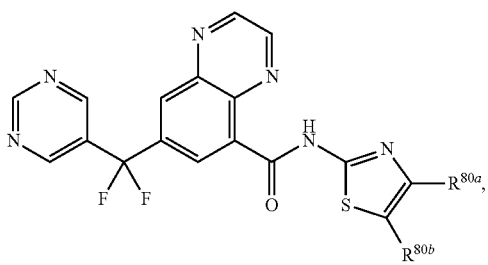
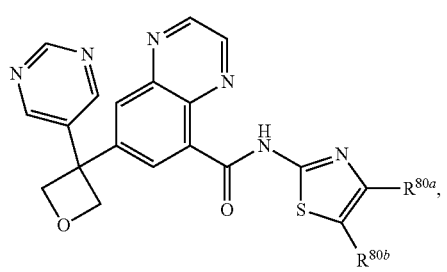
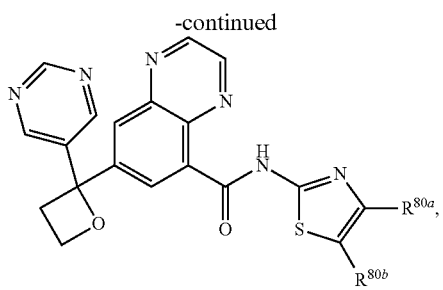
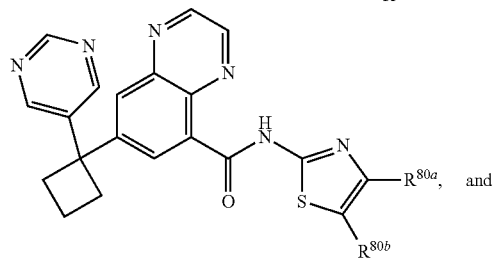
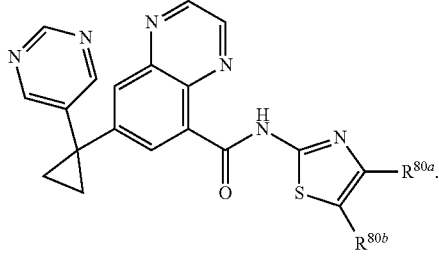

a. A Groups

In one aspect, A is N or $CR^5$. In a further aspect, A is N. In a still further aspect, A is $CR^5$.

b. Q Groups

In one aspect, Q is selected from N and $CR^6$. In a further aspect, Q is N. In a still further aspect, Q is $CR^6$.

c. V Groups

In one aspect, V is selected from N and $CR^7$, provided that Q and V are not simultaneously N. In a further aspect, V is N and Q is $CR^6$. In a still further aspect, V is $CR^7$ and Q is $CR^6$. In a yet further aspect, V is $CR^7$ and wherein Q is N.

d. Y Groups

In one aspect, Y is selected from —$CR^8R^9$—, —O—, —$S(O)_q$—, and —$NR^8$—; wherein q is 0, 1, or 2. In a further aspect, q is 0 or 1. In a still further aspect, q is 0 or 2. In yet a further aspect, q is 1 or 2.

In a further aspect, the sum of m and n is 1 or 2 when Y is —$CR^8R^9$—. In a still further aspect, the sum of m and n is 1 and Y is —$CR^8R^9$—. In yet a further aspect, the sum of m and n is 2 and Y is —$CR^8R^9$—.

In a further aspect, the sum of m and n is 2 when Y is —O—, —$S(O)_q$—, and —$NR^8$—; wherein q is 0, 1, or 2. In a still further aspect, the sum of m and n is 2 and Y is selected from —O—, —S—, and —$NR^8$—. In yet a further aspect, the sum of m and n is 2 and Y is selected from —O—, —(S=O)—, and —$NR^8$—. In an even further aspect, the sum of m and n is 2 and Y is selected from —O—, —$SO_2$—, and —$NR^8$—.

In a further aspect, the sum of m and n is 2 and Y is selected from —O— and —$S(O)_q$—; wherein q is 0, 1, or 2. In a still further aspect, the sum of m and n is 2 and Y is selected from —O— and —S—. In yet a further aspect, the sum of m and n is 2 and Y is selected from —O— and —(S=O)—. In an even further aspect, the sum of m and n is 2 and Y is selected from —O— and —$SO_2$—.

In a further aspect, the sum of m and n is 2 and wherein Y is selected from —S(O)$_q$— and —NR$^8$—; wherein q is 0, 1, or 2. In a still further aspect, the sum of m and n is 2 and wherein Y is selected from —S— and —NR$^8$—. In yet a further aspect, the sum of m and n is 2 and wherein Y is selected from —(S=O)— and —NR$^8$—. In an even further aspect, the sum of m and n is 2 and wherein Y is selected from —SO$_2$— and —NR$^8$—.

In a further aspect, the sum of m and n is 2 and Y is selected from —O— and —NR$^8$—.

e. Z Groups

In one aspect, Z is selected from —CR$^8$(O)$_r$R$^9$—, —CR$^8$NR$^{10a}$R$^{10b}$—, —(C=O)—, and a structure represented by a formula:

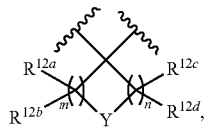

wherein m is an integer selected from 0, 1, and 2; wherein n is an integer selected from 0 and 1; wherein r is 0 or 1. In a further aspect, m is 0 or 1. In a still further aspect, m is 0 or 2. In yet a further aspect, m is 1 or 2. In an even further aspect, n is 0. In a still further aspect, n is 1. In an even further aspect, r is 0. In a still further aspect, r is 1.

In a further aspect, Z is selected from —CR$^8$NR$^{10a}$R$^{10b}$—, —(C=O)—, and a structure represented by a formula:

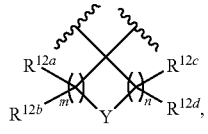

wherein m is an integer selected from 0, 1, and 2; wherein n is an integer selected from 0 and 1. In a further aspect, m is 0 or 1. In a still further aspect, m is 0 or 2. In yet a further aspect, m is 1 or 2. In an even further aspect, n is 0. In a still further aspect, n is 1.

In a still further aspect, Z is selected from —CR$^8$(O)$_r$R$^9$—, —(C=O)—, and a structure represented by a formula:

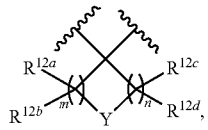

wherein m is an integer selected from 0, 1, and 2; wherein n is an integer selected from 0 and 1; wherein r is 0 or 1. In a further aspect, m is 0 or 1. In a still further aspect, m is 0 or 2. In yet a further aspect, m is 1 or 2. In an even further aspect, n is 0. In a still further aspect, n is 1. In an even further aspect, r is 0. In a still further aspect, r is 1.

In a yet further aspect, Z is selected from —CR$^8$OR$^9$—, —(C=O)—, and a structure represented by a formula:

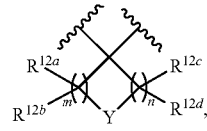

wherein m is an integer selected from 0, 1, and 2; wherein n is an integer selected from 0 and 1. In a further aspect, m is 0 or 1. In a still further aspect, m is 0 or 2. In yet a further aspect, m is 1 or 2. In an even further aspect, n is 0. In a still further aspect, n is 1.

In an even further aspect, Z is selected from —CR$^8$R$^9$—, —(C=O)—, and a structure represented by a formula:

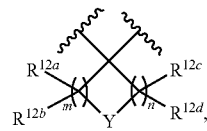

wherein m is an integer selected from 0, 1, and 2; wherein n is an integer selected from 0 and 1. In a further aspect, m is 0 or 1. In a still further aspect, m is 0 or 2. In yet a further aspect, m is 1 or 2. In an even further aspect, n is 0. In a still further aspect, n is 1.

In a further aspect, Z is selected from —CR$^8$(O)$_r$R$^9$—, —CR$^8$NR$^{10a}$R$^{10b}$—, and a structure represented by a formula:

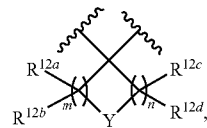

wherein m is an integer selected from 0, 1, and 2; wherein n is an integer selected from 0 and 1; wherein r is 0 or 1. In a further aspect, m is 0 or 1. In a still further aspect, m is 0 or 2. In yet a further aspect, m is 1 or 2. In an even further aspect, n is 0. In a still further aspect, n is 1. In an even further aspect, r is 0. In a still further aspect, r is 1.

In a still further aspect, Z is selected from —CR$^8$OR$^9$—, —CR$^8$NR$^{10a}$R$^{10b}$—, and a structure represented by a formula:

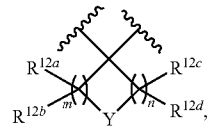

wherein m is an integer selected from 0, 1, and 2; wherein n is an integer selected from 0 and 1. In a further aspect, m is 0 or 1. In a still further aspect, m is 0 or 2. In yet a further aspect, m is 1 or 2. In an even further aspect, n is 0. In a still further aspect, n is 1.

In yet a further aspect, Z is selected from —CR$^8$R$^9$—, —CR$^8$NR$^{10a}$R$^{10b}$—, and a structure represented by a formula:

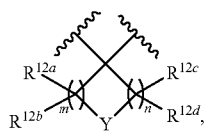

wherein m is an integer selected from 0, 1, and 2; wherein n is an integer selected from 0 and 1. In a further aspect, m is 0 or 1. In a still further aspect, m is 0 or 2. In yet a further aspect, m is 1 or 2. In an even further aspect, n is 0. In a still further aspect, n is 1.

In an even further aspect, Z is selected from —CR$^8$(O)$_r$R$^9$— and a structure represented by a formula:

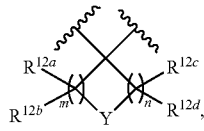

wherein m is an integer selected from 0, 1, and 2; wherein n is an integer selected from 0 and 1; wherein r is 0 or 1. In a further aspect, m is 0 or 1. In a still further aspect, m is 0 or 2. In yet a further aspect, m is 1 or 2. In an even further aspect, n is 0. In a still further aspect, n is 1. In an even further aspect, r is 0. In a still further aspect, r is 1.

In a further aspect, Z is selected from —CR$^8$OR$^9$— and a structure represented by a formula:

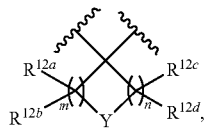

wherein m is an integer selected from 0, 1, and 2; wherein n is an integer selected from 0 and 1. In a further aspect, m is 0 or 1. In a still further aspect, m is 0 or 2. In yet a further aspect, m is 1 or 2. In an even further aspect, n is 0. In a still further aspect, n is 1.

In a still further aspect, Z is selected from —CR$^8$R$^9$— and a structure represented by a formula:

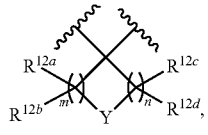

wherein m is an integer selected from 0, 1, and 2; wherein n is an integer selected from 0 and 1. In a further aspect, m is 0 or 1. In a still further aspect, m is 0 or 2. In yet a further aspect, m is 1 or 2. In an even further aspect, n is 0. In a still further aspect, n is 1.

In yet a further aspect, Z is selected from —CR$^8$NR$^{10a}$R$^{10b}$— and a structure represented by a formula:

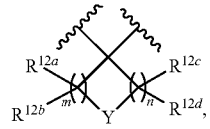

wherein m is an integer selected from 0, 1, and 2; wherein n is an integer selected from 0 and 1. In a further aspect, m is 0 or 1. In a still further aspect, m is 0 or 2. In yet a further aspect, m is 1 or 2. In an even further aspect, n is 0. In a still further aspect, n is 1.

In an even further aspect, Z is selected from —(C=O)— and a structure represented by a formula:

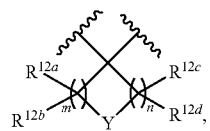

wherein m is an integer selected from 0, 1, and 2; wherein n is an integer selected from 0 and 1. In a further aspect, m is 0 or 1. In a still further aspect, m is 0 or 2. In yet a further aspect, m is 1 or 2. In an even further aspect, n is 0. In a still further aspect, n is 1.

In a still further aspect, Z is a structure represented by a formula:

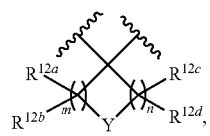

wherein m is an integer selected from 0, 1, and 2; wherein n is an integer selected from 0 and 1. In a further aspect, m is 0 or 1. In a still further aspect, m is 0 or 2. In yet a further aspect, m is 1 or 2. In an even further aspect, n is 0. In a still further aspect, n is 1.

In a further aspect, Z is a structure represented by a formula:

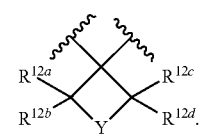

In a further aspect, Z is selected from a structure represented by a formula:

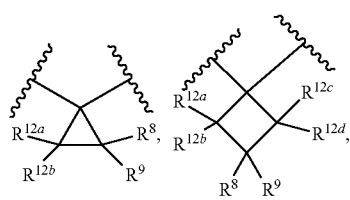

-continued
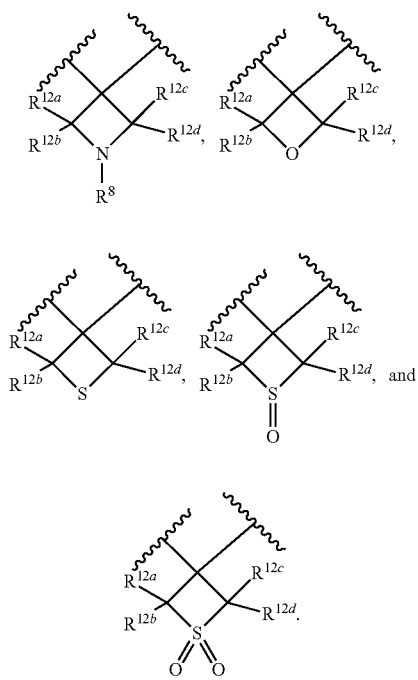
In a still further aspect, Z is selected from a structure represented by a formula:
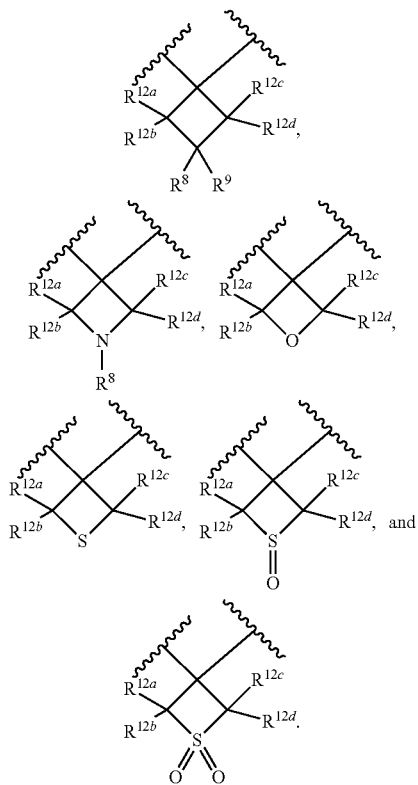
In yet a further aspect, Z is selected from a structure represented by a formula:
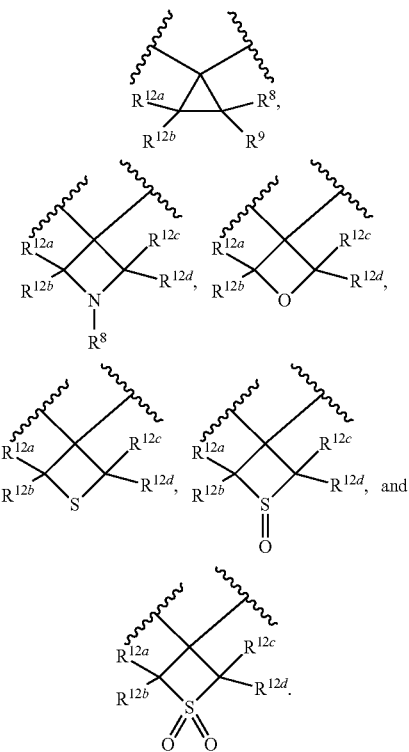
In an even further aspect, Z is selected from a structure represented by a formula:
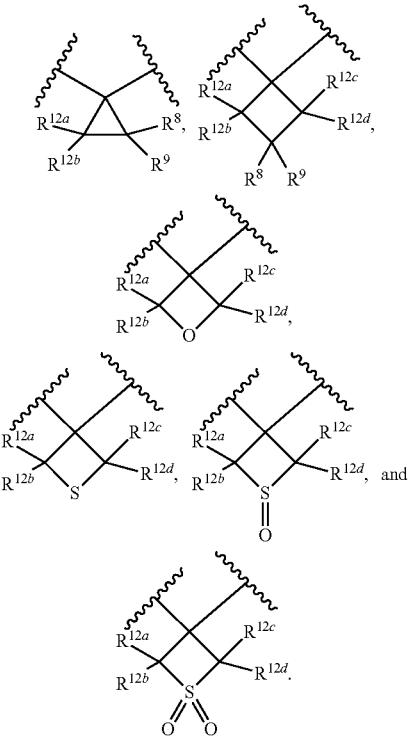
In a further aspect, Z is selected from a structure represented by a formula:

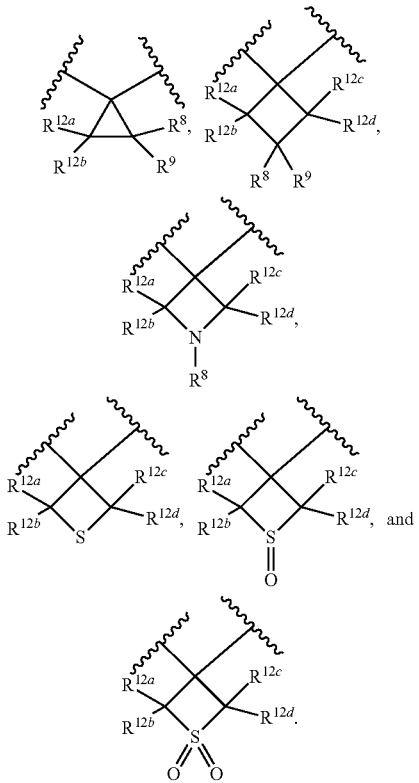
In a still further aspect, Z is selected from a structure represented by a formula:
In yet a further aspect, Z is selected from a structure represented by a formula:
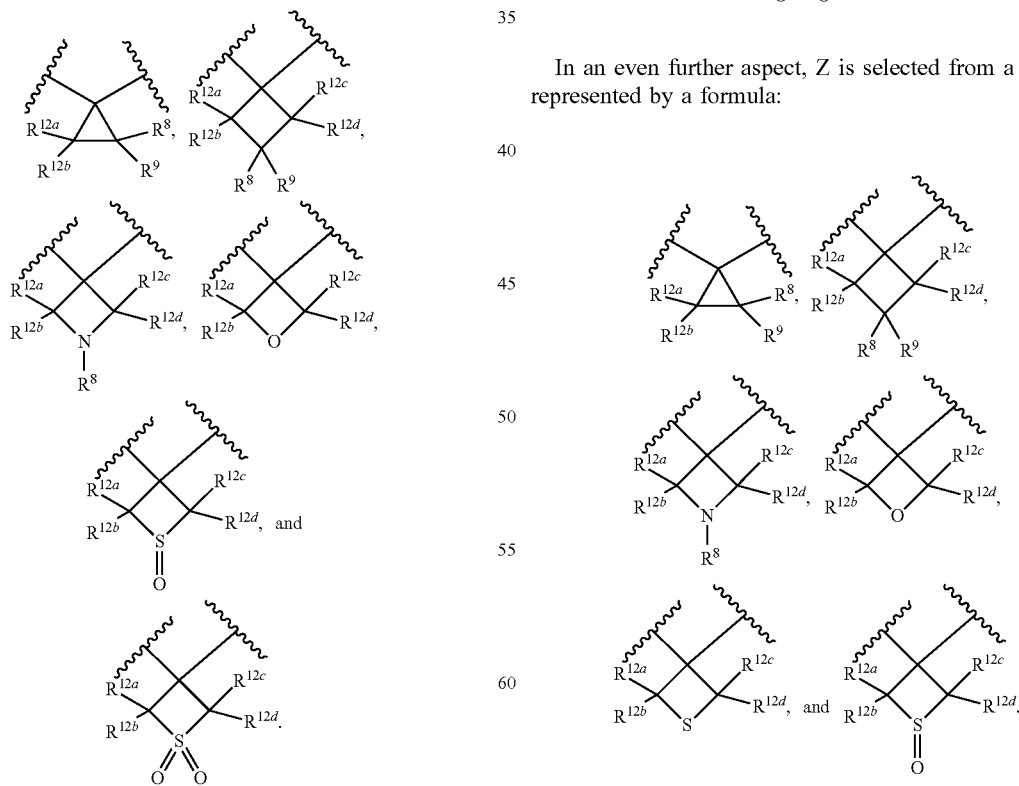
In an even further aspect, Z is selected from a structure represented by a formula:
In a further aspect, Z is selected from a structure represented by a formula:

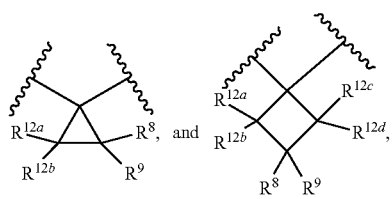

In a still further aspect, Z is selected from a structure represented by a formula:

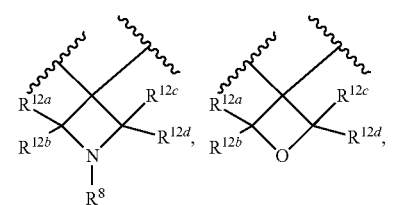

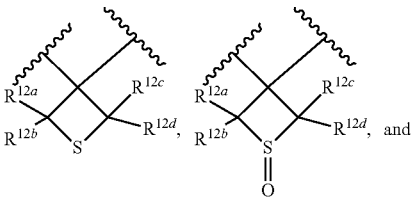

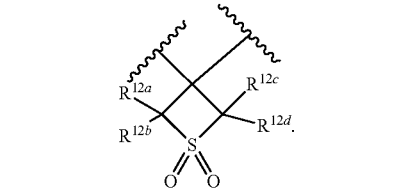

In yet a further aspect, Z is selected from a structure represented by a formula:

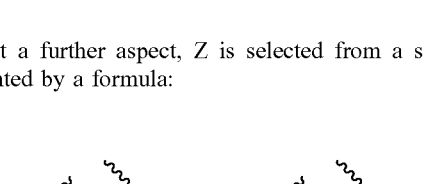

In an even further aspect, Z is selected from a structure represented by a formula:

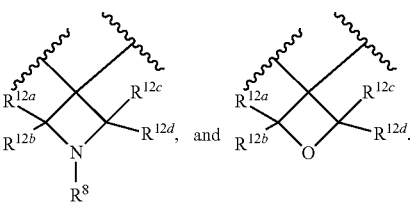

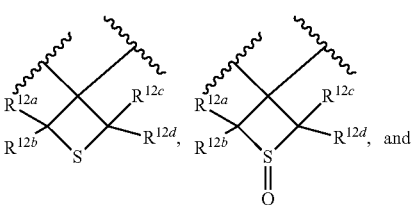

In a further aspect, Z is a structure represented by a formula:

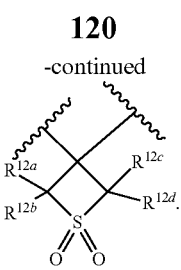

In a still further aspect, Z is a structure represented by a formula:

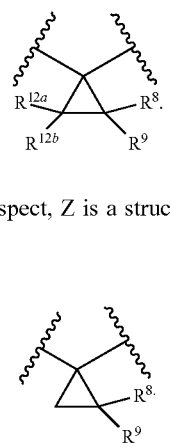

In yet a further aspect, Z is a structure represented by a formula:

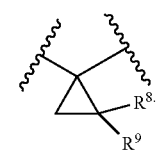

In an even further aspect, Z is a structure represented by a formula:

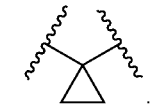

In a further aspect, Z is a structure represented by a formula:

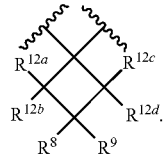

In a still further aspect, Z is a structure represented by a formula:

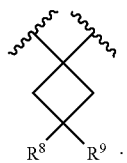

In yet a further aspect, wherein Z is a structure represented by a formula:

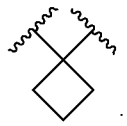 [SMILES: *C1(*)CCC1]

In an even further aspect, Z is a structure represented by a formula:

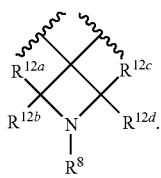

In a further aspect, Z is a structure represented by a formula:

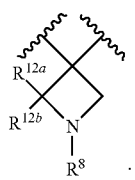

In a still further aspect, Z is a structure represented by a formula:

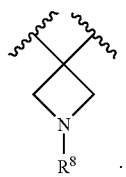

In yet a further aspect, Z is a structure represented by a formula:

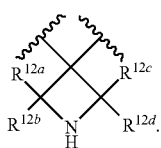

In an even further aspect, Z is a structure represented by a formula:

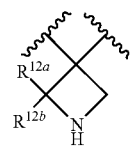

In a further aspect, Z is a structure represented by a formula:

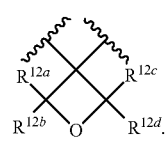

In a still further aspect, Z is a structure represented by a formula:

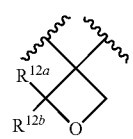

In yet a further aspect, Z is a structure represented by a formula:

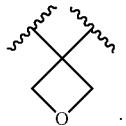 [SMILES: *C1(*)COC1]

In an even further aspect, Z is a structure represented by a formula:

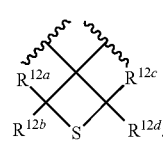

In a further aspect, Z is a structure represented by a formula:

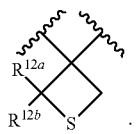

In yet a further aspect, Z is a structure represented by a formula:

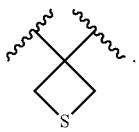 [SMILES: *C1(*)CSC1]

In an even further aspect, Z is a structure represented by a formula:

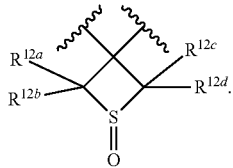

In a further aspect, Z is a structure represented by a formula:

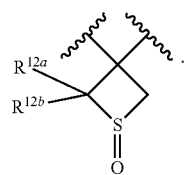

In a still further aspect, Z is a structure represented by a formula:

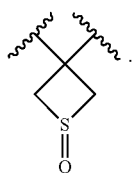 [SMILES: *C1(*)CS(=O)C1]

In yet a further aspect, Z is a structure represented by a formula:

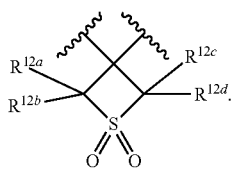

In an even further aspect, Z is a structure represented by a formula:

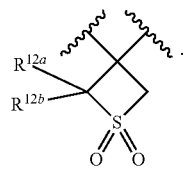

In a further aspect, Z is a structure represented by a formula:

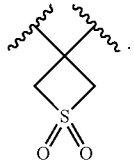 [SMILES: *C1(*)CS(=O)(=O)C1]

In a further aspect, Z is selected from —CR$^8$(O)$_r$R$^9$—, —CR$^8$NR$^{10a}$R$^{10b}$—, and —(C═O)—. In a still further aspect, Z is selected from —CR$^8$(O)$_r$R$^9$— and —CR$^8$NR$^{10a}$R$^{10b}$—. In yet a further aspect, Z is selected from —CR$^8$(O)$_r$R$^9$— and —(C═O)—. In an even further aspect, Z is —CR$^8$(O)$_r$R$^9$—. In a still further aspect, Z is —CR$^8$NR$^{10a}$R$^{10b}$—. In yet a further aspect, Z is —(C═O)—.

In a further aspect, Z is selected from —CR$^8$OR$^9$—, —CR$^8$NR$^{10a}$R$^{10b}$—, and —(C═O)—. In a still further aspect, Z is selected from —CR$^8$OR$^9$— and —(C═O)—. In yet a further aspect, Z is —CR$^8$OR$^9$—.

In a further aspect, Z is selected from —CR$^8$R$^9$—, —CR$^8$NR$^{10a}$R$^{10b}$—, and —(C═O)—. In a still further aspect, Z is selected from —CR$^8$R$^9$— and —(C═O)—. In yet a further aspect, Z is —CR$^8$R$^9$—.

f. R$^1$ Groups

In one aspect, R$^1$ is selected from aryl and heteroaryl, and wherein R$^1$ is substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C═O)R$^{53}$.

In a further aspect, R$^1$ is aryl substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, NR$^{51a}$R$^{51b}$, —SO$_2$R$^{52}$, and —(C═O)R$^{53}$. In a still further aspect, R$^1$ is phenyl substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C═O)R$^{53}$.

In a further aspect, R$^1$ is aryl substituted with 0, 1, or 2 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C═O)R$^{53}$. In a still further aspect, R$^1$ is phenyl substituted with 0, 1, or 2 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C═O)R$^{53}$.

In a further aspect, R$^1$ is aryl substituted with 0 or 1 group selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C═O)R$^{53}$. In a still further aspect, R$^1$ is phenyl substituted with 0 or 1 group selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$.

In a further aspect, R$^1$ is aryl monosubstituted with a group selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$. In a still further aspect, R$^1$ is phenyl monosubstituted with a group selected from halogen, —CN, C1-C3 alkyl, C1-C3 monohaloalkyl, C1-C3 polyhaloalkyl, cyclopropyl, —OR, —NR$^{51a}$R$^{51b}$, —SO$_2$R$^{52}$, and —(C=O)R$^{53}$.

In a further aspect, R$^1$ is unsubstituted aryl. In a still further aspect, R$^1$ is unsubstituted phenyl.

In a further aspect, R$^1$ is heteroaryl substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$. In a still further aspect, R$^1$ is pyridinyl substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$. In a yet further aspect, R$^1$ is pyrimidinyl substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$. In an even further aspect, R$^1$ is pyridinyl substituted with 0, 1, 2, or 3 groups independently selected from —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$Cl, —(C=O)CH$_2$CH$_2$F, —(C=O)CH$_2$CH$_2$Cl, —(C=O)CHF$_2$, —(C=O)CF$_3$, —(C=O)CHCl$_2$, —(C=O)CCl$_3$, —(C=O)NH$_2$, —(C=O)NHCH$_3$, and —(C=O)N(CH$_3$)$_2$.

In a further aspect, R$^1$ is heteroaryl substituted with 0, 1, or 2 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$. In a still further aspect, R$^1$ is pyridinyl substituted with 0, 1, or 2 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$. In yet further aspect, R$^1$ is pyrimidinyl substituted with 0, 1, or 2 groups independently selected from halogen, —CN, C1-C3 alkyl, C1-C3 monohaloalkyl, C1-C3 polyhaloalkyl, cyclopropyl, —OR, —NR$^{51a}$R$^{51b}$, —SO$_2$R$^{52}$, and —(C=O)R$^{53}$. In an even further aspect, R$^1$ is pyridinyl substituted with 0, 1, or 2 groups independently selected from —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$Cl, —(C=O)CH$_2$CH$_2$F, —(C=O)CH$_2$CH$_2$Cl, —(C=O)CHF$_2$, —(C=O)CF$_3$, —(C=O)CHCl$_2$, —(C=O)CCl$_3$, —(C=O)NH$_2$, —(C=O)NHCH$_3$, and —(C=O)N(CH$_3$)$_2$.

In a further aspect, R$^1$ is heteroaryl substituted with 0 or 1 group selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$. In a still further aspect, R$^1$ is pyridinyl substituted with 0 or 1 group selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$. In yet a further aspect, R$^1$ is pyrimidinyl substituted with 0 or 1 group selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$. In an even further aspect, R$^1$ is pyridinyl substituted with 0 or 1 group selected from —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$Cl, —(C=O)CH$_2$CH$_2$F, —(C=O)CH$_2$CH$_2$Cl, —(C=O)CHF$_2$, —(C=O)CF$_3$, —(C=O)CHCl$_2$, —(C=O)CCl$_3$, —(C=O)NH$_2$, —(C=O)NHCH$_3$, and —(C=O)N(CH$_3$)$_2$.

In a further aspect, R$^1$ is heteroaryl monosubstituted with a group selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$. In a still further aspect, R$^1$ is pyridinyl monosubstituted with a group selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$. In yet a further aspect, R$^1$ is pyrimidinyl monosubstituted with a group selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$. In an even further aspect, R$^1$ is pyridinyl monosubstituted a group selected from —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$Cl, —(C=O)CH$_2$CH$_2$F, —(C=O)CH$_2$CH$_2$Cl, —(C=O)CHF$_2$, —(C=O)CF$_3$, —(C=O)CHCl$_2$, —(C=O)CCl$_3$, —(C=O)NH$_2$, —(C=O)NHCH$_3$, and —(C=O)N(CH$_3$)$_2$. In a still further aspect, R$^1$ is pyridinyl monosubstituted a group selected from —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In yet a further aspect, R$^1$ is pyridinyl monosubstituted a group selected from —F, —Cl, methyl, —CF$_3$, —OH, —OCH$_3$, —OCF$_3$, —NH$_2$, —NHCH$_3$, and —N(CH$_3$)$_2$. In an even further aspect, R$^1$ is pyridinyl monosubstituted a group selected from —F, —Cl, methyl, and —CF$_3$. In a still further aspect, R$^1$ is pyridinyl monosubstituted a group selected from —F, —Cl, and methyl. In yet a further aspect, R$^1$ is pyridinyl monosubstituted with —F. In an even further aspect, R$^1$ is pyridinyl monosubstituted with —Cl. In a still further aspect, R$^1$ is pyridinyl monosubstituted with -methyl.

In a further aspect, R$^1$ is unsubstituted heteroaryl. In a still further aspect, R$^1$ is unsubstituted pyridinyl. In yet a further aspect, R$^1$ is unsubstituted pyrimidinyl. In an even further aspect, R$^1$ is pyridinyl monosubstituted a group selected from —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$.

In a further aspect, R$^1$ is pyridinyl substituted with 2 groups independently selected from —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$Cl, —(C=O)CH$_2$CH$_2$F, —(C=O)CH$_2$CH$_2$Cl, —(C=O)CHF$_2$, —(C=O)CF$_3$, —(C=O)CHCl$_2$, —(C=O)CCl$_3$, —(C=O)NH$_2$, —(C=O)NHCH$_3$, and —(C=O)N(CH$_3$)$_2$. In a still further aspect, R$^1$ is pyridinyl substituted with 2 groups independently selected from —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In yet a further aspect, R$^1$ is pyridinyl substituted with 2 groups independently selected from —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, R$^1$ is pyridinyl substituted with 2 groups independently selected from —F, —Cl, methyl, —CF$_3$, —OH, —OCH$_3$, —OCF$_3$, —NH$_2$, —NHCH$_3$, and —N(CH$_3$)$_2$. In a still further aspect, R$^1$ is pyridinyl substituted with 2 groups independently selected from —F, —Cl, methyl, and —CF$_3$. In yet a further aspect, R$^1$ is pyridinyl substituted with 2 groups independently selected from —F, —Cl, and methyl. In an even further aspect, R$^1$ is pyridinyl disubstituted with —F. In a still further aspect, R$^1$ is pyridinyl disubstituted with —Cl. In yet a further aspect, R$^1$ is pyridinyl disubstituted with -methyl.

g. R$^2$ Groups

In one aspect, R$^2$ is selected from hydrogen, C1-C3 alkyl, C1-C3 monohaloalkyl, C1-C3 polyhaloalkyl, and cyclopropyl. In a further aspect, R$^2$ is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, R$^2$ is selected from hydrogen, methyl, —CH$_2$F, —CH$_2$Cl, —CHF$_2$, —CF$_3$, —CHCl$_2$, —CCl$_3$, and cyclopropyl. In yet a further aspect, R$^2$ is selected from hydrogen, methyl, —CH$_2$F, —CHF$_2$, —CF$_3$, and cyclopropyl. In an even further aspect, R$^2$ is selected from hydrogen, methyl, —CF$_3$, and cyclopropyl.

In a further aspect, R$^2$ is selected from hydrogen, C1-C3 monohaloalkyl, C1-C3 polyhaloalkyl, and cyclopropyl. In a still further aspect, R$^2$ is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^2$ is selected from hydrogen, —CH$_2$F, —CH$_2$Cl, —CHF$_2$, —CF$_3$, —CHCl$_2$, —CCl$_3$, and cyclopropyl. In an even further aspect, R$^2$ is selected from hydrogen, —CH$_2$F, —CHF$_2$, —CF$_3$, and cyclopropyl. In a still further aspect, R$^2$ is selected from hydrogen, —CF$_3$ and cyclopropyl.

In a further aspect, R$^2$ is selected from hydrogen, C1-C3 alkyl, and cyclopropyl. In a still further aspect, R$^2$ is selected from hydrogen, methyl, ethyl, and cyclopropyl. In yet a further aspect, R$^2$ is selected from hydrogen, methyl, and cyclopropyl.

In a further aspect, R$^2$ is selected from hydrogen, C1-C3 alkyl, C1-C3 monohaloalkyl, and C1-C3 polyhaloalkyl. In a still further aspect, R$^2$ is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^2$ is selected from hydrogen, methyl, —CH$_2$F, —CH$_2$Cl, —CHF$_2$, —CF$_3$, —CHCl$_2$, and —CCl$_3$. In an even further aspect, R$^2$ is selected from hydrogen, methyl, —CH$_2$F, —CHF$_2$, and —CF$_3$. In a still further aspect, R$^2$ is selected from hydrogen, methyl, and —CF$_3$.

In a further aspect, R$^2$ is selected from hydrogen, C1-C3 monohaloalkyl, and C1-C3 polyhaloalkyl. In a still further aspect, R$^2$ is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^2$ is selected from hydrogen, —CH$_2$F, —CH$_2$Cl, —CHF$_2$, —CF$_3$, —CHCl$_2$, and —CCl$_3$. In an even further aspect, R$^2$ is selected from hydrogen, —CH$_2$F, —CHF$_2$, and —CF$_3$. In a still further aspect, R$^2$ is selected from hydrogen and —CF$_3$.

In a further aspect, R$^2$ is selected from hydrogen and C1-C3 alkyl. In a still further aspect, R$^2$ is selected from hydrogen, methyl, and ethyl. In yet a further aspect, R$^2$ is selected from hydrogen and methyl. In an even further aspect, R$^2$ is hydrogen.

h. R$^3$ Groups

In one aspect, R$^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$. In a further aspect, R$^3$ is selected from hydrogen, —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$Cl, —(C=O)CH$_2$CH$_2$F, —(C=O)CH$_2$CH$_2$Cl, —(C=O)CHF$_2$, —(C=O)CF$_3$, —(C=O)CHCl$_2$, —(C=O)CCl$_3$, —(C=O)NH$_2$, —(C=O)NHCH$_3$, and —(C=O)N(CH$_3$)$_2$. In a still further aspect, R$^3$ is selected from hydrogen, —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In yet a further aspect, R$^3$ is selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In an even further aspect, R$^3$ is selected from hydrogen, —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$.

In a further aspect, R$^3$ is selected from halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$. In a still further aspect, R$^3$ is selected from —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$Cl, —(C=O)CH$_2$CH$_2$F, —(C=O)CH$_2$CH$_2$Cl, —(C=O)CHF$_2$, —(C=O)CF$_3$, —(C=O)CHCl$_2$, —(C=O)CCl$_3$, —(C=O)NH$_2$, —(C=O)NHCH$_3$, and —(C=O)N(CH$_3$)$_2$. In yet a further aspect, R$^3$ is selected from —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In an even further aspect, R$^3$ is selected from —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In a still further aspect, R$^3$ is selected from —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$.

In a further aspect, R$^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, and —SO$_2$R$^{62}$. In a still further aspect, R$^3$ is selected from hydrogen, —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In yet a further aspect, R$^3$ is selected from hydrogen, —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, R$^3$ is selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, R$^3$ is selected from hydrogen, —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, R$^3$ is selected from hydrogen, halogen, C1-C3 alkyl, C1-C3 monohaloalkyl, C1-C3 polyhaloalkyl, —OR$^{60}$, —NR$^{61a}$R$^{61b}$, and —SO$_2$R$^{62}$. In a still further aspect, R$^3$ is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In yet a further aspect, R$^3$ is selected from hydrogen, —F, —Cl, methyl, —CH$_2$F, —CH$_2$Cl, —CHF$_2$, —CF$_3$, —CHCl$_2$, —CCl$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, R$^3$ is selected from hydrogen, —F, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, R$^3$ is selected from hydrogen, —F, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In yet a further aspect, R$^3$ is selected from hydrogen, —F, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, R$^3$ is selected from hydrogen, halogen, —CN, C1-C3 alkyl, C1-C3 monohaloalkyl, C1-C3 polyhaloalkyl, cyclopropyl, —OR$^{60}$, and —NR$^{61a}$R$^{61b}$. In a still further aspect, R$^3$ is selected from hydrogen, —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, and —N(CH$_3$)$_2$. In yet a further aspect, R$^3$ is selected from hydrogen, —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, and —N(CH$_3$)$_2$. In an even further aspect, R$^3$ is selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In a still further aspect, R$^3$ is selected from hydrogen, —F, —CN, methyl, —CF$_3$, cyclopropyl, —OH, —OCH$_3$, —OCF$_3$, —NH$_2$, —NHCH$_3$, and —N(CH$_3$)$_2$.

In a further aspect, R$^3$ is selected from hydrogen, halogen, C1-C3 alkyl, C1-C3 monohaloalkyl, C1-C3 polyhaloalkyl, cyclopropyl, —OR$^{60}$, and —NR$^{61a}$R$^{61b}$. In a still further aspect, R$^3$ is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, and —N(CH$_3$)$_2$. In yet a further aspect, R$^3$ is selected from hydrogen, —F, —Cl, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, and —N(CH$_3$)$_2$. In an even further aspect, R$^3$ is selected from hydrogen, —F, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In a still further aspect, R$^3$ is selected from hydrogen, —F, methyl, —CF$_3$, cyclopropyl, —OH, —OCH$_3$, —OCF$_3$, —NH$_2$, —NHCH$_3$, and —N(CH$_3$)$_2$.

In a further aspect, R$^3$ is selected from hydrogen, halogen, C1-C3 alkyl, C1-C3 monohaloalkyl, C1-C3 polyhaloalkyl, —OR$^{60}$, and —NR$^{61a}$R$^{61b}$. In a still further aspect, R$^3$ is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OH, —OCH$_3$, —OCH$_2$F, —OCHF$_2$, —OCF$_3$, —O-cyclopropyl, —NH$_2$, —NHCH$_3$, and —N(CH$_3$)$_2$. In yet a further aspect, R$^3$ is selected from hydrogen, —F, —Cl, methyl, —CH$_2$F, —CH$_2$Cl, —CHF$_2$, —CF$_3$, —CHCl$_2$, —CCl$_3$, —OH, —OCH$_3$, —OCF$_3$, —NH$_2$, —NHCH$_3$, and —N(CH$_3$)$_2$. In an even further aspect, R$^3$ is selected from hydrogen, —F, methyl, —CH$_2$F, —CHF$_2$, —CF$_3$, —OH, —OCH$_3$, —OCF$_3$, —NH$_2$, —NHCH$_3$, and —N(CH$_3$)$_2$. In a still further aspect, R$^3$ is selected from hydrogen, —F, —Cl, methyl, —CF$_3$, —OH, —OCH$_3$, —OCF$_3$, —NH$_2$, —NHCH$_3$, and —N(CH$_3$)$_2$. In yet a further aspect, R$^3$ is selected from hydrogen, —F, methyl, —CF$_3$, —OH, —OCH$_3$, —OCF$_3$, —NH$_2$, —NHCH$_3$, and —N(CH$_3$)$_2$.

In a further aspect, R$^3$ is selected from hydrogen, halogen, C1-C3 alkyl, C1-C3 monohaloalkyl, C1-C3 polyhaloalkyl, and cyclopropyl. In a still further aspect, R$^3$ is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, and cyclopropyl. In yet a further aspect, R$^3$ is selected from hydrogen, —F, —Cl, methyl, —CH$_2$F, —CH$_2$Cl, —CHF$_2$, —CF$_3$, —CHCl$_2$, —CCl$_3$, and cyclopropyl. In an even further aspect, R$^3$ is selected from hydrogen, —F, methyl, —CH$_2$F, —CHF$_2$, —CF$_3$, and cyclopropyl. In a still further aspect, R$^3$ is selected from hydrogen, —F, methyl, —CF$_3$, and cyclopropyl.

In a further aspect, R$^3$ is selected from hydrogen, halogen, C1-C3 alkyl, C1-C3 monohaloalkyl, and C1-C3 polyhaloalkyl. In a still further aspect, R$^3$ is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, and —CCl$_3$. In yet a further aspect, R$^3$ is selected from hydrogen, —F, —Cl, methyl, —CH$_2$F, —CH$_2$Cl, —CHF$_2$, —CF$_3$, —CHCl$_2$, and —CCl$_3$. In an even further aspect, R$^3$ is selected from hydrogen, —F, methyl, —CH$_2$F, —CHF$_2$, and —CF$_3$. In a still further aspect, R$^3$ is selected from hydrogen, —F, —Cl, methyl, and —CF$_3$. In yet a further aspect, R$^3$ is selected from hydrogen, —F, methyl, and —CF$_3$.

In a further aspect, R$^3$ is selected from hydrogen, halogen, and C1-C3 alkyl. In a still further aspect, R$^3$ is selected from hydrogen, —F, —Cl, methyl, and ethyl. In yet a further aspect, R$^3$ is selected from hydrogen, —F, —Cl, and methyl. In an even further aspect, R$^3$ is selected from hydrogen, —F, and methyl.

In a further aspect, R$^3$ is selected from hydrogen and C1-C3 alkyl. In a still further aspect, R$^3$ is selected from hydrogen, methyl, and ethyl. In yet a further aspect, R$^3$ is selected from hydrogen and methyl.

In a further aspect, R$^3$ is —F. In a still further aspect, R$^3$ is —Cl. In yet a further aspect, R$^3$ is methyl. In an even further aspect, R$^3$ is —CF$_3$. In a still further aspect, R$^3$ is hydrogen.

In a further aspect, each of R$^2$ and R$^3$ is hydrogen.

i. R$^4$ Groups

In one aspect, each of R$^{4a}$, R$^{4b}$, R$^{4c}$, and R$^{4d}$, is independently selected from hydrogen and fluoro. In a further aspect, each of R$^{4a}$, R$^{4b}$, and R$^{4c}$ is hydrogen, and wherein R$^{4d}$ is fluoro. In a still further aspect, each of R$^{4a}$, R$^{4b}$, and R$^{4d}$ is hydrogen, and wherein R$^{4c}$ is fluoro. In yet a further aspect, each of R$^{4a}$, R$^{4c}$, and R$^{4c}$ is hydrogen, and wherein R$^{4b}$ is fluoro. In an even further aspect, each of R$^{4b}$, R$^{4c}$, and R$^{4d}$ is hydrogen, and wherein R$^{4a}$ is fluoro. In a still further aspect, each of R$^{4a}$ and R$^{4b}$ is hydrogen, and wherein each of R$^{4c}$ and R$^{4d}$ is fluoro. In yet a further aspect, each of R$^{4a}$ and R$^{4c}$ is hydrogen, and wherein each of R$^{4b}$ and R$^{4d}$ is fluoro. In an even further aspect, each of R$^{4a}$ and R$^{4d}$ is hydrogen, and wherein each of R$^{4b}$ and R$^{4c}$ is fluoro. In a still further aspect, each of R$^{4b}$ and R$^{4c}$ is hydrogen, and wherein each of R$^{4a}$ and R$^{4d}$ is fluoro. In yet a further aspect, each of R$^{4b}$ and R$^{4d}$ is hydrogen, and wherein each of R$^{4a}$ and R$^{4c}$ is fluoro. In an even further aspect, each of R$^{4c}$ and R$^{4d}$ is hydrogen, and wherein each of R$^{4a}$ and R$^{4b}$ is fluoro. In a still further aspect, each of R$^{4a}$, R$^{4b}$, R$^{4c}$, and R$^{4d}$ is hydrogen. In yet a further aspect, each of R$^{4a}$, R$^{4b}$, R$^{4c}$, and R$^{4d}$ is fluoro.

In a further aspect, each of R$^2$, R$^{4a}$, R$^{4b}$, R$^{4c}$, and R$^{4d}$ is hydrogen.

In a further aspect, each of R$^3$, R$^{4a}$, R$^{4b}$, R$^{4c}$, and R$^{4d}$ is hydrogen.

In a further aspect, each of R$^2$, R$^3$, R$^{4a}$, R$^{4b}$, R$^{4c}$, and R$^{4d}$ is hydrogen.

j. R$^5$ Groups

In one aspect, R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$. In a further aspect, R$^5$, when present, is selected from hydrogen, —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$Cl, —(C=O)CH$_2$CH$_2$F, —(C=O)CH$_2$CH$_2$Cl, —(C=O)CHF$_2$, —(C=O)CF$_3$, —(C=O)CHCl$_2$, —(C=O)CCl$_3$, —(C=O)NH$_2$, —(C=O)NHCH$_3$, and —(C=O)N(CH$_3$)$_2$. In a still further aspect, R$^5$, when present, is selected from hydrogen, —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In yet a further aspect, R$^5$, when present, is selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In an even further aspect, R$^5$, when present, is selected from hydrogen, —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$.

In a further aspect, R$^5$, when present, is selected from halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$. In yet a further aspect, R$^5$, when present, is selected from —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—

$NH_2$, $-SO_2-NHCH_3$, $-SO_2-N(CH_3)_2$, $-(C=O)CH_3$, $-(C=O)CH_2CH_3$, $-(C=O)CH_2F$, $-(C=O)CH_2Cl$, $-(C=O)CH_2CH_2F$, $-(C=O)CH_2CH_2Cl$, $-(C=O)CHF_2$, $-(C=O)CF_3$, $-(C=O)CHCl_2$, $-(C=O)CCl_3$, $-(C=O)NH_2$, $-(C=O)NHCH_3$, and $-(C=O)N(CH_3)_2$. In an even further aspect, $R^5$, when present, is selected from $-F$, $-Cl$, $-CN$, methyl, $-CH_2F$, $-CH_2Cl$, $-CHF_2$, $-CF_3$, $-CHCl_2$, $-CCl_3$, cyclopropyl, $-OH$, $-OCH_3$, $-OCF_3$, $-NH_2$, $-NHCH_3$, $-N(CH_3)_2$, $-SO_2CH_3$, $-SO_2CF_3$, $-SO_2-NH_2$, $-SO_2-NHCH_3$, $-SO_2-N(CH_3)_2$, $-(C=O)CH_3$, $-(C=O)CF_3$, $-(C=O)NH_2$, $-(C=O)NHCH_3$, and $-(C=O)N(CH_3)_2$. In a still further aspect, $R^5$, when present, is selected from $-F$, $-CN$, methyl, $-CH_2F$, $-CHF_2$, $-CF_3$, cyclopropyl, $-OH$, $-OCH_3$, $-OCF_3$, $-NH_2$, $-NHCH_3$, $-N(CH_3)_2$, $-SO_2CH_3$, $-SO_2CF_3$, $-SO_2-NH_2$, $-SO_2-NHCH_3$, $-SO_2-N(CH_3)_2$, $-(C=O)CH_3$, $-(C=O)CF_3$, $-(C=O)NH_2$, $-(C=O)NHCH_3$, and $-(C=O)N(CH_3)_2$. In a yet further aspect, $R^5$, when present, is selected from $-F$, $-CN$, methyl, $-CF_3$, cyclopropyl, $-OH$, $-OCH_3$, $-OCF_3$, $-NH_2$, $-NHCH_3$, $-N(CH_3)_2$, $-SO_2CH_3$, $-SO_2CF_3$, $-SO_2-NH_2$, $-SO_2-NHCH_3$, $-SO_2-N(CH_3)_2$, $-(C=O)CH_3$, $-(C=O)CF_3$, $-(C=O)NH_2$, $-(C=O)NHCH_3$, and $-(C=O)N(CH_3)_2$.

In a further aspect, $R^5$, when present, is selected from hydrogen, halogen, $-CN$, C1-C3 alkyl, C1-C3 monohaloalkyl, C1-C3 polyhaloalkyl, cyclopropyl, $-OR^{20}$, $-NR^{21a}R^{21b}$, and $-SO_2R^{22}$. In a yet further aspect, $R^5$, when present, is selected from hydrogen, $-F$, $-Cl$, $-CN$, methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, cyclopropyl, $-OH$, $-OCH_3$, $-OCH_2F$, $-OCHF_2$, $-OCF_3$, $-O$-cyclopropyl, $-NH_2$, $-NHCH_3$, $-N(CH_3)_2$, $-SO_2CH_3$, $-SO_2CH_2F$, $-SO_2CHF_2$, $-SO_2CF_3$, $-SO_2$-cyclopropyl, $-SO_2-NH_2$, $-SO_2-NHCH_3$, and $-SO_2-N(CH_3)_2$. In an even further aspect, $R^5$, when present, is selected from hydrogen, $-F$, $-Cl$, $-CN$, methyl, $-CH_2F$, $-CH_2Cl$, $-CHF_2$, $-CF_3$, $-CHCl_2$, $-CCl_3$, cyclopropyl, $-OH$, $-OCH_3$, $-OCF_3$, $-NH_2$, $-NHCH_3$, $-N(CH_3)_2$, $-SO_2CH_3$, $-SO_2CF_3$, $-SO_2-NH_2$, $-SO_2-NHCH_3$, and $-SO_2-N(CH_3)_2$. In a still further aspect, $R^5$, when present, is selected from hydrogen, $-F$, $-CN$, methyl, $-CH_2F$, $-CHF_2$, $-CF_3$, cyclopropyl, $-OH$, $-OCH_3$, $-OCF_3$, $-NH_2$, $-NHCH_3$, $-N(CH_3)_2$, $-SO_2CH_3$, $-SO_2CF_3$, $-SO_2-NH_2$, $-SO_2-NHCH_3$, and $-SO_2-N(CH_3)_2$.

In a further aspect, $R^5$, when present, is selected from hydrogen, halogen, C1-C3 alkyl, C1-C3 monohaloalkyl, C1-C3 polyhaloalkyl, cyclopropyl, $-OR^{20}$, $-NR^{21a}R^{21b}$, and $-SO_2R^{22}$. In a still further aspect, $R^5$, when present, is selected from hydrogen, $-F$, $-Cl$, methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, cyclopropyl, $-OH$, $-OCH_3$, $-OCH_2F$, $-OCHF_2$, $-OCF_3$, $-O$-cyclopropyl, $-NH_2$, $-NHCH_3$, $-N(CH_3)_2$, $-SO_2CH_3$, $-SO_2CH_2F$, $-SO_2CHF_2$, $-SO_2CF_3$, $-SO_2$-cyclopropyl, $-SO_2-NH_2$, $-SO_2-NHCH_3$, and $-SO_2-N(CH_3)_2$. In an even further aspect, $R^5$, when present, is selected from selected from hydrogen, $-F$, $-Cl$, methyl, $-CH_2F$, $-CH_2Cl$, $-CHF_2$, $-CF_3$, $-CHCl_2$, $-CCl_3$, cyclopropyl, $-OH$, $-OCH_3$, $-OCF_3$, $-NH_2$, $-NHCH_3$, $-N(CH_3)_2$, $-SO_2CH_3$, $-SO_2CF_3$, $-SO_2-NH_2$, $-SO_2-NHCH_3$, and $-SO_2-N(CH_3)_2$. In a still further aspect, $R^5$, when present is selected from hydrogen, $-F$, methyl, $-CF_3$, cyclopropyl, $-OH$, $-OCH_3$, $-OCF_3$, $-NH_2$, $-NHCH_3$, $-N(CH_3)_2$, $-SO_2CH_3$, $-SO_2CF_3$, $-SO_2-NH_2$, $-SO_2-NHCH_3$, and $-SO_2-N(CH_3)_2$.

In a further aspect, $R^5$, when present, is selected from hydrogen, halogen, C1-C3 alkyl, C1-C3 monohaloalkyl, C1-C3 polyhaloalkyl, $-OR^{20}$, $-NR^{21a}R^{21b}$, and $-SO_2R^{22}$. In a yet further aspect, $R^5$, when present, is selected from hydrogen, $-F$, $-Cl$, methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, $-OH$, $-OCH_3$, $-OCH_2F$, $-OCHF_2$, $-OCF_3$, $-O$-cyclopropyl, $-NH_2$, $-NHCH_3$, $-N(CH_3)_2$, $-SO_2CH_3$, $-SO_2CH_2F$, $-SO_2CHF_2$, $-SO_2CF_3$, $-SO_2$-cyclopropyl, $-SO_2-NH_2$, $-SO_2-NHCH_3$, and $-SO_2-N(CH_3)_2$. In a still further aspect, $R^5$, when present, is selected from hydrogen, $-F$, $-Cl$, methyl, $-CH_2F$, $-CH_2Cl$, $-CHF_2$, $-CF_3$, $-CHCl_2$, $-CCl_3$, $-OH$, $-OCH_3$, $-OCF_3$, $-NH_2$, $-NHCH_3$, $-N(CH_3)_2$, $-SO_2CH_3$, $-SO_2CF_3$, $-SO_2-NH_2$, $-SO_2-NHCH_3$, and $-SO_2-N(CH_3)_2$. In a still further aspect, $R^5$, when present, is selected from hydrogen, $-F$, methyl, $-CF_3$, $-OH$, $-OCH_3$, $-OCF_3$, $-NH_2$, $-NHCH_3$, $-N(CH_3)_2$, $-SO_2CH_3$, $-SO_2CF_3$, $-SO_2-NH_2$, $-SO_2-NHCH_3$, and $-SO_2-N(CH_3)_2$.

In a further aspect, $R^5$, when present, is selected from hydrogen, halogen, $-CN$, C1-C3 alkyl, C1-C3 monohaloalkyl, C1-C3 polyhaloalkyl, cyclopropyl, $-OR^{20}$, and $-NR^{21a}R^{21b}$. In a yet further aspect, $R^5$, when present, is selected from hydrogen, $-F$, $-Cl$, $-CN$, methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, cyclopropyl, $-OH$, $-OCH_3$, $-OCH_2F$, $-OCHF_2$, $-OCF_3$, $-O$-cyclopropyl, $-NH_2$, $-NHCH_3$, and $-N(CH_3)_2$. In a still further aspect, $R^5$, when present is selected from hydrogen, $-F$, $-Cl$, $-CN$, methyl, $-CH_2F$, $-CH_2Cl$, $-CHF_2$, $-CF_3$, $-CHCl_2$, $-CCl_3$, cyclopropyl, $-OH$, $-OCH_3$, $-OCF_3$, $-NH_2$, $-NHCH_3$, and $-N(CH_3)_2$. In an even further aspect, $R^5$, when present, is selected from hydrogen, $-F$, $-CN$, methyl, $-CH_2F$, $-CHF_2$, $-CF_3$, cyclopropyl, $-OH$, $-OCH_3$, $-OCF_3$, $-NH_2$, $-NHCH_3$, and $-N(CH_3)_2$. In a yet further aspect, $R^5$, when present, is selected from hydrogen, $-F$, $-CN$, methyl, $-CF_3$, cyclopropyl, $-OH$, $-OCH_3$, $-OCF_3$, $-NH_2$, $-NHCH_3$, and $-N(CH_3)_2$.

In a further aspect, $R^5$, when present, is selected from hydrogen, halogen, C1-C3 alkyl, C1-C3 monohaloalkyl, C1-C3 polyhaloalkyl, cyclopropyl, $-OR^{20}$, and $-NR^{21a}R^{21b}$. In a yet further aspect, $R^5$, when present, is selected from hydrogen, $-F$, $-Cl$, methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, cyclopropyl, $-OH$, $-OCH_3$, $-OCH_2F$, $-OCHF_2$, $-OCF_3$, $-O$-cyclopropyl, $-NH_2$, $-NHCH_3$, and $-N(CH_3)_2$. In an even further aspect, $R^5$, when present, is selected from hydrogen, $-F$, $-Cl$, methyl, $-CH_2F$, $-CH_2Cl$, $-CHF_2$, $-CF_3$, $-CHCl_2$, $-CCl_3$, cyclopropyl, —OH, —OCH$_3$, —OCF$_3$, —NH$_2$, —NHCH$_3$, and —N(CH$_3$)$_2$. In a yet further aspect, R$^5$, when present, is selected from hydrogen, —F, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In a still further aspect, R$^5$, when present, is selected from hydrogen, —F, methyl, —CF$_3$, cyclopropyl, —OH, —OCH$_3$, —OCF$_3$, —NH$_2$, —NHCH$_3$, and —N(CH$_3$)$_2$.

In a further aspect, R$^5$, when present, is selected from hydrogen, halogen, C1-C3 alkyl, C1-C3 monohaloalkyl, C1-C3 polyhaloalkyl, —OR$^{20}$, and —NR$^{21a}$R$^{21b}$. In an even further aspect, R$^5$, when present, is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a yet further aspect, R$^5$, when present, is selected from hydrogen, —F, —Cl, methyl, —CH$_2$F, —CH$_2$Cl, —CHF$_2$, —CF$_3$, —CHCl$_2$, —CCl$_3$, —OH, —OCH$_3$, —OCF$_3$, —NH$_2$, —NHCH$_3$, and —N(CH$_3$)$_2$. In a still further aspect, R$^5$, when present, is selected from hydrogen, —F, methyl, —CH$_2$F, —CHF$_2$, —CF$_3$, —OH, —OCH$_3$, —OCF$_3$, —NH$_2$, —NHCH$_3$, and —N(CH$_3$)$_2$. In an even further aspect, R$^5$, when present, is selected from hydrogen, —F, —Cl, methyl, —CF$_3$, —OH, —OCH$_3$, —OCF$_3$, —NH$_2$, —NHCH$_3$, and —N(CH$_3$)$_2$. In a yet further aspect, R$^5$, when present, is selected from hydrogen, —F, methyl, —CF$_3$, —OH, —OCH$_3$, —OCF$_3$, —NH$_2$, —NHCH$_3$, and —N(CH$_3$)$_2$.

In a further aspect, R$^5$, when present, is selected from hydrogen, halogen, C1-C3 alkyl, C1-C3 monohaloalkyl, C1-C3 polyhaloalkyl, and cyclopropyl. In an even further aspect, R$^5$, when present, is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, and cyclopropyl. In a yet further aspect, R$^5$, when present, is selected from hydrogen, —F, —Cl, methyl, —CH$_2$F, —CH$_2$Cl, —CHF$_2$, —CF$_3$, —CHCl$_2$, —CCl$_3$, and cyclopropyl. In a still further aspect, R$^5$, when present, is selected from hydrogen, —F, methyl, —CH$_2$F, —CHF$_2$, —CF$_3$, and cyclopropyl. In an even further aspect, R$^5$, when present, is selected from hydrogen, —F, methyl, —CF$_3$, and cyclopropyl.

In a further aspect, R$^5$, when present, is selected from hydrogen, halogen, C1-C3 alkyl, C1-C3 monohaloalkyl, and C1-C3 polyhaloalkyl. In a still further aspect, R$^5$, when present, is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, and —CCl$_3$. In an even further aspect, R$^5$, when present, is selected from hydrogen, —F, —Cl, methyl, —CH$_2$F, —CH$_2$Cl, —CHF$_2$, —CF$_3$, —CHCl$_2$, and —CCl$_3$. In a yet further aspect, R$^5$, when present, is selected from hydrogen, —F, methyl, —CH$_2$F, —CHF$_2$, and —CF$_3$. In a still further aspect, R$^5$, when present, is selected from hydrogen, —F, —Cl, methyl, and —CF$_3$. In an even further aspect, R$^5$, when present, is selected from hydrogen, —F, methyl, and —CF$_3$.

In a further aspect, R$^5$, when present, is selected from hydrogen, halogen, and C1-C3 alkyl. In a still further aspect, R$^5$, when present, is selected from hydrogen, —F, —Cl, methyl, and ethyl. In an even further aspect, R$^5$, when present, is selected from hydrogen, —F, —Cl, and methyl. In a yet further aspect, R$^5$, when present, is selected from hydrogen, —F, and methyl.

In a further aspect, R$^5$, when present, is selected from hydrogen and C1-C3 alkyl. In still further aspect, R$^5$, when present, is selected from hydrogen, methyl, and ethyl. In an even further aspect, R$^5$, when present, is selected from hydrogen and methyl.

In a further aspect, R$^5$ is —CN. In a further aspect, R$^5$ is —F. In a still further aspect, R$^5$ is —Cl. In an even further aspect, R$^5$ is methyl. In a still further aspect, R$^5$ is —CF$_3$. In a yet further aspect, R$^5$ is hydrogen.

In a further aspect, R$^5$, when present, and R$^2$ is hydrogen. In a still further aspect, R$^5$, when present, and R$^3$ is hydrogen. In an even further aspect, each of R$^{4a}$, R$^{4b}$, R$^{4c}$, R$^{4d}$ and R$^5$, when present, is hydrogen. In a yet further aspect, each of R$^2$, R$^{4a}$, R$^{4b}$, R$^{4c}$, R$^{4d}$, and R$^5$, when present, is hydrogen. In a still further aspect, each of R$^3$, R$^{4a}$, R$^{4b}$, R$^{4c}$, R$^{4d}$, and R$^5$, when present, is hydrogen. In an even further aspect, each of R$^2$, R$^3$, R$^{4a}$, R$^{4b}$, R$^{4c}$, R$^{4d}$, and R$^5$, when present, is hydrogen.

k. R$^6$ Groups

In one aspect, R$^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C═O)R$^{33}$. In a further aspect, R$^6$, when present, is selected from hydrogen, —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C═O)CH$_3$, —(C═O)CH$_2$CH$_3$, —(C═O)CH$_2$F, —(C═O)CH$_2$Cl, —(C═O)CH$_2$CH$_2$F, —(C═O)CH$_2$CH$_2$Cl, —(C═O)CHF$_2$, —(C═O)CF$_3$, —(C═O)CHCl$_2$, —(C═O)CCl$_3$, —(C═O)NH$_2$, —(C═O)NHCH$_3$, and —(C═O)N(CH$_3$)$_2$. In a still further aspect, R$^6$, when present, is selected from hydrogen, —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C═O)CH$_3$, —(C═O)CF$_3$, —(C═O)NH$_2$, —(C═O)NHCH$_3$, and —(C═O)N(CH$_3$)$_2$. In a yet further aspect, R$^6$, when present, is selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C═O)CH$_3$, —(C═O)CF$_3$, —(C═O)NH$_2$, —(C═O)NHCH$_3$, and —(C═O)N(CH$_3$)$_2$. In an even further aspect, R$^6$, when present, is selected from hydrogen, —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C═O)CH$_3$, —(C═O)CF$_3$, —(C═O)NH$_2$, —(C═O)NHCH$_3$, and —(C═O)N(CH$_3$)$_2$.

In a further aspect, R$^6$, when present, is selected from halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C═O)R$^{23}$. In a still further aspect, R$^6$, when present, is selected from —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C═O)CH$_3$, —(C═O)CH$_2$CH$_3$, —(C═O)CH$_2$F, —(C═O)CH$_2$Cl, —(C═O)CH$_2$CH$_2$F, —(C═O)CH$_2$CH$_2$Cl, —(C═O)CHF$_2$, —(C═O)CF$_3$, —(C═O)CHCl$_2$, —(C═O)CCl$_3$, —(C═O)NH$_2$, —(C═O)NHCH$_3$, and —(C═O)N(CH$_3$)$_2$.

In a yet further aspect, $R^6$, when present, is selected from —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In an even further aspect, $R^6$, when present, is selected from —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In a still further aspect, $R^6$, when present, is selected from —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$.

In a further aspect, $R^6$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, and —SO$_2$R$^{22}$. In a still further aspect, $R^6$, when present, is selected from hydrogen, —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In a yet further aspect, $R^6$, when present, is selected from hydrogen, —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, $R^6$, when present, is selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, $R^6$, when present, is selected from hydrogen, —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, $R^6$, when present, is selected from hydrogen, halogen, C1-C3 alkyl, C1-C3 monohaloalkyl, C1-C3 polyhaloalkyl, cyclopropyl, —OR$^{20}$, —NR$^{21a}$R$^{21b}$, and —SO$_2$R$^{22}$. In a still further aspect, $R^6$, when present, is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In a yet further aspect, $R^6$, when present, is selected from hydrogen, —F, —Cl, methyl, —CH$_2$F, —CH$_2$Cl, —CHF$_2$, —CF$_3$, —CHCl$_2$, —CCl$_3$, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In a yet further aspect, $R^6$, when present, is selected from hydrogen, —F, —Cl, methyl, —CH$_2$F, —CH$_2$Cl, —CHF$_2$, —CF$_3$, —CHCl$_2$, —CCl$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, $R^6$, when present, is selected from hydrogen, —F, methyl, —CH$_2$F, —CHF$_2$, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, $R^6$, when present, is selected from hydrogen, —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a yet further aspect, $R^6$, when present, is selected from hydrogen, —F, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, $R^6$, when present, is selected from hydrogen, halogen, —CN, C1-C3 alkyl, C1-C3 monohaloalkyl, C1-C3 polyhaloalkyl, cyclopropyl, —OR$^{20}$, and —NR$^{21a}$R$^{21b}$. In a still further aspect, $R^6$, when present, is selected from hydrogen, —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a yet further aspect, $R^6$, when present, is selected from hydrogen, —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, and —N(CH$_3$)$_2$. In an even further aspect, $R^6$, when present, is selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In a still further aspect, $R^6$, when present, is selected from hydrogen, —F, —CN, methyl, —CF$_3$, cyclopropyl, —OH, —OCH$_3$, —OCF$_3$, —NH$_2$, —NHCH$_3$, and —N(CH$_3$)$_2$.

In a further aspect, $R^6$, when present, is selected from hydrogen, halogen, C1-C3 alkyl, C1-C3 monohaloalkyl, C1-C3 polyhaloalkyl, cyclopropyl, —OR$^{20}$, and —NR$^{21a}$R$^{21b}$. In a still further aspect, $R^6$, when present, s selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a yet further aspect, $R^6$, when present, is selected from hydrogen, —F, —Cl, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, and —N(CH$_3$)$_2$. In an even further aspect, $R^6$, when present, is selected from hydrogen, —F, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In a still further aspect, $R^6$, when present, is selected from hydrogen, —F, methyl, —CF$_3$, cyclopropyl, —OH, —OCH$_3$, —OCF$_3$, —NH$_2$, —NHCH$_3$, and —N(CH$_3$)$_2$.

In a further aspect, R$^6$, when present, is selected from hydrogen, halogen, C1-C3 alkyl, C1-C3 monohaloalkyl, C1-C3 polyhaloalkyl, —OR$^{20}$, and —NR$^{21a}$R$^{21b}$. In a still further aspect, R$^6$, when present, is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a yet further aspect, R$^6$, when present, is selected from hydrogen, —F, —Cl, methyl, —CH$_2$F, —CH$_2$Cl, —CHF$_2$, —CF$_3$, —CHCl$_2$, —CCl$_3$, —OH, —OCH$_3$, —OCF$_3$, —NH$_2$, —NHCH$_3$, and —N(CH$_3$)$_2$. In an even further aspect, R$^6$, when present, is selected from hydrogen, —F, methyl, —CH$_2$F, —CHF$_2$, —CF$_3$, —OH, —OCH$_3$, —OCF$_3$, —NH$_2$, —NHCH$_3$, and —N(CH$_3$)$_2$. In a still further aspect, R$^6$, when present, is selected from hydrogen, —F, —Cl, methyl, —CF$_3$, —OH, —OCH$_3$, —OCF$_3$, —NH$_2$, —NHCH$_3$, and —N(CH$_3$)$_2$. In a yet further aspect, R$^6$, when present, is selected from hydrogen, —F, methyl, —CF$_3$, —OH, —OCH$_3$, —OCF$_3$, —NH$_2$, —NHCH$_3$, and —N(CH$_3$)$_2$.

In a further aspect, R$^6$, when present, is selected from hydrogen, halogen, C1-C3 alkyl, C1-C3 monohaloalkyl, C1-C3 polyhaloalkyl, and cyclopropyl. In a still further aspect, R$^6$, when present, is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, and cyclopropyl. In a yet further aspect, R$^6$, when present, is selected from hydrogen, —F, —Cl, methyl, —CH$_2$F, —CH$_2$Cl, —CHF$_2$, —CF$_3$, —CHCl$_2$, —CCl$_3$, and cyclopropyl. In an even further aspect, R$^6$, when present, is selected from hydrogen, —F, methyl, —CH$_2$F, —CHF$_2$, —CF$_3$, and cyclopropyl. In a still further aspect, R$^6$, when present, is selected from hydrogen, —F, methyl, —CF$_3$, and cyclopropyl.

In a further aspect, R$^6$, when present, is selected from hydrogen, halogen, C1-C3 alkyl, C1-C3 monohaloalkyl, and C1-C3 polyhaloalkyl. In a still further aspect, R$^6$, when present, is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, and —CCl$_3$. In yet a further aspect, R$^6$, when present, is selected from hydrogen, —F, —Cl, methyl, —CH$_2$F, —CH$_2$Cl, —CHF$_2$, —CF$_3$, —CHCl$_2$, and —CCl$_3$. In an even further aspect, R$^6$, when present, is selected from hydrogen, —F, methyl, —CH$_2$F, —CHF$_2$, and —CF$_3$. In a still further aspect, R$^6$, when present, is selected from hydrogen, —F, —Cl, methyl, and —CF$_3$. In a yet further aspect, R$^6$, when present, is selected from hydrogen, —F, methyl, and —CF$_3$.

In a further aspect, R$^6$, when present, is selected from hydrogen, halogen, and C1-C3 alkyl. In a still further aspect, R$^6$, when present, is selected from hydrogen, —F, —Cl, methyl, and ethyl. In yet a further aspect, R$^6$, when present, is selected from hydrogen, —F, —Cl, and methyl. In an even further aspect, R$^6$, when present, is selected from hydrogen, —F, and methyl.

In a further aspect, R$^6$, when present, is selected from hydrogen and C1-C3 alkyl. In a still further aspect, R$^6$ is selected from hydrogen, methyl, and ethyl. In yet a further aspect, R$^6$, when present, is selected from hydrogen and methyl.

In a further aspect, R$^6$, when present, is —F. In a still further aspect, R$^6$, when present, is —Cl. In yet a further aspect, R$^6$, when present, is methyl. In an even further aspect, R$^6$, when present, is —CF$_3$. In still a further aspect, R$^6$, when present, is hydrogen.

In a further aspect, each of R$^2$ and R$^6$, when present, is hydrogen.

In a further aspect, each of R$^3$ and R$^6$, when present, is hydrogen.

In a further aspect, each of R$^5$ and R$^6$, when present, is hydrogen.

In a further aspect, each of R$^{4a}$, R$^{4b}$, R$^{4c}$, R$^{4d}$, and R$^6$, when present, is hydrogen.

In a further aspect, each of R$^2$, R$^{4a}$, R$^{4b}$, R$^{4c}$, R$^{4d}$, R$^5$, and R$^6$, when present, is hydrogen.

In a further aspect, each of R$^3$, R$^{4a}$, R$^{4b}$, R$^{4c}$, R$^{4d}$, R$^5$, and R$^6$, when present, is hydrogen.

In a further aspect, each of R$^2$, R$^3$, R$^{4a}$, R$^{4b}$, R$^{4c}$, R$^{4d}$, R$^5$, and R$^6$, when present, is hydrogen.

l. R$^7$ Groups

In one aspect, R$^7$, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C═O)R$^{43}$. In a still further aspect, R$^7$, when present, is selected from hydrogen, —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C═O)CH$_3$, —(C═O)CH$_2$CH$_3$, —(C═O)CH$_2$F, —(C═O)CH$_2$Cl, —(C═O)CH$_2$CH$_2$F, —(C═O)CH$_2$CH$_2$Cl, —(C═O)CHF$_2$, —(C═O)CF$_3$, —(C═O)CHCl$_2$, —(C═O)CCl$_3$, —(C═O)NH$_2$, —(C═O)NHCH$_3$, and —(C═O)N(CH$_3$)$_2$. In a yet further aspect, R$^7$, when present, is selected from hydrogen, —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C═O)CH$_3$, —(C═O)CF$_3$, —(C═O)NH$_2$, —(C═O)NHCH$_3$, and —(C═O)N(CH$_3$)$_2$. In an even further aspect, R$^7$, when present, is selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C═O)CH$_3$, —(C═O)CF$_3$, —(C═O)NH$_2$, —(C═O)NHCH$_3$, and —(C═O)N(CH$_3$)$_2$. In a still further aspect, R$^7$, when present, is selected from hydrogen, —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C═O)CH$_3$, —(C═O)CF$_3$, —(C═O)NH$_2$, —(C═O)NHCH$_3$, and —(C═O)N(CH$_3$)$_2$.

In a further aspect, R$^7$, when present, is selected from halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C═O)R$^{23}$. In a still further aspect, R$^7$, when present, is selected from —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C═O)CH$_3$, —(C═O)CH$_2$CH$_3$, —(C═O)CH$_2$F, —(C═O)CH$_2$Cl, —(C═O)CH$_2$CH$_2$F, —(C═O)CH$_2$CH$_2$Cl, —(C═O)CHF$_2$, —(C═O)CF$_3$, —(C═O)CHCl$_2$, —(C═O)CCl$_3$, —(C═O)NH$_2$, —(C═O)NHCH$_3$, and —(C═O)N(CH$_3$)$_2$.

In a yet further aspect, $R^7$, when present, is selected from —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C═O)CH$_3$, —(C═O)CF$_3$, —(C═O)NH$_2$, —(C═O)NHCH$_3$, and —(C═O)N(CH$_3$)$_2$. In an even further aspect, $R^7$, when present, is selected from —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C═O)CH$_3$, —(C═O)CF$_3$, —(C═O)NH$_2$, —(C═O)NHCH$_3$, and —(C═O)N(CH$_3$)$_2$. In a still further aspect, $R^7$, when present, is selected from —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C═O)CH$_3$, —(C═O)CF$_3$, —(C═O)NH$_2$, —(C═O)NHCH$_3$, and —(C═O)N(CH$_3$)$_2$.

In a further aspect, $R^7$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, and —SO$_2$R$^{22}$. In a still further aspect, $R^7$, when present, is selected from hydrogen, —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In a yet further aspect, $R^7$, when present, is selected from hydrogen, —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, $R^7$, when present, is selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, $R^7$, when present, is selected from hydrogen, —F, —CN, methyl, —CF$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, $R^7$, when present, is selected from hydrogen, halogen, C1-C3 alkyl, C1-C3 monohaloalkyl, C1-C3 polyhaloalkyl, cyclopropyl, —OR$^{20}$, —NR$^{21a}$R$^{21b}$, and —SO$_2$R$^{22}$. In a still further aspect, $R^7$, when present, is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, and —SO$_2$—N(CH$_3$)$_2$. In a yet further aspect, $R^7$, when present, is selected from hydrogen, —F, —Cl, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, $R^7$, when present, is selected from hydrogen, —F, methyl, —CH$_2$F, —CHF$_2$, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a still further aspect, $R^7$, when present, is selected from hydrogen, —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In a yet further aspect, $R^7$, when present, is selected from hydrogen, —F, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$.

In a further aspect, $R^7$, when present, is selected from hydrogen, halogen, —CN, C1-C3 alkyl, C1-C3 monohaloalkyl, C1-C3 polyhaloalkyl, cyclopropyl, —OR$^{20}$, and —NR$^{21a}$R$^{21b}$. In a still further aspect, $R^7$, when present, is selected from hydrogen, —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a yet further aspect, $R^7$, when present, is selected from hydrogen, —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, and —N(CH$_3$)$_2$. In an even further aspect, $R^7$, when present, is selected from hydrogen, —F, —CN, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In a still further aspect, $R^7$, when present, is selected from hydrogen, —F, —CN, methyl, —CF$_3$, cyclopropyl, —OH, —OCH$_3$, —OCF$_3$, —NH$_2$, —NHCH$_3$, and —N(CH$_3$)$_2$.

In a further aspect, $R^7$, when present, is selected from hydrogen, halogen, C1-C3 alkyl, C1-C3 monohaloalkyl, C1-C3 polyhaloalkyl, cyclopropyl, —OR$^{20}$, and —NR$^{21a}$R$^{21b}$. In a still further aspect, $R^7$, when present, is selected from hydrogen, —F, —Cl, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, and —N(CH$_3$)$_2$. In a yet further aspect, $R^7$, when present, is selected from hydrogen, —F, methyl, —CH$_2$F, —CHF$_2$, —CF$_3$, cyclopropyl, —OH, —OCH$_3$, —OCF$_3$, —NH$_2$, —NHCH$_3$, and —N(CH$_3$)$_2$. In an even further aspect, $R^7$, when present, is selected from hydrogen, —F, methyl, —CF$_3$, cyclopropyl, —OH, —OCH$_3$, —OCF$_3$, —NH$_2$, —NHCH$_3$, and —N(CH$_3$)$_2$.

In a further aspect, $R^7$, when present, is selected from hydrogen, halogen, C1-C3 alkyl, C1-C3 monohaloalkyl, C1-C3 polyhaloalkyl, —OR$^{20}$, and —NR$^{21a}$R$^{21b}$. In a still further aspect, $R^7$, when present, is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OH, —OCH$_3$, —OCH$_2$F, —OCHF$_2$, —OCF$_3$, —O-cyclopropyl, —NH$_2$, —NHCH$_3$, and —N(CH$_3$)$_2$. In a yet further aspect, $R^7$, when present, is selected from hydrogen, —F, —Cl, methyl, —CH$_2$F, —CH$_2$Cl, —CHF$_2$, —CF$_3$, —CHCl$_2$, —CCl$_3$, —OH, —OCH$_3$, —OCF$_3$, —NH$_2$, —NHCH$_3$, and —N(CH$_3$)$_2$. In an even further aspect, $R^7$, when present, is selected from hydrogen, —F, methyl, —CH$_2$F, —CHF$_2$, —CF$_3$, —OH, —OCH$_3$, —OCF$_3$, —NH$_2$, —NHCH$_3$, and —N(CH$_3$)$_2$. In a still further aspect, $R^7$, when present, is selected from hydrogen, —F, —Cl, methyl, —CF$_3$, —OH, —OCH$_3$, —OCF$_3$, —NH$_2$, —NHCH$_3$, and —N(CH$_3$)$_2$. In a yet further aspect, $R^7$, when present, is selected from hydrogen, —F, methyl, —CF$_3$, —OH, —OCH$_3$, —OCF$_3$, —NH$_2$, —NHCH$_3$, and —N(CH$_3$)$_2$.

In a further aspect, $R^7$, when present, is selected from hydrogen, halogen, C1-C3 alkyl, C1-C3 monohaloalkyl, C1-C3 polyhaloalkyl, and cyclopropyl. In a still further aspect, $R^7$, when present, is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, and cyclopropyl. In a yet further aspect, $R^7$, when present, is selected from hydrogen, —F, —Cl, methyl, —CH$_2$F, —CH$_2$Cl, —CHF$_2$, —CF$_3$, —CHCl$_2$, —CCl$_3$, and cyclopropyl. In an even further aspect, $R^7$, when present, is selected from hydrogen, —F, methyl, —CH$_2$F, —CHF$_2$, —CF$_3$, and cyclopropyl. In a still further aspect, $R^7$, when present, is selected from hydrogen, —F, methyl, —CF$_3$, and cyclopropyl.

In a further aspect, $R^7$, when present, is selected from hydrogen, halogen, C1-C3 alkyl, C1-C3 monohaloalkyl, and C1-C3 polyhaloalkyl. In a still further aspect, $R^7$, when present, is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, and —CCl$_3$. In a yet further aspect, $R^7$, when present, is selected from hydrogen, —F, —Cl, methyl, —CH$_2$F, —CH$_2$Cl, —CHF$_2$, —CF$_3$, —CHCl$_2$, and —CCl$_3$. In an even further aspect, $R^7$, when present, is selected from hydrogen, —F, methyl, —CH$_2$F, —CHF$_2$, and —CF$_3$. In a still further aspect, $R^7$, when present, is selected from hydrogen, —F, —Cl, methyl, and —CF$_3$. In a yet further aspect, $R^7$, when present, is selected from hydrogen, —F, methyl, and —CF$_3$.

In a further aspect, $R^7$, when present, is selected from hydrogen, halogen, and C1-C3 alkyl. In a still further aspect, $R^7$, when present, is selected from hydrogen, —F, —Cl, methyl, and ethyl. In a yet further aspect, $R^7$, when present, is selected from hydrogen, —F, —Cl, and methyl. In an even further aspect, $R^7$, when present, is selected from hydrogen, —F, and methyl.

In a further aspect, $R^7$, when present, is selected from hydrogen and C1-C3 alkyl. In a still further aspect, $R^7$, when present, is selected from hydrogen, methyl, and ethyl. In a yet further aspect, $R^7$, when present, is selected from hydrogen and methyl.

In a further aspect, $R^7$, when present, is —F. In a still further aspect, $R^7$, when present, is —Cl. In a yet further aspect, $R^7$, when present, is methyl. In an even further aspect, $R^7$, when present, is —CF$_3$. In a still further aspect, $R^7$, when present, is hydrogen.

In a further aspect, each of $R^2$ and $R^7$, when present, is hydrogen.

In a further aspect, each of $R^3$ and $R^7$, when present, is hydrogen.

In a further aspect, each of $R^{4a}$, $R^{4b}$, $R^{4c}$, $R^{4d}$, and $R^7$, when present, is hydrogen.

In a further aspect, each of $R^5$ and $R^7$, when present, is hydrogen.

In a further aspect, each of $R^6$ and $R^7$, when present, is hydrogen.

In a further aspect, each of $R^2$, $R^{4a}$, $R^{4b}$, $R^{4c}$, $R^{4d}$, $R^5$, $R^6$, and $R^7$, when present, is hydrogen.

In a further aspect, each of $R^3$, $R^{4a}$, $R^{4b}$, $R^{4c}$, $R^{4d}$, $R^5$, $R^6$, and $R^7$, when present, is hydrogen.

In a further aspect, each of $R^2$, $R^3$, $R^{4a}$, $R^{4b}$, $R^{4c}$, $R^{4d}$, $R^5$, $R^6$, and $R^7$, when present, is hydrogen.

m. $R^8$ Groups

In one aspect, $R^8$, when present, is selected from hydrogen, halogen, C1-C3 alkyl, C1-C3 monohaloalkyl, C1-C3 polyhaloalkyl, and cyclopropyl.

In a further aspect, $R^8$, when present, is selected from C1-C3 alkyl, C1-C3 monohaloalkyl, C1-C3 polyhaloalkyl, and cyclopropyl. In a still further aspect, $R^8$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, $R^8$, when present, is selected from methyl, —CH$_2$F, —CH$_2$Cl, —CHF$_2$, —CF$_3$, —CHCl$_2$, —CCl$_3$, and cyclopropyl. In an even further aspect, $R^8$, when present, is selected from methyl, —CH$_2$F, —CHF$_2$, —CF$_3$, and cyclopropyl. In a still further aspect, $R^8$, when present, is selected from methyl, —CF$_3$, and cyclopropyl.

In a further aspect, $R^8$, when present, is selected from hydrogen, C1-C3 alkyl, C1-C3 monohaloalkyl, and C1-C3 polyhaloalkyl. In a still further aspect, $R^8$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, $R^8$, when present, is selected from hydrogen, methyl, —CH$_2$F, —CH$_2$Cl, —CHF$_2$, —CF$_3$, —CHCl$_2$, and —CCl$_3$. In an even further aspect, $R^8$, when present, is selected from hydrogen, methyl, —CH$_2$F, —CHF$_2$, and —CF$_3$. In a still further aspect, $R^8$, when present, is selected from hydrogen, methyl, and —CF$_3$.

In a further aspect, $R^8$, when present, is selected from hydrogen, C1-C3 alkyl, and cyclopropyl. In a still further aspect, $R^8$, when present, is selected from hydrogen, methyl, ethyl, and cyclopropyl. In a yet further aspect, $R^8$, when present, is selected from hydrogen, methyl, and cyclopropyl.

In a further aspect, $R^8$, when present, is selected from hydrogen and C1-C3 alkyl. In a still further aspect, $R^8$, when present, is selected from hydrogen, methyl, and ethyl. In a yet further aspect, $R^8$, when present, is selected from hydrogen and methyl.

In a further aspect, $R^8$, when present, is selected from hydrogen, C1-C3 monohaloalkyl, C1-C3 polyhaloalkyl, and cyclopropyl.

In a further aspect, $R^8$ is F.

In a further aspect, each of $R^8$ and $R^9$, when present, is hydrogen. In a further aspect, —CR$^8$R$^9$ is selected from —CHF and —CF$_2$. In a further aspect, —CR$^8$R$^9$ is —CHF. In a further aspect, —CR$^8$R$^9$ is —CF$_2$.

n. $R^9$ Groups

In one aspect, $R^9$, when present, is selected from hydrogen, halogen, C1-C3 alkyl, C1-C3 monohaloalkyl, C1-C3 polyhaloalkyl, and cyclopropyl.

In a further aspect, $R^9$, when present, is selected from C1-C3 alkyl, C1-C3 monohaloalkyl, C1-C3 polyhaloalkyl, and cyclopropyl. In a still further aspect, $R^9$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl.

In yet a further aspect, R$^9$, when present, is selected from methyl, —CH$_2$F, —CH$_2$Cl, —CHF$_2$, —CF$_3$, —CHCl$_2$, —CCl$_3$, and cyclopropyl. In an even further aspect, R$^9$, when present, is selected from methyl, —CH$_2$F, —CHF$_2$, —CF$_3$, and cyclopropyl. In a still further aspect, R$^9$, when present, is selected from methyl, —CF$_3$, and cyclopropyl.

In a further aspect, R$^9$, when present, is selected from hydrogen, C1-C3 alkyl, C1-C3 monohaloalkyl, and C1-C3 polyhaloalkyl. In a still further aspect, R$^9$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^9$, when present, is selected from hydrogen, methyl, —CH$_2$F, —CH$_2$Cl, —CHF$_2$, —CF$_3$, —CHCl$_2$, and —CCl$_3$. In an even further aspect, R$^9$, when present, is selected from hydrogen, methyl, —CH$_2$F, —CHF$_2$, and —CF$_3$. In a still further aspect, R$^9$, when present, is selected from hydrogen, methyl, and —CF$_3$.

In a further aspect, R$^9$, when present, is selected from hydrogen, C1-C3 alkyl, and cyclopropyl. In a still further aspect, R$^9$, when present, is selected from hydrogen, methyl, ethyl, and cyclopropyl. In yet a further aspect, R$^9$, when present, is selected from hydrogen, methyl, and cyclopropyl.

In a further aspect, R$^9$, when present, is selected from hydrogen and C1-C3 alkyl. In a still further aspect, R$^9$, when present, is selected from hydrogen, methyl, and ethyl. In yet a further aspect, R$^9$, when present, is selected from hydrogen and methyl.

In a further aspect, R$^9$, when present, is selected from hydrogen, C1-C3 monohaloalkyl, C1-C3 polyhaloalkyl, and cyclopropyl. In a still further aspect, R$^9$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^9$, when present, is selected from hydrogen, —CH$_2$F, —CH$_2$Cl, —CHF$_2$, —CF$_3$, —CHCl$_2$, —CCl$_3$, and cyclopropyl. In an even further aspect, R$^9$, when present, is selected from hydrogen, —CH$_2$F, —CHF$_2$, —CF$_3$, and cyclopropyl. In a still further aspect, R$^9$, when present, is selected from hydrogen, —CF$_3$, and cyclopropyl. In yet a further aspect, R$^9$, when present, is hydrogen.

In a further aspect, R$^9$, when present, is selected from halogen, C1-C3 alkyl, C1-C3 monohaloalkyl, C1-C3 polyhaloalkyl, and cyclopropyl. In a still further aspect, R$^9$, when present, is selected from —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^9$, when present, is selected from —F, —Cl, methyl, —CH$_2$F, —CH$_2$Cl, —CHF$_2$, —CF$_3$, —CHCl$_2$, —CCl$_3$, and cyclopropyl. In an even further aspect, R$^9$, when present, is selected from —F, —Cl, methyl, —CH$_2$F, —CHF$_2$, —CF$_3$, and cyclopropyl. In a still further aspect, R$^9$, when present, is selected from —F, —Cl, methyl, —CF$_3$, and cyclopropyl.

In a further aspect, R$^9$, when present, is selected from hydrogen, halogen, C1-C3 alkyl, C1-C3 monohaloalkyl, and C1-C3 polyhaloalkyl. In a still further aspect, R$^9$, when present, is selected from hydrogen, —F, —Cl, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^9$, when present, is selected from hydrogen, —F, —Cl, methyl, —CH$_2$F, —CH$_2$Cl, —CHF$_2$, —CF$_3$, —CHCl$_2$, and —CCl$_3$. In an even further aspect, R$^9$, when present, is selected from hydrogen, —F, —Cl, methyl, —CH$_2$F, —CHF$_2$, and —CF$_3$. In a still further aspect, R$^9$, when present, is selected from hydrogen, —F, —Cl, methyl, and —CF$_3$. In yet a further aspect, R$^9$, when present, is selected from hydrogen, —F, methyl, and —CF$_3$.

In a further aspect, R$^9$, when present, is selected from hydrogen, halogen, C1-C3 alkyl, and cyclopropyl. In a still further aspect, R$^9$, when present, is selected from hydrogen, —F, —Cl, methyl, ethyl, and cyclopropyl. In yet a further aspect, R$^9$, when present, is selected from hydrogen, —F, —Cl, methyl, and cyclopropyl. In an even further aspect, R$^9$, when present, is selected from hydrogen, —F, methyl, and cyclopropyl.

In a further aspect, R$^9$, when present, is selected from hydrogen, halogen, and C1-C3 alkyl. In a still further aspect, R$^9$, when present, is selected from hydrogen, —F, —Cl, methyl, and ethyl. In yet a further aspect, R$^9$, when present, is selected from hydrogen, —F, —Cl, and methyl. In an even further aspect, R$^9$, when present, is selected from hydrogen, —F, and methyl.

In a further aspect, R$^9$, when present, is selected from hydrogen, halogen, C1-C3 monohaloalkyl, C1-C3 polyhaloalkyl, and cyclopropyl. In a still further aspect, R$^9$, when present, is selected from hydrogen, —F, —Cl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^9$, when present, is selected from hydrogen, —F, —Cl, —CH$_2$F, —CH$_2$Cl, —CHF$_2$, —CF$_3$, —CHCl$_2$, —CCl$_3$, and cyclopropyl. In an even further aspect, R$^9$, when present, is selected from hydrogen, —F, —Cl, —CH$_2$F, —CHF$_2$, —CF$_3$, and cyclopropyl. In a still further aspect, R$^9$, when present, is selected from hydrogen, —F, —Cl, —CF$_3$, and cyclopropyl. In yet a further aspect, R$^9$, when present, is selected from hydrogen, —F, —CF$_3$, and cyclopropyl. In an even further aspect, R$^9$, when present, is hydrogen.

In a further aspect, R$^9$ is F.

In a further aspect, each of R$^8$ and R$^9$, when present, is hydrogen. In a further aspect, —CR$^8$R$^9$ is selected from —CHF and —CF$_2$. In a further aspect, —CR$^8$R$^9$ is —CHF. In a further aspect, —CR$^8$R$^9$ is —CF$_2$.

o. R$^{10}$ Groups

In one aspect, each of R$^{10a}$ and R$^{10b}$, when present, is independently selected from hydrogen, C1-C3 alkyl, C1-C3 monohaloalkyl, C1-C3 polyhaloalkyl, and cyclopropyl. In a further aspect, each of R$^{10a}$ and R$^{10b}$ is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, each of R$^{10a}$ and R$^{10b}$ is independently selected from hydrogen, methyl, —CH$_2$F, —CH$_2$Cl, —CHF$_2$, —CF$_3$, —CHCl$_2$, —CCl$_3$, and cyclopropyl. In yet a further aspect, each of R$^{10a}$ and R$^{10b}$ is independently selected from methyl, —CH$_2$F, —CHF$_2$, —CF$_3$, and cyclopropyl. In an even further aspect, each of R$^{10a}$ and R$^{10b}$ is independently selected from methyl, —CF$_3$, and cyclopropyl.

In a further aspect, each of R$^{10a}$ and R$^{10b}$ is independently selected from C1-C3 alkyl, C1-C3 monohaloalkyl, C1-C3 polyhaloalkyl, and cyclopropyl. In a still further aspect, each of R$^{10a}$ and R$^{10b}$ is independently selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of $R^{10a}$ and $R^{10b}$ is independently selected from methyl, —$CH_2F$, —$CH_2Cl$, —$CHF_2$, —$CF_3$, —$CHCl_2$, —$CCl_3$, and cyclopropyl. In an even further aspect, each of $R^{10a}$ and $R^{10b}$ is independently selected from methyl, —$CH_2F$, —$CHF_2$, —$CF_3$, and cyclopropyl. In a still further aspect, each of $R^{10a}$ and $R^{10b}$ is independently selected from methyl, —$CF_3$, and cyclopropyl.

In a further aspect, each of $R^{10a}$ and $R^{10b}$ is independently selected from hydrogen, C1-C3 alkyl, C1-C3 monohaloalkyl, and C1-C3 polyhaloalkyl. In a still further aspect, each of $R^{10a}$ and $R^{10b}$ is independently selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, each of $R^{10a}$ and $R^{10b}$ is independently selected from hydrogen, methyl, —$CH_2F$, —$CH_2Cl$, —$CHF_2$, —$CF_3$, —$CHCl_2$, and —$CCl_3$. In an even further aspect, each of $R^{10a}$ and $R^{10b}$ is independently selected from hydrogen, methyl, —$CH_2F$, —$CHF_2$, and —$CF_3$. In a still further aspect, each of $R^{10a}$ and $R^{10b}$ is independently selected from hydrogen, methyl, and —$CF_3$.

In a further aspect, each of $R^{10a}$ and $R^{10b}$ is independently selected from hydrogen, C1-C3 alkyl, and cyclopropyl. In a still further aspect, each of $R^{10a}$ and $R^{10b}$ is independently selected from hydrogen, methyl, ethyl, and cyclopropyl. In yet a further aspect, each of $R^{10a}$ and $R^{10b}$ is independently selected from hydrogen, methyl, and cyclopropyl.

In a further aspect, each of $R^{10a}$ and $R^{10b}$ is independently selected from hydrogen and C1-C3 alkyl. In a still further aspect, each of $R^{10a}$ and $R^{10b}$ is independently selected from hydrogen, methyl, and ethyl. In yet a further aspect, each of $R^{10a}$ and $R^{10b}$ is independently selected from hydrogen and methyl.

In a further aspect, each of $R^{10a}$ and $R^{10b}$ is independently selected from hydrogen, C1-C3 monohaloalkyl, C1-C3 polyhaloalkyl, and cyclopropyl. In a still further aspect, each of $R^{10a}$ and $R^{10b}$ is independently selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, each of $R^{10a}$ and $R^{10b}$ is independently selected from hydrogen, —$CH_2F$, —$CH_2Cl$, —$CHF_2$, —$CF_3$, —$CHCl_2$, —$CCl_3$, and cyclopropyl. In an even further aspect, each of $R^{10a}$ and $R^{10b}$ is independently selected from hydrogen, —$CH_2F$, —$CHF_2$, —$CF_3$, and cyclopropyl. In a still further aspect, each of $R^{10a}$ and $R^{10b}$ is independently selected from hydrogen, —$CF_3$, and cyclopropyl. In yet a further aspect, each of $R^{10a}$ and $R^{10b}$ is hydrogen.

In a further aspect, $R^{10a}$ is hydrogen and $R^{10b}$ is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In a still further aspect, $R^{10a}$ is hydrogen and $R^{10b}$ is selected from hydrogen, methyl, —$CH_2F$, —$CH_2Cl$, —$CHF_2$, —$CF_3$, —$CHCl_2$, —$CCl_3$, and cyclopropyl. In yet a further aspect, $R^{10a}$ is hydrogen and $R^{10b}$ is selected from methyl, —$CH_2F$, —$CHF_2$, —$CF_3$, and cyclopropyl. In an even further aspect, $R^{10a}$ is hydrogen and $R^{10b}$ is selected from methyl, —$CF_3$, and cyclopropyl.

In a further aspect, $R^{10a}$ is hydrogen and $R^{10b}$ is selected from C1-C3 alkyl, C1-C3 monohaloalkyl, C1-C3 polyhaloalkyl, and cyclopropyl. In a still further aspect, $R^{10a}$ is hydrogen and $R^{10b}$ is selected from methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, $R^{10a}$ is hydrogen and $R^{10b}$ is selected from methyl, —$CH_2F$, —$CH_2Cl$, —$CHF_2$, —$CF_3$, —$CHCl_2$, —$CCl_3$, and cyclopropyl. In an even further aspect, $R^{10a}$ is hydrogen and $R^{10b}$ is selected from methyl, —$CH_2F$, —$CHF_2$, —$CF_3$, and cyclopropyl. In a still further aspect, $R^{10a}$ is hydrogen and $R^{10b}$ is selected from methyl, —$CF_3$, and cyclopropyl.

In a further aspect, $R^{10a}$ is hydrogen and $R^{10b}$ is selected from hydrogen, C1-C3 alkyl, C1-C3 monohaloalkyl, and C1-C3 polyhaloalkyl. In a still further aspect, $R^{10a}$ is hydrogen and $R^{10b}$ is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{10a}$ is hydrogen and $R^{10b}$ is selected from hydrogen, methyl, —$CH_2F$, —$CH_2Cl$, —$CHF_2$, —$CF_3$, —$CHCl_2$, and —$CCl_3$. In an even further aspect, $R^{10a}$ is hydrogen and $R^{10b}$ is selected from hydrogen, methyl, —$CH_2F$, —$CHF_2$, and —$CF_3$. In a still further aspect, $R^{10a}$ is hydrogen and $R^{10b}$ is selected from hydrogen, methyl, and —$CF_3$.

In a further aspect, $R^{10a}$ is hydrogen and $R^{10b}$ is selected from hydrogen, C1-C3 alkyl, and cyclopropyl. In a still further aspect, $R^{10a}$ is hydrogen and $R^{10b}$ is selected from hydrogen, methyl, ethyl, and cyclopropyl. In yet a further aspect, $R^{10a}$ is hydrogen and $R^{10b}$ is selected from hydrogen, methyl, and cyclopropyl.

In a further aspect, $R^{10a}$ is hydrogen and $R^{10b}$ is selected from hydrogen and C1-C3 alkyl. In a still further aspect, $R^{10a}$ is hydrogen and $R^{10b}$ is selected from hydrogen, methyl, and ethyl. In yet a further aspect, $R^{10a}$ is hydrogen and $R^{10b}$ is selected from hydrogen and methyl.

In a further aspect, $R^{10a}$ is hydrogen and $R^{10b}$ is selected from hydrogen, C1-C3 monohaloalkyl, C1-C3 polyhaloalkyl, and cyclopropyl. In a still further aspect, $R^{10a}$ is hydrogen and $R^{10b}$ is selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, $R^{10a}$ is hydrogen and $R^{10b}$ is selected from hydrogen, —$CH_2F$, —$CH_2Cl$, —$CHF_2$, —$CF_3$, —$CHCl_2$, —$CCl_3$, and cyclopropyl. In yet a further aspect, $R^{10a}$ is hydrogen and $R^{10b}$ is selected from hydrogen, —$CH_2F$, —$CHF_2$, —$CF_3$, and cyclopropyl. In an even further aspect, $R^{10a}$ is hydrogen and $R^{10b}$ is selected from hydrogen, —$CF_3$, and cyclopropyl.

p. $R^{12}$ Groups

In one aspect, each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl.

In a further aspect, each occurrence of $R^{12a}$, $R^{12a}$, $R^{12a}$, and $R^{12a}$, when present, is independently selected from hydrogen, C1-C3 alkyl, C1-C3 monohaloalkyl, and C1-C3 polyhaloalkyl. In a still further aspect, each occurrence of $R^{12a}$, $R^{12a}$, $R^{12a}$, and $R^{12a}$, when present, is independently selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, each occurrence of $R^{12a}$, $R^{12a}$, $R^{12a}$, and $R^{12a}$, when present, is independently selected from hydrogen, methyl, —$CH_2F$, —$CH_2Cl$, —$CHF_2$, —$CF_3$, —$CHCl_2$, and —$CCl_3$. In an even further aspect, each occurrence of $R^{12a}$, $R^{12a}$, $R^{12a}$, and $R^{12a}$, when present, is independently selected from hydrogen, methyl, —$CH_2F$, —$CHF_2$, and —$CF_3$. In a still further aspect, each occurrence of $R^{12a}$, $R^{12a}$, $R^{12a}$, and $R^{12a}$, when present, is independently selected from hydrogen, methyl, and —$CF_3$.

In a further aspect, each occurrence of $R^{12a}$, $R^{12a}$, $R^{12a}$, and $R^{12a}$, when present, is independently selected from hydrogen, C1-C3 monohaloalkyl, and C1-C3 polyhaloalkyl.

In a still further aspect, each occurrence of $R^{12a}$, $R^{12a}$, $R^{12a}$, and $R^{12a}$, when present, is independently selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, each occurrence of $R^{12a}$, $R^{12a}$, $R^{12a}$, and $R^{12a}$, when present, is independently selected from hydrogen, —$CH_2F$, —$CH_2Cl$, —$CHF_2$, —$CF_3$, —$CHCl_2$, and —$CCl_3$. In an even further aspect, each occurrence of $R^{12a}$, $R^{12a}$, $R^{12a}$, and $R^{12a}$, when present, is independently selected from hydrogen, —$CH_2F$, —$CHF_2$, and —$CF_3$. In a still further aspect, each occurrence of $R^{12a}$, $R^{12a}$, $R^{12a}$, and $R^{12a}$, when present, is independently selected from hydrogen and —$CF_3$.

In a further aspect, each occurrence of $R^{12a}$, $R^{12a}$, $R^{12a}$, and $R^{12a}$, when present, is independently selected from hydrogen and C1-C3 alkyl. In a still further aspect, each occurrence of $R^{12a}$, $R^{12a}$, $R^{12a}$, and $R^{12a}$, when present, is independently selected from hydrogen, methyl, and ethyl. In yet a further aspect, each occurrence of $R^{12a}$, $R^{12a}$, $R^{12a}$, and $R^{12a}$, when present, is independently selected from hydrogen and methyl.

In a further aspect, each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl. In a still further aspect, each occurrence of $R^{12a}$, $R^{12a}$, $R^{12a}$, and $R^{12a}$, when present, is independently selected from hydrogen, —F, —Cl, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, each occurrence of $R^{12a}$, $R^{12a}$, $R^{12a}$, and $R^{12a}$, when present, is independently selected from m hydrogen, —F, —Cl, methyl, —$CH_2F$, —$CH_2Cl$, —$CHF_2$, —$CF_3$, —$CHCl_2$, and —$CCl_3$. In an even further aspect, each occurrence of $R^{12a}$, $R^{12a}$, $R^{12a}$, and $R^{12a}$, when present, is independently selected from hydrogen, —F, —Cl, methyl, —$CH_2F$, —$CHF_2$, and —$CF_3$. In a still further aspect, each occurrence of $R^{12a}$, $R^{12a}$, $R^{12a}$, and $R^{12a}$, when present, is independently selected from hydrogen, —F, —Cl, methyl, and —$CF_3$. In yet a further aspect, each occurrence of $R^{12a}$, $R^{12a}$, $R^{12a}$, and $R^{12a}$, when present, is independently selected from hydrogen, —F, methyl, and —$CF_3$.

In a further aspect, each occurrence of $R^{12a}$, $R^{12a}$, $R^{12a}$, and $R^{12a}$, when present, is independently selected from hydrogen, halogen, C1-C3 monohaloalkyl, and C1-C3 polyhaloalkyl. In a still further aspect, each occurrence of $R^{12a}$, $R^{12a}$, $R^{12a}$, and $R^{12a}$, when present, is independently selected from hydrogen, —F, —Cl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, each occurrence of $R^{12a}$, $R^{12a}$, $R^{12a}$, and $R^{12a}$, when present, is independently selected from hydrogen, —F, —Cl, —$CH_2F$, —$CH_2Cl$, —$CHF_2$, —$CF_3$, —$CHCl_2$, and —$CCl_3$. In an even further aspect, each occurrence of $R^{12a}$, $R^{12a}$, $R^{12a}$, and $R^{12a}$, when present, is independently selected from hydrogen, —F, —Cl, —$CH_2F$, —$CHF_2$, and —$CF_3$. In a still further aspect, each occurrence of $R^{12a}$, $R^{12a}$, $R^{12a}$, and $R^{12a}$, when present, is independently selected from hydrogen, —F, —Cl, and —$CF_3$. In yet a further aspect, each occurrence of $R^{12a}$, $R^{12a}$, $R^{12a}$, and $R^{12a}$, when present, is independently selected from hydrogen, —F, and —$CF_3$.

In a further aspect, each occurrence of $R^{12a}$, $R^{12a}$, $R^{12a}$, and $R^{12a}$, when present, is independently selected from hydrogen, halogen, and C1-C3 alkyl. In a still further aspect, each occurrence of $R^{12a}$, $R^{12a}$, $R^{12a}$, and $R^{12a}$, when present, is independently selected from hydrogen, —F, —Cl, methyl, and ethyl. In yet a further aspect, each occurrence of $R^{12a}$, $R^{12a}$, $R^{12a}$, and $R^{12a}$, when present, is independently selected from hydrogen, —F, —Cl, and methyl.

In an even further aspect, each occurrence of $R^{12a}$, $R^{12a}$, $R^{12a}$, and $R^{12a}$, when present, is independently selected from hydrogen, —F, and methyl. In a still further aspect, each occurrence of $R^{12a}$, $R^{12a}$, $R^{12a}$, and $R^{12a}$, when present, is hydrogen.

q. $R^{20}$ Groups

In one aspect, $R^{20}$, when present, is selected from hydrogen, C1-C3 alkyl, C1-C3 monohaloalkyl, C1-C3 polyhaloalkyl, and cyclopropyl. In a further aspect, $R^{20}$, when present, is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In a still further aspect, $R^{20}$, when present, is selected from hydrogen, methyl, —$CH_2F$, —$CH_2Cl$, —$CHF_2$, —$CF_3$, —$CHCl_2$, —$CCl_3$, and cyclopropyl. In a yet further aspect, $R^{20}$, when present, is selected from hydrogen, methyl, —$CH_2F$, —$CHF_2$, —$CF_3$, and cyclopropyl. In an even further aspect, $R^{20}$, when present, is selected from hydrogen, methyl, —$CF_3$, and cyclopropyl.

In a further aspect, $R^{20}$, when present, is selected from hydrogen, C1-C3 monohaloalkyl, C1-C3 polyhaloalkyl, and cyclopropyl. In a still further aspect, $R^{20}$, when present, is selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In a yet further aspect, $R^{20}$, when present, is selected from hydrogen, —$CH_2F$, —$CH_2Cl$, —$CHF_2$, —$CF_3$, —$CHCl_2$, —$CCl_3$, and cyclopropyl. In an even further aspect, $R^{20}$, when present, is selected from hydrogen, —$CH_2F$, —$CHF_2$, —$CF_3$, and cyclopropyl. In a still further aspect, $R^{20}$, when present, is selected from hydrogen, —$CF_3$ and cyclopropyl.

In a further aspect, $R^{20}$, when present, is selected from hydrogen, C1-C3 alkyl, and cyclopropyl. In a still further aspect, $R^{20}$, when present, is selected from hydrogen, methyl, ethyl, and cyclopropyl. In a yet further aspect, $R^{20}$, when present, is selected from hydrogen, methyl, and cyclopropyl.

In a further aspect, $R^{20}$, when present, is selected from hydrogen, C1-C3 alkyl, C1-C3 monohaloalkyl, and C1-C3 polyhaloalkyl. In a still further aspect, $R^{20}$, when present, is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a yet further aspect, $R^{20}$, when present, is selected from hydrogen, methyl, —$CH_2F$, —$CH_2Cl$, —$CHF_2$, —$CF_3$, —$CHCl_2$, and —$CCl_3$. In an even further aspect, $R^{20}$, when present, is selected from hydrogen, methyl, —$CH_2F$, —$CHF_2$, and —$CF_3$. In a still further aspect, $R^{20}$, when present, is selected from hydrogen, methyl, and —$CF_3$.

In a further aspect, $R^{20}$, when present, is selected from hydrogen, C1-C3 monohaloalkyl, and C1-C3 polyhaloalkyl. In a still further aspect, $R^{20}$, when present, is selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a yet further aspect, $R^{20}$, when present, is selected from hydrogen, —$CH_2F$, —$CH_2Cl$, —$CHF_2$, —$CF_3$, —$CHCl_2$, and —$CCl_3$. In an even further aspect, $R^{20}$, when present, is selected from hydrogen, —$CH_2F$, —$CHF_2$, and —$CF_3$. In a still further aspect, $R^{20}$, when present, is selected from hydrogen and —$CF_3$.

In a further aspect, $R^{20}$, when present, is selected from hydrogen and C1-C3 alkyl. In a still further aspect, $R^{20}$, when present, is selected from hydrogen, methyl, and ethyl. In a yet further aspect, $R^{20}$, when present, is selected from hydrogen and methyl. In an even further aspect, $R^{20}$, when present, is hydrogen.

r. $R^{21}$ Groups

In one aspect, each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle.

In a further aspect, each of $R^{21a}$ and $R^{21b}$, when present, is independently selected from hydrogen, C1-C3 alkyl, C1-C3 monohaloalkyl, C1-C3 polyhaloalkyl, and cyclopropyl. In a still further aspect, each of $R^{21a}$ and $R^{21b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, each of $R^{21a}$ and $R^{21b}$, when present, is independently selected from hydrogen, methyl, —CH$_2$F, —CH$_2$Cl, —CHF$_2$, —CF$_3$, —CHCl$_2$, —CCl$_3$, and cyclopropyl. In an even further aspect, each of $R^{21a}$ and $R^{21b}$, when present, is independently selected from hydrogen, methyl, —CH$_2$F, —CHF$_2$, —CF$_3$, and cyclopropyl. In a still further aspect, each of $R^{21a}$ and $R^{21b}$, when present, is independently selected from hydrogen, methyl, —CF$_3$, and cyclopropyl.

In a further aspect, each of $R^{21a}$ and $R^{21b}$, when present, is independently selected from hydrogen, C1-C3 monohaloalkyl, C1-C3 polyhaloalkyl, and cyclopropyl. In a still further aspect, each of $R^{21a}$ and $R^{21b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, each of $R^{21a}$ and $R^{21b}$, when present, is independently selected from hydrogen, —CH$_2$F, —CH$_2$Cl, —CHF$_2$, —CF$_3$, —CHCl$_2$, —CCl$_3$, and cyclopropyl. In an even further aspect, each of $R^{21a}$ and $R^{21b}$, when present, is independently selected from hydrogen, —CH$_2$F, —CHF$_2$, —CF$_3$, and cyclopropyl. In a still further aspect, each of $R^{21a}$ and $R^{21b}$, when present, is independently selected from hydrogen, —CF$_3$ and cyclopropyl.

In a further aspect, each of $R^{21a}$ and $R^{21b}$, when present, is independently selected from hydrogen, C1-C3 alkyl, and cyclopropyl. In a still further aspect, each of $R^{21a}$ and $R^{21b}$, when present, is independently selected from hydrogen, methyl, ethyl, and cyclopropyl. In a yet further aspect, each of $R^{21a}$ and $R^{21b}$, when present, is independently selected from hydrogen, methyl, and cyclopropyl.

In a further aspect, each of $R^{21a}$ and $R^{21b}$, when present, is independently selected from hydrogen, C1-C3 alkyl, C1-C3 monohaloalkyl, and C1-C3 polyhaloalkyl. In a still further aspect, each of $R^{21a}$ and $R^{21b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each of $R^{21a}$ and $R^{21b}$, when present, is independently selected from hydrogen, methyl, —CH$_2$F, —CH$_2$Cl, —CHF$_2$, —CF$_3$, —CHCl$_2$, and —CCl$_3$. In an even further aspect, each of $R^{21a}$ and $R^{21b}$, when present, is independently selected from hydrogen, methyl, —CH$_2$F, —CHF$_2$, and —CF$_3$. In a still further aspect, each of $R^{21a}$ and $R^{21b}$, when present, is independently selected from hydrogen, methyl, and —CF$_3$.

In a further aspect, each of $R^{21a}$ and $R^{21b}$, when present, is independently selected from hydrogen, C1-C3 monohaloalkyl, and C1-C3 polyhaloalkyl. In a still further aspect, each of $R^{21a}$ and $R^{21b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each of $R^{21a}$ and $R^{21b}$, when present, is independently selected from hydrogen, —CH$_2$F, —CH$_2$Cl, —CHF$_2$, —CF$_3$, —CHCl$_2$, and —CCl$_3$. In an even further aspect, each of $R^{21a}$ and $R^{21b}$, when present, is independently selected from hydrogen, —CH$_2$F, —CHF$_2$, and —CF$_3$. In a still further aspect, each of $R^{21a}$ and $R^{21b}$, when present, is independently selected from hydrogen and —CF$_3$.

In a further aspect, each of $R^{21a}$ and $R^{21b}$, when present, is independently selected from hydrogen and C1-C3 alkyl. In a still further aspect, each of $R^{21a}$ and $R^{21b}$, when present, is independently selected from hydrogen, methyl, and ethyl. In a yet further aspect, each of $R^{21a}$ and $R^{21b}$, when present, is independently selected from hydrogen and methyl.

In a further aspect, $R^{21a}$, when present, is hydrogen and $R^{21b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, $R^{21a}$, when present, is hydrogen and $R^{21b}$, when present, is selected from hydrogen, methyl, —CH$_2$F, —CH$_2$Cl, —CHF$_2$, —CF$_3$, —CHCl$_2$, —CCl$_3$, and cyclopropyl. In a yet further aspect, $R^{21a}$, when present, is hydrogen and $R^{21b}$, when present, is selected from hydrogen, methyl, —CH$_2$F, —CHF$_2$, —CF$_3$, and cyclopropyl. In an even further aspect, $R^{21a}$, when present, is hydrogen and $R^{21b}$, when present, is selected from hydrogen, methyl, —CF$_3$, and cyclopropyl.

In a further aspect, $R^{21a}$, when present, is hydrogen and $R^{21b}$, when present, is selected from hydrogen, C1-C3 monohaloalkyl, C1-C3 polyhaloalkyl, and cyclopropyl. In a still further aspect, $R^{21a}$, when present, is hydrogen and $R^{21b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, $R^{21a}$, when present, is hydrogen and $R^{21b}$, when present, is selected from hydrogen, —CH$_2$F, —CH$_2$Cl, —CHF$_2$, —CF$_3$, —CHCl$_2$, —CCl$_3$, and cyclopropyl. In an even further aspect, $R^{21a}$, when present, is hydrogen and $R^{21b}$, when present, is selected from hydrogen, —CH$_2$F, —CHF$_2$, —CF$_3$, and cyclopropyl. In a still further aspect, $R^{21a}$, when present, is hydrogen and $R^{21b}$, when present, is selected from hydrogen, —CF$_3$ and cyclopropyl.

In a further aspect, $R^{21a}$, when present, is hydrogen and $R^{21b}$, when present, is selected from hydrogen, C1-C3 alkyl, and cyclopropyl. In a still further aspect, $R^{21a}$, when present, is hydrogen and $R^{21b}$, when present, is selected from hydrogen, methyl, ethyl, and cyclopropyl. In a yet further aspect, $R^{21a}$, when present, is hydrogen and $R^{21b}$, when present, is selected from hydrogen, methyl, and cyclopropyl.

In a further aspect, $R^{21a}$, when present, is hydrogen and $R^{21b}$, when present, is selected from hydrogen, C1-C3 alkyl, C1-C3 monohaloalkyl, and C1-C3 polyhaloalkyl. In a still further aspect, $R^{21a}$, when present, is hydrogen and $R^{21b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{21a}$, when present, is hydrogen and R$^{21b}$, when present, is selected from hydrogen, methyl, —CH$_2$F, —CH$_2$Cl, —CHF$_2$, —CF$_3$, —CHCl$_2$, and —CCl$_3$. In an even further aspect, R$^{21a}$, when present, is hydrogen and R$^{21b}$, when present, is selected from hydrogen, methyl, —CH$_2$F, —CHF$_2$, and —CF$_3$. In a still further aspect, R$^{21a}$, when present, is hydrogen and R$^{21b}$, when present, is selected from hydrogen, methyl, and —CF$_3$.

In a further aspect, R$^{21a}$, when present, is hydrogen and R$^{21b}$, when present, is selected from hydrogen, C1-C3 monohaloalkyl, and C1-C3 polyhaloalkyl. In a still further aspect, R$^{21a}$, when present, is hydrogen and R$^{21b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{21a}$, when present, is hydrogen and R$^{21b}$, when present, is selected from hydrogen, —CH$_2$F, —CH$_2$Cl, —CHF$_2$, —CF$_3$, —CHCl$_2$, and —CCl$_3$. In an even further aspect, R$^{21a}$, when present, is hydrogen and R$^{21b}$, when present, is selected from hydrogen, —CH$_2$F, —CHF$_2$, and —CF$_3$. In a still further aspect, R$^{21a}$, when present, is hydrogen and R$^{21b}$, when present, is selected from hydrogen and —CF$_3$.

In a further aspect, R$^{21a}$, when present, is hydrogen and R$^{21b}$, when present, is selected from hydrogen and C1-C3 alkyl. In a still further aspect, R$^{21a}$, when present, is hydrogen and R$^{21b}$, when present, is selected from hydrogen, methyl, and ethyl. In a yet further aspect, each of R$^{21a}$ and R$^{21b}$, when present, is hydrogen.

In a further aspect, R$^{21a}$ and R$^{21b}$, when present, are optionally covalently bonded and, together with the nitrogen atom to which they are attached, comprise a 3- to 6-membered heterocycle. In a still further aspect, R$^{21a}$ and R$^{21b}$, when present, are covalently bonded, and together with the nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In a yet further aspect, R$^{21a}$ and R$^{21b}$, when present, are covalently bonded, and together with nitrogen atom to which they are attached, comprise a heterocycle selected from pyrrolidinyl, piperidinyl, azepanyl, imidazolidinyl, and pyrazolidinyl. In an even further aspect, R$^{21a}$ and R$^{21b}$, when present, are covalently bonded, and together with nitrogen atom to which they are attached, comprise a heterocycle selected from imidazolyl, pyrazolyl, and pyrrolyl. In a still further aspect, R$^{21a}$ and R$^{21b}$, when present, are covalently bonded, and together with nitrogen atom to which they are attached, comprise a pyrrolidinyl. In a yet further aspect, R$^{21a}$ and R$^{21b}$, when present, are covalently bonded, and together with nitrogen atom to which they are attached, comprise a piperidinyl.

s. R$^{22}$ Groups

In one aspect, R$^{22}$, when present, is selected from C1-C3 alkyl, C1-C3 monohaloalkyl, C1-C3 polyhaloalkyl, cyclopropyl, and, —NR$^{24a}$R$^{24b}$. In a further aspect, R$^{22}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, R$^{22}$, when present, is selected from methyl, —CH$_2$F, —CH$_2$Cl, —CHF$_2$, —CF$_3$, —CHCl$_2$, —CCl$_3$, cyclopropyl, —NHCH$_3$, and —N(CH$_3$)$_2$. In a yet further aspect, R$^{22}$, when present, is selected from methyl, —CH$_2$F, —CHF$_2$, —CF$_3$, cyclopropyl, —NHCH$_3$, and —N(CH$_3$)$_2$. In an even further aspect, R$^{22}$, when present, is selected from methyl, —CF$_3$, cyclopropyl, and —NHCH$_3$.

In a further aspect, R$^{22}$, when present, is selected from C1-C3 alkyl, C1-C3 monohaloalkyl, C1-C3 polyhaloalkyl, and, —NR$^{24a}$R$^{24b}$. In a still further aspect, R$^{22}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, R$^{22}$, when present, is selected from methyl, —CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^{22}$, when present, is selected from methyl, —CH$_2$F, —CHF$_2$, —CF$_3$, —NHCH$_3$, and —N(CH$_3$)$_2$. In a still further aspect, R$^{22}$, when present, is selected from methyl, —CF$_3$, and —NHCH$_3$.

In a further aspect, R$^{22}$, when present, is selected from C1-C3 alkyl, C1-C3 monohaloalkyl, C1-C3 polyhaloalkyl, and cyclopropyl. In a still further aspect, R$^{22}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, R$^{22}$, when present, is selected from methyl, —CH$_2$F, —CH$_2$Cl, —CHF$_2$, —CF$_3$, —CHCl$_2$, —CC$_3$, and cyclopropyl. In an even further aspect, R$^{22}$, when present, is selected from methyl, —CH$_2$F, —CHF$_2$, —CF$_3$, and cyclopropyl. In a still further aspect, R$^{22}$, when present, is selected from methyl, —CF$_3$, and cyclopropyl.

In a further aspect, R$^{22}$, when present, is selected from C1-C3 monohaloalkyl, C1-C3 polyhaloalkyl, and cyclopropyl. In a still further aspect, R$^{22}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, R$^{22}$, when present, is selected from —CH$_2$F, —CH$_2$Cl, —CHF$_2$, —CF$_3$, —CHCl$_2$, —CCl$_3$, and cyclopropyl. In an even further aspect, R$^{22}$, when present, is selected from —CH$_2$F, —CHF$_2$, —CF$_3$, and cyclopropyl. In a still further aspect, R$^{22}$, when present, is selected from —CF$_3$ and cyclopropyl.

In a further aspect, R$^{22}$, when present, is selected from C1-C3 alkyl, and cyclopropyl. In a still further aspect, R$^{22}$, when present, is selected from methyl, ethyl, and cyclopropyl. In a yet further aspect, R$^{22}$, when present, is selected from methyl, and cyclopropyl.

In a further aspect, R$^{22}$, when present, is selected from C1-C3 alkyl, C1-C3 monohaloalkyl, and C1-C3 polyhaloalkyl. In a still further aspect, R$^{22}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{22}$, when present, is selected from methyl, —CH$_2$F, —CH$_2$Cl, —CHF$_2$, —CF$_3$, —CHCl$_2$, and —CCl$_3$. In an even further aspect, R$^{22}$, when present, is selected from methyl, —CH$_2$F, —CHF$_2$, and —CF$_3$. In a still further aspect, R$^{22}$, when present, is selected from methyl and —CF$_3$.

In a further aspect, R$^{22}$, when present, is selected from C1-C3 monohaloalkyl, and C1-C3 polyhaloalkyl. In a still further aspect, R$^{22}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{22}$, when present, is selected from —CH$_2$F, —CH$_2$Cl, —CHF$_2$, —CF$_3$, —CHCl$_2$, and —CCl$_3$. In an even further aspect, R$^2$, when present, is selected from —CH$_2$F, —CHF$_2$, and —CF$_3$. In a yet further aspect, R$^{22}$, when present, is —CF$_3$.

In a further aspect, R$^{22}$, when present, is C1-C3 alkyl. In a still further aspect, R$^{22}$ is selected from methyl, and ethyl. In a yet further aspect, R$^{22}$, when present, is methyl.

t. R$^{23}$ Groups

In one aspect, R$^{23}$, when present, is selected from C1-C3 alkyl, C1-C3 monohaloalkyl, C1-C3 polyhaloalkyl, cyclopropyl, and, —NR$^{25a}$R$^{25b}$. In a further aspect, R$^{23}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, R$^{23}$, when present, is selected from methyl, —CH$_2$F, —CH$_2$Cl, —CHF$_2$, —CF$_3$, —CHCl$_2$, —CCl$_3$, cyclopropyl, —NHCH$_3$, and —N(CH$_3$)$_2$. In a yet further aspect, R$^{23}$, when present, is selected from methyl, —CH$_2$F, —CHF$_2$, —CF$_3$, cyclopropyl, —NHCH$_3$, and —N(CH$_3$)$_2$. In an even further aspect, R$^{23}$, when present, is selected from methyl, —CF$_3$, cyclopropyl, and —NHCH$_3$.

In further aspect, R$^{23}$, when present, is selected from C1-C3 alkyl, C1-C3 monohaloalkyl, C1-C3 polyhaloalkyl, and, —NR$^{24a}$R$^{24b}$. In a still further aspect, R$^{23}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, R$^{23}$, when present, is selected from methyl, —CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^{23}$, when present, is selected from methyl, —CH$_2$F, —CHF$_2$, —CF$_3$, —NHCH$_3$, and —N(CH$_3$)$_2$. In a still further aspect, R$^{23}$, when present, is selected from methyl, —CF$_3$, and —NHCH$_3$.

In a further aspect, R$^{23}$, when present, is selected from C1-C3 alkyl, C1-C3 monohaloalkyl, C1-C3 polyhaloalkyl, and cyclopropyl. In a still further aspect, R$^{23}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, R$^{23}$, when present, is selected from methyl, —CH$_2$F, —CH$_2$Cl, —CHF$_2$, —CF$_3$, —CHCl$_2$, —CCl$_3$, and cyclopropyl. In an even further aspect, R$^{23}$, when present, is selected from methyl, —CH$_2$F, —CHF$_2$, —CF$_3$, and cyclopropyl. In a still further aspect, R$^{23}$, when present, is selected from methyl, —CF$_3$, and cyclopropyl.

In a further aspect, R$^{23}$, when present, is selected from C1-C3 monohaloalkyl, C1-C3 polyhaloalkyl, and cyclopropyl. In a still further aspect, R$^{23}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, R$^{23}$, when present, is selected from —CH$_2$F, —CH$_2$Cl, —CHF$_2$, —CF$_3$, —CHCl$_2$, —CCl$_3$, and cyclopropyl. In an even further aspect, R$^{23}$, when present, is selected from —CH$_2$F, —CHF$_2$, —CF$_3$, and cyclopropyl. In a still further aspect, R$^{23}$, when present, is selected from —CF$_3$ and cyclopropyl.

In a further aspect, R$^{23}$, when present, is selected from C1-C3 alkyl, and cyclopropyl. In a still further aspect, R$^{23}$, when present, is selected from methyl, ethyl, and cyclopropyl. In a yet further aspect, R$^{23}$, when present, is selected from methyl, and cyclopropyl.

In a further aspect, R$^{23}$, when present, is selected from C1-C3 alkyl, C1-C3 monohaloalkyl, and C1-C3 polyhaloalkyl. In a still further aspect, R$^{23}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{23}$, when present, is selected from methyl, —CH$_2$F, —CH$_2$Cl, —CHF$_2$, —CF$_3$, —CHCl$_2$, and —CCl$_3$. In an even further aspect, R$^{23}$, when present, is selected from methyl, —CH$_2$F, —CHF$_2$, and —CF$_3$. In a still further aspect, R$^{23}$, when present, is selected from methyl and —CF$_3$.

In a further aspect, R$^{23}$, when present, is selected from C1-C3 monohaloalkyl, and C1-C3 polyhaloalkyl. In a still further aspect, R$^{23}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{23}$, when present, is selected from —CH$_2$F, —CH$_2$Cl, —CHF$_2$, —CF$_3$, —CHCl$_2$, and —CCl$_3$. In an even further aspect, R$^{23}$, when present, is selected from —CH$_2$F, —CHF$_2$, and —CF$_3$. In a still further aspect, R$^{23}$, when present, is —CF$_3$.

In a further aspect, R$^{23}$, when present, is C1-C3 alkyl. In a still further aspect, R$^{23}$, when present, is selected from methyl, and ethyl. In a yet further aspect, R$^{23}$, when present, is methyl.

u. R$^{24}$ Groups

In one aspect, each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle. In a further aspect, each of R$^{24a}$ and R$^{24b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, each of R$^{24a}$ and R$^{24b}$, when present, is independently selected from hydrogen, methyl, —CH$_2$F, —CH$_2$Cl, —CHF$_2$, —CF$_3$, —CHCl$_2$, —CCl$_3$, and cyclopropyl. In a yet further aspect, each of R$^{24a}$ and R$^{24b}$, when present, is independently selected from hydrogen, methyl, —CH$_2$F, —CHF$_2$, —CF$_3$, and cyclopropyl. In an even further aspect, each of R$^{24a}$ and R$^{24b}$, when present, is independently selected from hydrogen, methyl, —CF$_3$, and cyclopropyl.

In a further aspect, each of R$^{24a}$ and R$^{24b}$, when present, is independently selected from hydrogen, C1-C3 monohaloalkyl, C1-C3 polyhaloalkyl, and cyclopropyl. In a still further aspect, each of R$^{24a}$ and R$^{24b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, each of R$^{24a}$ and R$^{24b}$, when present, is independently selected from hydrogen, —CH$_2$F, —CH$_2$Cl, —CHF$_2$, —CF$_3$, —CHCl$_2$, —CCl$_3$, and cyclopropyl. In an even further aspect, each of R$^{24a}$ and R$^{24b}$, when present, is independently selected from hydrogen, —CH$_2$F, —CHF$_2$, —CF$_3$, and cyclopropyl. In a still further aspect, each of $R^{24a}$ and $R^{24b}$, when present, is independently selected from hydrogen, —$CF_3$ and cyclopropyl.

In a further aspect, each of $R^{24a}$ and $R^{24b}$, when present, is independently selected from hydrogen, C1-C3 alkyl, and cyclopropyl. In a still further aspect, each of $R^{24a}$ and $R^{24b}$, when present, is independently selected from hydrogen, methyl, ethyl, and cyclopropyl. In a yet further aspect, each of $R^{24a}$ and $R^{24b}$, when present, is independently selected from hydrogen, methyl, and cyclopropyl.

In a further aspect, each of $R^{24a}$ and $R^{24b}$, when present, is independently selected from hydrogen, C1-C3 alkyl, C1-C3 monohaloalkyl, and C1-C3 polyhaloalkyl. In a still further aspect, each of $R^{24a}$ and $R^{24b}$, when present, is independently selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a yet further aspect, each of $R^{24a}$ and $R^{24b}$, when present, is independently selected from hydrogen, methyl, —$CH_2F$, —$CH_2Cl$, —$CHF_2$, —$CF_3$, —$CHCl_2$, and —$CCl_3$. In an even further aspect, each of $R^{24a}$ and $R^{24b}$, when present, is independently selected from hydrogen, methyl, —$CH_2F$, —$CHF_2$, and —$CF_3$. In a still further aspect, each of $R^{24a}$ and $R^{24b}$, when present, is independently selected from hydrogen, methyl, and —$CF_3$.

In a further aspect, each of $R^{24a}$ and $R^{24b}$, when present, is independently selected from hydrogen, C1-C3 monohaloalkyl, and C1-C3 polyhaloalkyl. In a still further aspect, each of $R^{24a}$ and $R^{24b}$, when present, is independently selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a yet further aspect, each of $R^{24a}$ and $R^{24b}$, when present, is independently selected from hydrogen, —$CH_2F$, —$CH_2Cl$, —$CHF_2$, —$CF_3$, —$CHCl_2$, and —$CCl_3$. In an even further aspect, each of $R^{24a}$ and $R^{24b}$, when present, is independently selected from hydrogen, —$CH_2F$, —$CHF_2$, and —$CF_3$. In a still further aspect, each of $R^{24a}$ and $R^{24b}$, when present, is independently selected from hydrogen and —$CF_3$.

In a further aspect, each of $R^{24a}$ and $R^{24b}$, when present, is independently selected from hydrogen and C1-C3 alkyl. In a still further aspect, each of $R^{24a}$ and $R^{24b}$, when present, is independently selected from hydrogen, methyl, and ethyl. In a yet further aspect, each of $R^{24a}$ and $R^{24b}$, when present, is independently selected from hydrogen and methyl.

In a further aspect, $R^{24a}$, when present, is hydrogen and $R^{24b}$, when present, is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In a still further aspect, $R^{24a}$, when present, is hydrogen and $R^{24b}$, when present, is selected from hydrogen, methyl, —$CH_2F$, —$CH_2Cl$, —$CHF_2$, —$CF_3$, —$CHCl_2$, —$CCl_3$, and cyclopropyl. In a yet further aspect, $R^{24a}$, when present, is hydrogen and $R^{24b}$, when present, is selected from hydrogen, methyl, —$CH_2F$, —$CHF_2$, —$CF_3$, and cyclopropyl. In an even further aspect, $R^{24a}$, when present, is hydrogen and $R^{24b}$, when present, is selected from hydrogen, methyl, —$CF_3$, and cyclopropyl.

In a further aspect, $R^{24a}$, when present, is hydrogen and $R^{24b}$, when present, is selected from hydrogen, C1-C3 monohaloalkyl, C1-C3 polyhaloalkyl, and cyclopropyl. In a still further aspect, $R^{24a}$, when present, is hydrogen and $R^{24b}$, when present, is selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In a yet further aspect, $R^{24a}$, when present, is hydrogen and $R^{24b}$, when present, is selected from hydrogen, —$CH_2F$, —$CH_2Cl$, —$CHF_2$, —$CF_3$, —$CHCl_2$, —$CCl_3$, and cyclopropyl. In an even further aspect, $R^{24a}$, when present, is hydrogen and $R^{24b}$, when present, is selected from hydrogen, —$CH_2F$, —$CHF_2$, —$CF_3$, and cyclopropyl. In a still further aspect, $R^{24a}$, when present, is hydrogen and $R^{24b}$, when present, is selected from hydrogen, —$CF_3$ and cyclopropyl.

In a further aspect, $R^{24a}$, when present, is hydrogen and $R^{24b}$, when present, is selected from hydrogen, C1-C3 alkyl, and cyclopropyl. In a still further aspect, $R^{24a}$, when present, is hydrogen and $R^{24b}$, when present, is selected from hydrogen, methyl, ethyl, and cyclopropyl. In a yet further aspect, $R^{24a}$, when present, is hydrogen and $R^{24b}$, when present, is selected from hydrogen, methyl, and cyclopropyl.

In a further aspect, $R^{24a}$, when present, is hydrogen and $R^{24b}$, when present, is selected from hydrogen, C1-C3 alkyl, C1-C3 monohaloalkyl, and C1-C3 polyhaloalkyl. In a still further aspect, $R^{24a}$, when present, is hydrogen and $R^{24b}$, when present, is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a yet further aspect, $R^{24a}$, when present, is hydrogen and $R^{24b}$, when present, is selected from hydrogen, methyl, —$CH_2F$, —$CH_2Cl$, —$CHF_2$, —$CF_3$, —$CHCl_2$, and —$CCl_3$. In an even further aspect, $R^{24a}$, when present, is hydrogen and $R^{24b}$, when present, is selected from hydrogen, methyl, —$CH_2F$, —$CHF_2$, and —$CF_3$. In a still further aspect, $R^{24a}$, when present, is hydrogen and $R^{24b}$, when present, is selected from hydrogen, methyl, and —$CF_3$.

In a further aspect, $R^{24a}$, when present, is hydrogen and $R^{24b}$, when present, is selected from hydrogen, C1-C3 monohaloalkyl, and C1-C3 polyhaloalkyl. In a still further aspect, $R^{24a}$, when present, is hydrogen and $R^{24b}$, when present, is selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a yet further aspect, $R^{24a}$, when present, is hydrogen and $R^{24b}$, when present, is selected from hydrogen, —$CH_2F$, —$CH_2Cl$, —$CHF_2$, —$CF_3$, —$CHCl_2$, and —$CCl_3$. In an even further aspect, $R^{24a}$, when present, is hydrogen and $R^{24b}$, when present, is selected from hydrogen, —$CH_2F$, —$CHF_2$, and —$CF_3$. In a still further aspect, $R^{24a}$, when present, is hydrogen and $R^{24b}$, when present, is selected from hydrogen and —$CF_3$.

In a further aspect, $R^{24a}$, when present, is hydrogen and $R^{24b}$, when present, is selected from hydrogen and C1-C3 alkyl. In a still further aspect, $R^{24a}$, when present, is hydrogen and $R^{24b}$, when present, is selected from hydrogen, methyl, and ethyl. In a yet further aspect, $R^{24a}$, when present, is hydrogen and $R^{24b}$ is selected from hydrogen and methyl. In an even further aspect, each of $R^{24a}$ and $R^{24b}$, when present, is hydrogen.

v. $R^{25}$ Groups

In one aspect, each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle.

In a further aspect, each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle. In a still further aspect, each of $R^{25a}$ and $R^{25b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, each of $R^{25a}$ and $R^{25b}$, when present, is independently selected from hydrogen, methyl, —CH$_2$F, —CH$_2$Cl, —CHF$_2$, —CF$_3$, —CHCl$_2$, —CCl$_3$, and cyclopropyl. In an even further aspect, each of $R^{25a}$ and $R^{25b}$, when present, is independently selected from hydrogen, methyl, —CH$_2$F, —CHF$_2$, —CF$_3$, and cyclopropyl. In a still further aspect, each of $R^{25a}$ and $R^{25b}$, when present, is independently selected from hydrogen, methyl, —CF$_3$, and cyclopropyl.

In a further aspect, each of $R^{25a}$ and $R^{25b}$, when present, is independently selected from hydrogen, C1-C3 monohaloalkyl, C1-C3 polyhaloalkyl, and cyclopropyl. In a still further aspect, each of $R^{25a}$ and $R^{25b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, each of $R^{25a}$ and $R^{25b}$, when present, is independently selected from hydrogen, —CH$_2$F, —CH$_2$Cl, —CHF$_2$, —CF$_3$, —CHCl$_2$, —CCl$_3$, and cyclopropyl. In an even further aspect, each of $R^{25a}$ and $R^{25b}$, when present, is independently selected from hydrogen, —CH$_2$F, —CHF$_2$, —CF$_3$, and cyclopropyl. In a still further aspect, each of $R^{25a}$ and $R^{25b}$, when present, is independently selected from hydrogen, —CF$_3$ and cyclopropyl.

In a further aspect, each of $R^{25a}$ and $R^{25b}$, when present, is independently selected from hydrogen, C1-C3 alkyl, and cyclopropyl. In a still further aspect, each of $R^{25a}$ and $R^{25b}$, when present, is independently selected from hydrogen, methyl, ethyl, and cyclopropyl. In a yet further aspect, each of $R^{25a}$ and $R^{25b}$, when present, is independently selected from hydrogen, methyl, and cyclopropyl.

In a further aspect, each of $R^{25a}$ and $R^{25b}$, when present, is independently selected from hydrogen, C1-C3 alkyl, C1-C3 monohaloalkyl, and C1-C3 polyhaloalkyl. In a still further aspect, each of $R^{25a}$ and $R^{25b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each of $R^{25a}$ and $R^{25b}$, when present, is independently selected from hydrogen, methyl, —CH$_2$F, —CH$_2$Cl, —CHF$_2$, —CF$_3$, —CHCl$_2$, and —CCl$_3$. In an even further aspect, each of $R^{25a}$ and $R^{25b}$, when present, is independently selected from hydrogen, methyl, —CH$_2$F, —CHF$_2$, and —CF$_3$. In a still further aspect, each of $R^{25a}$ and $R^{25b}$, when present, is independently selected from hydrogen, methyl, and —CF$_3$.

In a further aspect, each of $R^{25a}$ and $R^{25b}$, when present, is independently selected from hydrogen, C1-C3 monohaloalkyl, and C1-C3 polyhaloalkyl. In a still further aspect, each of $R^{25a}$ and $R^{25b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each of $R^{25a}$ and $R^{25b}$, when present, is independently selected from hydrogen, —CH$_2$F, —CH$_2$Cl, —CHF$_2$, —CF$_3$, —CHCl$_2$, and —CCl$_3$. In an even further aspect, each of $R^{25a}$ and $R^{25b}$, when present, is independently selected from hydrogen, —CH$_2$F, —CHF$_2$, and —CF$_3$. In a still further aspect, each of $R^{25a}$ and $R^{25b}$, when present, is independently selected from hydrogen and —CF$_3$.

In a further aspect, each of $R^{25a}$ and $R^{25b}$, when present, is independently selected from hydrogen and C1-C3 alkyl. In a still further aspect, each of $R^{25a}$ and $R^{25b}$, when present, is independently selected from hydrogen, methyl, and ethyl. In a yet further aspect, each of $R^{25a}$ and $R^{25b}$, when present, is independently selected from hydrogen and methyl.

In a further aspect, $R^{25a}$, when present, is hydrogen and $R^{25b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, $R^{25a}$, when present, is hydrogen and $R^{25b}$, when present, is selected from hydrogen, methyl, —CH$_2$F, —CH$_2$Cl, —CHF$_2$, —CF$_3$, —CHCl$_2$, —CCl$_3$, and cyclopropyl. In a yet further aspect, $R^{25a}$, when present, is hydrogen and $R^{25b}$, when present, is selected from hydrogen, methyl, —CH$_2$F, —CHF$_2$, —CF$_3$, and cyclopropyl. In an even further aspect, $R^{25a}$, when present, is hydrogen and $R^{25b}$, when present, is selected from hydrogen, methyl, —CF$_3$, and cyclopropyl.

In a further aspect, $R^{25a}$, when present, is hydrogen and $R^{25b}$, when present, is selected from hydrogen, C1-C3 monohaloalkyl, C1-C3 polyhaloalkyl, and cyclopropyl. In a still further aspect, $R^{25a}$, when present, is hydrogen and $R^{25b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, $R^{25a}$, when present, is hydrogen and $R^{25b}$, when present, is selected from hydrogen, —CH$_2$F, —CH$_2$Cl, —CHF$_2$, —CF$_3$, —CHCl$_2$, —CCl$_3$, and cyclopropyl. In an even further aspect, $R^{25a}$, when present, is hydrogen and $R^{25b}$, when present, is selected from hydrogen, —CH$_2$F, —CHF$_2$, —CF$_3$, and cyclopropyl. In a still further aspect, $R^{25a}$, when present, is hydrogen and $R^{25b}$, when present, is selected from hydrogen, —CF$_3$ and cyclopropyl.

In a further aspect, $R^{25a}$, when present, is hydrogen and $R^{25b}$, when present, is selected from hydrogen, C1-C3 alkyl, and cyclopropyl. In a still further aspect, $R^{25a}$, when present, is hydrogen and $R^{25b}$, when present, is selected from hydrogen, methyl, ethyl, and cyclopropyl. In a yet further aspect, $R^{25a}$, when present, is hydrogen and $R^{25b}$, when present, is selected from hydrogen, methyl, and cyclopropyl.

In a further aspect, $R^{25a}$, when present, is hydrogen and $R^{25b}$, when present, is selected from hydrogen, C1-C3 alkyl, C1-C3 monohaloalkyl, and C1-C3 polyhaloalkyl. In a still further aspect, $R^{25a}$, when present, is hydrogen and $R^{25b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, $R^{25a}$, when present, is hydrogen and $R^{25b}$, when present, is selected from hydrogen, methyl, —CH$_2$F, —CH$_2$Cl, —CHF$_2$, —CF$_3$, —CHCl$_2$, and —CCl$_3$. In an even further aspect, $R^{25a}$, when present, is hydrogen and $R^{25b}$, when present, is selected from hydrogen, methyl, —CH$_2$F, —CHF$_2$, and —CF$_3$. In a still further aspect, $R^{25a}$, when present, is hydrogen and $R^{25b}$, when present, is selected from hydrogen, methyl, and —CF$_3$.

In a further aspect, $R^{25a}$, when present, is hydrogen and $R^{25b}$, when present, is selected from hydrogen, C1-C3 monohaloalkyl, and C1-C3 polyhaloalkyl. In a still further aspect, $R^{25a}$, when present, is hydrogen and $R^{25b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{25a}$, when present, is hydrogen and R$^{25b}$, when present, is selected from hydrogen, —CH$_2$F, —CH$_2$Cl, —CHF$_2$, —CF$_3$, —CHCl$_2$, and —CCl$_3$. In an even further aspect, R$^{25a}$, when present, is hydrogen and R$^{25b}$, when present, is selected from hydrogen, —CH$_2$F, —CHF$_2$, and —CF$_3$. In a still further aspect, R$^{25a}$, when present, is hydrogen and R$^{25b}$, when present, is selected from hydrogen and —CF$_3$.

In a further aspect, R$^{25a}$, when present, is hydrogen and R$^{25b}$, when present, is selected from hydrogen and C1-C3 alkyl. In a still further aspect, R$^{25a}$, when present, is hydrogen and R$^{25b}$, when present, is selected from hydrogen, methyl, and ethyl. In a yet further aspect, R$^{25a}$, when present, is hydrogen and R$^{25b}$, when present, is selected from hydrogen and methyl. In an even further aspect, each of R$^{25a}$ and R$^{25b}$, when present, is hydrogen.

w. R$^{30}$ Groups

In one aspect, R$^{30}$, when present, is selected from hydrogen, C1-C3 alkyl, C1-C3 monohaloalkyl, C1-C3 polyhaloalkyl, and cyclopropyl. In a further aspect, R$^{30}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, R$^{30}$, when present, is selected from hydrogen, methyl, —CH$_2$F, —CH$_2$Cl, —CHF$_2$, —CF$_3$, —CHCl$_2$, —CCl$_3$, and cyclopropyl. In a yet further aspect, R$^{30}$, when present, is selected from hydrogen, methyl, —CH$_2$F, —CHF$_2$, —CF$_3$, and cyclopropyl. In an even further aspect, R$^{30}$, when present, is selected from hydrogen, methyl, —CF$_3$, and cyclopropyl.

In a further aspect, R$^{30}$, when present, is selected from hydrogen, C1-C3 monohaloalkyl, C1-C3 polyhaloalkyl, and cyclopropyl. In a still further aspect, R$^{30}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, R$^{30}$, when present, is selected from hydrogen, —CH$_2$F, —CH$_2$Cl, —CHF$_2$, —CF$_3$, —CHCl$_2$, —CCl$_3$, and cyclopropyl. In a still further aspect, R$^{30}$, when present, is selected from hydrogen, —CH$_2$F, —CHF$_2$, —CF$_3$, and cyclopropyl. In a yet further aspect, R$^{30}$, when present, is selected from hydrogen, —CF$_3$ and cyclopropyl.

In a further aspect, R$^{30}$, when present, is selected from hydrogen, C1-C3 alkyl, and cyclopropyl. In a still further aspect, R$^{30}$, when present, is selected from hydrogen, methyl, ethyl, and cyclopropyl. In a yet further aspect, R$^{30}$, when present, is selected from hydrogen, methyl, and cyclopropyl.

In a further aspect, R$^{30}$, when present, is selected from hydrogen, C1-C3 alkyl, C1-C3 monohaloalkyl, and C1-C3 polyhaloalkyl. In a still further aspect, R$^{30}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{30}$, when present, is selected from hydrogen, methyl, —CH$_2$F, —CH$_2$Cl, —CHF$_2$, —CF$_3$, —CHCl$_2$, and —CCl$_3$. In an even further aspect, R$^{30}$, when present, is selected from hydrogen, methyl, —CH$_2$F, —CHF$_2$, and —CF$_3$. In a still further aspect, R$^{30}$, when present, is selected from hydrogen, methyl, and —CF$_3$.

In a further aspect, R$^{30}$, when present, is selected from hydrogen, C1-C3 monohaloalkyl, and C1-C3 polyhaloalkyl. In a still further aspect, R$^{30}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{30}$, when present, is selected from hydrogen, —CH$_2$F, —CH$_2$Cl, —CHF$_2$, —CF$_3$, —CHCl$_2$, and —CCl$_3$. In an even further aspect, R$^{30}$, when present, is selected from hydrogen, —CH$_2$F, —CHF$_2$, and —CF$_3$. In a still further aspect, R$^{30}$, when present, is selected from hydrogen and —CF$_3$.

In a further aspect, R$^{30}$, when present, is selected from hydrogen and C1-C3 alkyl. In a still further aspect, R$^{30}$, when present, is selected from hydrogen, methyl, and ethyl. In a yet further aspect, R$^{30}$, when present, is selected from hydrogen and methyl. In an even further aspect, R$^{30}$, when present, is hydrogen.

x. R$^{31}$ Groups

In one aspect, each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle.

In a further aspect, each of R$^{31a}$ and R$^{31b}$, when present, is independently selected from hydrogen, C1-C3 alkyl, C1-C3 monohaloalkyl, C1-C3 polyhaloalkyl, and cyclopropyl. In a still further aspect, each of R$^{31a}$ and R$^{31b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of R$^{31a}$ and R$^{31b}$, when present, is independently selected from hydrogen, methyl, —CH$_2$F, —CH$_2$Cl, —CHF$_2$, —CF$_3$, —CHCl$_2$, —CCl$_3$, and cyclopropyl. In an even further aspect, each of R$^{31a}$ and R$^{31b}$, when present, is independently selected from hydrogen, methyl, —CH$_2$F, —CHF$_2$, —CF$_3$, and cyclopropyl. In a still further aspect, each of R$^{31a}$ and R$^{31b}$, when present, is independently selected from hydrogen, methyl, —CF$_3$, and cyclopropyl.

In a further aspect, each of R$^{31a}$ and R$^{31b}$, when present, is independently selected from hydrogen, C1-C3 monohaloalkyl, C1-C3 polyhaloalkyl, and cyclopropyl. In a still further aspect, each of R$^{31a}$ and R$^{31b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of R$^{31a}$ and R$^{31b}$, when present, is independently selected from hydrogen, —CH$_2$F, —CH$_2$Cl, —CHF$_2$, —CF$_3$, —CHCl$_2$, —CCl$_3$, and cyclopropyl. In an even further aspect, each of R$^{31a}$ and R$^{31b}$, when present, is independently selected from hydrogen, —CH$_2$F, —CHF$_2$, —CF$_3$, and cyclopropyl. In a still further aspect, each of R$^{31a}$ and R$^{31b}$, when present, is independently selected from hydrogen, —CF$_3$ and cyclopropyl.

In a further aspect, each of R$^{31a}$ and R$^{31b}$, when present, is independently selected from hydrogen, C1-C3 alkyl, and cyclopropyl. In a still further aspect, each of R$^{31a}$ and R$^{31b}$, when present, is independently selected from hydrogen, methyl, ethyl, and cyclopropyl. In yet a further aspect, each of R$^{31a}$ and R$^{31b}$, when present, is independently selected from hydrogen, methyl, and cyclopropyl.

In a further aspect, each of R$^{31a}$ and R$^{31b}$, when present, is independently selected from hydrogen, C1-C3 alkyl, C1-C3 monohaloalkyl, and C1-C3 polyhaloalkyl. In a still further aspect, each of R$^{31a}$ and R$^{31b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{31a}$ and R$^{31b}$, when present, is independently selected from hydrogen, methyl, —CH$_2$F, —CH$_2$Cl, —CHF$_2$, —CF$_3$, —CHCl$_2$, and —CCl$_3$. In an even further aspect, each of R$^{31a}$ and R$^{31b}$, when present, is independently selected from hydrogen, methyl, —CH$_2$F, —CHF$_2$, and —CF$_3$. In a still further aspect, each of R$^{31a}$ and R$^{31b}$, when present, is independently selected from hydrogen, methyl, and —CF$_3$.

In a further aspect, each of R$^{31a}$ and R$^{31b}$, when present, is independently selected from hydrogen, C1-C3 monohaloalkyl, and C1-C3 polyhaloalkyl. In a still further aspect, each of R$^{31a}$ and R$^{31b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{31a}$ and R$^{31b}$, when present, is independently selected from hydrogen, —CH$_2$F, —CH$_2$Cl, —CHF$_2$, —CF$_3$, —CHCl$_2$, and —CCl$_3$. In an even further aspect, each of R$^{31a}$ and R$^{31b}$, when present, is independently selected from hydrogen, —CH$_2$F, —CHF$_2$, and —CF$_3$. In still a further aspect, each of R$^{31a}$ and R$^{31b}$, when present, is independently selected from hydrogen and —CF$_3$.

In a further aspect, each of R$^{31a}$ and R$^{31b}$, when present, is independently selected from hydrogen and C1-C3 alkyl. In a still further aspect, each of R$^{31a}$ and R$^{31b}$, when present, is independently selected from hydrogen, methyl, and ethyl. In yet a further aspect, each of R$^{31a}$ and R$^{31b}$, when present, is independently selected from hydrogen and methyl. In an even further aspect, R$^{31a}$, when present, is hydrogen and R$^{31b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, R$^{31a}$, when present, is hydrogen and R$^{31b}$, when present, is selected from hydrogen, methyl, —CH$_2$F, —CH$_2$Cl, —CHF$_2$, —CF$_3$, —CHCl$_2$, —CCl$_3$, and cyclopropyl. In yet a further aspect, R$^{31a}$, when present, is hydrogen and R$^{31b}$, when present, is selected from hydrogen, methyl, —CH$_2$F, —CHF$_2$, —CF$_3$, and cyclopropyl. In an even further aspect, R$^{31a}$, when present, is hydrogen and R$^{31b}$, when present, is selected from hydrogen, methyl, —CF$_3$, and cyclopropyl.

In a further aspect, R$^{31a}$, when present, is hydrogen and R$^{31b}$, when present, is selected from hydrogen, C1-C3 monohaloalkyl, C1-C3 polyhaloalkyl, and cyclopropyl. In a still further aspect, R$^{31a}$, when present, is hydrogen and R$^{31b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{31a}$, when present, is hydrogen and R$^{31b}$, when present, is selected from hydrogen, —CH$_2$F, —CH$_2$Cl, —CHF$_2$, —CF$_3$, —CHCl$_2$, —CCl$_3$, and cyclopropyl. In an even further aspect, R$^{31a}$, when present, is hydrogen and R$^{31b}$, when present, is selected from hydrogen, —CH$_2$F, —CHF$_2$, —CF$_3$, and cyclopropyl. In a still further aspect, R$^{31a}$, when present, is hydrogen and R$^{31b}$, when present, is selected from hydrogen, —CF$_3$ and cyclopropyl.

In a further aspect, R$^{31a}$, when present, is hydrogen and R$^{31b}$, when present, is selected from hydrogen, C1-C3 alkyl, and cyclopropyl. In a still further aspect, R$^{31a}$, when present, is hydrogen and R$^{31b}$, when present, is selected from hydrogen, methyl, ethyl, and cyclopropyl. In yet a further aspect, R$^{31a}$, when present, is hydrogen and R$^{31b}$, when present, is selected from hydrogen, methyl, and cyclopropyl.

In a further aspect, R$^{31a}$, when present, is hydrogen and R$^{31b}$, when present, is selected from hydrogen, C1-C3 alkyl, C1-C3 monohaloalkyl, and C1-C3 polyhaloalkyl. In a still further aspect, R$^{31a}$, when present, is hydrogen and R$^{31b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{31a}$, when present, is hydrogen and R$^{31b}$, when present, is selected from hydrogen, methyl, —CH$_2$F, —CH$_2$Cl, —CHF$_2$, —CF$_3$, —CHCl$_2$, and —CCl$_3$. In an even further aspect, R$^{31a}$, when present, is hydrogen and R$^{31b}$, when present, is selected from hydrogen, methyl, —CH$_2$F, —CHF$_2$, and —CF$_3$. In a still further aspect, R$^{31a}$, when present, is hydrogen and R$^{31b}$, when present, is selected from hydrogen, methyl, and —CF$_3$.

In a further aspect, R$^{31a}$, when present, is hydrogen and R$^{31b}$, when present, is selected from hydrogen, C1-C3 monohaloalkyl, and C1-C3 polyhaloalkyl. In a still further aspect, R$^{31a}$, when present, is hydrogen and R$^{31b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{31a}$, when present, is hydrogen and R$^{31b}$, when present, is selected from hydrogen, —CH$_2$F, —CH$_2$Cl, —CHF$_2$, —CF$_3$, —CHCl$_2$, and —CCl$_3$. In an even further aspect, R$^{31a}$, when present, is hydrogen and R$^{31b}$, when present, is selected from hydrogen, —CH$_2$F, —CHF$_2$, and —CF$_3$. In a still further aspect, R$^{31a}$, when present, is hydrogen and R$^{31b}$, when present, is selected from hydrogen and —CF$_3$.

In a further aspect, R$^{31a}$, when present, is hydrogen and R$^{31b}$, when present, is selected from hydrogen and C1-C3 alkyl. In a still further aspect, R$^{31a}$, when present, is hydrogen and R$^{31b}$, when present, is selected from hydrogen, methyl, and ethyl. In yet a further aspect, R$^{31a}$, when present, is hydrogen and R$^{31b}$, when present, is selected from hydrogen and methyl. In an even further aspect, each of R$^{31a}$ and R$^{31b}$, when present, is hydrogen.

In a further aspect, R$^{31a}$ and R$^{31b}$, when present, are optionally covalently bonded and, together with nitrogen atom to which they are attached, comprise a 3- to 6-membered heterocycle. In a still further aspect, R$^{31a}$ and R$^{31b}$, when present, are covalently bonded, and together with nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In yet a further aspect, R$^{31a}$ and R$^{31b}$, when present, are covalently bonded, and together with nitrogen atom to which they are attached, comprise a heterocycle selected from pyrrolidinyl, piperidinyl, azepanyl, imidazolidinyl, and pyrazolidinyl. In an even further aspect, R$^{31a}$ and R$^{31b}$, when present, are covalently bonded, and together with nitrogen atom to which they are attached, comprise a heterocycle selected from imidazolyl, pyrazolyl, and pyrrolyl. In a still further aspect, R$^{31a}$ and R$^{31b}$, when present, are covalently bonded, and together with nitrogen atom to which they are attached, comprise a pyrrolidinyl. In yet a further aspect, R$^{31a}$ and R$^{31b}$, when present, are covalently bonded, and together with nitrogen atom to which they are attached, comprise a piperidinyl.

y. R$^{32}$ Groups

In one aspect, R$^{32}$, when present, is selected from C1-C3 alkyl, C1-C3 monohaloalkyl, C1-C3 polyhaloalkyl, cyclopropyl, and, —NR$^{34a}$R$^{34b}$. In a further aspect, R$^{32}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, R$^{32}$, when present, is selected from methyl, —CH$_2$F, —CH$_2$Cl, —CHF$_2$, —CF$_3$, —CHCl$_2$, —CCl$_3$, cyclopropyl, —NHCH$_3$, and —N(CH$_3$)$_2$. In yet a further aspect, R$^{32}$, when present, is selected from methyl, —CH$_2$F, —CHF$_2$, —CF$_3$, cyclopropyl, —NHCH$_3$, and —N(CH$_3$)$_2$. In an even further aspect, R$^{32}$, when present, is selected from methyl, —CF$_3$, cyclopropyl, and —NHCH$_3$.

In a further aspect, R$^{32}$, when present, is selected from C1-C3 alkyl, C1-C3 monohaloalkyl, C1-C3 polyhaloalkyl, and, —NR$^{34a}$R$^{34b}$. In a still further aspect, R$^{32}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In yet a further aspect, R$^{32}$, when present, is selected from methyl, —CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^{32}$, when present, is selected from methyl, —CH$_2$F, —CHF$_2$, —CF$_3$, —NHCH$_3$, and —N(CH$_3$)$_2$. In a still further aspect, R$^{32}$, when present, is selected from methyl, —CF$_3$, and —NHCH$_3$.

In a further aspect, R$^{32}$, when present, is selected from C1-C3 alkyl, C1-C3 monohaloalkyl, C1-C3 polyhaloalkyl, and cyclopropyl. In a still further aspect, R$^{32}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{32}$, when present, is selected from methyl, —CH$_2$F, —CH$_2$Cl, —CHF$_2$, —CF$_3$, —CHCl$_2$, —CCl$_3$, and cyclopropyl. In an even further aspect, R$^{32}$, when present, is selected from methyl, —CH$_2$F, —CHF$_2$, —CF$_3$, and cyclopropyl. In a still further aspect, R$^{32}$, when present, is selected from methyl, —CF$_3$, and cyclopropyl.

In a further aspect, R$^{32}$, when present, is selected from C1-C3 monohaloalkyl, C1-C3 polyhaloalkyl, and cyclopropyl. In a still further aspect, R$^{32}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{32}$, when present, is selected from —CH$_2$F, —CH$_2$Cl, —CHF$_2$, —CF$_3$, —CHCl$_2$, —CCl$_3$, and cyclopropyl. In an even further aspect, R$^{32}$, when present, is selected from —CH$_2$F, —CHF$_2$, —CF$_3$, and cyclopropyl. In a still further aspect, R$^{32}$, when present, is selected from —CF$_3$ and cyclopropyl.

In a further aspect, R$^{32}$, when present, is selected from C1-C3 alkyl, and cyclopropyl. In a still further aspect, R$^{32}$, when present, is selected from methyl, ethyl, and cyclopropyl. In yet a further aspect, R$^{32}$, when present, is selected from methyl, and cyclopropyl.

In a further aspect, R$^{32}$, when present, is selected from C1-C3 alkyl, C1-C3 monohaloalkyl, and C1-C3 polyhaloalkyl. In a still further aspect, R$^{32}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{32}$, when present, is selected from methyl, —CH$_2$F, —CH$_2$Cl, —CHF$_2$, —CF$_3$, —CHCl$_2$, and —CCl$_3$. In an even further aspect, R$^{32}$, when present, is selected from methyl, —CH$_2$F, —CHF$_2$, and —CF$_3$. In a still further aspect, R$^{32}$, when present, is selected from methyl and —CF$_3$.

In a further aspect, R$^{32}$, when present, is selected from C1-C3 monohaloalkyl, and C1-C3 polyhaloalkyl. In a still further aspect, R$^{32}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{32}$, when present, is selected from —CH$_2$F, —CH$_2$Cl, —CHF$_2$, —CF$_3$, —CHCl$_2$, and —CCl$_3$. In an even further aspect, R$^{32}$, when present, is selected from —CH$_2$F, —CHF$_2$, and —CF$_3$. In a still further aspect, R$^{32}$, when present, is —CF$_3$.

In a further aspect, R$^{32}$, when present, is C1-C3 alkyl. In a still further aspect, R$^{32}$, when present, is selected from methyl, and ethyl. In yet a further aspect, R$^{32}$, when present, is methyl.

z. R$^{33}$ Groups

In one aspect, R$^{33}$, when present, is selected from C1-C3 alkyl, C1-C3 monohaloalkyl, C1-C3 polyhaloalkyl, cyclopropyl, and, —NR$^{35a}$R$^{35b}$. In a further aspect, R$^{33}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, R$^{33}$, when present, is selected from methyl, —CH$_2$F, —CH$_2$Cl, —CHF$_2$, —CF$_3$, —CHCl$_2$, —CCl$_3$, cyclopropyl, —NHCH$_3$, and —N(CH$_3$)$_2$. In a yet further aspect, R$^{33$}$, when present, is selected from methyl, —CH$_2$F, —CHF$_2$, —CF$_3$, cyclopropyl, —NHCH$_3$, and —N(CH$_3$)$_2$. In an even further aspect, R$^{33}$, when present, is selected from methyl, —CF$_3$, cyclopropyl, and —NHCH$_3$.

In a further aspect, R$^{33}$, when present, is selected from C1-C3 alkyl, C1-C3 monohaloalkyl, C1-C3 polyhaloalkyl, and, —NR$^{34a}$R$^{34b}$. In a still further aspect, R$^{33}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a yet further aspect, R$^{33}$, when present, is selected from methyl, —CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^{33}$, when present, is selected from methyl, —CH$_2$F, —CHF$_2$, —CF$_3$, —NHCH$_3$, and —N(CH$_3$)$_2$. In a still further aspect, R$^{33}$, when present, is selected from methyl, —CF$_3$, and —NHCH$_3$.

In a further aspect, R$^{33}$, when present, is selected from C1-C3 alkyl, C1-C3 monohaloalkyl, C1-C3 polyhaloalkyl, and cyclopropyl. In a still further aspect, R$^{33}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, R$^{33}$, when present, is selected from methyl, —CH$_2$F, —CH$_2$Cl, —CHF$_2$, —CF$_3$, —CHCl$_2$, —CCl$_3$, and cyclopropyl. In an even further aspect, R$^{33}$, when present, is selected from methyl, —CH$_2$F, —CHF$_2$, —CF$_3$, and cyclopropyl. In a still further aspect, R$^{33}$, when present, is selected from methyl, —CF$_3$, and cyclopropyl.

In a further aspect, $R^{33}$, when present, is selected from C1-C3 monohaloalkyl, C1-C3 polyhaloalkyl, and cyclopropyl. In a still further aspect, $R^{33}$, when present, is selected from —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In a yet further aspect, $R^{33}$, when present, is selected from —$CH_2F$, —$CH_2Cl$, —$CHF_2$, —$CF_3$, —$CHCl_2$, —$CCl_3$, and cyclopropyl. In an even further aspect, $R^{33}$, when present, is selected from —$CH_2F$, —$CHF_2$, —$CF_3$, and cyclopropyl. $R^{33}$, when present, is selected from —$CF_3$ and cyclopropyl.

In a further aspect, $R^{33}$, when present, is selected from C1-C3 alkyl, and cyclopropyl. In a still further aspect, $R^{33}$, when present, is selected from methyl, ethyl, and cyclopropyl. In a yet further aspect, $R^{33}$, when present, is selected from methyl, and cyclopropyl.

In a further aspect, $R^{33}$, when present, is selected from C1-C3 alkyl, C1-C3 monohaloalkyl, and C1-C3 polyhaloalkyl. In a still further aspect, $R^{33}$, when present, is selected from methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a yet further aspect, $R^{33}$, when present, is selected from methyl, —$CH_2F$, —$CH_2Cl$, —$CHF_2$, —$CF_3$, —$CHCl_2$, and —$CCl_3$. In an even further aspect, $R^{33}$, when present, is selected from methyl, —$CH_2F$, —$CHF_2$, and —$CF_3$. In a still further aspect, $R^{33}$, when present, is selected from methyl and —$CF_3$.

In a further aspect, $R^{33}$, when present, is selected from C1-C3 monohaloalkyl, and C1-C3 polyhaloalkyl. In a still further aspect, $R^{33}$, when present, is selected from —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In a yet further aspect, $R^{33}$, when present, is selected from —$CH_2F$, —$CH_2Cl$, —$CHF_2$, —$CF_3$, —$CHCl_2$, and —$CCl_3$. In an even further aspect, $R^{33}$, when present, is selected from —$CH_2F$, —$CHF_2$, and —$CF_3$. In a still further aspect, $R^{33}$, when present, is —$CF_3$.

In a further aspect, $R^{33}$, when present, is C1-C3 alkyl. In a still further aspect, $R^{33}$, when present, is selected from methyl, and ethyl. In a yet further aspect, $R^{33}$, when present, is methyl.

aa. $R^{34}$ Groups

In one aspect, each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle.

In a further aspect, each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle. In a still further aspect, each of $R^{34a}$ and $R^{34b}$, when present, is independently selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, each of $R^{34a}$ and $R^{34b}$, when present, is independently selected from hydrogen, methyl, —$CH_2F$, —$CHF_2$, —$CF_3$, and cyclopropyl. In an even further aspect, each of $R^{34a}$ and $R^{34b}$, when present, is independently selected from hydrogen, methyl, —$CF_3$, and cyclopropyl.

In a further aspect, each of $R^{34a}$ and $R^{34b}$, when present, is independently selected from hydrogen, methyl, —$CF_3$, and cyclopropyl.

In a further aspect, each of $R^{34a}$ and $R^{34b}$, when present, is independently selected from hydrogen, C1-C3 monohaloalkyl, C1-C3 polyhaloalkyl, and cyclopropyl. In a still further aspect, each of $R^{34a}$ and $R^{34b}$, when present, is independently selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and cyclopropyl. In yet a further aspect, each of $R^{34a}$ and $R^{34b}$, when present, is independently selected from hydrogen, —$CH_2F$, —$CH_2Cl$, —$CHF_2$, —$CF_3$, —$CHCl_2$, —$CCl_3$, and cyclopropyl. In an even further aspect, each of $R^{34a}$ and $R^{34b}$, when present, is independently selected from hydrogen, —$CH_2F$, —$CHF_2$, —$CF_3$, and cyclopropyl. In a still further aspect, each of $R^{34a}$ and $R^{34b}$, when present, is independently selected from hydrogen, —$CF_3$ and cyclopropyl.

In a further aspect, each of $R^{34a}$ and $R^{34b}$, when present, is independently selected from hydrogen, C1-C3 alkyl, and cyclopropyl. In a still further aspect, each of $R^{34a}$ and $R^{34b}$, when present, is independently selected from hydrogen, methyl, ethyl, and cyclopropyl. In yet a further aspect, each of $R^{34a}$ and $R^{34b}$, when present, is independently selected from hydrogen, methyl, and cyclopropyl.

In a further aspect, each of $R^{34a}$ and $R^{34b}$, when present, is independently selected from hydrogen, C1-C3 alkyl, C1-C3 monohaloalkyl, and C1-C3 polyhaloalkyl. In a still further aspect, each of $R^{34a}$ and $R^{34b}$, when present, is independently selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, each of $R^{34a}$ and $R^{34b}$, when present, is independently selected from hydrogen, methyl, —$CH_2F$, —$CH_2Cl$, —$CHF_2$, —$CF_3$, —$CHCl_2$, and —$CCl_3$. In an even further aspect, each of $R^{34a}$ and $R^{34b}$, when present, is independently selected from hydrogen, methyl, —$CH_2F$, —$CHF_2$, and —$CF_3$. In a still further aspect, each of $R^{34a}$ and $R^{34b}$, when present, is independently selected from hydrogen, methyl, and —$CF_3$.

In a further aspect, each of $R^{34a}$ and $R^{34b}$, when present, is independently selected from hydrogen, C1-C3 monohaloalkyl, and C1-C3 polyhaloalkyl. In a still further aspect, each of $R^{34a}$ and $R^{34b}$, when present, is independently selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, each of $R^{34a}$ and $R^{34b}$, when present, is independently selected from hydrogen, —$CH_2F$, —$CH_2Cl$, —$CHF_2$, —$CF_3$, —$CHCl_2$, and —$CCl_3$. In an even further aspect, each of $R^{34a}$ and $R^{34b}$, when present, is independently selected from hydrogen, —$CH_2F$, —$CHF_2$, and —$CF_3$. In a still further aspect, each of $R^{34a}$ and $R^{34b}$, when present, is independently selected from hydrogen and —$CF_3$.

In a further aspect, each of $R^{34a}$ and $R^{34b}$, when present, is independently selected from hydrogen and C1-C3 alkyl. In a still further aspect, each of $R^{34a}$ and $R^{34b}$, when present, is independently selected from hydrogen, methyl, and ethyl. In yet a further aspect, each of $R^{34a}$ and $R^{34b}$, when present, is independently selected from hydrogen and methyl. In an even further aspect, $R^{34a}$, when present, is hydrogen and $R^{34b}$, when present, is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —CH$_2$CF$_3$, —CH$_2$CHCl$_2$, —CH$_2$CCl$_3$, and cyclopropyl. In a still further aspect, R$^{34a}$, when present, is hydrogen and R$^{34b}$, when present, is selected from hydrogen, methyl, —CH$_2$F, —CH$_2$Cl, —CHF$_2$, —CF$_3$, —CHCl$_2$, —CCl$_3$, and cyclopropyl. In yet a further aspect, R$^{34a}$, when present, is hydrogen and R$^{34b}$, when present, is selected from hydrogen, methyl, —CH$_2$F, —CHF$_2$, —CF$_3$, and cyclopropyl. In an even further aspect, R$^{34a}$, when present, is hydrogen and R$^{34b}$, when present, is selected from hydrogen, methyl, —CF$_3$, and cyclopropyl.

In a further aspect, R$^{34a}$, when present, is hydrogen and R$^{34b}$, when present, is selected from hydrogen, C1-C3 monohaloalkyl, C1-C3 polyhaloalkyl, and cyclopropyl. In a still further aspect, R$^{34a}$, when present, is hydrogen and R$^{34b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{34a}$, when present, is hydrogen and R$^{34b}$, when present, is selected from hydrogen, —CH$_2$F, —CH$_2$Cl, —CHF$_2$, —CF$_3$, —CHCl$_2$, —CCl$_3$, and cyclopropyl. In an even further aspect, R$^{34a}$, when present, is hydrogen and R$^{34b}$, when present, is selected from hydrogen, —CH$_2$F, —CHF$_2$, —CF$_3$, and cyclopropyl. In a still further aspect, R$^{34a}$, when present, is hydrogen and R$^{34b}$, when present, is selected from hydrogen, —CF$_3$ and cyclopropyl.

In a further aspect, R$^{34a}$, when present, is hydrogen and R$^{34b}$, when present, is selected from hydrogen, C1-C3 alkyl, and cyclopropyl. In a still further aspect, R$^{34a}$, when present, is hydrogen and R$^{34b}$, when present, is selected from hydrogen, methyl, ethyl, and cyclopropyl. In yet a further aspect, R$^{34a}$, when present, is hydrogen and R$^{34b}$, when present, is selected from hydrogen, methyl, and cyclopropyl.

In a further aspect, R$^{34a}$, when present, is hydrogen and R$^{34b}$, when present, is selected from hydrogen, C1-C3 alkyl, C1-C3 monohaloalkyl, and C1-C3 polyhaloalkyl. In a still further aspect, R$^{34a}$, when present, is hydrogen and R$^{34b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{34a}$, when present, is hydrogen and R$^{34b}$, when present, is selected from hydrogen, methyl, —CH$_2$F, —CH$_2$Cl, —CHF$_2$, —CF$_3$, —CHCl$_2$, and —CCl$_3$. In an even further aspect, R$^{34a}$, when present, is hydrogen and R$^{34b}$, when present, is selected from hydrogen, methyl, —CH$_2$F, —CHF$_2$, and —CF$_3$. In a still further aspect, R$^{34a}$, when present, is hydrogen and R$^{34b}$, when present, is selected from hydrogen, methyl, and —CF$_3$.

In a further aspect, R$^{34a}$, when present, is hydrogen and R$^{34b}$, when present, is selected from hydrogen, C1-C3 monohaloalkyl, and C1-C3 polyhaloalkyl. In a still further aspect, R$^{34a}$, when present, is hydrogen and R$^{34b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{34a}$, when present, is hydrogen and R$^{34b}$, when present, is selected from hydrogen, —CH$_2$F, —CH$_2$Cl, —CHF$_2$, —CF$_3$, —CHCl$_2$, and —CCl$_3$. In an even further aspect, R$^{34a}$, when present, is hydrogen and R$^{34b}$, when present, is selected from hydrogen, —CH$_2$F, —CHF$_2$, and —CF$_3$. In a still further aspect, R$^{34a}$, when present, is hydrogen and R$^{34b}$, when present, is selected from hydrogen and —CF$_3$.

In a further aspect, R$^{34a}$, when present, is hydrogen and R$^{34b}$, when present, is selected from hydrogen and C1-C3 alkyl. In a still further aspect, R$^{34a}$, when present, is hydrogen and R$^{34b}$, when present, is selected from hydrogen, methyl, and ethyl. In yet a further aspect, R$^{34a}$, when present, is hydrogen and R$^{34b}$, when present, is selected from hydrogen and methyl. In an even further aspect, each of R$^{34a}$ and R$^{34b}$, when present, is hydrogen.

bb. R$^{35}$ Groups

In one aspect, each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle.

In a further aspect, each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle. In a still further aspect, each of R$^{35a}$ and R$^{35b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, each of R$^{35a}$ and R$^{35b}$, when present, is independently selected from hydrogen, methyl, —CH$_2$F, —CH$_2$Cl, —CHF$_2$, —CF$_3$, —CHCl$_2$, —CCl$_3$, and cyclopropyl. In an even further aspect, each of R$^{35a}$ and R$^{35b}$, when present, is independently selected from hydrogen, methyl, —CH$_2$F, —CHF$_2$, —CF$_3$, and cyclopropyl. In a still further aspect, each of R$^{35a}$ and R$^{35b}$, when present, is independently selected from hydrogen, methyl, —CF$_3$, and cyclopropyl.

In a further aspect, each of R$^{35a}$ and R$^{35b}$, when present, is independently selected from hydrogen, C1-C3 monohaloalkyl, C1-C3 polyhaloalkyl, and cyclopropyl. In a still further aspect, each of R$^{35a}$ and R$^{35b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, each of R$^{35a}$ and R$^{35b}$, when present, is independently selected from hydrogen, —CH$_2$F, —CH$_2$Cl, —CHF$_2$, —CF$_3$, —CHCl$_2$, —CCl$_3$, and cyclopropyl. In an even further aspect, each of R$^{35a}$ and R$^{35b}$, when present, is independently selected from hydrogen, —CH$_2$F, —CHF$_2$, —CF$_3$, and cyclopropyl. In a still further aspect, each of R$^{35a}$ and R$^{35b}$, when present, is independently selected from hydrogen, —CF$_3$ and cyclopropyl.

In a further aspect, each of R$^{35a}$ and R$^{35b}$, when present, is independently selected from hydrogen, C1-C3 alkyl, and cyclopropyl. In a still further aspect, each of R$^{35a}$ and R$^{35b}$, when present, is independently selected from hydrogen, methyl, ethyl, and cyclopropyl. In a yet further aspect, each of R$^{35a}$ and R$^{35b}$, when present, is independently selected from hydrogen, methyl, and cyclopropyl.

In a further aspect, each of R$^{35a}$ and R$^{35b}$, when present, is independently selected from hydrogen, C1-C3 alkyl, C1-C3 monohaloalkyl, and C1-C3 polyhaloalkyl. In a still further aspect, each of R$^{35a}$ and R$^{35b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each of R$^{35a}$ and R$^{35b}$, when present, is independently selected from hydrogen, methyl, —CH$_2$F, —CH$_2$Cl, —CHF$_2$, —CF$_3$, —CHCl$_2$, and —CCl$_3$. In an even further aspect, each of R$^{35a}$ and R$^{35b}$, when present, is independently selected from hydrogen, methyl, —CH$_2$F, —CHF$_2$, and —CF$_3$. In a still further aspect, each of R$^{35a}$ and R$^{35b}$, when present, is independently selected from hydrogen, methyl, and —CF$_3$.

In a further aspect, each of R$^{35a}$ and R$^{35b}$, when present, is independently selected from hydrogen, C1-C3 monohaloalkyl, and C1-C3 polyhaloalkyl. In a still further aspect, each of R$^{35a}$ and R$^{35b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, each of R$^{35a}$ and R$^{35b}$, when present, is independently selected from hydrogen, —CH$_2$F, —CH$_2$Cl, —CHF$_2$, —CF$_3$, —CHCl$_2$, and —CCl$_3$. In an even further aspect, each of R$^{35a}$ and R$^{35b}$, when present, is independently selected from hydrogen, —CH$_2$F, —CHF$_2$, and —CF$_3$. In a still further aspect, each of R$^{35a}$ and R$^{35b}$, when present, is independently selected from hydrogen and —CF$_3$.

In a further aspect, each of R$^{35a}$ and R$^{35b}$, when present, is independently selected from hydrogen and C1-C3 alkyl. In a still further aspect, each of R$^{35a}$ and R$^{35b}$, when present, is independently selected from hydrogen, methyl, and ethyl. In a yet further aspect, each of R$^{35a}$ and R$^{35b}$, when present, is independently selected from hydrogen and methyl. In an even further aspect, R$^{35a}$ is hydrogen and R$^{35b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, R$^{35a}$, when present, is hydrogen and R$^{35b}$, when present, is selected from hydrogen, methyl, —CH$_2$F, —CH$_2$Cl, —CHF$_2$, —CF$_3$, —CHCl$_2$, —CCl$_3$, and cyclopropyl. In a yet further aspect, R$^{35a}$, when present, is hydrogen and R$^{35b}$, when present, is selected from hydrogen, methyl, —CH$_2$F, —CHF$_2$, —CF$_3$, and cyclopropyl. In an even further aspect, R$^{35a}$, when present, is hydrogen and R$^{35b}$, when present, is selected from hydrogen, methyl, —CF$_3$, and cyclopropyl.

In a further aspect, R$^{35a}$, when present, is hydrogen and R$^{35b}$, when present, is selected from hydrogen, C1-C3 monohaloalkyl, C1-C3 polyhaloalkyl, and cyclopropyl. In a still further aspect, R$^{35a}$, when present, is hydrogen and R$^{35b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a yet further aspect, R$^{35a}$, when present, is hydrogen and R$^{35b}$, when present, is selected from hydrogen, —CH$_2$F, —CH$_2$Cl, —CHF$_2$, —CF$_3$, —CHCl$_2$, —CCl$_3$, and cyclopropyl. In an even further aspect, R$^{35a}$, when present, is hydrogen and R$^{35b}$, when present, is selected from hydrogen, —CH$_2$F, —CHF$_2$, —CF$_3$, and cyclopropyl. In a still further aspect, R$^{35a}$, when present, is hydrogen and R$^{35b}$, when present, is selected from hydrogen, —CF$_3$ and cyclopropyl.

In a further aspect, R$^{35a}$, when present, is hydrogen and R$^{35b}$, when present, is selected from hydrogen, C1-C3 alkyl, and cyclopropyl. In a still further aspect, R$^{35a}$, when present, is hydrogen and R$^{35b}$, when present, is selected from hydrogen, methyl, ethyl, and cyclopropyl. In a yet further aspect, R$^{35a}$, when present, is hydrogen and R$^{35b}$, when present, is selected from hydrogen, methyl, and cyclopropyl.

In a further aspect, R$^{35a}$, when present, is hydrogen and R$^{35b}$, when present, is selected from hydrogen, C1-C3 alkyl, C1-C3 monohaloalkyl, and C1-C3 polyhaloalkyl. In a still further aspect, R$^{35a}$, when present, is hydrogen and R$^{35b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{35a}$, when present, is hydrogen and R$^{35b}$, when present, is selected from hydrogen, methyl, —CH$_2$F, —CH$_2$Cl, —CHF$_2$, —CF$_3$, —CHCl$_2$, and —CCl$_3$. In an even further aspect, R$^{35a}$, when present, is hydrogen and R$^{35b}$, when present, is selected from hydrogen, methyl, —CH$_2$F, —CHF$_2$, and —CF$_3$. In a still further aspect, R$^{35a}$, when present, is hydrogen and R$^{35b}$, when present, is selected from hydrogen, methyl, and —CF$_3$.

In a further aspect, R$^{35a}$, when present, is hydrogen and R$^{35b}$, when present, is selected from hydrogen, C1-C3 monohaloalkyl, and C1-C3 polyhaloalkyl. In a still further aspect, R$^{35a}$, when present, is hydrogen and R$^{35b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In a yet further aspect, R$^{35a}$, when present, is hydrogen and R$^{35b}$, when present, is selected from hydrogen, —CH$_2$F, —CH$_2$Cl, —CHF$_2$, —CF$_3$, —CHCl$_2$, and —CCl$_3$. In an even further aspect, R$^{35a}$, when present, is hydrogen and R$^{35b}$, when present, is selected from hydrogen, —CH$_2$F, —CHF$_2$, and —CF$_3$. In a still further aspect, R$^{35a}$, when present, is hydrogen and R$^{35b}$, when present, is selected from hydrogen and —CF$_3$.

In a further aspect, R$^{35a}$, when present, is hydrogen and R$^{35b}$, when present, is selected from hydrogen and C1-C3 alkyl. In a still further aspect, R$^{35a}$, when present, is hydrogen and R$^{35b}$, when present, is selected from hydrogen, methyl, and ethyl. In a yet further aspect, R$^{35a}$, when present, is hydrogen and R$^{35b}$, when present, is selected from hydrogen and methyl. In an even further aspect, each of R$^{35a}$ and R$^{35b}$, when present, is hydrogen.

cc. R$^{40}$ Groups

In one aspect, R$^{40}$, when present, is selected from hydrogen, C1-C3 alkyl, C1-C3 monohaloalkyl, C1-C3 polyhaloalkyl, and cyclopropyl. In a further aspect, R$^{40}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{40}$, when present, is selected from hydrogen, methyl, —CH$_2$F, —CH$_2$Cl, —CHF$_2$, —CF$_3$, —CHCl$_2$, —CCl$_3$, and cyclopropyl. In an even further aspect, R$^{40}$, when present, is selected from hydrogen, methyl, —CH$_2$F, —CHF$_2$, —CF$_3$, and cyclopropyl. In a still further aspect, R$^{40}$, when present, is selected from hydrogen, methyl, —CF$_3$, and cyclopropyl.

In a further aspect, R$^{40}$, when present, is selected from hydrogen, C1-C3 monohaloalkyl, C1-C3 polyhaloalkyl, and cyclopropyl. In a still further aspect, R$^{40}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{40}$, when present, is selected from hydrogen, —CH$_2$F, —CH$_2$Cl, —CHF$_2$, —CF$_3$, —CHCl$_2$, —CCl$_3$, and cyclopropyl. In an even further aspect, R$^{40}$, when present, is selected from hydrogen, —CH$_2$F, —CHF$_2$, —CF$_3$, and cyclopropyl. In a still further aspect, R$^{40}$, when present, is selected from hydrogen, —CF$_3$ and cyclopropyl.

In a further aspect, R$^{40}$, when present, is selected from hydrogen, C1-C3 alkyl, and cyclopropyl. In a still further aspect, R$^{40}$, when present, is selected from hydrogen, methyl, ethyl, and cyclopropyl. In yet a further aspect, R$^{40}$, when present, is selected from hydrogen, methyl, and cyclopropyl.

In a further aspect, $R^{40}$, when present, is selected from hydrogen, C1-C3 alkyl, C1-C3 monohaloalkyl, and C1-C3 polyhaloalkyl. In a still further aspect, $R^{40}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, $R^{40}$, when present, is selected from hydrogen, methyl, —CH$_2$F, —CH$_2$Cl, —CHF$_2$, —CF$_3$, —CHCl$_2$, and —CCl$_3$. In an even further aspect, $R^{40}$, when present, is selected from hydrogen, methyl, —CH$_2$F, —CHF$_2$, and —CF$_3$. In a still further aspect, $R^{40}$, when present, is selected from hydrogen, methyl, and —CF$_3$.

In a further aspect, $R^{40}$, when present, is selected from hydrogen, C1-C3 monohaloalkyl, and C1-C3 polyhaloalkyl. In a still further aspect, $R^{40}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, $R^{40}$, when present, is selected from hydrogen, —CH$_2$F, —CH$_2$Cl, —CHF$_2$, —CF$_3$, —CHCl$_2$, and —CCl$_3$. In an even further aspect, $R^{40}$, when present, is selected from hydrogen, —CH$_2$F, —CHF$_2$, and —CF$_3$. In a still further aspect, $R^{40}$, when present, is selected from hydrogen and —CF$_3$.

In a further aspect, $R^{40}$, when present, is selected from hydrogen and C1-C3 alkyl. In a still further aspect, $R^{40}$, when present, is selected from hydrogen, methyl, and ethyl. In yet a further aspect, $R^{40}$, when present, is selected from hydrogen and methyl. In an even further aspect, $R^{40}$, when present, is hydrogen.

dd. $R^{41}$ Groups

In one aspect, each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle.

In a further aspect, each of $R^{41a}$ and $R^{41b}$, when present, is independently selected from hydrogen, C1-C3 alkyl, C1-C3 monohaloalkyl, C1-C3 polyhaloalkyl, and cyclopropyl. In a still further aspect, each of $R^{41a}$ and $R^{41b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of $R^{41a}$ and $R^{41b}$, when present, is independently selected from hydrogen, methyl, —CH$_2$F, —CH$_2$Cl, —CHF$_2$, —CF$_3$, —CHCl$_2$, —CCl$_3$, and cyclopropyl. In an even further aspect, each of $R^{41a}$ and $R^{41b}$, when present, is independently selected from hydrogen, methyl, —CH$_2$F, —CHF$_2$, —CF$_3$, and cyclopropyl. In a still further aspect, each of $R^{41a}$ and $R^{41b}$, when present, is independently selected from hydrogen, methyl, —CF$_3$, and cyclopropyl.

In a further aspect, each of $R^{41a}$ and $R^{41b}$, when present, is independently selected from hydrogen, C1-C3 monohaloalkyl, C1-C3 polyhaloalkyl, and cyclopropyl. In a still further aspect, each of $R^{41a}$ and $R^{41b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of $R^{41a}$ and $R^{41b}$, when present, is independently selected from hydrogen, —CH$_2$F, —CH$_2$Cl, —CHF$_2$, —CF$_3$, —CHCl$_2$, —CCl$_3$, and cyclopropyl. In an even further aspect, each of $R^{41a}$ and $R^{41b}$, when present, is independently selected from hydrogen, —CH$_2$F, —CHF$_2$, —CF$_3$, and cyclopropyl. In a still further aspect, each of $R^{41a}$ and $R^{41b}$, when present, is independently selected from hydrogen, —CF$_3$ and cyclopropyl.

In a further aspect, each of $R^{41a}$ and $R^{41b}$, when present, is independently selected from hydrogen, C1-C3 alkyl, and cyclopropyl. In a still further aspect, each of $R^{41a}$ and $R^{41b}$, when present, is independently selected from hydrogen, methyl, ethyl, and cyclopropyl. In yet a further aspect, each of $R^{41a}$ and $R^{41b}$, when present, is independently selected from hydrogen, methyl, and cyclopropyl.

In a further aspect, each of $R^{41a}$ and $R^{41b}$, when present, is independently selected from hydrogen, C1-C3 alkyl, C1-C3 monohaloalkyl, and C1-C3 polyhaloalkyl. In a still further aspect, each of $R^{41a}$ and $R^{41b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of $R^{41a}$ and $R^{41b}$, when present, is independently selected from hydrogen, methyl, —CH$_2$F, —CH$_2$Cl, —CHF$_2$, —CF$_3$, —CHCl$_2$, and —CCl$_3$. In an even further aspect, each of $R^{41a}$ and $R^{41b}$, when present, is independently selected from hydrogen, methyl, —CH$_2$F, —CHF$_2$, and —CF$_3$. In a still further aspect, each of $R^{41a}$ and $R^{41b}$, when present, is independently selected from hydrogen, methyl, and —CF$_3$.

In a further aspect, each of $R^{41a}$ and $R^{41b}$, when present, is independently selected from hydrogen, C1-C3 monohaloalkyl, and C1-C3 polyhaloalkyl. In a still further aspect, each of $R^{41a}$ and $R^{41b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of $R^{41a}$ and $R^{41b}$, when present, is independently selected from hydrogen, —CH$_2$F, —CH$_2$Cl, —CHF$_2$, —CF$_3$, —CHCl$_2$, and —CCl$_3$. In an even further aspect, each of $R^{41a}$ and $R^{41b}$, when present, is independently selected from hydrogen, —CH$_2$F, —CHF$_2$, and —CF$_3$. In a still further aspect, each of $R^{41a}$ and $R^{41b}$, when present, is independently selected from hydrogen and —CF$_3$.

In a further aspect, each of $R^{41a}$ and $R^{41b}$, when present, is independently selected from hydrogen and C1-C3 alkyl. In a still further aspect, each of $R^{41a}$ and $R^{41b}$, when present, is independently selected from hydrogen and methyl.

In a further aspect, $R^{41a}$ is hydrogen and $R^{41b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, $R^{41a}$, when present, is hydrogen and $R^{41b}$, when present, is selected from hydrogen, methyl, —CH$_2$F, —CH$_2$Cl, —CHF$_2$, —CF$_3$, —CHCl$_2$, —CCl$_3$, and cyclopropyl. In yet a further aspect, $R^{41a}$, when present, is hydrogen and $R^{41b}$, when present, is selected from hydrogen, methyl, —CH$_2$F, —CHF$_2$, —CF$_3$, and cyclopropyl. In an even further aspect, $R^{41a}$, when present, is hydrogen and $R^{41b}$, when present, is selected from hydrogen, methyl, —CF$_3$, and cyclopropyl.

In a further aspect, $R^{41a}$, when present, is hydrogen and $R^{41b}$, when present, is selected from hydrogen, C1-C3 monohaloalkyl, C1-C3 polyhaloalkyl, and cyclopropyl. In a still further aspect, $R^{41a}$, when present, is hydrogen and $R^{41b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, $R^{41a}$, when present, is hydrogen and $R^{41b}$, when present, is selected from hydrogen, —CH$_2$F, —CH$_2$Cl, —CHF$_2$, —CF$_3$, —CHCl$_2$, —CCl$_3$, and cyclopropyl. In an even further aspect, $R^{41a}$, when present, is hydrogen and $R^{41b}$, when present, is selected from hydrogen, —CH$_2$F, —CHF$_2$, —CF$_3$, and cyclopropyl. In a still further aspect, $R^{41a}$, when present, is hydrogen and $R^{41b}$, when present, is selected from hydrogen, —CF$_3$ and cyclopropyl.

In a further aspect, $R^{41a}$, when present, is hydrogen and $R^{41b}$, when present, is selected from hydrogen, C1-C3 alkyl, and cyclopropyl. In a still further aspect, $R^{41a}$, when present, is hydrogen and $R^{41b}$, when present, is selected from hydrogen, methyl, ethyl, and cyclopropyl. In yet a further aspect, $R^{41a}$, when present, is hydrogen and $R^{41b}$, when present, is selected from hydrogen, methyl, and cyclopropyl.

In a further aspect, $R^{41a}$, when present, is hydrogen and $R^{41b}$, when present, is selected from hydrogen, C1-C3 alkyl, C1-C3 monohaloalkyl, and C1-C3 polyhaloalkyl. In a still further aspect, $R^{41a}$, when present, is hydrogen and $R^{41b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, $R^{41a}$, when present, is hydrogen and $R^{41b}$, when present, is selected from hydrogen, methyl, —CH$_2$F, —CH$_2$Cl, —CHF$_2$, —CF$_3$, —CHCl$_2$, and —CCl$_3$. In an even further aspect, $R^{41a}$, when present, is hydrogen and $R^{41b}$, when present, is selected from hydrogen, methyl, —CH$_2$F, —CHF$_2$, and —CF$_3$. In a still further aspect, $R^{41a}$, when present, is hydrogen and $R^{41b}$, when present, is selected from hydrogen, methyl, and —CF$_3$.

In a further aspect, $R^{41a}$, when present, is hydrogen and $R^{41b}$, when present, is selected from hydrogen, C1-C3 monohaloalkyl, and C1-C3 polyhaloalkyl. In a still further aspect, $R^{41a}$, when present, is hydrogen and $R^{41b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, $R^{41a}$, when present, is hydrogen and $R^{41b}$, when present, is selected from hydrogen, —CH$_2$F, —CH$_2$Cl, —CHF$_2$, —CF$_3$, —CHCl$_2$, and —CCl$_3$. In an even further aspect, $R^{41a}$, when present, is hydrogen and $R^{41b}$, when present, is selected from hydrogen, —CH$_2$F, —CHF$_2$, and —CF$_3$. In a still further aspect, $R^{41a}$, when present, is hydrogen and $R^{41b}$, when present, is selected from hydrogen and —CF$_3$.

In a further aspect, $R^{41a}$, when present, is hydrogen and $R^{41b}$, when present, is selected from hydrogen and C1-C3 alkyl. In a still further aspect, $R^{41a}$, when present, is hydrogen and $R^{41b}$, when present, is selected from hydrogen, methyl, and ethyl. In yet a further aspect, $R^{41a}$, when present, is hydrogen and $R^{41b}$, when present, is selected from hydrogen and methyl. In an even further aspect, each of $R^{41a}$ and $R^{41b}$, when present, is hydrogen.

In a further aspect, $R^{41a}$ and $R^{41b}$, when present, are optionally covalently bonded and, together with nitrogen atom to which they are attached, comprise a 3- to 6-membered heterocycle. In a still further aspect, $R^{41a}$ and $R^{41b}$, when present, are covalently bonded, and together with nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In yet a further aspect, $R^{41a}$ and $R^{41b}$, when present, are covalently bonded, and together with nitrogen atom to which they are attached, comprise a heterocycle selected from pyrrolidinyl, piperidinyl, azepanyl, imidazolidinyl, and pyrazolidinyl. In an even further aspect, $R^{41a}$ and $R^{41b}$, when present, are covalently bonded, and together with nitrogen atom to which they are attached, comprise a heterocycle selected from imidazolyl, pyrazolyl, and pyrrolyl. In a still further aspect, $R^{41a}$ and $R^{41b}$, when present, are covalently bonded, and together with nitrogen atom to which they are attached, comprise a pyrrolidinyl. In yet a further aspect, $R^{41a}$ and $R^{41b}$, when present, are covalently bonded, and together with nitrogen atom to which they are attached, comprise a piperidinyl.

ee. $R^{42}$ Groups

In one aspect, $R^{42}$, when present, is selected from C1-C3 alkyl, C1-C3 monohaloalkyl, C1-C3 polyhaloalkyl, cyclopropyl, and, —NR$^{44a}$R$^{44b}$. In a further aspect, $R^{42}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, $R^{42}$, when present, is selected from methyl, —CH$_2$F, —CH$_2$Cl, —CHF$_2$, —CF$_3$, —CHCl$_2$, —CCl$_3$, cyclopropyl, —NHCH$_3$, and —N(CH$_3$)$_2$. In yet a further aspect, $R^{42}$, when present, is selected from methyl, —CH$_2$F, —CHF$_2$, —CF$_3$, cyclopropyl, —NHCH$_3$, and —N(CH$_3$)$_2$. In an even further aspect, $R^{42}$, when present, is selected from methyl, —CF$_3$, cyclopropyl, and —NHCH$_3$.

In a further aspect, $R^{42}$, when present, is selected from C1-C3 alkyl, C1-C3 monohaloalkyl, C1-C3 polyhaloalkyl, and, —NR$^{44a}$R$^{44b}$. In a still further aspect, $R^{42}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In yet a further aspect, $R^{42}$, when present, is selected from methyl, —CH$_2$F, —CH$_2$Cl, —CHF$_2$, —CF$_3$, —CHCl$_2$, —CCl$_3$, —NHCH$_3$, and —N(CH$_3$)$_2$. In an even further aspect, $R^{42}$, when present, is selected from methyl, —CH$_2$F, —CHF$_2$, —CF$_3$, —NHCH$_3$, and —N(CH$_3$)$_2$. In a still further aspect, $R^{42}$, when present, is selected from methyl, —CF$_3$, and —NHCH$_3$.

In a further aspect, $R^{42}$, when present, is selected from C1-C3 alkyl, C1-C3 monohaloalkyl, C1-C3 polyhaloalkyl, and cyclopropyl. In a still further aspect, $R^{42}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, $R^{42}$, when present, is selected from methyl, —CH$_2$F, —CH$_2$Cl, —CHF$_2$, —CF$_3$, —CHCl$_2$, —CCl$_3$, and cyclopropyl. In an even further aspect, $R^{42}$, when present, is selected from methyl, —CH$_2$F, —CHF$_2$, —CF$_3$, and cyclopropyl. In a still further aspect, $R^{42}$, when present, is selected from methyl, —CF$_3$, and cyclopropyl.

In a further aspect, $R^{42}$, when present, is selected from C1-C3 monohaloalkyl, C1-C3 polyhaloalkyl, and cyclopropyl. In a still further aspect, $R^{42}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, $R^{42}$, when present, is selected from —CH$_2$F, —CH$_2$Cl, —CHF$_2$, —CF$_3$, —CHCl$_2$, —CCl$_3$, and cyclopropyl. In an even further aspect, $R^{42}$, when present, is selected from —CH$_2$F, —CHF$_2$, —CF$_3$, and cyclopropyl. In a still further aspect, R$^{42}$, when present, is selected from —CF$_3$ and cyclopropyl.

In a further aspect, R$^{42}$, when present, is selected from C1-C3 alkyl, and cyclopropyl. In a still further aspect, R$^{42}$, when present, is selected from methyl, ethyl, and cyclopropyl. In yet a further aspect, R$^{42}$, when present, is selected from methyl, and cyclopropyl.

In a further aspect, R$^{42}$, when present, is selected from C1-C3 alkyl, C1-C3 monohaloalkyl, and C1-C3 polyhaloalkyl. In a still further aspect, R$^{42}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{42}$, when present, is selected from methyl, —CH$_2$F, —CH$_2$Cl, —CHF$_2$, —CF$_3$, —CHCl$_2$, and —CCl$_3$. In an even further aspect, R$^{42}$, when present, is selected from methyl, —CH$_2$F, —CHF$_2$, and —CF$_3$. In a still further aspect, R$^{42}$, when present, is selected from methyl and —CF$_3$.

In a further aspect, R$^{42}$, when present, is selected from C1-C3 monohaloalkyl, and C1-C3 polyhaloalkyl. In a still further aspect, R$^{42}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{42}$, when present, is selected from —CH$_2$F, —CH$_2$Cl, —CHF$_2$, —CF$_3$, —CHCl$_2$, and —CCl$_3$. In an even further aspect, R$^{42}$, when present, is selected from —CH$_2$F, —CHF$_2$, and —CF$_3$. In a still further aspect, R$^{42}$, when present, is —CF$_3$.

In a further aspect, R$^{42}$, when present, is C1-C3 alkyl. In a still further aspect, R$^{42}$, when present, is selected from methyl, and ethyl. In yet a further aspect, R$^{42}$, when present, is methyl.

ff. R$^{43}$ Groups

In one aspect, R$^{43}$, when present, is selected from C1-C3 alkyl, C1-C3 monohaloalkyl, C1-C3 polyhaloalkyl, cyclopropyl, and, —NR$^{45a}$R$^{45b}$. In a further aspect, R$^{43}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, R$^{43}$, when present, is selected from methyl, —CH$_2$F, —CH$_2$Cl, —CHF$_2$, —CF$_3$, —CHCl$_2$, —CCl$_3$, cyclopropyl, —NHCH$_3$, and —N(CH$_3$)$_2$. In yet a further aspect, R$^{43}$, when present, is selected from methyl, —CH$_2$F, —CHF$_2$, —CF$_3$, cyclopropyl, —NHCH$_3$, and —N(CH$_3$)$_2$. In an even further aspect, R$^{43}$, when present, is selected from methyl, —CF$_3$, cyclopropyl, and —NHCH$_3$.

In a further aspect, R$^{43}$, when present, is selected from C1-C3 alkyl, C1-C3 monohaloalkyl, C1-C3 polyhaloalkyl, and, —NR$^{44a}$R$^{44b}$. In a still further aspect, R$^{43}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In yet a further aspect, R$^{43}$, when present, is selected from methyl, —CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^{43}$, when present, is selected from methyl, —CH$_2$F, —CHF$_2$, —CF$_3$, —NHCH$_3$, and —N(CH$_3$)$_2$. In a still further aspect, R$^{43}$, when present, is selected from methyl, —CF$_3$, and —NHCH$_3$.

In a further aspect, R$^{43}$, when present, is selected from C1-C3 alkyl, C1-C3 monohaloalkyl, C1-C3 polyhaloalkyl, and cyclopropyl. In a still further aspect, R$^{43}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{43}$, when present, is selected from methyl, —CH$_2$F, —CH$_2$Cl, —CHF$_2$, —CF$_3$, —CHCl$_2$, —CCl$_3$, and cyclopropyl. In an even further aspect, R$^{43}$, when present, is selected from methyl, —CH$_2$F, —CHF$_2$, —CF$_3$, and cyclopropyl. In a still further aspect, R$^{43}$, when present, is selected from methyl, —CF$_3$, and cyclopropyl.

In a further aspect, R$^{43}$, when present, is selected from C1-C3 monohaloalkyl, C1-C3 polyhaloalkyl, and cyclopropyl. In a still further aspect, R$^{43}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{43}$, when present, is selected from —CH$_2$F, —CH$_2$Cl, —CHF$_2$, —CF$_3$, —CHCl$_2$, —CCl$_3$, and cyclopropyl. In yet a further aspect, R$^{43}$, when present, is selected from —CH$_2$F, —CHF$_2$, —CF$_3$, and cyclopropyl. In an even further aspect, R$^{43}$, when present, is selected from —CF$_3$ and cyclopropyl.

In a further aspect, R$^{43}$, when present, is selected from C1-C3 alkyl, and cyclopropyl. In a still further aspect, R$^{43}$, when present, is selected from methyl, ethyl, and cyclopropyl. In yet a further aspect, R$^{43}$, when present, is selected from methyl, and cyclopropyl.

In a further aspect, R$^{43}$, when present, is selected from C1-C3 alkyl, C1-C3 monohaloalkyl, and C1-C3 polyhaloalkyl. In a still further aspect, R$^{43}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{43}$, when present, is selected from methyl, —CH$_2$F, —CH$_2$Cl, —CHF$_2$, —CF$_3$, —CHCl$_2$, and —CCl$_3$. In an even further aspect, R$^{43}$, when present, is selected from methyl, —CH$_2$F, —CHF$_2$, and —CF$_3$. In a still further aspect, R$^{43}$, when present, is selected from methyl and —CF$_3$.

In a further aspect, R$^{43}$, when present, is selected from C1-C3 monohaloalkyl, and C1-C3 polyhaloalkyl. In a still further aspect, R$^{43}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{43}$, when present, is selected from —CH$_2$F, —CH$_2$Cl, —CHF$_2$, —CF$_3$, —CHCl$_2$, and —CCl$_3$. In an even further aspect, R$^{43}$, when present, is selected from —CH$_2$F, —CHF$_2$, and —CF$_3$. In a still further aspect, R$^{43}$, when present, is —CF$_3$.

In a further aspect, R$^{43}$, when present, is C1-C3 alkyl. In a still further aspect, R$^{43}$, when present, is selected from methyl, and ethyl. In yet a further aspect, R$^{43}$, when present, is methyl.

gg. R$^{44}$ Groups

In one aspect, each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with nitrogen atom to which they are attached, comprise a 3- to 6-membered heterocycle.

In a further aspect, each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle. In a still further aspect, each of $R^{44a}$ and $R^{44b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of $R^{44a}$ and $R^{44b}$, when present, is independently selected from hydrogen, methyl, —CH$_2$F, —CH$_2$Cl, —CHF$_2$, —CF$_3$, —CHCl$_2$, —CCl$_3$, and cyclopropyl. In an even further aspect, each of $R^{44a}$ and $R^{44b}$, when present, is independently selected from hydrogen, methyl, —CH$_2$F, —CHF$_2$, —CF$_3$, and cyclopropyl. In a still further aspect, each of $R^{44a}$ and $R^{44b}$, when present, is independently selected from hydrogen, methyl, —CF$_3$, and cyclopropyl.

In a further aspect, each of $R^{44a}$ and $R^{44b}$, when present, is independently selected from hydrogen, C1-C3 monohaloalkyl, C1-C3 polyhaloalkyl, and cyclopropyl. In a still further aspect, each of $R^{44a}$ and $R^{44b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of $R^{44a}$ and $R^{44b}$, when present, is independently selected from hydrogen, —CH$_2$F, —CH$_2$Cl, —CHF$_2$, —CF$_3$, —CHCl$_2$, —CCl$_3$, and cyclopropyl. In an even further aspect, each of $R^{44a}$ and $R^{44b}$, when present, is independently selected from hydrogen, —CH$_2$F, —CHF$_2$, —CF$_3$, and cyclopropyl. In a still further aspect, each of $R^{44a}$ and $R^{44b}$, when present, is independently selected from hydrogen, —CF$_3$ and cyclopropyl.

In a further aspect, each of $R^{44a}$ and $R^{44b}$, when present, is independently selected from hydrogen, C1-C3 alkyl, and cyclopropyl. In a still further aspect, each of $R^{44a}$ and $R^{44b}$, when present, is independently selected from hydrogen, methyl, ethyl, and cyclopropyl. In yet a further aspect, each of $R^{44a}$ and $R^{44b}$, when present, is independently selected from hydrogen, methyl, and cyclopropyl.

In a further aspect, each of $R^{44a}$ and $R^{44b}$, when present, is independently selected from hydrogen, C1-C3 alkyl, C1-C3 monohaloalkyl, and C1-C3 polyhaloalkyl. In a still further aspect, each of $R^{44a}$ and $R^{44b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of $R^{44a}$ and $R^{44b}$, when present, is independently selected from hydrogen, methyl, —CH$_2$F, —CH$_2$Cl, —CHF$_2$, —CF$_3$, —CHCl$_2$, and —CCl$_3$. In an even further aspect, each of $R^{44a}$ and $R^{44b}$, when present, is independently selected from hydrogen, methyl, —CH$_2$F, —CHF$_2$, and —CF$_3$. In a still further aspect, each of $R^{44a}$ and $R^{44b}$, when present, is independently selected from hydrogen, methyl, and —CF$_3$.

In a further aspect, each of $R^{44a}$ and $R^{44b}$, when present, is independently selected from hydrogen, C1-C3 monohaloalkyl, and C1-C3 polyhaloalkyl. In a still further aspect, each of $R^{44a}$ and $R^{44b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of $R^{44a}$ and $R^{44b}$, when present, is independently selected from hydrogen, —CH$_2$F, —CH$_2$Cl, —CHF$_2$, —CF$_3$, —CHCl$_2$, and —CCl$_3$. In an even further aspect, each of $R^{44a}$ and $R^{44b}$, when present, is independently selected from hydrogen, —CH$_2$F, —CHF$_2$, and —CF$_3$. In a still further aspect, each of $R^{44a}$ and $R^{44b}$, when present, is independently selected from hydrogen and —CF$_3$.

In a further aspect, each of $R^{44a}$ and $R^{44b}$, when present, is independently selected from hydrogen and C1-C3 alkyl. In a still further aspect, each of $R^{44a}$ and $R^{44b}$, when present, is independently selected from hydrogen, methyl, and ethyl. In yet a further aspect, each of $R^{44a}$ and $R^{44b}$, when present, is independently selected from hydrogen and methyl.

In a further aspect, $R^{44a}$ is hydrogen and $R^{44b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, $R^{44a}$, when present, is hydrogen and $R^{44b}$, when present, is selected from hydrogen, methyl, —CH$_2$F, —CH$_2$Cl, —CHF$_2$, —CF$_3$, —CHCl$_2$, —CCl$_3$, and cyclopropyl. In yet a further aspect, $R^{44a}$, when present, is hydrogen and $R^{44b}$, when present, is selected from hydrogen, methyl, —CH$_2$F, —CHF$_2$, —CF$_3$, and cyclopropyl. In an even further aspect, $R^{44a}$, when present, is hydrogen and $R^{44b}$, when present, is selected from hydrogen, methyl, —CF$_3$, and cyclopropyl.

In a further aspect, $R^{44a}$, when present, is hydrogen and $R^{44b}$, when present, is selected from hydrogen, C1-C3 monohaloalkyl, C1-C3 polyhaloalkyl, and cyclopropyl. In a still further aspect, $R^{44a}$, when present, is hydrogen and $R^{44b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, $R^{44a}$, when present, is hydrogen and $R^{44b}$, when present, is selected from hydrogen, —CH$_2$F, —CH$_2$Cl, —CHF$_2$, —CF$_3$, —CHCl$_2$, —CCl$_3$, and cyclopropyl. In an even further aspect, $R^{44a}$, when present, is hydrogen and $R^{44b}$, when present, is selected from hydrogen, —CH$_2$F, —CHF$_2$, —CF$_3$, and cyclopropyl. In a still further aspect, $R^{44a}$, when present, is hydrogen and $R^{44b}$, when present, is selected from hydrogen, —CF$_3$ and cyclopropyl.

In a further aspect, $R^{44a}$, when present, is hydrogen and $R^{44b}$, when present, is selected from hydrogen, C1-C3 alkyl, and cyclopropyl. In a still further aspect, $R^{44a}$, when present, is hydrogen and $R^{44b}$, when present, is selected from hydrogen, methyl, ethyl, and cyclopropyl. In yet a further aspect, $R^{44a}$, when present, is hydrogen and $R^{44b}$, when present, is selected from hydrogen, methyl, and cyclopropyl.

In a further aspect, $R^{44a}$, when present, is hydrogen and $R^{44b}$, when present, is selected from hydrogen, C1-C3 alkyl, C1-C3 monohaloalkyl, and C1-C3 polyhaloalkyl. In a still further aspect, $R^{44a}$, when present, is hydrogen and $R^{44b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, $R^{44a}$, when present, is hydrogen and $R^{44b}$, when present, is selected from hydrogen, methyl, —CH$_2$F, —CH$_2$Cl, —CHF$_2$, —CF$_3$, —CHCl$_2$, and —CCl$_3$. In an even further aspect, $R^{44a}$, when present, is hydrogen and $R^{44b}$, when present, is selected from hydrogen, methyl, —CH$_2$F, —CHF$_2$, and —CF$_3$. In a still further aspect, $R^{44a}$, when present, is hydrogen and $R^{44b}$, when present, is selected from hydrogen, methyl, and —CF$_3$.

In a further aspect, $R^{44a}$, when present, is hydrogen and $R^{44b}$, when present, is selected from hydrogen, C1-C3 monohaloalkyl, and C1-C3 polyhaloalkyl. In a still further aspect, $R^{44a}$, when present, is hydrogen and $R^{44b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{44a}$, when present, is hydrogen and R$^{44b}$, when present, is selected from hydrogen, —CH$_2$F, —CH$_2$Cl, —CHF$_2$, —CF$_3$, —CHCl$_2$, and —CCl$_3$. In an even further aspect, R$^{44a}$, when present, is hydrogen and R$^{44b}$, when present, is selected from hydrogen, —CH$_2$F, —CHF$_2$, and —CF$_3$. In a still further aspect, R$^{44a}$, when present, is hydrogen and R$^{44b}$, when present, is selected from hydrogen and —CF$_3$.

In a further aspect, R$^{44a}$, when present, is hydrogen and R$^{44b}$, when present, is selected from hydrogen and C1-C3 alkyl. In a still further aspect, R$^{44a}$, when present, is hydrogen and R$^{44b}$, when present, is selected from hydrogen, methyl, and ethyl. In yet a further aspect, R$^{44a}$, when present, is hydrogen and R$^{44b}$, when present, is selected from hydrogen and methyl. In an even further aspect, each of R$^{44a}$ and R$^{44b}$, when present, is hydrogen.

hh. R$^{45}$ Groups

In one aspect, each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with nitrogen atom to which they are attached, comprise a 3- to 6-membered heterocycle.

In a further aspect, each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with nitrogen atom to which they are attached, comprise a 3- to 6-membered heterocycle. In a still further aspect, each of R$^{45a}$ and R$^{45b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of R$^{45a}$ and R$^{45b}$, when present, is independently selected from hydrogen, methyl, —CH$_2$F, —CH$_2$Cl, —CHF$_2$, —CF$_3$, —CHCl$_2$, —CCl$_3$, and cyclopropyl. In an even further aspect, each of R$^{45a}$ and R$^{45b}$, when present, is independently selected from hydrogen, methyl, —CH$_2$F, —CHF$_2$, —CF$_3$, and cyclopropyl. In a still further aspect, each of R$^{45a}$ and R$^{45b}$, when present, is independently selected from hydrogen, methyl, —CF$_3$, and cyclopropyl.

In a further aspect, each of R$^{45a}$ and R$^{45b}$, when present, is independently selected from hydrogen, C1-C3 monohaloalkyl, C1-C3 polyhaloalkyl, and cyclopropyl. In a still further aspect, each of R$^{45a}$ and R$^{45b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of R$^{45a}$ and R$^{45b}$, when present, is independently selected from hydrogen, —CH$_2$F, —CH$_2$Cl, —CHF$_2$, —CF$_3$, —CHCl$_2$, —CCl$_3$, and cyclopropyl. In an even further aspect, each of R$^{45a}$ and R$^{45b}$, when present, is independently selected from hydrogen, —CH$_2$F, —CHF$_2$, —CF$_3$, and cyclopropyl. In a still further aspect, each of R$^{45a}$ and R$^{45b}$, when present, is independently selected from hydrogen, —CF$_3$ and cyclopropyl.

In a further aspect, each of R$^{45a}$ and R$^{45b}$, when present, is independently selected from hydrogen, C1-C3 alkyl, and cyclopropyl. In a still further aspect, each of R$^{45a}$ and R$^{45b}$, when present, is independently selected from hydrogen, methyl, ethyl, and cyclopropyl. In yet a further aspect, each of R$^{45a}$ and R$^{45b}$, when present, is independently selected from hydrogen, methyl, and cyclopropyl.

In a further aspect, each of R$^{45a}$ and R$^{45b}$, when present, is independently selected from hydrogen, C1-C3 alkyl, C1-C3 monohaloalkyl, and C1-C3 polyhaloalkyl. In a still further aspect, each of R$^{45a}$ and R$^{45b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{45a}$ and R$^{45b}$, when present, is independently selected from hydrogen, methyl, —CH$_2$F, —CH$_2$Cl, —CHF$_2$, —CF$_3$, —CHCl$_2$, and —CCl$_3$. In an even further aspect, each of R$^{45a}$ and R$^{45b}$, when present, is independently selected from hydrogen, methyl, —CH$_2$F, —CHF$_2$, and —CF$_3$. In a still further aspect, each of R$^{45a}$ and R$^{45b}$, when present, is independently selected from hydrogen, methyl, and —CF$_3$.

In a further aspect, each of R$^{45a}$ and R$^{45b}$, when present, is independently selected from hydrogen, C1-C3 monohaloalkyl, and C1-C3 polyhaloalkyl. In a still further aspect, each of R$^{45a}$ and R$^{45b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{45a}$ and R$^{45b}$, when present, is independently selected from hydrogen, —CH$_2$F, —CH$_2$Cl, —CHF$_2$, —CF$_3$, —CHCl$_2$, and —CCl$_3$. In an even further aspect, each of R$^{45a}$ and R$^{45b}$, when present, is independently selected from hydrogen, —CH$_2$F, —CHF$_2$, and —CF$_3$. In a still further aspect, each of R$^{45a}$ and R$^{45b}$, when present, is independently selected from hydrogen and —CF$_3$.

In a further aspect, each of R$^{45a}$ and R$^{45b}$, when present, is independently selected from hydrogen and C1-C3 alkyl. In a still further aspect, each of R$^{45a}$ and R$^{45b}$, when present, is independently selected from hydrogen, methyl, and ethyl. In yet a further aspect, each of R$^{45a}$ and R$^{45b}$, when present, is independently selected from hydrogen and methyl.

In a further aspect, R$^{45a}$ is hydrogen and R$^{45b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, R$^{45a}$, when present, is hydrogen and R$^{45b}$, when present, is selected from hydrogen, methyl, —CH$_2$F, —CH$_2$Cl, —CHF$_2$, —CF$_3$, —CHCl$_2$, —CCl$_3$, and cyclopropyl. In yet a further aspect, R$^{45a}$, when present, is hydrogen and R$^{45b}$, when present, is selected from hydrogen, methyl, —CH$_2$F, —CHF$_2$, —CF$_3$, and cyclopropyl. In an even further aspect, R$^{45a}$, when present, is hydrogen and R$^{45b}$, when present, is selected from hydrogen, methyl, —CF$_3$, and cyclopropyl.

In a further aspect, R$^{45a}$, when present, is hydrogen and R$^{45b}$, when present, is selected from hydrogen, C1-C3 monohaloalkyl, C1-C3 polyhaloalkyl, and cyclopropyl. In a still further aspect, R$^{45a}$, when present, is hydrogen and R$^{45b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{45a}$, when present, is hydrogen and R$^{45b}$, when present, is selected from hydrogen, —CH$_2$F, —CH$_2$Cl, —CHF$_2$, —CF$_3$, —CHCl$_2$, —CCl$_3$, and cyclopropyl. In an even further aspect, R$^{45a}$, when present, is hydrogen and R$^{45b}$, when present, is selected from hydrogen, —CH$_2$F, —CHF$_2$, —CF$_3$, and cyclopropyl. In a still further aspect, R$^{45a}$, when present, is hydrogen and $R^{45b}$, when present, is selected from hydrogen, —$CF_3$ and cyclopropyl.

In a further aspect, $R^{45a}$, when present, is hydrogen and $R^{45b}$, when present, is selected from hydrogen, C1-C3 alkyl, and cyclopropyl. In a still further aspect, $R^{45a}$, when present, is hydrogen and $R^{45b}$, when present, is selected from hydrogen, methyl, ethyl, and cyclopropyl. In yet a further aspect, $R^{45a}$, when present, is hydrogen and $R^{45b}$, when present, is selected from hydrogen, methyl, and cyclopropyl.

In a further aspect, $R^{45a}$, when present, is hydrogen and $R^{45b}$, when present, is selected from hydrogen, C1-C3 alkyl, C1-C3 monohaloalkyl, and C1-C3 polyhaloalkyl. In a still further aspect, $R^{45a}$, when present, is hydrogen and $R^{45b}$, when present, is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{45a}$, when present, is hydrogen and $R^{45b}$, when present, is selected from hydrogen, methyl, —$CH_2F$, —$CH_2Cl$, —$CHF_2$, —$CF_3$, —$CHCl_2$, and —$CCl_3$. In an even further aspect, $R^{45a}$, when present, is hydrogen and $R^{45b}$, when present, is selected from hydrogen, methyl, —$CH_2F$, —$CHF_2$, and —$CF_3$. In a still further aspect, $R^{45a}$, when present, is hydrogen and $R^{45b}$, when present, is selected from hydrogen, methyl, and —$CF_3$.

In a further aspect, $R^{45a}$, when present, is hydrogen and $R^{45b}$, when present, is selected from hydrogen, C1-C3 monohaloalkyl, and C1-C3 polyhaloalkyl. In a still further aspect, $R^{45a}$, when present, is hydrogen and $R^{45b}$, when present, is selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{45a}$, when present, is hydrogen and $R^{45b}$, when present, is selected from hydrogen, —$CH_2F$, —$CH_2Cl$, —$CHF_2$, —$CF_3$, —$CHCl_2$, and —$CCl_3$. In an even further aspect, $R^{45a}$, when present, is hydrogen and $R^{45b}$, when present, is selected from hydrogen, —$CH_2F$, —$CHF_2$, and —$CF_3$. In a still further aspect, $R^{45a}$, when present, is hydrogen and $R^{45b}$, when present, is selected from hydrogen and —$CF_3$.

In a further aspect, $R^{45a}$, when present, is hydrogen and $R^{45b}$, when present, is selected from hydrogen and C1-C3 alkyl. In a still further aspect, $R^{45a}$, when present, is hydrogen and $R^{45b}$, when present, is selected from hydrogen, methyl, and ethyl. In yet a further aspect, $R^{45a}$, when present, is hydrogen and $R^{45b}$, when present, is selected from hydrogen and methyl. In an even further aspect, each of $R^{45a}$ and $R^{45b}$, when present, is hydrogen.

ii. $R^{50}$ Groups

In one aspect, $R^{50}$, when present, is independently selected from hydrogen, C1-C3 alkyl, C1-C3 monohaloalkyl, C1-C3 polyhaloalkyl, and cyclopropyl. In a still further aspect, $R^{50}$, when present, is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, $R^{50}$, when present, is selected from hydrogen, methyl, —$CH_2F$, —$CH_2Cl$, —$CHF_2$, —$CF_3$, —$CHCl_2$, —$CCl_3$, and cyclopropyl. In an even further aspect, $R^{50}$, when present, is selected from hydrogen, methyl, —$CH_2F$, —$CHF_2$, —$CF_3$, and cyclopropyl. In a still further aspect, $R^{50}$, when present, is selected from hydrogen, methyl, —$CF_3$, and cyclopropyl.

In a further aspect, $R^{50}$, when present, is selected from hydrogen, C1-C3 monohaloalkyl, C1-C3 polyhaloalkyl, and cyclopropyl. In a still further aspect, $R^{50}$, when present, is selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, $R^{50}$, when present, is selected from hydrogen, —$CH_2F$, —$CH_2Cl$, —$CHF_2$, —$CF_3$, —$CHCl_2$, —$CCl_3$, and cyclopropyl. In an even further aspect, $R^{50}$, when present, is selected from hydrogen, —$CH_2F$, —$CHF_2$, —$CF_3$, and cyclopropyl. In a still further aspect, $R^{50}$, when present, is selected from hydrogen, —$CF_3$ and cyclopropyl.

In a further aspect, $R^{50}$, when present, is selected from hydrogen, C1-C3 alkyl, and cyclopropyl. In a still further aspect, $R^{50}$, when present, is selected from hydrogen, methyl, ethyl, and cyclopropyl. In yet a further aspect, $R^{50}$, when present, is selected from hydrogen, methyl, and cyclopropyl.

In a further aspect, $R^{50}$, when present, is selected from hydrogen, C1-C3 alkyl, C1-C3 monohaloalkyl, and C1-C3 polyhaloalkyl. In a still further aspect, $R^{50}$, when present, is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{50}$, when present, is selected from hydrogen, methyl, —$CH_2F$, —$CH_2Cl$, —$CHF_2$, —$CF_3$, —$CHCl_2$, and —$CCl_3$. In an even further aspect, $R^{50}$, when present, is selected from hydrogen, methyl, —$CH_2F$, —$CHF_2$, and —$CF_3$. In a still further aspect, $R^{50}$, when present, is selected from hydrogen, methyl, and —$CF_3$.

In a further aspect, $R^{50}$, when present, is selected from hydrogen, C1-C3 monohaloalkyl, and C1-C3 polyhaloalkyl. In a still further aspect, $R^{50}$, when present, is selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{50}$, when present, is selected from hydrogen, —$CH_2F$, —$CH_2Cl$, —$CHF_2$, —$CF_3$, —$CHCl_2$, and —$CCl_3$. In an even further aspect, $R^{50}$, when present, is selected from hydrogen, —$CH_2F$, —$CHF_2$, and —$CF_3$. In a still further aspect, $R^{50}$, when present, is selected from hydrogen and —$CF_3$.

In a further aspect, $R^{50}$, when present, is selected from hydrogen and C1-C3 alkyl. In a still further aspect, $R^{50}$, when present, is selected from hydrogen, methyl, and ethyl. In yet a further aspect, $R^{50}$, when present, is selected from hydrogen and methyl. In an even further aspect, $R^{50}$, when present, is hydrogen.

jj. $R^{51}$ Groups

In one aspect, each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle.

In a further aspect, each of $R^{51a}$ and $R^{51b}$, when present, is independently selected from hydrogen, C1-C3 alkyl, C1-C3 monohaloalkyl, C1-C3 polyhaloalkyl, and cyclopropyl. In a still further aspect, each of $R^{51a}$ and $R^{51b}$, when present, is independently selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, each of $R^{51a}$ and $R^{51b}$, when present, is independently selected from hydrogen, methyl, —$CH_2F$, —$CH_2Cl$, —$CHF_2$, —$CF_3$, —$CHCl_2$, —$CCl_3$, and cyclopropyl. In an even further aspect, each of $R^{51a}$ and $R^{51b}$, when present, is independently selected from hydrogen, methyl, —$CH_2F$, —$CHF_2$, —$CF_3$, and cyclopropyl. In a still further aspect, each of $R^{51a}$ and $R^{51b}$, when present, is independently selected from hydrogen, methyl, —$CF_3$, and cyclopropyl.

In a further aspect, each of $R^{51a}$ and $R^{51b}$, when present, is independently selected from hydrogen, C1-C3 monohaloalkyl, C1-C3 polyhaloalkyl, and cyclopropyl. In a still further aspect, each of $R^{51a}$ and $R^{51b}$, when present, is independently selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, each of $R^{51a}$ and $R^{51b}$, when present, is independently selected from hydrogen, —$CH_2F$, —$CH_2Cl$, —$CHF_2$, —$CF_3$, —$CHCl_2$, —$CCl_3$, and cyclopropyl. In an even further aspect, each of $R^{51a}$ and $R^{51b}$, when present, is independently selected from hydrogen, —$CH_2F$, —$CHF_2$, —$CF_3$, and cyclopropyl. In a still further aspect, each of $R^{51a}$ and $R^{51b}$, when present, is independently selected from hydrogen, —$CF_3$ and cyclopropyl.

In a further aspect, each of $R^{51a}$ and $R^{51b}$, when present, is independently selected from hydrogen, C1-C3 alkyl, and cyclopropyl. In a still further aspect, each of $R^{51a}$ and $R^{51b}$, when present, is independently selected from hydrogen, methyl, ethyl, and cyclopropyl. In yet a further aspect, each of $R^{51a}$ and $R^{51b}$, when present, is independently selected from hydrogen, methyl, and cyclopropyl.

In a further aspect, each of $R^{51a}$ and $R^{51b}$, when present, is independently selected from hydrogen, C1-C3 alkyl, C1-C3 monohaloalkyl, and C1-C3 polyhaloalkyl. In a still further aspect, each of $R^{51a}$ and $R^{51b}$, when present, is independently selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, each of $R^{51a}$ and $R^{51b}$, when present, is independently selected from hydrogen, methyl, —$CH_2F$, —$CH_2Cl$, —$CHF_2$, —$CF_3$, —$CHCl_2$, and —$CCl_3$. In an even further aspect, each of $R^{51a}$ and $R^{51b}$, when present, is independently selected from hydrogen, methyl, —$CH_2F$, —$CHF_2$, and —$CF_3$. In a still further aspect, each of $R^{51a}$ and $R^{51b}$, when present, is independently selected from hydrogen, methyl, and —$CF_3$.

In a further aspect, each of $R^{51a}$ and $R^{51b}$, when present, is independently selected from hydrogen, C1-C3 monohaloalkyl, and C1-C3 polyhaloalkyl. In a still further aspect, each of $R^{51a}$ and $R^{51b}$, when present, is independently selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, each of $R^{51a}$ and $R^{51b}$, when present, is independently selected from hydrogen, —$CH_2F$, —$CH_2Cl$, —$CHF_2$, —$CF_3$, —$CHCl_2$, and —$CCl_3$. In an even further aspect, each of $R^{51a}$ and $R^{51b}$, when present, is independently selected from hydrogen, —$CH_2F$, —$CHF_2$, and —$CF_3$. In a still further aspect, each of $R^{51a}$ and $R^{51b}$, when present, is independently selected from hydrogen and —$CF_3$.

In a further aspect, each of $R^{51a}$ and $R^{51b}$, when present, is independently selected from hydrogen and C1-C3 alkyl. In a still further aspect, each of $R^{51a}$ and $R^{51b}$, when present, is independently selected from hydrogen, methyl, and ethyl. In yet a further aspect, each of $R^{51a}$ and $R^{51b}$, when present, is independently selected from hydrogen and methyl.

In a further aspect, $R^{51a}$ is hydrogen and $R^{51b}$, when present, is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In a still further aspect, $R^{51a}$, when present, is hydrogen and $R^{51b}$, when present, is selected from hydrogen, methyl, —$CH_2F$, —$CH_2Cl$, —$CHF_2$, —$CF_3$, —$CHCl_2$, —$CCl_3$, and cyclopropyl. In yet a further aspect, $R^{51a}$, when present, is hydrogen and $R^{51b}$, when present, is selected from hydrogen, methyl, —$CH_2F$, —$CHF_2$, —$CF_3$, and cyclopropyl. In an even further aspect, $R^{51a}$, when present, is hydrogen and $R^{51b}$, when present, is selected from hydrogen, methyl, —$CF_3$, and cyclopropyl.

In a further aspect, $R^{51a}$, when present, is hydrogen and $R^{51b}$, when present, is selected from hydrogen, C1-C3 monohaloalkyl, C1-C3 polyhaloalkyl, and cyclopropyl. In a still further aspect, $R^{51a}$, when present, is hydrogen and $R^{51b}$, when present, is selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, $R^{51a}$, when present, is hydrogen and $R^{51b}$, when present, is selected from hydrogen, —$CH_2F$, —$CH_2Cl$, —$CHF_2$, —$CF_3$, —$CHCl_2$, —$CCl_3$, and cyclopropyl. In an even further aspect, $R^{51a}$, when present, is hydrogen and $R^{51b}$, when present, is selected from hydrogen, —$CH_2F$, —$CHF_2$, —$CF_3$, and cyclopropyl. In a still further aspect, $R^{51a}$, when present, is hydrogen and $R^{51b}$, when present, is selected from hydrogen, —$CF_3$ and cyclopropyl.

In a further aspect, $R^{51a}$, when present, is hydrogen and $R^{51b}$, when present, is selected from hydrogen, C1-C3 alkyl, and cyclopropyl. In a still further aspect, $R^{51a}$, when present, is hydrogen and $R^{51b}$, when present, is selected from hydrogen, methyl, ethyl, and cyclopropyl. In yet a further aspect, $R^{51a}$, when present, is hydrogen and $R^{51b}$, when present, is selected from hydrogen, methyl, and cyclopropyl.

In a further aspect, $R^{51a}$, when present, is hydrogen and $R^{51b}$, when present, is selected from hydrogen, C1-C3 alkyl, C1-C3 monohaloalkyl, and C1-C3 polyhaloalkyl. In a still further aspect, $R^{51a}$, when present, is hydrogen and $R^{51b}$, when present, is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{51a}$, when present, is hydrogen and $R^{51b}$, when present, is selected from hydrogen, methyl, —$CH_2F$, —$CH_2Cl$, —$CHF_2$, —$CF_3$, —$CHCl_2$, and —$CCl_3$. In an even further aspect, $R^{51a}$, when present, is hydrogen and $R^{51b}$, when present, is selected from hydrogen, methyl, —$CH_2F$, —$CHF_2$, and —$CF_3$. In a still further aspect, $R^{51a}$, when present, is hydrogen and $R^{51b}$, when present, is selected from hydrogen, methyl, and —$CF_3$.

In a further aspect, $R^{51a}$, when present, is hydrogen and $R^{51b}$, when present, is selected from hydrogen, C1-C3 monohaloalkyl, and C1-C3 polyhaloalkyl. In a still further aspect, $R^{51a}$, when present, is hydrogen and $R^{51b}$, when present, is selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{51a}$, when present, is hydrogen and $R^{51b}$, when present, is selected from hydrogen, —$CH_2F$, —$CH_2Cl$, —$CHF_2$, —$CF_3$, —$CHCl_2$, and —$CCl_3$. In an even further aspect, $R^{51a}$, when present, is hydrogen and $R^{51b}$, when present, is selected from hydrogen, —$CH_2F$, —$CHF_2$, and —$CF_3$. In a still further aspect, $R^{51a}$, when present, is hydrogen and $R^{51b}$, when present, is selected from hydrogen and —$CF_3$.

In a further aspect, $R^{51a}$, when present, is hydrogen and $R^{51b}$, when present, is selected from hydrogen and C1-C3 alkyl. In a still further aspect, $R^{51a}$, when present, is hydrogen and $R^{51b}$, when present, is selected from hydrogen, methyl, and ethyl. In yet a further aspect, $R^{51a}$, when present, is hydrogen and $R^{51b}$, when present, is selected from hydrogen and methyl. In an even further aspect, each of $R^{51a}$ and $R^{51b}$, when present, is hydrogen.

In a further aspect, $R^{51a}$ and $R^{51b}$, when present, are optionally covalently bonded and, together with nitrogen atom to which they are attached, comprise a 3- to 6-membered heterocycle. In a still further aspect, $R^{51a}$ and $R^{51b}$, when present, are covalently bonded, and together with nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In yet a further aspect, $R^{51a}$ and $R^{51b}$, when present, are covalently bonded, and together with nitrogen atom to which they are attached, comprise a heterocycle selected from pyrrolidinyl, piperidinyl, azepanyl, imidazolidinyl, and pyrazolidinyl. In an even further aspect, $R^{51a}$ and $R^{51b}$, when present, are covalently bonded, and together with nitrogen atom to which they are attached, comprise a heterocycle selected from imidazolyl, pyrazolyl, and pyrrolyl. In a still further aspect, $R^{51a}$ and $R^{51b}$, when present, are covalently bonded, and together with nitrogen atom to which they are attached, comprise a pyrrolidinyl. $R^{51a}$ and $R^{51b}$, when present, are covalently bonded, and together with nitrogen atom to which they are attached, comprise a piperidinyl.

kk. $R^{52}$ Groups

In one aspect, $R^{52}$, when present, is independently selected from C1-C3 alkyl, C1-C3 monohaloalkyl, C1-C3 polyhaloalkyl, cyclopropyl, and, $-NR^{54a}R^{54b}$. In a further aspect, $R^{52}$, when present, is selected from methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, cyclopropyl, $-NHCH_3$, $-NHCH_2CH_3$, $-NH(CH_2)_2CH_3$, $-NHCH(CH_3)_2$, $-N(CH_3)_2$, $-N(CH_3)CH_2CH_3$, $-N(CH_3)(CH_2)_2CH_3$, $-N(CH_3)CH(CH_3)_2$, and $-N(CH_2CH_3)_2$. In a still further aspect, $R^{52}$, when present, is selected from methyl, $-CH_2F$, $-CH_2Cl$, $-CHF_2$, $-CF_3$, $-CHCl_2$, $-CCl_3$, cyclopropyl, $-NHCH_3$, and $-N(CH_3)_2$. In yet a further aspect, $R^{52}$, when present, is selected from methyl, $-CH_2F$, $-CHF_2$, $-CF_3$, cyclopropyl, $-NHCH_3$, and $-N(CH_3)_2$. In an even further aspect, $R^{52}$, when present, is selected from methyl, $-CF_3$, cyclopropyl, and $-NHCH_3$.

In a further aspect, $R^{52}$, when present, is selected from C1-C3 alkyl, C1-C3 monohaloalkyl, C1-C3 polyhaloalkyl, and, $-NR^{54a}R^{54b}$. In a still further aspect, $R^{52}$, when present, is selected from methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-NHCH_3$, $-NHCH_2CH_3$, $-NH(CH_2)_2CH_3$, $-NHCH(CH_3)_2$, $-N(CH_3)_2$, $-N(CH_3)CH_2CH_3$, $-N(CH_3)(CH_2)_2CH_3$, $-N(CH_3)CH(CH_3)_2$, and $-N(CH_2CH_3)_2$. In yet a further aspect, $R^{52}$, when present, is selected from methyl, $-CH_2F$, $-CH_2Cl$, $-CHF_2$, $-CF_3$, $-CHCl_2$, $-CCl_3$, $-NHCH_3$, and $-N(CH_3)_2$. In an even further aspect, $R^{52}$, when present, is selected from methyl, $-CH_2F$, $-CHF_2$, $-CF_3$, $-NHCH_3$, and $-N(CH_3)_2$. In a still further aspect, $R^{52}$, when present, is selected from methyl, $-CF_3$, and $-NHCH_3$.

In a further aspect, $R^{52}$, when present, is selected from C1-C3 alkyl, C1-C3 monohaloalkyl, C1-C3 polyhaloalkyl, and cyclopropyl. In a still further aspect, $R^{52}$, when present, is selected from methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, and cyclopropyl. In yet a further aspect, $R^{52}$, when present, is selected from methyl, $-CH_2F$, $-CH_2Cl$, $-CHF_2$, $-CF_3$, $-CHCl_2$, $-CCl_3$, and cyclopropyl. In an even further aspect, $R^{52}$, when present, is selected from methyl, $-CH_2F$, $-CHF_2$, $-CF_3$, and cyclopropyl. In a still further aspect, $R^{52}$, when present, is selected from methyl, $-CF_3$, and cyclopropyl.

In a further aspect, $R^{52}$, when present, is selected from C1-C3 monohaloalkyl, C1-C3 polyhaloalkyl, and cyclopropyl. In a still further aspect, $R^{52}$, when present, is selected from $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, and cyclopropyl. In yet a further aspect, $R^{52}$, when present, is selected from $-CH_2F$, $-CH_2Cl$, $-CHF_2$, $-CF_3$, $-CHCl_2$, $-CCl_3$, and cyclopropyl. In an even further aspect, $R^{52}$, when present, is selected from $-CH_2F$, $-CHF_2$, $-CF_3$, and cyclopropyl. In a still further aspect, $R^{52}$, when present, is selected from $-CF_3$ and cyclopropyl.

In a further aspect, $R^{52}$, when present, is selected from C1-C3 alkyl, and cyclopropyl. In a still further aspect, $R^{52}$, when present, is selected from methyl, ethyl, and cyclopropyl. In a yet further aspect, $R^{52}$, when present, is selected from methyl, and cyclopropyl.

In a further aspect, $R^{52}$, when present, is selected from C1-C3 alkyl, C1-C3 monohaloalkyl, and C1-C3 polyhaloalkyl. In a still further aspect, $R^{52}$, when present, is selected from methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, and $-CH_2CCl_3$. In yet a further aspect, $R^{52}$, when present, is selected from methyl, $-CH_2F$, $-CH_2Cl$, $-CHF_2$, $-CF_3$, $-CHCl_2$, and $-CCl_3$. In an even further aspect, $R^{52}$, when present, is selected from methyl, $-CH_2F$, $-CHF_2$, and $-CF_3$. In a still further aspect, $R^{52}$, when present, is selected from methyl and $-CF_3$.

In a further aspect, $R^{52}$, when present, is selected from C1-C3 monohaloalkyl, and C1-C3 polyhaloalkyl. In a still further aspect, $R^{52}$, when present, is selected from $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, and $-CH_2CCl_3$. In yet a further aspect, $R^{52}$, when present, is selected from $-CH_2F$, $-CH_2Cl$, $-CHF_2$, $-CF_3$, $-CHCl_2$, and $-CCl_3$. In an even further aspect, $R^{52}$, when present, is selected from $-CH_2F$, $-CHF_2$, and $-CF_3$. In a still further aspect, $R^{52}$, when present, is $-CF_3$.

In a further aspect, $R^{52}$, when present, is C1-C3 alkyl. In a still further aspect, $R^{52}$, when present, is selected from methyl, and ethyl. In an even further aspect, $R^{52}$, when present, is methyl.

ll. $R^{53}$ Groups

In one aspect, $R^{53}$, when present, is independently from C1-C3 alkyl, C1-C3 monohaloalkyl, C1-C3 polyhaloalkyl, cyclopropyl, and, $-NR^{55a}R^{55b}$. In a further aspect, $R^{53}$, when present, is selected from methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, cyclopropyl, $-NHCH_3$, $-NHCH_2CH_3$, $-NH(CH_2)_2CH_3$, $-NHCH(CH_3)_2$, $-N(CH_3)_2$, $-N(CH_3)CH_2CH_3$, $-N(CH_3)(CH_2)_2CH_3$, $-N(CH_3)CH(CH_3)_2$, and $-N(CH_2CH_3)_2$. In a still further aspect, $R^{53}$, when present, is selected from methyl, $-CH_2F$, $-CH_2Cl$, $-CHF_2$, $-CF_3$, $-CHCl_2$, $-CCl_3$, cyclopropyl, $-NHCH_3$, and $-N(CH_3)_2$. In yet a further aspect, $R^{53}$, when present, is selected from methyl, $-CH_2F$, $-CHF_2$, $-CF_3$, cyclopropyl, $-NHCH_3$, and $-N(CH_3)_2$. In an even further aspect, $R^{53}$, when present, is selected from methyl, $-CF_3$, cyclopropyl, and $-NHCH_3$.

In a further aspect, $R^{53}$, when present, is selected from C1-C3 alkyl, C1-C3 monohaloalkyl, C1-C3 polyhaloalkyl, and, —$NR^{54a}R^{54b}$. In a still further aspect, $R^{53}$, when present, is selected from methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$. In yet a further aspect, $R^{53}$, when present, is selected from methyl, —$CH_2F$, —$CH_2Cl$, —$CHF_2$, —$CF_3$, —$CHCl_2$, —$CCl_3$, —$NHCH_3$, and —$N(CH_3)_2$. In an even further aspect, $R^{53}$, when present, is selected from methyl, —$CH_2F$, —$CHF_2$, —$CF_3$, —$NHCH_3$, and —$N(CH_3)_2$. In a still further aspect, $R^{53}$, when present, is selected from methyl, —$CF_3$, and —$NHCH_3$.

In a further aspect, $R^{53}$, when present, is selected from C1-C3 alkyl, C1-C3 monohaloalkyl, C1-C3 polyhaloalkyl, and cyclopropyl. In a still further aspect, $R^{53}$, when present, is selected from methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, $R^{53}$, when present, is selected from methyl, —$CH_2F$, —$CH_2Cl$, —$CHF_2$, —$CF_3$, —$CHCl_2$, —$CCl_3$, and cyclopropyl. In an even further aspect, $R^{53}$, when present, is selected from methyl, —$CH_2F$, —$CHF_2$, —$CF_3$, and cyclopropyl. In a still further aspect, $R^{53}$, when present, is selected from methyl, —$CF_3$, and cyclopropyl.

In a further aspect, $R^{53}$, when present, is selected from C1-C3 monohaloalkyl, C1-C3 polyhaloalkyl, and cyclopropyl. In a still further aspect, $R^{53}$, when present, is selected from —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, $R^{53}$, when present, is selected from —$CH_2F$, —$CH_2Cl$, —$CHF_2$, —$CF_3$, —$CHCl_2$, —$CCl_3$, and cyclopropyl. In an even further aspect, $R^{53}$, when present, is selected from —$CH_2F$, —$CHF_2$, —$CF_3$, and cyclopropyl. In a still further aspect, $R^{53}$, when present, is selected from —$CF_3$ and cyclopropyl.

In a further aspect, $R^{53}$, when present, is selected from C1-C3 alkyl, and cyclopropyl. In a still further aspect, $R^{53}$, when present, is selected from methyl, ethyl, and cyclopropyl. In yet a further aspect, $R^{53}$, when present, is selected from methyl, and cyclopropyl.

In a further aspect, $R^{53}$, when present, is selected from C1-C3 alkyl, C1-C3 monohaloalkyl, and C1-C3 polyhaloalkyl. In a still further aspect, $R^{53}$, when present, is selected from methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{53}$, when present, is selected from methyl, —$CH_2F$, —$CH_2Cl$, —$CHF_2$, —$CF_3$, —$CHCl_2$, and —$CCl_3$. In an even further aspect, $R^{53}$, when present, is selected from methyl, —$CH_2F$, —$CHF_2$, and —$CF_3$. In a still further aspect, $R^{53}$, when present, is selected from methyl and —$CF_3$.

In a further aspect, $R^{53}$, when present, is selected from C1-C3 monohaloalkyl, and C1-C3 polyhaloalkyl. In a still further aspect, $R^{53}$, when present, is selected from —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{53}$, when present, is selected from —$CH_2F$, —$CH_2Cl$, —$CHF_2$, —$CF_3$, —$CHCl_2$, and —$CCl_3$. In an even further aspect, $R^{53}$, when present, is selected from —$CH_2F$, —$CHF_2$, and —$CF_3$. In a still further aspect, $R^{53}$, when present, is —$CF_3$.

In a further aspect, $R^{53}$, when present, is C1-C3 alkyl. In a still further aspect, $R^{53}$, when present, is selected from methyl, and ethyl. In yet a further aspect, $R^{53}$, when present, is methyl.

mm. $R^{54}$ Groups

In one aspect, each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle.

In a further aspect, each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle. In a still further aspect, each of $R^{54a}$ and $R^{54b}$, when present, is independently selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, each of $R^{54a}$ and $R^{54b}$, when present, is independently selected from hydrogen, methyl, —$CH_2F$, —$CH_2Cl$, —$CHF_2$, —$CF_3$, —$CHCl_2$, —$CCl_3$, and cyclopropyl. In an even further aspect, each of $R^{54a}$ and $R^{54b}$, when present, is independently selected from hydrogen, methyl, —$CH_2F$, —$CHF_2$, —$CF_3$, and cyclopropyl. In a still further aspect, each of $R^{54a}$ and $R^{54b}$, when present, is independently selected from hydrogen, methyl, —$CF_3$, and cyclopropyl.

In a further aspect, each of $R^{54a}$ and $R^{54b}$, when present, is independently selected from hydrogen, C1-C3 monohaloalkyl, C1-C3 polyhaloalkyl, and cyclopropyl. In a still further aspect, each of $R^{54a}$ and $R^{54b}$, when present, is independently selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, each of $R^{54a}$ and $R^{54b}$, when present, is independently selected from hydrogen, —$CH_2F$, —$CH_2Cl$, —$CHF_2$, —$CF_3$, —$CHCl_2$, —$CCl_3$, and cyclopropyl. In an even further aspect, each of $R^{54a}$ and $R^{54b}$, when present, is independently selected from hydrogen, —$CH_2F$, —$CHF_2$, —$CF_3$, and cyclopropyl. In a still further aspect, each of $R^{54a}$ and $R^{54b}$, when present, is independently selected from hydrogen, —$CF_3$ and cyclopropyl.

In a further aspect, each of $R^{54a}$ and $R^{54b}$, when present, is independently selected from hydrogen, C1-C3 alkyl, and cyclopropyl. In a still further aspect, each of $R^{54a}$ and $R^{54b}$, when present, is independently selected from hydrogen, methyl, ethyl, and cyclopropyl. In yet a further aspect, each of $R^{54a}$ and $R^{54b}$, when present, is independently selected from hydrogen, methyl, and cyclopropyl.

In a further aspect, each of $R^{54a}$ and $R^{54b}$, when present, is independently selected from hydrogen, C1-C3 alkyl, C1-C3 monohaloalkyl, and C1-C3 polyhaloalkyl. In a still further aspect, each of $R^{54a}$ and $R^{54b}$, when present, is independently selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, each of $R^{54a}$ and $R^{54b}$, when present, is independently selected from hydrogen, methyl, —$CH_2F$, —$CH_2Cl$, —$CHF_2$, —$CF_3$, —$CHCl_2$, and —$CCl_3$. In a still further aspect, each of $R^{54a}$ and $R^{54b}$, when present, is independently selected from hydrogen, methyl, —CH$_2$F, —CHF$_2$, and —CF$_3$. In yet a further aspect, each of $R^{54a}$ and $R^{54b}$, when present, is independently selected from hydrogen, methyl, and —CF$_3$.

In a further aspect, each of $R^{54a}$ and $R^{54b}$, when present, is independently selected from hydrogen, C1-C3 monohaloalkyl, and C1-C3 polyhaloalkyl. In a still further aspect, each of $R^{54a}$ and $R^{54b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of $R^{54a}$ and $R^{54b}$, when present, is independently selected from hydrogen, —CH$_2$F, —CH$_2$Cl, —CHF$_2$, —CF$_3$, —CHCl$_2$, and —CCl$_3$. In an even further aspect, each of $R^{54a}$ and $R^{54b}$, when present, is independently selected from hydrogen, —CH$_2$F, —CHF$_2$, and —CF$_3$. In a still further aspect, each of $R^{54a}$ and $R^{54b}$, when present, is independently selected from hydrogen and —CF$_3$.

In a further aspect, each of $R^{54a}$ and $R^{54b}$, when present, is independently selected from hydrogen and C1-C3 alkyl. In a still further aspect, each of $R^{54a}$ and $R^{54b}$, when present, is independently selected from hydrogen, methyl, and ethyl. In yet a further aspect, each of $R^{54a}$ and $R^{54b}$, when present, is independently selected from hydrogen and methyl.

In a further aspect, $R^{54a}$ is hydrogen and $R^{54b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, $R^{54a}$, when present, is hydrogen and $R^{54b}$, when present, is selected from hydrogen, methyl, —CH$_2$F, —CH$_2$Cl, —CHF$_2$, —CF$_3$, —CHCl$_2$, —CCl$_3$, and cyclopropyl. In yet a further aspect, $R^{54a}$, when present, is hydrogen and $R^{54b}$, when present, is selected from hydrogen, methyl, —CH$_2$F, —CHF$_2$, —CF$_3$, and cyclopropyl. In an even further aspect, $R^{54a}$, when present, is hydrogen and $R^{54b}$, when present, is selected from hydrogen, methyl, —CF$_3$, and cyclopropyl.

In a further aspect, $R^{54a}$, when present, is hydrogen and $R^{54b}$, when present, is selected from hydrogen, C1-C3 monohaloalkyl, C1-C3 polyhaloalkyl, and cyclopropyl. In a still further aspect, $R^{54a}$, when present, is hydrogen and $R^{54b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, $R^{54a}$, when present, is hydrogen and $R^{54b}$, when present, is selected from hydrogen, —CH$_2$F, —CH$_2$Cl, —CHF$_2$, —CF$_3$, —CHCl$_2$, —CCl$_3$, and cyclopropyl. In an even further aspect, $R^{54a}$, when present, is hydrogen and $R^{54b}$, when present, is selected from hydrogen, —CH$_2$F, —CHF$_2$, —CF$_3$, and cyclopropyl. In a still further aspect, $R^{54a}$, when present, is hydrogen and $R^{54b}$, when present, is selected from hydrogen, —CF$_3$ and cyclopropyl.

In a further aspect, $R^{54a}$, when present, is hydrogen and $R^{54b}$, when present, is selected from hydrogen, C1-C3 alkyl, and cyclopropyl. In a still further aspect, $R^{54a}$, when present, is hydrogen and $R^{54b}$, when present, is selected from hydrogen, methyl, ethyl, and cyclopropyl. In yet a further aspect, $R^{54a}$, when present, is hydrogen and $R^{54b}$, when present, is selected from hydrogen, methyl, and cyclopropyl.

In a further aspect, $R^{54a}$, when present, is hydrogen and $R^{54b}$, when present, is selected from hydrogen, C1-C3 alkyl, C1-C3 monohaloalkyl, and C1-C3 polyhaloalkyl. In a still further aspect, $R^{54a}$, when present, is hydrogen and $R^{54b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, $R^{54a}$, when present, is hydrogen and $R^{54b}$, when present, is selected from hydrogen, methyl, —CH$_2$F, —CH$_2$Cl, —CHF$_2$, —CF$_3$, —CHCl$_2$, and —CCl$_3$. In an even further aspect, $R^{54a}$, when present, is hydrogen and $R^{54b}$, when present, is selected from hydrogen, methyl, —CH$_2$F, —CHF$_2$, and —CF$_3$. In a still further aspect, $R^{54a}$, when present, is hydrogen and $R^{54b}$, when present, is selected from hydrogen, methyl, and —CF$_3$.

In a further aspect, $R^{54a}$, when present, is hydrogen and $R^{54b}$, when present, is selected from hydrogen, C1-C3 monohaloalkyl, and C1-C3 polyhaloalkyl. In a still further aspect, $R^{54a}$, when present, is hydrogen and $R^{54b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, $R^{54a}$, when present, is hydrogen and $R^{54b}$, when present, is selected from hydrogen, —CH$_2$F, —CH$_2$Cl, —CHF$_2$, —CF$_3$, —CHCl$_2$, and —CCl$_3$. In an even further aspect, $R^{54a}$, when present, is hydrogen and $R^{54b}$, when present, is selected from hydrogen, —CH$_2$F, —CHF$_2$, and —CF$_3$. In a still further aspect, $R^{54a}$, when present, is hydrogen and $R^{54b}$, when present, is selected from hydrogen and —CF$_3$.

In a further aspect, $R^{54a}$, when present, is hydrogen and $R^{54b}$, when present, is selected from hydrogen and C1-C3 alkyl. In a still further aspect, $R^{54a}$, when present, is hydrogen and $R^{54b}$, when present, is selected from hydrogen, methyl, and ethyl. In yet a further aspect, $R^{54a}$, when present, is hydrogen and $R^{54b}$, when present, is selected from hydrogen and methyl. In an even further aspect, each of $R^{54a}$ and $R^{54b}$, when present, is hydrogen.

nn. $R^{55}$ Groups

In one aspect, each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle In a further aspect, each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle. In a still further aspect, each of $R^{55a}$ and $R^{55b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of $R^{55a}$ and $R^{55b}$, when present, is independently selected from hydrogen, methyl, —CH$_2$F, —CH$_2$Cl, —CHF$_2$, —CF$_3$, —CHCl$_2$, —CCl$_3$, and cyclopropyl. In an even further aspect, each of $R^{55a}$ and $R^{55b}$, when present, is independently selected from hydrogen, methyl, —CH$_2$F, —CHF$_2$, —CF$_3$, and cyclopropyl. In a still further aspect, each of $R^{55a}$ and $R^{55b}$, when present, is independently selected from hydrogen, methyl, —CF$_3$, and cyclopropyl.

In a further aspect, each of $R^{55a}$ and $R^{55b}$, when present, is independently selected from hydrogen, C1-C3 monohaloalkyl, C1-C3 polyhaloalkyl, and cyclopropyl. In a still further aspect, each of $R^{55a}$ and $R^{55b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of R$^{55a}$ and R$^{55b}$, when present, is independently selected from hydrogen, —CH$_2$F, —CH$_2$Cl, —CHF$_2$, —CF$_3$, —CHCl$_2$, —CCl$_3$, and cyclopropyl. In an even further aspect, each of Rss$^{55a}$ and R$^{55b}$, when present, is independently selected from hydrogen, —CH$_2$F, —CHF$_2$, —CF$_3$, and cyclopropyl. In a still further aspect, each of R$^{55a}$ and R$^{55b}$, when present, is independently selected from hydrogen, —CF$_3$ and cyclopropyl.

In a further aspect, each of R$^{55a}$ and R$^{55b}$, when present, is independently selected from hydrogen, C1-C3 alkyl, and cyclopropyl. In a still further aspect, each of R$^{55a}$ and R$^{55b}$, when present, is independently selected from hydrogen, methyl, ethyl, and cyclopropyl. In yet a further aspect, each of R$^{55a}$ and R$^{55b}$, when present, is independently selected from hydrogen, methyl, and cyclopropyl.

In a further aspect, each of R$^{55a}$ and R$^{55b}$, when present, is independently selected from hydrogen, C1-C3 alkyl, C1-C3 monohaloalkyl, and C1-C3 polyhaloalkyl. In a still further aspect, each of R$^{55a}$ and R$^{55b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{55a}$ and R$^{55b}$, when present, is independently selected from hydrogen, methyl, —CH$_2$F, —CH$_2$Cl, —CHF$_2$, —CF$_3$, —CHCl$_2$, and —CCl$_3$. In an even further aspect, each of R$^{55a}$ and R$^{55b}$, when present, is independently selected from hydrogen, methyl, —CH$_2$F, —CHF$_2$, and —CF$_3$. In a still further aspect, each of R$^{55a}$ and R$^{55b}$, when present, is independently selected from hydrogen, methyl, and —CF$_3$.

In a further aspect, each of R$^{55a}$ and R$^{55b}$, when present, is independently selected from hydrogen, C1-C3 monohaloalkyl, and C1-C3 polyhaloalkyl. In a still further aspect, each of R$^{55a}$ and R$^{55b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{55a}$ and R$^{55b}$, when present, is independently selected from hydrogen, —CH$_2$F, —CH$_2$Cl, —CHF$_2$, —CF$_3$, —CHCl$_2$, and —CCl$_3$. In an even further aspect, each of R$^{55a}$ and R$^{55b}$, when present, is independently selected from hydrogen, —CH$_2$F, —CHF$_2$, and —CF$_3$. In a still further aspect, each of R$^{55a}$ and R$^{55b}$, when present, is independently selected from hydrogen and —CF$_3$.

In a further aspect, each of R$^{55a}$ and R$^{55b}$, when present, is independently selected from hydrogen and C1-C3 alkyl. In a still further aspect, each of R$^{55a}$ and R$^{55b}$, when present, is independently selected from hydrogen, methyl, and ethyl. In yet a further aspect, each of R$^{55a}$ and R$^{55b}$, when present, is independently selected from hydrogen and methyl.

In a further aspect, R$^{55a}$ is hydrogen and R$^{55b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, R$^{55a}$, when present, is hydrogen and R$^{55b}$, when present, is selected from hydrogen, methyl, —CH$_2$F, —CH$_2$Cl, —CHF$_2$, —CF$_3$, —CHCl$_2$, —CCl$_3$, and cyclopropyl. In yet a further aspect, R$^{55a}$, when present, is hydrogen and R$^{55b}$, when present, is selected from hydrogen, methyl, —CH$_2$F, —CHF$_2$, —CF$_3$, and cyclopropyl. In an even further aspect, R$^{55a}$, when present, is hydrogen and R$^{55b}$, when present, is selected from hydrogen, methyl, —CF$_3$, and cyclopropyl.

In a further aspect, R$^{55a}$, when present, is hydrogen and R$^{55b}$, when present, is selected from hydrogen, C1-C3 monohaloalkyl, C1-C3 polyhaloalkyl, and cyclopropyl. In a still further aspect, R$^{55a}$, when present, is hydrogen and R$^{55b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, Rssa, when present, is hydrogen and R$^{55b}$, when present, is selected from hydrogen, —CH$_2$F, —CH$_2$Cl, —CHF$_2$, —CF$_3$, —CHCl$_2$, —CCl$_3$, and cyclopropyl. In an even further aspect, R$^{55a}$, when present, is hydrogen and R$^{55b}$, when present, is selected from hydrogen, —CH$_2$F, —CHF$_2$, —CF$_3$, and cyclopropyl. In a still further aspect, R$^{55a}$, when present, is hydrogen and R$^{55b}$, when present, is selected from hydrogen, —CF$_3$ and cyclopropyl.

In a further aspect, R$^{55a}$, when present, is hydrogen and R$^{55b}$, when present, is selected from hydrogen, C1-C3 alkyl, and cyclopropyl. In a still further aspect, R$^{55a}$, when present, is hydrogen and R$^{55b}$, when present, is selected from hydrogen, methyl, ethyl, and cyclopropyl. In yet a further aspect, R$^{55a}$, when present, is hydrogen and R$^{55b}$, when present, is selected from hydrogen, methyl, and cyclopropyl.

In a further aspect, R$^{55a}$, when present, is hydrogen and R$^{55b}$, when present, is selected from hydrogen, C1-C3 alkyl, C1-C3 monohaloalkyl, and C1-C3 polyhaloalkyl. In a still further aspect, R$^{55a}$, when present, is hydrogen and R$^{55b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{55a}$, when present, is hydrogen and R$^{55b}$, when present, is selected from hydrogen, methyl, —CH$_2$F, —CH$_2$Cl, —CHF$_2$, —CF$_3$, —CHCl$_2$, and —CCl$_3$. In an even further aspect, R$^{55a}$, when present, is hydrogen and R$^{55b}$, when present, is selected from hydrogen, methyl, —CH$_2$F, —CHF$_2$, and —CF$_3$. In a still further aspect, R$^{55a}$, when present, is hydrogen and R$^{55b}$, when present, is selected from hydrogen, methyl, and —CF$_3$.

In a further aspect, R$^{55a}$, when present, is hydrogen and R$^{55b}$, when present, is selected from hydrogen, C1-C3 monohaloalkyl, and C1-C3 polyhaloalkyl. In a still further aspect, R$^{55a}$, when present, is hydrogen and R$^{55b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{55a}$, when present, is hydrogen and R$^{55b}$, when present, is selected from hydrogen, —CH$_2$F, —CH$_2$Cl, —CHF$_2$, —CF$_3$, —CHCl$_2$, and —CCl$_3$. In an even further aspect, R$^{55a}$, when present, is hydrogen and R$^{55b}$, when present, is selected from hydrogen, —CH$_2$F, —CHF$_2$, and —CF$_3$. In a still further aspect, R$^{55a}$, when present, is hydrogen and R$^{55b}$, when present, is selected from hydrogen and —CF$_3$.

In a further aspect, R$^{55a}$, when present, is hydrogen and R$^{55b}$, when present, is selected from hydrogen and C1-C3 alkyl. In a still further aspect, R$^{55a}$, when present, is hydrogen and R$^{55b}$, when present, is selected from hydrogen, methyl, and ethyl. In yet a further aspect, R$^{55a}$, when present, is hydrogen and R$^{55b}$, when present, is selected from hydrogen and methyl. In an even further aspect, each of R$^{55a}$ and R$^{55b}$, when present, is hydrogen.

oo. R$^{60}$ Groups

In one aspect, R$^{60}$, when present, is selected from hydrogen, C1-C3 alkyl, C1-C3 monohaloalkyl, C1-C3 polyhaloalkyl, and cyclopropyl. In a further aspect, R$^{60}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, R$^{60}$, when present, is selected from hydrogen, methyl, —CH$_2$F, —CH$_2$Cl, —CHF$_2$, —CF$_3$, —CHCl$_2$, —CCl$_3$, and cyclopropyl. In yet a further aspect, R$^{60}$, when present, is selected from hydrogen, methyl, —CH$_2$F, —CHF$_2$, —CF$_3$, and cyclopropyl. In an even further aspect, R$^{60}$, when present, is selected from hydrogen, methyl, —CF$_3$, and cyclopropyl.

In a further aspect, R$^{60}$, when present, is selected from hydrogen, C1-C3 monohaloalkyl, C1-C3 polyhaloalkyl, and cyclopropyl. In a still further aspect, R$^{60}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{60}$, when present, is selected from hydrogen, —CH$_2$F, —CH$_2$Cl, —CHF$_2$, —CF$_3$, —CHCl$_2$, —CCl$_3$, and cyclopropyl. In an even further aspect, R$^{60}$, when present, is selected from hydrogen, —CH$_2$F, —CHF$_2$, —CF$_3$, and cyclopropyl. In a still further aspect, R$^{60}$, when present, is selected from hydrogen, —CF$_3$ and cyclopropyl.

In a further aspect, R$^{60}$, when present, is selected from hydrogen, C1-C3 alkyl, and cyclopropyl. In a still further aspect, R$^{60}$, when present, is selected from hydrogen, methyl, ethyl, and cyclopropyl. In yet a further aspect, R$^{60}$, when present, is selected from hydrogen, methyl, and cyclopropyl.

In a further aspect, R$^{60}$, when present, is selected from hydrogen, C1-C3 alkyl, C1-C3 monohaloalkyl, and C1-C3 polyhaloalkyl. In a still further aspect, R$^{60}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{60}$, when present, is selected from hydrogen, methyl, —CH$_2$F, —CH$_2$Cl, —CHF$_2$, —CF$_3$, —CHCl$_2$, and —CCl$_3$. In an even further aspect, R$^{60}$, when present, is selected from hydrogen, methyl, —CH$_2$F, —CHF$_2$, and —CF$_3$. In a still further aspect, R$^{60}$, when present, is selected from hydrogen, methyl, and —CF$_3$.

In a further aspect, R$^{60}$, when present, is selected from hydrogen, C1-C3 monohaloalkyl, and C1-C3 polyhaloalkyl. In a still further aspect, R$^{60}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{60}$, when present, is selected from hydrogen, —CH$_2$F, —CH$_2$Cl, —CHF$_2$, —CF$_3$, —CHCl$_2$, and —CCl$_3$. In an even further aspect, R$^{60}$, when present, is selected from hydrogen, —CH$_2$F, —CHF$_2$, and —CF$_3$. In a still further aspect, R$^{60}$, when present, is selected from hydrogen and —CF$_3$.

In a further aspect, R$^{60}$, when present, is selected from hydrogen and C1-C3 alkyl. In a still further aspect, R$^{60}$, when present, is selected from hydrogen, methyl, and ethyl. In yet a further aspect, R$^{60}$, when present, is selected from hydrogen and methyl. In an even further aspect, R$^{60}$, when present, is hydrogen.

pp. R$^{61}$ Groups

In one aspect, each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle.

In a further aspect, each of R$^{61a}$ and R$^{61b}$, when present, is independently selected from hydrogen, C1-C3 alkyl, C1-C3 monohaloalkyl, C1-C3 polyhaloalkyl, and cyclopropyl. In a still further aspect, each of R$^{61a}$ and R$^{61b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of R$^{61a}$ and R$^{61b}$, when present, is independently selected from hydrogen, methyl, —CH$_2$F, —CH$_2$Cl, —CHF$_2$, —CF$_3$, —CHCl$_2$, —CCl$_3$, and cyclopropyl. In an even further aspect, each of R$^{61a}$ and R$^{61b}$, when present, is independently selected from hydrogen, methyl, —CH$_2$F, —CHF$_2$, —CF$_3$, and cyclopropyl. In a still further aspect, each of R$^{61a}$ and R$^{61b}$, when present, is independently selected from hydrogen, methyl, —CF$_3$, and cyclopropyl.

In a further aspect, each of R$^{61a}$ and R$^{61b}$, when present, is independently selected from hydrogen, C1-C3 monohaloalkyl, C1-C3 polyhaloalkyl, and cyclopropyl. In a still further aspect, each of R$^{61a}$ and R$^{61b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of R$^{61a}$ and R$^{61b}$, when present, is independently selected from hydrogen, —CH$_2$F, —CH$_2$Cl, —CHF$_2$, —CF$_3$, —CHCl$_2$, —CCl$_3$, and cyclopropyl. In an even further aspect, each of R$^{61a}$ and R$^{61b}$, when present, is independently selected from hydrogen, —CH$_2$F, —CHF$_2$, —CF$_3$, and cyclopropyl. In a still further aspect, each of R$^{61a}$ and R$^{61b}$, when present, is independently selected from hydrogen, —CF$_3$ and cyclopropyl.

In a further aspect, each of R$^{61a}$ and R$^{61b}$, when present, is independently selected from hydrogen, C1-C3 alkyl, and cyclopropyl. In a still further aspect, each of R$^{61a}$ and R$^{61b}$, when present, is independently selected from hydrogen, methyl, ethyl, and cyclopropyl. In yet a further aspect, each of R$^{61a}$ and R$^{61b}$, when present, is independently selected from hydrogen, methyl, and cyclopropyl.

In a further aspect, each of R$^{61a}$ and R$^{61b}$, when present, is independently selected from hydrogen, C1-C3 alkyl, C1-C3 monohaloalkyl, and C1-C3 polyhaloalkyl. In a still further aspect, each of R$^{61a}$ and R$^{61b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{61a}$ and R$^{61b}$, when present, is independently selected from hydrogen, methyl, —CH$_2$F, —CH$_2$Cl, —CHF$_2$, —CF$_3$, —CHCl$_2$, and —CCl$_3$. In an even further aspect, each of R$^{61a}$ and R$^{61b}$, when present, is independently selected from hydrogen, methyl, —CH$_2$F, —CHF$_2$, and —CF$_3$. In a still further aspect, each of R$^{61a}$ and R$^{61b}$, when present, is independently selected from hydrogen, methyl, and —CF$_3$.

In a further aspect, each of R$^{61a}$ and R$^{61b}$, when present, is independently selected from hydrogen, C1-C3 monohaloalkyl, and C1-C3 polyhaloalkyl. In a still further aspect, each of R$^{61a}$ and R$^{61b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{61a}$ and R$^{61b}$, when present, is independently selected from hydrogen, —CH$_2$F, —CH$_2$Cl, —CHF$_2$, —CF$_3$, —CHCl$_2$, and —CCl$_3$. In an even further aspect, each of R$^{61a}$ and R$^{61b}$, when present, is independently selected from hydrogen, —CH$_2$F, —CHF$_2$, and —CF$_3$. In a still further aspect, each of R$^{61a}$ and R$^{61b}$, when present, is independently selected from hydrogen and —CF$_3$.

In a further aspect, each of R$^{61a}$ and R$^{61b}$, when present, is independently selected from hydrogen and C1-C3 alkyl. In a still further aspect, each of R$^{61a}$ and R$^{61b}$, when present, is independently selected from hydrogen, methyl, and ethyl. In yet a further aspect, each of R$^{61a}$ and R$^{61b}$, when present, is independently selected from hydrogen and methyl.

In a further aspect, R$^{61a}$ is hydrogen and R$^{61b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, R$^{61a}$, when present, is hydrogen and R$^{61b}$, when present, is selected from hydrogen, methyl, —CH$_2$F, —CH$_2$Cl, —CHF$_2$, —CF$_3$, —CHCl$_2$, —CCl$_3$, and cyclopropyl. In yet a further aspect, R$^{61a}$, when present, is hydrogen and R$^{61b}$, when present, is selected from hydrogen, methyl, —CH$_2$F, —CHF$_2$, —CF$_3$, and cyclopropyl. In an even further aspect, R$^{61a}$, when present, is hydrogen and R$^{61b}$, when present, is selected from hydrogen, methyl, —CF$_3$, and cyclopropyl.

In a further aspect, R$^{61a}$, when present, is hydrogen and R$^{61b}$, when present, is selected from hydrogen, C1-C3 monohaloalkyl, C1-C3 polyhaloalkyl, and cyclopropyl. In a still further aspect, R$^{61a}$, when present, is hydrogen and R$^{61b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{61a}$, when present, is hydrogen and R$^{61b}$, when present, is selected from hydrogen, —CH$_2$F, —CH$_2$Cl, —CHF$_2$, —CF$_3$, —CHCl$_2$, —CCl$_3$, and cyclopropyl. In an even further aspect, R$^{61a}$, when present, is hydrogen and R$^{61b}$, when present, is selected from hydrogen, —CH$_2$F, —CHF$_2$, —CF$_3$, and cyclopropyl. In a still further aspect, R$^{61a}$, when present, is hydrogen and R$^{61b}$, when present, is selected from hydrogen, —CF$_3$ and cyclopropyl.

In a further aspect, R$^{61a}$, when present, is hydrogen and R$^{61b}$, when present, is selected from hydrogen, C1-C3 alkyl, and cyclopropyl. In a still further aspect, R$^{61a}$, when present, is hydrogen and R$^{61b}$, when present, is selected from hydrogen, methyl, ethyl, and cyclopropyl. In yet a further aspect, R$^{61a}$, when present, is hydrogen and R$^{61b}$, when present, is selected from hydrogen, methyl, and cyclopropyl.

In a further aspect, R$^{61a}$, when present, is hydrogen and R$^{61b}$, when present, is selected from hydrogen, C1-C3 alkyl, C1-C3 monohaloalkyl, and C1-C3 polyhaloalkyl. In a still further aspect, R$^{61a}$, when present, is hydrogen and R$^{61b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{61a}$, when present, is hydrogen and R$^{61b}$, when present, is selected from hydrogen, methyl, —CH$_2$F, —CH$_2$Cl, —CHF$_2$, —CF$_3$, —CHCl$_2$, and —CCl$_3$. In an even further aspect, R$^{61a}$, when present, is hydrogen and R$^{61b}$, when present, is selected from hydrogen, methyl, —CH$_2$F, —CHF$_2$, and —CF$_3$. In a still further aspect, R$^{61a}$, when present, is hydrogen and R$^{61b}$, when present, is selected from hydrogen, methyl, and —CF$_3$.

In a further aspect, R$^{61a}$, when present, is hydrogen and R$^{61b}$, when present, is selected from hydrogen, C1-C3 monohaloalkyl, and C1-C3 polyhaloalkyl. In a still further aspect, R$^{61a}$, when present, is hydrogen and R$^{61b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{61a}$, when present, is hydrogen and R$^{61b}$, when present, is selected from hydrogen, —CH$_2$F, —CH$_2$Cl, —CHF$_2$, —CF$_3$, —CHCl$_2$, and —CCl$_3$. In an even further aspect, R$^{61a}$, when present, is hydrogen and R$^{61b}$, when present, is selected from hydrogen, —CH$_2$F, —CHF$_2$, and —CF$_3$. In a still further aspect, R$^{61a}$, when present, is hydrogen and R$^{61b}$, when present, is selected from hydrogen and —CF$_3$.

In a further aspect, R$^{61a}$, when present, is hydrogen and R$^{61b}$, when present, is selected from hydrogen and C1-C3 alkyl. In a still further aspect, R$^{61a}$, when present, is hydrogen and R$^{61b}$, when present, is selected from hydrogen, methyl, and ethyl. In yet a further aspect, R$^{61a}$, when present, is hydrogen and R$^{61b}$, when present, is selected from hydrogen and methyl. In an even further aspect, each of R$^{61a}$ and R$^{61b}$, when present, is hydrogen.

In a further aspect, R$^{61a}$ and R$^{61b}$, when present, are optionally covalently bonded and, together with nitrogen atom to which they are attached, comprise a 3- to 6-membered heterocycle. In a still further aspect, R$^{61a}$ and R$^{61b}$, when present, are covalently bonded, and together with nitrogen atom to which they are attached, comprise a heterocycle selected from pyrrolidinyl, piperidinyl, azepanyl, imidazolidinyl, pyrazolidinyl, imidazolyl, pyrazolyl, and pyrrolyl. In yet a further aspect, R$^{61a}$ and R$^{61b}$, when present, are covalently bonded, and together with nitrogen atom to which they are attached, comprise a heterocycle selected from pyrrolidinyl, piperidinyl, azepanyl, imidazolidinyl, and pyrazolidinyl. In an even further aspect, R$^{61a}$ and R$^{61b}$, when present, are covalently bonded, and together with nitrogen atom to which they are attached, comprise a heterocycle selected from imidazolyl, pyrazolyl, and pyrrolyl. In a still further aspect, R$^{61a}$ and R$^{61b}$, when present, are covalently bonded, and together with nitrogen atom to which they are attached, comprise a pyrrolidinyl. In yet a further aspect, R$^{61a}$ and R$^{61b}$, when present, are covalently bonded, and together with nitrogen atom to which they are attached, comprise a piperidinyl.

qq. R$^{62}$ Groups

In one aspect, R$^{62}$, when present, is selected from C1-C3 alkyl, C1-C3 monohaloalkyl, C1-C3 polyhaloalkyl, cyclopropyl, and, —NR$^{64a}$R$^{64b}$. In a further aspect, R$^{62}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, R$^{62}$, when present, is selected from methyl, —CH$_2$F, —CH$_2$Cl, —CHF$_2$, —CF$_3$, —CHCl$_2$, —CCl$_3$, cyclopropyl, —NHCH$_3$, and —N(CH$_3$)$_2$. In yet a further aspect, R$^{62}$, when present, is selected from methyl, —CH$_2$F, —CHF$_2$, —CF$_3$, cyclopropyl, —NHCH$_3$, and —N(CH$_3$)$_2$. In an even further aspect, R$^{62}$, when present, is selected from methyl, —CF$_3$, cyclopropyl, and —NHCH$_3$.

In a further aspect, R$^{62}$, when present, is selected from C1-C3 alkyl, C1-C3 monohaloalkyl, C1-C3 polyhaloalkyl, and, —NR$^{64a}$R$^{64b}$. In a still further aspect, R$^{62}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In yet a further aspect, R$^{62}$, when present, is selected from methyl, —CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^{62}$, when present, is selected from methyl, —CH$_2$F, —CHF$_2$, —CF$_3$, —NHCH$_3$, and —N(CH$_3$)$_2$. In a still further aspect, R$^{62}$, when present, is selected from methyl, —CF$_3$, and —NHCH$_3$.

In a further aspect, R$^{62}$, when present, is selected from C1-C3 alkyl, C1-C3 monohaloalkyl, C1-C3 polyhaloalkyl, and cyclopropyl. In a still further aspect, R$^{62}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{62}$, when present, is selected from methyl, —CH$_2$F, —CH$_2$Cl, —CHF$_2$, —CF$_3$, —CHCl$_2$, —CCl$_3$, and cyclopropyl. In an even further aspect, R$^{62}$, when present, is selected from methyl, —CH$_2$F, —CHF$_2$, —CF$_3$, and cyclopropyl. In a still further aspect, R$^{62}$, when present, is selected from methyl, —CF$_3$, and cyclopropyl.

In a further aspect, R$^{62}$, when present, is selected from C1-C3 monohaloalkyl, C1-C3 polyhaloalkyl, and cyclopropyl. In a still further aspect, R$^{62}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{62}$, when present, is selected from —CH$_2$F, —CH$_2$Cl, —CHF$_2$, —CF$_3$, —CHCl$_2$, —CCl$_3$, and cyclopropyl. In an even further aspect, R$^{62}$, when present, is selected from —CH$_2$F, —CHF$_2$, —CF$_3$, and cyclopropyl. In a still further aspect, R$^{62}$, when present, is selected from —CF$_3$ and cyclopropyl.

In a further aspect, R$^{62}$, when present, is selected from C1-C3 alkyl, and cyclopropyl. In a still further aspect, R$^{62}$, when present, is selected from methyl, ethyl, and cyclopropyl. In yet a further aspect, R$^{62}$, when present, is selected from methyl, and cyclopropyl.

In a further aspect, R$^{62}$, when present, is selected from C1-C3 alkyl, C1-C3 monohaloalkyl, and C1-C3 polyhaloalkyl. In a still further aspect, R$^{62}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{62}$, when present, is selected from methyl, —CH$_2$F, —CH$_2$Cl, —CHF$_2$, —CF$_3$, —CHCl$_2$, and —CCl$_3$. In an even further aspect, R$^{62}$, when present, is selected from methyl, —CH$_2$F, —CHF$_2$, and —CF$_3$. In a still further aspect, R$^{62}$, when present, is selected from methyl and —CF$_3$.

In a further aspect, R$^{62}$, when present, is selected from C1-C3 monohaloalkyl, and C1-C3 polyhaloalkyl. In a still further aspect, R$^{62}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{62}$, when present, is selected from —CH$_2$F, —CH$_2$Cl, —CHF$_2$, —CF$_3$, —CHCl$_2$, and —CCl$_3$. In an even further aspect, R$^{62}$, when present, is selected from —CH$_2$F, —CHF$_2$, and —CF$_3$. In a still further aspect, R$^{62}$, when present, is —CF$_3$.

In a further aspect, R$^{62}$, when present, is C1-C3 alkyl. In a still further aspect, R$^{62}$, when present, is selected from methyl, and ethyl. In yet a further aspect, R$^{62}$, when present, is methyl.

rr. R$^{63}$ Groups

In one aspect, R$^{63}$, when present, is selected from C1-C3 alkyl, C1-C3 monohaloalkyl, C1-C3 polyhaloalkyl, cyclopropyl, and, —NR$^{65a}$R$^{65b}$. In a further aspect, R$^{63}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, cyclopropyl, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In a still further aspect, R$^{63}$, when present, is selected from methyl, —CH$_2$F, —CH$_2$Cl, —CHF$_2$, —CF$_3$, —CHCl$_2$, —CCl$_3$, cyclopropyl, —NHCH$_3$, and —N(CH$_3$)$_2$. In yet a further aspect, R$^{63}$, when present, is selected from methyl, —CH$_2$F, —CHF$_2$, —CF$_3$, cyclopropyl, —NHCH$_3$, and —N(CH$_3$)$_2$. In an even further aspect, R$^{63}$, when present, is selected from methyl, —CF$_3$, cyclopropyl, and —NHCH$_3$.

In a further aspect, R$^{63}$, when present, is selected from C1-C3 alkyl, C1-C3 monohaloalkyl, C1-C3 polyhaloalkyl, and, —NR$^{64a}$R$^{64b}$. In a still further aspect, R$^{63}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$. In yet a further aspect, R$^{63}$, when present, is selected from methyl, —CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^{63}$, when present, is selected from methyl, —CH$_2$F, —CHF$_2$, —CF$_3$, —NHCH$_3$, and —N(CH$_3$)$_2$. In a still further aspect, R$^{63}$, when present, is selected from methyl, —CF$_3$, and —NHCH$_3$.

In a further aspect, R$^{63}$, when present, is selected from C1-C3 alkyl, C1-C3 monohaloalkyl, C1-C3 polyhaloalkyl, and cyclopropyl. In a still further aspect, R$^{63}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{63}$, when present, is selected from methyl, —CH$_2$F, —CH$_2$Cl, —CHF$_2$, —CF$_3$, —CHCl$_2$, —CCl$_3$, and cyclopropyl. In an even further aspect, R$^{63}$, when present, is selected from methyl, —CH$_2$F, —CHF$_2$, —CF$_3$, and cyclopropyl. In a still further aspect, R$^{63}$, when present, is selected from methyl, —CF$_3$, and cyclopropyl.

In a further aspect, R$^{63}$, when present, is selected from C1-C3 monohaloalkyl, C1-C3 polyhaloalkyl, and cyclopropyl. In a still further aspect, R$^{63}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{63}$, when present, is selected from —CH$_2$F, —CH$_2$Cl, —CHF$_2$, —CF$_3$, —CHCl$_2$, —CCl$_3$, and cyclopropyl. In an even further aspect, R$^{63}$, when present, is selected from —CH$_2$F, —CHF$_2$, —CF$_3$, and cyclopropyl. In a still further aspect, R$^{63}$, when present, is selected from —CF$_3$ and cyclopropyl.

In a further aspect, R$^{63}$, when present, is selected from C1-C3 alkyl, and cyclopropyl. In a still further aspect, R$^{63}$, when present, is selected from methyl, ethyl, and cyclopropyl. In yet a further aspect, R$^{63}$, when present, is selected from methyl, and cyclopropyl.

In a further aspect, R$^{63}$, when present, is selected from C1-C3 alkyl, C1-C3 monohaloalkyl, and C1-C3 polyhaloalkyl. In a still further aspect, R$^{63}$, when present, is selected from methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{63}$, when present, is selected from methyl, —CH$_2$F, —CH$_2$Cl, —CHF$_2$, —CF$_3$, —CHCl$_2$, and —CCl$_3$. In an even further aspect, R$^{63}$, when present, is selected from methyl, —CH$_2$F, —CHF$_2$, and —CF$_3$. In a still further aspect, R$^{63}$, when present, is selected from methyl and —CF$_3$.

In a further aspect, R$^{63}$, when present, is selected from C1-C3 monohaloalkyl, and C1-C3 polyhaloalkyl. In a still further aspect, R$^{63}$, when present, is selected from —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, R$^{63}$, when present, is selected from —CH$_2$F, —CH$_2$Cl, —CHF$_2$, —CF$_3$, —CHCl$_2$, and —CCl$_3$. In an even further aspect, R$^{63}$, when present, is selected from —CH$_2$F, —CHF$_2$, and —CF$_3$. In a still further aspect, R$^{63}$, when present, is —CF$_3$.

In a further aspect, R$^{63}$, when present, is C1-C3 alkyl. In a still further aspect, R$^{63}$, when present, is selected from methyl, and ethyl. In yet a further aspect, R$^{63}$, when present, is methyl.

ss. R$^{64}$ Groups

In one aspect, each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle In a further aspect, each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle. In a still further aspect, each of R$^{64a}$ and R$^{64b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of R$^{64a}$ and R$^{64b}$, when present, is independently selected from hydrogen, methyl, —CH$_2$F, —CH$_2$Cl, —CHF$_2$, —CF$_3$, —CHCl$_2$, —CCl$_3$, and cyclopropyl. In an even further aspect, each of R$^{64a}$ and R$^{64b}$, when present, is independently selected from hydrogen, methyl, —CH$_2$F, —CHF$_2$, —CF$_3$, and cyclopropyl. In a still further aspect, each of R$^{64a}$ and R$^{64b}$, when present, is independently selected from hydrogen, methyl, —CF$_3$, and cyclopropyl.

In a further aspect, each of R$^{64a}$ and R$^{64b}$, when present, is independently selected from hydrogen, C1-C3 monohaloalkyl, C1-C3 polyhaloalkyl, and cyclopropyl. In a still further aspect, each of R$^{64a}$ and R$^{64b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, each of R$^{64a}$ and R$^{64b}$, when present, is independently selected from hydrogen, —CH$_2$F, —CH$_2$Cl, —CHF$_2$, —CF$_3$, —CHCl$_2$, —CCl$_3$, and cyclopropyl. In an even further aspect, each of R$^{64a}$ and R$^{64b}$, when present, is independently selected from hydrogen, —CH$_2$F, —CHF$_2$, —CF$_3$, and cyclopropyl. In a still further aspect, each of R$^{64a}$ and R$^{64b}$, when present, is independently selected from hydrogen, —CF$_3$ and cyclopropyl.

In a further aspect, each of R$^{64a}$ and R$^{64b}$, when present, is independently selected from hydrogen, C1-C3 alkyl, and cyclopropyl. In a still further aspect, each of R$^{64a}$ and R$^{64b}$, when present, is independently selected from hydrogen, methyl, ethyl, and cyclopropyl. In yet a further aspect, each of R$^{64a}$ and R$^{64b}$, when present, is independently selected from hydrogen, methyl, and cyclopropyl.

In a further aspect, each of R$^{64a}$ and R$^{64b}$, when present, is independently selected from hydrogen, C1-C3 alkyl, C1-C3 monohaloalkyl, and C1-C3 polyhaloalkyl. In a still further aspect, each of R$^{64a}$ and R$^{64b}$, when present, is independently selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{64a}$ and R$^{64b}$, when present, is independently selected from hydrogen, methyl, —CH$_2$F, —CH$_2$Cl, —CHF$_2$, —CF$_3$, —CHCl$_2$, and —CCl$_3$. In an even further aspect, each of R$^{64a}$ and R$^{64b}$, when present, is independently selected from hydrogen, methyl, —CH$_2$F, —CHF$_2$, and —CF$_3$. In a still further aspect, each of R$^{64a}$ and R$^{64b}$, when present, is independently selected from hydrogen, methyl, and —CF$_3$.

In a further aspect, each of R$^{64a}$ and R$^{64b}$, when present, is independently selected from hydrogen, C1-C3 monohaloalkyl, and C1-C3 polyhaloalkyl. In a still further aspect, each of R$^{64a}$ and R$^{64b}$, when present, is independently selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, each of R$^{64a}$ and R$^{64b}$, when present, is independently selected from hydrogen, —CH$_2$F, —CH$_2$Cl, —CHF$_2$, —CF$_3$, —CHCl$_2$, and —CCl$_3$. In an even further aspect, each of R$^{64a}$ and R$^{64b}$, when present, is independently selected from hydrogen, —CH$_2$F, —CHF$_2$, and —CF$_3$. In a still further aspect, each of R$^{64a}$ and R$^{64b}$, when present, is independently selected from hydrogen and —CF$_3$.

In a further aspect, each of R$^{64a}$ and R$^{64b}$, when present, is independently selected from hydrogen and C1-C3 alkyl. In a still further aspect, each of R$^{64a}$ and R$^{64b}$, when present, is independently selected from hydrogen, methyl, and ethyl. In yet a further aspect, each of R$^{64a}$ and R$^{64b}$, when present, is independently selected from hydrogen and methyl.

In a further aspect, R$^{64a}$ is hydrogen and R$^{64b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, R$^{64a}$, when present, is hydrogen and R$^{64b}$, when present, is selected from hydrogen, methyl, —CH$_2$F, —CH$_2$Cl, —CHF$_2$, —CF$_3$, —CHCl$_2$, —CCl$_3$, and cyclopropyl. In yet a further aspect, R$^{64a}$, when present, is hydrogen and R$^{64b}$, when present, is selected from hydrogen, methyl, —CH$_2$F, —CHF$_2$, —CF$_3$, and cyclopropyl. In an even further aspect, R$^{64a}$, when present, is hydrogen and R$^{64b}$, when present, is selected from hydrogen, methyl, —CF$_3$, and cyclopropyl.

In a further aspect, R$^{64a}$, when present, is hydrogen and R$^{64b}$, when present, is selected from hydrogen, C1-C3 monohaloalkyl, C1-C3 polyhaloalkyl, and cyclopropyl. In a still further aspect, R$^{64a}$, when present, is hydrogen and R$^{64b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, R$^{64a}$, when present, is hydrogen and R$^{64b}$, when present, is selected from hydrogen, —CH$_2$F, —CH$_2$Cl, —CHF$_2$, —CF$_3$, —CHCl$_2$, —CCl$_3$, and cyclopropyl. In an even further aspect, R$^{64a}$, when present, is hydrogen and R$^{64b}$, when present, is selected from hydrogen, —CH$_2$F, —CHF$_2$, —CF$_3$, and cyclopropyl. In a still further aspect, R$^{64a}$, when present, is hydrogen and $R^{64b}$, when present, is selected from hydrogen, —$CF_3$ and cyclopropyl.

In a further aspect, $R^{64a}$, when present, is hydrogen and $R^{64b}$, when present, is selected from hydrogen, C1-C3 alkyl, and cyclopropyl. In a still further aspect, $R^{64a}$, when present, is hydrogen and $R^{64b}$, when present, is selected from hydrogen, methyl, ethyl, and cyclopropyl. In yet a further aspect, $R^{64a}$, when present, is hydrogen and $R^{64b}$, when present, is selected from hydrogen, methyl, and cyclopropyl.

In a further aspect, $R^{64a}$, when present, is hydrogen and $R^{64b}$, when present, is selected from hydrogen, C1-C3 alkyl, C1-C3 monohaloalkyl, and C1-C3 polyhaloalkyl. In a still further aspect, $R^{64a}$, when present, is hydrogen and $R^{64b}$, when present, is selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{64a}$, when present, is hydrogen and $R^{64b}$, when present, is selected from hydrogen, methyl, —$CH_2F$, —$CH_2Cl$, —$CHF_2$, —$CF_3$, —$CHCl_2$, and —$CCl_3$. In an even further aspect, $R^{64a}$, when present, is hydrogen and $R^{64b}$, when present, is selected from hydrogen, methyl, —$CH_2F$, —$CHF_2$, and —$CF_3$. In a still further aspect, $R^{64a}$, when present, is hydrogen and $R^{64b}$, when present, is selected from hydrogen, methyl, and —$CF_3$.

In a further aspect, $R^{64a}$, when present, is hydrogen and $R^{64b}$, when present, is selected from hydrogen, C1-C3 monohaloalkyl, and C1-C3 polyhaloalkyl. In a still further aspect, $R^{64a}$, when present, is hydrogen and $R^{64b}$, when present, is selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, $R^{64a}$, when present, is hydrogen and $R^{64b}$, when present, is selected from hydrogen, —$CH_2F$, —$CH_2Cl$, —$CHF_2$, —$CF_3$, —$CHCl_2$, and —$CCl_3$. In an even further aspect, $R^{64a}$, when present, is hydrogen and $R^{64b}$, when present, is selected from hydrogen, —$CH_2F$, —$CHF_2$, and —$CF_3$. In a still further aspect, $R^{64a}$, when present, is hydrogen and $R^{64b}$, when present, is selected from hydrogen and —$CF_3$.

In a further aspect, $R^{64a}$, when present, is hydrogen and $R^{64b}$, when present, is selected from hydrogen and C1-C3 alkyl. In a still further aspect, $R^{64a}$, when present, is hydrogen and $R^{64b}$, when present, is selected from hydrogen, methyl, and ethyl. In yet a further aspect, $R^{64a}$, when present, is hydrogen and $R^{64b}$, when present, is selected from hydrogen and methyl. In an even further aspect, each of $R^{64a}$ and $R^{64b}$, when present, is hydrogen.

tt. $R^{65}$ Groups

In one aspect, each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle.

In a further aspect, ach of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle. In a still further aspect, each of $R^{65a}$ and $R^{65b}$, when present, is independently selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, each of $R^{65a}$ and $R^{65b}$, when present, is independently selected from hydrogen, methyl, —$CH_2F$, —$CH_2Cl$, —$CHF_2$, —$CF_3$, —$CHCl_2$, —$CCl_3$, and cyclopropyl. In an even further aspect, each of $R^{65a}$ and $R^{65b}$, when present, is independently selected from hydrogen, methyl, —$CH_2F$, —$CHF_2$, —$CF_3$, and cyclopropyl. In a still further aspect, each of $R^{65a}$ and $R^{65b}$, when present, is independently selected from hydrogen, methyl, —$CF_3$, and cyclopropyl.

In a further aspect, each of $R^{65a}$ and $R^{65b}$, when present, is independently selected from hydrogen, C1-C3 monohaloalkyl, C1-C3 polyhaloalkyl, and cyclopropyl. In a still further aspect, each of $R^{65a}$ and $R^{65b}$, when present, is independently selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, and cyclopropyl. In yet a further aspect, each of $R^{65a}$ and $R^{65b}$, when present, is independently selected from hydrogen, —$CH_2F$, —$CH_2Cl$, —$CHF_2$, —$CF_3$, —$CHCl_2$, —$CCl_3$, and cyclopropyl. In an even further aspect, each of $R^{65a}$ and $R^{65b}$, when present, is independently selected from hydrogen, —$CH_2F$, —$CHF_2$, —$CF_3$, and cyclopropyl. In a still further aspect, each of $R^{65a}$ and $R^{65b}$, when present, is independently selected from hydrogen, —$CF_3$ and cyclopropyl.

In a further aspect, each of $R^{65a}$ and $R^{65b}$, when present, is independently selected from hydrogen, C1-C3 alkyl, and cyclopropyl. In a still further aspect, each of $R^{65a}$ and $R^{65b}$, when present, is independently selected from hydrogen, methyl, ethyl, and cyclopropyl. In yet a further aspect, each of $R^{65a}$ and $R^{65b}$, when present, is independently selected from hydrogen, methyl, and cyclopropyl.

In a further aspect, each of $R^{65a}$ and $R^{65b}$, when present, is independently selected from hydrogen, C1-C3 alkyl, C1-C3 monohaloalkyl, and C1-C3 polyhaloalkyl. In a still further aspect, each of $R^{65a}$ and $R^{65b}$, when present, is independently selected from hydrogen, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, each of $R^{65a}$ and $R^{65b}$, when present, is independently selected from hydrogen, methyl, —$CH_2F$, —$CH_2Cl$, —$CHF_2$, —$CF_3$, —$CHCl_2$, and —$CCl_3$. In an even further aspect, each of $R^{65a}$ and $R^{65b}$, when present, is independently selected from hydrogen, methyl, —$CH_2F$, —$CHF_2$, and —$CF_3$. In a still further aspect, each of $R^{65a}$ and $R^{65b}$, when present, is independently selected from hydrogen, methyl, and —$CF_3$.

In a further aspect, each of $R^{65a}$ and $R^{65b}$, when present, is independently selected from hydrogen, C1-C3 monohaloalkyl, and C1-C3 polyhaloalkyl. In a still further aspect, each of $R^{65a}$ and $R^{65b}$, when present, is independently selected from hydrogen, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, and —$CH_2CCl_3$. In yet a further aspect, each of $R^{65a}$ and $R^{65b}$, when present, is independently selected from hydrogen, —$CH_2F$, —$CH_2Cl$, —$CHF_2$, —$CF_3$, —$CHCl_2$, and —$CCl_3$. In an even further aspect, each of $R^{65a}$ and $R^{65b}$, when present, is independently selected from hydrogen, —$CH_2F$, —$CHF_2$, and —$CF_3$. In a still further aspect, each of $R^{65a}$ and $R^{65b}$, when present, is independently selected from hydrogen and —$CF_3$.

In a further aspect, each of $R^{65a}$ and $R^{65b}$, when present, is independently selected from hydrogen and C1-C3 alkyl. In a still further aspect, each of $R^{65a}$ and $R^{65b}$, when present, is independently selected from hydrogen, methyl, and ethyl. In yet a further aspect, each of $R^{65a}$ and $R^{65b}$, when present, is independently selected from hydrogen and methyl.

In a further aspect, $R^{65a}$ is hydrogen and $R^{65b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In a still further aspect, $R^{65a}$, when present, is hydrogen and $R^{65b}$, when present, is selected from hydrogen, methyl, —CH$_2$F, —CH$_2$Cl, —CHF$_2$, —CF$_3$, —CHCl$_2$, —CCl$_3$, and cyclopropyl. In yet a further aspect, $R^{65a}$, when present, is hydrogen and $R^{65b}$, when present, is selected from hydrogen, methyl, —CH$_2$F, —CHF$_2$, —CF$_3$, and cyclopropyl. In an even further aspect, $R^{65a}$, when present, is hydrogen and $R^{65b}$, when present, is selected from hydrogen, methyl, —CF$_3$, and cyclopropyl.

In a further aspect, $R^{65a}$, when present, is hydrogen and $R^{65b}$, when present, is selected from hydrogen, C1-C3 monohaloalkyl, C1-C3 polyhaloalkyl, and cyclopropyl. In a still further aspect, $R^{65a}$, when present, is hydrogen and $R^{65b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, and cyclopropyl. In yet a further aspect, $R^{65a}$, when present, is hydrogen and $R^{65b}$, when present, is selected from hydrogen, —CH$_2$F, —CH$_2$Cl, —CHF$_2$, —CF$_3$, —CHCl$_2$, —CCl$_3$, and cyclopropyl. In an even further aspect, $R^{65a}$, when present, is hydrogen and $R^{65b}$, when present, is selected from hydrogen, —CH$_2$F, —CHF$_2$, —CF$_3$, and cyclopropyl. In a still further aspect, $R^{65a}$, when present, is hydrogen and $R^{65b}$, when present, is selected from hydrogen, —CF$_3$ and cyclopropyl.

In a further aspect, $R^{65a}$, when present, is hydrogen and $R^{65b}$, when present, is selected from hydrogen, C1-C3 alkyl, and cyclopropyl. In a still further aspect, $R^{65a}$, when present, is hydrogen and $R^{65b}$, when present, is selected from hydrogen, methyl, ethyl, and cyclopropyl. In yet a further aspect, $R^{65a}$, when present, is hydrogen and $R^{65b}$, when present, is selected from hydrogen, methyl, and cyclopropyl.

In a further aspect, $R^{65a}$, when present, is hydrogen and $R^{65b}$, when present, is selected from hydrogen, C1-C3 alkyl, C1-C3 monohaloalkyl, and C1-C3 polyhaloalkyl. In a still further aspect, $R^{65a}$, when present, is hydrogen and $R^{65b}$, when present, is selected from hydrogen, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, $R^{65a}$, when present, is hydrogen and $R^{65b}$, when present, is selected from hydrogen, methyl, —CH$_2$F, —CH$_2$Cl, —CHF$_2$, —CF$_3$, —CHCl$_2$, and —CCl$_3$. In an even further aspect, $R^{65a}$, when present, is hydrogen and $R^{65b}$, when present, is selected from hydrogen, methyl, —CH$_2$F, —CHF$_2$, and —CF$_3$. In a still further aspect, $R^{65a}$, when present, is hydrogen and $R^{65b}$, when present, is selected from hydrogen, methyl, and —CF$_3$.

In a further aspect, $R^{65a}$, when present, is hydrogen and $R^{65b}$, when present, is selected from hydrogen, C1-C3 monohaloalkyl, and C1-C3 polyhaloalkyl. In a still further aspect, $R^{65a}$, when present, is hydrogen and $R^{65b}$, when present, is selected from hydrogen, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, and —CH$_2$CCl$_3$. In yet a further aspect, $R^{65a}$, when present, is hydrogen and $R^{65b}$, when present, is selected from hydrogen, —CH$_2$F, —CH$_2$Cl, —CHF$_2$, —CF$_3$, —CHCl$_2$, and —CCl$_3$. In an even further aspect, $R^{65a}$, when present, is hydrogen and $R^{65b}$, when present, is selected from hydrogen, —CH$_2$F, —CHF$_2$, and —CF$_3$. In a still further aspect, $R^{65a}$, when present, is hydrogen and $R^{65b}$, when present, is selected from hydrogen and —CF$_3$.

In a further aspect, $R^{65a}$, when present, is hydrogen and $R^{65b}$, when present, is selected from hydrogen and C1-C3 alkyl. In a still further aspect, $R^{65a}$, when present, is hydrogen and $R^{65b}$, when present, is selected from hydrogen, methyl, and ethyl. In yet a further aspect, $R^{65a}$, when present, is hydrogen and $R^{65b}$, when present, is selected from hydrogen and methyl. In an even further aspect, $R^{65a}$ and $R^{65b}$, when present, is hydrogen.

uu. $R^{66}$ Groups

In one aspect, $R^{66}$ is Cl, CN, CO$_2$R$^{41}$, or CH=CH$_2$. In a further aspect, $R^{66}$ is Cl. In a further aspect, $R^{66}$ is CN. In a further aspect, $R^{66}$ is CO$_2$R$^{41}$. In a further aspect, $R^{66}$ is CH=CH$_2$.

vv. $R^{67}$ Groups

In one aspect, $R^{67}$ is C1-C3 alkyl. In a further aspect, $R^{67}$ is C1-C2 alkyl. In a further aspect, $R^{67}$ is C2-C3 alkyl. In a further aspect, $R^{67}$ is methyl, ethyl, n-propyl, i-propyl, or cyclopropyl.

ww. $R^{70}$ Groups

In one aspect, each of $R^{70a}$, $R^{70b}$, $R^{70c}$, and $R^{70d}$ is independently selected from hydrogen, halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$, provided that at least one of $R^{70a}$, $R^{70b}$, $R^{70a}$, and $R^{70a}$ is hydrogen. In a further aspect, each of $R^{70a}$, $R^{70b}$, $R^{70c}$, and $R^{70d}$ is independently selected from hydrogen, —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$Cl, —(C=O)CH$_2$CH$_2$F, —(C=O)CH$_2$CH$_2$Cl, —(C=O)CHF$_2$, —(C=O)CF$_3$, —(C=O)CHCl$_2$, —(C=O)CCl$_3$, —(C=O)NH$_2$, —(C=O)NHCH$_3$, and —(C=O)N(CH$_3$)$_2$. In a still further aspect, each of $R^{70a}$, $R^{70b}$, $R^{70c}$, and $R^{70d}$ is independently selected from hydrogen, —F, —Cl, —CN, methyl, —CH$_2$F, —CH$_2$Cl, —CHF$_2$, —CF$_3$, —CHCl$_2$, —CCl$_3$, cyclopropyl, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, —SO$_2$—N(CH$_3$)$_2$, —(C=O)CH$_3$, —(C=O)CF$_3$, —(C=O)NH$_2$, —(C=O)NHCH$_3$, and —(C=O)N(CH$_3$)$_2$. In yet a further aspect, each of $R^{70a}$, $R^{70b}$, $R^{70c}$, and $R^{70d}$ is independently selected from hydrogen, —F, —Cl, methyl, —CF$_3$, —OH, —OCH$_3$, —OCF$_3$, —NH$_2$, —NHCH$_3$, —N(CH$_3$)$_2$, —SO$_2$CH$_3$, —SO$_2$CF$_3$, —SO$_2$—NH$_2$, —SO$_2$—NHCH$_3$, and —SO$_2$—N(CH$_3$)$_2$. In an even further aspect, each of $R^{70a}$, $R^{70b}$, $R^{70c}$, and $R^{70d}$ is independently selected from hydrogen, —F, —Cl, methyl, —CF$_3$, —OH, —OCH$_3$, —OCF$_3$, —NH$_2$, —NHCH$_3$, and —N(CH$_3$)$_2$. In a still further aspect, each of $R^{70a}$, $R^{70b}$, $R^{70c}$, and $R^{70d}$ is independently selected from hydrogen, —F, —Cl, methyl, and —CF$_3$. In yet a further aspect, each of $R^{70a}$, $R^{70b}$, $R^{70c}$, and $R^{70d}$ is independently selected from hydrogen, —F, —Cl, and methyl.

In a further aspect, each of $R^{70b}$, $R^{70c}$, and $R^{70d}$ is hydrogen and wherein $R^{70a}$ is selected from hydrogen, —F, —Cl, —CN, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, cyclopropyl, —OH, —OCH$_3$, —OCH$_2$F, —OCHF$_2$, —OCF$_3$, —O-cyclopropyl, —NH$_2$, —NHCH$_3$, —N(CH$_3$)$_2$, —SO$_2$CH$_3$, —SO$_2$CH$_2$F, —SO$_2$CHF$_2$, —SO$_2$CF$_3$, —SO$_2$-cyclopropyl, —SO$_2$—NH$_2$, —SO$_2$—NHCH$_3$, —SO$_2$—N(CH$_3$)$_2$, —(C=O)CH$_3$, —(C=O)CH$_2$CH$_3$, —(C=O)CH$_2$F, —(C=O)CH$_2$Cl, —(C=O)

$CH_2CH_2F$, —(C=O)$CH_2CH_2Cl$, —(C=O)$CHF_2$, —(C=O)$CF_3$, —(C=O)$CHCl_2$, —(C=O)$CCl_3$, —(C=O)$NH_2$, —(C=O)$NHCH_3$, and —(C=O)$N(CH_3)_2$. In a still further aspect, each of $R^{70b}$, $R^{70c}$, and $R^{70d}$ is hydrogen and wherein $R^{70a}$ is selected from hydrogen, —F, —Cl, —CN, methyl, —$CH_2F$, —$CH_2Cl$, —$CHF_2$, —$CF_3$, —$CHCl_2$, —$CCl_3$, cyclopropyl, —OH, —$OCH_3$, —$OCF_3$, —$NH_2$, —$NHCH_3$, —$N(CH_3)_2$, —$SO_2CH_3$, —$SO_2CF_3$, —$SO_2$—$NH_2$, —$SO_2$—$NHCH_3$, —$SO_2$—$N(CH_3)_2$, —(C=O)$CH_3$, —(C=O)$CF_3$, —(C=O)$NH_2$, —(C=O)$NHCH_3$, and —(C=O)$N(CH_3)_2$. In yet a further aspect, each of $R^{70b}$, $R^{70c}$, and $R^{70d}$ is hydrogen and wherein $R^{70a}$ is selected from hydrogen, —F, —Cl, methyl, —$CF_3$, —OH, —$OCH_3$, —$OCF_3$, —$NH_2$, —$NHCH_3$, —$N(CH_3)_2$, —$SO_2CH_3$, —$SO_2CF_3$, —$SO_2$—$NH_2$, —$SO_2$—$NHCH_3$, and —$SO_2$—$N(CH_3)_2$. In an even further aspect, each of $R^{70b}$, $R^{70c}$, and $R^{70d}$ is hydrogen and wherein $R^{70a}$ is selected from hydrogen, —F, —Cl, methyl, —$CF_3$, —OH, —$OCH_3$, —$OCF_3$, —$NH_2$, —$NHCH_3$, and —$N(CH_3)_2$. In a still further aspect, each of $R^{70b}$, $R^{70c}$, and $R^{70d}$ is hydrogen and wherein $R^{70a}$ is selected from hydrogen, —F, —Cl, methyl, and —$CF_3$. In yet a further aspect, each of $R^{70b}$, $R^{70c}$, and $R^{70d}$ is hydrogen and wherein $R^{70a}$ is selected from hydrogen, —F, —Cl, and methyl. In an even further aspect, each of $R^{70b}$, $R^{70c}$, and $R^{70d}$ is hydrogen and wherein $R^{70a}$ is —F. In a still further aspect, each of $R^{70b}$, $R^{70c}$, and $R^{70d}$ is hydrogen and wherein $R^{70a}$ is —Cl. In yet a further aspect, each of $R^{70b}$, $R^{70c}$, and $R^{70d}$ is hydrogen and wherein $R^{70a}$ is methyl. In an even further aspect, each of $R^{70b}$, $R^{70c}$, and $R^{70d}$ is hydrogen and wherein $R^{70a}$ is —$CF_3$.

In a further aspect, each of $R^{70a}$, $R^{70c}$, and $R^{70d}$ is hydrogen and wherein $R^{70b}$ is selected from hydrogen, —F, —Cl, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, cyclopropyl, —OH, —$OCH_3$, —$OCH_2F$, —$OCHF_2$, —$OCF_3$, —O-cyclopropyl, —$NH_2$, —$NHCH_3$, —$N(CH_3)_2$, —$SO_2CH_3$, —$SO_2CH_2F$, —$SO_2CHF_2$, —$SO_2CF_3$, —$SO_2$-cyclopropyl, —$SO_2$—$NH_2$, —$SO_2$—$NHCH_3$, —$SO_2$—$N(CH_3)_2$, —(C=O)$CH_3$, —(C=O)$CH_2CH_3$, —(C=O)$CH_2F$, —(C=O)$CH_2Cl$, —(C=O)$CH_2CH_2F$, —(C=O)$CH_2CH_2Cl$, —(C=O)$CHF_2$, —(C=O)$CF_3$, —(C=O)$CHCl_2$, —(C=O)$CCl_3$, —(C=O)$NH_2$, —(C=O)$NHCH_3$, and —(C=O)$N(CH_3)_2$. In a still further aspect, each of $R^{70a}$, $R^{70c}$, and $R^{70d}$ is hydrogen and wherein $R^{70b}$ is selected from hydrogen, —F, —Cl, —CN, methyl, —$CH_2F$, —$CH_2Cl$, —$CHF_2$, —$CF_3$, —$CHCl_2$, —$CCl_3$, cyclopropyl, —OH, —$OCH_3$, —$OCF_3$, —$NH_2$, —$NHCH_3$, —$N(CH_3)_2$, —$SO_2CH_3$, —$SO_2CF_3$, —$SO_2$—$NH_2$, —$SO_2$—$NHCH_3$, —$SO_2$—$N(CH_3)_2$, —(C=O)$CH_3$, —(C=O)$CF_3$, —(C=O)$NH_2$, —(C=O)$NHCH_3$, and —(C=O)$N(CH_3)_2$. In yet a further aspect, each of $R^{70a}$, $R^{70c}$, and $R^{70d}$ is hydrogen and wherein $R^{70b}$ is selected from hydrogen, —F, —Cl, methyl, —$CF_3$, —OH, —$OCH_3$, —$OCF_3$, —$NH_2$, —$NHCH_3$, —$N(CH_3)_2$, —$SO_2CH_3$, —$SO_2CF_3$, —$SO_2$—$NH_2$, —$SO_2$—$NHCH_3$, and —$SO_2$—$N(CH_3)_2$. In an even further aspect, each of $R^{70a}$, $R^{70c}$, and $R^{70d}$ is hydrogen and wherein $R^{70b}$ is selected from hydrogen, —F, —Cl, methyl, —$CF_3$, —OH, —$OCH_3$, —$OCF_3$, —$NH_2$, —$NHCH_3$, and —$N(CH_3)_2$. In a still further aspect, each of $R^{70a}$, $R^{70c}$, and $R^{70d}$ is hydrogen and wherein $R^{70b}$ is selected from hydrogen, —F, —Cl, methyl, and —$CF_3$. In yet a further aspect, each of $R^{70a}$, $R^{70c}$, and $R^{70d}$ is hydrogen and wherein $R^{70b}$ is selected from hydrogen, —F, —Cl, and methyl. In an even further aspect, each of $R^{70a}$, $R^{70c}$, and $R^{70d}$ is hydrogen and wherein $R^{70b}$ is —F. In a still further aspect, each of $R^{70a}$, $R^{70c}$, and $R^{70d}$ is hydrogen and wherein $R^{70b}$ is —Cl. In yet a further aspect, each of $R^{70a}$, $R^{70c}$, and $R^{70d}$ is hydrogen and wherein $R^{70b}$ is —$CF_3$. In an even further aspect, each of $R^{70a}$, $R^{70b}$, $R^{70c}$, and $R^{70d}$ is hydrogen.

xx. $R^{80}$ Groups

In one aspect, each of $R^{80a}$ and $R^{80b}$ is independently selected from hydrogen, halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O)$R^{53}$. In a further aspect, each of $R^{80a}$ and $R^{80b}$ is independently selected from hydrogen, —F, —Cl, —CN, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, cyclopropyl, —OH, —$OCH_3$, —$OCH_2F$, —$OCHF_2$, —$OCF_3$, —O-cyclopropyl, —$NH_2$, —$NHCH_3$, and —$N(CH_3)_2$. In a still further aspect, each of $R^{80a}$ and $R^{80b}$ is independently selected from hydrogen, —F, —Cl, —CN, methyl, —$CH_2F$, —$CH_2Cl$, —$CHF_2$, —$CF_3$, —$CHCl_2$, —$CCl_3$, cyclopropyl, —OH, —$OCH_3$, —$OCF_3$, —$NH_2$, —$NHCH_3$, and —$N(CH_3)_2$. In yet a further aspect, each of $R^{80a}$ and $R^{80b}$ is independently selected from hydrogen, —F, —Cl, methyl, —$CF_3$, —OH, —$OCH_3$, —$OCF_3$, —$NH_2$, —$NHCH_3$, and —$N(CH_3)_2$. In an even further aspect, each of $R^{80a}$ and $R^{80b}$ is independently selected from hydrogen, —F, —Cl, methyl, —$CF_3$, —OH, —$OCH_3$, —$OCF_3$, —$NH_2$, —$NHCH_3$, and —$N(CH_3)_2$. In a still further aspect, each of $R^{80a}$ and $R^{80b}$ is independently selected from hydrogen, —F, —Cl, and methyl.

In a further aspect, $R^{80b}$ is hydrogen and $R^{80a}$ is selected from hydrogen, methyl, ethyl, propyl, isopropyl, —$CH_2F$, —$CH_2Cl$, —$CH_2CH_2F$, —$CH_2CH_2Cl$, —$CHF_2$, —$CF_3$, —$CHCl_2$, —$CCl_3$, and cyclopropyl. In a still further aspect, $R^{80b}$ is hydrogen and $R^{80a}$ is selected from hydrogen, methyl, ethyl, propyl, isopropyl, —$CH_2F$, —$CH_2Cl$, —$CHF_2$, —$CF_3$, —$CHCl_2$, —$CCl_3$, and cyclopropyl. In yet a further aspect, $R^{80b}$ is hydrogen and $R^{80a}$ is selected from hydrogen, methyl, and —$CF_3$. In an even further aspect, $R^{80b}$ is hydrogen and $R^{80a}$ is methyl. In a still further aspect, $R^{80b}$ is hydrogen and $R^{80a}$ is —$CF_3$. In yet a further aspect, each of $R^{80a}$ and $R^{80b}$ is hydrogen.

2. Example Structures

In one aspect, a compound can be present as:

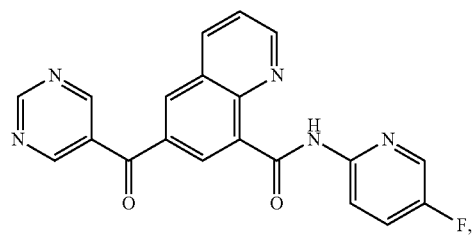

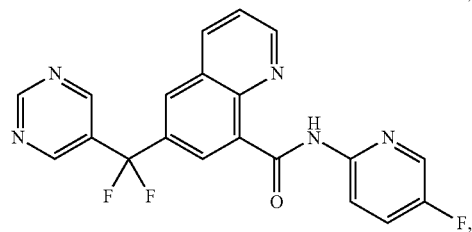

-continued
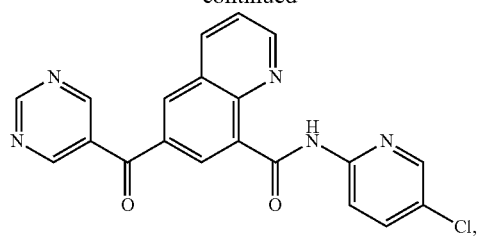
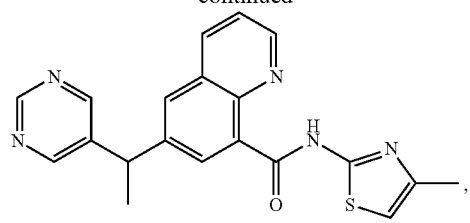
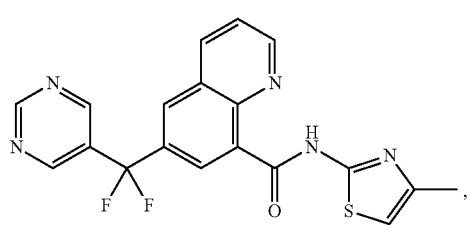
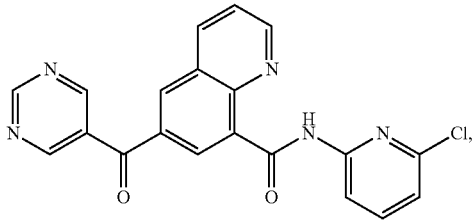
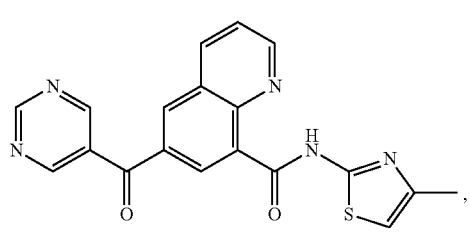
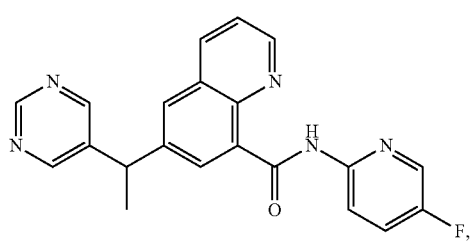
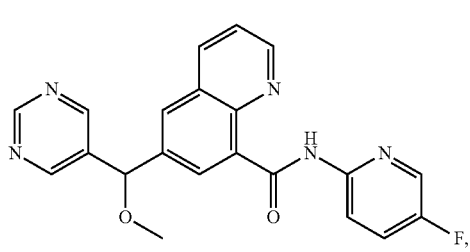
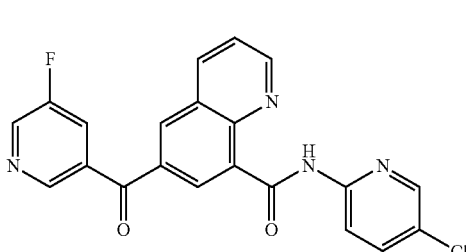
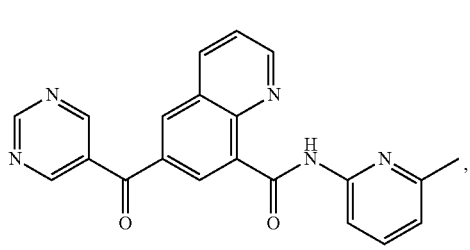
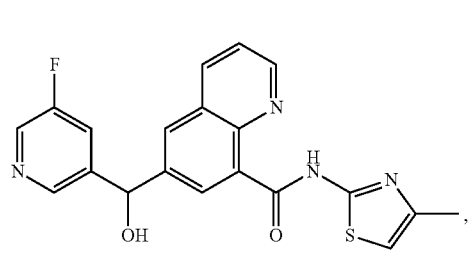
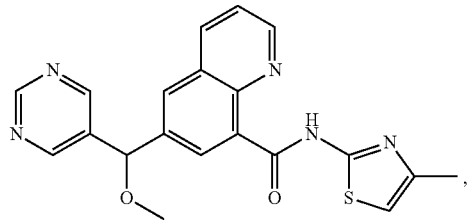
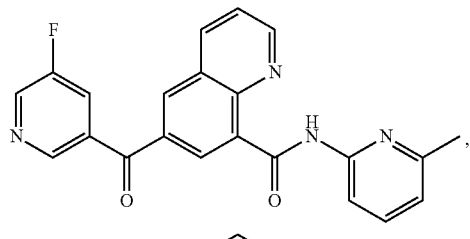
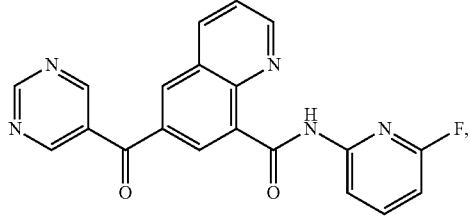
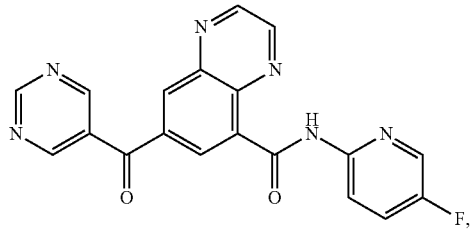

-continued
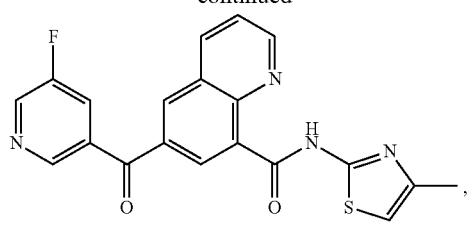
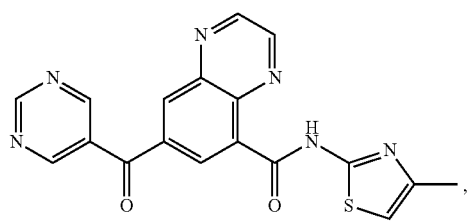
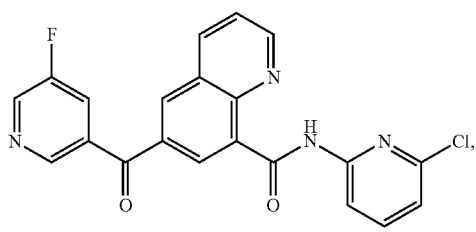
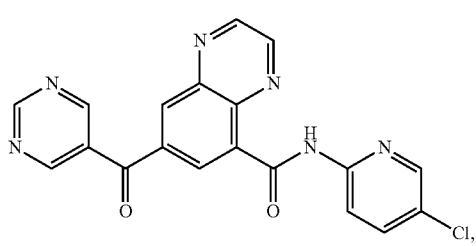
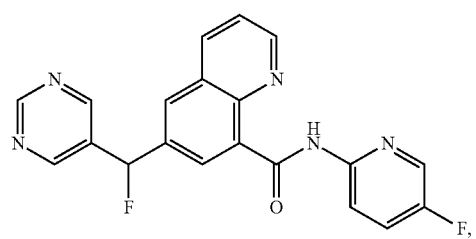
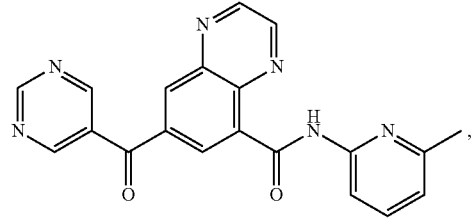
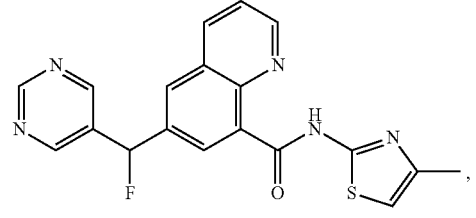
-continued
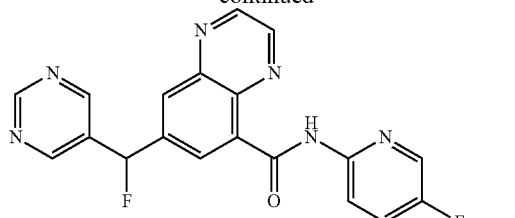
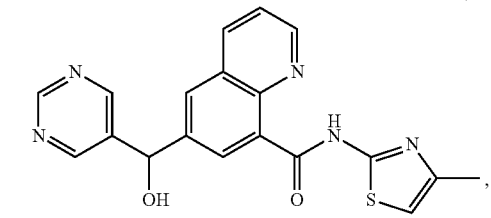
or a subgroup thereof.
In a further aspect, a compound can be present as:
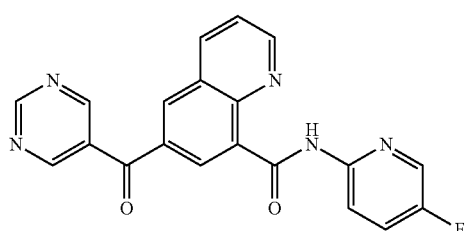
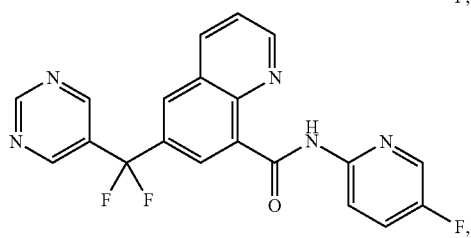
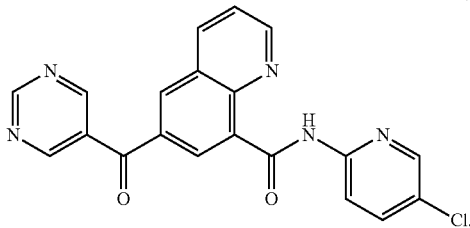
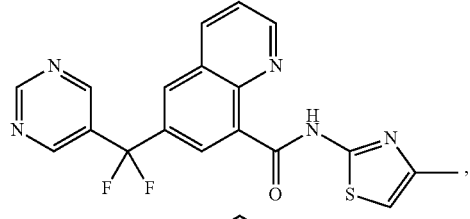
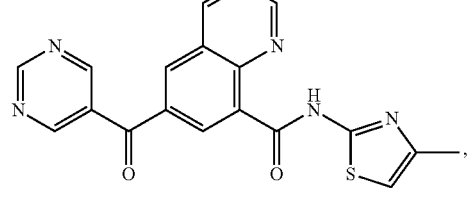

213
-continued
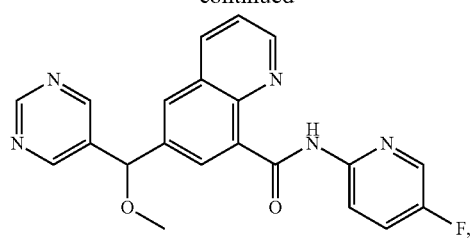
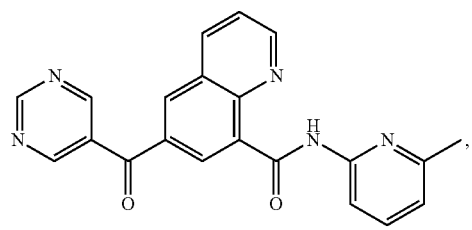 [SMILES: Cc1cccc(NC(=O)c2cc(C(=O)c3cncnc3)cc3nccnc23)n1]
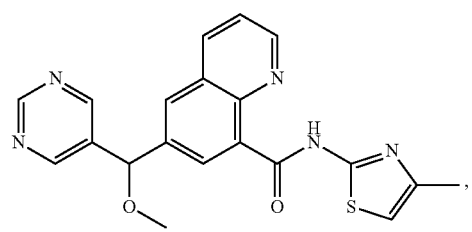
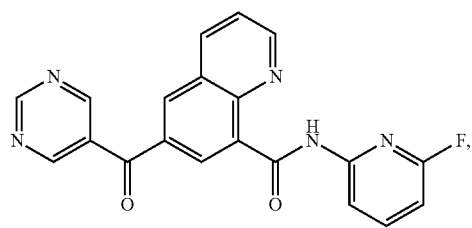
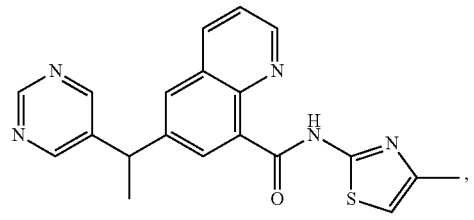
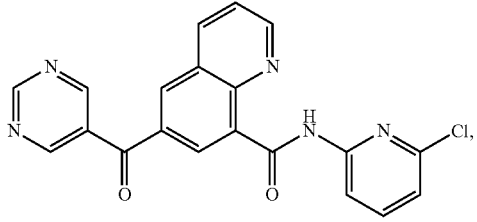
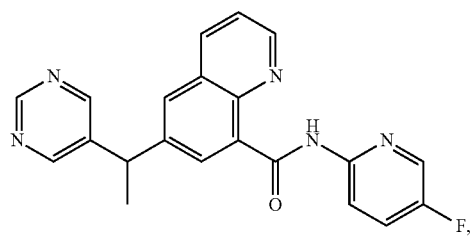
214
-continued
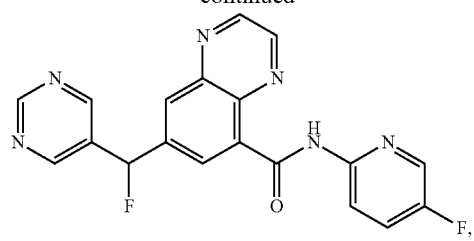
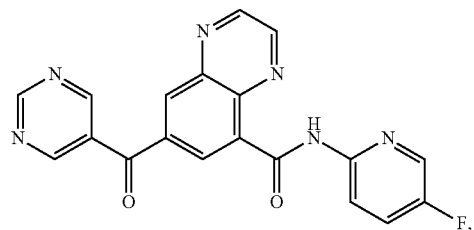
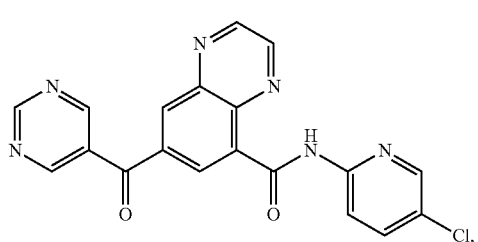
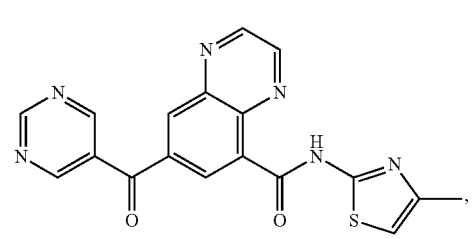
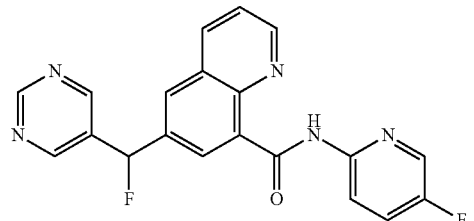
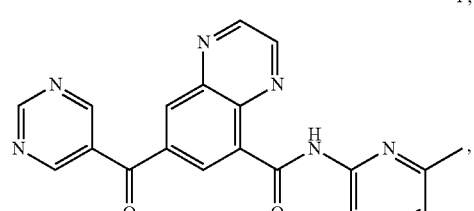
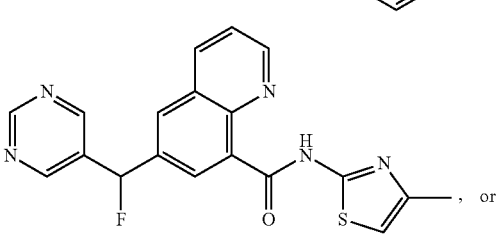, or

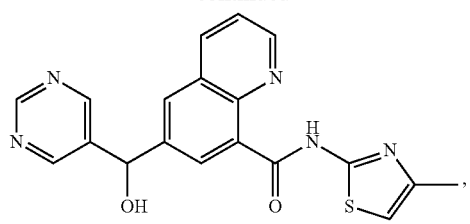
or a subgroup thereof.
In a yet further aspect, a compound can be present as:
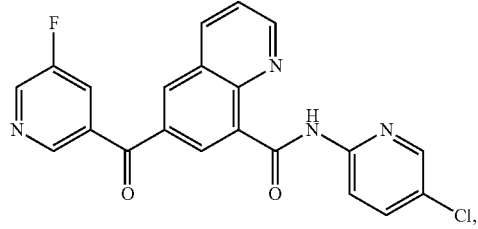
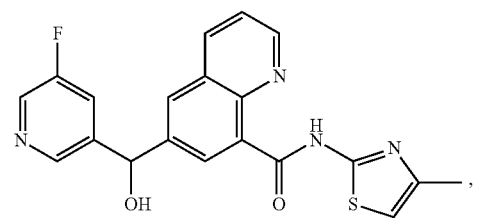
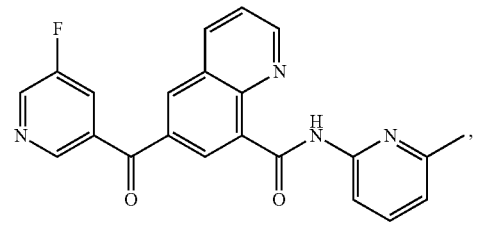
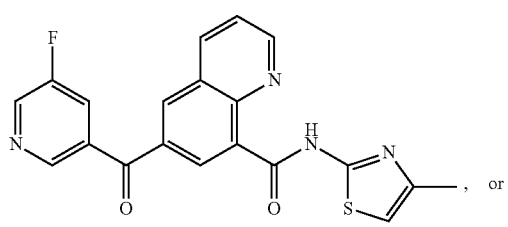
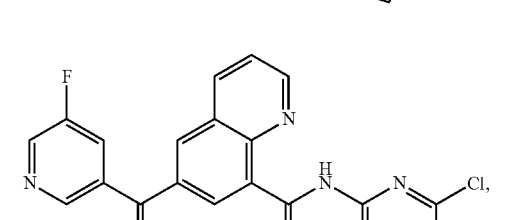
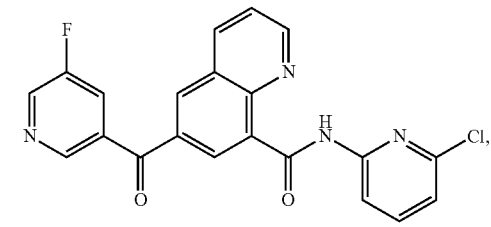
or a subgroup thereof.
In a still further aspect, a compound can be present as:
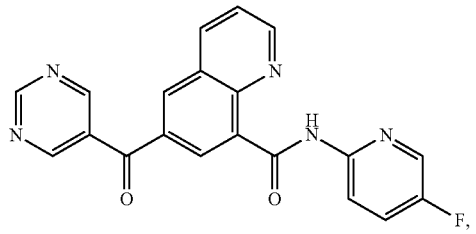
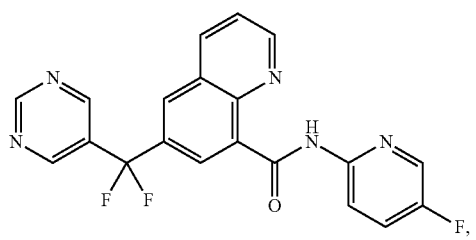
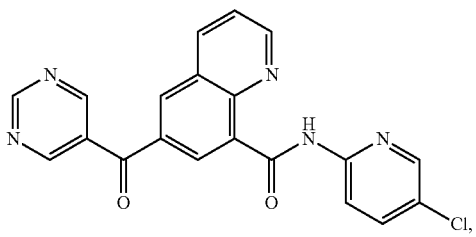
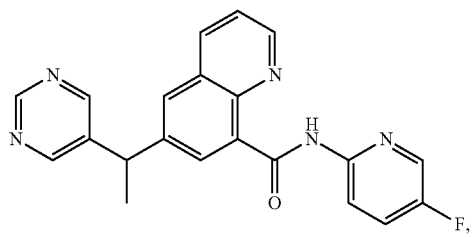
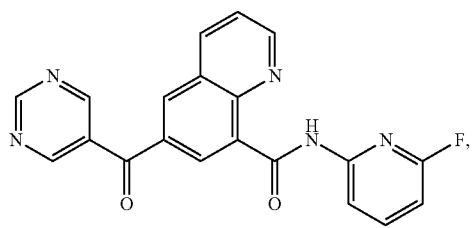
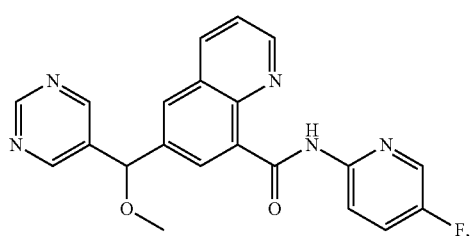
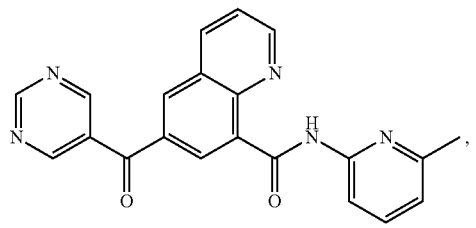

217
-continued
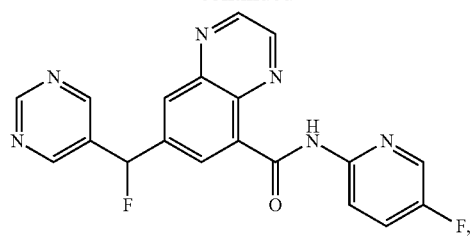
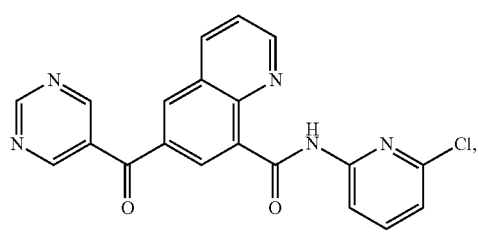
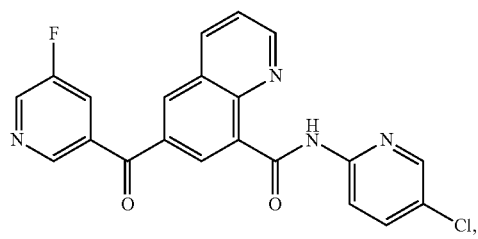
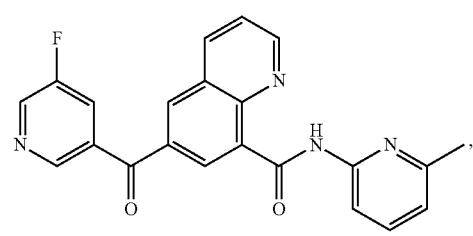
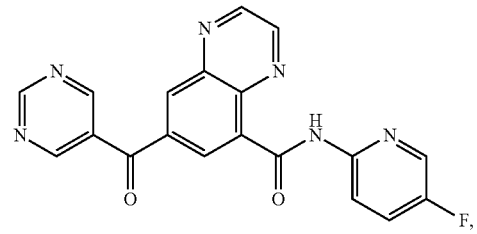
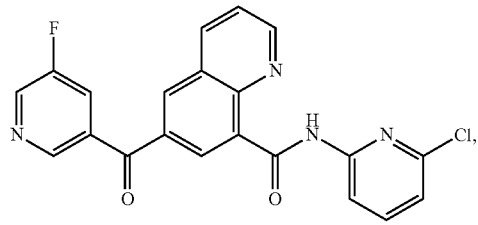
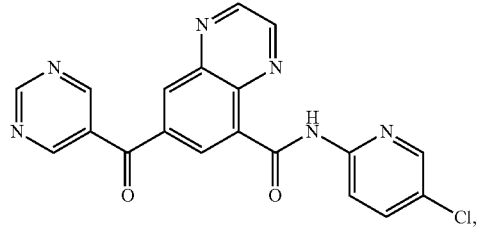
218
-continued
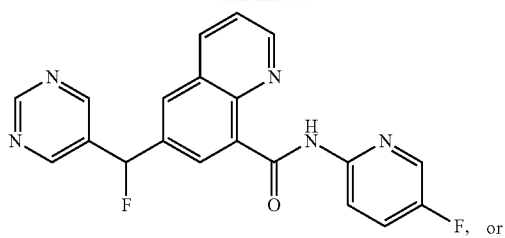
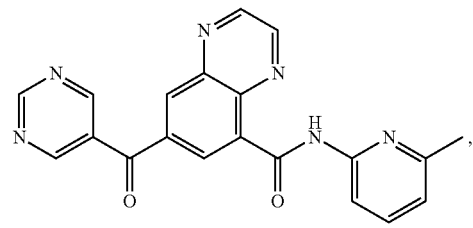
or a subgroup thereof.
In an even further aspect, a compound can be present as:
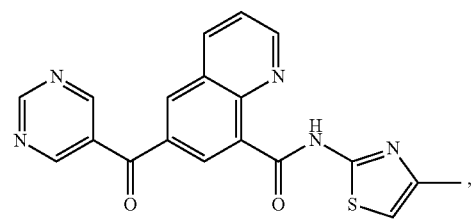
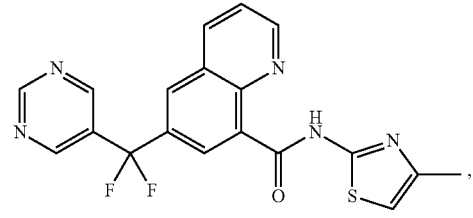
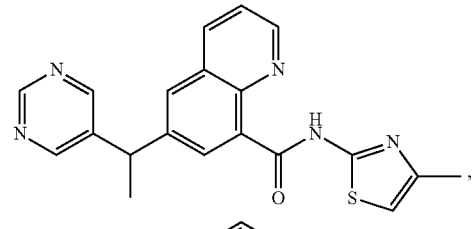
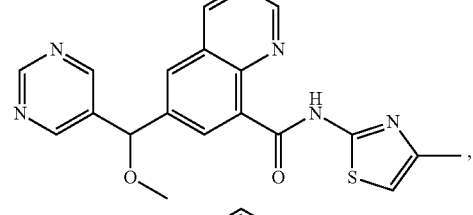
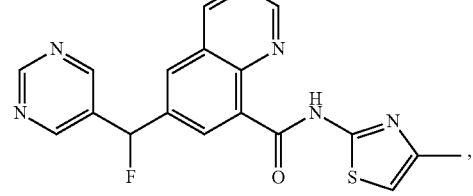

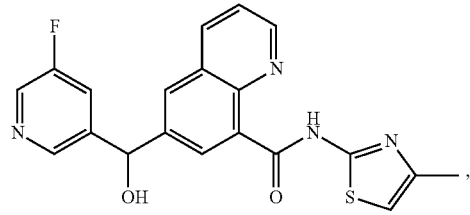
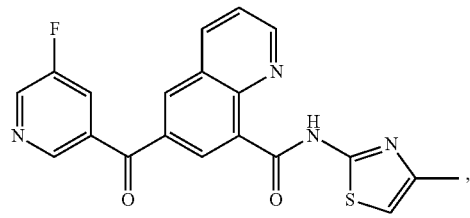
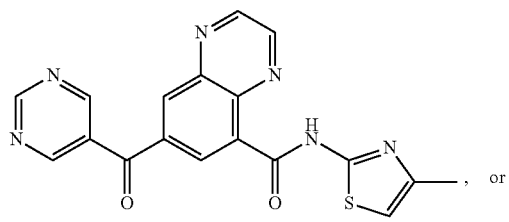, or
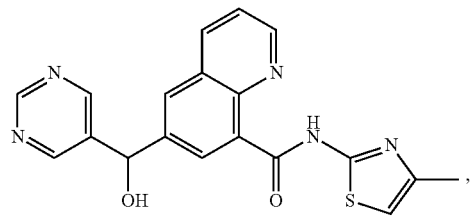
or a subgroup thereof.
In a further aspect, a compound can be present as:
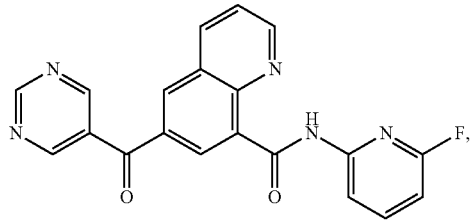
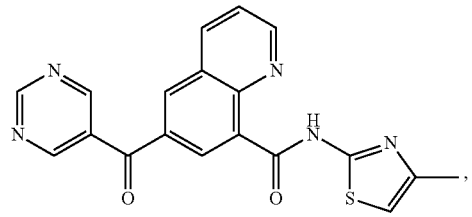
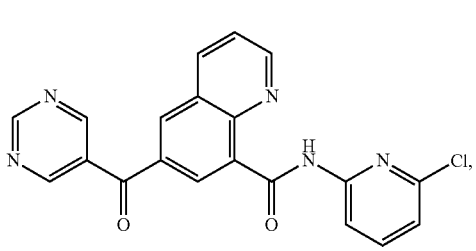
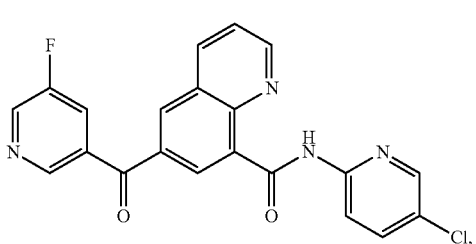
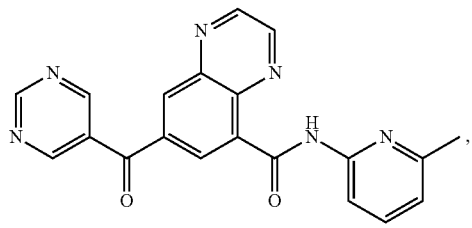
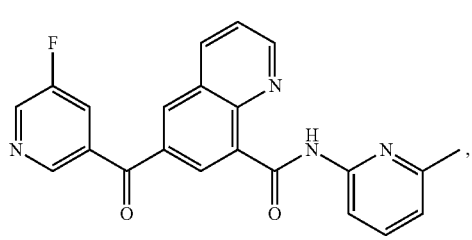
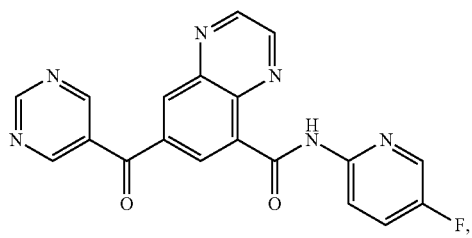

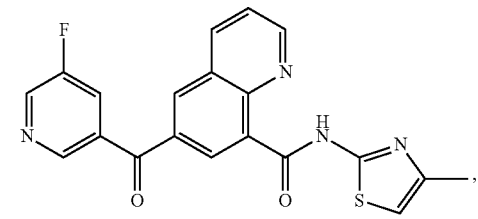
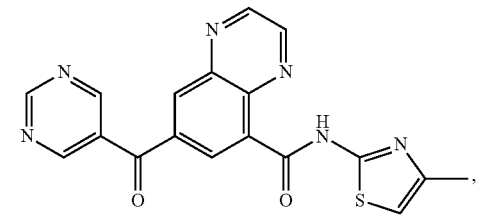
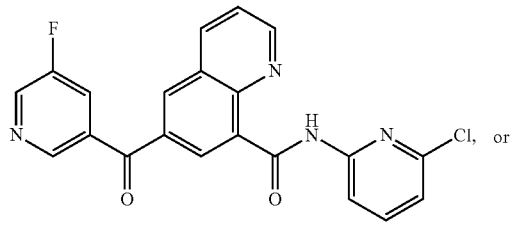
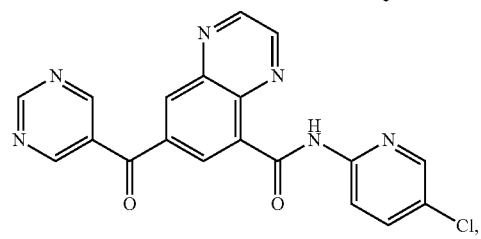
or a subgroup thereof.
In a yet further aspect, a compound can be present as:
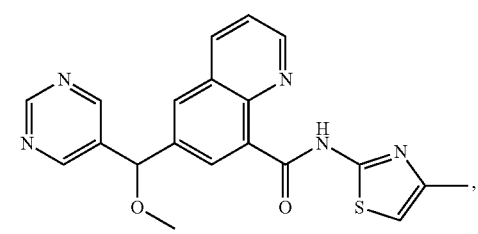
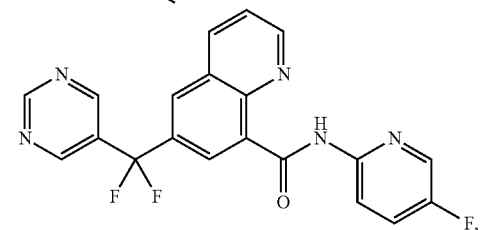
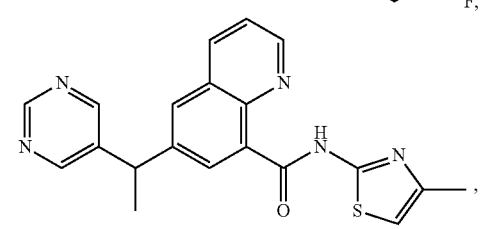
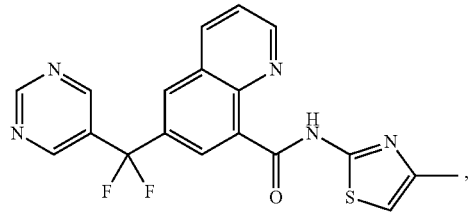
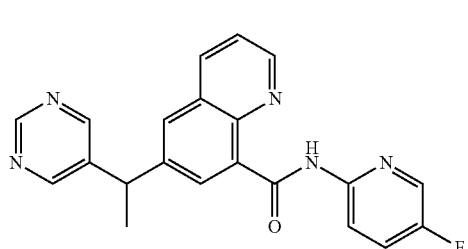
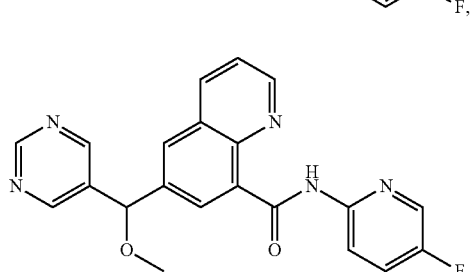
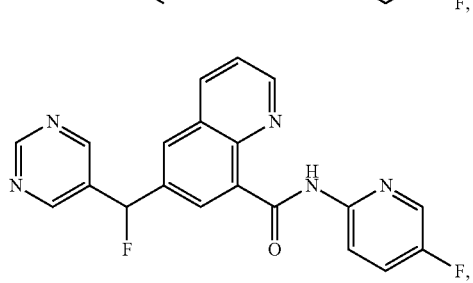

-continued
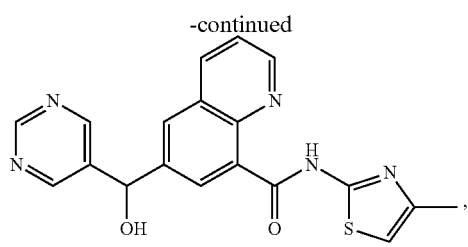
or a subgroup thereof.
In a still further aspect, a compound can be present as:
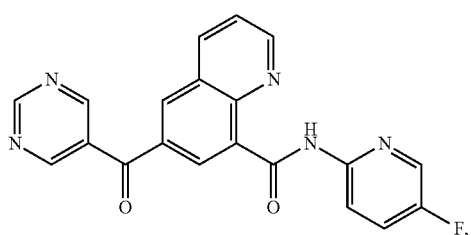
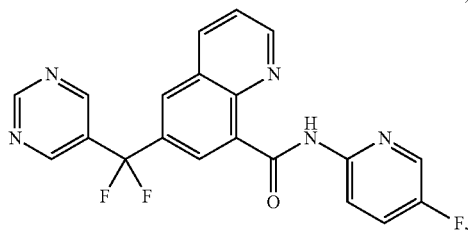
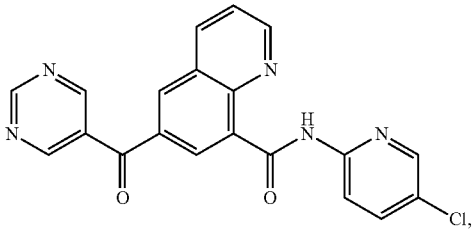
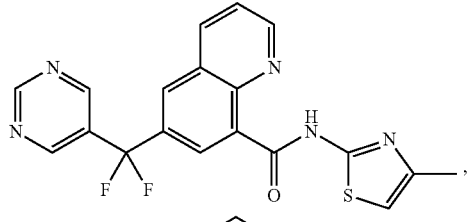
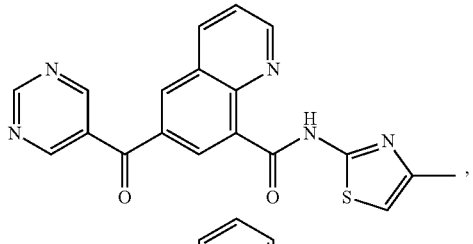
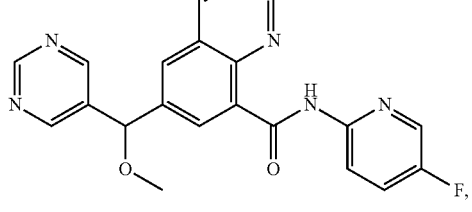
-continued
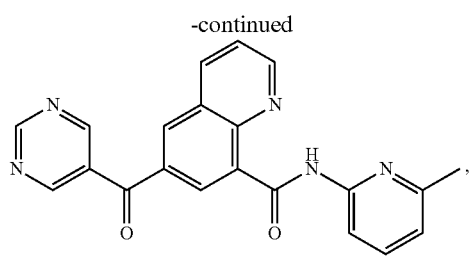
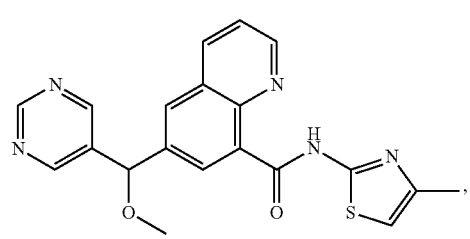
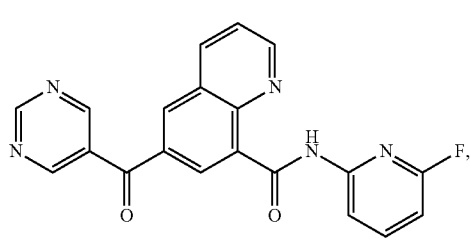
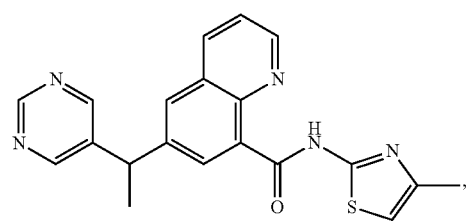
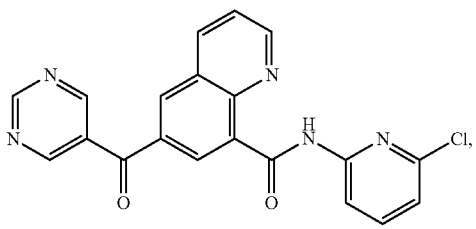
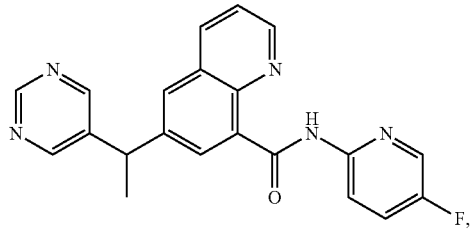
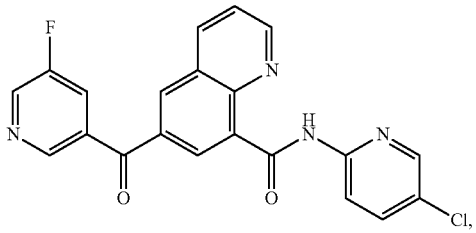

-continued
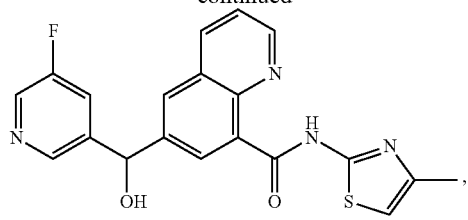
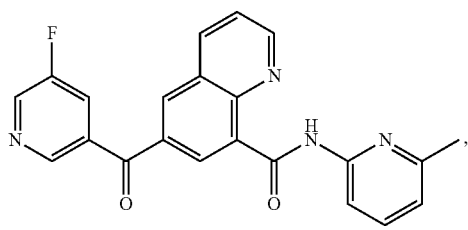
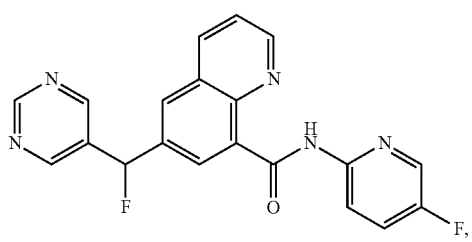
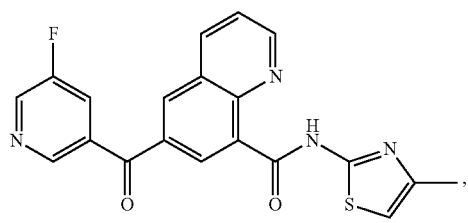
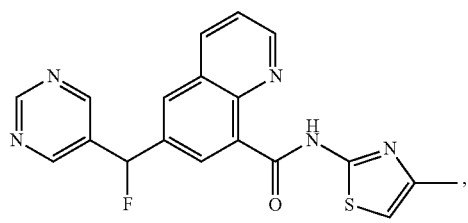
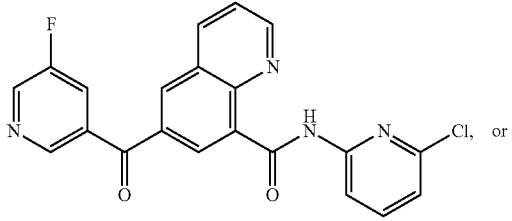
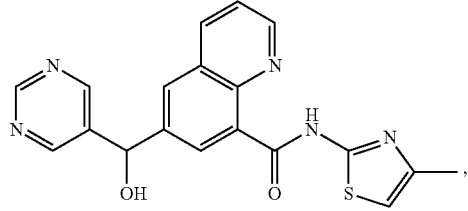
or a subgroup thereof.
In an even further aspect, a compound can be present as:
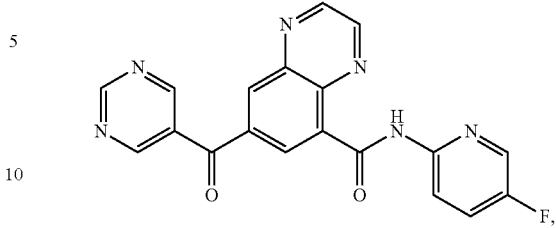
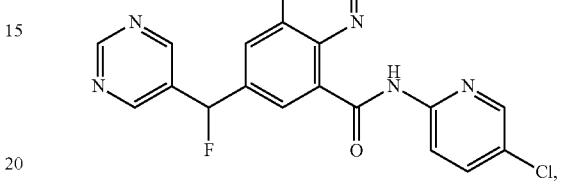
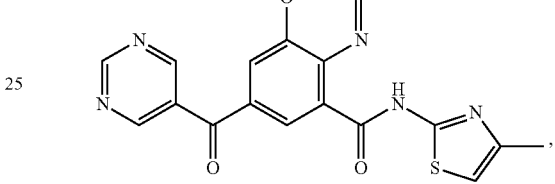
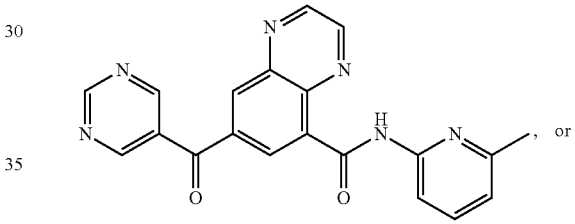
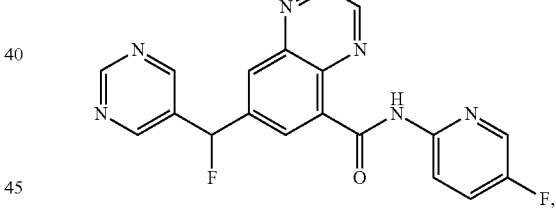
or a subgroup thereof.
In a further aspect, a compound can be present as:
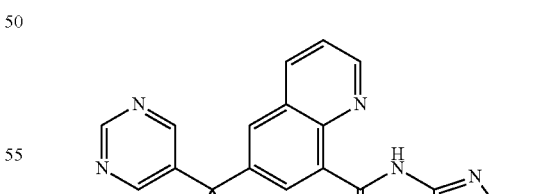
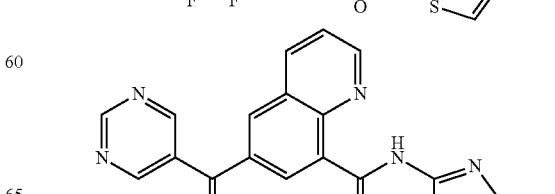

-continued
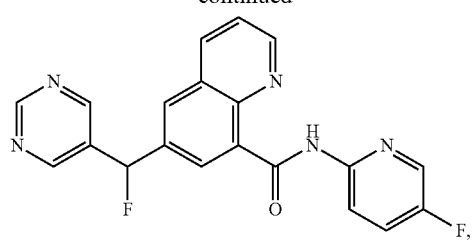
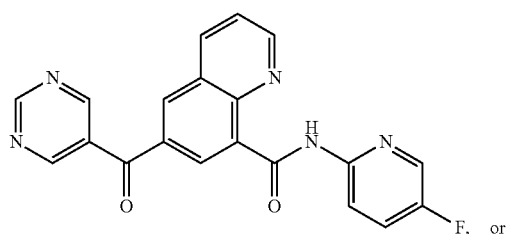
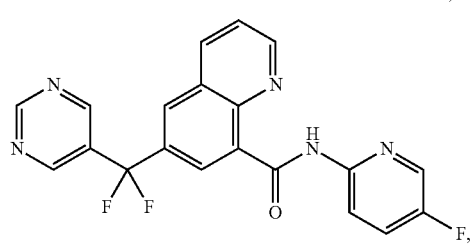
F, or
or a subgroup thereof.
In a yet further aspect, a compound can be present as:
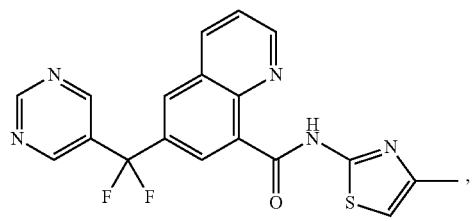
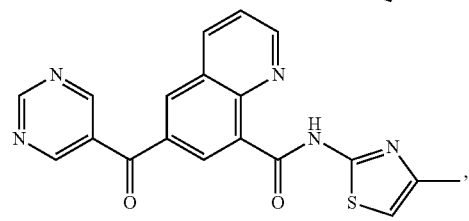
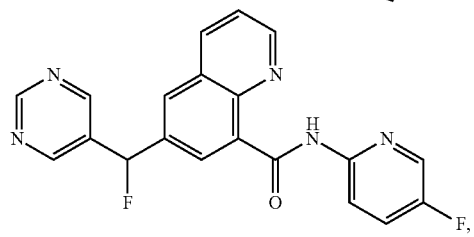
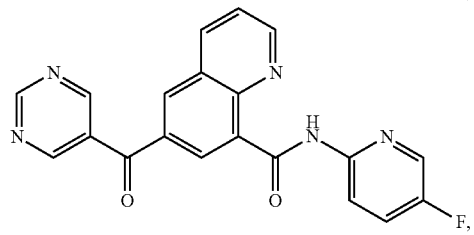
-continued
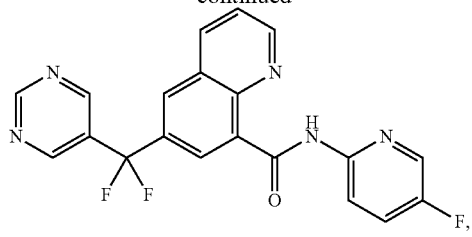
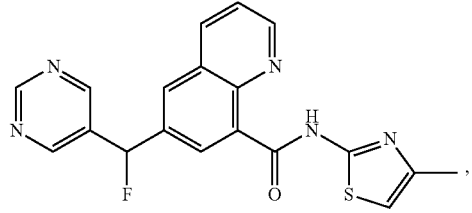
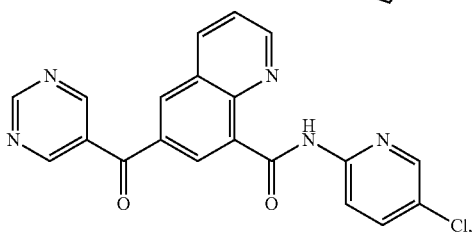
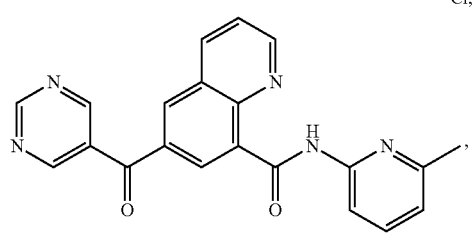
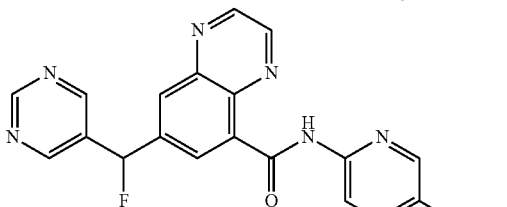
Cl, or
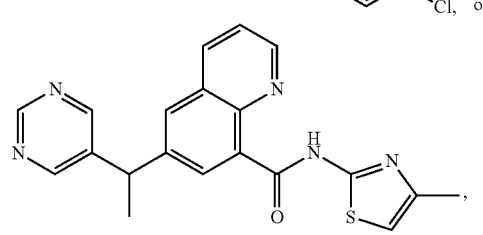
or a subgroup thereof.
In an even further aspect, a compound can be present as:
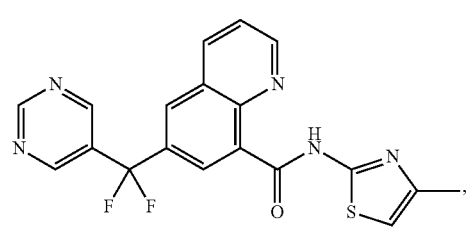

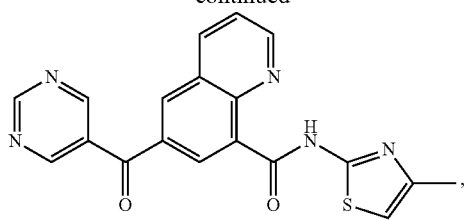
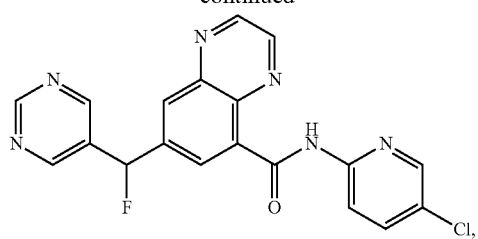
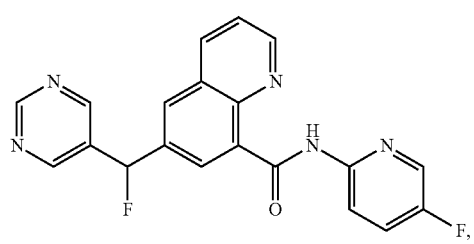
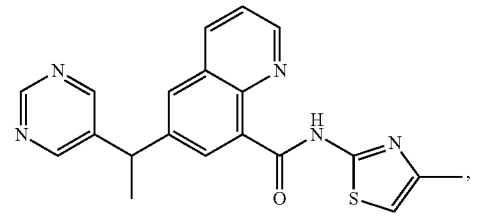
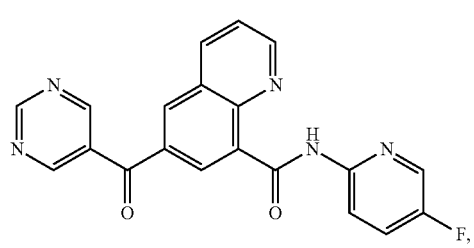
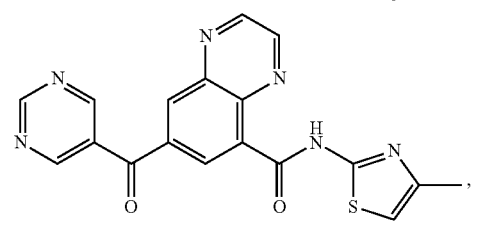
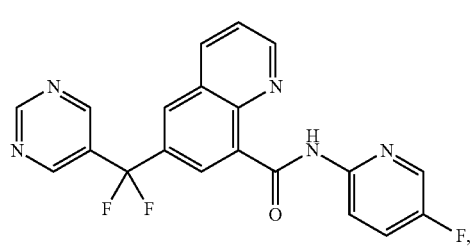
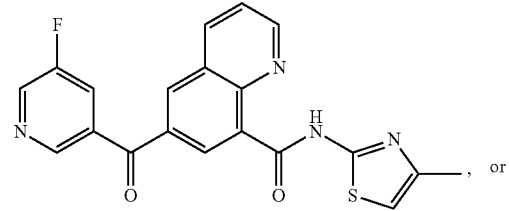, or
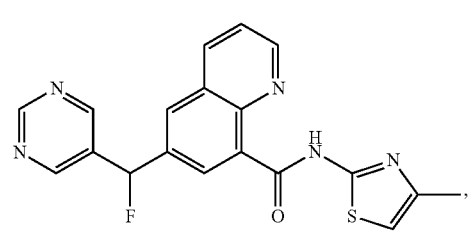
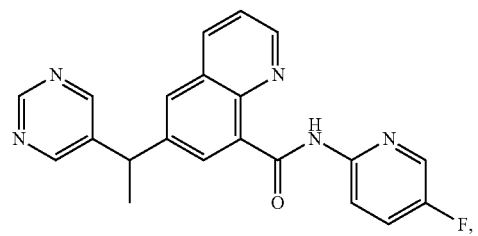
or a subgroup thereof.
In a further aspect, a compound can be present as:
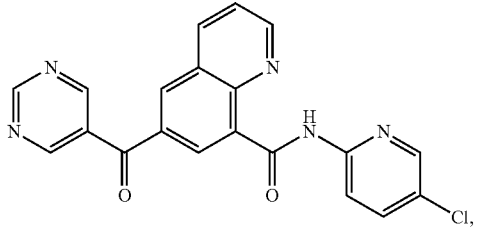
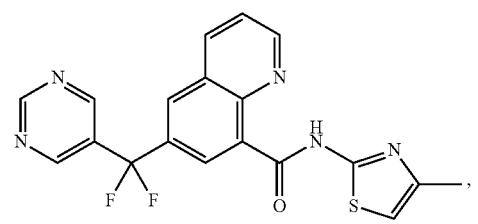
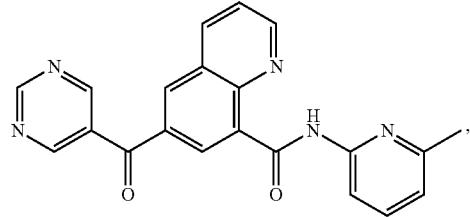
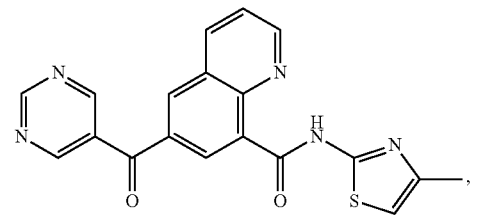

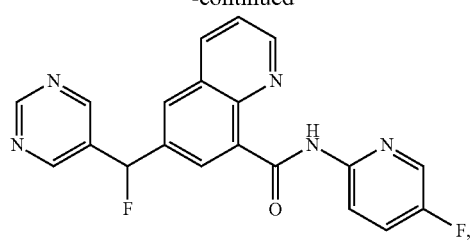
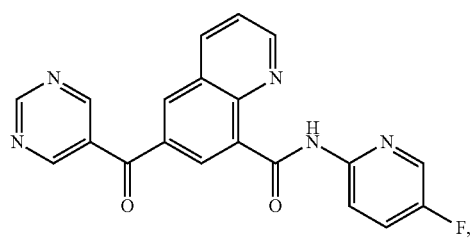
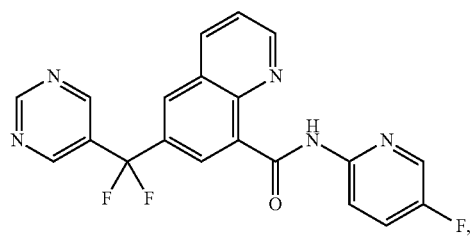
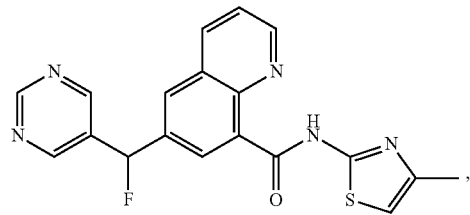
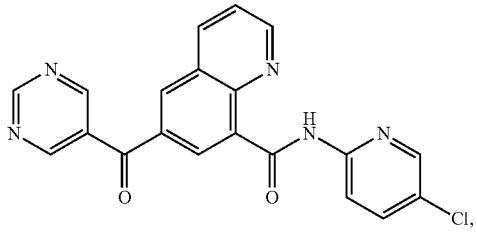
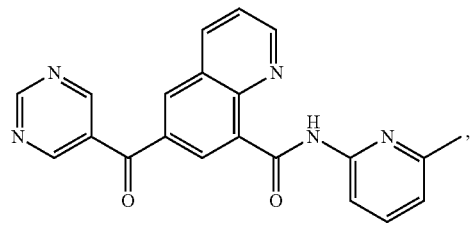
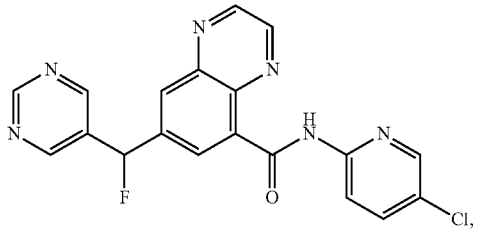
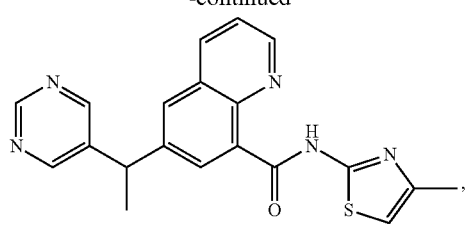
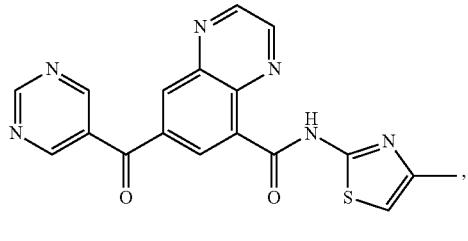
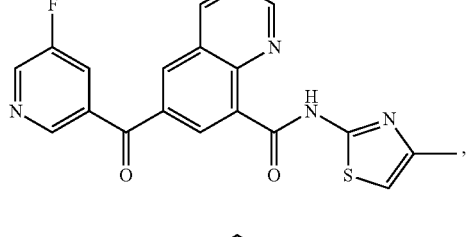
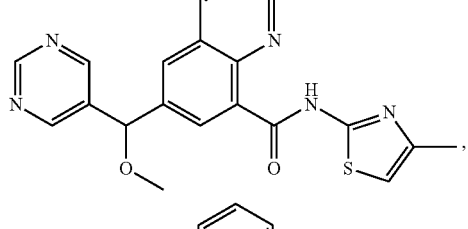
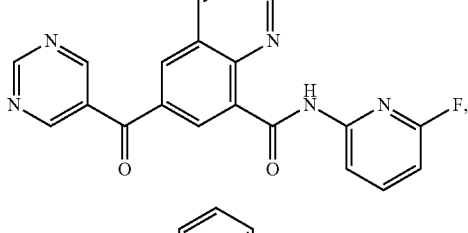
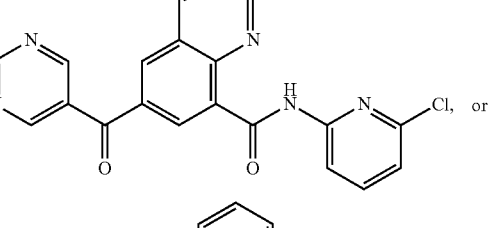
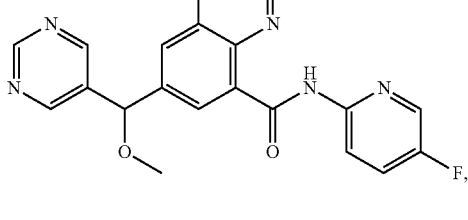
or a subgroup thereof.

In a still further aspect, a compound can be present as:
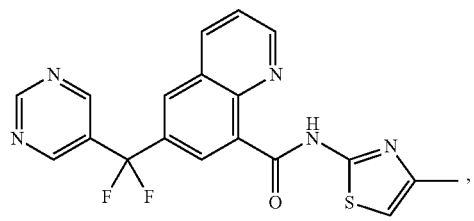
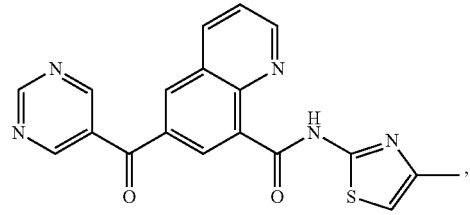
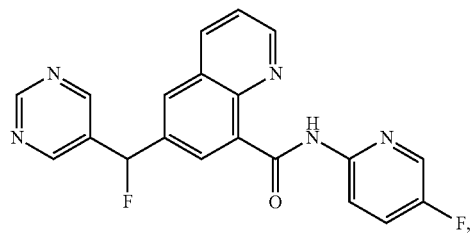
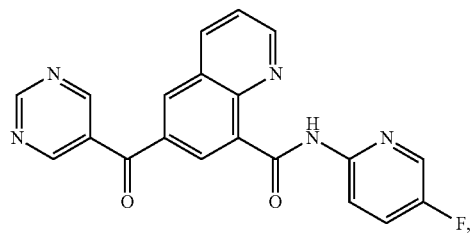
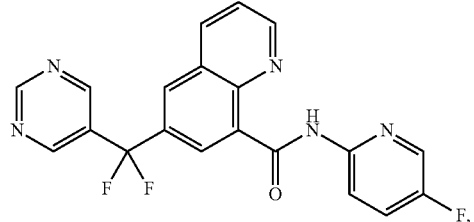
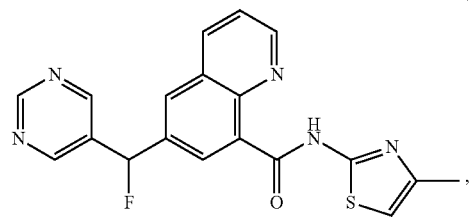
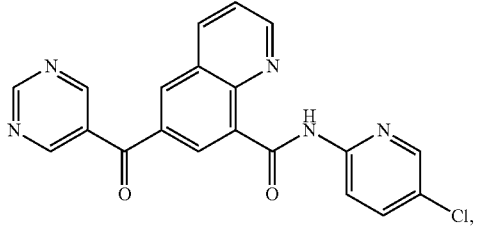
-continued
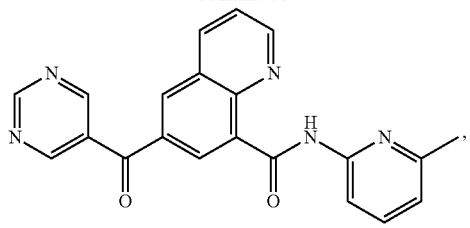
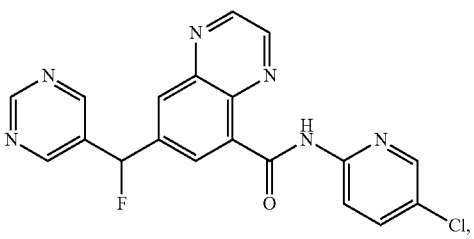
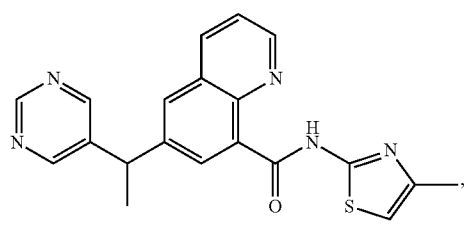
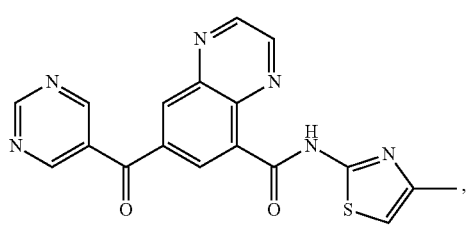
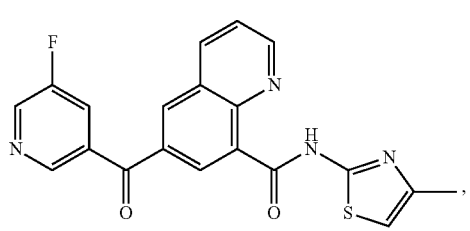
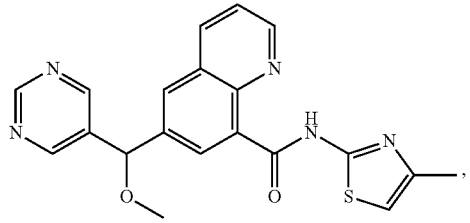
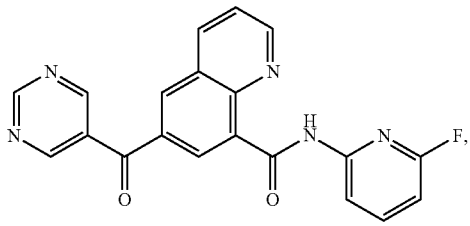

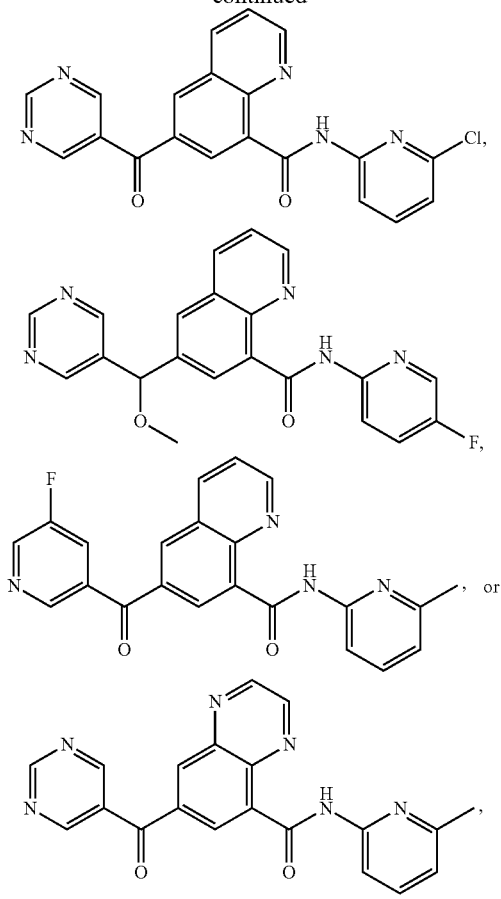

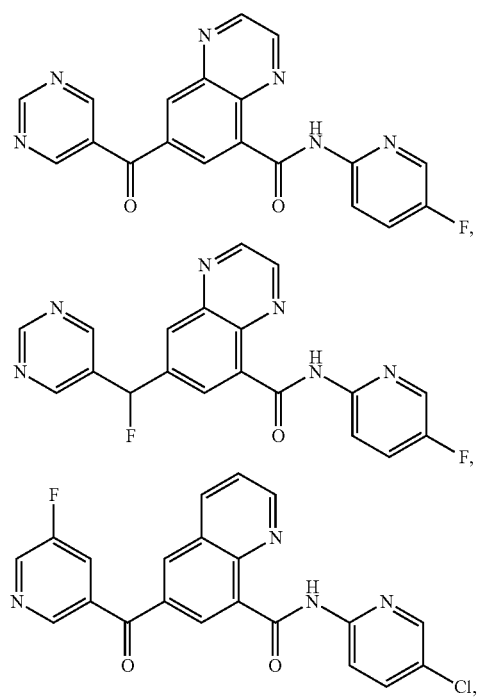

or a subgroup thereof.

In yet a further aspect, a compound can be present as:

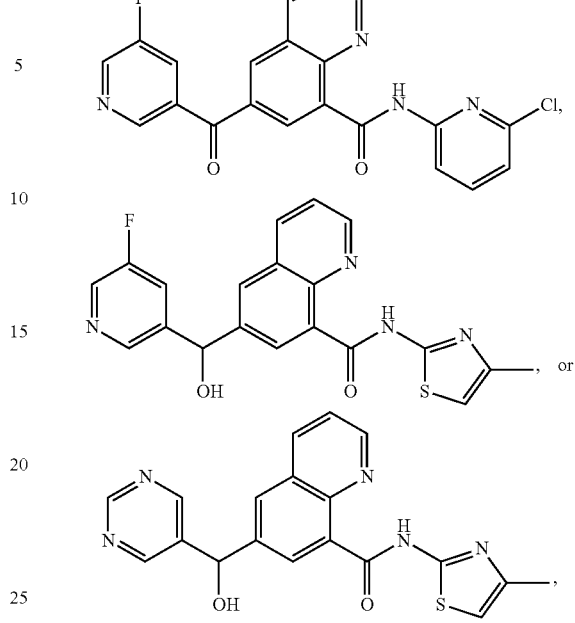

or a subgroup thereof.

In yet a further aspect, the compound exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound exhibits negative allosteric modulation of mGluR5 after contacting a cell expressing mGluR5. In a further aspect, the compound produced exhibits partial or total inhibition of mGluR5 after contacting a cell expressing mGluR5.

In a further aspect, the compound exhibits partial inhibition of mGluR5 response. In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits noncompetitive antagonism. In a still further aspect, the compound exhibits negative allosteric modulation. In a yet further aspect, the compound exhibits noncompetitive inhibition. In an even further aspect, the compound exhibits allosteric antagonism.

In a further aspect, the compound exhibits negative allosteric modulation with an $IC_{50}$ of less than about $30 \times 10^{-6}$ M. In an even further aspect, the compound exhibits negative allosteric modulation with an $IC_{50}$ of less than about $10 \times 10^{-6}$ M. In a yet further aspect, the compound exhibits negative allosteric modulation with an $IC_{50}$ of less than about $1.0 \times 10^{-6}$ M. In a still further aspect, the compound exhibits negative allosteric modulation with an $IC_{50}$ of less than about $1.0\times10^{-7}$ M. In an even further aspect, the compound exhibits negative allosteric modulation with an $IC_{50}$ of less than about $1.0\times10^{-8}$ M. In a yet further aspect, the compound exhibits negative allosteric modulation with an $IC_{50}$ of less than about $1.0\times10^{-9}$ M. In a still further aspect, the compound exhibits negative allosteric modulation inhibition with an $IC_{50}$ of between about $1\times10^{-5}$ M to about $1\times10^{-9}$ M. In an even further aspect, the compound exhibits negative allosteric modulation with an $IC_{50}$ of between about from about $1\times10^{-6}$ M to about $1\times10^{-9}$ M. In a yet further aspect, the compound exhibits negative allosteric modulation with an $IC_{50}$ of between about from about $1\times10^{-7}$ M to about $1\times10^{-9}$ M. In a still further aspect, the compound exhibits negative allosteric modulation with an $IC_{50}$ of between about $1\times10^{-8}$ M to about $1\times10^{-9}$ M.

In a further aspect, the compound exhibits partial or total inhibition with an $IC_{50}$ of less than about $30\times10^{-6}$ M. In an even further aspect, the compound exhibits partial or total inhibition with an $IC_{50}$ of less than about $10\times10^{-6}$ M. In a yet further aspect, the compound exhibits partial or total inhibition with an $IC_{50}$ of less than about $1.0\times10^{-6}$ M. In a still further aspect, the compound exhibits partial or total inhibition with an $IC_{50}$ of less than about $1.0\times10^{-7}$ M. In an even further aspect, the compound exhibits partial or total inhibition with an $IC_{50}$ of less than about $1.0\times10^{-8}$ M. In a yet further aspect, the compound exhibits partial or total inhibition with an $IC_{50}$ of less than about $1.0\times10^{-9}$ M. In a still further aspect, the compound exhibits partial or total inhibition with an $IC_{50}$ of between about $1\times10^{-5}$ M to about $1\times10^{-9}$ M. In an even further aspect, the compound exhibits partial or total inhibition with an $IC_{50}$ of between about from about $1\times10^{-6}$ M to about $1\times10^{-9}$ M. In a yet further aspect, the compound exhibits partial or total inhibition with an $IC_{50}$ of between about from about $1\times10^{-7}$ M to about $1\times10^{-9}$ M. In a still further aspect, the compound exhibits partial or total inhibition with an $IC_{50}$ of between about $1\times10^{-8}$ M to about $1\times10^{-9}$ M.

In a further aspect, a pharmaceutical composition comprising a therapeutically effective amount of the compound and a pharmaceutically acceptable carrier.

It is contemplated that one or more example structures can be optionally omitted from the disclosed invention.

3. Atropisomeric Forms

Atropisomers are stereoisomers resulting from hindered rotation about single bonds where the steric strain barrier to rotation is high enough to allow for the isolation of the conformers. Atropisomers display axial chirality, but differ from other chiral compounds in that they can be equilibrated thermally, whereas in the other forms of chirality isomerization is usually only possible chemically. In certain aspects, the disclosed compounds can be provided as atropisomeric compounds. For example, disclosed compounds can be provided as single atropisomers or as a mixture of atropisomers.

It is contemplated that one atropisomer can exhibit greater negative allosteric modulation of mGluR5 response to glutamate than another, otherwise structurally identical, atropisomer. Thus, individual atropisomers of disclosed compounds can be isolated and used in disclosed methods. Separation of atropisomers can be achieved by chiral resolution methods such as selective crystallization.

In an atropo-enantioselective or atropo-selective synthesis, one atropisomer is formed at the expense of the other. Thus, it is also contemplated that a specific atropisomer can be preferentially prepared: atropo-selective synthesis can be carried out by use of chiral auxiliaries or by approaches based on thermodynamic equilibration when an isomerization reaction favors one atropisomer over the other.

4. Negative Allosteric Modulation of mGluR5 Response

In a further aspect, the compound exhibits partial inhibition of mGluR5 response. In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits noncompetitive antagonism. In a still further aspect, the compound exhibits negative allosteric modulation. In a yet further aspect, the compound exhibits noncompetitive inhibition. In an even further aspect, the compound exhibits allosteric antagonism.

In a further aspect, the compound exhibits negative allosteric modulation with an $IC_{50}$ of less than about $30\times10^{-6}$ M. In an even further aspect, the compound exhibits negative allosteric modulation with an $IC_{50}$ of less than about $10\times10^{-6}$ M. In a yet further aspect, the compound exhibits negative allosteric modulation with an $IC_{50}$ of less than about $1.0\times10^{-6}$ M. In a still further aspect, the compound exhibits negative allosteric modulation with an $IC_{50}$ of less than about $1.0\times10^{-7}$ M. In an even further aspect, the compound exhibits negative allosteric modulation with an $IC_{50}$ of less than about $1.0\times10^{-8}$ M. In a yet further aspect, the compound exhibits negative allosteric modulation with an $IC_{50}$ of less than about $1.0\times10^{-9}$ M. In a still further aspect, the compound exhibits negative allosteric modulation inhibition with an $IC_{50}$ of between about $1\times10^{-5}$ M to about $1\times10^{-9}$ M. In an even further aspect, the compound exhibits negative allosteric modulation with an $IC_{50}$ of between about from about $1\times10^{-6}$ M to about $1\times10^{-9}$ M. In a yet further aspect, the compound exhibits negative allosteric modulation with an $IC_{50}$ of between about from about $1\times10^{-7}$ M to about $1\times10^{-9}$ M. In a still further aspect, the compound exhibits negative allosteric modulation with an $IC_{50}$ of between about $1\times10^{-8}$ M to about $1\times10^{-9}$ M.

In a further aspect, the compound exhibits partial or total inhibition with an $IC_{50}$ of less than about $30\times10^{-6}$ M. In an even further aspect, the compound exhibits partial or total inhibition with an $IC_{50}$ of less than about $10\times10^{-6}$ M. In a yet further aspect, the compound exhibits partial or total inhibition with an $IC_{50}$ of less than about $1.0\times10^{-6}$ M. In a still further aspect, the compound exhibits partial or total inhibition with an $IC_{50}$ of less than about $1.0\times10^{-7}$ M. In an even further aspect, the compound exhibits partial or total inhibition with an $IC_{50}$ of less than about $1.0\times10^{-8}$ M. In a yet further aspect, the compound exhibits partial or total inhibition with an $IC_{50}$ of less than about $1.0\times10^{-9}$ M. In a still further aspect, the compound exhibits partial or total inhibition with an $IC_{50}$ of between about $1\times10^{-5}$ M to about $1\times10^{-9}$ M. In an even further aspect, the compound exhibits partial or total inhibition with an $IC_{50}$ of between about from about $1\times10^{-6}$ M to about $1\times10^{-9}$ M. In a yet further aspect, the compound exhibits partial or total inhibition with an $IC_{50}$ of between about from about $1\times10^{-7}$ M to about $1\times10^{-9}$ M. In a still further aspect, the compound exhibits partial or total inhibition with an $IC_{50}$ of between about $1\times10^{-8}$ M to about $1\times10^{-9}$ M.

C. Metabotropic Glutamate Receptor Activity

The utility of the compounds in accordance with the present invention as negative allosteric modulators of metabotropic glutamate receptor activity, in particular mGluR5 activity, can be demonstrated by methodology known in the art. Human embryonic kidney (HEK) cells transfected with rat or human mGluR5 were plated in clear bottom assay plates for assay in a Functional Drug Screening System (FDSS). The cells were loaded with a $Ca^{2+}$- sensitive fluorescent dye (e.g., Fluo-4), and the plates were washed and placed in the FDSS instrument. Test compound was applied to cells 3 seconds after baseline readings were taken. Cells were incubated with the test compounds for 140 seconds and then stimulated with an $EC_{20}$ concentration of an mGluR5 agonist (e.g., glutamate, 3,5-dihydroxyphenylglycine, or quisqualate); 60-80 seconds later an $EC_{80}$ concentration of agonist was added and readings taken for an additional 40 seconds. Data were collected at 1 Hz. Negative allosteric modulation of the agonist response of mGluR5 by the compounds in the present invention was observed as a decrease in response to non-maximal concentrations of agonist (here, glutamate) in the presence of compound compared to the response to agonist in the absence of compound. Concentration response curves were generated using a four parameter logistical equation.

The above described assay was operated in two modes. In the first mode (utilizing a triple add protocol), a range of concentrations of the present compounds were added to cells, followed by two single fixed concentrations of agonist ($EC_{20}$ followed by $EC_{80}$). If a compound acted as a potentiator, an $EC_{50}$ value for potentiation of the $EC_{20}$ response and a maximum extent of potentiation by the compound at this concentration of agonist was determined by non-linear curve fitting. If a compound acted as an antagonist, an $IC_{50}$ value for antagonism of the $EC_{80}$ response and a maximum extent of antagonism by the compound at this concentration of agonist was determined by non-linear curve fitting. In the second mode (utilizing a double add protocol), several fixed concentrations of the present compounds were added to various wells on a plate, followed by a range of concentrations of agonist for each concentration of present compound; the $EC_{50}$ values for the agonist at each concentration of compound were determined by nonlinear curve fitting. A decrease in the $EC_{50}$ value of the agonist with increasing concentrations of the present compounds (a leftward shift of the agonist concentration-response curve) is an indication of the degree of mGluR5 positive allosteric modulation at a given concentration of the present compound. An increase in the $EC_{50}$ value of the agonist with increasing concentrations of the present compounds (a rightward shift of the agonist concentration response curve) is an indication of the degree of mGluR5 antagonism at a given concentration of the present compound. The second mode also indicates whether the present compounds also affect the maximum response to mGluR5 to agonists. Exemplary data are provided in Table 1 below.

In particular, the disclosed compounds had activity in modulating the mGluR5 receptor in the aforementioned assays, generally with an $IC_{50}$ for modulation of less than about 30 µM. Preferred compounds within the present invention had activity in modulating the mGluR5 receptor with an $IC_{50}$ for negative allosteric modulation of less than about 500 nM. Preferred compounds reduced the response to an $EC_{80}$ concentration of glutamate to less than 50% of the maximal response and also induced a rightward and downward shift of the glutamate concentration response curve. These compounds are negative allosteric modulators of human and rat mGluR5 and were selective for mGluR5 compared to the other six subtypes of metabotropic glutamate receptors.

D. Methods of Making the Compounds

In one aspect, the invention relates to methods of making compounds useful as negative allosteric modulators of the metabotropic glutamate receptor subtype 5 (mGluR5), which can be useful in the treatment neurological and psychiatric disorders associated with glutamate dysfunction and other diseases in which metabotropic glutamate receptors are involved.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Route I and Route II, as described and exemplified below. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

In a further aspect, the compound produced exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound.

1. Intermediate Route I

In one aspect, bromoquinoxaline intermediates can be prepared as shown below.

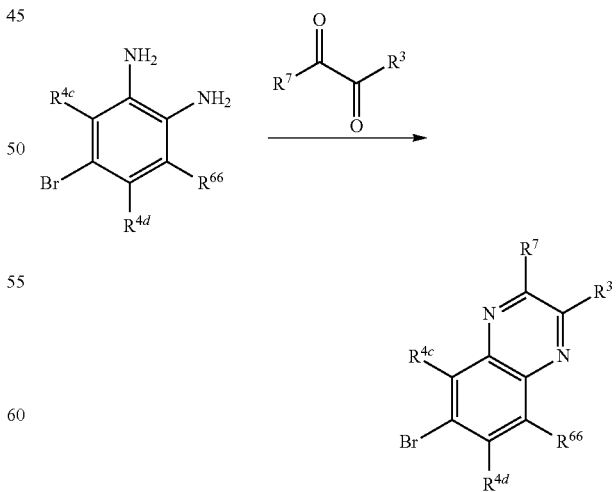

Compounds are represented in generic form, with substituents as noted in compound descriptions elsewhere herein. A more specific example is set forth below.

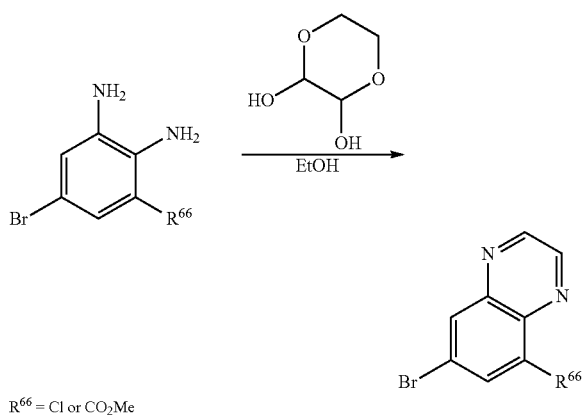

R⁶⁶ = Cl or CO₂Me

In one aspect, Intermediate Route I begins with a substituted benzene-1,2-diamine. Such benzene-1,2-diamines can be purchased commercially or prepared by one skilled in the art according to methods well described in the literature. Reaction with 1,4-dioxan-2,3-diol (a glyoxal equivalent) provides the quinoxaline intermediate. The reaction may be optionally heated with conventional heating or microwave irradiation.

Thus, in one aspect, the invention relates to a method of making a compound comprising the step of reacting a compound having a structure represented by a formula:

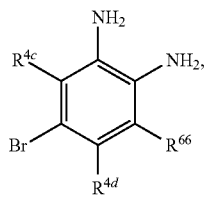

wherein each of $R^{4c}$ and $R^{4d}$ is independently selected from hydrogen and fluoro; wherein $R^{66}$ is chloro or $CO_2R^{67}$; wherein $R^{67}$ is C1-C3 alkyl; with a second compound having a structure represented by a formula:

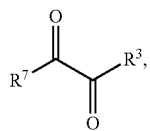

wherein $R^3$ is selected from hydrogen, halogen, —CN, C1-C3 alkyl, C1-C3 monohaloalkyl, C1-C3 polyhaloalkyl, cyclopropyl, —OR⁶⁰, —NR⁶¹ᵃR⁶¹ᵇ, —SO₂R⁶², and —(C=O)R⁶³; wherein R⁶⁰, when present, is selected from hydrogen, C1-C3 alkyl, C1-C3 monohaloalkyl, C1-C3 polyhaloalkyl, and cyclopropyl; wherein each of R⁶¹ᵃ and R⁶¹ᵇ, when present, is independently selected from hydrogen, C1-C3 alkyl, C1-C3 monohaloalkyl, C1-C3 polyhaloalkyl, and cyclopropyl; or wherein R⁶¹ᵃ and R⁶¹ᵇ, when present, are optionally covalently bonded and, together with nitrogen atom to which they are attached, comprise a 3- to 6-membered heterocycle; wherein R⁶², when present, is selected from C1-C3 alkyl, C1-C3 monohaloalkyl, C1-C3 polyhaloalkyl, cyclopropyl, and, —NR⁶⁴ᵃR⁶⁴ᵇ; wherein each of R⁶⁴ᵃ and R⁶⁴ᵇ, when present, is independently selected from hydrogen, C1-C3 alkyl, C1-C3 monohaloalkyl, C1-C3 polyhaloalkyl, and cyclopropyl; or wherein R⁶⁴ᵃ and R⁶⁴ᵇ, when present, are optionally covalently bonded and, together with nitrogen atom to which they are attached, comprise a 3- to 6-membered heterocycle; wherein R⁶³, when present, is selected from C1-C3 alkyl, C1-C3 monohaloalkyl, C1-C3 polyhaloalkyl, cyclopropyl, and, —NR⁶⁵ᵃR⁶⁵ᵇ; wherein each of R⁶⁵ᵃ and R⁶⁵ᵇ, when present, is independently selected from hydrogen, C1-C3 alkyl, C1-C3 monohaloalkyl, C1-C3 polyhaloalkyl, and cyclopropyl; or wherein R⁶⁵ᵃ and R⁶⁵ᵇ, when present, are optionally covalently bonded and, together with nitrogen atom to which they are attached, comprise a 3- to 6-membered heterocycle; wherein R⁷, when present, is selected from hydrogen, halogen, —CN, C1-C3 alkyl, C1-C3 monohaloalkyl, C1-C3 polyhaloalkyl, cyclopropyl, —OR⁴⁰, —NR⁴¹ᵃR⁴¹ᵇ, —SO₂R⁴², and —(C=O)R⁴³; wherein R⁴⁰, when present, is selected from hydrogen, C1-C3 alkyl, C1-C3 monohaloalkyl, C1-C3 polyhaloalkyl, and cyclopropyl; wherein each of R⁴¹ᵃ and R⁴¹ᵇ, when present, is independently selected from hydrogen, C1-C3 alkyl, C1-C3 monohaloalkyl, C1-C3 polyhaloalkyl, and cyclopropyl; or wherein R⁴¹ᵃ and R⁴¹ᵇ, when present, are optionally covalently bonded and, together with nitrogen atom to which they are attached, comprise a 3- to 6-membered heterocycle; wherein R⁴², when present, is selected from C1-C3 alkyl, C1-C3 monohaloalkyl, C1-C3 polyhaloalkyl, cyclopropyl, and, —NR⁴⁴ᵃR⁴⁴ᵇ; wherein each of R⁴⁴ᵃ and R⁴⁴ᵇ, when present, is independently selected from hydrogen, C1-C3 alkyl, C1-C3 monohaloalkyl, C1-C3 polyhaloalkyl, and cyclopropyl; or wherein R⁴⁴ᵃ and R⁴⁴ᵇ, when present, are optionally covalently bonded and, together with nitrogen atom to which they are attached, comprise a 3- to 6-membered heterocycle; wherein R⁴³, when present, is selected from C1-C3 alkyl, C1-C3 monohaloalkyl, C1-C3 polyhaloalkyl, cyclopropyl, and, —NR⁴⁵ᵃR⁴⁵ᵇ; wherein each of R⁴⁵ᵃ and R⁴⁵ᵇ, when present, is independently selected from hydrogen, C1-C3 alkyl, C1-C3 monohaloalkyl, C1-C3 polyhaloalkyl, and cyclopropyl; or wherein R⁴⁵ᵃ and R⁴⁵ᵇ, when present, are optionally covalently bonded and, together with nitrogen atom to which they are attached, comprise a 3- to 6-membered heterocycle.

In a further aspect, the compound produced has a structure represented by a formula:

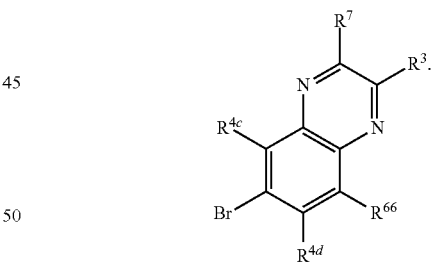

2. Intermediate Route II

In one aspect, aldehyde intermediates can be prepared as shown below.

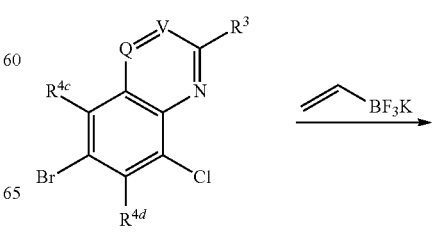

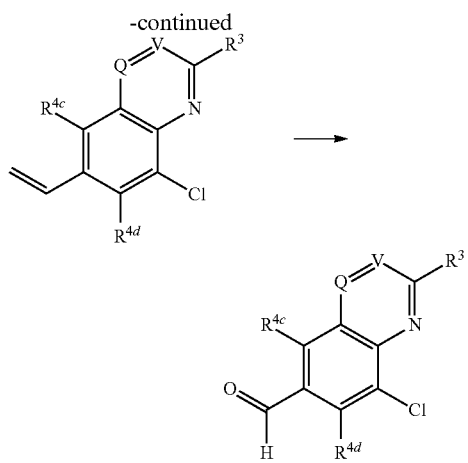

Compounds are represented in generic form, with substituents as noted in compound descriptions elsewhere herein. A more specific example is set forth below.

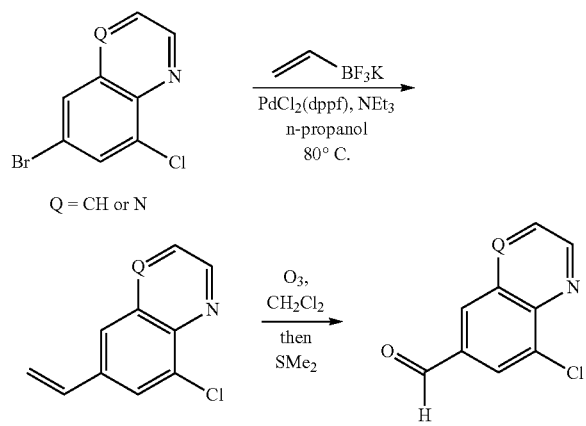

Q = CH or N

In one aspect, Intermediate Route II begins with a bromoquinoline or bromoquinoxaline. Bromoquinolines are commercially available or readily prepared by one skilled in the art. Bromoquinoxalines may be prepared as outlined in Intermediate Route I. Reaction with potassium vinyltrifluoroborate and a palladium catalyst affords the substituted vinyl intermediate (Molander, G. A.; Rivero, M. R. *Org. Lett.* 2002, 4, 107-109). The reaction may be optionally heated with conventional heating or microwave irradiation. It will be appreciated that a variety of palladium catalysts, phosphine ligands, and bases may be suitable for this coupling reaction. The vinyl intermediate can be treated with ozone and subsequently a reducing agent to yield the aldehyde intermediate. It will be appreciated that a variety of reducing agents, including but not limited to dimethyl sulfide, triphenylphosphine and zinc, may be used for this transformation.

Thus, in one aspect, the invention relates to a method of making a compound comprising the step of reacting a compound having a structure represented by a formula:

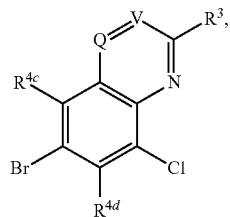

wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4c}$ and R$^{4d}$ is independently selected from hydrogen and fluoro; with potassium vinyltrifluoroborate and a palladium catalyst, thereby forming vinyl intermediate, having a structure represented by a formula:

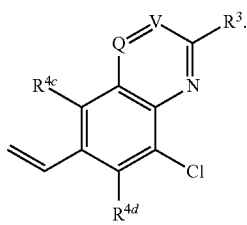

In a further aspect, the method further comprises the step of reacting the vinyl group with ozone and a reducing agent, thereby forming an aldehyde, having a structure represented by a formula:

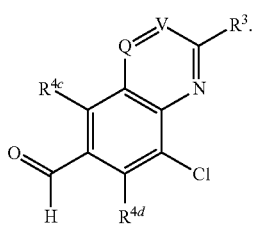

3. Intermediate Route III

In one aspect, vinyl bromide intermediates can be prepared as shown below.

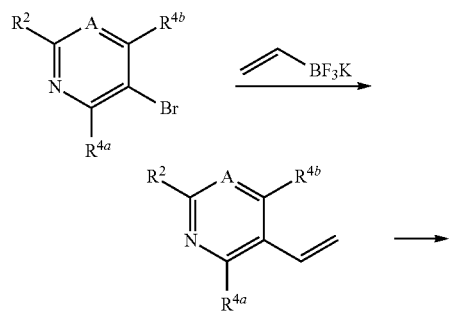

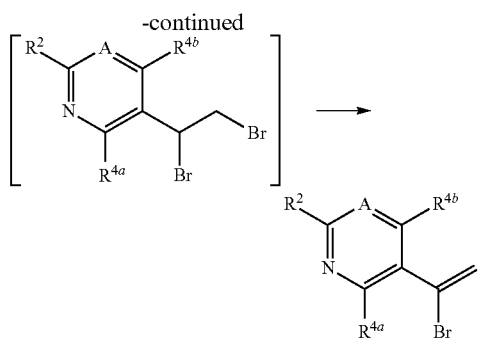

Compounds are represented in generic form, with substituents as noted in compound descriptions elsewhere herein. A more specific example is set forth below.

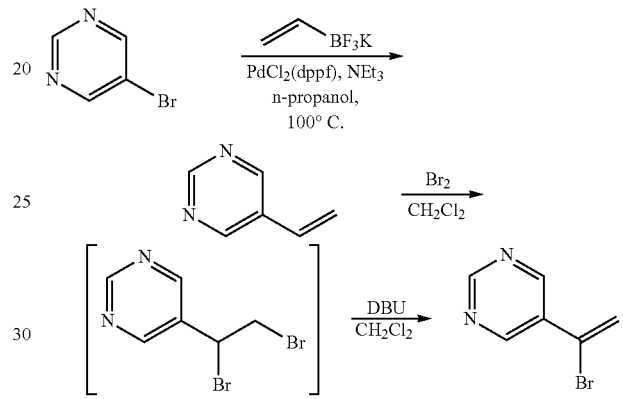

In one aspect, Intermediate Route III begins with a heteroaryl bromide. Such heteroaryl bromides are commercially available or readily prepared by one skilled in the art. Reaction with potassium vinyltrifluoroborate and a palladium catalyst affords the substituted vinyl intermediate (Molander, G. A.; Rivero, M. R. Org. Lett. 2002, 4, 107-109). The reaction may be optionally heated with conventional heating or microwave irradiation. It will be appreciated that a variety of palladium catalysts, phosphine ligands, and bases may be suitable for this coupling reaction. The vinyl intermediate can be treated with bromine to afford a dibromide intermediate. It will be appreciated that a variety of brominating reagents are commercially available and may serve as alternatives to bromine. The dibromide intermediate may or may not be isolated. Treatment with a suitable base will afford the vinyl bromide intermediate. It will be appreciated that a variety of bases may be effective in this transformation. Examples of suitable bases include but are not limited to 1,8-diazabicycloundec-7-ene, 1,8-bis(dimethylamino)naphthalene, and 1,4-diazabicyclo[2.2.2]octane.

Thus, in one aspect, the invention relates to a method of making a compound comprising the step of reacting a compound having a structure represented by a formula:

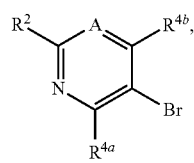

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR²⁰, —NR²¹ᵃR²¹ᵇ, —SO₂R²², and —(C=O) R²³; wherein R²⁰, when present, is selected from hydrogen, C1-C3 alkyl, C1-C3 monohaloalkyl, C1-C3 polyhaloalkyl, and cyclopropyl; wherein each of R²¹ᵃ and R²¹ᵇ, when present, is independently selected from hydrogen, C1-C3 alkyl, C1-C3 monohaloalkyl, C1-C3 polyhaloalkyl, and cyclopropyl; or wherein R²¹ᵃ and R²¹ᵇ, when present, are optionally covalently bonded and, together with nitrogen atom to which they are attached, comprise a 3- to 6-membered heterocycle; wherein R²², when present, is selected from C1-C3 alkyl, C1-C3 monohaloalkyl, C1-C3 polyhaloalkyl, cyclopropyl, and, —NR²⁴ᵃR²⁴ᵇ; wherein each of R²⁴ᵃ and R²⁴ᵇ, when present, is independently selected from hydrogen, C1-C3 alkyl, C1-C3 monohaloalkyl, C1-C3 polyhaloalkyl, and cyclopropyl; or wherein R²⁴ᵃ and R²⁴ᵇ, when present, are optionally covalently bonded and, together with nitrogen atom to which they are attached, comprise a 3- to 6-membered heterocycle; wherein R²³, when present, is selected from C1-C3 alkyl, C1-C3 monohaloalkyl, C1-C3 polyhaloalkyl, cyclopropyl, and, —NR²⁵ᵃR²⁵ᵇ; wherein each of R²⁵ᵃ and R²⁵ᵇ, when present, is independently selected from hydrogen, C1-C3 alkyl, C1-C3 monohaloalkyl, C1-C3 polyhaloalkyl, and cyclopropyl; or wherein R²⁵ᵃ and R²⁵ᵇ, when present, are optionally covalently bonded and, together with nitrogen atom to which they are attached, comprise a 3- to 6-membered heterocycle; wherein R² is selected from hydrogen, C1-C3 alkyl, C1-C3 monohaloalkyl, C1-C3 polyhaloalkyl, and cyclopropyl; wherein each of R⁴ᵃ and R⁴ᵇ is independently selected from hydrogen and fluoro; with potassium vinyltrifluoroborate and a palladium catalyst, thereby forming a vinyl intermediate, having a structure represented by a formula:

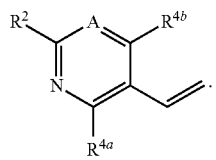

In a further aspect, the method further comprises the step of reacting the vinyl compound with a brominating reagent, thereby forming a dibromide intermediate, having a structure represented by a formula:

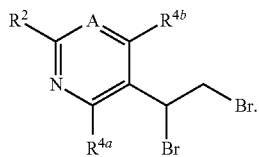

In a further aspect, the method further comprises the step of reacting the dibromide intermediate with a suitable base, thereby forming a vinyl bromide intermediate, having a structure represented by a formula:

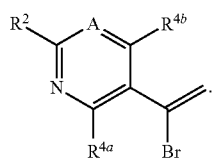

4. Intermediate Route IV

In one aspect, ketone intermediates can be prepared as shown below.

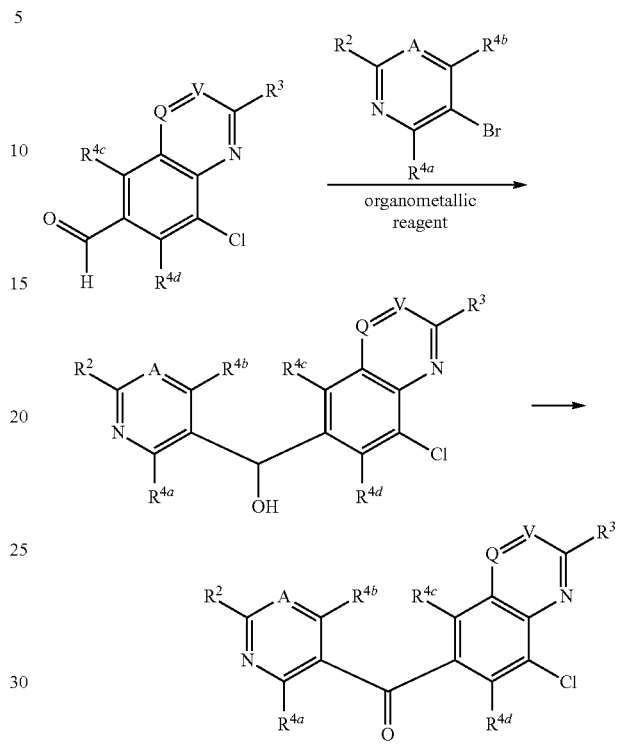

Compounds are represented in generic form, with substituents as noted in compound descriptions elsewhere herein. A more specific example is set forth below.

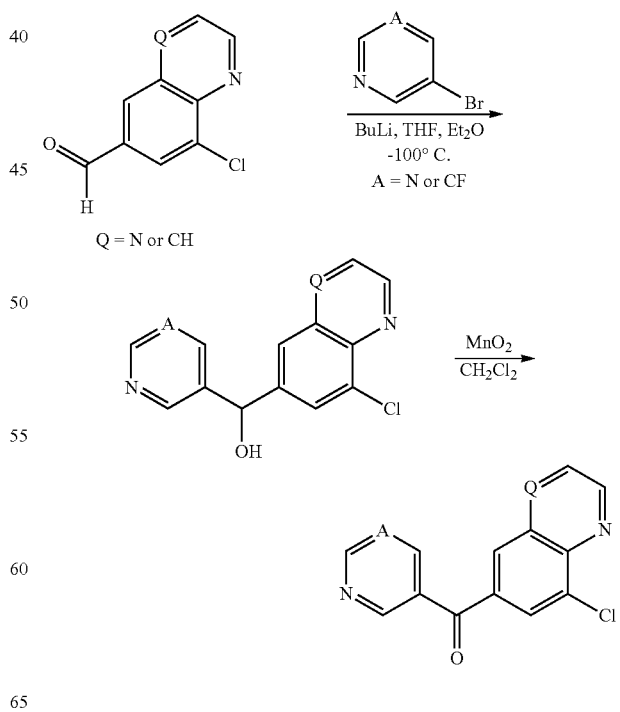

In one aspect, Intermediate Route IV begins with a heteroaryl bromide. Such heteroaryl bromides are commercially available or readily prepared by one skilled in the art. Treatment of the heteroaryl bromide with n-butyl lithium and subsequent reaction with an aldehyde intermediate provides a secondary alcohol intermediate. The aldehyde intermediate can be prepared according to the procedure described in Intermediate Route II. It will be appreciated that organometallic reagents including but not limited to sec-butyl lithium, tert-butyl lithium, and isopropyl magnesium bromide, may be used as an alternative to n-butyl lithium. The secondary alcohol intermediate can be oxidized to afford the ketone intermediate. It will be appreciated that a variety of oxidizing conditions may be used for this transformation. Examples of suitable oxidizing conditions include but are not limited to manganese dioxide, Dess-Martin periodinane, tetrapropylammonium perruthenate/N-methylmorpholine-N-oxide, and oxalyl chloride/dimethylsulfoxide/triethylamine.

Thus, in one aspect, the invention relates to a method of making a compound comprising the step of reacting a compound having a structure represented by a formula:

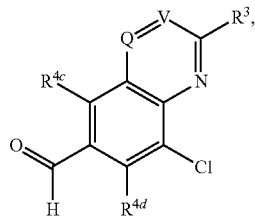

wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4c}$ and $R^{4d}$ is independently selected from hydrogen and fluoro; with a second compound having a structure represented by a formula:

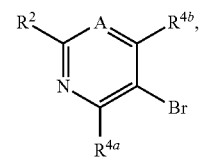

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C═O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein R$^2$ is selected from hydrogen, C1-C3 alkyl, C1-C3 monohaloalkyl, C1-C3 polyhaloalkyl, and cyclopropyl; wherein R$^2$ is selected from hydrogen, C1-C3 alkyl, C1-C3 monohaloalkyl, C1-C3 polyhaloalkyl, and cyclopropyl; wherein each of R$^{4a}$ and R$^{4b}$ is independently selected from hydrogen and fluoro; in the presence of an organometallic reagent thereby forming a secondary alcohol intermediate.

In a further aspect, the compound produced has a structure represented by a formula:

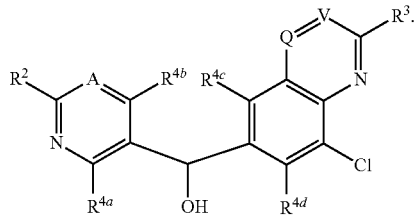

In a further aspect, the method further comprises the step of reacting the secondary alcohol with a suitable oxidizing agent to produce a ketone intermediate, having a structure represented by a formula:

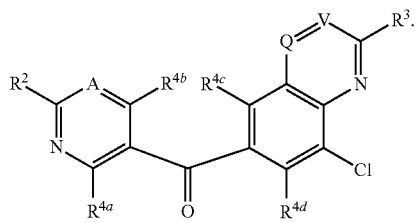

5. Intermediate Route V

In one aspect, carboxylic acid intermediates can be prepared as shown below.

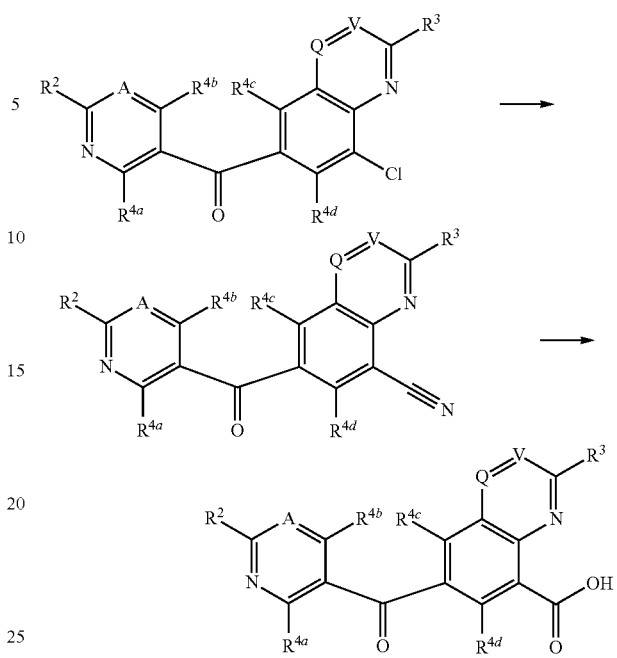

Compounds are represented in generic form, with substituents as noted in compound descriptions elsewhere herein. A more specific example is set forth below.

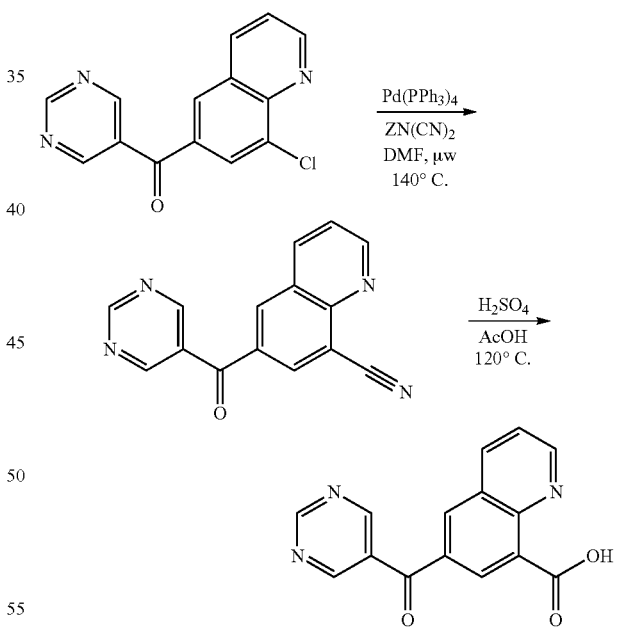

In one aspect, Intermediate Route V begins with a ketone intermediate prepared according to methods described in Intermediate Route IV. A palladium catalyzed cyanation reaction can be used to generate the nitrile compound. It will be appreciated that a variety of palladium catalysts, ligands, and cyanide sources may be suitable for this coupling reaction (see *Synthetic Comm.* 2007, 37, 431-438 and references therein). The reaction may be optionally heated with conventional heating or microwave irradiation. Acid hydrolysis of the cyano group will provide the carboxylic acid. It will be appreciated that a variety of aqueous acids may be used for this transformation and that the reaction may be optionally heated.

Thus, in one aspect, the invention relates to a method of making a compound comprising the step of reacting a compound having a structure represented by a formula:

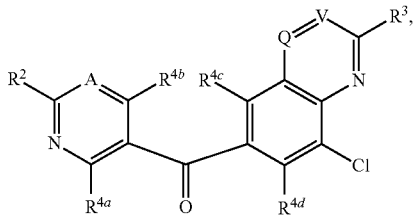

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$ is independently selected from hydrogen and fluoro; in a palladium catalyzed cyanation reaction, thereby forming a nitrile intermediate, having a structure represented by a formula:

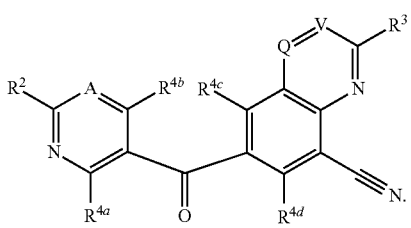

In a further aspect, the method further comprises the step of reacting the nitrile compound with aqueous acid to produce a carboxylic acid intermediate, having a structure represented by a formula:

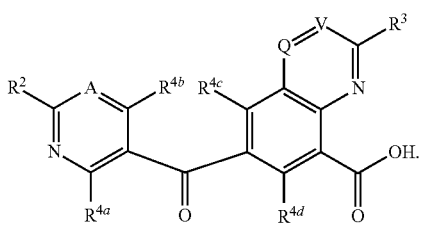

6. Intermediate Route VI

In one aspect, vinyl intermediates can be prepared as shown below.

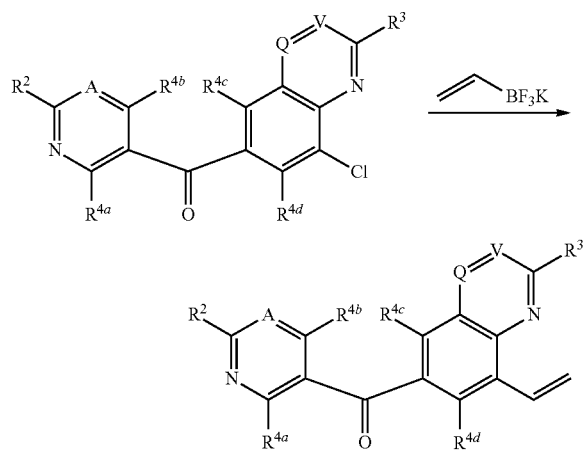

Compounds are represented in generic form, with substituents as noted in compound descriptions elsewhere herein. A more specific example is set forth below.

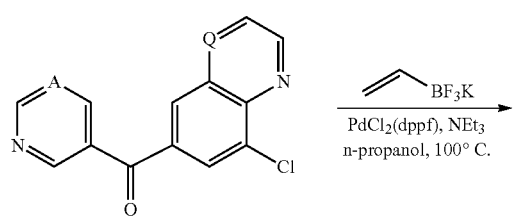

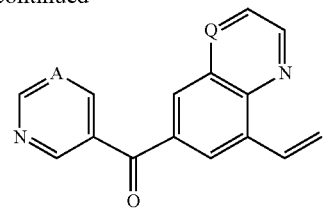

A = N; Q = CH
A = CF; Q = CH
A = N; Q = N

In one aspect, Intermediate Route VI begins with a ketone intermediate prepared according to methods described in Intermediate Route IV. Reaction with potassium vinyltrifluoroborate and a palladium catalyst affords the substituted vinyl intermediate (Molander, G. A.; Rivero, M. R. Org. Lett. 2002, 4, 107-109). The reaction may be optionally heated with conventional heating or microwave irradiation. It will be appreciated that a variety of palladium catalysts, phosphine ligands, and bases may be suitable for this coupling reaction.

Thus, in one aspect, the invention relates to a method of making a compound comprising the step of reacting a compound having a structure represented by a formula:

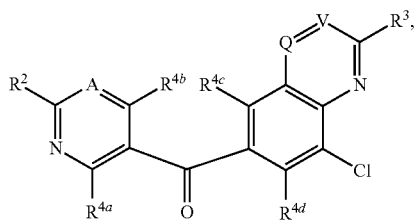

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle; wherein R$^{32}$, when present, is selected from C1-C3 alkyl, C1-C3 monohaloalkyl, C1-C3 polyhaloalkyl, cyclopropyl, and, —NR$^{34a}$R$^{34b}$; wherein each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with nitrogen atom to which they are attached, comprise a 3- to 6-membered heterocycle; wherein R$^{33}$, when present, is selected from C1-C3 alkyl, C1-C3 monohaloalkyl, C1-C3 polyhaloalkyl, cyclopropyl, and, —NR$^{35a}$R$^{35b}$; wherein each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; wherein V is selected from N and CR$^7$, provided that Q and V are not simultaneously N; wherein R$^7$, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and, —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and, —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with nitrogen atom to which they are attached, comprise a 3- to 6-membered heterocycle; wherein R$^2$ is selected from hydrogen, C1-C3 alkyl, C1-C3 monohaloalkyl, C1-C3 polyhaloalkyl, and cyclopropyl; wherein R$^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle;

wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$ is independently selected from hydrogen and fluoro; with potassium vinyltrifluoroborate and a palladium catalyst, thereby forming a vinyl intermediate, having a structure represented by a formula:

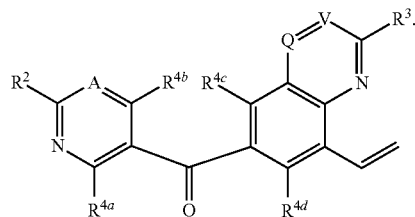

7. Intermediate Route VII

In one aspect, fluorinated intermediates can be prepared as shown below.

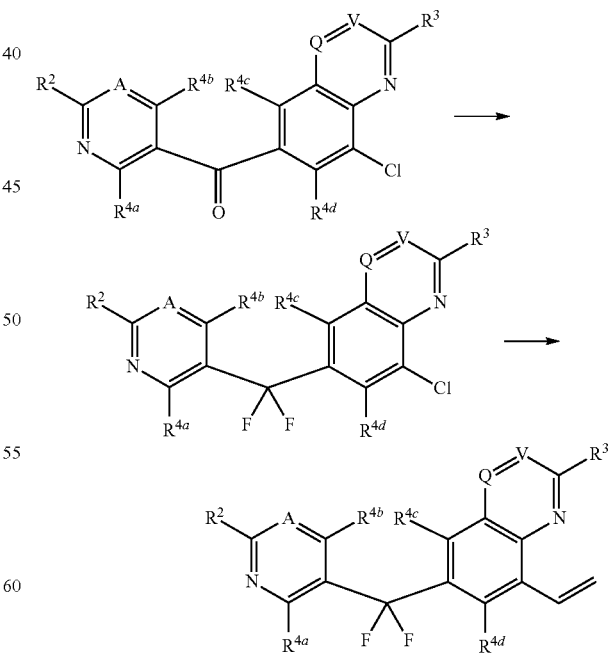

Compounds are represented in generic form, with substituents as noted in compound descriptions elsewhere herein. A more specific example is set forth below.

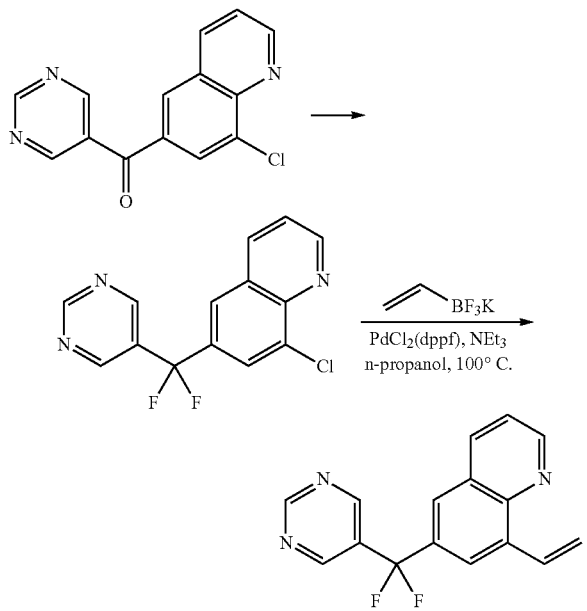

In one aspect, Intermediate Route VII begins with a ketone intermediate prepared according to methods described in Intermediate Route IV. Reaction with a fluorinating agent such as diethylaminosulfur trifluoride will afford the fluorinated compound. It will be appreciated that a variety of reagents, including but not limited to bis-(2-methoxyethyl)aminosulfur trifluoride and morpholinosulfur trifluoride, may be effective alternatives to diethylaminosulfur trifluoride for this transformation. Reaction of the difluoride compound with potassium vinyltrifluoroborate and a palladium catalyst affords the substituted vinyl intermediate (Molander, G. A.; Rivero, M. R. *Org. Lett.* 2002, 4, 107-109). The reaction may be optionally heated with conventional heating or microwave irradiation. It will be appreciated that a variety of palladium catalysts, phosphine ligands, and bases may be suitable for this coupling reaction.

Thus, in one aspect, the invention relates to a method of making a compound comprising the step of reacting a compound having a structure represented by a formula:

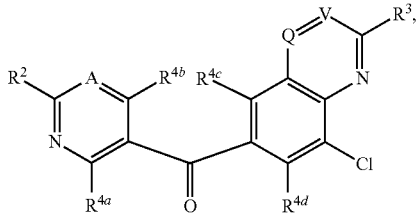

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$ is independently selected from hydrogen and fluoro; with a fluorinating agent, thereby forming a fluorinated intermediate, having a structure represented by a formula:

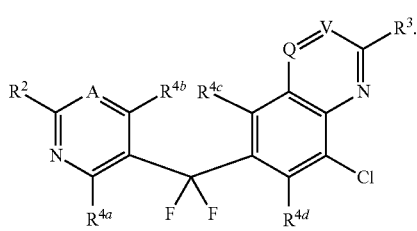

In a further aspect, the method further comprises the step of reacting the fluorinated compound with potassium vinyltrifluoroborate and a palladium catalyst thereby producing an intermediate, having a structure represented by a formula:

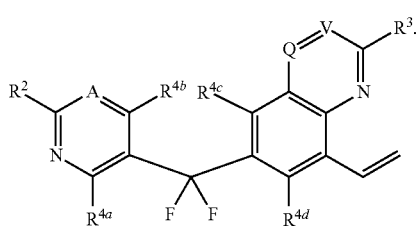

8. Intermediate Route VIII

In one aspect, ketone intermediates can be prepared as shown below.

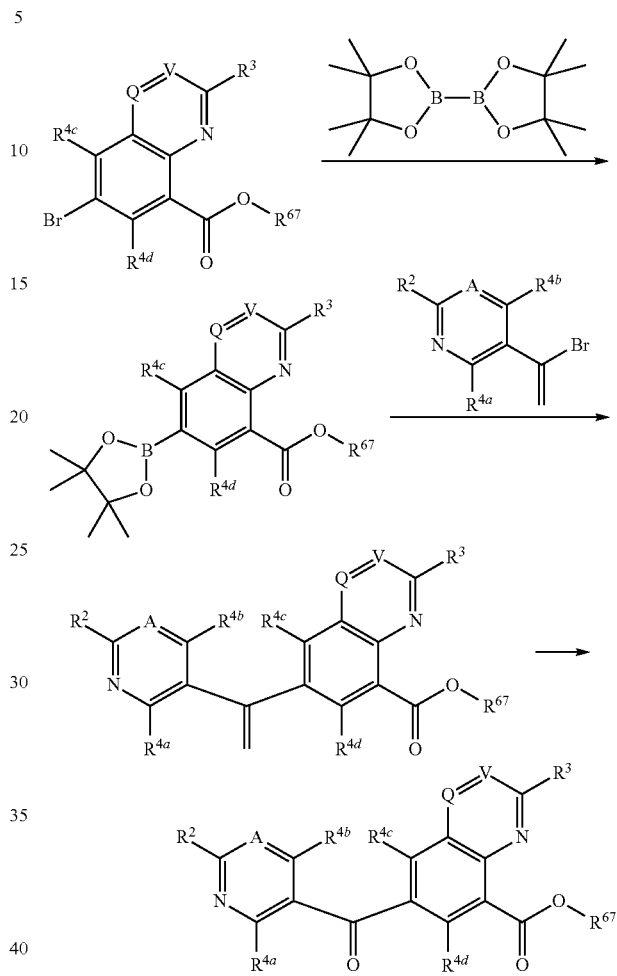

Compounds are represented in generic form, with substituents as noted in compound descriptions elsewhere herein. A more specific example is set forth below.

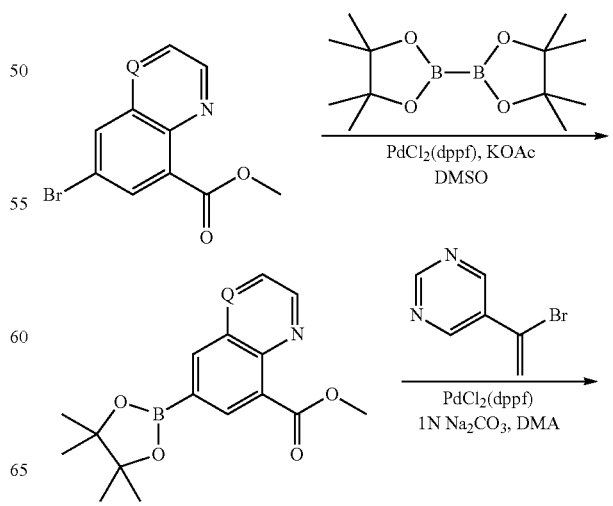

-continued

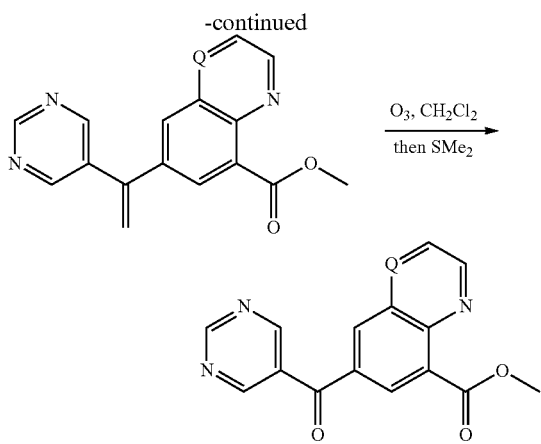

In one aspect, Intermediate Route VIII begins with a bromoquinoline or bromoquinoxaline. Bromoquinolines are commercially available or readily prepared by one skilled in the art. Bromoquinoxalines may be prepared as outlined in Intermediate Route I. Reaction with bis(pinacolato)diboron and a palladium catalyst affords the boronic ester intermediate (Ishiyama, T.; Murata, M.; Miyaura, N. *J. Org. Chem.* 1995, 60, 7508-7510). The reaction may be optionally heated with conventional heating or microwave irradiation. It will be appreciated that a variety of palladium catalysts, phosphine ligands, and bases may be suitable for this coupling reaction. Reaction of the boronic acid intermediate with a heteroaryl vinyl bromide and a palladium catalyst will yield the coupled product. The heteroaryl vinyl bromide may be prepared according to the method described in Intermediate Route III. The reaction may be optionally heated with conventional heating or microwave irradiation. It will be appreciated that a variety of palladium catalysts, phosphine ligands, and bases may be suitable for this Suzuki coupling reaction. The coupled product can be treated with ozone and subsequently a reducing agent to yield the ketone intermediate. It will be appreciated that a variety of reducing agents, including but not limited to dimethyl sulfide, triphenylphosphine and zinc, may be used for this transformation.

Thus, in one aspect, the invention relates to a method of making a compound comprising the step of reacting a compound having a structure represented by a formula:

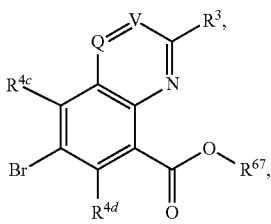

wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, $—NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4c}$ and $R^{4d}$ is independently selected from hydrogen and fluoro; wherein $R^{67}$ is C1-C3 alkyl; with bis(pinacolato)diboron and a palladium catalyst, thereby forming a boronic ester intermediate, having a structure represented by a formula:

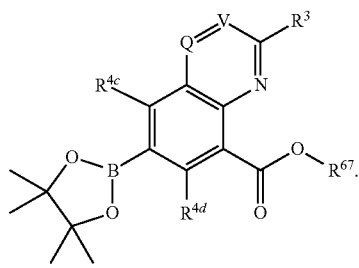

In a further aspect, the method further comprises the step of reacting the boronic ester intermediate with a palladium catalyst and a second compound having a structure represented by a formula:

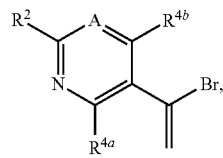

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, $—OR^{20}$, $—NR^{21a}R^{21b}$, $—SO_2R^{22}$, and $—(C=O)R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, $—NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, $—NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein each of $R^{4a}$ and $R^{4b}$ is independently selected from hydrogen and fluoro.

In a further aspect, the compound produced has a structure represented by a formula:

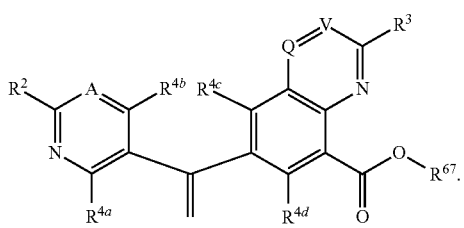

In a further aspect, the method further comprises the step of reacting the vinyl intermediate with ozone and a reducing agent, thereby forming a ketone, having a structure represented by a formula:

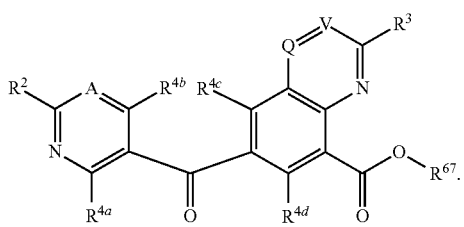

9. Intermediate Route IX

In one aspect, fluorinated intermediates can be prepared as shown below.

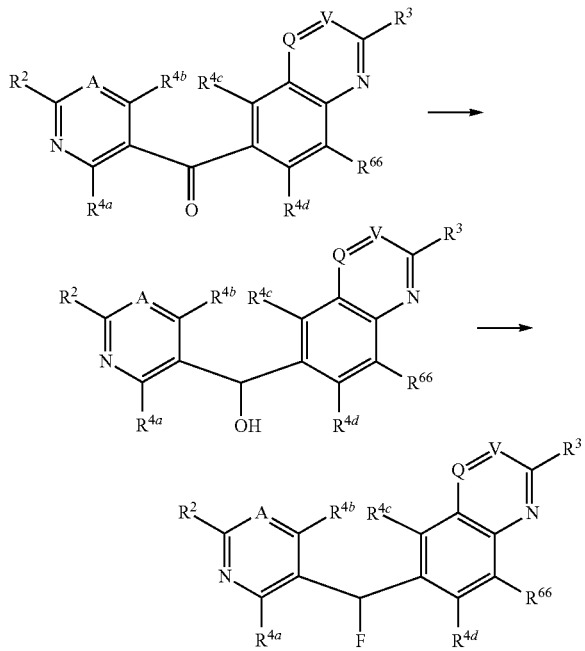

Compounds are represented in generic form, with substituents as noted in compound descriptions elsewhere herein. A more specific example is set forth below.

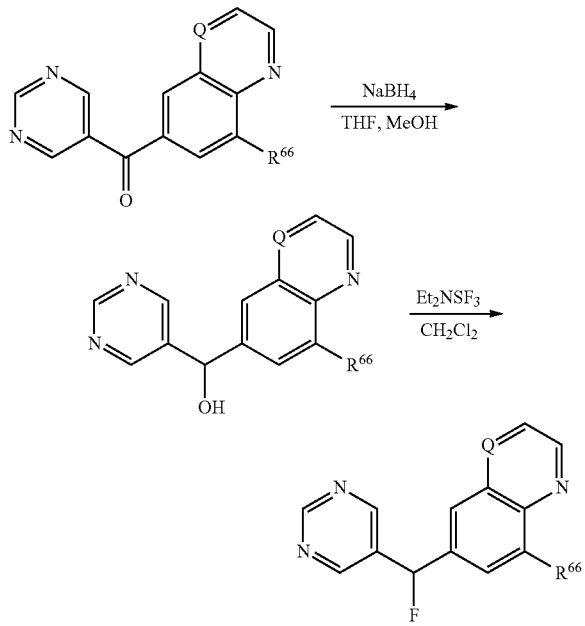

$R^{66}$ = CO$_2$Me, CH = CH$_2$
Q = CH or N

In one aspect, Intermediate Route IX begins with a ketone intermediate. Such ketone intermediates can be prepared according to methods described in Intermediate Route VI and Intermediate Route VIII. Reaction with a reducing agent will provide the secondary alcohol intermediate. It will be appreciated that a variety of reducing agents, including but not limited to sodium borohydride and lithium borohydride, may be useful for this transformation. Reaction of the secondary alcohol intermediate with a fluorinating agent such as diethylaminosulfur trifluoride will afford the fluorinated compound. It will be appreciated that a variety of reagents, including but not limited to bis-(2-methoxyethyl) aminosulfur trifluoride and morpholinosulfur trifluoride, may be effective alternatives to diethylaminosulfur trifluoride for this transformation.

Thus, in one aspect, the invention relates to a method of making a compound comprising the step of reacting a compound having a structure represented by a formula:

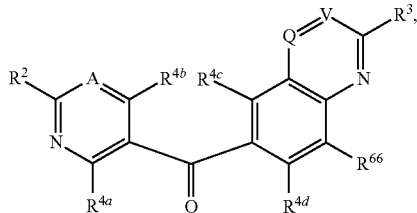

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein Q is selected from N and CR$^6$; wherein R$^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle; wherein R$^{32}$, when present, is selected from C1-C3 alkyl, C1-C3 monohaloalkyl, C1-C3 polyhaloalkyl, cyclopropyl, and, —NR$^{34a}$R$^{34b}$; wherein each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with nitrogen atom to which they are attached, comprise a 3- to 6-membered heterocycle; wherein R$^{33}$, when present, is selected from C1-C3 alkyl, C1-C3 monohaloalkyl, C1-C3 polyhaloalkyl, cyclopropyl, and, —NR$^{35a}$R$^{35b}$; wherein each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; wherein V is selected from N and CR$^7$, provided that Q and V are not simultaneously N; wherein R$^7$, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and, —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and, —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with nitrogen atom to which they are attached, comprise a 3- to 6-membered heterocycle; wherein R$^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$ is independently selected from hydrogen and fluoro; wherein R$^{66}$ is CH=CH$_2$ or CO$^2$R$^{67}$; wherein R$^{67}$ is C1-C3 alkyl; with a reducing agent, thereby forming a secondary alcohol intermediate, having a structure represented by a formula:

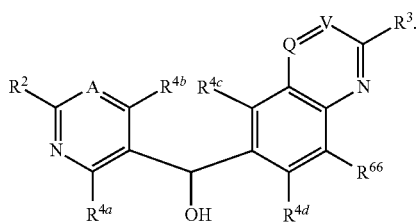

In a further aspect, the method further comprises the step of reacting the secondary alcohol intermediate with a fluorinating agent thereby producing a fluorinated intermediate, having a structure represented by a formula:

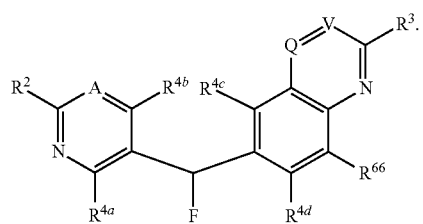

10. Intermediate Route X

In one aspect, methylated intermediates can be prepared as shown below.

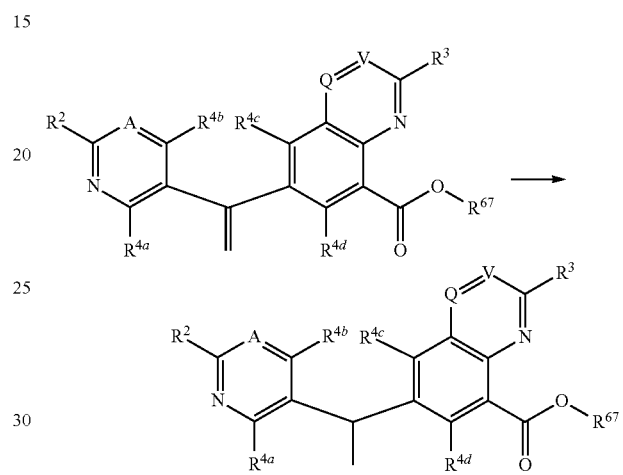

Compounds are represented in generic form, with substituents as noted in compound descriptions elsewhere herein. A more specific example is set forth below.

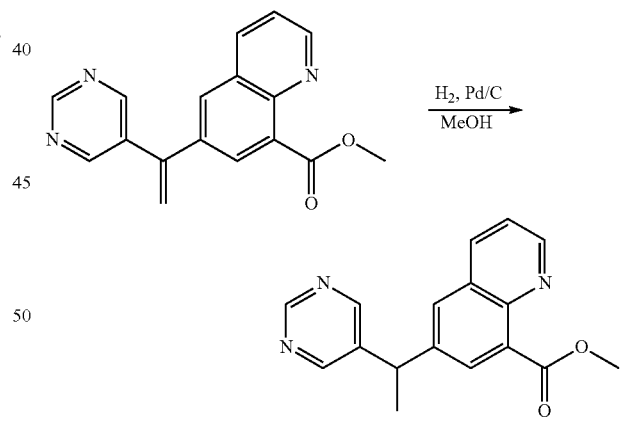

In one aspect, Intermediate Route X begins with a vinyl intermediate. Such vinyl intermediates can be prepared according to methods described in Intermediate Route VIII. A hydrogenation of the double bond will produce the methylated intermediate. It will be appreciated that a variety of catalysts may be effective for this hydrogenation reaction. Examples of suitable catalysts included but are not limited to palladium on carbon, palladium hydroxide on carbon, platinum on carbon, and rhodium on carbon.

Thus, in one aspect, the invention relates to a method of making a compound comprising the step of reacting a compound having a structure represented by a formula:

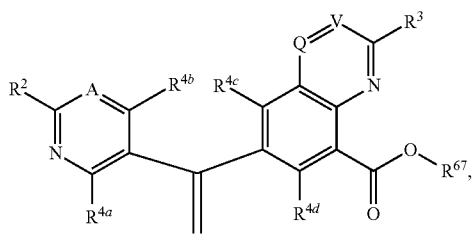

wherein A is selected from N and CR⁵; wherein R⁵, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein Q is selected from N and CR⁶; wherein R⁶, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle; wherein R$^{32}$, when present, is selected from C1-C3 alkyl, C1-C3 monohaloalkyl, C1-C3 polyhaloalkyl, cyclopropyl, and, —NR$^{34a}$R$^{34b}$; wherein each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with nitrogen atom to which they are attached, comprise a 3- to 6-membered heterocycle; wherein R$^{33}$, when present, is selected from C1-C3 alkyl, C1-C3 monohaloalkyl, C1-C3 polyhaloalkyl, cyclopropyl, and, —NR$^{35a}$R$^{35b}$; wherein each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; wherein V is selected from N and CR⁷, provided that Q and V are not simultaneously N; wherein R⁷, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and, —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and, —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with nitrogen atom to which they are attached, comprise a 3- to 6-membered heterocycle; wherein R³ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$ is independently selected from hydrogen and fluoro; wherein R$^{67}$ is C1-C3 alkyl; with hydrogen in the presence of a suitable catalyst, thereby producing a methylated intermediate having a structure represented by a formula:

11. Intermediate Route XI

In one aspect, ether intermediates can be prepared as shown below.

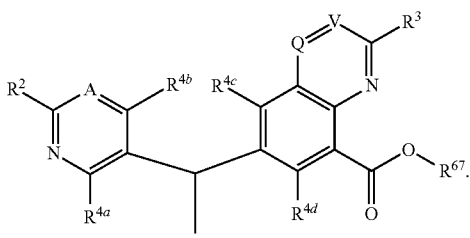

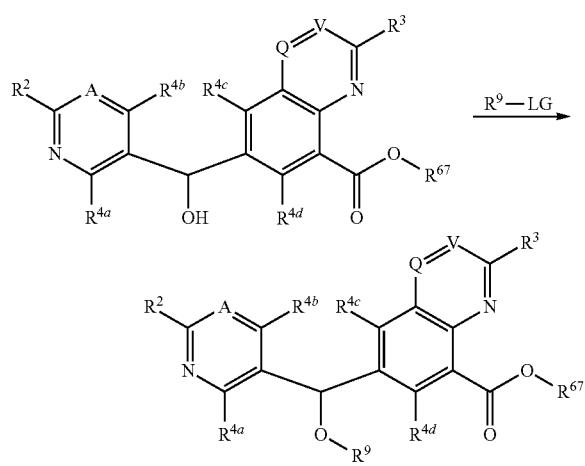

Compounds are represented in generic form, with substituents as noted in compound descriptions elsewhere herein. A more specific example is set forth below.

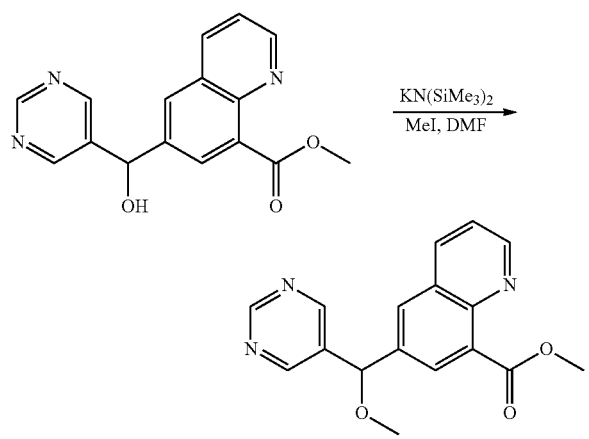

In one aspect, Intermediate Route XI begins with a secondary alcohol intermediate. Such intermediates can be prepared according to methods described in Intermediate Route IX. Reaction with a suitable base and an alkyl compound with a suitable leaving group will afford the ether intermediate. It will be appreciated that a variety of bases may be suitable for this reaction, including but not limited to sodium hydride, potassium hydride, sodium bis(trimethylsilyl)amide, and potassium bis(trimethylsilyl)amide. It will be further appreciated that a variety of leaving groups may be suitable for this reaction, including but not limited to chlorides, bromides, iodides, mesylates, tosylates, and triflates.

Thus, in one aspect, the invention relates to a method of making a compound comprising the step of reacting a compound having a structure represented by a formula:

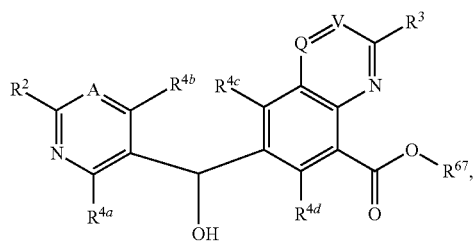

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, $-NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, $-CN$, C1-C3 alkyl, C1-C3 monohaloalkyl, C1-C3 polyhaloalkyl, cyclopropyl, $-OR^{40}$, $-NR^{41a}R^{41b}$, $-SO_2R^{42}$, and $-(C=O)R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, $-NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, $-NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein $R^3$ is selected from hydrogen, halogen, $-CN$, C1-C3 alkyl, C1-C3 monohaloalkyl, C1-C3 polyhaloalkyl, cyclopropyl, $-OR^{60}$, $-NR^{61a}R^{61b}$, $-SO_2R^{62}$, and $-(C=O)R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, $-NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, $-NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$ is independently selected from hydrogen and fluoro; wherein $R^{67}$ is C1-C3 alkyl; with a suitable base and $R^9$-LG; wherein $R^9$ is C1-C3 alkyl, C1-C3 monohaloalkyl, C1-C3 polyhaloalkyl, and cyclopropyl; wherein LG is a suitable leaving group, thereby producing an ether intermediate having a structure represented by a formula:

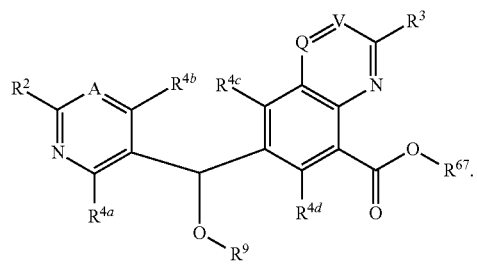

12. Intermediate Route XII

In one aspect, aldehyde intermediates can be prepared as shown below.

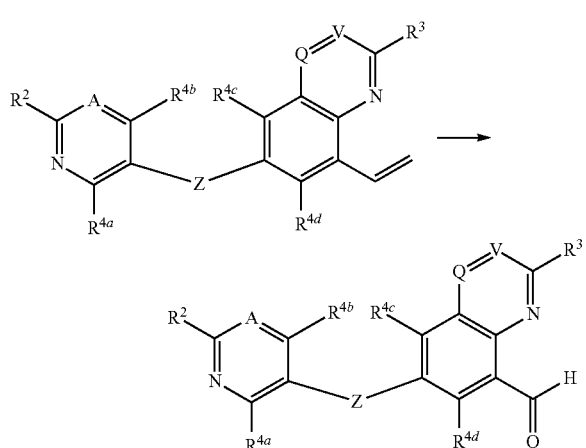

Compounds are represented in generic form, with substituents as noted in compound descriptions elsewhre herin. A mre specific example is set forth below.

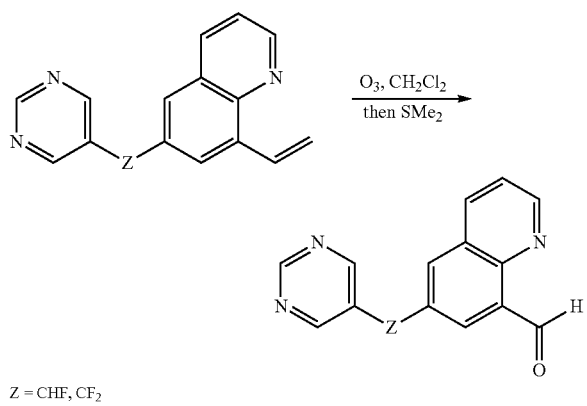

Z = CHF, CF$_2$

In one aspect, Intermediate Route XII begins with a vinyl intermediate. Such vinyl intermediates can be prepared according to methods described in Intermediate Route VI, Intermediate Route VII, and Intermediate Route IX. The vinyl intermediate can be treated with ozone and subsequently a reducing agent to yield the aldehyde intermediate. It will be appreciated that a variety of reducing agents, including but not limited to dimethyl sulfide, triphenylphosphine and zinc, may be used for this transformation.

Thus, in one aspect, the invention relates to a method of making a compound comprising the step of reacting a compound having a structure represented by a formula:

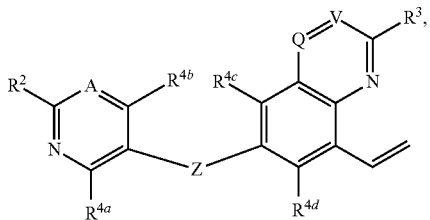

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8$(O)$_rR^9$—, —$CR^8NR^{10a}R^{10b}$—, —(C=O)—, and a structure represented by a formula:

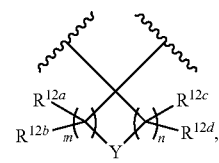

wherein Y is selected from —$CR^8R^9$—, —O—, —S(O)$_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —S(O)$_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8$(O)$_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —CR⁸(O)ᵣR⁹— and r is 1, R⁹ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —OR⁶⁰, —NR⁶¹ᵃR⁶¹ᵇ, —SO₂R⁶², and —(C═O)R⁶³; wherein R⁶⁰, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein R⁶², when present, is selected from C1-C3 alkyl, C1-C3 monohaloalkyl, C1-C3 polyhaloalkyl, cyclopropyl, and, —NR⁶⁴ᵃR⁶⁴ᵇ; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein R⁶³, when present, is selected from C1-C3 alkyl, C1-C3 monohaloalkyl, C1-C3 polyhaloalkyl, cyclopropyl, and, —NR⁶⁵ᵃR⁶⁵ᵇ; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$ is independently selected from hydrogen and fluoro; with ozone and a reducing agent, thereby forming an aldehyde, having a structure represented by a formula:

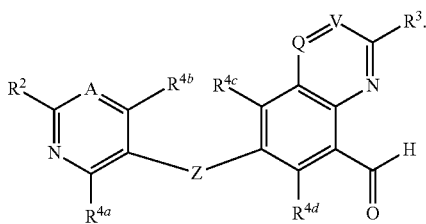

13. Intermediate Route XIII

In one aspect, aldehyde intermediates can be prepared as shown below.

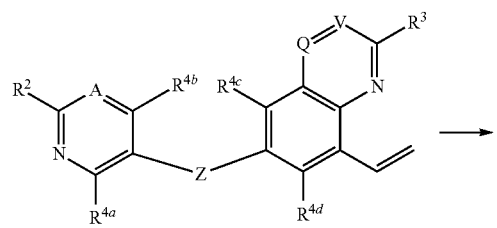

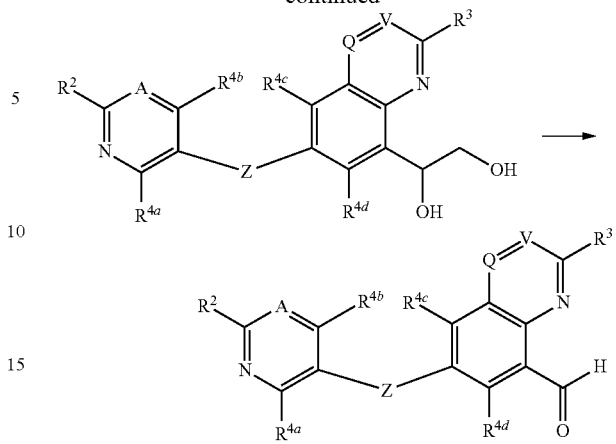

Compounds are represented in generic form, with substituents as noted in compound descriptions elsewhere herein. A more specific example is set forth below.

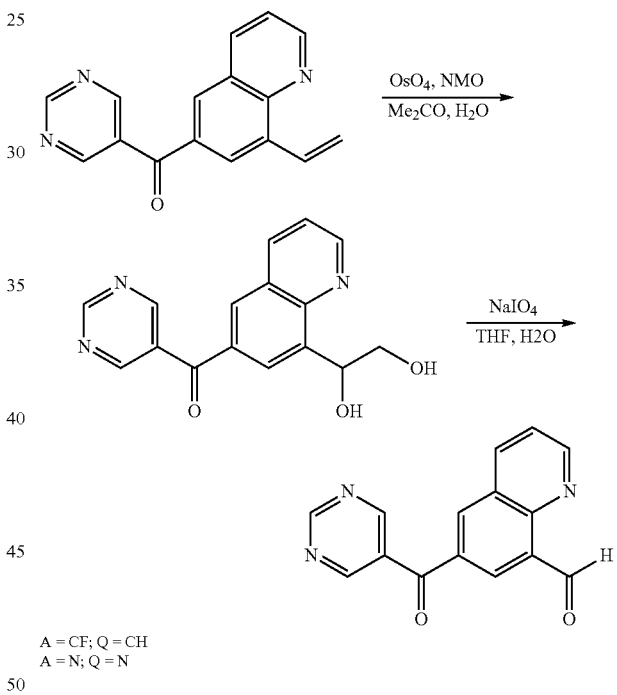

A = CF; Q = CH
A = N; Q = N

In one aspect, Intermediate Route XIII begins with a vinyl intermediate. Such vinyl intermediates can be prepared according to methods described in Intermediate Route VI, Intermediate Route VII, and Intermediate Route IX. Reaction of the vinyl intermediate with a catalytic amount of osmium tetroxide in the presence of a suitable oxidizing agent will generate the vicinal diol intermediate. It will be appreciated that a variety of oxidizing agents may be useful in this transformation, including but not limited to N-methylmorpholine-N-oxide, hydrogen peroxide, and potassium ferricyanide. Treatment of the vicinal diol intermediate with an oxidizing agent suitable for cleaving the diol will produce the aldehyde intermediate. It will be appreciated that a variety of oxidizing agents may be useful in this cleavage, including but not limited to sodium periodate, periodic acid, and lead tetracetate.

Thus, in one aspect, the invention relates to a method of making a compound comprising the step of reacting a compound having a structure represented by a formula:

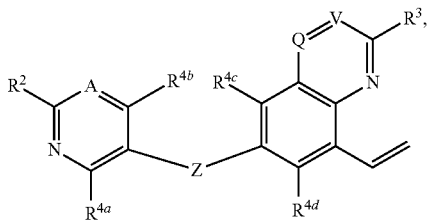

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O) $R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8$(O)$_rR^9$—, —$CR^8NR^{10a}R^{10b}$—, —(C=O)—, and a structure represented by a formula:

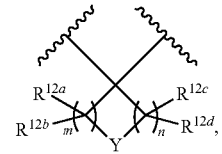

wherein Y is selected from —$CR^8R^9$—, —O—, —S(O)$_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —S(O)$_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8$(O)$_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8$(O)$_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$ is independently selected from hydrogen and fluoro; with a catalytic amount of osmium tetroxide and an oxidizing agent, thereby forming a vicinal diol intermediate, having a structure represented by a formula:

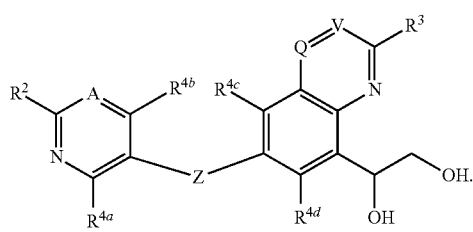

In a further aspect, the method further comprises the step of reacting the vicinal diol intermediate with a suitable oxidizing agent thereby cleaving the diol producing an aldehyde intermediate, having a structure represented by a formula:

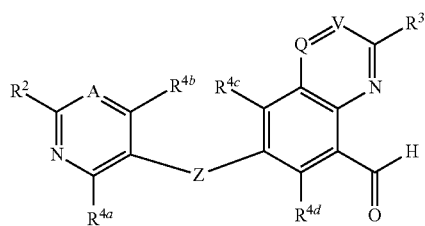

14. Intermediate Route XIV

In one aspect, carboxylic acid intermediates can be prepared as shown below.

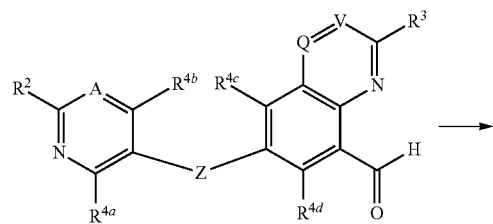

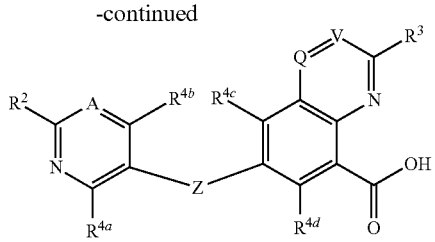

Compounds are represented in generic form, with substituents as noted in compound descriptions elsewhere herein. A more specific example is set forth below.

A = CF; Q = CH; Z = CO
A = N; Q = CH; Z = CHF
A = N; Q = CH; Z = CF$_2$
A = N; Q = N; Z = CO

In one aspect, Intermediate Route XIV begins with an aldehyde intermediate. Such aldehyde intermediates can be prepared according to methods described in Intermediate Route XII and Intermediate Route XIII. Reaction of the aldehyde intermediate with a suitable oxidizing agent will yield the carboxylic acid intermediate. It will be appreciated that a variety of oxidizing agents may be useful for this transformation, including but not limited to sodium chlorite, oxone, Jones reagent, potassium permanganate, and sodium perborate in acetic acid.

Thus, in one aspect, the invention relates to a method of making a compound comprising the step of reacting a compound having a structure represented by a formula:

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, $-NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, $-NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, $-CN$, C1-C3 alkyl, C1-C3 monohaloalkyl, C1-C3 polyhaloalkyl, cyclopropyl, $-OR^{30}$, $-NR^{31a}R^{31b}$, $-SO_2R^{32}$, and $-(C=O)R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, $-NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, $-NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, $-CN$, C1-C3 alkyl, C1-C3 monohaloalkyl, C1-C3 polyhaloalkyl, cyclopropyl, $-OR^{40}$, $-NR^{41a}R^{41b}$, $-SO_2R^{42}$, and $-(C=O)R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, $-NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, $-NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from $-CR^8(O)_rR^9-$, $-CR^8NR^{10a}R^{10b}-$, $-(C=O)-$, and a structure represented by a formula:

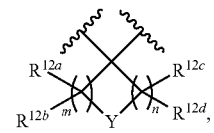

wherein Y is selected from $-CR^8R^9-$, $-O-$, $-S(O)_q-$, and $-NR^8-$; wherein m is an integer selected from 0, 1, and 2; wherein n is an integer selected from 0 and 1; wherein the sum of m and n is 1 or 2 when Y is $-CR^8R^9-$; wherein the sum of m and n is 2 when Y is $-O-$, $-S(O)_q-$, and $-NR^8-$; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is $-CR^8(O)_rR^9-$ and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is $-CR^8(O)_rR^9-$ and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, $-CN$, C1-C3 alkyl, C1-C3 monohaloalkyl, C1-C3 polyhaloalkyl, cyclopropyl, $-OR^{60}$, $-NR^{61a}R^{61b}$, $-SO_2R^{62}$, and $-(C=O)R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, $-NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, $-NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$ is independently selected from hydrogen and fluoro; with a suitable oxidizing agent, thereby forming a carboxylic acid intermediate, having a structure represented by a formula:

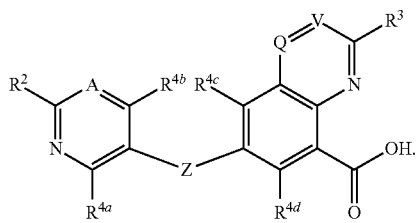

15. Intermediate Route XV

In one aspect, carboxylic acid intermediates can be prepared as shown below.

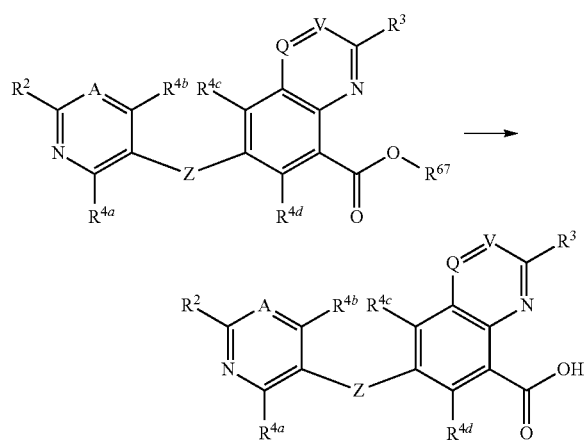

Compounds are represented in generic form, with substituents as noted in compound descriptions elsewhere herein. A more specific example is set forth below.

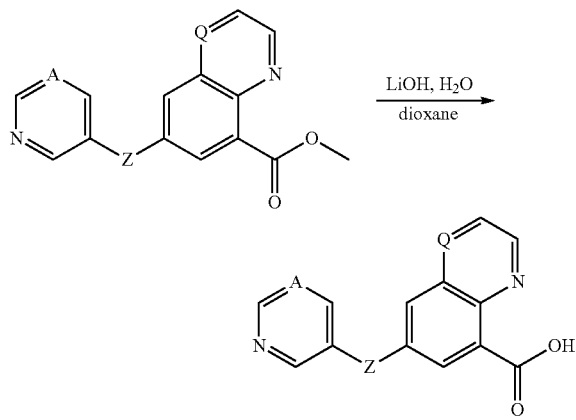

A = N; Q = CH; Z = CHMe
A = N; Q = CH; Z = CHOMe
A = N; Q = N; Z = CHF

In one aspect, Intermediate Route XIV begins with an ester intermediate. Such ester intermediates can be prepared according to methods described in Intermediate Route VIII, Intermediate Route IX, Intermediate Route X, and Intermediate Route XI. Reaction of the ester with aqueous hydroxide will provide the carboxylic acid intermediate. It will be appreciated that many hydroxide sources may be useful for this transformation including but not limited to lithium hydroxide, sodium hydroxide, and potassium hydroxide.

Thus, in one aspect, the invention relates to a method of making a compound comprising the step of reacting a compound having a structure represented by a formula:

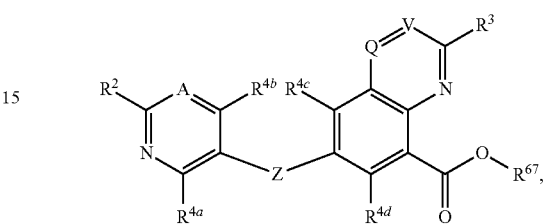

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8(O)_rR^9$—, —$CR^8NR^{10a}R^{10b}$—, —(C=O)—, and a structure represented by a formula:

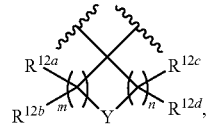

wherein Y is selected from —$CR^8R^9$—, —O—, —$S(O)_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —$S(O)_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$ is independently selected from hydrogen and fluoro; wherein $R^{67}$ is C1-C3 alkyl; with aqueous hydroxide, thereby forming a carboxylic acid intermediate, having a structure represented by a formula:

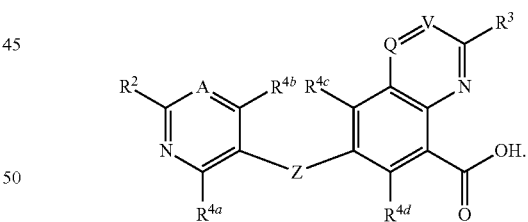

16. Analog Route I

In one aspect, analogs can be prepared as shown below.

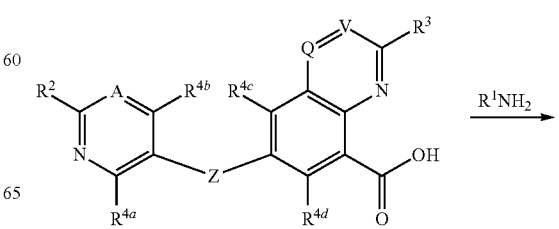

-continued

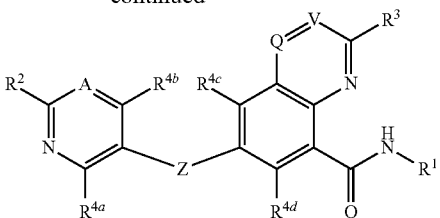

Compounds are represented in generic form, with substituents as noted in compound descriptions elsewhere herein. A more specific example is set forth below.

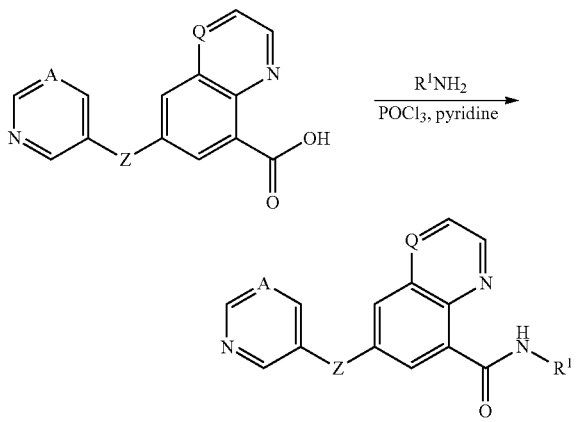

A = N; Q = CH; Z = CO
A = N; Q = CH; Z = CHF
A = N; Q = CH; Z = CF$_2$
A = N; Q = CH; Z = CHOMe
A = N; Q = CH; Z = CO
A = CF; Q = CH; Z = CO
A = N; Q = N; Z = CO
A = N; Q = N; Z = CHF

In one aspect, Analog Route I begins with a carboxylic acid intermediate. Such acid intermediates can be prepared according to methods described in Intermediate Route V, Intermediate Route XIV, and Intermediate Route XV. Coupling of the carboxylic acid with an aryl or heteroaryl amine can yield the amide product. Such aryl or heteroaryl amines are commercially available or readily prepared by one skilled in the art. Such coupling reactions are generally well known. For example, carboxylic acids can be treated with activating reagents such as 2-(1H-7-azabenzotriazol-1-yl)-1,1,3,3-tetramethyl uronium hexafluoro-phosphate methanaminium (HATU), Ghosez's Reagent (1-chloro-N,N,2-trimethyl-1-propenylamine), and phosphorous oxychloride/pyridine including mixtures thereof, and then reacted with the amine. Functional group transformation of the remaining substituents can yield further analogs.

Thus, in one aspect, the invention relates to a method of making a compound comprising the step of reacting a compound having a structure represented by a formula:

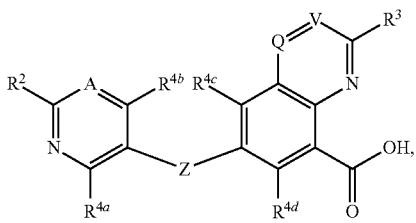

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein Q is selected from N and CR$^6$; wherein R$^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle; wherein R$^{32}$, when present, is selected from C1-C3 alkyl, C1-C3 monohaloalkyl, C1-C3 polyhaloalkyl, cyclopropyl, and, —NR$^{34a}$R$^{34b}$; wherein each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with nitrogen atom to which they are attached, comprise a 3- to 6-membered heterocycle; wherein R$^{33}$, when present, is selected from C1-C3 alkyl, C1-C3 monohaloalkyl, C1-C3 polyhaloalkyl, cyclopropyl, and, —NR$^{35a}$R$^{35b}$; wherein each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; wherein V is selected from N and CR$^7$, provided that Q and V are not simultaneously N; wherein R$^7$, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and, —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and, —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with nitrogen atom to which they are attached, comprise a 3- to 6-membered heterocycle; wherein Z is selected from —CR$^8$(O)$_r$R$^9$—, —CR$^8$NR$^{10a}$R$^{10b}$—, —(C=O)—, and a structure represented by a formula:

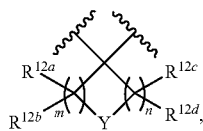

wherein Y is selected from —CR$^8$R$^9$—, —O—, —S(O)$_q$—, and —NR$^8$—; wherein m is an integer selected from 0, 1, and 2; wherein n is an integer selected from 0 and 1; wherein the sum of m and n is 1 or 2 when Y is —CR$^8$R$^9$—; wherein the sum of m and n is 2 when Y is —O—, —S(O)$_q$—, and —NR$^8$—; wherein q is 0, 1, or 2; wherein r is 0 or 1; wherein R$^8$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^8$ is not halogen; wherein R$^9$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^9$ is not halogen; wherein each of R$^{10a}$ and R$^{10b}$, when present, is independently selected from hydrogen, C1-C3 alkyl, C1-C3 monohaloalkyl, C1-C3 polyhaloalkyl, and cyclopropyl; wherein each occurrence of R$^{12a}$, R$^{12a}$, R$^{12a}$, and R$^{12a}$, when present, is independently selected from hydrogen, halogen, C1-C3 alkyl, C1-C3 monohaloalkyl, and C1-C3 polyhaloalkyl; wherein R$^2$ is selected from hydrogen, C1-C3 alkyl, C1-C3 monohaloalkyl, C1-C3 polyhaloalkyl, and cyclopropyl; wherein R$^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$ is independently selected from hydrogen and fluoro; with a second compound R$^1$NH$_2$; wherein R$^1$ is selected from aryl and heteroaryl, and wherein R$^1$ is substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$; wherein each occurrence of R$^{50}$, when present, is independently selected from hydrogen, C1-C3 alkyl, C1-C3 monohaloalkyl, C1-C3 polyhaloalkyl, and cyclopropyl; wherein each occurrence of each of R$^{51a}$ and R$^{51b}$, when present, is independently selected from hydrogen, C1-C3 alkyl, C1-C3 monohaloalkyl, C1-C3 polyhaloalkyl, and cyclopropyl; or wherein R$^{51a}$ and R$^{51b}$, when present, are optionally covalently bonded and, together with nitrogen atom to which they are attached, comprise a 3- to 6-membered heterocycle; wherein each occurrence of R$^{52}$, when present, is independently selected from C1-C3 alkyl, C1-C3 monohaloalkyl, C1-C3 polyhaloalkyl, cyclopropyl, and, —NR$^{54a}$R$^{54b}$; wherein each occurrence of each of R$^{54a}$ and R$^{54b}$, when present, is independently selected from hydrogen, C1-C3 alkyl, C1-C3 monohaloalkyl, C1-C3 polyhaloalkyl, and cyclopropyl; or wherein R$^{54a}$ and R$^{54b}$, when present, are optionally covalently bonded and, together with nitrogen atom to which they are attached, comprise a 3- to 6-membered heterocycle; wherein each occurrence of R$^{53}$, when present, is independently from C1-C3 alkyl, C1-C3 monohaloalkyl, C1-C3 polyhaloalkyl, cyclopropyl, and, —NR$^{55a}$R$^{55b}$; wherein each occurrence of each of R$^{55a}$ and R$^{55b}$, when present, is independently selected from hydrogen, C1-C3 alkyl, C1-C3 monohaloalkyl, C1-C3 polyhaloalkyl, and cyclopropyl; or wherein R$^{55a}$ and R$^{55b}$, when present, are optionally covalently bonded and, together with nitrogen atom to which they are attached, comprise a 3- to 6-membered heterocycle; thereby forming an amide.

In a further aspect, the compound produced has a structure represented by a formula:

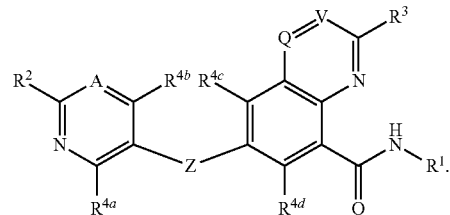

In a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

17. Analog Route II

In one aspect, analogs can be prepared as shown below.

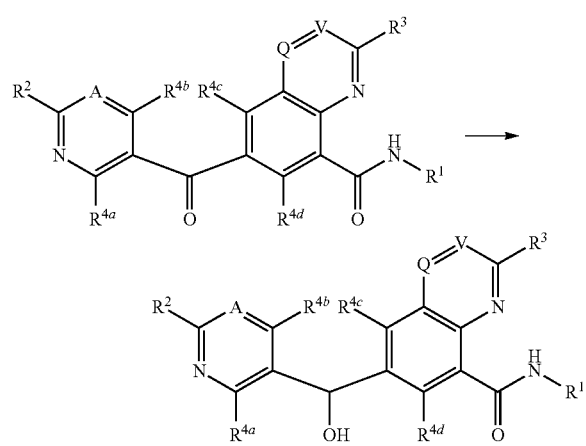

Compounds are represented in generic form, with substituents as noted in compound descriptions elsewhere herein. A more specific example is set forth below.

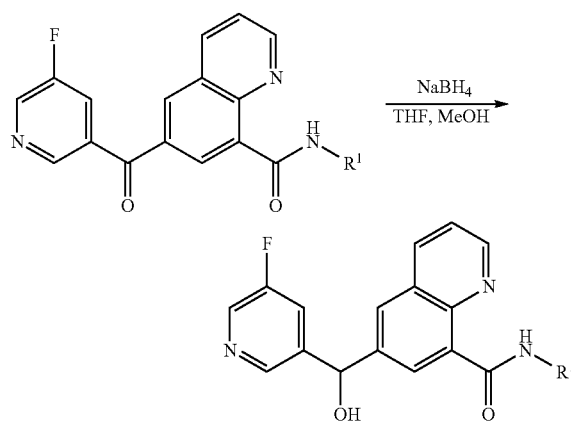

In one aspect, Intermediate Route XIV begins with an amide analog. Such amide analogs can be prepared according to the method described in Analog Route I. Reaction with a reducing agent will provide the secondary alcohol intermediate. It will be appreciated that a variety of reducing agents, including but not limited to sodium borohydride and lithium borohydride, may be useful for this transformation. Functional group transformation of the remaining substituents can yield further analogs.

18. Prophetic Example I

In one aspect, tertiary alcohol intermediates can be prepared as shown below.

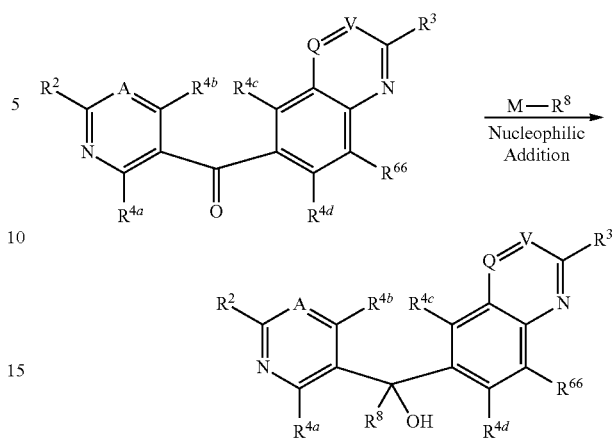

Compounds are represented in generic form, with substituents as noted in compound descriptions elsewhere herein. $R^{66}$ is Cl, CN, $CO_2R^{67}$, or $CH=CH_2$. $R^{67}$ is C1-C3 alkyl. M is any atom or group of atoms that renders $R^8$ nucleophilic. In this example $R^8$ is not H. Reaction of the ketone with M-$R^8$ will afford a tertiary alcohol intermediate. Examples of M-$R^8$ include but are not limited to Grignard reagents ($R^8$MgCl, $R^8$MgBr), alkyl lithiums ($R^8$Li), and organocerium reagents ($R^8$CeCl$_2$). Such reagents are often commercially available or can be readily prepared according to methods well known to one skilled in the art. For methods suitable for preparing examples where $R^8$ is trifluoromethyl see Kawai, H. *Org. Lett.* 2010, 12, 5104-5107; Singh, R. P. et al. *J. Org. Chem.* 1999, 64, 2873-2876; Prakash, G. K. S. et al. *J. Am. Chem. Soc.* 1989, 111, 393-395; and references therein. Conversion of the tertiary alcohol intermediate into final analogs can be accomplished according to methods described elsewhere herein.

19. Prophetic Example II

In one aspect, amine intermediates can be prepared as shown below.

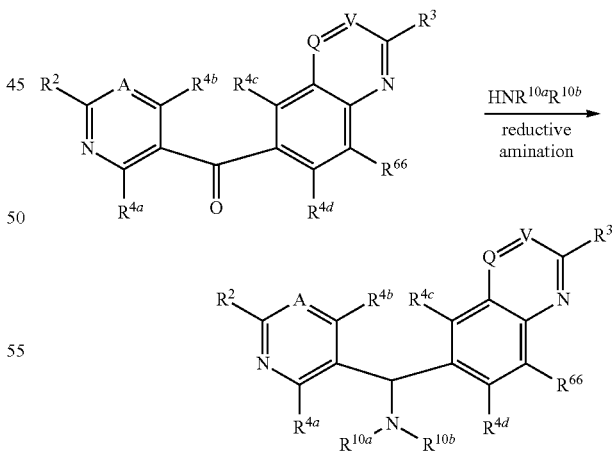

Compounds are represented in generic form, with substituents as noted in compound descriptions elsewhere herein. $R^{66}$ is Cl, CN, $CO_2R^{67}$, or $CH=CH_2$. $R^{67}$ is C1-C3 alkyl. Reaction of the ketone with a substituted amine under reductive amination conditions will provide an amine intermediate. For suitable reductive amination conditions see Abdel-Magid, A. F. et al. *J. Org. Chem.* 1996, 61, 3849-3862 and references therein. Conversion of the amine intermediate into final analogs can be accomplished according to methods described elsewhere herein.

20. Prophetic Example III

In one aspect, amine intermediates can be prepared as shown below.

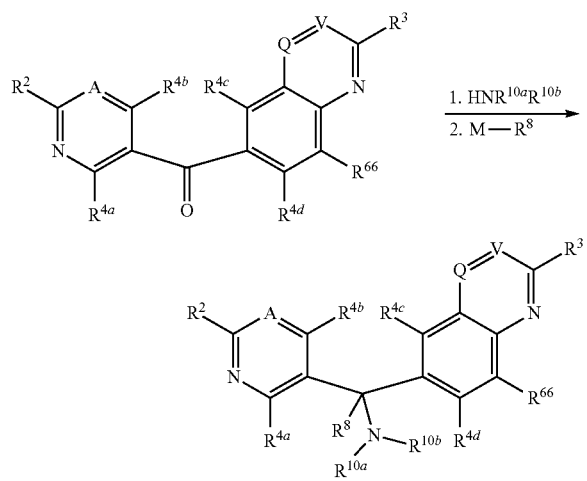

Compounds are represented in generic form, with substituents as noted in compound descriptions elsewhere herein. $R^{66}$ is Cl, CN, $CO_2R^{67}$, or $CH=CH_2$. $R^{67}$ is C1-C3 alkyl. M is any atom or group of atoms that renders $R^8$ nucleophilic. Reaction of the ketone with a substituted amine under suitable conditions will provide an imine intermediate, which may or may not be isolated. Reaction of the imine intermediate with M-$R^8$ will provide a tertiary amine intermediate. Examples of M-$R^8$ include but are not limited to Grignard reagents ($R^8$MgCl, $R^8$MgBr), alkyl lithiums ($R^8$Li), organozinc reagents (Zn$R^8_2$) and organocerium reagents ($R^8$CeCl$_2$). Such reagents are often commercially available or can be readily prepared according to methods well known to one skilled in the art. For conditions suitable for carrying out such transformations see Bloch, R. *Chem. Rev.* 1998, 98, 1407-1438; De Kimpe, N.; De Smaele, D. *Tetrahedron Lett.* 1994, 35, 8023-8026; Saidi, M. R.; Nazari, M. *Monatshefte für Chem.* 2004, 135, 309-312; and references therein. Conversion of the amine intermediate into final analogs can be accomplished according to methods described elsewhere herein.

21. Prophetic Example IV

In one aspect, alkyl intermediates can be prepared as shown below.

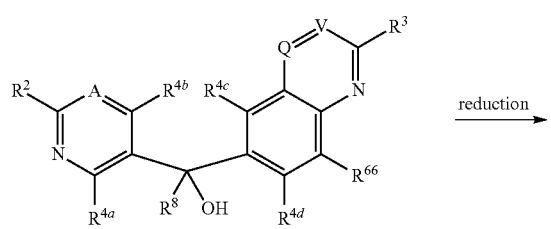

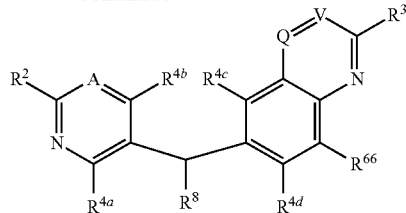

Compounds are represented in generic form, with substituents as noted in compound descriptions elsewhere herein. $R^{66}$ is Cl, CN, $CO_2R^{67}$, or $CH=CH_2$. $R^{67}$ is C1-C3 alkyl. Reaction of the alcohol under suitable reducing conditions will provide an alkyl intermediate. Examples of suitable reducing conditions include but are not limited to catalytic hydrogenation (Botteghi, C. et al. *Tetrahedron* 2001, 57, 1631-1637), a trialkylsilane in the presence of a suitable acid (Orfanopoulos, M.; Smonou, I. *Synth. Comm.* 1988, 18, 833-839), and sodium borohydride in acidic media (Gribble, G.; Leese, R. M. *Synthesis* 1997, 172-176). Conversion of the alkyl intermediate into final analogs can be accomplished according to methods described elsewhere herein.

22. Prophetic Example V

In one aspect, alkyl intermediates can be prepared as shown below.

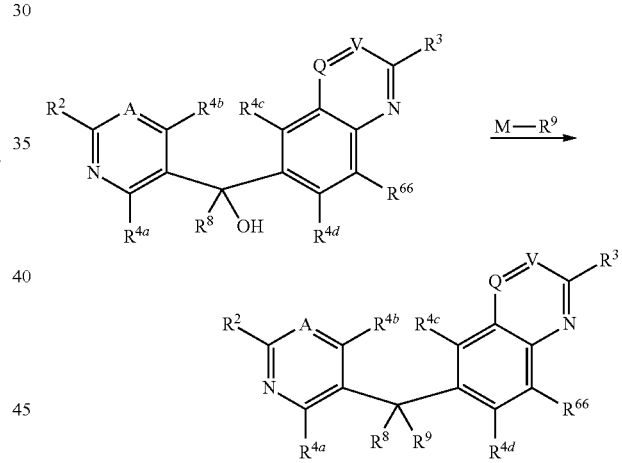

Compounds are represented in generic form, with substituents as noted in compound descriptions elsewhere herein. $R^{66}$ is Cl, CN, $CO_2R^{67}$, or $CH=CH_2$. $R^{67}$ is C1-C3 alkyl. M is any atom or group of atoms that renders $R^9$ nucleophilic. Reaction of the alcohol with M-$R^9$ under suitable conditions will provided an alkyl intermediate. Examples of M-$R^9$ and suitable conditions include but are not limited to an organosilane and a Lewis acid (De, S. K.; Gibbs, R. A. *Tetrahedron Lett.* 2005, 46, 8345-8350 and Cella, J. A. *J. Org. Chem.* 1982, 47, 2125-2130), a trialkylaluminum reagent (Obrey, S. J. et al. *Organometallics* 2001, 20, 5162-5170), and a dialkylzinc reagent and a Lewis acid (Tanaka H.; Shishido, Y. *Bioorg. Med. Chem. Lett.* 2007, 17, 6079-6085). Conversion of the alkyl intermediate into final analogs can be accomplished according to methods described elsewhere herein.

23. Prophetic Example VI

In one aspect, cyclopropyl intermediates can be prepared as shown below.

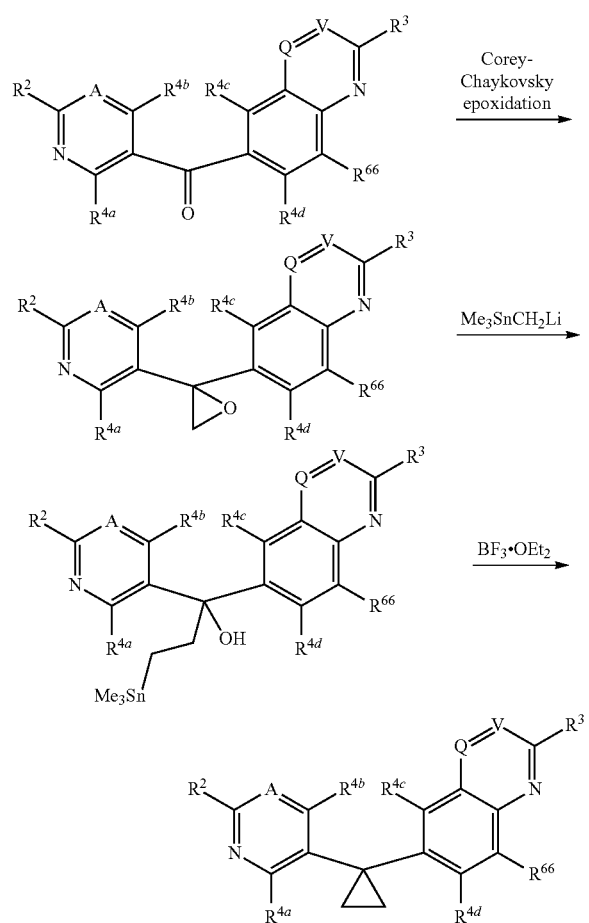

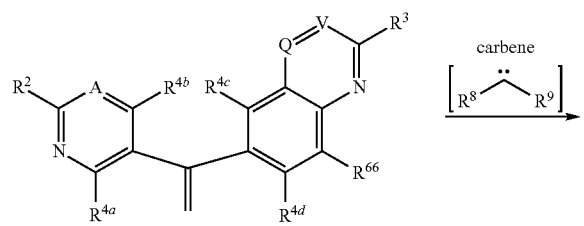

Compounds are represented in generic form, with substituents as noted in compound descriptions elsewhere herein. $R^{66}$ is Cl, CN, $CO_2R^{67}$, or $CH=CH_2$. $R^{67}$ is C1-C3 alkyl. Reaction of the ketone under Corey-Chaykovsky conditions will afford an epoxide intermediate. For suitable conditions for this transformation see Ciaccio, J. A. et al. *Synthetic Comm.* 2003, 33, 2135-2143 and references therein. Reaction of the epoxide with a trialkylstannylmethyllithium and subsequent treatment with a Lewis acid such as boron trifluoride etherate will yield a cyclopropyl intermediate. For suitable conditions for these transformations see Fleming, I.; Urch, C. J. *J. Organomet. Chem.* 1985, 285, 173-191; Murayama, E. et al. *Chem. Lett.* 1984, 1897-1900; and references therein. Conversion of the cyclopropyl intermediate into final analogs can be accomplished according to methods described elsewhere herein.

24. Prophetic Example VII

In one aspect, cyclopropyl intermediates can be prepared as shown below.

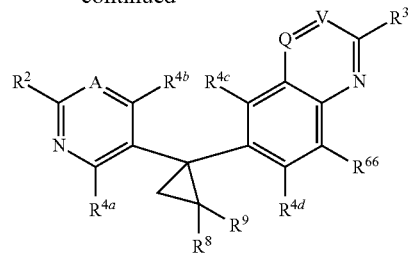

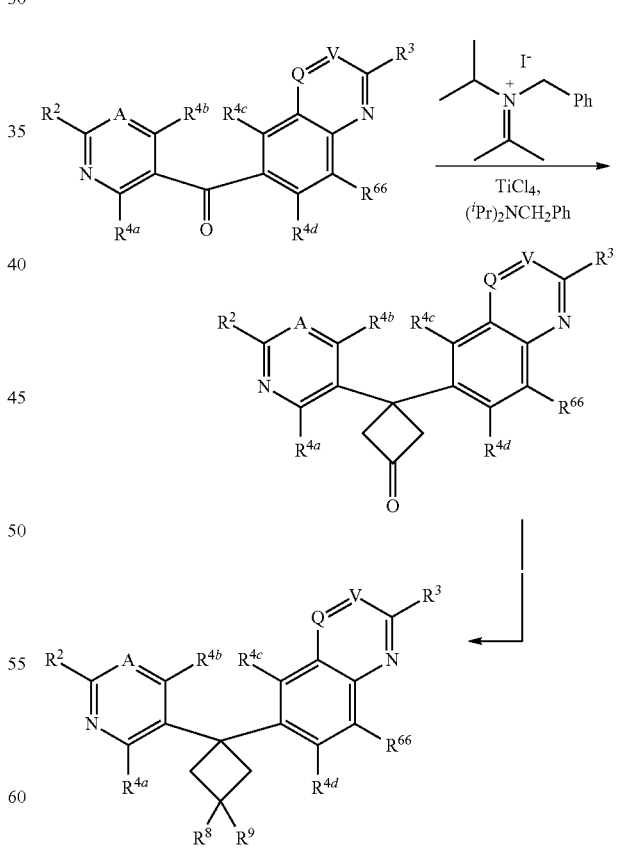

Compounds are represented in generic form, with substituents as noted in compound descriptions elsewhere herein. $R^{66}$ is Cl, CN, or $CO_2R^{67}$. $R^{67}$ is C1-C3 alkyl. Reaction of the olefin intermediate with a carbene will provide a cyclopropyl intermediates. For examples of useful carbenes and suitable conditions for the cyclopropanation reaction see Grygorenko, O. O. et al. *Tetrahedron* 2011, 67, 803-823; Virender, S. L. J.; Sain, B. *Tetrahedron Lett.* 2005, 46, 37-38; Dolbier, W. R., Jr. et al. *J. Fluorine Chem.* 2004, 125, 459-469; Singh, V. K.; et al. *Synthesis* 1997, 137-149; Brookhart, M.; Studabaker, W. B. et al. *Chem. Rev.* 1987, 87, 411-432; and references therein. Conversion of the cyclopropyl intermediate into final analogs can be accomplished according to methods described elsewhere herein.

25. Prophetic Example VIII

In one aspect, cyclobutyl intermediates can be prepared as shown below.

Compounds are represented in generic form, with substituents as noted in compound descriptions elsewhere herein. $R^{66}$ is Cl, CN, $CO_2R^{67}$, or $CH=CH_2$. $R^{67}$ is C1-C3 alkyl. The iminium ion prepared through the oxidation of N,N-diisopropyl-N-benzylamine is reacted with TiCl$_4$—N,N-diisopropyl-N-benzylamine and subsequently the ketone intermediate to afford a cyclobutanone intermediate. For suitable conditions for such a transformation see Periasamy, M. et al. *J. Org. Chem.* 2005, 70, 5420-5425; Periasamy, M. et al. *Chem. Commun.* 2001, 1728-1729; and references therein. Conversion of the cyclobutanone intermediate into a cyclobutyl intermediate can be accomplished according to methods outlined elsewhere herein. Conversion of the cyclobutyl intermediate into final analogs can be accomplished according to methods described elsewhere herein.

26. Prophetic Example IX

In one aspect, cyclobutyl intermediates can be prepared as shown below.

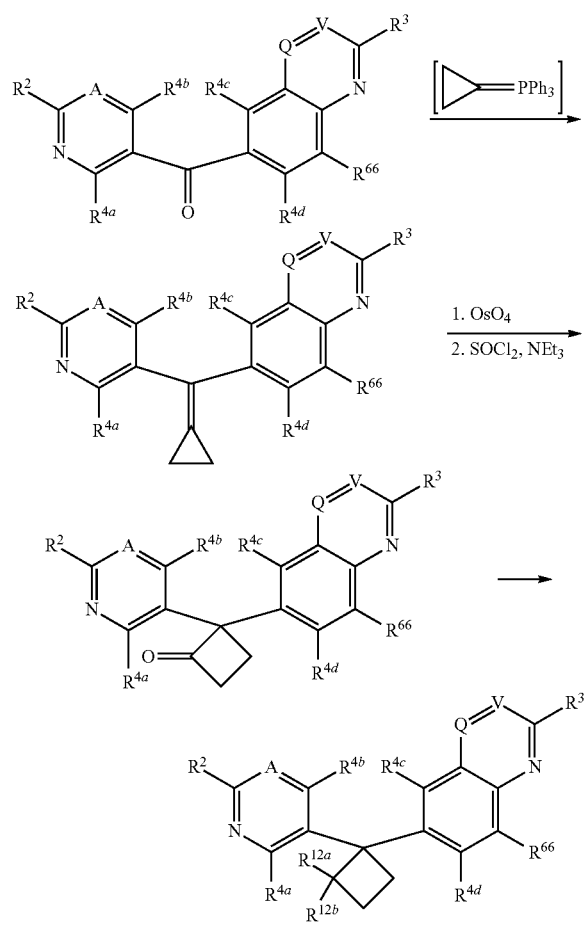

Compounds are represented in generic form, with substituents as noted in compound descriptions elsewhere herein. R$^{66}$ is Cl, CN, or CO$_2$R$^{67}$. R$^{67}$ is C1-C3 alkyl. Reaction of the ketone intermediate with cyclopropylidenetriphenylphosphorane will afford an olefin intermediate. For suitable conditions for such a transformation see Stafford, J. A.; McMurry, J. E. *Tetrahedron Lett.* 1988, 21, 2531-2534 and references therein. Reaction of the olefin under dihydroxylation conditions will afford a diol that can be treated with thionyl chloride to provide a cyclobutanone intermediate. For suitable conditions for such a transformation see Nemoto, H. et al. *Tetrahedron* 1995, 51, 5511-5522 and references therein. Conversion of the cyclobutanone intermediate into a cyclobutyl intermediate can be accomplished according to methods outlined elsewhere herein. Conversion of the cyclobutyl intermediate into final analogs can be accomplished according to methods described elsewhere herein.

27. Prophetic Examples X

In one aspect, oxetane intermediates can be prepared as shown below.

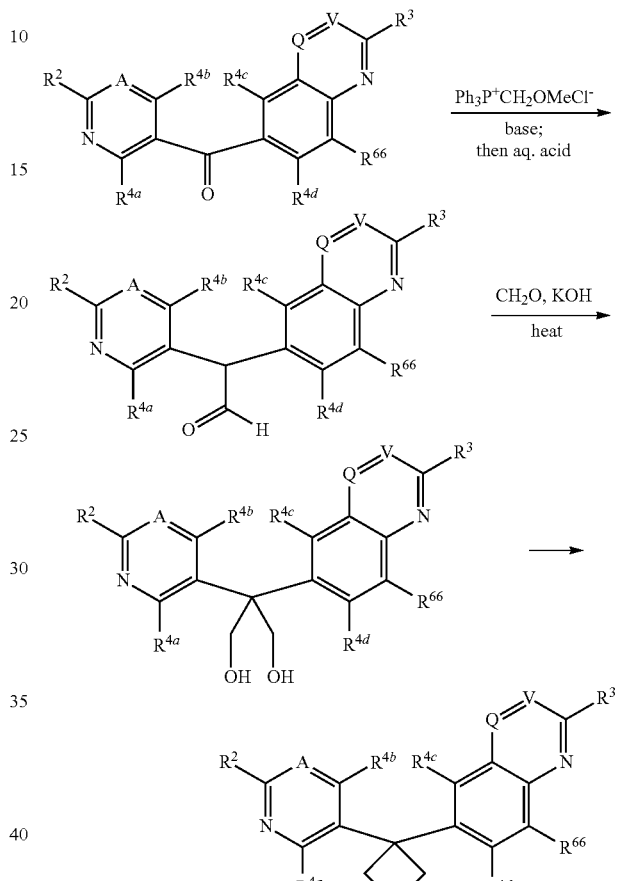

Compounds are represented in generic form, with substituents as noted in compound descriptions elsewhere herein. R$^{66}$ is Cl, CN, or CH=CH$_2$. Reaction of the ketone intermediate in a one carbon homologation Wittig reaction will afford an aldehyde intermediate. For suitable conditions for such a transformation see Sorensen, U. S. et al. *Bioorg. Med. Chem.* 2003, 11, 197-205 and references therein. Reaction of the aldehyde intermediate with formaldehyde and base under heating conditions will afford a diol intermediate. For suitable conditions for such a transformation see Winter, B. *Helv. Chim. Acta* 2004, 87, 1616-1627 and references therein. Synthesis of the oxetane from the diol can be accomplished by a number of conditions including but not limited to Mitsunobu reaction (Christlieb, M. et al. *J. Chem Soc. Perkin Trans.* 1, 2001, 2983-2996) and tosyl chloride and base (Picard, P. et al. *Synthesis* 1981, 550-551 and references therein). Conversion of the oxetane intermediate into final analogs can be accomplished according to methods described elsewhere herein.

28. Prophetic Examples XI

In one aspect, oxetane intermediates can be prepared as shown below.

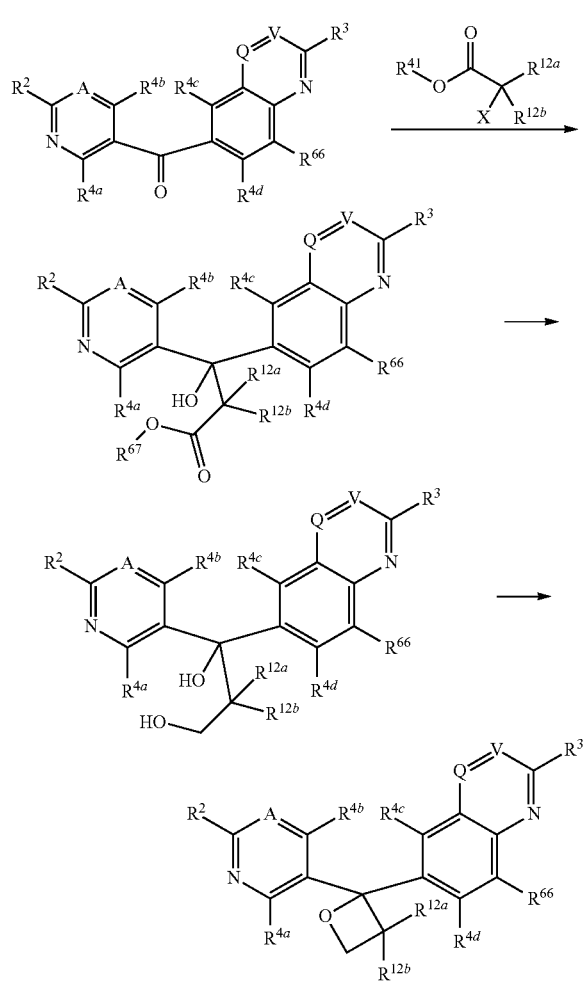

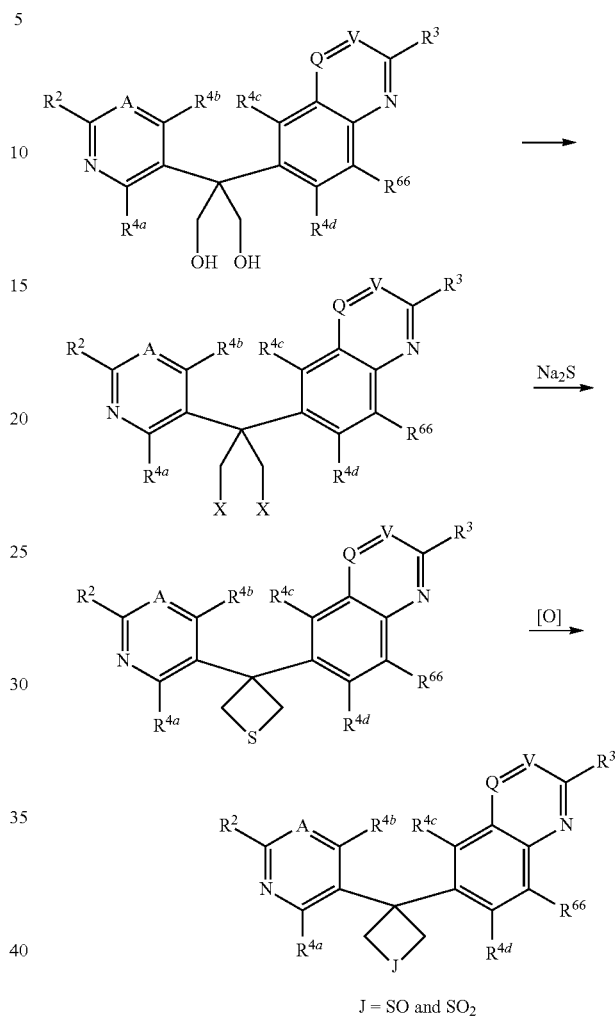

J = SO and SO$_2$

29. Prophetic Examples XII

In one aspect, thietane, thietaneoxide, and thietanedioxide intermediates can be prepared as shown below.

Compounds are represented in generic form, with substituents as noted in compound descriptions elsewhere herein. R$^{66}$ is Cl, CN, or CH=CH$_2$. R$^{67}$ is C1-C3 alkyl. Reaction of the ketone intermediate with a metal ester enolate will afford a β-hydroxy ester intermediate. The metal ester enolate may be generated from a number of ways well known to one skilled in the art. Examples of such methods include but are not limited to treatment of an ester (X=H) with a lithium bases such as lithium diisopropylamide or lithium (bistrimethylsilyl)amide (see Suri, S. C. et al. *Synth. Comm.* 2005, 35, 379-387; Groundwater, P. W. et al. *J. Chem. Soc., Perkin Trans. 1*, 2001, 2781-2787), treatment of an α-haloester (X=Cl, Br, or I) with zinc (see Ross, N. A.; Bartsch, R. A. *J. Org. Chem.* 2003, 68, 360-366; Rollin, Y. et al. *J. Organom. Chem.* 1993, 461, 9-13), treatment of an α-haloester (X=Cl, Br, or I) with manganese (Suh, Y. S.; Rieke, R. D. *Tetrahedron Lett.* 2004, 45, 1807-1809), and treatment of an α-haloester (X=Cl, Br, or I) with samarium iodide (Yoshida, M. et al. *J. Chem. Soc., Perkin Trans. 1*, 1997, 643-648). The β-hydroxy ester intermediate can be treated with a suitable hydride reducing agent to afford a diol intermediate. Examples of such reducing agents are well known to one skilled in the art and include but are not limited to lithium aluminum hydride, lithium borohydride, and diisobutylaluminum hydride. Conversation of the diol intermediate into an oxetane intermediate can be accomplished according to methods outlined elsewhere herein. Conversion of the oxetane intermediate into final analogs can be accomplished according to methods described elsewhere herein.

Compounds are represented in generic form, with substituents as noted in compound descriptions elsewhere herein. R$^{66}$ is Cl, CN, or CH=CH$_2$. Conversion of both of the hydroxyl groups present the diol intermediate into halides (X=Cl, Br, or I) or alkylsulfonates (X=OSO$_2$R$^{42}$, wherein R$^{42}$ is methyl, trifluoromethyl, phenyl, or 4-methylphenyl). Methods for such conversions are well known to one skilled in the art and include but are not limited to thionyl chloride, phosphorous oxychloride, carbon tetrabromide-triphenylphosphine, phosphorous tribromide, and iodine-triphenylphosphine-imidazole. Reaction of the dihalide or dialkylsufonate intermediate with sodium sulfide under appropriate conditions will afford a thietane intermediate. For examples of suitable conditions see Burkhard, J. A. et al. *Angew. Chem. Int. Ed.* 2010, 49, 3524-3527; Nishizono, N. *Tetrahedron* 2007, 63, 11622-11625; and references therein. The thietane intermediate may be converted into thietaneoxide or thietanedioxide intermediates by treatment with a suitable oxidizing agent. Examples of such oxidizing agents are well known to one skilled in the art and include but are not limited to hydrogen peroxide, oxone, and m-chloroperoxybenzoic acid. Conversion of the thietane, thietaneoxide, and thietanedioxide intermediates into final analogs can be accomplished according to methods described elsewhere herein.

30. Prophetic Examples XIII

In one aspect, thietane, thietaneoxide, and thietanedioxide intermediates can be prepared as shown below.

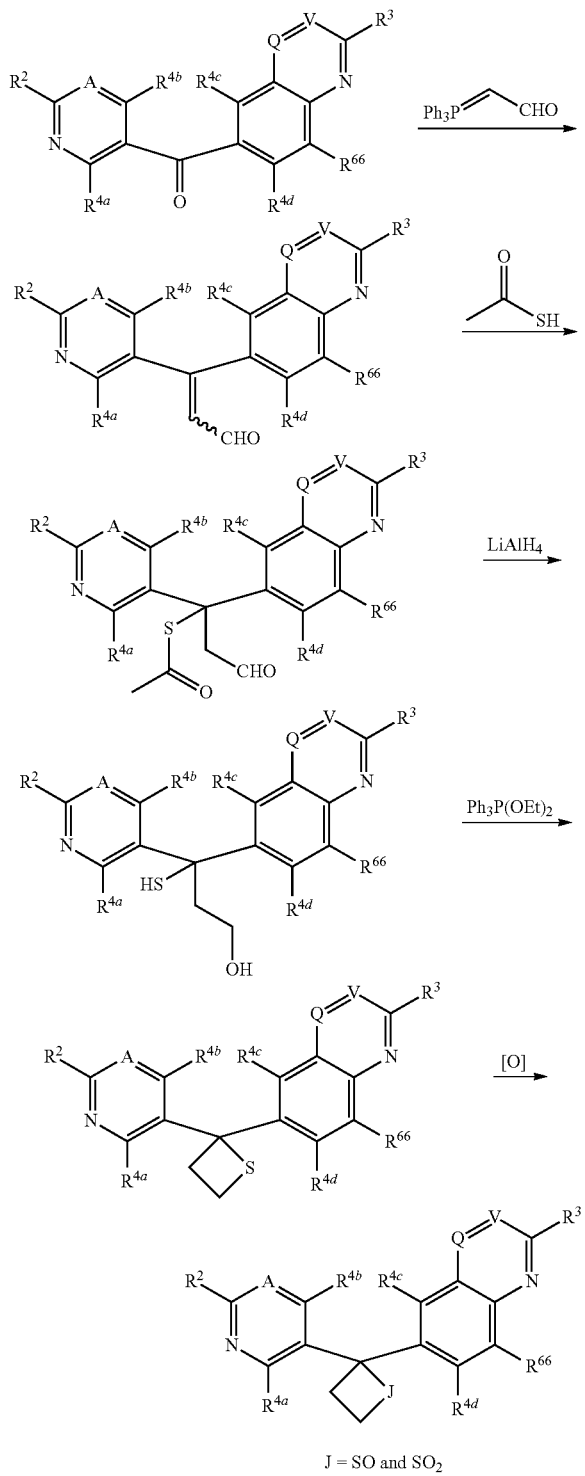

J = SO and SO₂

Compounds are represented in generic form, with substituents as noted in compound descriptions elsewhere herein. $R^{66}$ is Cl, CN, or CH=CH₂. The sequence of transformations shown here is described in Burkhard, J. A. et al. *Org. Lett.* 2010, 12, 1944-1947 and references therein.

Reaction of the ketone intermediate with 2-(triphenylphosphoranylidene)acetaldehyde will furnish an α,β-unsaturated aldehyde intermediate. Reaction of the aldehyde intermediate with thioacetic acid under basic conditions will facilitate a conjugate addition and provide the thioester intermediate. Reaction of the thioester intermediate with lithium aluminum hydride will afford a thiol alcohol intermediate. Treatment of the thiol alcohol intermediate with diethoxytriphenylphosphorane will afford a thietane intermediate. The thietane intermediate may be converted into thietaneoxide or thietanedioxide intermediates by treatment with a suitable oxidizing agent. Examples of such oxidizing agents are well known to one skilled in the art and include but are not limited to hydrogen peroxide, oxone, and m-chloroperoxybenzoic acid. Conversion of the thietane, thietaneoxide, and thietanedioxide intermediates into final analogs can be accomplished according to methods described elsewhere herein.

31. Prophetic Examples XIV

In one aspect, azetidine intermediates can be prepared as shown below.

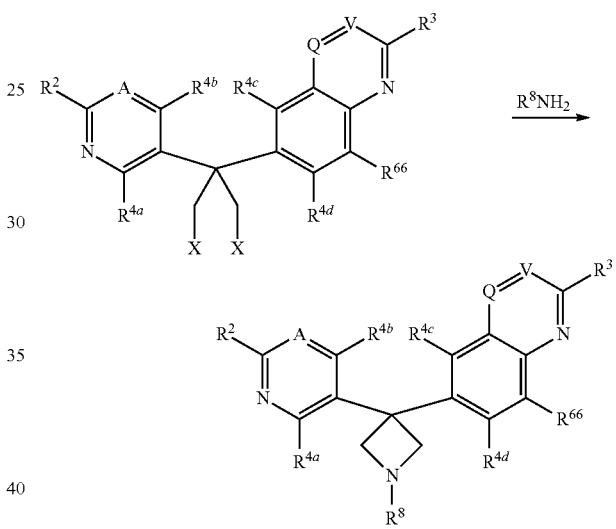

Compounds are represented in generic form, with substituents as noted in compound descriptions elsewhere herein. $R^{66}$ is Cl, CN, or CH=CH₂. X=Cl, Br, I, or OSO₂R⁴². wherein $R^{42}$ is methyl, trifluoromethyl, phenyl, or 4-methylphenyl. Reaction of the dihalide or dialkylsufonate intermediate with a primary amine under appropriate conditions will afford an azetidine intermediate. For examples of suitable conditions see Burkhard, J. A. et al. *Angew. Chem. Int. Ed.* 2010, 49, 3524-3527 and references therein. Conversion of the azetidine intermediates into final analogs can be accomplished according to methods described elsewhere herein.

32. Prophetic Examples XV

In one aspect, azetidine intermediates can be prepared as shown below.

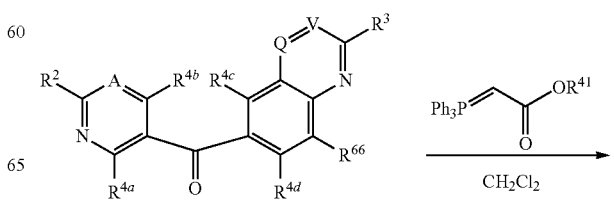

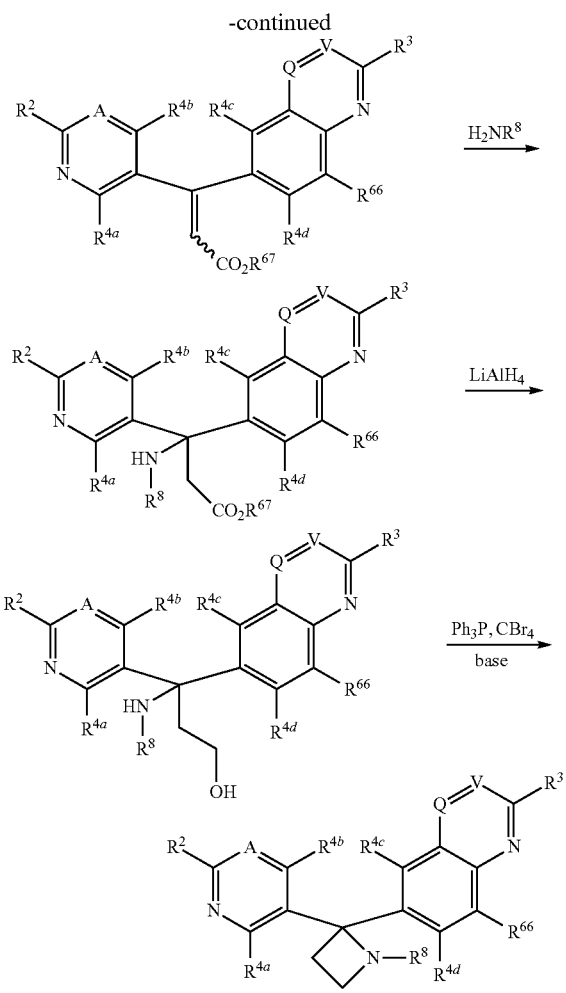

Compounds are represented in generic form, with substituents as noted in compound descriptions elsewhere herein. $R^{66}$ is Cl, CN, or CH=CH$_2$. $R^{67}$ is C1-C3 alkyl. The sequence of transformations shown here is described in Burkhard, J. A. et al. *Org. Lett.* 2010, 12, 1944-1947 and references therein. Reaction of the ketone intermediate with a suitable stabilized ylide reagent will furnish an α,β-unsaturated ester intermediate. Reaction of the α,β-unsaturated ester intermediate with a suitable primary amine will facilitate a conjugate addition and provide a β-aminoester intermediate. Reaction of the β-aminoester intermediate with lithium aluminum hydride will afford an amino alcohol intermediate. Treatment of the amino alcohol intermediate with carbon tetrabromide and triphenylphosphine followed by a suitable base will afford an azetidine intermediate. Conversion of the azetidine intermediates into final analogs can be accomplished according to methods described elsewhere herein.

Thus, in one aspect, the invention relates to a method of making a compound comprising the step of reacting a compound having a structure represented by a formula:

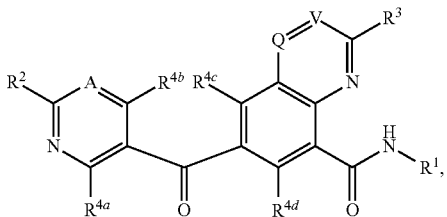

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein Q is selected from N and CR$^6$; wherein R$^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle; wherein R$^{32}$, when present, is selected from C1-C3 alkyl, C1-C3 monohaloalkyl, C1-C3 polyhaloalkyl, cyclopropyl, and, —NR$^{34a}$R$^{34b}$; wherein each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with nitrogen atom to which they are attached, comprise a 3- to 6-membered heterocycle; wherein R$^{33}$, when present, is selected from C1-C3 alkyl, C1-C3 monohaloalkyl, C1-C3 polyhaloalkyl, cyclopropyl, and, —NR$^{35a}$R$^{35b}$; wherein each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; wherein V is selected from N and CR$^7$, provided that Q and V are not simultaneously N; wherein R$^7$, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$ is independently selected from hydrogen and fluoro; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O)$R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —$NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, $NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; with a reducing agent, thereby forming a secondary alcohol.

In a further aspect, the compound produced has a structure represented by a formula:

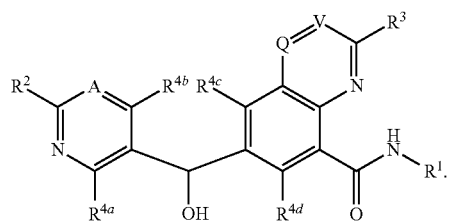

In a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

In a further aspect, the compound produced exhibits noncompetitive antagonism. In a yet further aspect, the compound produced exhibits noncompetitive inhibition. In an even further aspect, the compound produced exhibits allosteric antagonism.

In a further aspect, the compound produced exhibits negative allosteric modulation with an $IC_{50}$ of less than about $30 \times 10^{-6}$ M. In an even further aspect, the compound produced exhibits negative allosteric modulation with an $IC_{50}$ of less than about $10 \times 10^{-6}$ M. In a yet further aspect, the compound produced exhibits negative allosteric modulation with an $IC_{50}$ of less than about $1.0 \times 10^{-6}$ M. In a still further aspect, the compound produced exhibits negative allosteric modulation with an $IC_{50}$ of less than about $1.0 \times 10^{-7}$ M. In an even further aspect, the compound produced exhibits negative allosteric modulation with an $IC_{50}$ of less than about $1.0 \times 10^{-8}$ M. In a yet further aspect, the compound produced exhibits negative allosteric modulation with an $IC_{50}$ of less than about $1.0 \times 10^{-9}$ M. In a still further aspect, the compound produced exhibits negative allosteric modulation inhibition with an $IC_{50}$ of between about $1 \times 10^{-5}$ M to about $1 \times 10^{-9}$ M. In an even further aspect, the compound produced exhibits negative allosteric modulation with an $IC_{50}$ of between about from about $1\times10^{-6}$ M to about $1\times10^{-9}$ M. In a yet further aspect, the compound produced exhibits negative allosteric modulation with an $IC_{50}$ of between about from about $1\times10^{-7}$ M to about $1\times10^{-9}$ M. In a still further aspect, the compound produced exhibits negative allosteric modulation with an $IC_{50}$ of between about $1\times10^{-8}$ M to about $1\times10^{-9}$ M.

In a further aspect, the compound produced exhibits partial or total inhibition with an $IC_{50}$ of less than about $30\times10^{-6}$ M. In an even further aspect, the compound produced exhibits partial or total inhibition with an $IC_{50}$ of less than about $10\times10^{-6}$ M. In a yet further aspect, the compound produced exhibits partial or total inhibition with an $IC_{50}$ of less than about $1.0\times10^{-6}$ M. In a still further aspect, the compound produced exhibits partial or total inhibition with an $IC_{50}$ of less than about $1.0\times10^{-7}$ M. In an even further aspect, the compound produced exhibits partial or total inhibition with an $IC_{50}$ of less than about $1.0\times10^{-8}$ M. In a yet further aspect, the compound produced exhibits partial or total inhibition with an $IC_{50}$ of less than about $1.0\times10^{-9}$ M. In a still further aspect, the compound produced exhibits partial or total inhibition with an $IC_{50}$ of between about $1\times10^{-5}$ M to about $1\times10^{-9}$ M. In an even further aspect, the compound produced exhibits partial or total inhibition with an $IC_{50}$ of between about from about $1\times10^{-6}$ M to about $1\times10^{-9}$ M. In a yet further aspect, the compound produced exhibits partial or total inhibition with an $IC_{50}$ of between about from about $1\times10^{-7}$ M to about $1\times10^{-9}$ M. In a still further aspect, the compound produced exhibits partial or total inhibition with an $IC_{50}$ of between about $1\times10^{-8}$ M to about $1\times10^{-9}$ M.

In a further aspect, a compound produced is a component in a pharmaceutical composition. In a still further aspect, a pharmaceutical composition comprises a therapeutically effective amount of a compound produced and a pharmaceutically acceptable carrier. In a still further aspect, a compound produced is a component is used in the manufacture of a medicament comprising combining at least one compound produced with a pharmaceutically acceptable carrier or diluent.

It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

Table 1 below lists specific compounds as well as a preferred route for its synthesis, experimentally determined molecular mass, and mGluR5 activity determined in a cell-based assay. The mGluR5 activity was determined using the metabotropic glutamate receptor activity assays in human embryonic kidney cells as described herein, wherein the human embryonic kidney cells were transfected with rat mGluR5. The mGluR5 activity data for some compounds are shown as the average of at least three experiments with the standard error in these cases. If no error is indicated for the mGluR5 activity, the values given represent the results from a single experiment or the average of two experiments. The compounds in Table 1 were synthesized with methods identical or analogous to those shown herein. The requisite starting materials were commercially available, described in the literature, or readily synthesized by one skilled in the art of organic synthesis.

TABLE 1

| Structure | mGluR5 $IC_{50}$ (nM) | $[M + H]^+$ | Intermediate Route Reference | Analog Synthetic Route Reference |
|---|---|---|---|---|
| 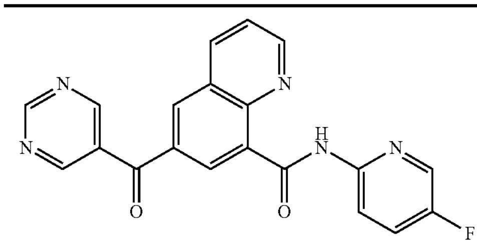 | 106 | 374.2 | II, IV, V | I |
| 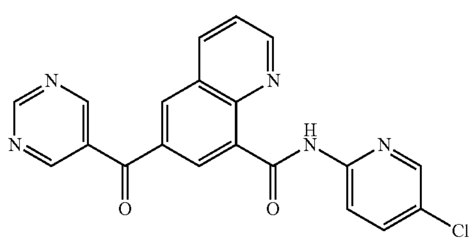 | 148 | 390.1 | II, IV, V | I |
| 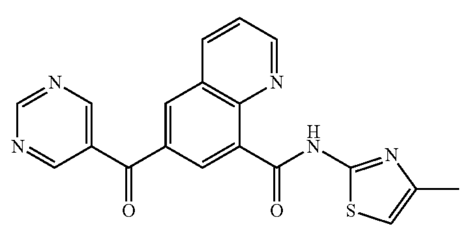 [SMILES: Cc1csc(NC(=O)c2cc(C(=O)c3cncnc3)cc3cccnc23)n1] | 73 | 376.2 | II, IV, V | I |

TABLE 1-continued

| Structure | mGluR5 IC$_{50}$ (nM) | [M + H]$^+$ | Intermediate Route Reference | Analog Synthetic Route Reference |
| --- | --- | --- | --- | --- |
| 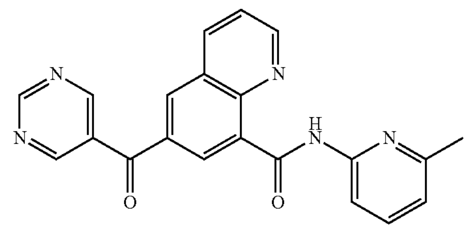 [SMILES: Cc1cccc(NC(=O)c2cc(C(=O)c3cncnc3)cc3cccnc23)n1] | 163 | 370.2 | II, IV, V | I |
| 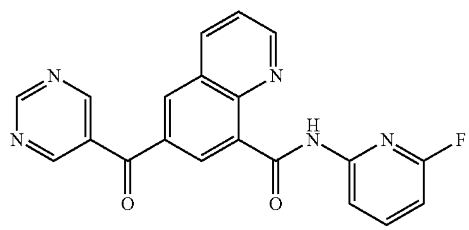 [SMILES: O=C(c1cncnc1)c1cc(C(=O)Nc2cccc(F)n2)c2ncccc2c1] | 645 | 374.2 | II, IV, V | I |
| 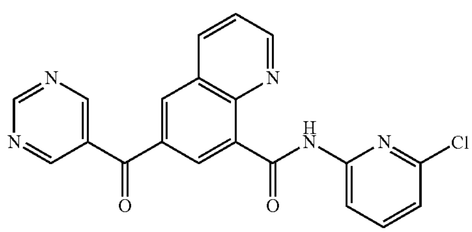 [SMILES: O=C(c1cncnc1)c1cc(C(=O)Nc2cccc(Cl)n2)c2ncccc2c1] | 696 | 390.1 | II, IV, V | I |
| 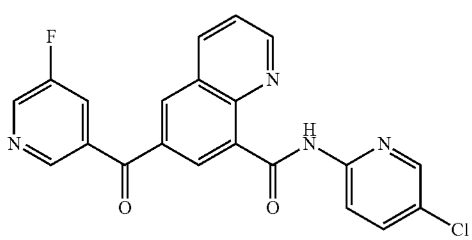 [SMILES: O=C(c1cncc(F)c1)c1cc(C(=O)Nc2ccc(Cl)cn2)c2ncccc2c1] | >30,000 | 406.9 | II, IV, VI, XIII, XIV | I |
| 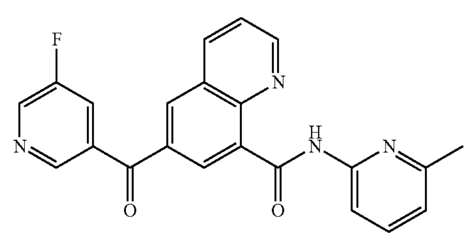 [SMILES: Cc1cccc(NC(=O)c2cc(C(=O)c3cncc(F)c3)cc3cccnc23)n1] | 1620 | 387.0 | II, IV, VI, XIII, XIV | I |
| 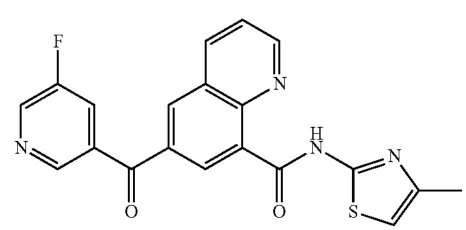 [SMILES: Cc1csc(NC(=O)c2cc(C(=O)c3cncc(F)c3)cc3cccnc23)n1] | 444 | 393.0 | II, IV, VI, XIII, XIV | I |

TABLE 1-continued
| Structure | mGluR5 IC$_{50}$ (nM) | [M + H]$^+$ | Intermediate Route Reference | Analog Synthetic Route Reference |
|---|---|---|---|---|
| 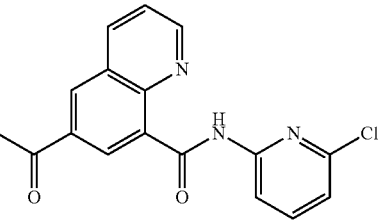 | >30,000 | 406.9 | II, IV, VI, XIII, XIV | I |
| 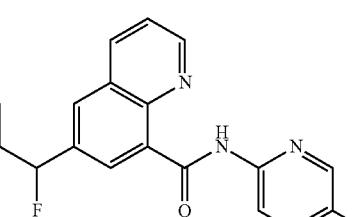 | 83 | 378.0 | II, IV, VI, XIII, XIV | I |
| 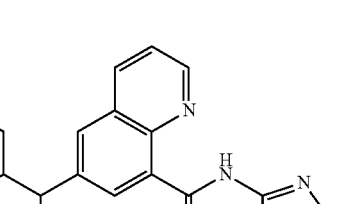 | 127 | 379.9 | II, IV, VI, XIII, XIV | I |
| 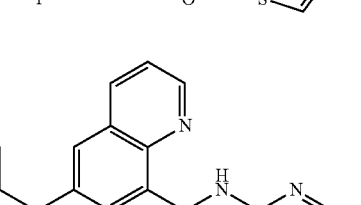 | 109 | 395.9 | II, IV, VI, XIII, XIV | I |
| 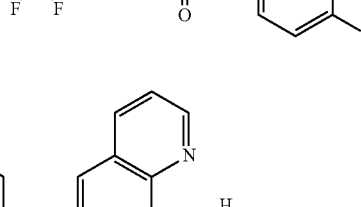 | 39 | 398.1 | II, IV, VI, XIII, XIV | I |
| 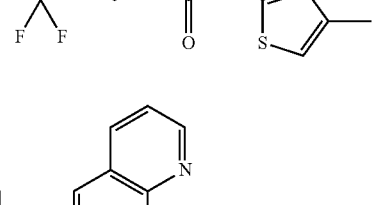 | 890 | 390.0 | III, VIII, IX, XI, XV | I |

TABLE 1-continued

| Structure | mGluR5 IC$_{50}$ (nM) | [M + H]$^+$ | Intermediate Route Reference | Analog Synthetic Route Reference |
|---|---|---|---|---|
| 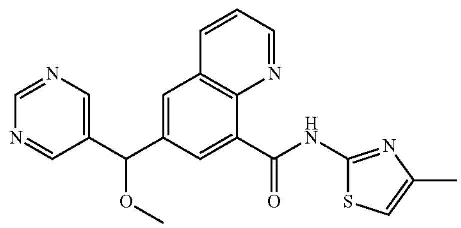 [SMILES: COC(c1cncnc1)c1cc(C(=O)Nc2nc(C)cs2)c2ncccc2c1] | 552 | 392.0 | III, VIII, IX, XI, XV | I |
| 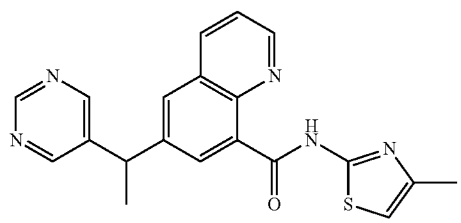 | 258 | 376.0 | III, VIII, X, XV | I |
| 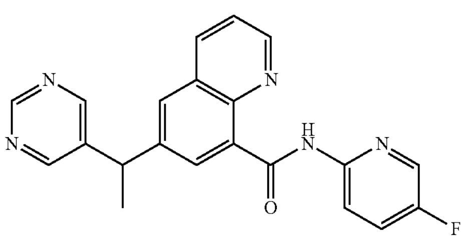 [SMILES: CC(c1cncnc1)c1cc(C(=O)Nc2ccc(F)cn2)c2ncccc2c1] | 540 | 374.0 | III, VIII, X, XV | I |
| 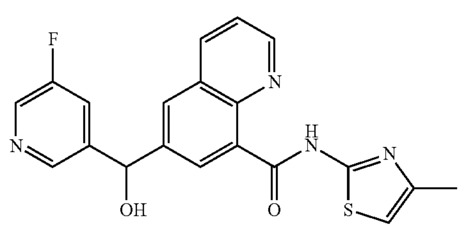 [SMILES: Cc1csc(NC(=O)c2cc(C(O)c3cncc(F)c3)cc3cccnc23)n1] | >30,000 | 395.0 | II, IV, VI, XIII, XIV | I & II |
| | >10,000$^b$ | 375.0 | I, II, IV, VI, XIII, XIV | I |
| 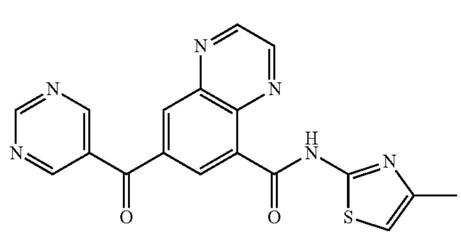 | 380 | 377.0 | I, II, IV, VI, XIII, XIV | I |

TABLE 1-continued

| Structure | mGluR5 IC$_{50}$ (nM) | [M + H]$^+$ | Intermediate Route Reference | Analog Synthetic Route Reference |
|---|---|---|---|---|
| (structure) | 176 | 390.9 | I, II, IV, VI, XIII, XIV | I |
| (structure) | 3090 | 371.0 | I, II, IV, VI, XIII, XIV | I |
| (structure) | >10,000$^b$ | 379.0 | I, III, VIII, IX, XV | I |
| (structure) | >10,000$^b$ | 378.1 | II, IV, V | I & II |

E. Pharmaceutical Compositions

In one aspect, the invention relates to pharmaceutical compositions comprising the disclosed compounds. That is, a pharmaceutical composition can be provided comprising a therapeutically effective amount of at least one disclosed compound, at least one product of a disclosed method, or a pharmaceutically acceptable salt, solvate, hydrate, or polymorph thereof, and a pharmaceutically acceptable carrier.

In one aspect, the invention relates to pharmaceutical compositions comprising a pharmaceutically acceptable carrier and an effective amount of a compound represented by a formula:

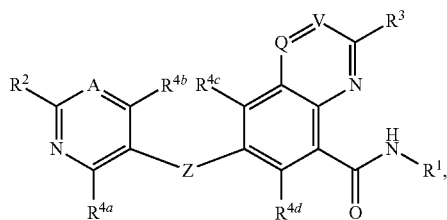

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —$(C=O)R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —$(C=O)R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8(O)_rR^9$—, —$CR^8NR^{10a}R^{10b}$—, —(C=O)—, and a structure represented by a formula:

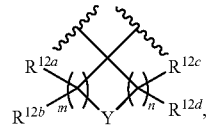

wherein Y is selected from —$CR^8R^9$—, —O—, —$S(O)_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —$S(O)_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O)$R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —$NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, —$NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof.

In a further aspect, the effective amount is a therapeutically effective amount. In a still further aspect, the effective amount is a prophylactically effective amount.

In a further aspect, the pharmaceutical composition comprises a disclosed compound. In a yet further aspect, the pharmaceutical composition comprises a product of a disclosed method of making.

In a further aspect, the pharmaceutical composition comprises a compound that exhibits partial or total inhibition of mGluR5 response to glutamate as a decrease in response to non-maximal concentrations of glutamate in human embryonic kidney cells transfected with mGluR5 in the presence of the compound, compared to the response to glutamate in the absence of the compound. In a still further aspect, the human embryonic kidney cells transfected with rat mGluR5. In a yet further aspect, the human embryonic kidney cells transfected with human mGluR5.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, *acacia*, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require negative allosteric modulation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating glutamate receptor activity (e.g., treatment of one or more neurological and/or psychiatric disorder associated with glutamate dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

F. Methods of Using the Compounds and Compositions

The amino acid L-glutamate (referred to herein simply as glutamate) is the principal excitatory neurotransmitter in the mammalian central nervous system (CNS). Within the CNS, glutamate plays a key role in synaptic plasticity (e.g., long term potentiation (the basis of learning and memory)), motor control and sensory perception. It is now well understood that a variety of neurological and psychiatric disorders are associated with dysfunctions in the glutamatergic system. Thus, modulation of the glutamatergic system is an important therapeutic goal. Glutamate acts through two distinct receptors: ionotropic and metabotropic glutamate receptors. The first class, the ionotropic glutamate receptors, is comprised of multi-subunit ligand-gated ion channels that mediate excitatory post-synaptic currents. Three subtypes of ionotropic glutamate receptors have been identified, and despite glutamate serving as agonist for all three receptor subtypes, selective ligands have been discovered that activate each subtype. The ionotropic glutamate receptors are named after their respective selective ligands: kainite receptors, AMPA receptors and NMDA receptors.

The second class of glutamate receptor, termed metabotropic glutamate receptors, (mGluRs), are G-protein coupled receptors (GPCRs) that modulate neurotransmitter release or the strength of synaptic transmission, based on their location (pre- or post-synaptic). The mGluRs are family C GPCR, characterized by a large (~560 amino acid) "venus fly trap" agonist binding domain in the amino-terminal domain of the receptor. This unique agonist binding domain distinguishes family C GPCRs from family A and B GPCRs wherein the agonist binding domains are located within the 7-strand transmembrane spanning (7TM) region or within the extracellular loops that connect the strands to this region. To date, eight distinct mGluRs have been identified, cloned and sequenced. Based on structural similarity, primary coupling to intracellular signaling pathways and pharmacology, the mGluRs have been assigned to three groups: Group I (mGluR1 and mGluR5), Group II (mGluR2 and mGluR3) and Group III (mGluR4, mGluR6, mGluR7 and mGluR8). Group I mGluRs are coupled through G$\alpha$q/11 to increase inositol phosphate and metabolism and resultant increases in intracellular calcium. Group I mGluRs are primarily located post-synaptically and have a modulatory effect on ion channel activity and neuronal excitability. Group II (mGluR2 and mGluR3) and Group III (mGluR4, mGluR6, mGluR7 and mGluR8) mGluRs are primarily located pre-synaptically where they regulate the release of neurotransmitters, such as glutamate. Group II and Group III mGluRs are coupled to G$\alpha$i and its associated effectors such as adenylate cyclase.

Post-synaptic mGluRs are known to functionally interact with post-synaptic ionotropic glutamate receptors, such as the NMDA receptor. For example, activation of mGluR5 by a selective agonist has been shown to increase post-synaptic NMDA currents (Mannaioni et al., *J. Neurosci.* (2001) 21:5925-5934). Therefore, modulation of mGluRs is an approach to modulating glutamatergic transmission. Numerous reports indicate that mGluR5 plays a role in a number of disease states including anxiety (Spooren et al., *J. Pharmacol. Exp. Therapeut.* (2000) 295:1267-1275, Tatarczynska et al., *Br. J. Pharmacol.* (2001) 132:1423-1430), addiction to cocaine (Chiamulera et al., *Nature Neurosci.* (2001) 4:873-874), Parkinson's disease (Awad et al., *J. Neurosci.* 20:7871-7879 (2000), Ossowska et al., *Neuropharmacol.* (2001) 41: 413-420), pain (Salt and Binns, *Neurosci.* 100:375-380 (2001)), Fragile X syndrome ("FXS", see de Vrij F M S, et al. *Neurobiol Disease* (2008) 31(1):127-132; Yan Q J, et al. *Neuropharmacol* (2005) 49(7):1053-1066), GERD (Jensen, J., Lehmann, A., Uvebrant, A., Carlsson, A., Jerndal, G., Nilsson, K., Frisby, C., Blackshaw, L. A., and Mattsson, J. P. Eur. J. Pharmacol. (2005) 519, 154-157), nicotine addiction (Tronci, V., et al. Psychopharmacology (2010) 211, 33-42), morphine addiction (Kotlinska, J. and Bochenski, M. Eur. J. Pharmacol. (2007) 558, 113-118), methamphetamine addiction (Gass, J. T., et al. Neuropsychopharmacology (2009) 34, 820-833), and alcohol addiction (Lominac, K. D., et al. Drug Alcohol Depend. 85, 142-156).

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In one aspect, the subject compounds can be coadministered with anti-Alzheimer's agents, beta-secretase inhibitors, gamma-secretase inhibitors, muscarinic agonists, muscarinic potentiators, HMG-CoA reductase inhibitors, NSAIDs and anti-amyloid antibodies.

In a further aspect, the subject compounds can be administered in combination with sedatives, hypnotics, anxiolytics, antipsychotics, anti-epileptics, selective serotonin reuptake inhibitors ("SSRI") and/or selective serotonin and norepinephrine reuptake inhibitors ("SSNRI"), tricyclic antidepressant drugs, monoamine oxidase inhibitors (MAOIs), 5-HT2 agonists or antagonists, GlyT1 inhibitors and the like such as, but not limited to: risperidone, clozapine, olanzapine, haloperidol, fluoxetine, prazepam, xanomeline, lithium, phenobarbitol, and salts thereof and combinations thereof.

In a further aspect, the subject compound can be used in combination with levodopa (with or without a selective extracerebral decarboxylase inhibitor), anti-cholinergics such as biperiden, COMT inhibitors such as entacapone, A2a adenosine antagonists, cholinergic agonists, NMDA receptor agonists or antagonists and dopamine agonists.

In a further aspect, the subject compound can be administered in combination with opiate agonists or antagonists, calcium channel antagonists, sodium channel antagonists, COX-2 selective inhibitors, NK1 antagonists, non-steroidal anti-inflammatory drugs ("NSAID"), GABA-A receptor modulators, dopamine agonists or antagonists, norepinephrine modulators, nicotinic agonists or antagonists including nicotine, and muscarinic agonists or antagonists. In a yet further aspect, the subject compound can be administered in combination with heroin substituting drugs such as methadone, levo-alpha-acetylmethadol, buprenorphine and naltrexone, and disulfiram and acamprosate. In a further aspect, the subject compound can be administered in combination with L-DOPA, buspirone, valproate, and gabapentin.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of neurological and psychiatric disorders associated with glutamate dysfunction. Thus, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more neurological and/or psychiatric disorders associated with glutamate dysfunction in a subject comprising the step of administering to the subject at least one disclosed compound; at least one disclosed pharmaceutical composition; and/or at least one disclosed product in a dosage and amount effective to treat the disorder in the subject.

Examples of disorders associated with glutamate dysfunction include: acute and chronic neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, addictive behavior, including addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.), obesity, psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder. In a further aspect, examples of disorders associated with glutamate dysfunction include, of mood disorders, specifically depression, treatment-resistant depression, and depressive-like states that respond to ketamine treatment.

Anxiety disorders that can be treated or prevented by the compositions disclosed herein include generalized anxiety disorder, panic disorder, and obsessive compulsive disorder. Addictive behaviors include addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.) and substance tolerance.

Also provided is a method for treating or prevention anxiety, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder, and anxiety disorder not otherwise specified.

Further disorders that can be treated or prevented by the compositions disclosed herein include Autism spectrum disorders, which are neuropsychiatric conditions characterized by widespread abnormalities of social interactions and communication, as well as severely restricted interests and highly repetitive behavior. Autism spectrum disorders include Autism, Asperger syndrome, Childhood Disintegrative Disorders, Pervasive Developmental Disorder Not Otherwise Specified (PDD-NOS), sometimes called atypical autism, and Rett Syndrome. Fragile X syndrome (FXS) is a single gene disorder almost universally associated with symptoms of autism spectrum disorder, the most common form of inherited mental retardation, and the most common known cause of autism, affecting 1 in 6,000 births. Therapeutic agents for treatment of patients with FXS are among the most critical of unmet medical needs, and there are very few proven effective treatment strategies for this patient population. Again, without wishing to be bound by theory, increasing evidence has identified a connection between the fragile X phenotype and mGluR signaling Compounds of the invention can be used, for example, for the treatment of fragile X syndrome and autism spectrum disorders in a manner that can improve symptoms (e.g., reduce anxiety and irritability; increase cognitive function, communication and/or social interaction). Thus, the methods of the invention can provide an effective manner to treat a subject having fragile X syndrome or autism spectrum disorder.

a. Treating a Disorder Associated with Metabotropic Glutamate Receptor Activity

In one aspect, the invention relates to a method for the treatment of a disorder associated with metabotropic glutamate receptor activity in a mammal comprising the step of administering to the mammal an amount of at least one disclosed compound, at least one disclosed product in a dosage, or at least one product of a disclosed method of making a compound. In a further aspect, the amount administered to the mammal is a therapeutically effective amount to treat a disorder in the mammal, wherein the disorder is associated with metabotropic glutamate receptor activity. In a yet further aspect, the mammal is a human. In a still further aspect, the metabotropic glutamate receptor is mGluR5.

Thus, in one aspect, the invention relates to a method for the treatment of a disorder associated with metabotropic glutamate receptor activity in a mammal comprising the step of administering to the mammal a therapeutically effective amount of a compound having a structure represented by a formula:

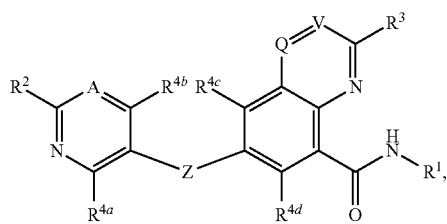

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, $NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8(O)_rR^9$—, —$CR^8NR^{10a}R^{10b}$—, —(C=O)—, and a structure represented by a formula:

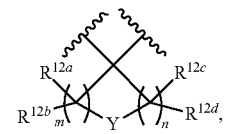

wherein Y is selected from —$CR^8R^9$—, —O—, —$S(O)_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —$S(O)_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^5$, —$NR^{51a}R^{51b}$, —$SO_2R^{52}$, and —(C=O)$R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —NR$^{54a}$R$^{54b}$; wherein each occurrence of each of R$^{54a}$ and R$^{54b}$, when present, is independently selected from hydrogen, C1-C3 alkyl, C1-C3 monohaloalkyl, C1-C3 polyhaloalkyl, and cyclopropyl; or wherein R$^{54a}$ and R$^{54b}$, when present, are optionally covalently bonded and, together with nitrogen atom to which they are attached, comprise a 3- to 6-membered heterocycle; wherein each occurrence of R$^{53}$, when present, is independently from C1-C3 alkyl, C1-C3 monohaloalkyl, C1-C3 polyhaloalkyl, cyclopropyl, and, —NR$^{55a}$R$^{55b}$; wherein each occurrence of each of R$^{55a}$ and R$^{55b}$, when present, is independently selected from hydrogen, C1-C3 alkyl, C1-C3 monohaloalkyl, C1-C3 polyhaloalkyl, and cyclopropyl; or wherein R$^{55a}$ and R$^{55b}$, when present, are optionally covalently bonded and, together with nitrogen atom to which they are attached, comprise a 3- to 6-membered heterocycle; wherein R$^2$ is selected from hydrogen, C1-C3 alkyl, C1-C3 monohaloalkyl, C1-C3 polyhaloalkyl, and cyclopropyl; wherein R$^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$, is independently selected from hydrogen and fluoro; or a pharmaceutically acceptable salt, solvate, or polymorph thereof.

In a further aspect, the compound administered is any disclosed compound or at least one product of a disclosed method.

In a further aspect, the mammal is a human. In a still further aspect, the metabotropic glutamate receptor is mGluR5.

In a further aspect, the compound exhibits partial inhibition of mGluR5 response.

In a still further aspect, the compound exhibits total inhibition of mGluR5 response.

In a further aspect, the compound exhibits noncompetitive antagonism of metabotropic glutamate receptor activity. In a yet further aspect, the compound exhibits negative allosteric modulation of metabotropic glutamate receptor activity. In a still further aspect, the compound exhibits noncompetitive inhibition of metabotropic glutamate receptor activity. In an even further aspect, the compound exhibits allosteric inhibition of metabotropic glutamate receptor activity. In a still further aspect, the compound exhibits allosteric antagonism of metabotropic glutamate receptor activity. In a yet further aspect, the compound exhibits inhibition of metabotropic glutamate receptor activity.

In a further aspect, the compound exhibits partial inhibition of mGluR5 response.

In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits negative allosteric modulation with an IC$_{50}$ of less than about $30 \times 10^{-6}$ M. In an even further aspect, the compound exhibits negative allosteric modulation with an IC$_{50}$ of less than about $10 \times 10^{-6}$ M. In a yet further aspect, the compound exhibits negative allosteric modulation with an IC$_{50}$ of less than about $1.0 \times 10^{-6}$ M. In a still further aspect, the compound exhibits negative allosteric modulation with an IC$_{50}$ of less than about $1.0 \times 10^{-7}$ M. In an even further aspect, the compound exhibits negative allosteric modulation with an IC$_{50}$ of less than about $1.0 \times 10^{-8}$ M. In a yet further aspect, the compound exhibits negative allosteric modulation with an IC$_{50}$ of less than about $1.0 \times 10^{-9}$ M. In a still further aspect, the compound exhibits negative allosteric modulation inhibition with an IC$_{50}$ of between about $1 \times 10^{-5}$ M to about $1 \times 10^{-9}$ M. In an even further aspect, the compound exhibits negative allosteric modulation with an IC$_{50}$ of between about from about $1 \times 10^{-6}$ M to about $1 \times 10^{-9}$ M. In a yet further aspect, the compound exhibits negative allosteric modulation with an IC$_{50}$ of between about from about $1 \times 10^{-7}$ M to about $1 \times 10^{-9}$ M. In a still further aspect, the compound exhibits negative allosteric modulation with an IC$_{50}$ of between about $1 \times 10^{-8}$ M to about $1 \times 10^{-9}$ M.

In a further aspect, the compound exhibits partial or total inhibition with an IC$_{50}$ of less than about $30 \times 10^{-6}$ M. In an even further aspect, the compound exhibits partial or total inhibition with an IC$_{50}$ of less than about $10 \times 10^{-6}$ M. In a yet further aspect, the compound exhibits partial or total inhibition with an IC$_{50}$ of less than about $1.0 \times 10^{-6}$ M. In a still further aspect, the compound exhibits partial or total inhibition with an IC$_{50}$ of less than about $1.0 \times 10^{-7}$ M. In an even further aspect, the compound exhibits partial or total inhibition with an IC$_{50}$ of less than about $1.0 \times 10^{-8}$ M. In a yet further aspect, the compound exhibits partial or total inhibition with an IC$_{50}$ of less than about $1.0 \times 10^{-9}$ M. In a still further aspect, the compound exhibits partial or total inhibition with an IC$_{50}$ of between about $1 \times 10^{-5}$ M to about $1 \times 10^{-9}$ M. In an even further aspect, the compound exhibits partial or total inhibition with an IC$_{50}$ of between about from about $1 \times 10^{-6}$ M to about $1 \times 10^{-9}$ M. In a yet further aspect, the compound exhibits partial or total inhibition with an IC$_{50}$ of between about from about $1 \times 10^{-7}$ M to about $1 \times 10^{-9}$ M. In a still further aspect, the compound exhibits partial or total inhibition with an IC$_{50}$ of between about $1 \times 10^{-8}$ M to about $1 \times 10^{-9}$ M.

In a further aspect, the mammal has been diagnosed with a need for treatment of the disorder prior to the administering step. In a still further aspect, the method further comprises the step of identifying a mammal in need of treatment of the disorder.

In a yet further aspect, the mammal has been diagnosed with a need for treatment of a disorder related to metabotropic glutamate receptor activity prior to the administering step. In a still further aspect, the method further comprises the step of identifying a mammal in need of treating a metabotropic glutamate receptor activity dysfunction. In a yet further aspect, the treating metabotropic glutamate receptor activity treats a disorder associated with metabotropic glutamate receptor activity in the mammal.

In a further aspect, the disorder is a neurological and/or psychiatric disorder associated with glutamate dysfunction. In a still further aspect, neurological and/or psychiatric disorder is selected from addiction, anxiety, fragile x syndrome, gastroesophageal reflux disease (GERD), Parkinson's disease, and pain. In a yet further aspect, the neurological and/or psychiatric disorder is selected from affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, Huntington's-related chorea, levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression.

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder is a disease of uncontrolled cellular proliferation. In a still further aspect, the disease of uncontrolled cellular proliferation is cancer. In a yet further aspect, the disease of uncontrolled cellular proliferation is selected from breast cancer, renal cancer, gastric cancer, and colorectal cancer. In an even further aspect, the disease of uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

b. Decreasing Metabotropic Glutamate Receptor Activity

In one aspect, the invention relates to a method for decreasing metabotropic glutamate receptor activity in a mammal comprising the step of administering to the mammal an amount of at least one disclosed compound, at least one disclosed product in a dosage, or at least one product of a disclosed method of making a compound. In a further aspect, the amount administered to the mammal is a therapeutically effective amount to treat a disorder in the mammal, wherein the disorder is associated with metabotropic glutamate receptor activity. In a yet further aspect, the mammal is a human. In a still further aspect, the metabotropic glutamate receptor is mGluR5

Thus, in one aspect, the invention relates to a method for decreasing metabotropic glutamate receptor activity in a mammal comprising the step of administering to the mammal a therapeutically effective amount of at least one compound having a structure represented by a formula:

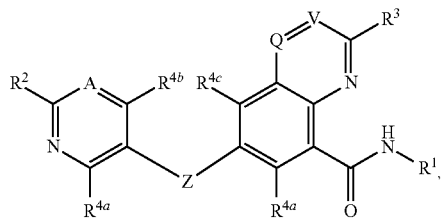

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, $-NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, $-NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from $-CR^8(O)_rR^9-$, $-CR^8NR^{10a}R^{10b}-$, $-(C=O)-$, and a structure represented by a formula:

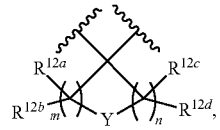

wherein Y is selected from $-CR^8R^9-$, $-O-$, $-S(O)_q-$, and $-NR^8-$; wherein m is an integer selected from 0, 1, and 2; wherein n is an integer selected from 0 and 1; wherein the sum of m and n is 1 or 2 when Y is $-CR^8R^9-$; wherein the sum of m and n is 2 when Y is $-O-$, $-S(O)_q-$, and $-NR^8-$; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is $-CR^8(O)_rR^9-$ and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is $-CR^8(O)_rR^9-$ and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, $-CN$, C1-C3 alkyl, C1-C3 monohaloalkyl, C1-C3 polyhaloalkyl, cyclopropyl, $-OR^{50}$, $-NR^{51a}R^{51b}$, $-SO_2R^{52}$, and $-(C=O)R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, $-NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, $-NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, $-CN$, C1-C3 alkyl, C1-C3 monohaloalkyl, C1-C3 polyhaloalkyl, cyclopropyl, $-OR^{60}$, $-NR^{61a}R^{61b}$, $-SO_2R^{62}$, and $-(C=O)R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, $-NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, $-NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof.

In a further aspect, the compound administered is any disclosed compound or at least one product of a disclosed method.

In a further aspect, the mammal is a human. In a still further aspect, the metabotropic glutamate receptor is mGluR5.

In a further aspect, the compound exhibits partial inhibition of mGluR5 response.

In a still further aspect, the compound exhibits total inhibition of mGluR5 response.

In a further aspect, the compound exhibits noncompetitive antagonism of metabotropic glutamate receptor activity. In a yet further aspect, the compound exhibits negative allosteric modulation of metabotropic glutamate receptor activity. In a still further aspect, the compound exhibits noncompetitive inhibition of metabotropic glutamate receptor activity. In an even further aspect, the compound exhibits allosteric inhibition of metabotropic glutamate receptor activity. In a still further aspect, the compound exhibits allosteric antagonism of metabotropic glutamate receptor activity. In a yet further aspect, the compound exhibits inhibition of metabotropic glutamate receptor activity.

In a further aspect, the compound exhibits partial inhibition of mGluR5 response. In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits negative allosteric modulation with an $IC_{50}$ of less than about $30\times10^{-6}$ M. In an even further aspect, the compound exhibits negative allosteric modulation with an $IC_{50}$ of less than about $10\times10^{-6}$ M. In a yet further aspect, the compound exhibits negative allosteric modulation with an $IC_{50}$ of less than about $1.0\times10^{-6}$ M. In a still further aspect, the compound exhibits negative allosteric modulation with an $IC_{50}$ of less than about $1.0\times10^{-7}$ M. In an even further aspect, the compound exhibits negative allosteric modulation with an $IC_{50}$ of less than about $1.0\times10^{-8}$ M. In a yet further aspect, the compound exhibits negative allosteric modulation with an $IC_{50}$ of less than about $1.0\times10^{-9}$ M. In a still further aspect, the compound exhibits negative allosteric modulation inhibition with an $IC_{50}$ of between about $1\times10^{-5}$ M to about $1\times10^{-9}$ M. In an even further aspect, the compound exhibits negative allosteric modulation with an $IC_{50}$ of between about from about $1\times10^{-6}$ M to about $1\times10^{-9}$ M. In a yet further aspect, the compound exhibits negative allosteric modulation with an $IC_{50}$ of between about from about $1\times10^{-7}$ M to about $1\times10^{-9}$ M. In a still further aspect, the compound exhibits negative allosteric modulation with an $IC_{50}$ of between about $1\times10^{-8}$ M to about $1\times10^{-9}$ M.

In a further aspect, the compound exhibits partial or total inhibition with an $IC_{50}$ of less than about $30\times10^{-6}$ M. In an even further aspect, the compound exhibits partial or total inhibition with an $IC_{50}$ of less than about $10\times10^{-6}$ M. In a yet further aspect, the compound exhibits partial or total inhibition with an $IC_{50}$ of less than about $1.0\times10^{-6}$ M. In a still further aspect, the compound exhibits partial or total inhibition with an $IC_{50}$ of less than about $1.0\times10^{-7}$ M. In an even further aspect, the compound exhibits partial or total inhibition with an $IC_{50}$ of less than about $1.0\times10^{-7}$ M. In a yet further aspect, the compound exhibits partial or total inhibition with an $IC_{50}$ of less than about $1.0\times10^{-9}$ M. In a still further aspect, the compound exhibits partial or total inhibition with an $IC_{50}$ of between about $1\times10^{-5}$ M to about $1\times10^{-9}$ M. In an even further aspect, the compound exhibits partial or total inhibition with an $IC_{50}$ of between about from about $1\times10^{-6}$ M to about $1\times10^{-9}$ M. In a yet further aspect, the compound exhibits partial or total inhibition with an $IC_{50}$ of between about from about $1\times10^{-7}$ M to about $1\times10^{-9}$ M. In a still further aspect, the compound exhibits partial or total inhibition with an $IC_{50}$ of between about $1\times10^{-8}$ M to about $1\times10^{-9}$ M.

In a further aspect, the mammal has been diagnosed with a need for treatment of a disorder prior to the administering step. In a still further aspect, the method further comprises the step of identifying a mammal in need of treatment of a disorder.

In a further aspect, the mammal has been diagnosed with a need for decreasing metabotropic glutamate receptor activity prior to the administering step. In a still further aspect, the method further comprises the step of identifying a mammal in need of decreasing metabotropic glutamate receptor activity. In an even further aspect, the decrease in metabotropic glutamate receptor activity treats a disorder associated with metabotropic glutamate receptor activity in the mammal. In a yet further aspect, the mammal has been diagnosed with a need for treatment of a disorder related to metabotropic glutamate receptor activity prior to the administering step.

In a further aspect, the disorder is a neurological and/or psychiatric disorder associated with glutamate dysfunction. In a still further aspect, neurological and/or psychiatric disorder is selected from addiction, anxiety, fragile x syndrome, gastroesophageal reflux disease (GERD), Parkinson's disease, and pain. In a yet further aspect, the neurological and/or psychiatric disorder is selected from affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, Huntington's-related chorea, levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression.

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder is a disease of uncontrolled cellular proliferation. In a still further aspect, the disease of uncontrolled cellular proliferation is cancer. In a yet further aspect, the disease of uncontrolled cellular proliferation is selected from breast cancer, renal cancer, gastric cancer, and colorectal cancer. In an even further aspect, the disease of uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

c. Inhibiting Metabotropic Glutamate Receptor Activity

In one aspect, the invention relates to a method for inhibiting metabotropic glutamate receptor activity in a mammal comprising the step of administering to the mammal an amount of at least one disclosed compound, at least one disclosed product in a dosage, or at least one product of a disclosed method of making a compound. In a further aspect, the amount administered to the mammal is a therapeutically effective amount to treat a disorder in the mammal, wherein the disorder is associated with metabotropic glutamate receptor activity. In a yet further aspect, the mammal is a human. In a still further aspect, the metabotropic glutamate receptor is mGluR5.

Thus, in one aspect, the invention relates to a method for inhibiting metabotropic glutamate receptor activity in a mammal comprising the step of administering to the mammal a therapeutically effective amount of least one compound having a structure represented by a formula:

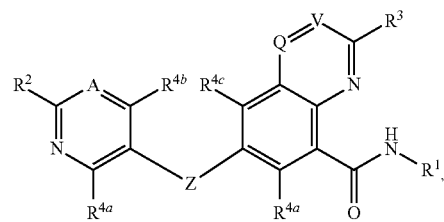

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein Q is selected from N and CR$^6$; wherein R$^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle; wherein R$^{32}$, when present, is selected from C1-C3 alkyl, C1-C3 monohaloalkyl, C1-C3 polyhaloalkyl, cyclopropyl, and, —NR$^{34a}$R$^{34b}$; wherein each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with nitrogen atom to which they are attached, comprise a 3- to 6-membered heterocycle; wherein R$^{33}$, when present, is selected from C1-C3 alkyl, C1-C3 monohaloalkyl, C1-C3 polyhaloalkyl, cyclopropyl, and, —NR$^{35a}$R$^{35b}$; wherein each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; wherein V is selected from N and CR$^7$, provided that Q and V are not simultaneously N; wherein R$^7$, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and, —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and, —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with nitrogen atom to which they are attached, comprise a 3- to 6-membered heterocycle; wherein Z is selected from —CR$^8$(O)$_r$R$^9$—, —CR$^8$NR$^{10a}$R$^{10b}$—, —(C=O)—, and a structure represented by a formula:

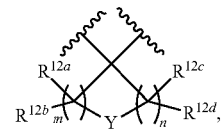

wherein Y is selected from —CR$^8$R$^9$—, —O—, —S(O)$_q$—, and —NR$^8$—; wherein m is an integer selected from 0, 1, and 2; wherein n is an integer selected from 0 and 1; wherein the sum of m and n is 1 or 2 when Y is —CR$^8$R$^9$—; wherein the sum of m and n is 2 when Y is —O—, —S(O)$_q$—, and —NR$^8$—; wherein q is 0, 1, or 2; wherein r is 0 or 1; wherein R$^8$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^8$ is not halogen; wherein R$^9$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^9$ is not halogen; wherein each of R$^{10a}$ and R$^{10b}$, when present, is independently selected from hydrogen, C1-C3 alkyl, C1-C3 monohaloalkyl, C1-C3 polyhaloalkyl, and cyclopropyl; wherein each occurrence of R$^{12a}$, R$^{12a}$, R$^{12a}$, and R$^{12a}$, when present, is independently selected from hydrogen, halogen, C1-C3 alkyl, C1-C3 monohaloalkyl, and C1-C3 polyhaloalkyl; wherein R$^1$ is selected from aryl and heteroaryl, and wherein R$^1$ is substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$; wherein each occurrence of R$^{50}$, when present, is independently selected from hydrogen, C1-C3 alkyl, C1-C3 monohaloalkyl, C1-C3 polyhaloalkyl, and cyclopropyl; wherein each occurrence of each of R$^{51a}$ and R$^{51b}$, when present, is independently selected from hydrogen, C1-C3 alkyl, C1-C3 monohaloalkyl, C1-C3 polyhaloalkyl, and cyclopropyl; or wherein R$^{51a}$ and R$^{51b}$, when present, are optionally covalently bonded and, together with nitrogen atom to which they are attached, comprise a 3- to 6-membered heterocycle; wherein each occurrence of R$^{52}$, when present, is independently selected from C1-C3 alkyl, C1-C3 monohaloalkyl, C1-C3 polyhaloalkyl, cyclopropyl, and, —NR$^{54a}$R$^{54b}$; wherein each occurrence of each of R$^{54a}$ and R$^{54b}$, when present, is independently selected from hydrogen, C1-C3 alkyl, C1-C3 monohaloalkyl, C1-C3 polyhaloalkyl, and cyclopropyl; or wherein R$^{54a}$ and R$^{54b}$, when present, are optionally covalently bonded and, together with nitrogen atom to which they are attached, comprise a 3- to 6-membered heterocycle; wherein each occurrence of R$^{53}$, when present, is independently from C1-C3 alkyl, C1-C3 monohaloalkyl, C1-C3 polyhaloalkyl, cyclopropyl, and, —NR$^{55a}$R$^{55b}$; wherein each occurrence of each of R$^{55a}$ and R$^{55b}$, when present, is independently selected from hydrogen, C1-C3 alkyl, C1-C3 monohaloalkyl, C1-C3 polyhaloalkyl, and cyclopropyl; or wherein R$^{55a}$ and R$^{55b}$, when present, are optionally covalently bonded and, together with nitrogen atom to which they are attached, comprise a 3- to 6-membered heterocycle; wherein R$^{2}$ is selected from hydrogen, C1-C3 alkyl, C1-C3 monohaloalkyl, C1-C3 polyhaloalkyl, and cyclopropyl; wherein R$^{3}$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$, is independently selected from hydrogen and fluoro; or a pharmaceutically acceptable salt, solvate, or polymorph thereof.

In a further aspect, the compound administered is any disclosed compound or at least one product of a disclosed method.

In a further aspect, the mammal is a human. In a still further aspect, the metabotropic glutamate receptor is mGluR5.

In a further aspect, the compound exhibits noncompetitive antagonism of metabotropic glutamate receptor activity. In a yet further aspect, the compound exhibits negative allosteric modulation of metabotropic glutamate receptor activity. In a still further aspect, the compound exhibits noncompetitive inhibition of metabotropic glutamate receptor activity. In an even further aspect, the compound exhibits allosteric inhibition of metabotropic glutamate receptor activity. In a still further aspect, the compound exhibits allosteric antagonism of metabotropic glutamate receptor activity.

In a further aspect, the compound exhibits partial inhibition of mGluR5 response.

In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits negative allosteric modulation with an IC$_{50}$ of less than about 30×10$^{-6}$ M. In an even further aspect, the compound exhibits negative allosteric modulation with an IC$_{50}$ of less than about 10×10$^{-6}$ M. In a yet further aspect, the compound exhibits negative allosteric modulation with an IC$_{50}$ of less than about 1.0×10$^{-6}$ M. In a still further aspect, the compound exhibits negative allosteric modulation with an IC$_{50}$ of less than about 1.0×10$^{-7}$ M. In an even further aspect, the compound exhibits negative allosteric modulation with an IC$_{50}$ of less than about 1.0×10$^{-8}$ M. In a yet further aspect, the compound exhibits negative allosteric modulation with an IC$_{50}$ of less than about 1.0×10$^{-9}$ M. In a still further aspect, the compound exhibits negative allosteric modulation inhibition with an IC$_{50}$ of between about 1×10$^{-5}$ M to about 1×10$^{-9}$ M. In an even further aspect, the compound exhibits negative allosteric modulation with an IC$_{50}$ of between about from about 1×10$^{-6}$ M to about 1×10$^{-9}$ M. In a yet further aspect, the compound exhibits negative allosteric modulation with an IC$_{50}$ of between about from about 1×10$^{-7}$ M to about 1×10$^{-9}$ M. In a still further aspect, the compound exhibits negative allosteric modulation with an IC$_{50}$ of between about 1×10$^{-8}$ M to about 1×10$^{-9}$ M.

In a further aspect, the compound exhibits partial or total inhibition with an IC$_{50}$ of less than about 30×10$^{-6}$ M. In an even further aspect, the compound exhibits partial or total inhibition with an IC$_{50}$ of less than about 10×10$^{-6}$ M. In a yet further aspect, the compound exhibits partial or total inhibition with an IC$_{50}$ of less than about 1.0×10$^{-6}$ M. In a still further aspect, the compound exhibits partial or total inhibition with an IC$_{50}$ of less than about 1.0×10$^{-7}$ M. In an even further aspect, the compound exhibits partial or total inhibition with an IC$_{50}$ of less than about 1.0×10$^{-8}$ M. In a yet further aspect, the compound exhibits partial or total inhibition with an IC$_{50}$ of less than about 1.0×10$^{-9}$ M. In a still further aspect, the compound exhibits partial or total inhibition with an IC$_{50}$ of between about 1×10$^{-5}$ M to about 1×10$^{-9}$ M. In an even further aspect, the compound exhibits partial or total inhibition with an IC$_{50}$ of between about from about 1×10$^{-6}$ M to about 1×10$^{-9}$ M. In a yet further aspect, the compound exhibits partial or total inhibition with an IC$_{50}$ of between about from about 1×10$^{-7}$ M to about 1×10$^{-9}$ M. In a still further aspect, the compound exhibits partial or total inhibition with an IC$_{50}$ of between about 1×10$^{-8}$ M to about 1×10$^{-9}$ M.

In a further aspect, the mammal has been diagnosed with a need for treatment of a disorder prior to the administering step. In a still further aspect, the method further comprises the step of identifying a mammal in need of treatment of a disorder.

In a further aspect, the mammal has been diagnosed with a need for inhibiting metabotropic glutamate receptor activity prior to the administering step. In a still further aspect, the method further comprises the step of identifying a mammal in need of inhibiting metabotropic glutamate receptor activity. In an even further aspect, the inhibition of metabotropic glutamate receptor activity treats a disorder associated with metabotropic glutamate receptor activity in the mammal. In a yet further aspect, the mammal has been diagnosed with a need for treatment of a disorder related to metabotropic glutamate receptor activity prior to the administering step.

In a further aspect, the disorder related to metabotropic glutamate receptor activity is a neurological and/or psychiatric disorder associated with glutamate dysfunction. In a still further aspect, neurological and/or psychiatric disorder is selected from addiction, anxiety, fragile x syndrome, gastroesophageal reflux disease (GERD), Parkinson's disease, and pain. In a yet further aspect, the neurological and/or psychiatric disorder is selected from affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, Huntington's-related chorea, levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression.

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder related to metabotropic glutamate receptor activity is a disease of uncontrolled cellular proliferation. In a still further aspect, the disease of uncontrolled cellular proliferation is cancer. In a yet further aspect, the disease of uncontrolled cellular proliferation is selected from breast cancer, renal cancer, gastric cancer, and colorectal cancer. In an even further aspect, the disease of uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

d. Negative Allosteric Modulation of Metabotropic Glutamate Receptor Activity

In one aspect, the invention relates to a method for negative allosteric modulation of metabotropic glutamate receptor activity in a mammal comprising the step of administering to the mammal an amount of at least one disclosed compound, at least one disclosed product in a dosage, or at least one product of a disclosed method of making a compound. In a further aspect, the amount administered to the mammal is a therapeutically effective amount to treat a disorder in the mammal, wherein the disorder is associated with metabotropic glutamate receptor activity. In a yet further aspect, the mammal is a human. In a still further aspect, the metabotropic glutamate receptor is mGluR5.

Thus, in one aspect, the invention relates to a method for negative allosteric modulation of metabotropic glutamate receptor activity in a mammal comprising the step of administering to the mammal a therapeutically effective amount of at least one compound having a structure represented by a formula:

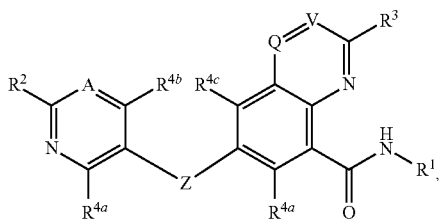

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —$(C=O)R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8(O)_rR^9$—, —$CR^8NR^{10a}R^{10b}$—, —(C=O)—, and a structure represented by a formula:

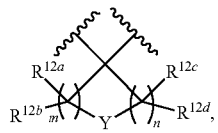

wherein Y is selected from —$CR^8R^9$—, —O—, —$S(O)_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —$S(O)_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O)$R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —$NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, —$NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof.

In a further aspect, the compound administered is any disclosed compound or at least one product of a disclosed method.

In a further aspect, the mammal is a human. In a still further aspect, the metabotropic glutamate receptor is mGluR5.

In a further aspect, the compound exhibits partial inhibition of mGluR5 response. In a still further aspect, the compound exhibits total inhibition of mGluR5 response.

In a further aspect, the compound exhibits noncompetitive antagonism of metabotropic glutamate receptor activity. In a still further aspect, the compound exhibits noncompetitive inhibition of metabotropic glutamate receptor activity. In an even further aspect, the compound exhibits inhibition of metabotropic glutamate receptor activity. In a still further aspect, the compound exhibits allosteric antagonism of metabotropic glutamate receptor activity. In a yet further aspect, the compound exhibits inhibition of metabotropic glutamate receptor activity.

In a further aspect, the compound exhibits partial inhibition of mGluR5 response. In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits negative allosteric modulation with an $IC_{50}$ of less than about $30\times10^{-6}$ M. In an even further aspect, the compound exhibits negative allosteric modulation with an $IC_{50}$ of less than about $10\times10^{-6}$ M. In a yet further aspect, the compound exhibits negative allosteric modulation with an $IC_{50}$ of less than about $1.0\times10^{-6}$ M. In a still further aspect, the compound exhibits negative allosteric modulation with an $IC_{50}$ of less than about $1.0\times10^{-7}$ M. In an even further aspect, the compound exhibits negative allosteric modulation with an $IC_{50}$ of less than about $1.0\times10^{-8}$ M. In a yet further aspect, the compound exhibits negative allosteric modulation with an $IC_{50}$ of less than about $1.0\times10^{-9}$ M. In a still further aspect, the compound exhibits negative allosteric modulation inhibition with an $IC_{50}$ of between about $1\times10^{-5}$ M to about $1\times10^{-9}$ M. In an even further aspect, the compound exhibits negative allosteric modulation with an $IC_{50}$ of between about from about $1\times10^{-6}$ M to about $1\times10^{-9}$ M. In a yet further aspect, the compound exhibits negative allosteric modulation with an $IC_{50}$ of between about from about $1\times10^{-7}$ M to about $1\times10^{-9}$ M. In a still further aspect, the compound exhibits negative allosteric modulation with an $IC_{50}$ of between about $1\times10^{-8}$ M to about $1\times10^{-9}$ M.

In a further aspect, the compound exhibits partial or total inhibition with an $IC_{50}$ of less than about $30\times10^{-6}$ M. In an even further aspect, the compound exhibits partial or total inhibition with an $IC_{50}$ of less than about $10\times10^{-6}$ M. In a yet further aspect, the compound exhibits partial or total inhibition with an $IC_{50}$ of less than about $1.0\times10^{-6}$ M. In a still further aspect, the compound exhibits partial or total inhibition with an $IC_{50}$ of less than about $1.0\times10^{-7}$ M. In an even further aspect, the compound exhibits partial or total inhibition with an $IC_{50}$ of less than about $1.0\times10^{-8}$ M. In a yet further aspect, the compound exhibits partial or total inhibition with an $IC_{50}$ of less than about $1.0\times10^{-9}$ M. In a still further aspect, the compound exhibits partial or total inhibition with an $IC_{50}$ of between about $1\times10^{-5}$ M to about $1\times10^{-9}$ M. In an even further aspect, the compound exhibits partial or total inhibition with an $IC_{50}$ of between about from about $1\times10^{-6}$ M to about $1\times10^{-9}$ M. In a yet further aspect, the compound exhibits partial or total inhibition with an $IC_{50}$ of between about from about $1\times10^{-7}$ M to about $1\times10^{-9}$ M. In a still further aspect, the compound exhibits partial or total inhibition with an $IC_{50}$ of between about $1\times10^{-8}$ M to about $1\times10^{-9}$ M.

In a further aspect, the mammal has been diagnosed with a need for treatment of a disorder prior to the administering step. In a still further aspect, the method further comprises the step of identifying a mammal in need of treatment of a disorder.

In a further aspect, the mammal has been diagnosed with a need for negative allosteric modulation of metabotropic glutamate receptor activity prior to the administering step. In a still further aspect, the method further comprises the step of identifying a mammal in need of negative allosteric modulation of metabotropic glutamate receptor activity. In an even further aspect, the negative allosteric modulation of metabotropic glutamate receptor activity treats a disorder associated with metabotropic glutamate receptor activity in the mammal. In a yet further aspect, the mammal has been diagnosed with a need for treatment of a disorder related to metabotropic glutamate receptor activity prior to the administering step.

In a further aspect, the disorder related to metabotropic glutamate receptor activity is a neurological and/or psychiatric disorder associated with glutamate dysfunction. In a still further aspect, neurological and/or psychiatric disorder is selected from addiction, anxiety, fragile x syndrome, gastroesophageal reflux disease (GERD), Parkinson's disease, and pain. In a yet further aspect, the neurological and/or psychiatric disorder is selected from affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, Huntington's-related chorea, levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression.

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder related to metabotropic glutamate receptor activity is a disease of uncontrolled cellular proliferation. In a still further aspect, the disease of uncontrolled cellular proliferation is cancer. In a yet further aspect, the disease of uncontrolled cellular proliferation is selected from breast cancer, renal cancer, gastric cancer, and colorectal cancer. In an even further aspect, the disease of uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

e. Noncompetitive Antagonism of Metabotropic Glutamate Receptor Activity

In one aspect, the invention relates to a method for noncompetitive antagonism of metabotropic glutamate receptor activity in a mammal comprising the step of administering to the mammal an amount of at least one disclosed compound, at least one disclosed product in a dosage, or at least one product of a disclosed method of making a compound. In a further aspect, the amount administered to the mammal is a therapeutically effective amount to treat a disorder in the mammal, wherein the disorder is associated with metabotropic glutamate receptor activity. In a yet further aspect, the mammal is a human. In a still further aspect, the metabotropic glutamate receptor is mGluR5.

Thus, in one aspect, the invention relates to a method for noncompetitive antagonism of metabotropic glutamate receptor activity in a mammal comprising the step of administering to the mammal a therapeutically effective amount of least one compound having a structure represented by a formula:

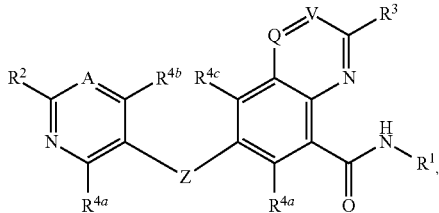

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O) $R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, $NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8$ (O)$_r R^9$—, —$CR^8 NR^{10a}R^{10b}$—, —(C=O)—, and a structure represented by a formula:

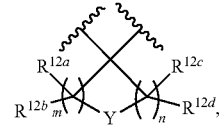

wherein Y is selected from —$CR^8R^9$—, —O—, —$S(O)_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —$S(O)_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_r R^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_r R^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O)$R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —$NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, —$NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof.

In a further aspect, the compound administered is any disclosed compound or at least one product of a disclosed method.

In a further aspect, the mammal is a human. In a still further aspect, the metabotropic glutamate receptor is mGluR5.

In a further aspect, the compound exhibits partial inhibition of mGluR5 response.

In a still further aspect, the compound exhibits total inhibition of mGluR5 response.

In a further aspect, the compound exhibits negative allosteric modulation of metabotropic glutamate receptor activity. In a still further aspect, the compound exhibits noncompetitive inhibition of metabotropic glutamate receptor activity. In an even further aspect, the compound exhibits allosteric inhibition of metabotropic glutamate receptor activity. In a still further aspect, the compound exhibits allosteric antagonism. In a yet further aspect, the compound exhibits inhibition of metabotropic glutamate receptor activity.

In a further aspect, the compound exhibits partial inhibition of mGluR5 response. In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits negative allosteric modulation with an $IC_{50}$ of less than about $30 \times 10^{-6}$ M. In an even further aspect, the compound exhibits negative allosteric modulation with an $IC_{50}$ of less than about $10 \times 10^{-6}$ M. In a yet further aspect, the compound exhibits negative allosteric modulation with an $IC_{50}$ of less than about $1.0 \times 10^{-6}$ M. In a still further aspect, the compound exhibits negative allosteric modulation with an $IC_{50}$ of less than about $1.0 \times 10^{-7}$ M. In an even further aspect, the compound exhibits negative allosteric modulation with an $IC_{50}$ of less than about $1.0 \times 10^{-8}$ M. In a yet further aspect, the compound exhibits negative allosteric modulation with an $IC_{50}$ of less than about $1.0 \times 10^{-9}$ M. In a still further aspect, the compound exhibits negative allosteric modulation inhibition with an $IC_{50}$ of between about $1 \times 10^{-5}$ M to about $1 \times 10^{-9}$ M. In an even further aspect, the compound exhibits negative allosteric modulation with an $IC_{50}$ of between about from about $1 \times 10^{-6}$ M to about $1 \times 10^{-9}$ M. In a yet further aspect, the compound exhibits negative allosteric modulation with an $IC_{50}$ of between about from about $1 \times 10^{-7}$ M to about $1 \times 10^{-9}$ M. In a still further aspect, the compound exhibits negative allosteric modulation with an $IC_{50}$ of between about $1 \times 10^{-8}$ M to about $1 \times 10^{-9}$ M.

In a further aspect, the compound exhibits partial or total inhibition with an $IC_{50}$ of less than about $30 \times 10^{-6}$ M. In an even further aspect, the compound exhibits partial or total inhibition with an $IC_{50}$ of less than about $10 \times 10^{-6}$ M. In a yet further aspect, the compound exhibits partial or total inhibition with an $IC_{50}$ of less than about $1.0 \times 10^{-6}$ M. In a still further aspect, the compound exhibits partial or total inhibition with an $IC_{50}$ of less than about $1.0 \times 10^{-7}$ M. In an even further aspect, the compound exhibits partial or total inhibition with an $IC_{50}$ of less than about $1.0 \times 10^{-8}$ M. In a yet further aspect, the compound exhibits partial or total inhibition with an $IC_{50}$ of less than about $1.0 \times 10^{-9}$ M. In a still further aspect, the compound exhibits partial or total inhibition with an $IC_{50}$ of between about $1 \times 10^{-5}$ M to about 1×10⁻⁹ M. In an even further aspect, the compound exhibits partial or total inhibition with an IC$_{50}$ of between about from about 1×10⁻⁶ M to about 1×10⁻⁹ M. In a yet further aspect, the compound exhibits partial or total inhibition with an IC$_{50}$ of between about from about 1×10⁻⁷ M to about 1×10⁻⁹ M. In a still further aspect, the compound exhibits partial or total inhibition with an IC$_{50}$ of between about 1×10⁻⁸ M to about 1×10⁻⁹ M.

In a further aspect, the mammal has been diagnosed with a need for treatment of a disorder prior to the administering step. In a still further aspect, the method further comprises the step of identifying a mammal in need of treatment of a disorder.

In a further aspect, the mammal has been diagnosed with a need for partial antagonism of metabotropic glutamate receptor activity prior to the administering step. In a still further aspect, the method further comprises the step of identifying a mammal in need of partial antagonism of metabotropic glutamate receptor activity. In an even further aspect, the partial antagonism of metabotropic glutamate receptor activity treats a disorder associated with metabotropic glutamate receptor activity in the mammal. In a yet further aspect, the mammal has been diagnosed with a need for treatment of a disorder related to metabotropic glutamate receptor activity prior to the administering step.

In a further aspect, the disorder related to metabotropic glutamate receptor activity is a neurological and/or psychiatric disorder associated with glutamate dysfunction. In a still further aspect, neurological and/or psychiatric disorder is selected from addiction, anxiety, fragile x syndrome, gastroesophageal reflux disease (GERD), Parkinson's disease, and pain. In a yet further aspect, the neurological and/or psychiatric disorder is selected from affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, Huntington's-related chorea, levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression.

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder related to metabotropic glutamate receptor activity is a disease of uncontrolled cellular proliferation. In a still further aspect, the disease of uncontrolled cellular proliferation is cancer. In a yet further aspect, the disease of uncontrolled cellular proliferation is selected from breast cancer, renal cancer, gastric cancer, and colorectal cancer. In an even further aspect, the disease of uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

f. Modulating Metabotropic Glutamate Receptor Activity

In one aspect, the invention relates to a method for modulating metabotropic glutamate receptor activity in a mammal comprising the step of administering to the mammal an amount of at least one disclosed compound, at least one disclosed product in a dosage, or at least one product of a disclosed method of making a compound. In a further aspect, the amount administered to the mammal is a therapeutically effective amount to treat a disorder in the mammal, wherein the disorder is associated with metabotropic glutamate receptor activity. In a yet further aspect, the mammal is a human. In a still further aspect, the metabotropic glutamate receptor is mGluR5.

Thus, in one aspect, the invention relates to a method for modulating metabotropic glutamate receptor activity in a mammal comprising the step of administering to the mammal a therapeutically effective amount of least one compound having a structure represented by a formula:

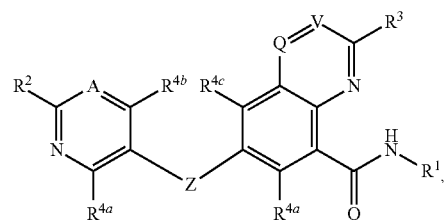

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein Q is selected from N and CR$^6$; wherein R$^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, $-NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, $-NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, $-CN$, C1-C3 alkyl, C1-C3 monohaloalkyl, C1-C3 polyhaloalkyl, cyclopropyl, $-OR^{40}$, $-NR^{41a}R^{41b}$, $-SO_2R^{42}$, and $-(C=O)R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, $-NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, $-NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from $-CR^8(O)_rR^9-$, $-CR^8NR^{10a}R^{10b}-$, $-(C=O)-$, and a structure represented by a formula:

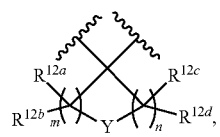

wherein Y is selected from $-CR^8R^9-$, $-O-$, $-S(O)_q-$, and $-NR^8-$; wherein m is an integer selected from 0, 1, and 2; wherein n is an integer selected from 0 and 1; wherein the sum of m and n is 1 or 2 when Y is $-CR^8R^9-$; wherein the sum of m and n is 2 when Y is $-O-$, $-S(O)_q-$, and $-NR^8-$; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is $-CR^8(O)_rR^9-$ and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is $-CR^8(O)_rR^9-$ and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, $-CN$, C1-C3 alkyl, C1-C3 monohaloalkyl, C1-C3 polyhaloalkyl, cyclopropyl, $-OR^{50}$, $-NR^{51a}R^{51b}$, $-SO_2R^{52}$, and $-(C=O)R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, $-NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, $-NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, $-CN$, C1-C3 alkyl, C1-C3 monohaloalkyl, C1-C3 polyhaloalkyl, cyclopropyl, $-OR^{60}$, $-NR^{61a}R^{61b}$, $-SO_2R^{62}$, and $-(C=O)R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, $-NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof.

In a further aspect, the compound administered is any disclosed compound or at least one product of a disclosed method.

In a further aspect, the mammal is a human. In a still further aspect, the metabotropic glutamate receptor is mGluR5.

In a further aspect, the compound exhibits partial inhibition of mGluR5 response. In a still further aspect, the compound exhibits total inhibition of mGluR5 response.

In a further aspect, the compound exhibits noncompetitive antagonism of metabotropic glutamate receptor activity. In a yet further aspect, the compound exhibits negative allosteric modulation of metabotropic glutamate receptor activity. In a still further aspect, the compound exhibits noncompetitive inhibition of metabotropic glutamate receptor activity. In an even further aspect, the compound exhibits allosteric inhibition of metabotropic glutamate receptor activity. In a still further aspect, the compound exhibits allosteric antagonism. In a yet further aspect, the compound exhibits inhibition of metabotropic glutamate receptor activity.

In a further aspect, the compound exhibits partial inhibition of mGluR5 response. In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits negative allosteric modulation with an $IC_{50}$ of less than about $30 \times 10^{-6}$ M. In an even further aspect, the compound exhibits negative allosteric modulation with an $IC_{50}$ of less than about $10 \times 10^{-6}$ M. In a yet further aspect, the compound exhibits negative allosteric modulation with an $IC_{50}$ of less than about $1.0 \times 10^{-6}$ M. In a still further aspect, the compound exhibits negative allosteric modulation with an $IC_{50}$ of less than about $1.0 \times 10^{-7}$ M. In an even further aspect, the compound exhibits negative allosteric modulation with an $IC_{50}$ of less than about $1.0 \times 10^{-8}$ M. In a yet further aspect, the compound exhibits negative allosteric modulation with an $IC_{50}$ of less than about $1.0 \times 10^{-9}$ M. In a still further aspect, the compound exhibits negative allosteric modulation inhibition with an $IC_{50}$ of between about $1 \times 10^{-5}$ M to about $1 \times 10^{-9}$ M. In an even further aspect, the compound exhibits negative allosteric modulation with an $IC_{50}$ of between about from about $1 \times 10^{-6}$ M to about $1 \times 10^{-9}$ M. In a yet further aspect, the compound exhibits negative allosteric modulation with an $IC_{50}$ of between about from about $1 \times 10^{-7}$ M to about $1 \times 10^{-9}$ M. In a still further aspect, the compound exhibits negative allosteric modulation with an $IC_{50}$ of between about $1 \times 10^{-8}$ M to about $1 \times 10^{-9}$ M.

In a further aspect, the compound exhibits partial or total inhibition with an $IC_{50}$ of less than about $30 \times 10^{-6}$ M. In an even further aspect, the compound exhibits partial or total inhibition with an $IC_{50}$ of less than about $10 \times 10^{-6}$ M. In a yet further aspect, the compound exhibits partial or total inhibition with an $IC_{50}$ of less than about $1.0 \times 10^{-6}$ M. In a still further aspect, the compound exhibits partial or total inhibition with an $IC_{50}$ of less than about $1.0 \times 10^{-7}$ M. In an even further aspect, the compound exhibits partial or total inhibition with an $IC_{50}$ of less than about $1.0 \times 10^{-7}$ M. In a yet further aspect, the compound exhibits partial or total inhibition with an $IC_{50}$ of less than about $1.0 \times 10^{-9}$ M. In a still further aspect, the compound exhibits partial or total inhibition with an $IC_{50}$ of between about $1 \times 10^{-5}$ M to about $1 \times 10^{-9}$ M. In an even further aspect, the compound exhibits partial or total inhibition with an $IC_{50}$ of between about from about $1 \times 10^{-6}$ M to about $1 \times 10^{-9}$ M. In a yet further aspect, the compound exhibits partial or total inhibition with an $IC_{50}$ of between about from about $1 \times 10^{-7}$ M to about $1 \times 10^{-9}$ M. In a still further aspect, the compound exhibits partial or total inhibition with an $IC_{50}$ of between about $1 \times 10^{-8}$ M to about $1 \times 10^{-9}$ M.

In a further aspect, the mammal has been diagnosed with a need for treatment of a disorder prior to the administering step. In a still further aspect, the method further comprises the step of identifying a mammal in need of treatment of a disorder.

In a further aspect, the mammal has been diagnosed with a need for modulation of metabotropic glutamate receptor activity prior to the administering step. In a still further aspect, the method further comprises the step of identifying a mammal in need of modulation of metabotropic glutamate receptor activity. In an even further aspect, the modulation of metabotropic glutamate receptor activity treats a disorder associated with metabotropic glutamate receptor activity in the mammal. In a yet further aspect, the mammal has been diagnosed with a need for treatment of a disorder related to metabotropic glutamate receptor activity prior to the administering step.

In a further aspect, the disorder related to metabotropic glutamate receptor activity is a neurological and/or psychiatric disorder associated with glutamate dysfunction. In a still further aspect, neurological and/or psychiatric disorder is selected from addiction, anxiety, fragile x syndrome, gastroesophageal reflux disease (GERD), Parkinson's disease, and pain. In a yet further aspect, the neurological and/or psychiatric disorder is selected from affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, Huntington's-related chorea, levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression.

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder related to metabotropic glutamate receptor activity is a disease of uncontrolled cellular proliferation. In a still further aspect, the disease of uncontrolled cellular proliferation is cancer. In a yet further aspect, the disease of uncontrolled cellular proliferation is selected from breast cancer, renal cancer, gastric cancer, and colorectal cancer. In an even further aspect, the disease of uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

g. Modulating Metabotropic Glutamate Receptor Activity in Cells

In one aspect, the invention relates to a method for modulating metabotropic glutamate receptor activity in at least one cell, comprising the step of contacting the at least one cell with an amount of at least one disclosed compound, at least one disclosed product in a dosage, or at least one product of a disclosed method of making a compound. In a further aspect, the cell is in a mammal. In a still further aspect, the mammal is human. In an even further aspect, the amount contacting the cell is effective to inhibit mGluR5 activity in the at least one cell. In a yet further aspect, the amount contacting the cell is a therapeutically effective amount to treat a disorder in the mammal, wherein the disorder is associated with metabotropic glutamate receptor activity in at least one cell. In a further aspect, the metabotropic glutamate receptor is mGluR5.

Thus, in one aspect, the invention relates to a method for modulating metabotropic glutamate receptor activity in at least one cell, comprising the step of contacting the at least one cell with an effective amount of least one compound having a structure represented by a formula:

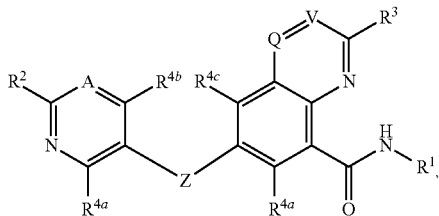

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8$(O)$_xR^9$—, —$CR^8NR^{10a}R^{10b}$—, —(C=O)—, and a structure represented by a formula:

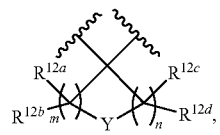

wherein Y is selected from —CR$^8$R$^9$—, —O—, —S(O)$_q$—, and —NR$^8$—; wherein m is an integer selected from 0, 1, and 2; wherein n is an integer selected from 0 and 1; wherein the sum of m and n is 1 or 2 when Y is —CR$^8$R$^9$—; wherein the sum of m and n is 2 when Y is —O—, —S(O)$_q$—, and —NR$^8$—; wherein q is 0, 1, or 2; wherein r is 0 or 1; wherein R$^8$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^8$ is not halogen; wherein R$^9$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^9$ is not halogen; wherein each of R$^{10a}$ and R$^{10b}$, when present, is independently selected from hydrogen, C1-C3 alkyl, C1-C3 monohaloalkyl, C1-C3 polyhaloalkyl, and cyclopropyl; wherein each occurrence of R$^{12a}$, R$^{12a}$, R$^{12a}$, and R$^{12a}$, when present, is independently selected from hydrogen, halogen, C1-C3 alkyl, C1-C3 monohaloalkyl, and C1-C3 polyhaloalkyl; wherein R$^1$ is selected from aryl and heteroaryl, and wherein R$^1$ is substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$; wherein each occurrence of R$^{50}$, when present, is independently selected from hydrogen, C1-C3 alkyl, C1-C3 monohaloalkyl, C1-C3 polyhaloalkyl, and cyclopropyl; wherein each occurrence of each of R$^{51a}$ and R$^{51b}$, when present, is independently selected from hydrogen, C1-C3 alkyl, C1-C3 monohaloalkyl, C1-C3 polyhaloalkyl, and cyclopropyl; or wherein R$^{51a}$ and R$^{51b}$, when present, are optionally covalently bonded and, together with nitrogen atom to which they are attached, comprise a 3- to 6-membered heterocycle; wherein each occurrence of R$^{52}$, when present, is independently selected from C1-C3 alkyl, C1-C3 monohaloalkyl, C1-C3 polyhaloalkyl, cyclopropyl, and, —NR$^{54a}$R$^{54b}$; wherein each occurrence of each of R$^{54a}$ and R$^{54b}$, when present, is independently selected from hydrogen, C1-C3 alkyl, C1-C3 monohaloalkyl, C1-C3 polyhaloalkyl, and cyclopropyl; or wherein R$^{54a}$ and R$^{54b}$, when present, are optionally covalently bonded and, together with nitrogen atom to which they are attached, comprise a 3- to 6-membered heterocycle; wherein each occurrence of R$^{53}$, when present, is independently from C1-C3 alkyl, C1-C3 monohaloalkyl, C1-C3 polyhaloalkyl, cyclopropyl, and, —NR$^{55a}$R$^{55b}$; wherein each occurrence of each of R$^{55a}$ and R$^{55b}$, when present, is independently selected from hydrogen, C1-C3 alkyl, C1-C3 monohaloalkyl, C1-C3 polyhaloalkyl, and cyclopropyl; or wherein R$^{55a}$ and R$^{55b}$, when present, are optionally covalently bonded and, together with nitrogen atom to which they are attached, comprise a 3- to 6-membered heterocycle; wherein R$^2$ is selected from hydrogen, C1-C3 alkyl, C1-C3 monohaloalkyl, C1-C3 polyhaloalkyl, and cyclopropyl; wherein R$^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$, is independently selected from hydrogen and fluoro; or a pharmaceutically acceptable salt, solvate, or polymorph thereof.

In a further aspect, the compound contacting the cell is any disclosed compound or at least one product of a disclosed method.

In a further aspect, the cell is mammalian. In a still further aspect, the cell is a human. In a still further aspect, the metabotropic glutamate receptor is mGluR5. In a yet further aspect, the cell has been isolated from a mammal prior to the contacting step. In a further aspect, modulating metabotropic glutamate receptor activity in the at least one cell modulates metabotropic glutamate receptor activity in the mammal. In a yet further aspect, modulating metabotropic glutamate receptor activity in the mammal treats a disorder associated with mGluR5 activity in the mammal.

In a further aspect, the compound exhibits noncompetitive antagonism of metabotropic glutamate receptor activity. In a yet further aspect, the compound exhibits negative allosteric modulation of metabotropic glutamate receptor activity. In a still further aspect, the compound exhibits noncompetitive inhibition of metabotropic glutamate receptor activity. In an even further aspect, the compound exhibits allosteric inhibition of metabotropic glutamate receptor activity. In a still further aspect, the compound exhibits allosteric antagonism. In a yet further aspect, the compound exhibits inhibition of metabotropic glutamate receptor activity.

In a further aspect, the compound exhibits partial inhibition of mGluR5 response. In a still further aspect, the compound exhibits total inhibition of mGluR5 response.

In a further aspect, the compound exhibits partial inhibition of mGluR5 response. In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits negative allosteric modulation with an IC$_{50}$ of less than about $30\times10^{-6}$ M. In an even further aspect, the compound exhibits negative allosteric modulation with an IC$_{50}$ of less than about $10\times10^{-6}$ M. In a yet further aspect, the compound exhibits negative allosteric modulation with an IC$_{50}$ of less than about $1.0\times10^{-6}$ M. In a still further aspect, the compound exhibits negative allosteric modulation with an IC$_{50}$ of less than about $1.0\times10^{-7}$ M. In an even further aspect, the compound exhibits negative allosteric modulation with an $IC_{50}$ of less than about $1.0 \times 10^{-8}$ M. In a yet further aspect, the compound exhibits negative allosteric modulation with an $IC_{50}$ of less than about $1.0 \times 10^{-9}$ M. In a still further aspect, the compound exhibits negative allosteric modulation inhibition with an $IC_{50}$ of between about $1 \times 10^{-5}$ M to about $1 \times 10^{-9}$ M. In an even further aspect, the compound exhibits negative allosteric modulation with an $IC_{50}$ of between about from about $1 \times 10^{-6}$ M to about $1 \times 10^{-9}$ M. In a yet further aspect, the compound exhibits negative allosteric modulation with an $IC_{50}$ of between about from about $1 \times 10^{-7}$ M to about $1 \times 10^{-9}$ M. In a still further aspect, the compound exhibits negative allosteric modulation with an $IC_{50}$ of between about $1 \times 10^{-8}$ M to about $1 \times 10^{-9}$ M.

In a further aspect, the compound exhibits partial or total inhibition with an $IC_{50}$ of less than about $30 \times 10^{-6}$ M. In an even further aspect, the compound exhibits partial or total inhibition with an $IC_{50}$ of less than about $10 \times 10^{-6}$ M. In a yet further aspect, the compound exhibits partial or total inhibition with an $IC_{50}$ of less than about $1.0 \times 10^{-6}$ M. In a still further aspect, the compound exhibits partial or total inhibition with an $IC_{50}$ of less than about $1.0 \times 10^{-7}$ M. In an even further aspect, the compound exhibits partial or total inhibition with an $IC_{50}$ of less than about $1.0 \times 10^{-8}$ M. In a yet further aspect, the compound exhibits partial or total inhibition with an $IC_{50}$ of less than about $1.0 \times 10^{-9}$ M. In a still further aspect, the compound exhibits partial or total inhibition with an $IC_{50}$ of between about $1 \times 10^{-5}$ M to about $1 \times 10^{-9}$ M. In an even further aspect, the compound exhibits partial or total inhibition with an $IC_{50}$ of between about from about $1 \times 10^{-6}$ M to about $1 \times 10^{-9}$ M. In a yet further aspect, the compound exhibits partial or total inhibition with an $IC_{50}$ of between about from about $1 \times 10^{-7}$ M to about $1 \times 10^{-9}$ M. In a still further aspect, the compound exhibits partial or total inhibition with an $IC_{50}$ of between about $1 \times 10^{-8}$ M to about $1 \times 10^{-9}$ M.

In a further aspect, contacting is via administration to a mammal. In a further aspect, the mammal has been diagnosed with a need for treatment of a disorder prior to the administering step. In a still further aspect, the method further comprises the step of identifying a mammal in need of treatment of a disorder.

In a further aspect, the mammal has been diagnosed with a need for modulation of metabotropic glutamate receptor activity prior to the administering step. In a still further aspect, the method further comprises the step of identifying a mammal in need of modulation of metabotropic glutamate receptor activity. In an even further aspect, the modulation of metabotropic glutamate receptor activity treats a disorder associated with metabotropic glutamate receptor activity in the mammal. In a yet further aspect, the mammal has been diagnosed with a need for treatment of a disorder related to metabotropic glutamate receptor activity prior to the administering step.

In a further aspect, the disorder related to metabotropic glutamate receptor activity is a neurological and/or psychiatric disorder associated with glutamate dysfunction. In a still further aspect, neurological and/or psychiatric disorder is selected from addiction, anxiety, fragile x syndrome, gastroesophageal reflux disease (GERD), Parkinson's disease, and pain. In a yet further aspect, the neurological and/or psychiatric disorder is selected from affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, Huntington's-related chorea, levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression.

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder related to metabotropic glutamate receptor activity is a disease of uncontrolled cellular proliferation. In a still further aspect, the disease of uncontrolled cellular proliferation is cancer. In a yet further aspect, the disease of uncontrolled cellular proliferation is selected from breast cancer, renal cancer, gastric cancer, and colorectal cancer. In an even further aspect, the disease of uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

h. Inhibiting Metabotropic Glutamate Receptor Activity in Cells

In one aspect, the invention relates to a method for inhibiting metabotropic glutamate receptor activity in at least one cell, comprising the step of contacting the at least one cell with an amount of at least one disclosed compound, at least one disclosed product in a dosage, or at least one product of a disclosed method of making a compound. In a further aspect, the cell is in a mammal. In a still further aspect, the mammal is human. In an even further aspect, the amount contacting the cell is effective to inhibit mGluR5 activity in the at least one cell. In a yet further aspect, the amount contacting the cell is a therapeutically effective amount to treat a disorder in the mammal, wherein the disorder is associated with metabotropic glutamate receptor activity in at least one cell. In a further aspect, the metabotropic glutamate receptor is mGluR5.

Thus, in one aspect, the invention relates to a method for inhibiting metabotropic glutamate receptor activity in at least one cell, comprising the step of contacting the at least one cell with at least one compound having a structure represented by a formula:

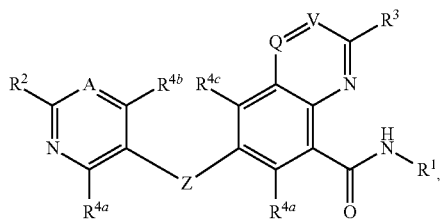

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8(O)_rR^9$—, —$CR^8NR^{10a}R^{10b}$—, —(C=O)—, and a structure represented by a formula:

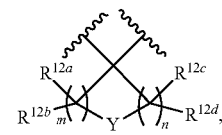

wherein Y is selected from —$CR^8R^9$—, —O—, —$S(O)_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —$S(O)_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O)$R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —$NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, $-NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —$(C=O)R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof.

In a further aspect, the compound contacting the cell is any disclosed compound or at least one product of a disclosed method.

In a further aspect, the cell is mammalian. In a still further aspect, the cell is a human. In a still further aspect, the metabotropic glutamate receptor is mGluR5. In a yet further aspect, the cell has been isolated from a mammal prior to the contacting step. In a further aspect, inhibiting metabotropic glutamate receptor activity in the at least one cell inhibits metabotropic glutamate receptor activity in the mammal. In a yet further aspect, inhibiting metabotropic glutamate receptor activity in the mammal treats a disorder associated with mGluR5 activity in the mammal.

In a further aspect, inhibiting is noncompetitive inhibition. In a still further aspect, inhibiting is noncompetitive antagonism. In an even further aspect, inhibiting is negative allosteric modulation. In an even further aspect, inhibiting is antagonism.

In a further aspect, the compound exhibits partial inhibition of mGluR5 response.

In a still further aspect, the compound exhibits total inhibition of mGluR5 response.

In a further aspect, the compound exhibits noncompetitive antagonism of metabotropic glutamate receptor activity. In a still further aspect, the compound exhibits noncompetitive inhibition of metabotropic glutamate receptor activity. In an even further aspect, the compound exhibits inhibition of metabotropic glutamate receptor activity. In a still further aspect, the compound exhibits allosteric antagonism of metabotropic glutamate receptor activity.

In a further aspect, the compound exhibits partial inhibition of mGluR5 response. In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits negative allosteric modulation with an $IC_{50}$ of less than about $30\times10^{-6}$ M. In an even further aspect, the compound exhibits negative allosteric modulation with an $IC_{50}$ of less than about $10\times10^{-6}$ M. In a yet further aspect, the compound exhibits negative allosteric modulation with an $IC_{50}$ of less than about $1.0\times10^{-6}$ M. In a still further aspect, the compound exhibits negative allosteric modulation with an $IC_{50}$ of less than about $1.0\times10^{-7}$ M. In an even further aspect, the compound exhibits negative allosteric modulation with an $IC_{50}$ of less than about $1.0\times10^{-8}$ M. In a yet further aspect, the compound exhibits negative allosteric modulation with an $IC_{50}$ of less than about $1.0\times10^{-9}$ M. In a still further aspect, the compound exhibits negative allosteric modulation inhibition with an $IC_{50}$ of between about $1\times10^{-5}$ M to about $1\times10^{-9}$ M. In an even further aspect, the compound exhibits negative allosteric modulation with an $IC_{50}$ of between about from about $1\times10^{-6}$ M to about $1\times10^{-9}$ M. In a yet further aspect, the compound exhibits negative allosteric modulation with an $IC_{50}$ of between about from about $1\times10^{-7}$ M to about $1\times10^{-9}$ M. In a still further aspect, the compound exhibits negative allosteric modulation with an $IC_{50}$ of between about $1\times10^{-8}$ M to about $1\times10^{-9}$ M.

In a further aspect, the compound exhibits partial or total inhibition with an $IC_{50}$ of less than about $30\times10^{-6}$ M. In an even further aspect, the compound exhibits partial or total inhibition with an $IC_{50}$ of less than about $10\times10^{-6}$ M. In a yet further aspect, the compound exhibits partial or total inhibition with an $IC_{50}$ of less than about $1.0\times10^{-6}$ M. In a still further aspect, the compound exhibits partial or total inhibition with an $IC_{50}$ of less than about $1.0\times10^{-7}$ M. In an even further aspect, the compound exhibits partial or total inhibition with an $IC_{50}$ of less than about $1.0\times10^{-8}$ M. In a yet further aspect, the compound exhibits partial or total inhibition with an $IC_{50}$ of less than about $1.0\times10^{-9}$ M. In a still further aspect, the compound exhibits partial or total inhibition with an $IC_{50}$ of between about $1\times10^{-5}$ M to about $1\times10^{-9}$ M. In an even further aspect, the compound exhibits partial or total inhibition with an $IC_{50}$ of between about from about $1\times10^{-6}$ M to about $1\times10^{-9}$ M. In a yet further aspect, the compound exhibits partial or total inhibition with an $IC_{50}$ of between about from about $1\times10^{-7}$ M to about $1\times10^{-9}$ M. In a still further aspect, the compound exhibits partial or total inhibition with an $IC_{50}$ of between about $1\times10^{-8}$ M to about $1\times10^{-9}$ M.

In a further aspect, contacting is via administration to a mammal. In a further aspect, the mammal has been diagnosed with a need for treatment of a disorder prior to the administering step. In a still further aspect, the method further comprises the step of identifying a mammal in need of treatment of a disorder.

In a further aspect, the mammal has been diagnosed with a need for inhibition of metabotropic glutamate receptor activity prior to the administering step. In a still further aspect, the method further comprises the step of identifying a mammal in need of inhibition of metabotropic glutamate receptor activity. In an even further aspect, the inhibition of metabotropic glutamate receptor activity treats a disorder associated with metabotropic glutamate receptor activity in the mammal. In a yet further aspect, the mammal has been diagnosed with a need for treatment of a disorder related to metabotropic glutamate receptor activity prior to the administering step.

In a further aspect, the disorder related to metabotropic glutamate receptor activity is a neurological and/or psychiatric disorder associated with glutamate dysfunction. In a still further aspect, neurological and/or psychiatric disorder is selected from addiction, anxiety, fragile x syndrome, gastroesophageal reflux disease (GERD), Parkinson's disease, and pain. In a yet further aspect, the neurological and/or psychiatric disorder is selected from affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, Huntington's-related chorea, levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression.

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the disorder related to metabotropic glutamate receptor activity is a disease of uncontrolled cellular proliferation. In a still further aspect, the disease of uncontrolled cellular proliferation is cancer. In a yet further aspect, the disease of uncontrolled cellular proliferation is selected from breast cancer, renal cancer, gastric cancer, and colorectal cancer. In an even further aspect, the disease of uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

2. Use of Compounds

Also provided are the uses of the disclosed compounds and products. In one aspect, the use relates to a treatment of a disorder in a mammal. In one aspect, the use is characterized in that the mammal is a human. In one aspect, the use is characterized in that the disorder is a neurological and/or psychiatric disorder associated with glutamate dysfunction. In one aspect, the use relates to negative allosteric modulation of metabotropic glutamate receptor activity in a mammal.

In one aspect, the invention relates to use of a compound having a structure represented by a formula:

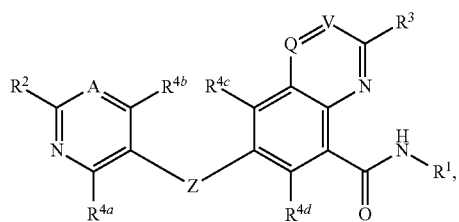

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C═O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C═O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C═O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8(O)_rR^9$—, —$CR^8NR^{10a}R^{10b}$—, —(C=O)—, and a structure represented by a formula:

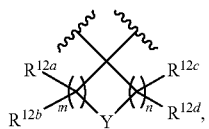

wherein Y is selected from —$CR^8R^9$—, —O—, —$S(O)_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —$S(O)_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O)$R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —$NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, —$NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof.

In a further aspect, the compound is any disclosed compound or at least one product of a disclosed method.

In a further aspect, compound exhibits partial or total inhibition of mGluR5 response to glutamate as a decrease in response to non-maximal concentrations of glutamate in human embryonic kidney cells transfected with mGluR5 in the presence of the compound, compared to the response to glutamate in the absence of the compound. In a still further aspect, human embryonic kidney cells transfected with rat mGluR5. In a yet further aspect, human embryonic kidney cells transfected with human mGluR5.

In a further aspect, the compound treats a neurological and/or psychiatric disorder associated with glutamate dysfunction. In a still further aspect, neurological and/or psychiatric disorder is selected from addiction, anxiety, fragile x syndrome, gastroesophageal reflux disease (GERD), Parkinson's disease, and pain. In a yet further aspect, the neurological and/or psychiatric disorder is selected from affective disorder, age-related cognitive decline, Alzheimer's disease, amnestic disorders, amyotrophic lateral sclerosis, anxiety disorders, Angelman's syndrome, Asperger's syndrome, attention deficit hyperactivity disorder, bipolar disorder, brain edema, chronic pain, delirium, dementia, depression, diabetes, Down Syndrome, dystonia, eating disorders, epilepsy, fibromyalgia, Huntington's-related chorea, levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, senile dementia, sleep disorder, substance-related disorder, or unipolar depression.

In a further aspect, the neurological and/or psychiatric disorder is an autism spectrum disorder. In a still further aspect, the autism spectrum disorder is selected from autism, classical autism, Asperger syndrome, Pervasive Developmental Disorder Not Otherwise Specified (PDD-NOS), sometimes called atypical autism, Fragile X syndrome, Rett syndrome, and Childhood Disintegrative Disorder.

In a further aspect, the compound treats a disease of uncontrolled cellular proliferation. In a still further aspect, disease of uncontrolled cellular proliferation is cancer. In a yet further aspect, the disease of uncontrolled cellular proliferation is selected from breast cancer, renal cancer, gastric cancer, and colorectal cancer. In an even further aspect, the disease of uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

In a further aspect, the compound exhibits partial inhibition of mGluR5 response. In a still further aspect, the compound exhibits total inhibition of mGluR5 response. In an even further aspect, the mGluR5 is rat mGluR5. In a yet further aspect, the mGluR5 is human mGluR5.

In a further aspect, the compound exhibits negative allosteric modulation with an $IC_{50}$ of less than about $30 \times 10^{-6}$ M. In an even further aspect, the compound exhibits negative allosteric modulation with an $IC_{50}$ of less than about $10 \times 10^{-6}$ M. In a yet further aspect, the compound exhibits negative allosteric modulation with an $IC_{50}$ of less than about $1.0 \times 10^{-6}$ M. In a still further aspect, the compound exhibits negative allosteric modulation with an $IC_{50}$ of less than about $1.0 \times 10^{-7}$ M. In an even further aspect, the compound exhibits negative allosteric modulation with an $IC_{50}$ of less than about $1.0 \times 10^{-8}$ M. In a yet further aspect, the compound exhibits negative allosteric modulation with an $IC_{50}$ of less than about $1.0 \times 10^{-9}$ M. In a still further aspect, the compound exhibits negative allosteric modulation inhibition with an $IC_{50}$ of between about $1 \times 10^{-5}$ M to about $1 \times 10^{-9}$ M. In an even further aspect, the compound exhibits negative allosteric modulation with an $IC_{50}$ of between about from about $1 \times 10^{-6}$ M to about $1 \times 10^{-9}$ M. In a yet further aspect, the compound exhibits negative allosteric modulation with an $IC_{50}$ of between about from about $1 \times 10^{-7}$ M to about $1 \times 10^{-9}$ M. In a still further aspect, the compound exhibits negative allosteric modulation with an $IC_{50}$ of between about $1 \times 10^{-8}$ M to about $1 \times 10^{-9}$ M.

In a further aspect, the compound exhibits partial or total inhibition with an $IC_{50}$ of less than about $30 \times 10^{-6}$ M. In an even further aspect, the compound exhibits partial or total inhibition with an $IC_{50}$ of less than about $10 \times 10^{-6}$ M. In a yet further aspect, the compound exhibits partial or total inhibition with an $IC_{50}$ of less than about $1.0 \times 10^{-6}$ M. In a still further aspect, the compound exhibits partial or total inhibition with an $IC_{50}$ of less than about $1.0 \times 10^{-7}$ M. In an even further aspect, the compound exhibits partial or total inhibition with an $IC_{50}$ of less than about $1.0 \times 10^{-8}$ M. In a yet further aspect, the compound exhibits partial or total inhibition with an $IC_{50}$ of less than about $1.0 \times 10^{-9}$ M. In a still further aspect, the compound exhibits partial or total inhibition with an $IC_{50}$ of between about $1 \times 10^{-5}$ M to about $1 \times 10^{-9}$ M. In an even further aspect, the compound exhibits partial or total inhibition with an $IC_{50}$ of between about from about $1 \times 10^{-6}$ M to about $1 \times 10^{-9}$ M. In a yet further aspect, the compound exhibits partial or total inhibition with an $IC_{50}$ of between about from about $1 \times 10^{-7}$ M to about $1 \times 10^{-9}$ M. In a still further aspect, the compound exhibits partial or total inhibition with an $IC_{50}$ of between about $1 \times 10^{-8}$ M to about $1 \times 10^{-9}$ M.

In a further aspect, the invention relates to the use of a disclosed compound or a disclosed product in the manufacture of a medicament for the treatment of a disorder associated with glutamate dysfunction in a mammal. In a still further aspect, the disorder is a neurological and/or psychiatric disorder. In a yet further aspect, the disorder is a disease of uncontrolled cellular proliferation.

3. Kits

In one aspect, the invention relates to a kit comprising at least one disclosed compound or at least one disclosed product and one or more of at least one agent known to increase mGluR5 activity; at least one agent known to decrease mGluR5 activity; at least one agent known to treat a neurological and/or psychiatric disorder; at least one agent known to treat a disease of uncontrolled cellular proliferation; or instructions for treating a disorder associated with glutamate dysfunction. In a further aspect, the at least one compound or the at least one product and the at least one agent are co-formulated. In a further aspect, the at least one compound or the at least one product and the at least one agent are co-packaged.

In one aspect, the invention relates to a kit comprising at least one compound having a structure represented by a formula:

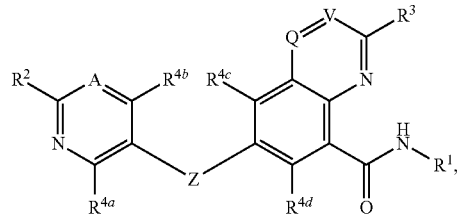

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein R²³, when present, is selected from C1-C3 alkyl, C1-C3 monohaloalkyl, C1-C3 polyhaloalkyl, cyclopropyl, and, —NR²⁵ᵃR²⁵ᵇ; wherein each of R²⁵ᵃ and R²⁵ᵇ, when present, is independently selected from hydrogen, C1-C3 alkyl, C1-C3 monohaloalkyl, C1-C3 polyhaloalkyl, and cyclopropyl; or wherein R²⁵ᵃ and R²⁵ᵇ, when present, are optionally covalently bonded and, together with nitrogen atom to which they are attached, comprise a 3- to 6-membered heterocycle; wherein Q is selected from N and CR⁶; wherein R⁶, when present, is selected from hydrogen, halogen, —CN, C1-C3 alkyl, C1-C3 monohaloalkyl, C1-C3 polyhaloalkyl, cyclopropyl, —OR³⁰, —NR³¹ᵃR³¹ᵇ, —SO₂R³², and —(C=O)R³³; wherein R³⁰, when present, is selected from hydrogen, C1-C3 alkyl, C1-C3 monohaloalkyl, C1-C3 polyhaloalkyl, and cyclopropyl; wherein each of R³¹ᵃ and R³¹ᵇ, when present, is independently selected from hydrogen, C1-C3 alkyl, C1-C3 monohaloalkyl, C1-C3 polyhaloalkyl, and cyclopropyl; or wherein R³¹ᵃ and R³¹ᵇ, when present, are optionally covalently bonded and, together with nitrogen atom to which they are attached, comprise a 3- to 6-membered heterocycle; wherein R³², when present, is selected from C1-C3 alkyl, C1-C3 monohaloalkyl, C1-C3 polyhaloalkyl, cyclopropyl, and, —NR³⁴ᵃR³⁴ᵇ; wherein each of R³⁴ᵃ and R³⁴ᵇ, when present, is independently selected from hydrogen, C1-C3 alkyl, C1-C3 monohaloalkyl, C1-C3 polyhaloalkyl, and cyclopropyl; or wherein R³⁴ᵃ and R³⁴ᵇ, when present, are optionally covalently bonded and, together with nitrogen atom to which they are attached, comprise a 3- to 6-membered heterocycle; wherein R³³, when present, is selected from C1-C3 alkyl, C1-C3 monohaloalkyl, C1-C3 polyhaloalkyl, cyclopropyl, and, —NR³⁵ᵃR³⁵ᵇ; wherein each of R³⁵ᵃ and R³⁵ᵇ, when present, is independently selected from hydrogen, C1-C3 alkyl, C1-C3 monohaloalkyl, C1-C3 polyhaloalkyl, and cyclopropyl; or wherein R³⁵ᵃ and R³⁵ᵇ, when present, are optionally covalently bonded and, together with nitrogen atom to which they are attached, comprise a 3- to 6-membered heterocycle; wherein V is selected from N and CR⁷, provided that Q and V are not simultaneously N; wherein R⁷, when present, is selected from hydrogen, halogen, —CN, C1-C3 alkyl, C1-C3 monohaloalkyl, C1-C3 polyhaloalkyl, cyclopropyl, —OR⁴⁰, —NR⁴¹ᵃR⁴¹ᵇ, —SO₂R⁴², and —(C=O)R⁴³; wherein R⁴⁰, when present, is selected from hydrogen, C1-C3 alkyl, C1-C3 monohaloalkyl, C1-C3 polyhaloalkyl, and cyclopropyl; wherein each of R⁴¹ᵃ and R⁴¹ᵇ, when present, is independently selected from hydrogen, C1-C3 alkyl, C1-C3 monohaloalkyl, C1-C3 polyhaloalkyl, and cyclopropyl; or wherein R⁴¹ᵃ and R⁴¹ᵇ, when present, are optionally covalently bonded and, together with nitrogen atom to which they are attached, comprise a 3- to 6-membered heterocycle; wherein R⁴², when present, is selected from C1-C3 alkyl, C1-C3 monohaloalkyl, C1-C3 polyhaloalkyl, cyclopropyl, and, —NR⁴⁴ᵃR⁴⁴ᵇ; wherein each of R⁴⁴ᵃ and R⁴⁴ᵇ, when present, is independently selected from hydrogen, C1-C3 alkyl, C1-C3 monohaloalkyl, C1-C3 polyhaloalkyl, and cyclopropyl; or wherein R⁴⁴ᵃ and R⁴⁴ᵇ, when present, are optionally covalently bonded and, together with nitrogen atom to which they are attached, comprise a 3- to 6-membered heterocycle; wherein R⁴³, when present, is selected from C1-C3 alkyl, C1-C3 monohaloalkyl, C1-C3 polyhaloalkyl, cyclopropyl, and, —NR⁴⁵ᵃR⁴⁵ᵇ; wherein each of R⁴⁵ᵃ and R⁴⁵ᵇ, when present, is independently selected from hydrogen, C1-C3 alkyl, C1-C3 monohaloalkyl, C1-C3 polyhaloalkyl, and cyclopropyl; or wherein R⁴⁵ᵃ and R⁴⁵ᵇ, when present, are optionally covalently bonded and, together with nitrogen atom to which they are attached, comprise a 3- to 6-membered heterocycle; wherein Z is selected from —CR⁸(O)ᵣR⁹—, —CR⁸NR¹⁰ᵃR¹⁰ᵇ—, —(C=O)—, and a structure represented by a formula:

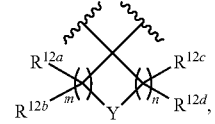

wherein Y is selected from —CR⁸R⁹—, —O—, —S(O)_q—, and —NR⁸—; wherein m is an integer selected from 0, 1, and 2; wherein n is an integer selected from 0 and 1; wherein the sum of m and n is 1 or 2 when Y is —CR⁸R⁹—; wherein the sum of m and n is 2 when Y is —O—, —S(O)_q—, and —NR⁸—; wherein q is 0, 1, or 2; wherein r is 0 or 1; wherein R⁸, when present, is selected from hydrogen, halogen, C1-C3 alkyl, C1-C3 monohaloalkyl, C1-C3 polyhaloalkyl, and cyclopropyl; provided that, when Z is —CR⁸(O)ᵣR⁹— and r is 1, R⁸ is not halogen; wherein R⁹, when present, is selected from hydrogen, halogen, C1-C3 alkyl, C1-C3 monohaloalkyl, C1-C3 polyhaloalkyl, and cyclopropyl; provided that, when Z is —CR⁸(O)ᵣR⁹— and r is 1, R⁹ is not halogen; wherein each of R¹⁰ᵃ and R¹⁰ᵇ, when present, is independently selected from hydrogen, C1-C3 alkyl, C1-C3 monohaloalkyl, C1-C3 polyhaloalkyl, and cyclopropyl; wherein each occurrence of R¹²ᵃ, R¹²ᵃ, R¹²ᵃ, and R¹²ᵃ, when present, is independently selected from hydrogen, halogen, C1-C3 alkyl, C1-C3 monohaloalkyl, and C1-C3 polyhaloalkyl; wherein R¹ is selected from aryl and heteroaryl, and wherein R¹ is substituted with 0, 1, 2, or 3 groups independently selected from halogen, —CN, C1-C3 alkyl, C1-C3 monohaloalkyl, C1-C3 polyhaloalkyl, cyclopropyl, —OR⁵⁰, —NR⁵¹ᵃR⁵¹ᵇ, —SO₂R⁵², and —(C=O)R⁵³; wherein each occurrence of R⁵⁰, when present, is independently selected from C1-C3 alkyl, C1-C3 monohaloalkyl, C1-C3 polyhaloalkyl, and cyclopropyl; wherein each occurrence of each of R⁵¹ᵃ and R⁵¹ᵇ, when present, is independently selected from hydrogen, C1-C3 alkyl, C1-C3 monohaloalkyl, C1-C3 polyhaloalkyl, and cyclopropyl; or wherein R⁵¹ᵃ and R⁵¹ᵇ, when present, are optionally covalently bonded and, together with nitrogen atom to which they are attached, comprise a 3- to 6-membered heterocycle; wherein each occurrence of R⁵², when present, is independently selected from C1-C3 alkyl, C1-C3 monohaloalkyl, C1-C3 polyhaloalkyl, cyclopropyl, and, —NR⁵⁴ᵃR⁵⁴ᵇ; wherein each occurrence of each of R⁵⁴ᵃ and R⁵⁴ᵇ, when present, is independently selected from hydrogen, C1-C3 alkyl, C1-C3 monohaloalkyl, C1-C3 polyhaloalkyl, and cyclopropyl; or wherein R⁵⁴ᵃ and R⁵⁴ᵇ, when present, are optionally covalently bonded and, together with nitrogen atom to which they are attached, comprise a 3- to 6-membered heterocycle; wherein each occurrence of R⁵³, when present, is independently from C1-C3 alkyl, C1-C3 monohaloalkyl, C1-C3 polyhaloalkyl, cyclopropyl, and, —NR⁵⁵ᵃR⁵⁵ᵇ; wherein each occurrence of each of R⁵⁵ᵃ and R⁵⁵ᵇ, when present, is independently selected from hydrogen, C1-C3 alkyl, C1-C3 monohaloalkyl, C1-C3 polyhaloalkyl, and cyclopropyl; or wherein R⁵⁵ᵃ and R⁵⁵ᵇ, when present, are optionally covalently bonded and, together with nitrogen atom to which they are attached, comprise a 3- to 6-membered heterocycle; wherein R² is selected from hydrogen, C1-C3 alkyl, C1-C3 monohaloalkyl, C1-C3 polyhaloalkyl, and cyclopropyl; wherein R³ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$, is independently selected from hydrogen and fluoro; or a pharmaceutically acceptable salt, solvate, or polymorph thereof.

In a further aspect, the kit comprises any disclosed compound or at least one product of a disclosed method of making.

In a further aspect, the pharmaceutical composition comprises a compound that exhibits partial or total inhibition of mGluR5 response to glutamate as a decrease in response to non-maximal concentrations of glutamate in human embryonic kidney cells transfected with mGluR5 in the presence of the compound, compared to the response to glutamate in the absence of the compound. In a still further aspect, the human embryonic kidney cells transfected with rat mGluR5. In a yet further aspect, the human embryonic kidney cells transfected with human mGluR5.

In a further aspect, the at least one agent is selected from an antipsychotic, a selective serotonin reuptake inhibitor, a central sympathomimetic, an imidazoline receptor agonists, a proprionic acid derivative, a benzodiazepine, sympathomimetics, a fatty acid derivative, a vitamin or multivitamin (with or without minerals), a piperazine derivative, an anilide, a lipid modifying agent, an aminoalkyl ether analogue, a macrolide, a melatonin receptor agonist, a penicillin derivative, a tetracycline analogue, an expectorant, an antihistamine, an azaspirodecanedione derivative, a central acting agent, a carboxamide, an opium alkaloid or derivative, an antidepressant, an antiepileptic, a beta blocker, a psychostimulant, a proton pump inhibitor, a 5HT3 antagonist, a vitamin D analogue, a diazepine, an indole derivative, an HMG CoA reductase inhibitor, a topical antibiotic, a progesterone analogue, an estrogen analogue, an angiotensin-converting enzyme inhibitor, an anesthetic, an antifungal, an antidiarrheal, an oxazepine, a thiazepine, a vaccine, a sulfonamide, a leukotriene receptor antagonist, a lincosamide, a neuroamidase inhibitor, a non-selective monoamine reuptake inhibitor, and a salicylic acid analogue.

In a further aspect, the at least one agent is selected from Aripiprazole, Acetominophen, Acetylcarnitine, Acetylsalicylic acid, Alprazolam, Amitryptyline, Amoxicillin, Augmentin, Azithromycin, Baclofen, Benzylpenicllin, Bupropion, Buspirone, Carbamazepine, Cetirizine, Cimetidine, Ciprofloxacin, Citalopram, Clonidine, Clozapine, Contac, Dexamfetamine, Dexmethylphenidate, Dextromethorphan, Diazepam, Dimetapp, Diphenhydramine, Donepezil, Drospirenone with ethinylestradiol, Ergocalciferol, Escitalopram, Excedrin, Fish oil, Fluoxetine, Fluvoxamine, Guaifenesin, Guanfacine, Haloperidol, Ibuprofen, Imipramine, Lamotrigine, Lansoprazole, Levoceterizine, Lisdexamfetamine, Loratadine, Lorazepam, Melatonin, Methylphenidate, Midazolam, Minocycline, Modafinil, Mupirocin, Naproxen, Obetrol, Olanzapine, Omega-3 TG, Omeprazole, Ondansetron, Oxcarbazepine, Paliperidone, Paracetamol, Pediacare, Phenobarbital, Phenylephrine, Phenytoin, Promethazine with codeine, Propranolol, Pseudoephedrine, Risperidone, Sertraline, Simvastatin, Statins, Topiramate, Trazodone, Tricyclic AD, Valproate, Venlafaxine, Ziprasidone, and Zonisamide.

In a further aspect, the at least one compound and the at least one agent are co-formulated.

In a further aspect, the at least one compound and the at least one agent are co-formulated, wherein the at least one agent is selected from an antipsychotic, a selective serotonin reuptake inhibitor, a central sympathomimetic, an imidazoline receptor agonists, a proprionic acid derivative, a benzodiazepine, sympathomimetics, a fatty acid derivative, a vitamin or multivitamin (with or without minerals), a piperazine derivative, an anilide, a lipid modifying agent, an aminoalkyl ether analogue, a macrolide, a melatonin receptor agonist, a penicillin derivative, a tetracycline analogue, an expectorant, an antihistamine, an azaspirodecanedione derivative, a central acting agent, a carboxamide, an opium alkaloid or derivative, an antidepressant, an antiepileptic, a beta blocker, a psychostimulant, a proton pump inhibitor, a 5HT3 antagonist, a vitamin D analogue, a diazepine, an indole derivative, an HMG CoA reductase inhibitor, a topical antibiotic, a progesterone analogue, an estrogen analogue, an angiotensin-converting enzyme inhibitor, an anesthetic, an antifungal, an antidiarrheal, an oxazepine, a thiazepine, a vaccine, a sulfonamide, a leukotriene receptor antagonist, a lincosamide, a neuroamidase inhibitor, a non-selective monoamine reuptake inhibitor, and a salicylic acid analogue.

In a further aspect, the at least one compound and the at least one agent are co-formulated, wherein the at least one agent is selected from Aripiprazole, Acetominophen, Acetylcarnitine, Acetylsalicylic acid, Alprazolam, Amitryptyline, Amoxicillin, Augmentin, Azithromycin, Baclofen, Benzylpenicillin, Bupropion, Buspirone, Carbamazepine, Cetirizine, Cimetidine, Ciprofloxacin, Citalopram, Clonidine, Clozapine, Contac, Dexamfetamine, Dexmethylphenidate, Dextromethorphan, Diazepam, Dimetapp, Diphenhydramine, Donepezil, Drospirenone with ethinylestradiol, Ergocalciferol, Escitalopram, Excedrin, Fish oil, Fluoxetine, Fluvoxamine, Guaifenesin, Guanfacine, Haloperidol, Ibuprofen, Imipramine, Lamotrigine, Lansoprazole, Levoceterizine, Lisdexamfetamine, Loratadine, Lorazepam, Melatonin, Methylphenidate, Midazolam, Minocycline, Modafinil, Mupirocin, Naproxen, Obetrol, Olanzapine, Omega-3 TG, Omeprazole, Ondansetron, Oxcarbazepine, Paliperidone, Paracetamol, Pediacare, Phenobarbital, Phenylephrine, Phenytoin, Promethazine with codeine, Propranolol, Pseudoephedrine, Risperidone, Sertraline, Simvastatin, Statins, Topiramate, Trazodone, Tricyclic AD, Valproate, Venlafaxine, Ziprasidone, and Zonisamide.

In a further aspect, the at least one compound and the at least one agent are co-packaged.

In a further aspect, the at least one compound and the at least one agent are co-packaged, wherein the at least one agent is selected from an antipsychotic, a selective serotonin reuptake inhibitor, a central sympathomimetic, an imidazoline receptor agonists, a proprionic acid derivative, a benzodiazepine, sympathomimetics, a fatty acid derivative, a vitamin or multivitamin (with or without minerals), a piperazine derivative, an anilide, a lipid modifying agent, an aminoalkyl ether analogue, a macrolide, a melatonin receptor agonist, a penicillin derivative, a tetracycline analogue, an expectorant, an antihistamine, an azaspirodecanedione derivative, a central acting agent, a carboxamide, an opium alkaloid or derivative, an antidepressant, an antiepileptic, a beta blocker, a psychostimulant, a proton pump inhibitor, a 5HT3 antagonist, a vitamin D analogue, a diazepine, an indole derivative, an HMG CoA reductase inhibitor, a topical antibiotic, a progesterone analogue, an estrogen analogue, an angiotensin-converting enzyme inhibitor, an anesthetic, an antifungal, an antidiarrheal, an oxazepine, a thiazepine, a vaccine, a sulfonamide, a leukotriene receptor antagonist, a lincosamide, a neuroamidase inhibitor, a non-selective monoamine reuptake inhibitor, and a salicylic acid analogue.

In a further aspect, the at least one compound and the at least one agent are co-packaged, wherein the at least one agent is selected from Aripiprazole, Acetominophen, Acetylcarnitine, Acetylsalicylic acid, Alprazolam, Amitryptyline, Amoxicillin, Augmentin, Azithromycin, Baclofen, Benzylpenicillin, Bupropion, Buspirone, Carbamazepine, Cetirizine, Cimetidine, Ciprofloxacin, Citalopram, Clonidine, Clozapine, Contac, Dexamfetamine, Dexmethylphenidate, Dextromethorphan, Diazepam, Dimetapp, Diphenhydramine, Donepezil, Drospirenone with ethinylestradiol, Ergocalciferol, Escitalopram, Excedrin, Fish oil, Fluoxetine, Fluvoxamine, Guaifenesin, Guanfacine, Haloperidol, Ibuprofen, Imipramine, Lamotrigine, Lansoprazole, Levocetirizine, Lisdexamfetamine, Loratadine, Lorazepam, Melatonin, Methylphenidate, Midazolam, Minocycline, Modafinil, Mupirocin, Naproxen, Obetrol, Olanzapine, Omega-3 TG, Omeprazole, Ondansetron, Oxcarbazepine, Paliperidone, Paracetamol, Pediacare, Phenobarbital, Phenylephrine, Phenytoin, Promethazine with codeine, Propranolol, Pseudoephedrine, Risperidone, Sertraline, Simvastatin, Statins, Topiramate, Trazodone, Tricyclic AD, Valproate, Venlafaxine, Ziprasidone, and Zonisamide.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

4. Non-Medical Uses

Also provided are the uses of the disclosed compounds and products as pharmacological tools in the development and standardization of in vitro and in vivo test systems for the evaluation of the effects of modulators of mGluR related activity in laboratory animals such as cats, dogs, rabbits, monkeys, rats and mice, as part of the search for new therapeutic agents of mGluR. In a further aspect, the invention relates to the use of a disclosed compound or a disclosed product as pharmacological tools in the development and standardization of in vitro and in vivo test systems for the evaluation of the effects of modulators of mGluR5 related activity in laboratory animals such as cats, dogs, rabbits, monkeys, rats and mice, as part of the search for new therapeutic agents of mGluR5.

G. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. All $^1$H NMR spectra were obtained on instrumentation at a field strength of 300 to 500 MHz.

1. Intermediate Route I a. Preparation of methyl 7-bromoquinoxaline-5-carboxylate

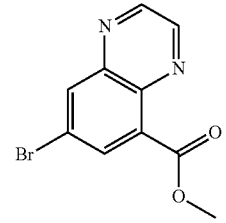

Methyl 2,3-diamino-5-bromobenzoate (2.51 g, 11.3 mmol, 1.0 eq) and 1,4-dioxane-2,3-diol (0.123 g, 11.3 mmol, 1.0 eq) were dissolved in ethanol (51 mL) in a microwave vial and heated in a microwave reactor at 110° C. for 10 minutes. The reaction was concentrated and purified by flash column chromatography on silica gel using hexanes/ethyl acetate to afford 2.35 g (85%) of the title compound as a white solid. $^1$H NMR (400 MHz, DMSO-d$_6$) δ 9.04 (s, 2H), 8.51 (d, J=2.3 Hz, 1H), 8.25 (d, J=2.3 Hz, 1H), 3.93 (s, 3H); ES-MS [M+1]$^+$: 266.9.

2. Intermediate Route II a. Preparation of 8-chloro-6-vinylquinoline

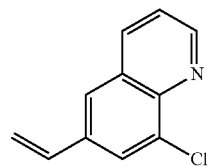

6-Bromo-8-chloroquinoline (1.49 g, 6.14 mmol, 1.0 eq), [1,1'-Bis(diphenylphosphino)-ferrocene]dichloropalladium (100 mg, 0.122 mmol), 0.020 eq), potassium vinyltrifluoroborate (823 mg, 6.14 mmol, 1.0 eq) and triethylamine (857 μL, 6.15 mmol, 1.0 eq) were dissolved in ethanol (61 mL) in a round-bottom flask and heated to 80° C. until complete by LCMS (~2 hours). The reaction was cooled, filtered over Celite and washed with 1:1 hexanes:ethyl acetate. The solvents were removed in vacuo and the crude material was purified by flash column chromatography on silica gel using hexanes/ethyl acetate to afford 1.17 g (>99%) of the title compound as an off-white solid. $^1$H NMR (400 MHz, DMSO-$d_6$) δ 8.96 (dd, J=4.2, 1.6 Hz, 1H), 8.40 (dd, J=8.3, 1.6 Hz, 1H), 8.19 (d, J=1.8 Hz, 1H), 7.96 (d, J=1.6 Hz, 1H), 7.63 (dd, J=8.3, 4.2 Hz, 1H), 6.89 (dd, J=17.7, 10.9 Hz, 1H), 6.10 (d, J=17.6 Hz, 1H), 5.46 (d, J=11.0 Hz, 1H); ES-MS [M+1]$^+$: 190.0.

b. Preparation of 8-chloroquinoline-6-carbaldehyde

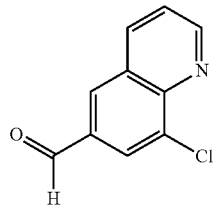 [SMILES: O=Cc1cc(Cl)c2ncccc2c1]

8-Chloro-6-vinylquinoline (4.08 g, 21.5 mmol, 1.0 eq) was dissolved in CH$_2$Cl$_2$ (108 mL) and methanol (108 mL) and cooled to −78° C. Ozone was bubbled through the reaction until disappearance of starting material was observed by TLC. Oxygen was bubbled through the reaction to remove the excess ozone and dimethyl sulfide (47.7 mL, 645 mmol, 30 eq) was added. The reaction was allowed to warm to room temperature and stirred for 2 hours. Water was added and the reaction was extracted with CH$_2$Cl$_2$ (3×). The combined organics were dried (MgSO$_4$) and concentrated in vacuo. Purification by flash chromatography on silica gel afforded 3.19 g (77%) of the title compound as a white solid. $^1$H NMR (400 MHz, DMSO-$d_6$) δ 10.15 (s, 1H), 9.17 (dd, J=4.12, 1.7 Hz, 1H), 8.70 (dd, J=8.3 Hz, 1.6 Hz, 1H), 8.66 (d, J=1.6 Hz, 1H), 8.26 (d, J=1.7 Hz, 1H), 7.79 (dd, J=8.3, 4.2 Hz, 1H); ES-MS [M+1]$^+$: 192.1.

3. Intermediate Route III a. Preparation of 5-vinylpyrimidine

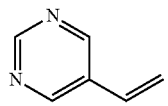

5-Bromopyrimidine (7.0 g, 44 mmol, 1.0 eq), [1,1'-Bis(diphenylphosphino)-ferrocene]dichloropalladium (1.44 g, 1.76 mmol, 0.040 eq), and potassium vinyltrifluoroborate (7.08 g, 52.9 mmol, 1.2 eq) were added to a pressure vessel. The vessel was purged with argon and degassed n-propanol (220 mL) and triethylamine (7.4 mL, 53 mmol, 1.2 eq) were added. The reaction was heated at 100° C. overnight at which point it was cooled to room temperature and diethyl ether (300 mL) was added. The combined organics were washed with H$_2$O (3×), dried (MgSO$_4$), and concentrated taking care to keep the flask cold as the product is somewhat volatile. Purification by flash chromatography on silica gel using ether/hexanes afforded 2.5 g (53%) of the title compound as a red oil. $^1$H NMR (400 MHz, DMSO-$d_6$) δ 9.06 (s, 1H), 8.93 (s, 2H), 6.74 (dd, J=17.9, 11.2 Hz, 1H), 6.13 (d, J=17.9 Hz, 1H), 5.51 (d, J=11.2 Hz, 1H); ES-MS [M+1]$^+$: 107.2.

b. Preparation of 5-(1-bromovinyl)pyrimidine

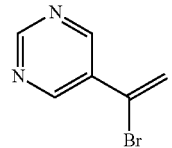

6-Vinylpyrimidine (2.03 g, 19.1 mmol, 1.0 eq) was dissolved in CHCl$_3$ (95 mL) and cooled to 0° C. Bromine (0.986 mL, 19.1 mmol, 1.0 eq) was added dropwise and the reaction was allowed to stir at 0° C. for 1.5 hours. Argon was bubbled through the reaction to remove excess bromine and 1,8-diazabicycloundec-7-ene (2.86 mL, 19.1 mmol, 1.0 eq) was added in one portion. The reaction was poured into a separatory funnel and washed with H$_2$O. The aqueous layer was back extracted with CH$_2$Cl$_2$ and the combined organics were dried (MgSO$_4$) and concentrated in vacuo. Purification by flash column chromatography on silica gel afforded 2.3 g (65%) of the title compound as a red solid. $^1$H NMR (400 MHz, DMSO-$d_6$) δ 9.18 (s, 1H), 9.05 (s, 2H), 6.71 (d, J=3.1 Hz, 1H), 6.10 (d, J=3.1 Hz, 1H); ES-MS [M+1]$^+$: 185.0.

4. Intermediate Route IV a. Preparation of (8-chloroquinolin-6-yl)(pyrimidin-5-yl)methanol.

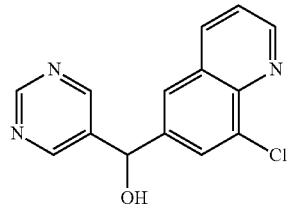 [SMILES: OC(c1cncnc1)c1cc(Cl)c2ncccc2c1]

5-Bromopyrimidine (2.65 g, 16.7 mmol, 1.0 eq) was dissolved in THF (34 mL) and ether (34 mL) in an oven-dried round bottom flask and cooled to −100° C. n-Butyllithium (1.6 M in hexanes) (10.4 mL, 16.6 mmol, 1.0 eq) was added dropwise while keeping the internal reaction temperature below −90° C. After addition the reaction was stirred for 15 minutes at −100° C. and 8-chloroquinoline-6-carbaldehyde (3.19 g, 16.7 mmol, 1.0 eq) was added dropwise as a solution in THF (34 mL) while keeping the internal reaction temperature below −90° C. After addition the reaction was allowed to gradually warm to room temperature. The reaction was quenched with water and extracted with ethyl acetate (3×). The combined organics were dried (MgSO$_4$) and concentrated in vacuo. Purification by flash chromatography on silica gel afforded 3.67 g (81%) of the title compound as a white solid. $^1$H NMR (400 MHz, DMSO-$d_6$) δ 9.09 (s, 1H), 8.99 (dd, J=4.2, 1.6 Hz, 1H), 8.86 (s, 2H), 8.46 (dd, J=8.4, 1.6 Hz, 1H), 8.06 (d, J=1.4 Hz, 1H), 7.98 (d, J=1.7 Hz, 1H), 7.64 (dd, J=8.3, 4.2 Hz, 1H), 6.58 (d, J=4.2 Hz, 1H), 6.06 (d, J=4.2 Hz, 1H); ES-MS [M+1]$^+$: 272.1.

b. Preparation of (8-chloroquinolin-6-yl)(pyrimidin-5-yl)methanone.

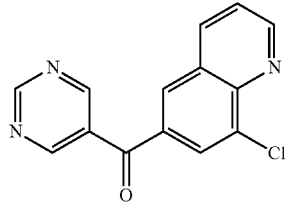 [SMILES: O=C(c1cncnc1)c1cc(Cl)c2ncccc2c1]

(8-Chloroquinolin-6-yl)pyrimidin-5-yl)methanol (3.67 g, 13.5 mmol, 1.0 eq) was dissolved in CH₂Cl₂ (113 mL) and MnO₂ (8.22 g, 94.5 mmol, 7.0 eq) was added. The reaction was stirred overnight, filtered and concentrated to afford 3.63 g (99%) of the title compound as a white solid. $^1$H NMR (400 MHz, DMSO-$d_6$) δ 9.48 (s, 1H), 9.21 (s, 2H), 9.17 (dd, J=4.2, 1.7 Hz, 1H), 8.68 (dd, J=8.3, 4.2 Hz, 1H); ES-MS [M+1]⁺: 270.1

5. Intermediate Route V a. Preparation of 6-(pyrimidine-5-carbonyl)quinoline-8-carbonitrile.

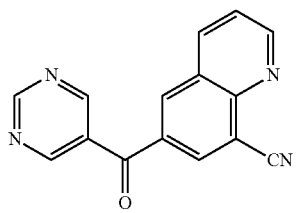 [SMILES: N#Cc1cc(C(=O)c2cncnc2)cc2cccnc12]

(8-Chloroquinolin-6-yl)(pyrimidin-5-yl)methanone (1.20 g, 4.45 mmol, 1.0 eq), tetrakis(triphenylphosphine)palladium(0) (514 mg, 0.445 mmol, 0.10 eq) and zinc cyanide (575 mg, 4.90 mmol, 1.1 eq) were dissolved in DMF (30 mL) in a microwave vial. The vial was purged with argon and heated in a microwave reactor at 140° C. for 20 minutes. The reaction was filtered, concentrated and purified by flash chromatography on silica gel to afford 809 mg (70%) of the title compound as a yellow solid. $^1$H NMR (400 MHz, CDCl₃) δ 9.48 (s, 1H), 9.24-9.21 (m, 3H), 8.89 (d, J=1.8 Hz, 1H), 8.76 (dd, J=8.4, 1.5, 1H), 8.73 (d, J=1.8 Hz, 1H), 7.85 (dd, J=8.3, 4.3 Hz, 1H); ES-MS [M+1]⁺: 261.0.

b. Preparation of 6-pyrimidine-5-carbonyl)quinoline-8-carboxylic acid.

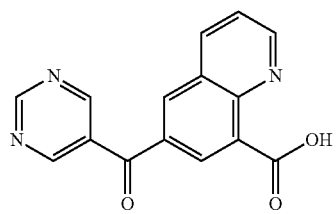 [SMILES: O=C(c1cncnc1)c1cc(C(=O)O)c2ncccc2c1]

6-(Pyrimidine-5-carbonyl)quinolone-8-carbonitrile (80 mg, 0.31 mmol, 1.0 eq) was dissolved in H₂SO₄ (1.6 mL) and AcOH (1.6 mL) in a sealed vessel and heated at 120° C. overnight. The reaction was cooled to room temperature and poured on ice. The solution was neutralized to pH 4-5 with 2N NaOH and extracted with 3:1 CHCl₃:isopropanol (3×). The combined organics were dried (MgSO₄) and concentrated in vacuo to afford 55 mg (64%) of the title compound as a white solid. $^1$H NMR (400 MHz, DMSO-$d_6$) δ 9.49 (s, 1H), 9.27-9.19 (m, 3H), 8.95-8.93 (m, 3H), 7.97-7.91 (m, 1H); ES-MS [M+1]⁺: 280.1.

6. Intermediate Route VI a. Preparation of pyrimidin-5-yl(8-vinylquinolin-6-yl)methanone.

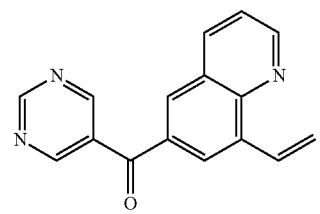 [SMILES: C=Cc1cc(C(=O)c2cncnc2)cc2cccnc12]

(8-Chloroquinolin-6-yl)(pyrimidin-5-yl)methanone (500 mg, 1.85 mmol, 1.0 eq), [1,1'-Bis(diphenyllphosphino)ferrocene]dichloropalladium (61 mg, 0.075 mmol, 0.040 eq), potassium vinyltrifluoroborate (298 mg, 2.22 mmol, 1.2 eq) and triethylamine (258 μL, 1.85 mmol, 1.0 eq) were dissolved in isopropanol (19 mL) in a round bottom flask and heated to 100° C. until complete by LCMS (~2 hours). The reaction was cooled, filtered over Celite and washed with 5% methanol/CH₂Cl₂. The solvents were removed in vacuo and the crude material was purified by flash chromatography on silica gel using hexanes/ethyl acetate to afford 330 mg (68%) of the title compound as a white solid. $^1$H NMR (400 MHz, CDCl₃) δ 9.47 (s, 1H), 9.20 (s, 2H), 9.09 (dd, J=4.2, 1.6 Hz, 1H), 8.59 (dd, J=8.3, 1.6 Hz, 1H), 8.45 (d, J=1.8 Hz, 1H), 8.38 (d, J=1.8 Hz, 1H), 7.96 (dd, J=18.0, 11.2 Hz, 1H), 7.69 (dd, J=8.3, 4.2 Hz, 1H), 6.17 (d, J=17.9 Hz, 1H), 5.58 (d, J=11.5 Hz, 1H); ES-MS [M+1]⁺: 262.0.

7. Intermediate Route VII a. Preparation of 8-chloro-6-(difluoro(pyrimidin-5-yl)methyl)quinoline

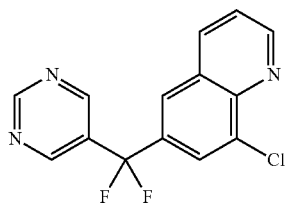 [SMILES: FC(F)(c1cncnc1)c1cc(Cl)c2ncccc2c1]

Diethylaminosulfur trifluoride (1.7 mL, 13 mmol, 7.0 eq) was added to (8-chloroquinolin-6-yl)(pyrimidin-5-yl)methanone (500 mg, 1.85 mmol, 1.0 eq) dissolved in CH₂Cl₂ (12.5 mL) in a sealed vessel and the reaction was heated to 40° C. overnight. An additional portion of diethylaminosulfur trifluoride (500 μL, 6.5 mmol, 3.5 eq) was added and the reaction was heated at 40 OC for an additional 24 hours. The reaction was cooled and quenched by dripping slowly onto ice. The layers were separated and the aqueous extracted with CH$_2$Cl$_2$. The combined organics were dried (MgSO$_4$) and concentrated in vacuo. Purification by flash chromatography on silica gel afforded 152 mg (28%) of the title compound as a yellow solid. $^1$H NMR (400 MHz, DMSO-d$_6$) δ 9.39 (s, 1H), 9.19 (dd J=4.3, 1.7 Hz, 1H), 9.17 (s, 2H), 8.75-8.69 (m, 2H), 8.67 (dd, J=8.4, 1.6 Hz, 1H), 7.83 (dd, J=8.4, 4.3 Hz, 1H); ES-MS [M+1]$^+$: 291.9.

b. Preparation of 6-difluoro(pyrimidin-5-yl)methyl)-8-vinylquinoline

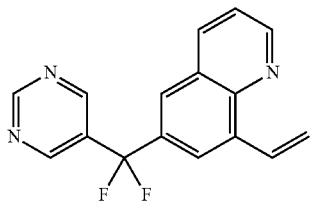 [SMILES: C=Cc1cc(C(F)(F)c2cncnc2)cc2cccnc12]

8-Chloro-6-(difluoro(pyrimidin-5-yl)methyl)quinoline (152 mg, 0.521 mmol, 1.0 eq), [1,1'-Bis(diphenylphosphino)ferrocene]dichloropalladium (17 mg, 0.021 mmol, 0.040 eq), potassium vinyltrifluoroborate (84 mg, 0.63 mmol, 1.2 eq) and triethylamine (73 μL, 0.52 mmol, 1.0 eq) were dissolved in isopropanol (3.5 mL) in a round-bottom flask and heated to 100° C. until complete by LCMS (~2 hours). The reaction was cooled, filtered over Celite and washed with 5% methanol/CH$_2$Cl$_2$. The solvents were removed in vacuo and the crude material was purified by flash chromatography on silica gel using hexanes/ethyl acetate to afford 71 mg (48%) of the title compound as a pale-yellow solid. $^1$H NMR (400 MHz, DMSO-d$_6$) δ 9.38 (s, 1H), 9.18 (s, 2H), 9.04 (dd, J=4.2, 1.7 Hz, 1H), 8.50 (dd, J=8.3, 1.6 Hz, 1H), 8.27-8.17 (m, 2H), 7.93 (dd, J=18.0, 11.3 Hz, 1H), 7.66 (dd, J=8.3, 4.2 Hz, 1H), 6.21 (d, J=18.0 Hz, 1H), 5.56 (d, J=11.3 Hz, 1H); ES-MS [M+1]$^+$: 284.0.

8. Intermediate Route VIII a. Preparation of methyl 6-(4,4,5,5-tetramethyl-1,3,2-dioxaborolan-2-yl)quinoline-8-carboxylate

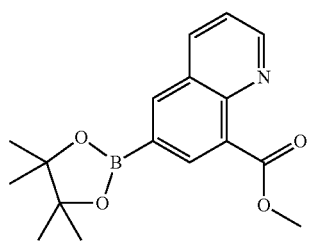

Methyl 6-bromoquinoline-8-carboxylate (1.00 g, 3.76 mmol, 1.0 eq), Bis(pinacaloto)diboron (1.05 g, 4.13 mmol, 1.10 eq), [1,1'-Bis(diphenylphosphino)ferrocene]-dichloropalladium (92 mg, 0.11 mmol, 0.030 eq) and dry potassium acetate (1.11 g, 11.3 mmol, 3.0 eq) were added to a microwave vial and the vial was purged with argon. Anhydrous DMSO (19 mL) was added and the vial heated in microwave reactor at 120° C. for 10 minutes. Water was added and the mixture extracted with ethyl acetate (3×). The combined organics were dried (MgSO$_4$) and concentrated in vacuo. Purification by flash chromatography on silica gel afforded 1.21 g (>99%) of the title compound as a black solid. $^1$H NMR (400 MHz, DMSO-d$_6$) δ 9.07 (dd, J=4.3, 1.8 Hz, 1H), 8.45-8.38 (dd, J=2H), 8.21 (dd, J=8.3, 1.8 Hz, 1H), 7.46 (dd, J=8.3, 4.2 Hz, 1H), 4.04 (s, 3H), 1.38 (s, 12H), 1.23 (s, 4H); Mass of boronic acid observed in LCMS ES-MS [M+1]$^+$: 232.0.

b. Preparation of methyl 6-(1-(pyrimidin-5-yl)vinyl)quinoline-8-carboxylate

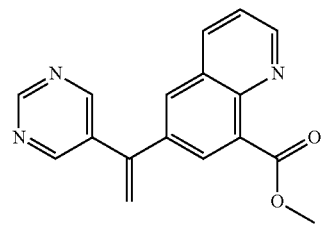 [SMILES: C=C(c1cncnc1)c1cc(C(=O)OC)c2ncccc2c1]

Methyl 6-(4,4,5,5-tetramethyl-1,3,2-dioxaborolan-2-yl)quinoline-8-carboxylate (600 mg, 1.92 mmol, 1.2 eq), 5-(1-bromovinyl)pyrimidine (295 mg, 1.60 mmol, 1.0 eq), Bis(diphenylphosphino)ferrocene]dichloropalladium (130 mg, 0.159 mmol, 0.10 eq) were dissolved in dimethylacetamide (8 mL) and 1N Na$_2$CO$_3$ (2.7 mL) in a microwave vial. The vial was heated in a microwave reactor at 100° C. for 10 minutes. The reaction was diluted with ethyl acetate and washed with water. The aqueous layer was back extracted with ethyl acetate and the combined organics were dried (MgSO$_4$) and concentrated in vacuo. Purification by flash chromatography on silica gel afforded 338 mg (61%) of the title compound as a white solid. $^1$H NMR (400 MHz, DMSO-d$_6$) δ 9.22 (s, 1H), 8.96 (d, J=4.3 Hz, 1H), 8.83 (s, 2H), 8.44 (d, J=8.3 Hz, 1H), 8.04 (s, 1H), 8.00 (s, 1H), 7.62 (dd, J=8.3, 4.2 Hz, 1H), 5.99 (s, 1H), 5.86 (s, 1H), 3.90 (s, 3H); ES-MS [M+1]$^+$: 292.1.

c. Preparation of methyl 6-(pyrimidine-5-carbonyl)quinoline-8-carboxylate

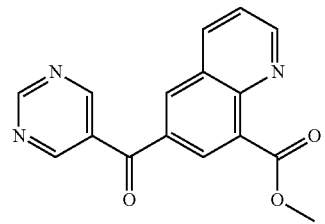 [SMILES: COC(=O)c1cc(C(=O)c2cncnc2)cc2cccnc12]

Methyl 6-(1-(pyrimidin-5-yl)vinyl)quinoline-8-carboxylate (338 mg, 1.16 mmol, 1.0 eq) was dissolved in CH$_2$Cl$_2$ (12 mL) and methanol (12 mL) and cooled to −76° C. Ozone was bubbled through the reaction until disappearance of starting material was observed by TLC. Oxygen was bubbled through the reaction to remove the excess ozone and dimethyl sulfide (2.57 mL, 34.8 mmol, 30 eq) was added. The reaction was allowed to warm to room temperature and stirred for 2 hours. The reaction was concentrated and purification by flash chromatography on silica gel afforded 131 mg (39%) of the title compound as an off-white solid. $^1$H NMR (400 MHz, DMSO-d$_6$) δ 9.48 (s, 1H), 9.21 (s, 2H), 9.11 (dd, J=4.3, 1.7 Hz, 1H), 8.69 (d, J=2.0 Hz, 1H), 8.67 (dd, J=8.4, 1.7 Hz, 1H), 8.32 (d, J=2.0 Hz, 1H), 7.74 (dd, J=8.3, 4.3 Hz, 1H), 3.94 (s, 3H); ES-MS [M+1]$^+$: 294.0.

9. Intermediate Route IX a. Preparation of pyrimidin-5-yl(8-vinylquinolin-6-yl)methanol

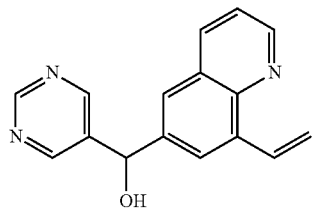 [SMILES: C=Cc1cc(C(O)c2cncnc2)cc2cccnc12]

Pyrimidin-5-yl(8-vinylquinolin-6-yl)methanone (330 mg, 1.26 mmol, 1.0 eq) was dissolved in THF (3.6 mL) and methanol (2.5 mL) and cooled to 0° C. Sodium borohydride (48 mg, 1.3 mmol, 1.0 eq) was added and the reaction was allowed to warm to room temperature. Upon determination of completion by LCMS, water was added and the reaction extracted with ethyl acetate (3×). The combined organics were dried (MgSO$_4$) and concentrated in vacuo. Purification by flash chromatography on silica gel afforded 335 mg (>99%) of the title compound as a white solid. $^1$H NMR (400 MHz, DMSO-d$_6$) δ 9.20 (s, 1H), 8.94-8.90 (m, 3H), 8.42 (dd, J=8.4, 1.6 Hz, 1H), 8.04 (s, 1H), 8.00 (s, 1H), 7.93 (dd, J=18.0, 11.3 Hz, 1H), 7.57 (dd, J=8.4, 4.2 Hz, 1H), 6.68 (d, J=4.2 Hz, 1H), 6.14-6.08 (m, 2H), 5.51 (d, J=11.3 Hz, 1H); ES-MS [M+1]$^+$: 264.0.

b. Preparation of 6-(fluoro(pyrimidin-5-yl)methyl)-8-vinylquinoline

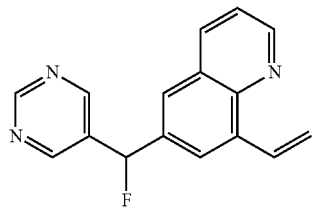 [SMILES: C=Cc1cc(C(F)c2cncnc2)cc2cccnc12]

Diethylaminosulfur trifluoride (252 μL, 1.91 mmol, 1.5 eq) was added to Pyrimidin-5-yl(8-vinylquinolin-6-yl)methanol (335 mg, 1.27 mmol, 1.0 eq) dissolved in CH$_2$Cl$_2$ (6.4 mL) in a sealed vessel and the reaction was heated to 40° C. overnight. The reaction was cooled and quenched by dripping slowly onto ice. The layers were separated and the aqueous extracted with CH$_2$Cl$_2$. The combined organics were dried (MgSO$_4$) and concentrated in vacuo. Purification by flash chromatography on silica gel afforded 125 mg (37%) of the title compound as a yellow solid. $^1$H NMR (400 MHz, DMSO-d$_6$) δ 9.22 (s, 1H), 8.98-8.92 (m, 3H), 8.42 (dd, J=8.4, 1.6 Hz, 1H), 8.08 (s, 1H), 8.04 (s, 1H), 7.93 (dd, J=18.0, 11.3 Hz, 1H), 7.60 (dd, J=8.4, 4.2 Hz, 1H), 7.14-7.02 (d, J=45.7 Hz, 1H), 6.11 (d, J=18.0 Hz, 1H), 5.51 (d, J=11.3 Hz, 1H); ES-MS [M+1]$^+$: 266.0.

10. Intermediate Route X a. Preparation of methyl 6-(1-(pyrimidin-5-yl)ethyl)quinoline-8-carboxylate

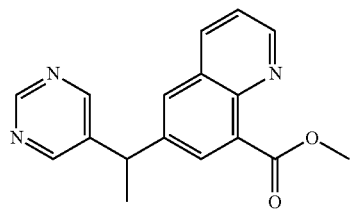 [SMILES: COC(=O)c1cc(C(C)c2cncnc2)cc2cccnc12]

Methyl 6-(1-(pyrimidin-5-yl)vinyl)quinoline-8-carboxylate (139 mg, 0.477 mmol, 1.0 eq) was dissolved in methanol (2.4 mL) in a round-bottom flask and Pd/C 10 wt % (5 mg) was added. The flash was pumped and purged with H$_2$ and the reaction was allowed to stir at room temperature overnight. The reaction was filtered over Celite and concentrated in vacuo to afford 135 mg (96%) of the title compound as a white solid. ES-MS [M+1]$^+$: 294.1.

11. Intermediate Route XI a. Preparation of methyl 6-(methoxy(pyrimidin-5-yl)methyl)quinoline-8-carboxylate

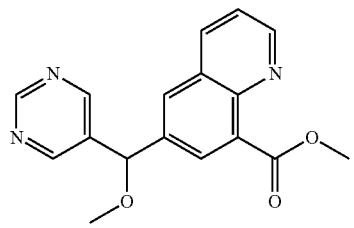 [SMILES: COC(=O)c1cc(C(OC)c2cncnc2)cc2cccnc12]

Methyl 6-(hydroxy(pyrimidin-5-yl)methyl)quinoline-8-carboxylate (55 mg, 0.19 mmol, 1.0 eq) and methyl iodide (11.6 μL, 0.19 mmol, 1.0 eq) were dissolved in DMF (1 mL) and cooled to 0° C. Potassium bis(trimethylsilyl)amide (0.5 M in toluene) (373 L, 0.186 mmol, 1.00 eq) was added and the reaction was allowed to stir for 2 hours. Another portion of potassium bis(trimethylsilyl)amide (0.5 M in toluene) (187 μL, 0.0931 mmol, 0.500 eq) was added and the reaction stirred for 1 hour. Water was added and the reaction was extracted with ethyl acetate (3×). The combined organics were dried (MgSO$_4$) and concentrated in vacuo. Purification by flash chromatography on silica gel afforded 15 mg (26%) of the title compound as a white solid. $^1$H NMR (400 MHz, DMSO-d$_6$) δ 9.13 (s, 1H), 8.95 (dd, J=4.2, 1.6 Hz, 1H), 8.87 (s, 2H), 8.47 (dd, J=8.4, 1.7 Hz, 1H), 8.23 (d, J=1.7 Hz, 1H), 7.93 (d, J=1.9 Hz, 1H), 7.62 (dd, J=8.4, 4.2 Hz, 1H), 5.76 (s, 1H), 3.88 (s, 3H), 3.37 (s, 3H); ES-MS [M+1]⁺: 310.0.

12. Intermediate Route XII a. Preparation of 6-(difluoro(pyrimidin-5-yl)methyl)quinoline-8-carbaldehyde

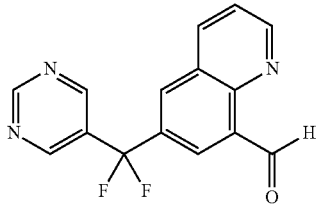 [SMILES: O=Cc1cc(C(F)(F)c2cncnc2)cc2cccnc12]

6-(Difluoro(pyrimidin-5-yl)methyl)-8-vinylquinoline (71 mg, 0.25 mmol, 1.0 eq) was dissolved in CH₂Cl₂ (2.5 mL) and cooled to −76° C. Ozone was bubbled through the reaction until disappearance of starting material was observed by TLC. Oxygen was bubbled through the reaction to remove the excess ozone and dimethyl sulfide (556 μL, 7.52 mmol, 30 eq) was added. The reaction was allowed to warm to room temperature and stirred for 2 hours. The reaction was concentrated and purification by flash chromatography on silica gel afforded 21 mg (29%) of the title compound as a yellow solid. ¹H NMR (400 MHz, CDCl₃) δ 9.52 (s, 1H), 7.63 (s, 1H), 7.48 (d, J=3.6 Hz, 1H), 7.26 (s, 2H), 6.71 (d, J=8.2 Hz, 1H), 6.66-6.60 (m, 2H), 5.98 (dd, J=8.4, 4.3 Hz, 1H); ES-MS [M+1]⁺: 286.0.

13. Intermediate Route XIII a. Preparation of (8-(1,2-dihydroxyethyl)quinoxalin-6-yl)(pyrimidin-5-yl)methanone

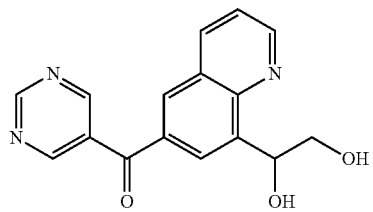 [SMILES: O=C(c1cncnc1)c1cc(C(O)CO)c2ncccc2c1]

Pyrimidin-5-yl(8-vinylquinoxalin-6-yl)methanone (20 mg, 0.076 mmol, 1.0 eq) and N-methylmorpholine-N-oxide (13.4 mg, 0.114 mmol, 1.5 eq) were dissolved in 3:1 acetone/H₂O (600 μL). Osmium tetraoxide (2.5 wt % in t-butanol) (15.5 μL, 0.00153 mmol, 0.020 eq) was added and the reaction was allowed to stir at room temperature overnight. The reaction was diluted with ethyl acetate and 10% NaS₂O₃ was added. The layers were separated and the aqueous phase extracted with 3:1 CHCl₃/IPA (2×). The combined organics were dried (MgSO₄) and concentrated in vacuo to give a crude brown oil that was used directly. ES-MS [M+1]⁺: 297.0.

b. Preparation of 7-(pyrimidine-5-carbonyl)quinoxaline-5-carbaldehyde

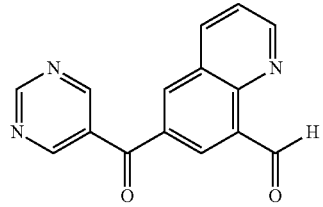 [SMILES: O=Cc1cc(C(=O)c2cncnc2)cc2cccnc12]

(8-(1,2-Dihydroxyethyl)quinoxalin-6-yl)(pyrimidin-5-yl)methanone (22 mg, 0.074 mmol, 1.0 eq) was dissolved in 3:1 THF/methanol (600 μL). Sodium periodate (17.5 mg, 0.0818 mmol, 1.0 eq) was added and the reaction was stirred at room temperature for 2 hours. The reaction was diluted with ethyl acetate water was added. The layers were separated and the aqueous layer was extracted with an additional portion of ethyl acetate and again with CH₂Cl₂. The combined organics were dried (MgSO₄) and concentrated in vacuo. Purification by flash chromatography on silica gel afforded 10 mg (51%) of the title compound as a white solid. ¹H NMR (400 MHz, DMSO-d₆) δ 9.48 (s, 1H), 9.27 (d, J=1.6 Hz, 1H), 9.23 (d, J=1.6 Hz, 1H), 9.21 (s, 2H), 8.78 (d, J=1.9 Hz, 1H), 8.58 (d, J=1.9 Hz, 1H); ES-MS [M+1]⁺: 265.0.

14. Intermediate Route XIV a. Preparation of 6-(pyrimidine-5-carbonyl)quinoline-8-carboxylic acid

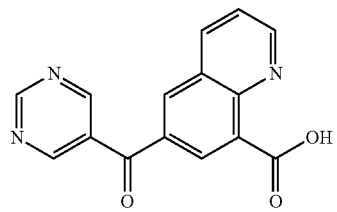 [SMILES: O=C(c1cncnc1)c1cc(C(=O)O)c2ncccc2c1]

6-(Pyrimidine-5-carbonyl)quinoline-8-carbaldehyde (5.0 mg, 0.019 mmol, 1.0 eq) was dissolved in dioxane (393 μL) and a solution of sodium acetate (5.5 mg, 0.067 mmol, 3.5 eq) in AcOH (125 μL) and H₂O (125 μL) was added followed by a solution of sulfamic acid (3.7 mg, 0.038 mmol, 2.0 eq) in H₂O (282 μL) and a solution of sodium chlorite (4.3 mg, 0.048 mmol, 2.0 eq) in H₂O (352 μL). The reaction was stirred for 1.5 hours and concentrated to around ⅓ volume. The resulting solution was extracted with CH₂Cl₂ (3×) and the combined organics were dried (MgSO₄) and concentrated in vacuo to afford 3.5 mg (66%) of the title compound as an off-white solid. ¹H NMR (400 MHz, DMSO-d₆) δ 9.49 (s, 1H), 9.25 (d, J=3.8 Hz, 1H), 9.22

(s, 2H), 8.92 (s, 8.3 Hz, 1H), 8.90-8.83 (m, 2H), 7.98-7.89 (m, 1H); ES-MS [M+1]⁺: 280.0.

15. Intermediate Route XV a. Preparation of 6-(methoxy(pyrimidin-5-yl)methyl)quinoline-8-carboxylic acid

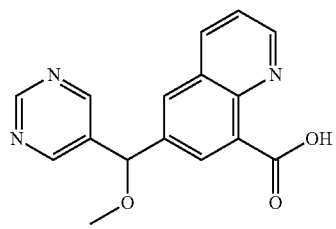 [SMILES: COC(c1cncnc1)c1cc(C(=O)O)c2ncccc2c1]

Methyl 6-(methoxy(pyrimidin-5-yl)methyl)quinoline-8-carboxylate (15 mg, 0.048 mmol, 1.0 eq) was dissolved in dioxane (250 μL) and 1N LiOH (125 μL) was added. The reaction was stirred for 1 hour and concentrated in vacuo. The solid was dissolved in 10% MeOH/CH$_2$Cl$_2$ and the undissolved salt was filtered off and the solvents were removed in vacuo to afford the title compound as a pale-yellow solid. ES-MS [M+1]⁺: 296.0.

16. Analog Route I a. Preparation of N-(5-fluoropyridin-2-yl)-6-(pyrimidine-5-carbonyl)quinoline-8-carboxamide

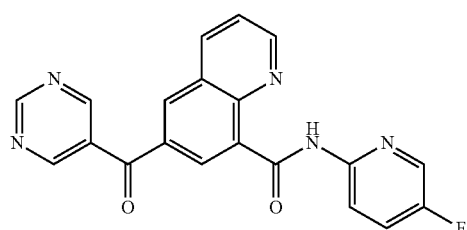

6-(Pyrimidine-5-carbonyl)quinoline-8-carboxylic acid (12 mg, 0.043 mmol, 1.0 eq) and 5-fluoro-2-aminopyridine (5.3 mg, 0.047 mmol, 1.1 eq) were dissolved in pyridine (1 mL) in a flame-dried round-bottom flask. The reaction was cooled to −15° C. and phosphorus oxychloride (4.4 μL, 0.047 mmol, 1.1 eq) was added while keeping the temperature below −15° C. After stirring for 30 min. at −15° C. and the reaction was quenched with ice-water and neutralized with 10% K$_2$CO$_3$. The mixture was extracted with EtOAc (3×) and the combined organics were dried (MgSO$_4$), filtered and concentrated in vacuo. Purification by flash chromatography on silica gel afforded 6.7 mg (42%) of the title compound as a white solid. ¹H NMR (400 MHz, DMSO-d$_6$) δ 9.50 (s, 1H), 9.30 (dd, J=4.3, 1.6 Hz, 1H), 9.24 (s, 2H), 9.10 (d, J=2.0 Hz, 1H), 8.88-8.83 (m, 2H), 8.47-8.41 (m, 2H), 7.90-7.83 (m, 2H); ES-MS [M+1]⁺: 374.2.

17. Analog Route II a. Preparation of 6-((5-fluoropyridin-3-yl)(hydroxy)methyl)-N-(4-methylthiazol-2-yl)quinoline-8-carboxamide

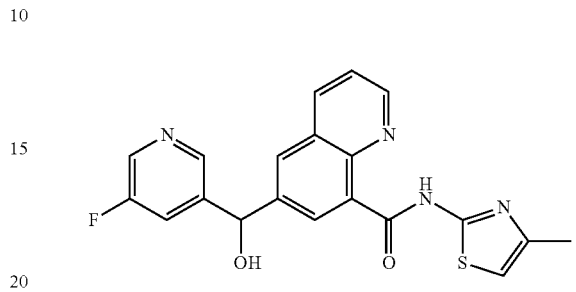

6-(5-Fluoronicotinoyl)-N-(4-methylthiazol-2-yl)quinoline-8-carboxamide (7.0 mg, 0.018 mmol, 1.0 eq) was dissolved in THF (300 L) and methanol (200 L) and cooled to 0° C. Sodium borohydride (0.74 mg, 0.019 mmol, 1.1 eq) was added and the reaction was allowed to warm to room temperature. Upon determination of completion by LCMS, water was added and the reaction extracted with ethyl acetate (3×). The combined organics were dried (MgSO$_4$) and concentrated in vacuo. Purification by flash chromatography on silica gel afforded 3.0 mg (42%) of the title compound as a white solid. ES-MS [M+1]⁺: 395.0.

18. Generation of mGluR5 Stable Cell Lines

Typically, the mGluR5 activity of the disclosed compounds is determined a stable cell line transected with rat mGluR5. The preparation of rat mGluR5 stable cell-lines is as previously described (e.g. see Romano et al. J. Biol. Chem. 1996 Nov. 8; 271(45):28612-6). Data generated using this cell-line in the mGluR5 assay (described below) are shown in Table 1.

mGluR5 activity of the disclosed cell-lines can also be determined using a stable cell-line transected with human mGluR5. Briefly, human mGluR5a cDNA in pCMV6-XL6 mammalian expression plasmid was purchased from OriGene Technologies, Inc. (catalogue number SC326357) and subcloned into pcDNA3.1(−). Human embryonic kidney (HEK)293A cells were then transfected with human mGluR5a pcDNA3.1(−) using LipofectAmine® 2000 (Invitrogen) and monoclones were selected and tested for functional response using a Ca$^{2+}$ mobilization assay. Monoclones were named for the species ("H" for human) plus the location on the plate (e.g. "10H").

19. Metabotropic Glutamate Receptor Activity: Calcium Mobilization Assay

HEK 293A cells stably expressing rat mGluR5 were plated in black-walled, clear-bottomed, poly-D-lysine coated 384-well plates in 20 L of assay medium (DMEM containing 10% dialyzed FBS, 20 mM HEPES, and 1 mM sodium pyruvate) at a density of 20,000 cells/well. The cells were grown overnight at 37° C. in the presence of 5% CO$_2$. The next day, medium was removed and the cells incubated with 20 μL of 2 μM Fluo-4, AM prepared as a 2.3 mM stock in DMSO and mixed in a 1:1 ratio with 10% (w/v) pluronic acid F-127 and diluted in assay buffer (Hank's balanced salt solution, 20 mM HEPES, and 2.5 mM probenecid) for 45 minutes at 37° C. Dye was removed, 20 L of assay buffer was added, and the plate was incubated for 10 minutes at room temperature.

$Ca^{2+}$ flux was measured using the Functional Drug Screening System (FDSS6000, Hamamatsu, Japan). After establishment of a fluorescence baseline for about 3 seconds, the compounds of the present invention were added to the cells, and the response in cells was measured. 2.3 minutes later an $EC_{20}$ concentration of the mGluR5 receptor agonist glutamate was added to the cells, and the response of the cells was measured for about 1.2 minutes; an $EC_{80}$ concentration of agonist was added and readings taken for an additional 40 seconds. All test compounds were dissolved and diluted to a concentration of 10 mM in 100% DMSO and then serially diluted into assay buffer for a 2× stock solution in 0.6% DMSO; stock compounds were then added to the assay for a final DMSO concentration of 0.3% after the first addition to the assay well. Calcium fluorescence measures were recorded as fold over basal fluorescence; raw data was then normalized to the maximal response to glutamate. Antagonism of the agonist response of the mGluR5 receptor in the present invention was observed as a decrease in response to nearly maximal concentrations of glutamate in the presence of compound compared to the response to glutamate in the absence of compound.

The raw data file containing all time points was used as the data source in the analysis template. This was saved by the FDSS as a tab-delimited text file. Data were normalized using a static ratio function ($F/F_0$) for each measurement of the total 250 values per well divided by each well's initial value. Data were then reduced as to peak amplitudes (Max−Initial Min) using a time range that starts approximately 3 seconds prior to the glutamate $EC_{80}$ addition and continues for approximately 40 seconds. This is sufficient time to capture the peak amplitude of the cellular calcium response. Individual amplitudes were expressed as % $E_{Max}$ by multiplying each amplitude by 100 and then dividing the product by the mean of the amplitudes derived from the glutamate $EC_{Max}$-treated wells. $EC_{50}$ values for test compounds were generated by fitting the normalized values versus the log of the test compound concentration (in mol/L) using a 4 parameter logistic equation where none of the parameters were fixed. Each of the three values collected at each concentration of test compound were weighted evenly. A compound was designated as a negative allosteric modulator if the compound showed a concentration-dependent decrease in the glutamate $EC_{80}$ addition. Potency ($IC_{50}$) and maximum response (% Glu Max) for compounds were determined using a four parameter logistical equation. For data that show a decrease in the $EC_{80}$ response, but do not hit a plateau, the average of the maximum response at a single concentration (30 M) was determined and potencies were not quantified.

The above described assay was also operated in a second mode where an appropriate fixed concentration of the present compounds were added to the cells after establishment of a fluorescence baseline for about 3 seconds, and the response in cells was measured. 2.3 min later the appropriate concentration of agonist was added and readings taken for an additional 2.6 minutes. Data were reduced as described above and the $EC_{50}$ values for the agonist in the presence of test compound were determined by nonlinear curve fitting. A decrease in the $EC_{50}$ value of the agonist with increasing concentrations of the present compounds (a leftward shift of the agonist concentration-response curve) is an indication of the degree of mGluR5 positive allosteric modulation at a given concentration of the present compound. An increase in the EC50 value of the agonist with increasing concentrations of the present compounds (a rightward shift of the agonist concentration response curve) is an indication of the degree of mGluR5 antagonism at a given concentration of the present compound. The second mode also indicates whether the present compounds also affect the maximum response to mGluR5 to agonists.

20. Prospective Metabotropic Glutamate Receptor Activity: Radioligand Binding Assay The following examples of the in vitro effects of the disclosed compounds are prophetic. An example of an in vitro assay method for assessing the receptor ligand binding activity of the disclosed compounds is given below.

Competition binding studies can be performed with the allosteric antagonist [$^3$H]methoxyPEPy to determine if the disclosed compounds interact with the well-characterized allosteric binding site for the mGluR5 NAM MPEP.

The allosteric antagonist MPEP analog [$^3$H]methoxyPEPy is used to evaluate the ability of test compounds to interact with the MPEP site on mGluR5 (Cosford et al., 2003a). Membranes are prepared from rat mGluR5 HEK293 cells (Rodriguez et al., 2005). Compounds are diluted in assay buffer (50 mM Tris/0.9% NaCl, pH 7.4) to a 5× stock and 100 μL test compound is added to each well of a 96 deep-well assay plate. 300 L aliquots of membranes diluted in assay buffer (40 g/well) are added to each well. 100 μL [$^3$H]methoxyPEPy (2 nM final concentration) is added and the reaction is incubated at room temperature for 1 hour with shaking. After the incubation period, the membrane-bound ligand is separated from free ligand by filtration through glass-fiber 96 well filter plates (Unifilter-96, GF/B, PerkinElmer Life and Analytical Sciences, Boston, Mass.). The contents of each well are transferred simultaneously to the filter plate and washed 3-4 times with assay buffer using a cell harvester (Brandel Cell Harvester, Brandel Inc., Gaithersburg, Md.). 40 L scintillation fluid is added to each well and the membrane-bound radioactivity determined by scintillation counting (TopCount, PerkinElmer Life and Analytical Sciences). Non-specific binding is estimated using 5 μM MPEP. Concentration response curves were generated using a four parameter logistical equation in GraphPad Prism (GraphPad Software, Inc., La Jolla, Calif.).

For example, compounds having a structure represented by a formula:

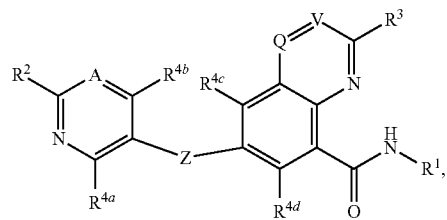

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$SO_2R^{22}$, and —(C═O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, —$NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, —$NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, —$NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, —$NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, —$NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, —$NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from —$CR^8(O)_rR^9$—, —$CR^8NR^{10a}R^{10b}$—, —(C=O)—, and a structure represented by a formula:

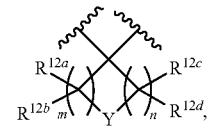

wherein Y is selected from —$CR^8R^9$—, —O—, —$S(O)_q$—, and —$NR^8$—; wherein m is an integer selected from 0, 1, and 2; wherein n is an integer selected from 0 and 1; wherein the sum of m and n is 1 or 2 when Y is —$CR^8R^9$—; wherein the sum of m and n is 2 when Y is —O—, —$S(O)_q$—, and —$NR^8$—; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O)$R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, —$NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, —$NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein R$^{64a}$ and R$^{64b}$, when present, are optionally covalently bonded and, together with nitrogen atom to which they are attached, comprise a 3- to 6-membered heterocycle; wherein R$^{63}$, when present, is selected from C1-C3 alkyl, C1-C3 monohaloalkyl, C1-C3 polyhaloalkyl, cyclopropyl, and, —NR$^{65a}$R$^{65b}$; wherein each of R$^{65a}$ and R$^{65b}$, when present, is independently selected from hydrogen, C1-C3 alkyl, C1-C3 monohaloalkyl, C1-C3 polyhaloalkyl, and cyclopropyl; or wherein R$^{65a}$ and R$^{65b}$, when present, are optionally covalently bonded and, together with nitrogen atom to which they are attached, comprise a 3- to 6-membered heterocycle; wherein each of R$^{4a}$, R$^{4b}$, R$^{4c}$, and R$^{4d}$, is independently selected from hydrogen and fluoro; or a pharmaceutically acceptable salt, solvate, or polymorph thereof, are expected to show at least partial displacement of [$^3$H]methoxyPEPy in the radioligand binding assay. Moreover, compounds prepared using the disclosed synthetic methods are also expected to show such effects.

21. Prospective Metabotropic Glutamate Receptor Activity: Selectivity Assays

The following examples of the in vitro effects of the disclosed compounds are prophetic. Typical examples of in vitro assay methods for assessing the receptor selectivity of the disclosed compounds are given below.

a. Rat mGluR1 Assay

Compound activity at the group I mGluRs can be assessed in the assay described herein. HEK293 cells stably expressing rat mGluR1 are cultured and assayed as described above for mGluR5-expressing cells. For these assays, after establishment of a fluorescence baseline for about 3 seconds, the compounds of the present invention are added to the cells at 2× final concentration, and the response in cells is measured. 2.3 min later the appropriate concentration of agonist is added at 5× the final concentration and readings taken for an additional 2.6 minutes. Data are analyzed as described for mGluR5 assays.

b. Rat mGlu Receptors 2, 3, 4, 7, and 8, and Human mGluR6 Assays

Compound activity at the group II and group III mGluRs can be assessed using thallium flux through G-protein-coupled inwardly rectifying potassium (GIRK) channels, a method that has been described in detail (Niswender et al. (2008) Mol. Pharmacol. 73, 1213-1224). These cell lines are grown in growth media containing 45% DMEM, 45% F-12, 10% FBS, 20 mM HEPES, 2 mM Ll-glutamine, antibiotic/antimycotic, nonessential amino acids, 700 µg/mL G418, and 0.6 g/mL puromycin at 37° C. in the presence of 5% CO$_2$. Briefly, HEK/GIRK cells expressing the mGluR subtype 2, 3, 4, 6, 7, or 8 are plated into 384 well, black-walled, clear-bottom poly-D-lysine coated plates at a density of 15,000 cells/20 L/well in assay medium and incubated overnight at 37° C. in the presence of 5% CO$_2$. The following day, the medium from the cells and 20 µL/well of 1.7 µM concentration of the indicator dye BTC-AM (Invitrogen, Carlsbad, Calif.) in assay buffer is added. Cells are incubated for 1 hour at room temperature and the dye is replaced with 20 µL/well of assay buffer. After establishment of a fluorescence baseline for about 3 seconds, the compounds of the present invention are added to the cells at 2× final concentration, and the response in cells is measured. 2.3 min later the appropriate concentration of agonist is added and readings taken for an additional 2.6 minutes. Agonists are diluted in thallium buffer (125 mM sodium bicarbonate, 1 mM magnesium sulfate, 1.8 mM calcium sulfate, 5 mM glucose, 12 mM thallium sulfate, 10 mM HEPES) at 5× the final concentration to be assayed. Data are analyzed as described in Niswender et al. 2008.

c. Prospective Activity of the Disclosed Compounds and Products of the Disclosed Methods of Making It is anticipated that compounds having a structure represented by a formula:

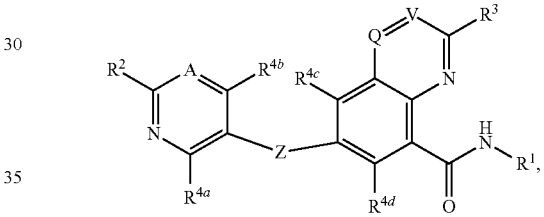

wherein A is selected from N and CR$^5$; wherein R$^5$, when present, is selected from hydrogen, halogen, —CN, C1-C3 alkyl, C1-C3 monohaloalkyl, C1-C3 polyhaloalkyl, cyclopropyl, —OR$^{20}$, —NR$^{21a}$R$^{21b}$, —SO$_2$R$^{22}$, and —(C=O)R$^{23}$; wherein R$^{20}$, when present, is selected from hydrogen, C1-C3 alkyl, C1-C3 monohaloalkyl, C1-C3 polyhaloalkyl, and cyclopropyl; wherein each of R$^{21a}$ and R$^{21b}$, when present, is independently selected from hydrogen, C1-C3 alkyl, C1-C3 monohaloalkyl, C1-C3 polyhaloalkyl, and cyclopropyl; or wherein R$^{21a}$ and R$^{21b}$, when present, are optionally covalently bonded and, together with nitrogen atom to which they are attached, comprise a 3- to 6-membered heterocycle; wherein R$^{22}$, when present, is selected from C1-C3 alkyl, C1-C3 monohaloalkyl, C1-C3 polyhaloalkyl, cyclopropyl, and, —NR$^{24a}$R$^{24b}$; wherein each of R$^{24a}$ and R$^{24b}$, when present, is independently selected from hydrogen, C1-C3 alkyl, C1-C3 monohaloalkyl, C1-C3 polyhaloalkyl, and cyclopropyl; or wherein R$^{24a}$ and R$^{24b}$, when present, are optionally covalently bonded and, together with nitrogen atom to which they are attached, comprise a 3- to 6-membered heterocycle; wherein R$^{23}$, when present, is selected from C1-C3 alkyl, C1-C3 monohaloalkyl, C1-C3 polyhaloalkyl, cyclopropyl, and, —NR$^{25a}$R$^{25b}$; wherein each of R$^{25a}$ and R$^{25b}$, when present, is independently selected from hydrogen, C1-C3 alkyl, C1-C3 monohaloalkyl, C1-C3 polyhaloalkyl, and cyclopropyl; or wherein R$^{25a}$ and R$^{25b}$, when present, are optionally covalently bonded and, together with nitrogen atom to which they are attached, comprise a 3- to 6-membered heterocycle; wherein Q is selected from N and CR$^6$; wherein R$^6$, when present, is selected from hydrogen, halogen, —CN, C1-C3 alkyl, C1-C3 monohaloalkyl, C1-C3 polyhaloalkyl, cyclopropyl, —OR$^{30}$, —NR$^{31a}$R$^{31b}$, —SO$_2$R$^{32}$, and —(C=O)R$^{33}$; wherein R$^{30}$, when present, is selected from hydrogen, C1-C3 alkyl, C1-C3 monohaloalkyl, C1-C3 polyhaloalkyl, and cyclopropyl; wherein each of R$^{31a}$ and R$^{31b}$, when present, is independently selected from hydrogen, C1-C3 alkyl, C1-C3 monohaloalkyl, C1-C3 polyhaloalkyl, and cyclopropyl; or wherein R$^{31a}$ and R$^{31b}$, when present, are optionally covalently bonded and, together with nitrogen atom to which they are attached, comprise a 3- to 6-membered heterocycle; wherein R$^{32}$, when present, is selected from C1-C3 alkyl, C1-C3 monohaloalkyl, C1-C3 polyhaloalkyl, cyclopropyl, and, —NR$^{34a}$R$^{34b}$; wherein each of R$^{34a}$ and R$^{34b}$, when present, is independently selected from hydrogen, C1-C3 alkyl, C1-C3 monohaloalkyl, C1-C3 polyhaloalkyl, and cyclopropyl; or wherein R$^{34a}$ and R$^{34b}$, when present, are optionally covalently bonded and, together with nitrogen atom to which they are attached, comprise a 3- to 6-membered heterocycle; wherein R$^{33}$, when present, is selected from C1-C3 alkyl, C1-C3 monohaloalkyl, C1-C3 polyhaloalkyl, cyclopropyl, and, —NR$^{35a}$R$^{35b}$; wherein each of R$^{35a}$ and R$^{35b}$, when present, is independently selected from hydrogen, C1-C3 alkyl, C1-C3 monohaloalkyl, C1-C3 polyhaloalkyl, and cyclopropyl; or wherein R$^{35a}$ and R$^{35b}$, when present, are optionally covalently bonded and, together with nitrogen atom to which they are attached, comprise a 3- to 6-membered heterocycle; wherein V is selected from N and CR$^7$, provided that Q and V are not simultaneously N; wherein R$^7$, when present, is selected from hydrogen, halogen, —CN, C1-C3 alkyl, C1-C3 monohaloalkyl, C1-C3 polyhaloalkyl, cyclopropyl, —OR$^{40}$, —NR$^{41a}$R$^{41b}$, —SO$_2$R$^{42}$, and —(C=O)R$^{43}$; wherein R$^{40}$, when present, is selected from hydrogen, C1-C3 alkyl, C1-C3 monohaloalkyl, C1-C3 polyhaloalkyl, and cyclopropyl; wherein each of R$^{41a}$ and R$^{41b}$, when present, is independently selected from hydrogen, C1-C3 alkyl, C1-C3 monohaloalkyl, C1-C3 polyhaloalkyl, and cyclopropyl; or wherein R$^{41a}$ and R$^{41b}$, when present, are optionally covalently bonded and, together with nitrogen atom to which they are attached, comprise a 3- to 6-membered heterocycle; wherein R$^{42}$, when present, is selected from C1-C3 alkyl, C1-C3 monohaloalkyl, C1-C3 polyhaloalkyl, cyclopropyl, and, —NR$^{44a}$R$^{44b}$; wherein each of R$^{44a}$ and R$^{44b}$, when present, is independently selected from hydrogen, C1-C3 alkyl, C1-C3 monohaloalkyl, C1-C3 polyhaloalkyl, and cyclopropyl; or wherein R$^{44a}$ and R$^{44b}$, when present, are optionally covalently bonded and, together with nitrogen atom to which they are attached, comprise a 3- to 6-membered heterocycle; wherein R$^{43}$, when present, is selected from C1-C3 alkyl, C1-C3 monohaloalkyl, C1-C3 polyhaloalkyl, cyclopropyl, and, —NR$^{45a}$R$^{45b}$; wherein each of R$^{45a}$ and R$^{45b}$, when present, is independently selected from hydrogen, C1-C3 alkyl, C1-C3 monohaloalkyl, C1-C3 polyhaloalkyl, and cyclopropyl; or wherein R$^{45a}$ and R$^{45b}$, when present, are optionally covalently bonded and, together with nitrogen atom to which they are attached, comprise a 3- to 6-membered heterocycle; wherein Z is selected from —CR$^8$(O)$_r$R$^9$—, —CR$^8$NR$^{10a}$R$^{10b}$—, —(C=O)—, and a structure represented by a formula:

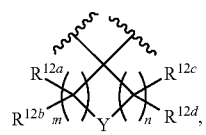

wherein Y is selected from —CR$^8$R$^9$—, —O—, —S(O)$_q$—, and —NR$^8$—; wherein m is an integer selected from 0, 1, and 2; wherein n is an integer selected from 0 and 1; wherein the sum of m and n is 1 or 2 when Y is —CR$^8$R$^9$—; wherein the sum of m and n is 2 when Y is —O—, —S(O)$_q$—, and —NR$^8$—; wherein q is 0, 1, or 2; wherein r is 0 or 1; wherein R$^8$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^8$ is not halogen; wherein R$^9$, when present, is selected from hydrogen, halogen, C1-C3 alkyl, C1-C3 monohaloalkyl, C1-C3 polyhaloalkyl, and cyclopropyl; provided that, when Z is —CR$^8$(O)$_r$R$^9$— and r is 1, R$^9$ is not halogen; wherein each of R$^{10a}$ and R$^{10b}$, when present, is independently selected from hydrogen, C1-C3 alkyl, C1-C3 monohaloalkyl, C1-C3 polyhaloalkyl, and cyclopropyl; wherein each occurrence of R$^{12a}$, R$^{12a}$, R$^{12a}$, and R$^{12a}$, when present, is independently selected from hydrogen, halogen, C1-C3 alkyl, C1-C3 monohaloalkyl, and C1-C3 polyhaloalkyl; wherein R$^1$ is selected from aryl and heteroaryl, and wherein R$^1$ is substituted with 0, 1, 2, or 3 groups independently selected from halogen, —CN, C1-C3 alkyl, C1-C3 monohaloalkyl, C1-C3 polyhaloalkyl, cyclopropyl, —OR$^{50}$, —NR$^{51a}$R$^{51b}$, —SO$_2$R$^{52}$, and —(C=O)R$^{53}$; wherein each occurrence of R$^{50}$, when present, is independently selected from hydrogen, C1-C3 alkyl, C1-C3 monohaloalkyl, C1-C3 polyhaloalkyl, and cyclopropyl; wherein each occurrence of each of R$^{51a}$ and R$^{51b}$, when present, is independently selected from hydrogen, C1-C3 alkyl, C1-C3 monohaloalkyl, C1-C3 polyhaloalkyl, and cyclopropyl; or wherein R$^{51a}$ and R$^{51b}$, when present, are optionally covalently bonded and, together with nitrogen atom to which they are attached, comprise a 3- to 6-membered heterocycle; wherein each occurrence of R$^{52}$, when present, is independently selected from C1-C3 alkyl, C1-C3 monohaloalkyl, C1-C3 polyhaloalkyl, cyclopropyl, and, —NR$^{54a}$R$^{54b}$; wherein each occurrence of each of R$^{54a}$ and R$^{54b}$, when present, is independently selected from hydrogen, C1-C3 alkyl, C1-C3 monohaloalkyl, C1-C3 polyhaloalkyl, and cyclopropyl; or wherein R$^{54a}$ and R$^{54b}$, when present, are optionally covalently bonded and, together with nitrogen atom to which they are attached, comprise a 3- to 6-membered heterocycle; wherein each occurrence of R$^{53}$, when present, is independently from C1-C3 alkyl, C1-C3 monohaloalkyl, C1-C3 polyhaloalkyl, cyclopropyl, and, —NR$^{55a}$R$^{55b}$; wherein each occurrence of each of R$^{55a}$ and R$^{55b}$, when present, is independently selected from hydrogen, C1-C3 alkyl, C1-C3 monohaloalkyl, C1-C3 polyhaloalkyl, and cyclopropyl; or wherein R$^{55a}$ and R$^{55b}$, when present, are optionally covalently bonded and, together with nitrogen atom to which they are attached, comprise a 3- to 6-membered heterocycle; wherein R$^2$ is selected from hydrogen, C1-C3 alkyl, C1-C3 monohaloalkyl, C1-C3 polyhaloalkyl, and cyclopropyl; wherein R$^3$ is selected from hydrogen, halogen, —CN, C1-C3 alkyl, C1-C3 monohaloalkyl, C1-C3 polyhaloalkyl, cyclopropyl, —OR$^{60}$, —NR$^{61a}$R$^{61b}$, —SO$_2$R$^{62}$, and —(C=O)R$^{63}$; wherein R$^{60}$, when present, is selected from hydrogen, C1-C3 alkyl, C1-C3 monohaloalkyl, C1-C3 polyhaloalkyl, and cyclopropyl; wherein each of R$^{61a}$ and R$^{61b}$, when present, is independently selected from hydrogen, C1-C3 alkyl, C1-C3 monohaloalkyl, C1-C3 polyhaloalkyl, and cyclopropyl; or wherein R$^{61a}$ and R$^{61b}$, when present, are optionally covalently bonded and, together with nitrogen atom to which they are attached, comprise a 3- to 6-membered heterocycle; wherein R$^{62}$, when present, is selected from C1-C3 alkyl, C1-C3 monohaloalkyl, C1-C3 polyhaloalkyl, cyclopropyl, and, —NR$^{64a}$R$^{64b}$; wherein each of R$^{64a}$ and R$^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof, are expected to show selective inhibition of mGluR5 compared to rat mGlu receptors R1, R2, R3, R4, R7, and R8, and Human mGluR6. In one aspect, the disclosed compounds are anticipated to show at least about 1.5 fold greater selectivity for rat mGluR5 compared rat mGlu receptors R1, R2, R3, R4, R7, and R8, and Human mGluR6 based on $IC_{50}$. In a further aspect, the disclosed compounds are anticipated to show about at least 5 fold greater selectivity for rat mGluR5 compared rat mGlu receptors R1, R2, R3, R4, R7, and R8, and Human mGluR6 based on $IC_{50}$. In a still further aspect, the disclosed compounds are anticipated to show at least about 10 fold greater selectivity for rat mGluR5 compared rat mGlu receptors R1, R2, R3, R4, R7, and R8, and Human mGluR6 based on $IC_{50}$. In an even further aspect, the disclosed compounds are anticipated to show at least about 50 fold greater selectivity for rat mGluR5 compared rat mGlu receptors R1, R2, R3, R4, R7, and R8, and Human mGluR6 based on $IC_{50}$. In a still further aspect, the disclosed compounds are anticipated to show at least about 100 fold greater selectivity for rat mGluR5 compared rat mGlu receptors R1, R2, R3, R4, R7, and R8, and Human mGluR6 based on $IC_{50}$. Moreover, compounds prepared using the disclosed synthetic methods are also expected to show such effects.

22. Mouse Model of Anxiolytic Behavior: Inhibition of Marble Burying Activity in Mice (Prophetic)

It is well known that mice will bury foreign objects such as glass marbles in deep bedding (Deacon, R. M. J. *Nature Protocols* 2006, 1, 122-124). Low doses of anxiolytic benzodiazepines have been demonstrated to inhibit this behavior (Njung'e, K.; Handley, S. L. *Brit. J. Pharmacol.* 1991, 104, 105-112; Broekkamp, C. L.; Rijk, H. W.; Joly-Gelouin, D.; Lloyd, K. L. *Eur. J. Pharmacol.* 1986, 126, 223-229). Moreover, the known mGlu₅ NAMs MPEP (3-((2-Methyl-4-thiazolyl)ethynyl)-pyridine) and fenobam (1-(3-chlorophenyl)-3-(1-methyl-4-oxo-4,5-dihydro-1H-imidazol-2-yl) urea) are effective in this model (Spooren W. P. J. M.; Vassout A.; Neijt H. C.; Kuhn R.; Gasparini F.; Roux S.; Porsolt R. D.; Gentsch C. *J. Pharmacol. Exp. Ther.* 2000, 295, 1267-1275; Nicolas, L. B.; Kolb, Y.; Prinssen, E. P. M. *Eur. J. Pharmacol.* 2006, 547, 106-115). These facts along with the relative convenience of this assay make it a useful in vivo screening tool.

Doses of compound are suspended in vehicle (10% Tween 80 for intraperitoneal dosing and 0.5% methylcellulose for oral dosing), vortexed vigorously, heated gently with a Master Heat Gun (Master Appliance Corp., Racine, Wis.), and sonicated at 37° C. for 30 minutes. The pH was checked using 0-14 EMD strips and adjusted to approximately 7. All doses are administered at approximately 10 mL/kg.

Studies are conducted using male Harlan CD-1 mice (Harlan Sprague Dawley, Indianapolis, Ind.), weighing 30 to 35 grams. Subjects are housed in a large colony room under a 12 hour light/dark cycle (lights on at 6:00 a.m.) with food and water provided ad libitum. Test sessions are performed between 10:00 a.m. and 4:00 p.m. All dose groups consists of ≥10 mice. All experiments are conducted in accordance with the National Institute of Health regulations of animal care covered in Principles of Laboratory Animal Care (National Institutes of Health publication 85-23, revised 1985) and are approved by the Institutional Animal Care and Use Committee.

Plexiglass cages (32×17×14 cm) were arranged on top of a large, round table. Mice are transported from the colony room to the testing room and are allowed to habituate for 30 minutes. Mice are pretreated with a dose of a standard compound (MTEP, 2-methyl-4-(pyridin-3-ylethynyl)thiazole) or novel compound for 15 or 30 minutes and individually placed in the cages in which 12 black glass marbles (14 mm diameter) are evenly distributed (spaced 6.4 cm vertically and 4.25 cm horizontally from each other and the walls of the cage) on top of 2.5 cm Diamond Soft Bedding (Harlan Teklad, Madison, Wis.). The novel compound and comparator are evaluated in a counterbalanced design, in which all doses of compounds are tested in each session. Mice receiving the same dose are placed in cages on opposite sides of the table to control for effects of lighting and context. Clear, perforated plastic lids are set on top of each cage and the amount of marble burying is recorded over a 30 minute interval. The mice are then removed from the cages and the number of buried marbles is counted using the criteria of greater than ⅔ covered by bedding. Each session is videotaped with a Sony MiniDV camcorder equipped with a Sony wide-angle lens mounted on a 1.5 m tripod.

The data for the dose-response studies are analyzed by a between-group analysis of variance. If there is a main effect of dose, then each dose group is compared with the vehicle control group using a Dunnett's comparison. The calculations are performed using JMP IN 8 (SAS Institute, Cary, N.C.) statistical software and graphed using SigmaPlot9 (Sasgua, MA).

23. Prophetic Pharmaceutical Composition Examples

"Active ingredient" as used throughout these examples relates to one or more compounds having a structure represented by a formula:

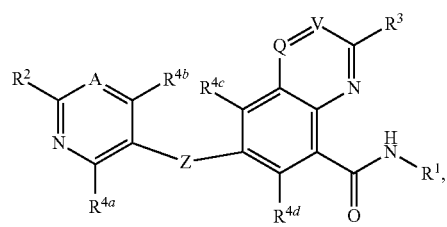

wherein A is selected from N and $CR^5$; wherein $R^5$, when present, is selected from hydrogen, halogen, —CN, C1-C3 alkyl, C1-C3 monohaloalkyl, C1-C3 polyhaloalkyl, cyclopropyl, —$OR^{20}$, —$NR^{21a}R^{21b}$, —$S_2R^{22}$, and —(C=O)$R^{23}$; wherein $R^{20}$, when present, is selected from hydrogen, C1-C3 alkyl, C1-C3 monohaloalkyl, C1-C3 polyhaloalkyl, and cyclopropyl; wherein each of $R^{21a}$ and $R^{21b}$, when present, is independently selected from hydrogen, C1-C3 alkyl, C1-C3 monohaloalkyl, C1-C3 polyhaloalkyl, and cyclopropyl; or wherein $R^{21a}$ and $R^{21b}$, when present, are optionally covalently bonded and, together with nitrogen atom to which they are attached, comprise a 3- to 6-membered heterocycle; wherein $R^{22}$, when present, is selected from C1-C3 alkyl, C1-C3 monohaloalkyl, C1-C3 polyhaloalkyl, cyclopropyl, and, $-NR^{24a}R^{24b}$; wherein each of $R^{24a}$ and $R^{24b}$, when present, is independently selected from hydrogen, C1-C3 alkyl, C1-C3 monohaloalkyl, C1-C3 polyhaloalkyl, and cyclopropyl; or wherein $R^{24a}$ and $R^{24b}$, when present, are optionally covalently bonded and, together with nitrogen atom to which they are attached, comprise a 3- to 6-membered heterocycle; wherein $R^{23}$, when present, is selected from C1-C3 alkyl, C1-C3 monohaloalkyl, C1-C3 polyhaloalkyl, cyclopropyl, and, $-NR^{25a}R^{25b}$; wherein each of $R^{25a}$ and $R^{25b}$, when present, is independently selected from hydrogen, C1-C3 alkyl, C1-C3 monohaloalkyl, C1-C3 polyhaloalkyl, and cyclopropyl; or wherein $R^{25a}$ and $R^{25b}$, when present, are optionally covalently bonded and, together with nitrogen atom to which they are attached, comprise a 3- to 6-membered heterocycle; wherein Q is selected from N and $CR^6$; wherein $R^6$, when present, is selected from hydrogen, halogen, $-CN$, C1-C3 alkyl, C1-C3 monohaloalkyl, C1-C3 polyhaloalkyl, cyclopropyl, $-OR^{30}$, $-NR^{31a}R^{31b}$, $-SO_2R^{32}$, and $-(C=O)R^{33}$; wherein $R^{30}$, when present, is selected from hydrogen, C1-C3 alkyl, C1-C3 monohaloalkyl, C1-C3 polyhaloalkyl, and cyclopropyl; wherein each of $R^{31a}$ and $R^{31b}$, when present, is independently selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle; wherein $R^{32}$, when present, is selected from C1-C3 alkyl, C1-C3 monohaloalkyl, C1-C3 polyhaloalkyl, cyclopropyl, and, $-NR^{34a}R^{34b}$; wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle; wherein $R^{33}$, when present, is selected from C1-C3 alkyl, C1-C3 monohaloalkyl, C1-C3 polyhaloalkyl, cyclopropyl, and, $-NR^{35a}R^{35b}$; wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle; wherein V is selected from N and $CR^7$, provided that Q and V are not simultaneously N; wherein $R^7$, when present, is selected from hydrogen, halogen, $-CN$, C1-C3 alkyl, C1-C3 monohaloalkyl, C1-C3 polyhaloalkyl, cyclopropyl, $-OR^{40}$, $-NR^{41a}R^{41b}$, $-SO_2R^{42}$, and $-(C=O)R^{43}$; wherein $R^{40}$, when present, is selected from hydrogen, C1-C3 alkyl, C1-C3 monohaloalkyl, C1-C3 polyhaloalkyl, and cyclopropyl; wherein each of $R^{41a}$ and $R^{41b}$, when present, is independently selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle; wherein $R^{42}$, when present, is selected from C1-C3 alkyl, C1-C3 monohaloalkyl, C1-C3 polyhaloalkyl, cyclopropyl, and, $-NR^{44a}R^{44b}$; wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle; wherein $R^{43}$, when present, is selected from C1-C3 alkyl, C1-C3 monohaloalkyl, C1-C3 polyhaloalkyl, cyclopropyl, and, $-NR^{45a}R^{45b}$; wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle; wherein Z is selected from $-CR^8(O)_rR^9-$, $-CR^8NR^{10a}R^{10b}-$, $-(C=O)-$, and a structure represented by a formula:

$$\begin{array}{c} R^{12a} \diagdown \diagup R^{12c} \\ R^{12b} {}_m^{\diagup} Y \diagdown {}_n^{\diagup} R^{12d} \end{array}$$

wherein Y is selected from $-CR^8R^9-$, $-O-$, $-S(O)_q-$, and $-NR^8-$; wherein m is an integer selected from 0, 1, and 2; wherein n is an integer selected from 0 and 1; wherein the sum of m and n is 1 or 2 when Y is $-CR^8R^9-$; wherein the sum of m and n is 2 when Y is $-O-$, $-S(O)_q-$, and $-NR^8-$; wherein q is 0, 1, or 2; wherein r is 0 or 1; wherein $R^8$, when present, is selected from hydrogen, halogen, C1-C3 alkyl, C1-C3 monohaloalkyl, C1-C3 polyhaloalkyl, and cyclopropyl; provided that, when Z is $-CR^8(O)_rR^9-$ and r is 1, $R^8$ is not halogen; wherein $R^9$, when present, is selected from hydrogen, halogen, C1-C3 alkyl, C1-C3 monohaloalkyl, C1-C3 polyhaloalkyl, and cyclopropyl; provided that, when Z is $-CR^8(O)_rR^9-$ and r is 1, $R^9$ is not halogen; wherein each of $R^{10a}$ and $R^{10b}$, when present, is independently selected from hydrogen, C1-C3 alkyl, C1-C3 monohaloalkyl, C1-C3 polyhaloalkyl, and cyclopropyl; wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl; wherein $R^1$ is selected from aryl and heteroaryl, and wherein $R^1$ is substituted with 0, 1, 2, or 3 groups independently selected from halogen, $-CN$, C1-C3 alkyl, C1-C3 monohaloalkyl, C1-C3 polyhaloalkyl, cyclopropyl, $-OR^{50}$, $-NR^{51a}R^{51b}$, $-SO_2R^{52}$, and $-(C=O)R^{53}$; wherein each occurrence of $R^{50}$, when present, is independently selected from hydrogen, C1-C3 alkyl, C1-C3 monohaloalkyl, C1-C3 polyhaloalkyl, and cyclopropyl; wherein each occurrence of each of $R^{51a}$ and $R^{51b}$, when present, is independently selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle; wherein each occurrence of $R^{52}$, when present, is independently selected from C1-C3 alkyl, C1-C3 monohaloalkyl, C1-C3 polyhaloalkyl, cyclopropyl, and, $-NR^{54a}R^{54b}$; wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle; wherein each occurrence of $R^{53}$, when present, is independently from C1-C3 alkyl, C1-C3 monohaloalkyl, C1-C3 polyhaloalkyl, cyclopropyl, and, $-NR^{55a}R^{55b}$; wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle; wherein $R^2$ is selected from hydrogen, C1-C3 alkyl, C1-C3 monohaloalkyl, C1-C3 polyhaloalkyl, and cyclopropyl; wherein $R^3$ is selected from hydrogen, halogen, —CN, C1-C3 alkyl, C1-C3 monohaloalkyl, C1-C3 polyhaloalkyl, cyclopropyl, —$OR^{60}$, —$NR^{61a}R^{61b}$, —$SO_2R^{62}$, and —(C=O)$R^{63}$; wherein $R^{60}$, when present, is selected from hydrogen, C1-C3 alkyl, C1-C3 monohaloalkyl, C1-C3 polyhaloalkyl, and cyclopropyl; wherein each of $R^{61a}$ and $R^{61b}$, when present, is independently selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle; wherein $R^{62}$, when present, is selected from C1-C3 alkyl, C1-C3 monohaloalkyl, C1-C3 polyhaloalkyl, cyclopropyl, and, —$NR^{64a}R^{64b}$; wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle; wherein $R^{63}$, when present, is selected from C1-C3 alkyl, C1-C3 monohaloalkyl, C1-C3 polyhaloalkyl, cyclopropyl, and, —$NR^{65a}R^{65b}$; wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle; wherein each of $R^{4a}$, $R^{4b}$, $R^{4c}$, and $R^{4d}$, is independently selected from hydrogen and fluoro; or a pharmaceutically acceptable salt, solvate, or polymorph thereof. The following examples of the formulation of the disclosed compounds of the present invention in tablets, suspension, injectables and ointments are prophetic. Typical examples of recipes for the formulation of the invention are as given below.

a. Tablets

A tablet can be prepared as follows:

| Component | Amount |
|---|---|
| Active ingredient | 5 to 50 mg |
| Di-calcium phosphate | 20 mg |
| Lactose | 30 mg |
| Talcum | 10 mg |
| Magnesium stearate | 5 |
| Potato starch | add to make total weight 200 mg |

In this Example, active ingredient can be replaced with the same amount of any of the compounds according to the present invention, in particular by the same amount of any of the exemplified compounds.

b. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

c. Injectable

A parenteral composition is prepared by stirring 1.5% by weight of active ingredient of the invention in 10% by volume propylene glycol in water.

d. Ointment

An ointment can be prepared as follows:

| Component | Amount |
|---|---|
| Active ingredient | 5 to 1000 mg |
| Stearyl alcohol | 3 g |
| Lanoline | 5 g |
| White petroleum | 15 g |
| Water | add to make total weight 100 g |

In this Example, active ingredient can be replaced with the same amount of any of the compounds according to the present invention, in particular by the same amount of any of the exemplified compounds.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

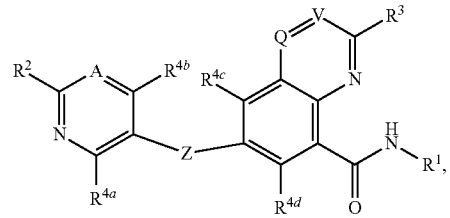

wherein A is N;
wherein Q is selected from N and $CR^6$;
  wherein $R^6$, when present, is selected from hydrogen, halogen, —CN, C1-C3 alkyl, C1-C3 monohaloalkyl, C1-C3 polyhaloalkyl, cyclopropyl, —$OR^{30}$, —$NR^{31a}R^{31b}$, —$SO_2R^{32}$, and —(C=O)$R^{33}$;
  wherein $R^{30}$, when present, is selected from is selected from hydrogen, C1-C3 alkyl, C1-C3 monohaloalkyl, C1-C3 polyhaloalkyl, and cyclopropyl;
  wherein each of $R^{31a}$ and $R^{31b}$, when present, is independently selected from is selected from hydrogen, C1-C3 alkyl, C1-C3 monohaloalkyl, C1-C3 polyhaloalkyl, and cyclopropyl; or wherein $R^{31a}$ and $R^{31b}$, when present, are optionally covalently bonded and, together with nitrogen atom to which they are attached, comprise a 3- to 6-membered heterocycle;
  wherein $R^{32}$, when present, is selected from C1-C3 alkyl, C1-C3 monohaloalkyl, C1-C3 polyhaloalkyl, cyclopropyl, and, —$NR^{34a}R^{34b}$;
    wherein each of $R^{34a}$ and $R^{34b}$, when present, is independently selected from hydrogen, C1-C3 alkyl, C1-C3 monohaloalkyl, C1-C3 polyhaloalkyl, and cyclopropyl; or wherein $R^{34a}$ and $R^{34b}$, when present, are optionally covalently bonded and, together with nitrogen atom to which they are attached, comprise a 3- to 6-membered heterocycle;
  wherein $R^{33}$, when present, is selected from C1-C3 alkyl, C1-C3 monohaloalkyl, C1-C3 polyhaloalkyl, cyclopropyl, and, —$NR^{35a}R^{35b}$;

wherein each of $R^{35a}$ and $R^{35b}$, when present, is independently selected from hydrogen, C1-C3 alkyl, C1-C3 monohaloalkyl, C1-C3 polyhaloalkyl, and cyclopropyl; or wherein $R^{35a}$ and $R^{35b}$, when present, are optionally covalently bonded and, together with nitrogen atom to which they are attached, comprise a 3- to 6-membered heterocycle;

wherein V is selected from N and $CR^7$, provided that Q and V are not simultaneously N;

wherein $R^7$, when present, is selected from hydrogen, halogen, —CN, C1-C3 alkyl, C1-C3 monohaloalkyl, C1-C3 polyhaloalkyl, cyclopropyl, —$OR^{40}$, —$NR^{41a}R^{41b}$, —$SO_2R^{42}$, and —(C=O)$R^{43}$;

wherein $R^{40}$, when present, is selected from is selected from hydrogen, C1-C3 alkyl, C1-C3 monohaloalkyl, C1-C3 polyhaloalkyl, and cyclopropyl;

wherein each of $R^{41a}$ and $R^{41b}$, when present, is independently selected from is selected from hydrogen, C1-C3 alkyl, C1-C3 monohaloalkyl, C1-C3 polyhaloalkyl, and cyclopropyl; or wherein $R^{41a}$ and $R^{41b}$, when present, are optionally covalently bonded and, together with nitrogen atom to which they are attached, comprise a 3- to 6-membered heterocycle;

wherein $R^{42}$, when present, is selected from C1-C3 alkyl, C1-C3 monohaloalkyl, C1-C3 polyhaloalkyl, cyclopropyl, and, —$NR^{44a}R^{44b}$;

wherein each of $R^{44a}$ and $R^{44b}$, when present, is independently selected from hydrogen, C1-C3 alkyl, C1-C3 monohaloalkyl, C1-C3 polyhaloalkyl, and cyclopropyl; or wherein $R^{44a}$ and $R^{44b}$, when present, are optionally covalently bonded and, together with nitrogen atom to which they are attached, comprise a 3- to 6-membered heterocycle;

wherein $R^{43}$, when present, is selected from C1-C3 alkyl, C1-C3 monohaloalkyl, C1-C3 polyhaloalkyl, cyclopropyl, and, —$NR^{45a}R^{45b}$;

wherein each of $R^{45a}$ and $R^{45b}$, when present, is independently selected from hydrogen, C1-C3 alkyl, C1-C3 monohaloalkyl, C1-C3 polyhaloalkyl, and cyclopropyl; or wherein $R^{45a}$ and $R^{45b}$, when present, are optionally covalently bonded and, together with nitrogen atom to which they are attached, comprise a 3- to 6-membered heterocycle;

wherein Z is selected from —$CR^8(O)_rR^9$—, —$CR^8NR^{10a}R^{10b}$—, —(C=O)—, and a structure represented by a formula:

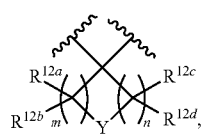

wherein Y is selected from —$CR^8R^9$—, —O—, —$S(O)_q$—, and —$NR^8$—;
wherein m is an integer selected from 0, 1, and 2;
wherein n is an integer selected from 0 and 1;
wherein the sum of m and n is 1 or 2 when Y is —$CR^8R^9$—;
wherein the sum of m and n is 2 when Y is —O—, —$S(O)_q$—, and —$NR^8$—;
wherein q is 0, 1, or 2;
wherein r is 0 or 1;
wherein $R^8$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^8$ is not halogen;

wherein $R^9$, when present, is selected from hydrogen, halogen, C1-C3 alkyl, C1-C3 monohaloalkyl, C1-C3 polyhaloalkyl, and cyclopropyl; provided that, when Z is —$CR^8(O)_rR^9$— and r is 1, $R^9$ is not halogen;

wherein each of $R^{10a}$ and $R^{10b}$, when present, is independently selected from hydrogen, C1-C3 alkyl, C1-C3 monohaloalkyl, C1-C3 polyhaloalkyl, and cyclopropyl;

wherein each occurrence of $R^{12a}$, $R^{12a}$, $R^{12a}$, and $R^{12a}$, when present, is independently selected from hydrogen, halogen, C1-C3 alkyl, C1-C3 monohaloalkyl, and C1-C3 polyhaloalkyl;

wherein $R^1$ is selected from aryl and heteroaryl, and wherein $R^1$ is substituted with 0, 1, 2, or 3 groups independently selected from halogen, —CN, C1-C3 alkyl, C1-C3 monohaloalkyl, C1-C3 polyhaloalkyl, cyclopropyl, —$OR^{50}$, —$NR^{51a}R^{51b}$, —$SO_2R^{52}$, and —(C=O)$R^{53}$;

wherein each occurrence of $R^{50}$, when present, is independently selected from is selected from hydrogen, C1-C3 alkyl, C1-C3 monohaloalkyl, C1-C3 polyhaloalkyl, and cyclopropyl;

wherein each occurrence of each of $R^{51a}$ and $R^{51b}$, when present, is independently selected from is selected from hydrogen, C1-C3 alkyl, C1-C3 monohaloalkyl, C1-C3 polyhaloalkyl, and cyclopropyl; or wherein $R^{51a}$ and $R^{51b}$, when present, are optionally covalently bonded and, together with nitrogen atom to which they are attached, comprise a 3- to 6-membered heterocycle;

wherein each occurrence of $R^{52}$, when present, is independently selected from C1-C3 alkyl, C1-C3 monohaloalkyl, C1-C3 polyhaloalkyl, cyclopropyl, and, —$NR^{54a}R^{54b}$;

wherein each occurrence of each of $R^{54a}$ and $R^{54b}$, when present, is independently selected from hydrogen, C1-C3 alkyl, C1-C3 monohaloalkyl, C1-C3 polyhaloalkyl, and cyclopropyl; or wherein $R^{54a}$ and $R^{54b}$, when present, are optionally covalently bonded and, together with nitrogen atom to which they are attached, comprise a 3- to 6-membered heterocycle;

wherein each occurrence of $R^{53}$, when present, is independently from C1-C3 alkyl, C1-C3 monohaloalkyl, C1-C3 polyhaloalkyl, cyclopropyl, and, —$NR^{55a}R^{55b}$;

wherein each occurrence of each of $R^{55a}$ and $R^{55b}$, when present, is independently selected from hydrogen, C1-C3 alkyl, C1-C3 monohaloalkyl, C1-C3 polyhaloalkyl, and cyclopropyl; or wherein $R^{55a}$ and $R^{55b}$, when present, are optionally covalently bonded and, together with nitrogen atom to which they are attached, comprise a 3- to 6-membered heterocycle;

wherein $R^2$ is selected from hydrogen, C1-C3 alkyl, C1-C3 monohaloalkyl, C1-C3 polyhaloalkyl, and cyclopropyl;

wherein $R^3$ is selected from hydrogen, halogen, —CN, C1-C3 alkyl, C1-C3 monohaloalkyl, C1-C3 polyhaloalkyl, cyclopropyl, $OR^{60}$, —$NR^{61a}R^{61b}$, —$SO_2R^{62}$, and —(C=O)$R^{63}$;

wherein $R^{60}$, when present, is selected from is selected from hydrogen, C1-C3 alkyl, C1-C3 monohaloalkyl, C1-C3 polyhaloalkyl, and cyclopropyl;

wherein each of $R^{61a}$ and $R^{61b}$, when present, is independently selected from is selected from hydrogen, C1-C3 alkyl, C1-C3 monohaloalkyl, C1-C3 polyhaloalkyl, and cyclopropyl; or wherein $R^{61a}$ and $R^{61b}$, when present, are optionally covalently bonded and, together with nitrogen atom to which they are attached, comprise a 3- to 6-membered heterocycle;

wherein $R^{62}$, when present, is selected from C1-C3 alkyl, C1-C3 monohaloalkyl, C1-C3 polyhaloalkyl, cyclopropyl, and, $-NR^{64a}R^{64b}$;

wherein each of $R^{64a}$ and $R^{64b}$, when present, is independently selected from hydrogen, C1-C3 alkyl, C1-C3 monohaloalkyl, C1-C3 polyhaloalkyl, and cyclopropyl; or wherein $R^{64a}$ and $R^{64b}$, when present, are optionally covalently bonded and, together with nitrogen atom to which they are attached, comprise a 3- to 6-membered heterocycle;

wherein $R^{63}$, when present, is selected from C1-C3 alkyl, C1-C3 monohaloalkyl, C1-C3 polyhaloalkyl, cyclopropyl, and, $-NR^{65a}R^{65b}$;

wherein each of $R^{65a}$ and $R^{65b}$, when present, is independently selected from hydrogen, C1-C3 alkyl, C1-C3 monohaloalkyl, C1-C3 polyhaloalkyl, and cyclopropyl; or wherein $R^{65a}$ and $R^{65b}$, when present, are optionally covalently bonded and, together with nitrogen atom to which they are attached, comprise a 3- to 6-membered heterocycle;

wherein each of $R^{4a}$, $R^{4b}$, $R^{4c}$, and $R^{4d}$, is independently selected from hydrogen and fluoro;

or a pharmaceutically acceptable salt thereof.

2. The compound of claim 1, wherein Z is $-CR^8(O)_rR^9-$, wherein r is 0, and wherein at least one of $R^8$ and $R^9$ is $-F$.

3. The compound of claim 1, wherein Z is a structure represented by a formula:

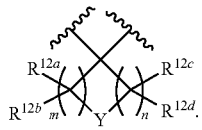

4. The compound of claim 1, wherein $R^1$ is heteroaryl substituted with 0, 1, 2, or 3 groups independently selected from halogen, $-CN$, C1-C3 alkyl, C1-C3 monohaloalkyl, C1-C3 polyhaloalkyl, cyclopropyl, $-OR^{50}$, $-NR^{51a}R^{51b}$, $-SO_2R^{52}$, and $-(C=O)R^{53}$.

5. The compound of claim 1, wherein $R^2$ is selected from hydrogen, methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, and cyclopropyl.

6. The compound of claim 1, wherein $R^3$ is selected from hydrogen, $-F$, $-Cl$, $-CN$, methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, cyclopropyl, $-OH$, $-OCH_3$, $-OCH_2F$, $-OCHF_2$, $-OCF_3$, $-O-$cyclopropyl, $-NH_2$, $-NHCH_3$, $-N(CH_3)_2$, $-SO_2CH_3$, $-SO_2CH_2F$, $-SO_2CHF_2$, $-SO_2CF_3$, $-SO_2-$cyclopropyl, $-SO_2-NH_2$, $-SO_2-NHCH_3$, $-SO_2-N(CH_3)_2$, $-(C=O)CH_3$, $-(C=O)CH_2CH_3$, $-(C=O)CH_2F$, $-(C=O)CH_2Cl$, $-(C=O)CH_2CH_2F$, $-(C=O)CH_2CH_2Cl$, $-(C=O)CHF_2$, $-(C=O)CF_3$, $-(C=O)CHCl_2$, $-(C=O)CCl_3$, $-(C=O)NH_2$, $-(C=O)NHCH_3$, and $-(C=O)N(CH_3)_2$.

7. The compound of claim 1, wherein each of $R^{4a}$, $R^{4b}$, and $R^{4c}$ is hydrogen, and wherein $R^{4d}$ is fluoro.

8. The compound of claim 1, wherein $R^6$, when present, is selected from hydrogen, $-F$, $-Cl$, $-CN$, methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, cyclopropyl, $-OH$, $-OCH_3$, $-OCH_2F$, $-OCHF_2$, $-OCF_3$, $-O-$cyclopropyl, $-NH_2$, $-NHCH_3$, $-N(CH_3)_2$, $-SO_2CH_3$, $-SO_2CH_2F$, $-SO_2CHF_2$, $-SO_2CF_3$, $-SO_2-$cyclopropyl, $-SO_2-NH_2$, $-SO_2-NHCH_3$, $-SO_2-N(CH_3)_2$, $-(C=O)CH_3$, $-(C=O)CH_2CH_3$, $-(C=O)CH_2F$, $-(C=O)CH_2Cl$, $-(C=O)CH_2CH_2F$, $-(C=O)CH_2CH_2Cl$, $-(C=O)CHF_2$, $-(C=O)CF_3$, $-(C=O)CHCl_2$, $-(C=O)CCl_3$, $-(C=O)NH_2$, $-(C=O)NHCH_3$, and $-(C=O)N(CH_3)_2$.

9. The compound of claim 1, wherein $R^7$, when present, is selected from hydrogen, $-F$, $-Cl$, $-CN$, methyl, ethyl, $-CH_2F$, $-CH_2Cl$, $-CH_2CH_2F$, $-CH_2CH_2Cl$, $-CHF_2$, $-CF_3$, $-CHCl_2$, $-CCl_3$, cyclopropyl, $-OH$, $-OCH_3$, $-OCH_2F$, $-OCHF_2$, $-OCF_3$, $-O-$cyclopropyl, $-NH_2$, $-NHCH_3$, $-N(CH_3)_2$, $-SO_2CH_3$, $-SO_2CH_2F$, $-SO_2CHF_2$, $-SO_2CF_3$, $-SO_2-$cyclopropyl, $-SO_2-NH_2$, $-SO_2-NHCH_3$, $-SO_2-N(CH_3)_2$, $-(C=O)CH_3$, $-(C=O)CH_2CH_3$, $-(C=O)CH_2F$, $-(C=O)CH_2Cl$, $-(C=O)CH_2CH_2F$, $-(C=O)CH_2CH_2Cl$, $-(C=O)CHF_2$, $-(C=O)CF_3$, $-(C=O)CHCl_2$, $-(C=O)CCl_3$, $-(C=O)NH_2$, $-(C=O)NHCH_3$, and $-(C=O)N(CH_3)_2$.

10. The compound of claim 1, wherein $R^8$, when present, is selected from C1-C3 alkyl, C1-C3 monohaloalkyl, C1-C3 polyhaloalkyl, and cyclopropyl.

11. The compound of claim 1, wherein $R^9$, when present, is selected from C1-C3 alkyl, C1-C3 monohaloalkyl, C1-C3 polyhaloalkyl, and cyclopropyl.

12. The compound of claim 1, having a structure represented by a formula:

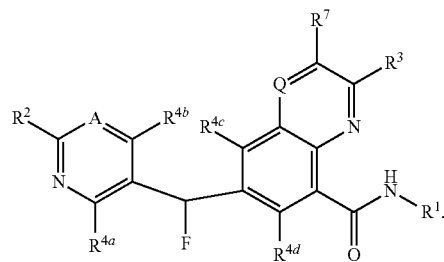

13. The compound of claim 1, having a structure represented by a formula:

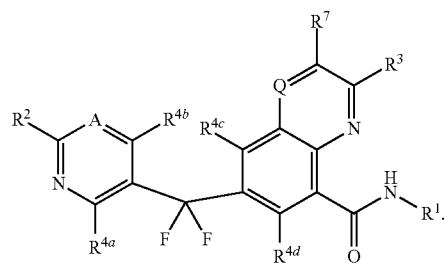

14. The compound of claim 1, having a structure represented by a formula:

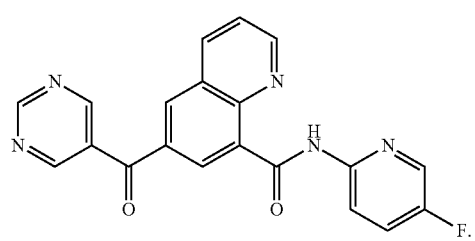

15. The compound of claim 1, having a structure represented by a formula:

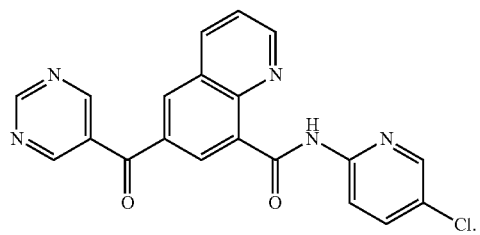 [SMILES: O=C(c1cncnc1)c1cc(C(=O)Nc2ccc(Cl)cn2)c2ncccc2c1]

16. The compound of claim 1, having a structure represented by a formula:

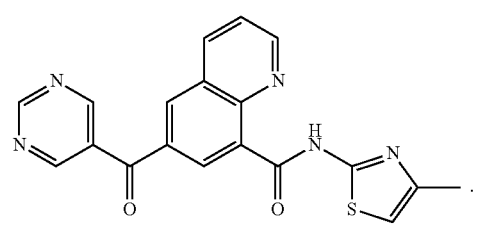 [SMILES: Cc1csc(NC(=O)c2cc(C(=O)c3cncnc3)cc3cccnc23)n1]

17. The compound of claim 1, having a structure represented by a formula:

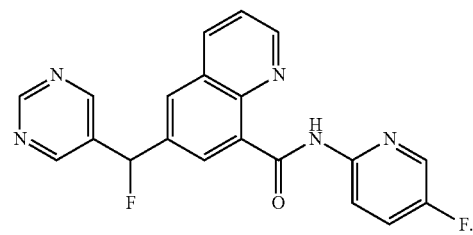

18. The compound of claim 1, having a structure represented by a formula:

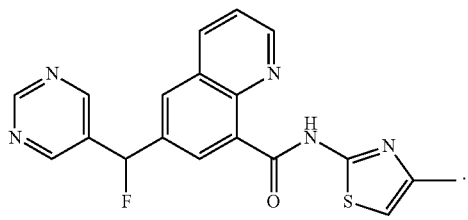

19. The compound of claim 1, having a structure represented by a formula:

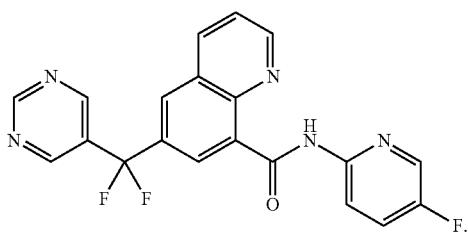 [SMILES: O=C(Nc1ccc(F)cn1)c1cc(C(F)(F)c2cncnc2)cc2cccnc12]

20. The compound of claim 1, having a structure represented by a formula:

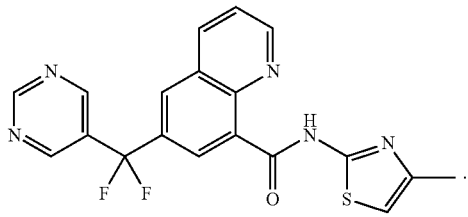 [SMILES: Cc1csc(NC(=O)c2cc(C(F)(F)c3cncnc3)cc3cccnc23)n1]

\* \* \* \* \*

UNITED STATES PATENT AND TRADEMARK OFFICE
CERTIFICATE OF CORRECTION

PATENT NO. : 9,533,982 B2
APPLICATION NO. : 14/664792
DATED : January 3, 2017
INVENTOR(S) : P. Jeffrey Conn et al.

Page 1 of 1

It is certified that error appears in the above-identified patent and that said Letters Patent is hereby corrected as shown below:

In the Specification

Column 1, Lines 15-24, replace:
"This invention was made with government support under Grant No. 2R01-MH062646-12 awarded by the National Institute of Mental Health (NIMH), under Grant No. 5R01-MH073676-04 awarded by the National Institute of Mental Health (NIMH), under Grant No. 5R01-NS031373-15 awarded by the National Institute of Neurological Disorders and Stroke (NINDS), and Grant no. 1R01-DA023947-01 awarded by the National Institute on Drug Abuse (NIDA). The United States government has certain rights in the invention."

With:
-- This invention was made with government support under grant numbers MH062646, MH073676, NS031373 and DA023947 awarded by the National Institutes of Health. The government has certain rights in the invention. --

Signed and Sealed this
Nineteenth Day of November, 2019

Andrei Iancu
*Director of the United States Patent and Trademark Office*